(12) United States Patent
Keck et al.

(10) Patent No.: US 8,415,393 B2
(45) Date of Patent: Apr. 9, 2013

(54) ANTI-BACTERIAL DRUG TARGETING OF GENOME MAINTENANCE INTERFACES

(75) Inventors: James L. Keck, Monona, WI (US); Douglas A. Bernstein, Somerville, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1358 days.

(21) Appl. No.: 12/124,251

(22) Filed: May 21, 2008

(65) Prior Publication Data

US 2009/0203754 A1 Aug. 13, 2009

Related U.S. Application Data

(60) Provisional application No. 60/931,411, filed on May 22, 2007.

(51) Int. Cl.
*A61K 31/03* (2006.01)
*A61K 31/085* (2006.01)
*A61K 31/136* (2006.01)
*A61K 31/192* (2006.01)
*C07C 229/58* (2006.01)

(52) U.S. Cl. ........ 514/567; 514/568; 514/658; 514/716; 514/721; 514/741; 514/759; 562/453

(58) Field of Classification Search .................. None
See application file for complete search history.

(56) References Cited

U.S. PATENT DOCUMENTS

| | | | | |
|---|---|---|---|---|
| 2,950,325 | A * | 8/1960 | Britton et al. | 568/775 |
| 3,042,579 | A * | 7/1962 | Jacobi et al. | 514/658 |
| 3,405,184 | A * | 10/1968 | Widiger, Jr. et al. | 568/637 |
| 4,260,506 | A * | 4/1981 | Munch et al. | 252/78.1 |
| 5,789,444 | A * | 8/1998 | Choi et al. | 514/567 |
| 6,022,698 | A * | 2/2000 | Chen et al. | 435/24 |
| 6,251,943 | B1 * | 6/2001 | Barrett et al. | 514/564 |
| 6,342,630 | B1 * | 1/2002 | Brown et al. | 562/435 |
| 6,646,181 | B1 * | 11/2003 | Eastin | 800/278 |
| 7,588,909 | B2 * | 9/2009 | Robichon | 435/18 |
| 2002/0147432 | A1 * | 10/2002 | Baker | 604/359 |
| 2003/0003444 | A1 | 1/2003 | Pelletier et al. | |
| 2004/0185009 | A1 * | 9/2004 | Penhasi et al. | 424/49 |
| 2004/0186174 | A1 * | 9/2004 | Holzl et al. | 514/543 |
| 2006/0004086 | A1 * | 1/2006 | Mang Koo et al. | 514/420 |
| 2006/0241103 | A1 * | 10/2006 | White et al. | 514/221 |
| 2009/0208535 | A1 * | 8/2009 | Sloane et al. | 424/260.1 |
| 2009/0306021 | A1 * | 12/2009 | Nizet et al. | 514/126 |
| 2010/0204161 | A1 * | 8/2010 | Huse et al. | 514/23 |

FOREIGN PATENT DOCUMENTS

| | | |
|---|---|---|
| EP | 1 190 662 A1 | 3/2002 |
| WO | WO 01/49721 A2 | 7/2001 |
| WO | WO 2009008906 A2 * | 1/2009 |

OTHER PUBLICATIONS

U.S. Appl. No. 60/899,633, filed Feb. 6, 2007.*
Gryglewski et al article. The Fibrinolytic Activity of N-Arylanthranilates. Biochemical Pharmacology. 1966, vol. 15, pp. 1171-1175.*
Breyer and Matthews, "Structure of *Escherichia coli* exonuclease I suggests how processivity is achieved," *Nat. Struct. Biol.*, 7(12):1125-1128 (2000).

Butland et al., "Interaction network containing conserved and essential protein complexes in *Escherichia coli*," *Nature*, 433:531-537 (2005).
Cadman and McGlynn, "PriA helicase and SSB interact physically and functionally," *Nucleic Acids Res.*, 32(21):6378-6387 (2004).
Curth et al., "In vitro and invivo function of the C-terminus of *Escherichia coli* single-stranded DNA binding protein," *Nucleic Acids Res.*, 24(14):2706-2711 (1996).
Genschel et al., "Interaction of *E.coli* Single-Stranded DNA Binding Protein (SSB) with Exonuclease I. The Carboxy-Terminus of SSB is the Recognition Site for the Nuclease," *Biol. Chem.*, 381:183-192 (2000).
Handa et al., "Chimeras between Single-stranded DNA-binding Proteins from *Escherichia coli* and *Mycobacterium tuberculosis* Reveal That Their C-terminal Domans Interact with Uracil DNA Glycosylases," *J. Biol. Chem.*, 276(20):16992-16997 (2001).
Katz et al., "Where have all the antibiotic patents gone," *Nat. Biotech.*, 24(12):1529-1531 (2006).
Lecointe et al., "Anticipating chromosomal replication fork arrest: SSB targets repair DNA helicases to active forks," *EMBO J.*, 26:4239-4251 (2007).
Lehman, "The Deoxyribonucleases of *Escherichia coli*," *J. Biol. Chem.*, 235(5): 1479-1487 (1960).
Lohman and Ferrari, "*Escherichia coli* Single-Stranded DNA-Binding Protein: Multiple DNA-Binding Modes and Cooperatives," *Annu. Rev. Biochem.*, 63: 527-570 (1994).
Lu and Keck, "Structural basis of *Escherichia coli* single-stranded DNA-binding protein stimulation of exonuclease I," *Proc. Natl. Acad. Sci. USA*, 105(27):9169-9174 (2008).
Molineux and Gefter, "Properties of the *Escherichia coli* DNA-binding (Unwinding) Protein Interaction with Nucleolytic Enzymes and DNA," *J. Mol. Biol.*, 98:811-825 (1975).
Nikolovska-Coleska et al., "Development and optimization of a binding assay for the XIAP BIR3 domain using fluorescence polarization," *Anal. Biochem.*, 332:261-273 (2004).

(Continued)

*Primary Examiner* — Jeffrey E Russel
(74) *Attorney, Agent, or Firm* — Allison Johnson; Allison Johnson, P.A.

(57) ABSTRACT

The present invention provides methods for the design and identification of novel antimicrobial compounds, and provides antimicrobial compounds identified using these methods. These antimicrobial compounds inhibit the binding of a prokaryotic single-stranded DNA binding protein to a polypeptide that binds to the prokaryotic single-stranded DNA binding protein. In some examples, the prokaryotic single-stranded DNA binding protein is prokaryotic Exonuclease I. In one embodiment, the antimicrobial compound has the structure

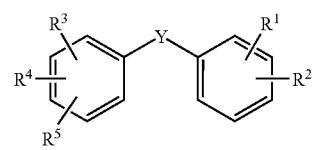

wherein Y is selected from the group consisting of $CH_2$, O, and NH,
$R^1$ is selected from the group consisting of H, F, Cl, Br, and I,
$R^2$ is selected from the group consisting of H and $CF_3$,
$R^3$ is selected from the group consisting of H and $CO_2H$,
$R^4$ is selected from the group consisting of H and OH, and
$R^5$ is selected from the group consisting of H, alkoxy, and $NO_2$.

15 Claims, 18 Drawing Sheets

OTHER PUBLICATIONS

Payne et al., "Drugs for bad bugs: confronting the challenges of antibacterial discovery," *Nat. Rev. Drug Discovery*, 6:29-40 (2007).

Sandigursky et al., "Protein-Protein Interactions between the *Escherichia coli* Single-Stranded DNA-Binding Protein and Exonuclease I," *Radiation Res.*, 145:619-623 (1996).

Shereda et al., "A Central Role for SSB in *Escherichia coli* RecQ DNA Helicase Function," *J. Biol. Chem.*, 282(26):19247-19258 (2007).

Witte et al., "DNA polymerase $III_\chi$ subunit ties single-stranded DNA bnding protein to the bacterial replication machinery," *Nucleic Acids Res.*, 31(15):4434-4440 (2003).

Yuzhakov et al., "Trading Places on DNA-A Three-Point Switch Underlies Primer Handoff from Primase to the Replicative DNA Polymerase," *Cell*, 96: 153-163 (1999).

Andrews, M.J.I. et al., "REPLACE: A Strategy for Iterative Design of Cyclin-Binding Groove Inhibitors," *ChemBioChem*, 7:1909-1915 (2006).

Han, E. et al., "RecJ Exonuclease: Substrates, Products and Interaction with SSB," *Nucleic Acids Research*, 34(4):1084-1091 (2006).

Shereda, R. et al., "SSB as an Organizer/Mobilizer of Genome Maintenance Complexes," *Biochemistry and Molecular Biology*, 43:289-318 (2008).

Communication relating to the Results of the Partial International Search (Annex Form PCT/ISA/206 to Invitation to Pay Additional Fees) dated Apr. 28, 2009 received in related PCT Application No. PCT/US2008/0643655.

\* cited by examiner

ANTI-BACTERIAL DRUG TARGETING OF GENOME MAINTENANCE INTERFACES

CROSS-REFERENCE TO RELATED APPLICATIONS

This invention claims priority to U.S. Provisional Patent Application Ser. No. 60/931,411, filed May 22, 2007, which is herein incorporated by reference.

GOVERNMENT INTERESTS

This invention was made with United States government support awarded by the National Institutes of Health, grant No. GM068061. The United States government has certain rights in this invention.

FIELD OF THE INVENTION

The present invention relates generally to the field of screening for novel antimicrobial compounds.

BACKGROUND

Antibiotic resistant strains of bacteria as well as emerging bacterial pathogens pose a growing threat to world health, and the development of antibiotics necessary to counter these threats has dramatically slowed over the previous decades, leaving the population more vulnerable to these risks (Katz et al., 2006, Nat. Biotech. 24: 1529-1531; Payne et al., 2007, Nat. Rev. Drug Discovery 6: 29-40). Most newly developed antibiotics merely target one of the proven vulnerable pathways previously exploited by prior generations of antibiotics. While these drugs are effective, resistance to them is rising at an alarming rate, suggesting the need for antibiotics that target additional bacterial molecules or cellular processes.

Single-stranded DNA-binding proteins (SSBs) in bacteria form essential intermolecular complexes with at least a dozen other DNA replication, DNA recombination, and DNA repair proteins (Molineux and Gefter, 1975, J. Mol. Biol. 98: 811-825; Butland et al., 2005, Nature 433: 531-537). In addition, SSB proteins play important organizational roles through their interactions with many different genome maintenance proteins. Several, if not all, of these interactions are known to be mediated by the carboxy-terminal-most 8-10 residues from SSB, which form a peptide sequence that is highly conserved among bacterial SSBs but is not found in eukaryotic SSBs (Sandigursky et al., 1996, Radiation Res. 145: 619-623; Curth et al., 1996, Nucleic Acids Res. 24: 2706-2711; Genschel et al., 2000, Biol. Chem. 381: 183-192). Previous studies have shown that mutations within, or deletions of, this interaction sequence from SSB, have drastic effects on bacterial viability, indicating that formation of proper protein interactions with this site is critical for bacterial growth.

SSBs are a conserved protein family found throughout all forms of life, playing a variety of essential roles in nearly all aspects of DNA metabolism. SSBs bind and protect sensitive single-stranded DNA (ssDNA) intermediates that occur during DNA replication, recombination, and repair. SSBs recruit genome maintenance proteins to ssDNA, and play instrumental regulatory roles in ssDNA degradation, replication initiation, initiation of homologous recombination, relaxation of supercoiled DNA, and numerous other genome maintenance processes. Deletions of SSBs have been shown to be lethal and since all known SSBs play similar roles in cells, finding compounds that inhibit bacterial SSBs could have similar effects on eukaryotic cells.

BRIEF SUMMARY

It has been discovered that interfaces involving SSBs may be used as targets to generate promising new classes of antimicrobial compounds. Methods are provided that include reacting polypeptides comprising prokaryotic single-stranded DNA binding proteins, polypeptides that bind to the prokaryotic single-stranded DNA binding proteins, and candidate compounds, and assaying for binding of the polypeptides comprising the prokaryotic single-stranded DNA binding proteins to the polypeptides that bind to the prokaryotic single-stranded DNA binding proteins, where a decrease in binding, relative to the binding of the polypeptides comprising the prokaryotic single-stranded DNA binding proteins to the polypeptides that bind to the prokaryotic single-stranded DNA binding proteins in absence of the candidate compounds, identifies the candidate compounds as antimicrobial compounds. In the practice of the methods, the polypeptides comprising the prokaryotic single-stranded DNA binding proteins may include carboxy-tails that are at least 90% identical to the carboxy-tails of the polypeptides with an amino acid sequence of SEQ ID NO:2, or to the carboxy-tails of the polypeptides with an amino acid sequence of SEQ ID NO:2 having 1 to 4 conservative amino acid substitutions. The polypeptides comprising the prokaryotic single-stranded DNA binding proteins polypeptides may include carboxy-tails comprising the amino acid sequence Asp-Ile-Pro-Phe (SEQ ID NO:5), or the amino acid sequence Asp-Ile-Pro-Phe (SEQ ID NO:5) having 1 to 2 conservative amino acid substitutions.

In the practice of the methods, the polypeptides that bind to the prokaryotic single-stranded DNA binding proteins may include exonucleases, DNA polymerase subunits, primases, helicases, topoisomerases, DNA repair enzymes, etc. In one example, the polypeptides that bind to the prokaryotic single-stranded DNA binding proteins include Exonuclease I. The polypeptides that bind to the prokaryotic single-stranded DNA binding proteins may be at least 90% identical to the amino acid sequence of SEQ ID NO:4. The methods may include assaying that comprises measuring fluorescence polarization.

Methods of inhibiting the binding of SSB-binding proteins to the C-terminal tails of prokaryotic SSBs are provided. The methods include contacting the antimicrobial compounds identified as described above with the SSB-binding proteins and with the C-terminal tails of prokaryotic SSBs, where the antimicrobial compounds inhibit the binding of the prokaryotic SSBs to the SSB-binding proteins. The SSB-binding proteins may be exonucleases, and in some embodiments the SSB-binding proteins may be prokaryotic Exonuclease I.

Methods of inhibiting the growth of microorganisms are provided, which include contacting the antimicrobial compounds identified as described above with the microorganisms, thereby inhibiting the growth of the microorganisms.

Three-dimensional models of crystal structures of prokaryotic Exonucleases I bound to the C-terminal tails of prokaryotic SSBs are provided. In one embodiment, the models substantially represent the atomic coordinates specified in the Protein Data Bank under the accession code 3C94. Methods are provided, which include: a) identifying candidate compounds using three-dimensional models of crystal structures of Exonuclease I bound to C-terminal tails of prokaryotic single-stranded DNA binding proteins, where the models substantially represent the atomic coordinates specified in the Protein Data Bank under the accession code 3C94; b) contacting the candidate compounds with polypeptides comprising the prokaryotic single-stranded DNA binding proteins and with polypeptides that bind to the prokaryotic single-stranded DNA binding proteins; and c) assaying for binding of the polypeptides comprising the prokaryotic single-stranded DNA binding proteins to the polypeptides that bind to the prokaryotic single-stranded DNA binding proteins; where a decrease in binding, relative to the binding of the polypeptides comprising the prokaryotic single-stranded DNA binding proteins to the polypeptides that bind to the prokaryotic single-stranded DNA binding proteins in absence of the candidate compounds, identifies the candidate compounds as antimicrobial compounds. The contacting may be performed in solution. Alternatively, the contacting may be simulated in silico. The methods may also include the step (d) of administering the identified antimicrobial compounds to subjects to determine if the compounds reduce growth of microorganisms in the subjects. Compounds identified by these methods are provided. Antimicrobial pharmaceutical compositions that include as active agents the compounds identified by these methods are also provided.

Methods of inhibiting the binding of prokaryotic Exonucleases I to the C-terminal tails of prokaryotic SSBs are provided, which include: a) designing candidate compounds using three-dimensional models of crystal structures of the prokaryotic Exonucleases I bound to the C-terminal tails of the prokaryotic SSBs, where the models substantially represent the atomic coordinates specified in the Protein Data Bank under the accession code 3C94; and b) contacting the candidate compounds with the Exonucleases I and with the prokaryotic SSBs, where the candidate compounds inhibit the binding of the prokaryotic Exonucleases I to the prokaryotic SSBs. The contacting may be performed in solution. Alternatively, the contacting may be simulated in silico.

Three-dimensional models of crystal structures of prokaryotic Exonuclease I bound to compounds identified according to the present invention are provided. For example, the three-dimensional model of crystal structure of prokaryotic Exonuclease I bound to compound 9 is provided, where the models substantially represent the atomic coordinates specified in Table 6. As well, the three-dimensional models of crystal structure of prokaryotic Exonuclease I bound to compound 10 is provided, where the models substantially represent the atomic coordinates specified in Table 7. Methods are provided, which include: a) identifying candidate compounds using three-dimensional models of crystal structures of Exonuclease I bound to compound 9 or compound 10, where the models substantially represent the atomic coordinates specified in Tables 7 and 8, respectively; b) contacting the candidate compounds with polypeptides comprising the prokaryotic single-stranded DNA binding proteins and with polypeptides that bind to the prokaryotic single-stranded DNA binding proteins; and c) assaying for binding of the polypeptides comprising the prokaryotic single-stranded DNA binding proteins to the polypeptides that bind to the prokaryotic single-stranded DNA binding proteins; where a decrease in binding, relative to the binding of the polypeptides comprising the prokaryotic single-stranded DNA binding proteins to the polypeptides that bind to the prokaryotic single-stranded DNA binding proteins in absence of the candidate compounds, identifies the candidate compounds as antimicrobial compounds. The contacting may be performed in solution. Alternatively, the contacting may be simulated in silico. The methods may also include the step (d) of administering the identified antimicrobial compounds to subjects to determine if the compounds reduce growth of microorganisms in the subjects. Compounds identified by these methods are provided. Antimicrobial pharmaceutical compositions that include as active agents the compounds identified by these methods are also provided.

Methods of inhibiting the growth of microorganisms are provided, which include contacting the antimicrobial compounds identified as described herein with the microorganisms, thereby inhibiting the growth of the microorganisms.

Antimicrobial pharmaceutical compositions comprising as the active agent the antimicrobial compounds identified as described herein are provided. Also provided are methods of treating subjects that have microbial infections, which include the step of administering to the subjects therapeutically effective amounts of these novel pharmaceutical compositions.

DETAILED DESCRIPTION OF THE PRESENTLY PREFERRED EMBODIMENTS

Figure 1:
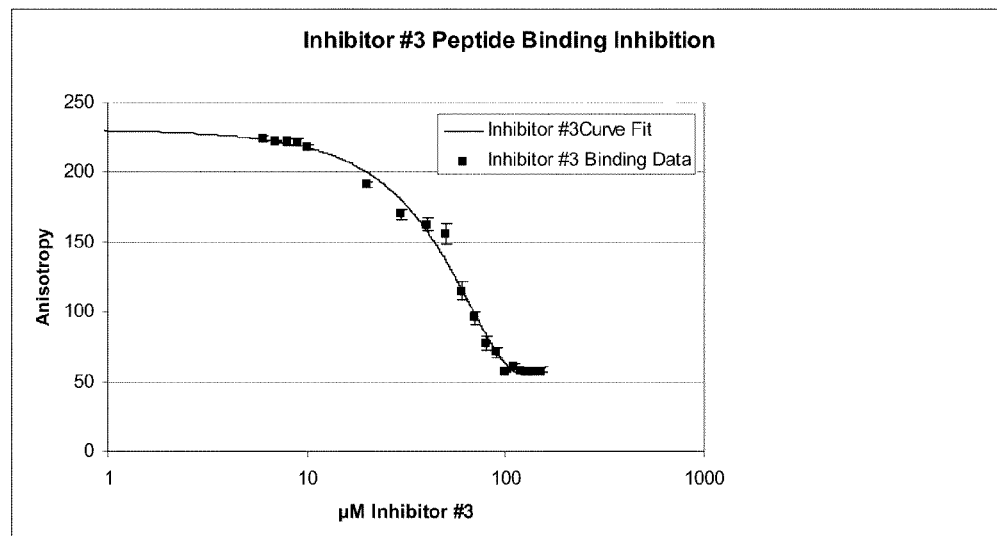
FIG. 1 is a graph showing peptide binding inhibition by inhibitor 3.
Figure 2:
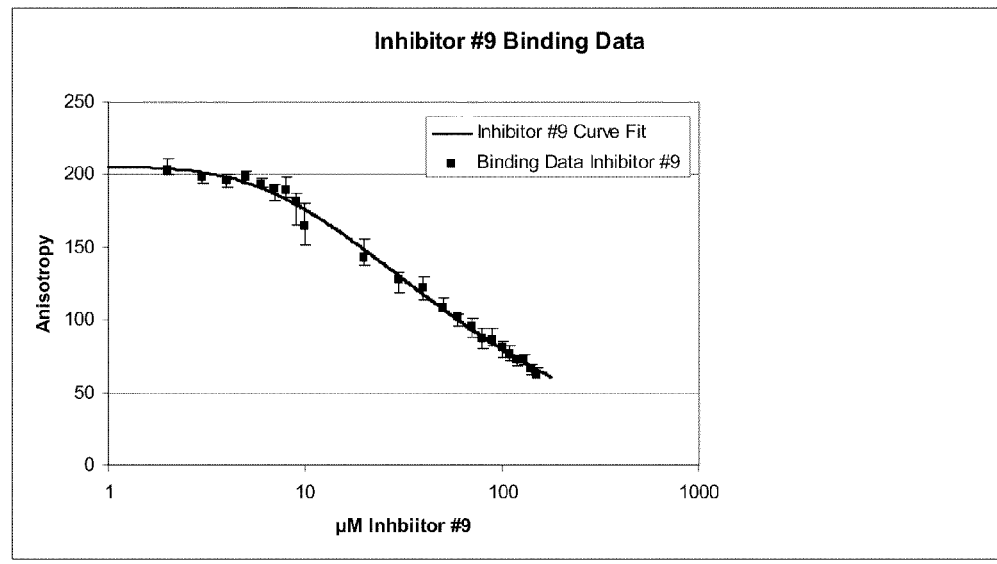
FIG. 2 is a graph showing peptide binding inhibition by inhibitor 9.
Figure 3:
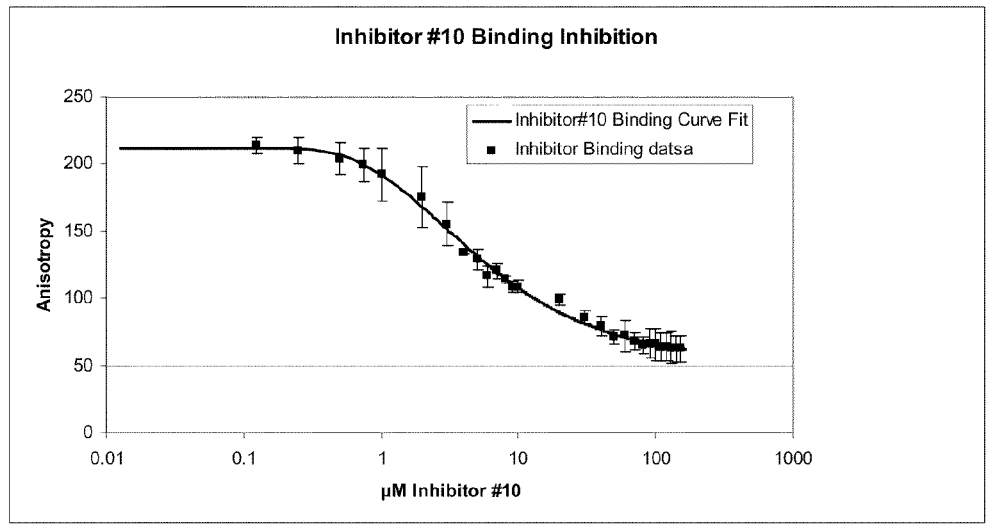
FIG. 3 is a graph showing peptide binding inhibition by inhibitor 10.
Figure 4:
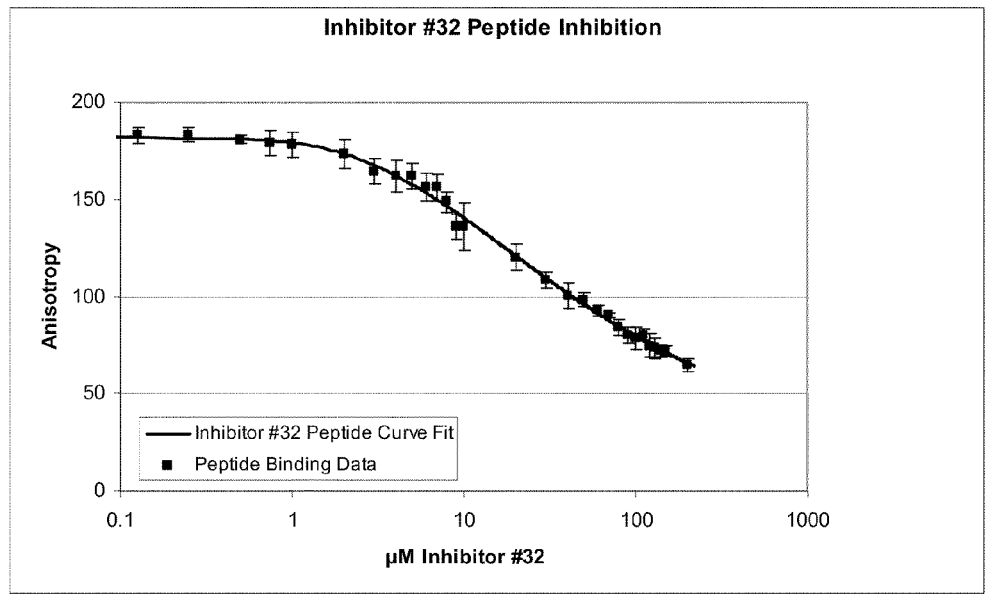
FIG. 4 is a graph showing peptide binding inhibition by inhibitor 32.
Figure 5:
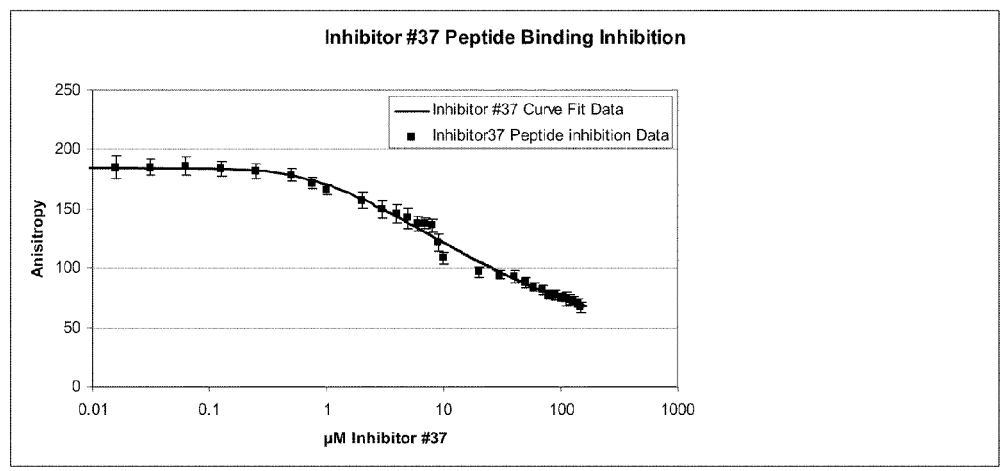
FIG. 5 is a graph showing peptide binding inhibition by inhibitor 37.

Novel and selective targets for antibiotic development are provided. The compounds and assays of the present invention can be used for identification of molecules that selectively inhibit interaction between SSB and its target proteins. Such molecules may be used as novel, broad-spectrum antibiotics. Alternatively, such molecules may be chemically modified, i.e. they may be used as starting points for the development of novel, broad-spectrum antibiotics. The compositions of the present invention find use in methods to inhibit the growth of microorganisms. They find use as disinfectants. They find use as active agents that can be used in pharmaceutical compositions, and they also find use in methods of treating subjects with microbial infections. The term "subject" is intended to include patients, normal volunteers, non-human mammals such as primates, and also other animals.

In one aspect, the present invention relates to novel antimicrobial compounds and to methods of identifying same. An "antimicrobial" is a substance that kills or inhibits the growth of microbes such as bacteria (antibacterial activity), fungi (antifungal activity), viruses (antiviral activity), or parasites (anti-parasitic activity). "Antibiotic" is an antimicrobial substance that is generally used to treat bacterial infections.

The invention is particularly well-suited for the identification of antimicrobial compounds in the form of small molecules that can inhibit the growth of bacteria. In some examples, the bacteria whose growth is inhibited using the compounds of the present invention are Gram-negative bacteria, e.g. *Escherichia coli*. In other examples, the bacteria whose growth is inhibited using the compounds of the present invention are Gram-positive bacteria, e.g. *Staphylococcus aureus*. The present invention may be practiced with bacteria that are not necessarily classified as Gram-positive or Gram-negative, e.g. *Deinococcus radiodurans* and Mycobactedia such as *Mycobacterium tuberculosis*, and also with any other bacteria that have conserved C-terminal residues as described herein.

In one embodiment, the present invention provides for the identification of compounds that inhibit protein complex formation mediated by the single-stranded DNA binding protein's highly conserved C-terminal tail, which could lead to a novel class of chemotherapeutics. The term "SSB" refers to a single-stranded DNA-binding protein. In some embodiments of the present invention, the *E. coli* SSB has the nucleotide sequence of SEQ ID NO:1, and has the amino acid sequence of SEQ ID NO:2.

Prokaryotic SSBs of the present invention include polypeptides that are polymorphic variants, mutants, and interspecies homologs of SEQ ID NO:2. Prokaryotic SSBs of the present invention also include functional equivalents or fragments of SEQ ID NO:2. A "functional fragment" or "functional equivalent" or "functional homolog" of a polypeptide of the present invention is a polypeptide that is homologous to the specified polypeptide but has one or more amino acid differences from the specified polypeptide. A functional fragment or equivalent of a polypeptide retains at least some, if not all, of the activity of the specified polypeptide.

The term "genome maintenance" as used herein refers to the maintenance of the structure and integrity of a genome. Proteins such as the single-stranded DNA-binding protein (SSB) may be involved in genome maintenance.

"Carboxy tail" (also known as the carboxy-tail, carboxyl-terminus, carboxy-terminus, C-terminal end, C-terminus, or COOH-terminus) of a protein or polypeptide is the end of the amino acid chain terminated by a free carboxyl group (—COOH). For purposes of the present invention, the C-terminus of a protein encompasses approximately 10-20 amino acids of the C-terminus of a protein. The SSB's C-terminus is herein also referred to as SSB-Ct.

The canonical prokaryotic SSBs are homotetramers composed of four identical subunits, with each monomeric unit consisting of an oligonucleotide/oligosaccharide binding (OB)-fold followed by a disordered C-terminal tail. The final ten amino acids of the C-terminal tail are very highly conserved among bacteria, and are essential for viability in *E. coli*, yet they are notably absent from both eukaryotic and mitochondrial SSBs. The C-terminal tail of *E. coli* SSB is the primary interaction site between SSB and many, if not all, of its functional partners including Topoisomerase III, PriA DNA helicase, Chi subunit of DNA polymerase III, RecQ DNA helicase, and Exonuclease I. Removal of the C-terminal tail of SSB has little effect on SSB's DNA binding capabilities, but it is nonetheless lethal to *E. coli*.

Methods are provided for the identification of compounds that inhibit protein-protein interactions mediated by the C-terminal tail of SSB. The present invention also provides compounds that are identified using these methods, which compounds can inhibit protein-protein interactions mediated by the C-terminal tail of SSB. These compounds can serve as broad-spectrum antibiotics by disrupting the formation of genome maintenance protein complexes in prokaryotes, and in particular in bacteria. These compounds are not detrimental to eukaryotic genome maintenance complexes since eukaryotic RPA (Replication Protein A) does not contain a similar C-terminal tail, and likely uses a distinct method to recruit binding partners.

Alignment of SSB Tails from Different Prokaryotic Organisms

The alignment of the carboxy-tails of approximately 280 prokaryotic SSBs is shown in Table 1, which shows the conservation of the approximately ten amino acid residues that comprise the carboxy-tails of prokaryotic SSBs. In particular, the alignment of the C-terminal 20 residues of approximately 280 prokaryotic SSBs shows that the four extreme C-terminal residues (DIPF, i.e. Asp-Ile-Pro-Phe; also shown in SEQ ID NO:5) are the most highly conserved residues in the carboxy-tail of these prokaryotic SSBs (Table 1). These final C-terminal residues from the carboxy-tail of prokaryotic SSBs appear to be the most important for binding of proteins.

The present invention contemplates the use of polypeptides with carboxy-tails as shown in Table 1. The present invention contemplates the use of polypeptides with carboxy-tails homologous to the carboxy-tails shown in Table 1. For example, other useful polypeptides may have carboxy-tails as indicated in Table 1 with amino acid sequences comprising one or more conservative amino acid substitutions.

TABLE 1

Alignment of the carboxy-tails (C-termini) of known prokaryotic SSBs

```
Desulfovibrio_desulfuricans--------FDDLGPAFPSEVSGMDDVPF  (SEQ ID NO: 9)

Desulfovibrio_vulgaris------------DDDLGPAFPSEASGMDDVPF   (SEQ ID NO: 10)

Lawsonia_intracellularis----------GFEDISP-FPSEASGMDDVPF  (SEQ ID NO: 11)

Deinococcus_geothermalis----------GLDIDQGLDDFPPEEEDLPF   (SEQ ID NO: 12)

Deinococcus_radiodurans-----------GLDIDQGLDDFPPEEDDLPF   (SEQ ID NO: 13)

Thermus_thermophilus--------------GGVDIDEGLEDFPPEE-DLPF  (SEQ ID NO: 14)

Streptococcus_pneumoniae----------ENNAGQDLADLVLEEEELPF   (SEQ ID NO: 15)

Caldicellulosiruptor_saccharol----DIGTSSKLDLDENPEDDLPF   (SEQ ID NO: 16)

Streptococcus_pyogenes------------NTSSLADSMPDYGPEPDLPF   (SEQ ID NO: 17)

Bacteroides_thetaiotaomicron------QAQPSQAQPIQDNPADDLPF   (SEQ ID NO: 18)

Bacteroides_fragilis--------------SQQPQQPVSSQDNSADDLPF   (SEQ ID NO: 19)

Gramella_forsetii-----------------NFANKNEFYSQDEEEDDLPF   (SEQ ID NO: 20)

Escherichia_coli_K12-------------SAPAAPSNEPPMD---FDDDIPF (SEQ ID NO: 21)

Shigella_dysenteriae_Sd197-------SAPAAPSNEPPMD---FDDDIPF (SEQ ID NO: 22)

Shigella_flexneri----------------SAPAAPSNEPPMD---FDDDIPF (SEQ ID NO: 23)

Shigella_sonnei_Ss046------------SAPAAPSNEPPMD---FDDDIPF (SEQ ID NO: 24)

Shigella_boydii_Sb227------------SAPAAPSNEPPMD---FDDDIPF (SEQ ID NO: 25)

Haemophilus_influenzae-----------QQAAPQAEPPMDG--FDDDIPF  (SEQ ID NO: 26)

Pseudoalteromonas_atlantica------QNKPAPMAEPDFD---FDDDIPF (SEQ ID NO: 27)

Mannheimia_succiniciproducens----TRPAPAAEPAMDN--FDDDIPF  (SEQ ID NO: 28)

Pasteurella_mult-----------------PAPQNEPPMDMGFEBDNIPF   (SEQ ID NO: 29)

Salmonella_enterica-------------QSAPAPSNEPPMD---FDDDIPF  (SEQ ID NO: 30)

Salmonella_typhimurium----------QSAPAPSNEPPMD---FDDDIPF  (SEQ ID NO: 31)

Sodalis_glossinidius------------NSAPAPSNEPPMD---FDDDIPF  (SEQ ID NO: 32)

Erwinia_carotovora--------------NNAPAQSNEPPMD---FDDDIPF  (SEQ ID NO: 33)

Aeromonas_hydrophila------------QSAPPVYNEPPMD---FDDDIPF  (SEQ ID NO: 34)
```

TABLE 1-continued

Alignment of the carboxy-tails (C-termini)
of known prokaryotic SSBs

```
Aeromonas_salmonicida-----------QSAPPVYNEPPMD---FDDDIPF (SEQ ID
NO: 35)

Vibrio_parahaemolyticus---------QQPQQQYNEPPMD---FDDDIPF (SEQ ID
NO: 36)

Photobacterium_profundum--------QQPQQQYNEPPMD---FDDDIPF (SEQ ID
NO: 37)

Vibrio_cholerae-----------------QYSQPQYNEPPMD---FDDDIPF (SEQ ID
NO: 38)

Vibrio_vulnificus---------------MQSQPQYNEPPMD---FDDDIPF (SEQ ID
NO: 39)

Vibrio_fischeri-----------------QAAQPQYNEPPMD---FDDDIPF (SEQ ID
NO: 40)

Psychromonas_ingrahamii---------QPTQTQYNEPSMD---FDDDIPF (SEQ ID
NO: 41)

Yersinia_enterocolitica---------AAQPQGGNEPPMD---FDDDIPF (SEQ ID
NO: 42)

Shewanella_oneidensis-------------QPQQNFTPDLDDG-WDDDIPF (SEQ ID
NO: 43)

Shewanella_loihica----------------QPQQNFTPDLDDG-WDDDIPF (SEQ ID
NO: 44)

Shewanella_putrefaciens-----------QPQQNFTPDLDDG-WDDDIPF (SEQ ID
NO: 45)

Shewanella_baltica----------------QPQQNFTPDLDDG-WDDDIPF (SEQ ID
NO: 46)

Shewanella_amazonensis------------PQQQNYTPDLDDG-WDDDIPF (SEQ ID
NO: 47)

Xanthomonas_campestris------------PAQQQSAPPMDDF-ADDDIPF (SEQ ID
NO: 48)

Xanthomonas_axonopodis------------PAQQQSAPPMDDF-ADDDIPF (SEQ ID
NO: 49)

Xanthomonas_oryzae----------------PAQQQSVPPMDDF-ADDDIPF (SEQ ID
NO: 50)

Xylella_fastidiosa----------------QSPQSSPPPMDDF-ADDDIPF (SEQ ID
NO: 51)

Hahella_chejuensis----------------QQPKPPMPEPMDD-FDDDIPF (SEQ ID
NO: 52)

Marinobacter_aquaeolei------------QQQGGGMPEPIDD-FDDDIPF (SEQ ID
NO: 53)

Alcanivorax_borkumensis---------TNQGGGFSGPADD---FDDDIPF (SEQ ID
NO: 54)

Magnetococcus_MC-1-------------FSSPADTFN-EGPD---FDDDIPF (SEQ ID
NO: 55)

Geobacter_metallireducens-------FGGGPAYDEPAFN---PDDDIPF (SEQ ID
NO: 56)

Geobacter_sulfurreducens-------GFGG-PSYDEPAFN---PDDDIPF (SEQ ID
NO: 57)

Pelobacter_carbinolicus---------QPQQNQYEEPPFN---PDDDIPF (SEQ ID
NO: 58)

Syntrophobacter_fumaroxidans----SRADELPPHPGGG---PDDDIPF (SEQ ID
NO: 59)
```

TABLE 1-continued

Alignment of the carboxy-tails (C-termini)
of known prokaryotic SSBs

```
Leptospira_borgpetersenii-------SSSPESYNPPAPD---GDDDIPF (SEQ ID
NO: 60)

Buchnera_aphidicola----------------PKKIEKIDSSEIDFDDEIPF (SEQ ID
NO: 61)

Coxiella_burnetii-----------------QTPTAGDDSSVADFDDDIPF (SEQ ID
NO: 62)

Photorhabdus_luminescens----------SSVPPRGSEPPIDFDELIPF (SEQ ID
NO: 63)

Nitrosococcus_oceani-------------PRPSAPPSSSND--DFEDDIPF (SEQ ID
NO: 64)

Colwellia_psychrerythraea----------QAPKVNPQEPSIDFDDDIPF (SEQ ID
NO: 65)

Pseudoalteromonas_haloplanktis-----QGGASNPMEPTIDFDDDIPF (SEQ ID
NO: 66)

Wigglesworthia_glossinidia---------KESKKNKIEEEINFDDDIPF (SEQ ID
NO: 67)

Pseudomonas_entomophila------------QQPAPQPAADFDSFDDDIPF (SEQ ID
NO: 68)

Pseudomonas_putida----------------QQPAPQPAADFDSFDDDIPF (SEQ ID
NO: 69)

Pseudomonas_syringae--------------QQQAPQPAADFDSFDDDIPF (SEQ ID
NO: 70)

Pseudomonas_fluorescens-----------QQAAPQPAPDFDSFDDDIPF (SEQ ID
NO: 71)

Pseudomonas_aeruginosa------------QQPAPQPAQDYDSFDDDIPF (SEQ ID
NO: 72)

Pseudomonas_stutzeri---------------PAARQQPAPDYDSEDDDIPF (SEQ ID
NO: 73)

Pseudomonas_mendocina-------------APQQAQPAPDYDSFDDDIPF (SEQ ID
NO: 74)

Saccharophagus_degradans----------PAPAAPPAPDMDSFDDDIPF (SEQ ID
NO: 75)

Methylibium_petroleiphilum--------RQQARQPATAGDGFDDEIPF (SEQ ID
NO: 76)

Thiomicrospira_crunogena----------PAQQVPAYTANDFDDDDVPF (SEQ ID
NO: 77)

Solibacter_usitatus---------------APAQHNDDFNQG-ITDDDVPF (SEQ ID
NO: 78)

Idiomarina_loihiensis-------------KPAEPAPFSPDNDF-DDDIPF (SEQ ID
NO: 79)

Burkholderia_383------------------SRPSAPAGGGFDEMDDDIPF (SEQ ID
NO: 80)

Burkholderia_cepacia--------------SRPSAPAGGGFDEMDDDIPF (SEQ ID
NO: 81)

Burkholderia_pseudomallei---------SRPSAPAGGGFDEMDDDIPF (SEQ ID
NO: 82)

Burkholderia_mallei---------------SRPSAPAGGGFDEMDDDIPF (SEQ ID
NO: 83)

Burkholderia_cenocepacia----------SRPSAPAGGGFDEMDDDIPF (SEQ ID
NO: 84)
```

TABLE 1-continued

Alignment of the carboxy-tails (C-termini)
of known prokaryotic SSBs

Burkhoideria_xenovorans-----------SRPSAPAGGGFDEMDDDIPF (SEQ ID NO: 85)

Burkholderia_vietnamiensis---------SRPSAPAGGGFDEMDDDIPF (SEQ ID NO: 86)

Acidovorax_avenae-----------------AAQAPRAASGFDDMDDDIPF (SEQ ID NO: 87)

Verminephrobacter_eiseniae---------AAPGPRAASGFDDMDDDIPF (SEQ ID NO: 88)

Polaromonas_JS666-----------------APAPTKAASGFDDMDDDIPF (SEQ ID NO: 89)

Rhodoferax_ferrireducens----------APAQAKPSSGFDDMDDDIPF (SEQ ID NO: 90)

Thiobacillus_denitrificans---------AGSQRPASSGFDDMDDDIPF (SEQ ID NO: 91)

Polaromonas_naphthalenivorans------PAASRASPSGFDDMDDDIPF (SEQ ID NO: 92)

Nitrosomonas_eutropha--------------KTGTTGSSTGFDDMEDDIPF (SEQ ID NO: 93)

Nitrosomonas_europaea--------------STPPAKSNTGFDDMEDDIPF (SEQ ID NO: 94)

Nitrosospira_multiformis----------GRAPARSSTGFDDMDDDIPF (SEQ ID NO: 95)

Azoarcus_EbN1---------------------KAPTKSSGAGFGDFDDDIPF (SEQ ID NO: 96)

Methylobacillus_flagellatus--------AASKPAGGSNFDDFEDDIPF (SEQ ID NO: 97)

Rhodospirillum_rubrum-------------TAPASGPAGGP-VDMDDDIPF (SEQ ID NO: 98)

Ralstonia_eutropha----------------RRQQQAPSNGF-EDMDDDIPF (SEQ ID NO: 99)

Ralstonia_solanacearum------------ARRQQAPSNGF-EDMDDDIPF (SEQ ID NO: 100)

Agrobacterium_tumefaciens----------RGGGQPSGGFSNDMDDDIPF (SEQ ID NO: 101)

Neisseria_gonorrhoeae--------------RRQPVPAAAPVEDIDDDIPF (SEQ ID NO: 102)

Neisseria_meningitidis-------------RRQPVPAAAPVEDIDDDIPF (SEQ ID NO: 103)

Herminiimonas_arsenicoxydans-------RPAAKPAASNFNDMDDDIPF (SEQ ID NO: 104)

Nitrobacter_hamburgensis----------PRRTVAAGARRSDMDDDIPF (SEQ ID NO: 105)

Nitrobacter_winogradskyi----------PRRAAPASSHRGDMDDDIPF (SEQ ID NO: 106)

Bordetella_parapertussis----------PAPQAAPAANLADMDDDIPF (SEQ ID NO: 107)

Bordetella_pertussis---------------PAPQAAPAANLADMDDDIPF (SEQ ID NO: 108)

Bordetelia_bronchiseptica----------PAPQAAPAANLADMDDDIPF (SEQ ID NO: 109)

TABLE 1-continued

Alignment of the carboxy-tails (C-termini)
of known prokaryotic SSBs

```
Polynucleobacter_QLW-P1DMWA-1------SAPSASNAASLGAMDDDIPF (SEQ ID
NO: 110)

Acidobacteria_bacterium-----------NDFDSAPAASTGITDDDIPF (SEQ ID
NO: 111)

Candidatus_pelagibacter-----------ANNFEDSPQTSN-DMDDEIPF (SEQ ID
NO: 112)

Psychrobacter_arcticus------------PAQSKPTAMLDGPVDDDIPF (SEQ ID
NO: 113)

Psychrobacter_cryohalolentis------PAQSKPTAMPDGPVDDDIPF (SEQ ID
NO: 114)

Haemophilus_ducreyi---------------NKSSKKSTTQQPEVDDDIPF (SEQ ID
NO: 115)

Dechloromonas_aromatica-----------APPKNKPKPSFDDLGDDIPF (SEQ ID
NO: 116)

Neorickettsia_sennetsu-----------DLGTPTNHVNDTLDD--DDIPF (SEQ ID
NO: 117)

Baumannia_cicadellinicola---------NKILQDMGNEQPIEFDDEIPF (SEQ ID
NO: 118)

Bdellovibrio_bacteriovorus--------FNFQDFGPEPSFNSNDEIPF (SEQ ID
NO: 119)

Chromohalobacter_salexigens-------DNYGAPNPGNFDDFDDEIPF (SEQ ID
NO: 120)

Dichelobacter_nodosus------------SSPDYGP--DGAFDPDDEIPF (SEQ ID
NO: 121)

Aquifex_aeolicus------------------EKLGKEEEKPFTDEEDEIPF (SEQ ID
NO: 122)

Hyphomonas_neptunium-------------QQMSGPKESFS-QDLDDEIPF (SEQ ID
NO: 123)

Caulobacter_crescentus-----------SQPSGPRESES-ADLDDEIPF (SEQ ID
NO: 124)

Maricaulis_mans------------------SMDGPKEDFRNADLDDEIPF (SEQ ID
NO: 125)

Rickettsia_felis-----------------HPEAKNHSFDHSDLDDEIPF (SEQ ID
NO: 126)

Rickettsia_conorii---------------HPETKNHSFDHSDLDDEIPF (SEQ ID
NO: 127)

Rickettsia_typhi-----------------YPEIKNHSFDHSDLDDEIPF (SEQ ID
NO: 128)

Rickettsia_prowazekii------------YPETKNHSFDHSDLDDEIPF (SEQ ID
NO: 129)

Rickettsia_bellii----------------EYKHSKPSFDHSDLDDEIPF (SEQ ID
NO: 130)

Halorhodospira_halophila---------GSGGGGMQEAPADFDDDIPF (SEQ ID
NO: 131)

Paracoccus_denitrificans---------SGGGGGQSQSRPDFDDDIPF (SEQ ID
NO: 132)

Rhodopseudomonas_palustris-------RPMPASSGGGRSDMDDDIPF (SEQ ID
NO: 133)

Bradyrhizobium_japonicum---------RAVAAGGGGRNSDMDDDIPF (SEQ ID
NO: 134)
```

TABLE 1-continued

Alignment of the carboxy-tails (C-termini)
of known prokaryotic SSBs

*Granulibacter_bethesdensis*--------SGGSGWEPSHGG-DLDDEIPF (SEQ ID NO: 135)

*Rhodobacter_sphaeroides*-----------RGNAPSGCGRRS-DLDDEIPF (SEQ ID NO: 136)

*Silicibacter_pomeroyi*-------------GGGRGRGPASGG-IDDDEIPF (SEQ ID NO: 137)

*Roseobacter_denitrificans*---------GGGNAPSPAPSR-DLDDEIPF (SEQ ID NO: 138)

*Magnetospirillum_magneticum*-------GGGCGQSWEPPA-DLDDEIPF (SEQ ID NO: 139)

*Mesorhizobium_BNC1*----------------PAESGGGGHSR-DLDDEIPF (SEQ ID NO: 140)

*Mesorhizobium_loti*----------------APRGGGGGSSR-ELDDEIPF (SEQ ID NO: 141)

*Brucella_melitensis*---------------GPSSGSSGGFSR-DLDDEIPF (SEQ ID NO: 142)

*Brucella_suis*--------------------GPSSGSSGGFSR-DLDDEIPF (SEQ ID NO: 143)

*Brucella_abortus*-----------------GPSSGSSGGFSR-DLDDEIPF (SEQ ID NO: 144)

*Jannaschia_CCS1*-------------------SGGGYGGGGGSSDLDDEIPF (SEQ ID NO: 145)

*Silicibacter_TM1040*---------------NRGGGYGSGSQSID-DDEIPF (SEQ ID NO: 146)

*Novosphingobium_aromaticivoran*----NQGGGSGGGFGD-DLDDDIPF (SEQ ID NO: 147)

*Myxococcus_xanthus*-------------PPDDMGGGHGGGNGD----DDIPF (SEQ ID NO: 148)

*Erythrobacter_litoralis*-----------GGSGGGGGSNYD-DLDDDIPF (SEQ ID NO: 149)

*Anaeromyxobacter_dehalogenans*-----GPGFGSGGGAGG-GGPDDIPF (SEQ ID NO: 150)

*Desulfotomaculum_reducens*--------SGSGSGFGSEISF-NG-DDIPF (SEQ ID NO: 151)

*Sphingopyxis_alaskensis*-----------GAPGGGR-PPFDDDLDDDVPF (SEQ ID NO: 152)

*Pelobacter_propionicus*----------AGTSGGGYEPPPFQD---DDIPF (SEQ ID NO: 153)

*Gluconobacter_oxydans*--------------GSNGGWDAPPDNDLDDEIPF (SEQ ID NO: 154)

*Bartonella_quintana*---------------QNNSQSEESFSHKLDDDVPF (SEQ ID NO: 155)

*Bartonella_henselae*---------------SNNSQLGESFSHKLDDDVPF (SEQ ID NO: 156)

*Bartonella_bacilliformis*----------QNNQSGGSFSHQLDDDVPF (SEQ ID NO: 157)

*Rhizobium_etli*--------------------SSNRGGGGNFSRDLDDDIPF (SEQ ID NO: 158)

*Rhizobium_leguminosarum*------------SRGGGGGGNFSRDLDDDIPF (SEQ ID NO: 159)

TABLE 1-continued

Alignment of the carboxy-tails (C-termini)
of known prokaryotic SSBs

```
Sinorhizobium_meliloti-------------SNQPNQGGNFSRDLDDDIPF (SEQ ID
NO: 160)

Desulfitobacterium_hafniense------HTASGEAYGHEMSLDDDIPF (SEQ ID
NO: 161)

Shewanella_denitrificans-----------KSHLVDSTSKIDFDDEDIPF (SEQ ID
NO: 162)

Candidatus_blochmannia------------NNHELNSESILVNFNEDDIPF (SEQ ID
NO: 163)

Wolbachia_endosyinbiont------------QYENFDSEVKEELIDDEIPF (SEQ ID
NO: 164)

Tropheryma_whipplei----------------KVLVGDNVSYEDFDSDEVPF (SEQ ID
NO: 165)

Ehrlichia_chaffeensis--------------KENSLNSSCDDIIIDDEIPF (SEQ ID
NO: 166)

Ehrlichia_canis--------------------KENFQDSSCDDIIIDDEIPF (SEQ ID
NO: 167)

Ehrlichia_ruminantium--------------NKMPFQNSCEDVIIDDEIPF (SEQ ID
NO: 168)

Helicobacter_acinonychis-----------PSKYQNSVPEINIDEEEIPF (SEQ ID
NO: 169)

Helicobacter_pylori----------------PSKYQNSVPEINIDEEEIPF (SEQ ID
NO: 170)

Thiomicrospira_denitrificans-------QMPSNSSIPEIDIDEDEIPF (SEQ ID
NO: 171)

Wolinella_succinogenes-------------APYKEPQIPEINIDDDEIPF (SEQ ID
NO: 172)

Helicobacter_hepaticus-------------TGNYPQNIPEINIDDEDIPF (SEQ ID
NO: 173)

Campylobacter_fetus----------------RQNKPKQNIDVNIDDEEIPF (SEQ ID
NO: 174)

Dehalococcoides_ethenogenes-------MDARDDDNGGGELEP---EDIPF (SEQ ID
NO: 175)

Dehalococcoides_CBDB1-------------IDAREDDNGGGELEP---EDIPF (SEQ ID
NO: 176)

Symbiobacterium_thermophilum-------RREDGMGSELTLGDDEDVPF (SEQ ID
NO: 177)

Clostridium_novyi------------------IFDQGYDEEITPIDDGDIPF (SEQ ID
NO: 178)

Clostridium_acetobutylicum---------DFGVPVQEDITPVDNSDIPF (SEQ ID
NO: 179)

Clostridium_perfringens------------DSSFNSNDDMTPIDDGDIPF (SEQ ID
NO: 180)

Clostridium_tetani-----------------NNEDNYNDDITPVDEGEVPF (SEQ ID
NO: 181)

Borrelia_afzelii-------------------EDVIKDIDIVDDKFNEDIPF (SEQ ID
NO: 182)

Borrelia_burgdorferi---------------EDVVKDIDIVDDKFSEDIPF (SEQ ID
NO: 183)

Borrelia_garinii-------------------EDAIKNIDIVDDKFNEDIPF (SEQ ID
NO: 184)
```

TABLE 1-continued

Alignment of the carboxy-tails (C-termini)
of known prokaryotic SSBs

*Syntrophomonas_wolfei*--------------EVNMDNIDLVDQHEDEDIPF (SEQ ID NO: 185)

*Anaplasma_marginale*---------------ENAIVEEVSFADEDMDEIPF (SEQ ID NO: 186)

*Anaplasma_phagocytophilum*----------AGSFGGGVDFLDPDVDEIPF (SEQ ID NO: 187)

*Treponema_pallidum*----------------ATSSLDEADFSSSDLDTVPF (SEQ ID NO: 188)

*Rubrobacter_xylanophilus*-----------GRGAGDEVDINESDFDDIPF (SEQ ID NO: 189)

*Treponema_denticola*---------------PSYDDYQPDMGNSDLDNIPF (SEQ ID NO: 190)

*Mycoplasma_penetrans*--------------DDEDPDQVVSNLDWLDEFKF (SEQ ID NO: 191)

*Candidatus_ruthia*----------------PVLDPIAPVDNSEFDDDIPF (SEQ ID NO: 192)

*Acidovorax_JS42*------------------PVLDPIAPVDNSEFDDDIPF (SEQ ID NO: 193)

*Francisella_tularensis*-------------DNMPDFAEINSSNFDDDIPF (SEQ ID NO: 194)

*Porphyromonas_gingivalis*-----------SSVRDTAKEESSEPPSDLPF (SEQ ID NO: 195)

*Acinetobacter_ADP1*---------------YVPKAPQQP--APADLDDDLPF (SEQ ID NO: 196)

*Acinetobacter_baumannii*------------PKAPQQPASAPADLDDDLPF (SEQ ID NO: 197)

*Synechococcus_elongates*------------GSRRDQEGGMAPRDPDSDLF (SEQ ID NO: 198)

*Clostridium_thermocellum*----------EPENTDGEGFFPAE-DDELPF (SEQ ID NO: 199)

*Clostridium_difficile*-------------EPQGLDPQGFQAID-DDDIPF (SEQ ID NO: 200)

*Thermoanaerobacter_tengcongens*-----DIPDDFDGFTPIESEDDLPF (SEQ ID NO: 201)

*Streptococcus_sanguinis*----------DESPFGNSN--PMDISDDDLPF (SEQ ID NO: 202)

*Streptococcus_thermophilus*-------DESPFGNSN--PMDISDDDLPF (SEQ ID NO: 203)

*Streptococcus_agalactiae*---------DESPFGNSN--PMDISDDDLPF (SEQ ID NO: 204)

*Streptococcus_mutans*-------------DESPFGDSN--PMDISDDDLPF (SEQ ID NO: 205)

*Streptococcus_suis*--------------EESPFGASN--PMDISDDDLPF (SEQ ID NO: 206)

*Lactococcus_lactis*--------------QNNDSFG-SD--PMEISDDDLPF (SEQ ID NO: 207)

*Zymomonas_inobilis*--------------SSNTNHDPF--GMDDLDDDVPF (SEQ ID NO: 208)

*Oenococcus_oeni*-----------------PFNTDTGND--SLDISDDDLPF (SEQ ID NO: 209)

TABLE 1-continued

Alignment of the carboxy-tails (C-termini)
of known prokaryotic SSBs

Carboxydothermus_hydrogenoform----DFDPSDFG-TEIEISDEDIPF (SEQ ID NO: 210)

Moorella_therinoacetica-----------NQDFSDLG-TEVEIGEDDLPF (SEQ ID NO: 211)

Geobacillus_kaustophilus----------DDPFANDG-QPIDISDDDLPF (SEQ ID NO: 212)

Geobacillus_thermodenitrifican----EDPFANDG-QPIDISDDDLPF (SEQ ID NO: 213)

Bacillus_licheniformis------------DDPFANDG-KPIDISDDDLPF (SEQ ID NO: 214)

Bacillus_subtilis-----------------DDPFANDG-KPIDISDDDLPF (SEQ ID NO: 215)

Bacillus_halodurans---------------EDPFANDG-KPIDISDDDLPF (SEQ ID NO: 216)

Listeria_welshimeri---------------NDPFASDG-KPIDISDDDLPF (SEQ ID NO: 217)

Lactobacillus_casei---------------PDPFANNG-KPIDISDDDLPF (SEQ ID NO: 218)

Oceanobacillus_iheyensis----------EDPFKNNG-EPIDISDDDLPF (SEQ ID NO: 219)

Bacillus_thuringiensis------------DDPFSNVG-QPIDISDDDLPF (SEQ ID NO: 220)

Bacillus_anthracis----------------DDPFSNVG-QPIDISDDDLPF (SEQ ID NO: 221)

Bacillus_cereus-------------------DDPFSNVG-QPIDISDDDLPF (SEQ ID NO: 222)

Bacillus_clausii-----------------DNDPFSNDG--SIDISDDDLPF (SEQ ID NO: 223)

Pediococcus_pentosaceus-----------NDPFANSG-QSIDISDDDLPF (SEQ ID NO: 224)

Lactobacillus_plantarum-----------ADPFANNG-DQIDISDDDLPF (SEQ ID NO: 225)

Lactobacillus_brevis--------------ADPFANSG-DSIDISDDDLPF (SEQ ID NO: 226)

Lactobacillus_sakei---------------ADPFANNG-QAIDISDDDLPF (SEQ ID NO: 227)

Lactobacillus_salivarius----------ADPFADNG-QSIDISDDDLPF (SEQ ID NO: 228)

Leuconostoc_mesenteroides----------NPFAASGNTEIDISDDDLPF (SEQ ID NO: 229)

Lactobacillus_gasseri-------------QDPFADSG-STIDISDDDLPF (SEQ ID NO: 230)

Enterococcus_faecalis-------------SDPFGGSG-SSIDISDDDLPF (SEQ ID NO: 231)

Staphylococcus_haemolyticus-------DNPFANAN-GPIDISDDDLPF (SEQ ID NO: 232)

Staphylococcus_saprophyticus------DNPFANAN-GPIDISDDDLPF (SEQ ID NO: 233)

Staphylococcus_epidermidis--------DNPFANAN-GPIDISDDDLPF (SEQ ID NO: 234)

TABLE 1-continued

Alignment of the carboxy-tails (C-termini) of known prokaryotic SSBs

```
Listeria_innocua------------------SDSFANEG-KPIDINPDDLPF (SEQ ID
NO: 235)

Listeria_monocytogenes------------SDSFASEG-KPIDINEDDLPF (SEQ ID
NO: 236)

Prosthecochloris_vibrioformis------TSQPPSGPMIENNDKDDLPF (SEQ ID
NO: 237)

Pelodictyon_luteolum--------------PPQTAPSAPMIEN-DKDDLPF (SEQ ID
NO: 238)

Chlorobium_phaeobacteroides-------DYPQQSSGPMIES-EKDDLPF (SEQ ID
NO: 239)

Chlorobium_tepidum----------------YGASPSSGGAQEFEKDDLPF (SEQ ID
NO: 240)

Chlorobium_chlorochromatii--------PPATPTVPTMIDTDKDDLPF (SEQ ID
NO: 241)

Staphylococcus_aureus-------------TQTGNNPFDNTEEDFSDLPF (SEQ ID
NO: 242)

Lactobacillus_delbrueckii---------TNPFDSSDDAINVSNDDLPF (SEQ ID
NO: 243)

Salinibacter_rubber---------------GGDGQPGSDETFEPDDDLPF (SEQ ID
NO: 244)

Cytophaga_hutchinsonii------------AMESAGSFEPQTSGADDLPF (SEQ ID
NO: 245)

Methylococcus_capsulatus----------GGSGAGSSQFDEGFDDDVPF (SEQ ID
NO: 246)

Alkalilimnicola_ehrlichei---------GGRQDNMGDDAGAFEDDIPF (SEQ ID
NO: 247)

Rhodopirellula_baltica------------SSDSQPTGDGPGYDEPDIPF (SEQ ID
NO: 248)

Synechococcus_WH_8102-------------DNQEAAGSFG-GQASDEEIPF (SEQ ID
NO: 249)

Synechococcus_CC9902--------------DNQESGGNFG-GQASDEDIPF (SEQ ID
NO: 250)

Synechococcus_CC9311--------------SEAGSGGFGGGSPSDEEVPF (SEQ ID
NO: 251)

Prochlorococcus_marinus-----------ASNFGGGGFGDG-PSBEEVPF (SEQ ID
NO: 252)

Arthrobacter_aurescens-----------NPSANAGSSWGNS-P-DSEPPF (SEQ ID
NO: 253)

Arthrobacter_FB24-----------------PGVSNAGGGWGNG-P-DSEPPF (SEQ ID
NO: 254)

Mycobacterium_tuberculosis--------PWGSAPASGSFGGG---DDEPPF (SEQ ID
NO: 255)

Mycobacterium_avium---------------PWGSAPASGSFGGG---DDEPPF (SEQ ID
NO: 256)

Mycobacterium_bovis---------------PWGSAPASGSFGGG---DDEPPF (SEQ ID
NO: 257)

Mycobacterium_vanbaalenii---------PWGSAPASGSFGGA---DDEPPF (SEQ ID
NO: 258)

Mycobacterium_gilvum--------------PWGSAPASGSFGGA---DDEPPF (SEQ ID
NO: 259)
```

TABLE 1-continued

Alignment of the carboxy-tails (C-termini)
of known prokaryotic SSBs

*Mycobacterium_smegmatis*---------PWGSAPASGSFSGA---DDEPPF (SEQ ID NO: 260)

*Nocardia_farcinica*----------------GSAPAAGSFGGGRM-DDEPPF (SEQ ID NO: 261)

*Mycobacterium_ulcerans*---------DPWGSAPASGSFG-G---DDEPPF (SEQ ID NO: 262)

*Mycobacterium_leprae*------------PWGSAPTSGSEGVG---DEEPPF (SEQ ID NO: 263)

*Corynebacterium_jeikeium*-------DPWNSAPQSG-FGDG---DDEPPF (SEQ ID NO: 264)

*Corynebacterium_diphtheriae*-----PWSSAPQAGGFGGA---EQDPPF (SEQ ID NO: 265)

*Salinispora_tropica*---------------APAPSRGGSGGGNF-DEEPPF (SEQ ID NO: 266)

*Corynebacterium_efficiens*---------NSAPPAGSGGFGGA-DDEPPF (SEQ ID NO: 267)

*Corynebacterium_glutamicum*--------NSAPPAGSGGFGGA-DDEPPF (SEQ ID NO: 268)

*Rhodococcus_RHA1*----------------APQASGSFGGSGGG---SDEPPF (SEQ ID NO: 269)

*Streptomyces_avermitilis*---------GSSGGSSGGSGGG-Y-SDEPPF (SEQ ID NO: 270)

*Thermobifida_fusca*--------------WATGGGGFGG-GGG-Y-SDEPPF (SEQ ID NO: 271)

*Frankia_CcI3*--------------------APIDDPWSQPAGG--YSDEPPF (SEQ ID NO: 272)

*Nocardioides_JS614*--------------SAPANDPWGAPGVG---SDEPPF (SEQ ID NO: 273)

*Acidothermus_cellulolyticus*--------AEDPWAAGSATGNFSDEPPF (SEQ ID NO: 274)

*Propionibacterium_acnes*-------ANRGGGVDPWASAQT-----DEPPF (SEQ ID NO: 275)

*Leifsonia_xyli*-----------------PSAGTDVWNTPGAYN---DSTPF (SEQ ID NO: 276)

Aster_yellows_witches_broom--NKTATKVIVQKVIFLDNKDK (SEQ ID NO: 277)

Onion_yellows_2--------------------VIVHKVIFLDNKSQTDNLPF (SEQ ID NO: 278)

*Anabaena_variabilis*----------------EESTSTSLPNETQAVANANF (SEQ ID NO: 279)

*Nostoc_PCC_7120*-------------------EESTSTSAPNETQAVANANF (SEQ ID NO: 280)

*Synechocystis_*--------------------LLGSKRDNAEATMNNYPEEF (SEQ ID NO: 281)

*Trichodesinium_erythraeum*----------ELLGSKRDSEQAALASYNEF (SEQ ID NO: 282)

*Flavobacterium_johnsoniae*----------AKNTNFDAPSEGLPINDLPF (SEQ ID NO: 283)

*Thermotoga_maritime*----------------LEIPEEDFSSDTFSEDEPPF (SEQ ID NO: 284)

TABLE 1-continued

Alignment of the carboxy-tails (C-termini)
of known prokaryotic SSBs

```
Syntrophus_aciditrophicus----------EGHFSPFNDLPPLPEDDVPF (SEQ ID
NO: 285)

Leptospira_interrogans-------------VVGQMIRFDGLPGKKEREVA (SEQ ID
NO: 286)

Desulfotalea_psychrophila----------SFPEPTGPDAYGGTGNDVPF (SEQ ID
NO: 287)

Onion_yellows_phytoplasma_OY-M-----CNNVQFLESKKNPDNAYDNF (SEQ ID
NO: 288)

Campylobacter_jejuni---------------EKLKEIDIDAYDSDDTNLPF (SEQ ID
NO: 289)

Thermosynechococcus_elongates-------LSSKRDTDPNAVPAGYVPEI (SEQ ID
NO: 290)

Shewanella_W3-18-1-----------------PADDASSQANWAQTYPEPDF (SEQ ID
NO: 291)

Gloeobacter_violaceus--------------KVDQLELLGRAARPDEPESF (SEQ ID
NO: 292)

Shewanella_ANA-3--------------------AQPQGGHQQNTQQQAYNYHR (SEQ ID
NO: 293)
```

In one aspect, the present invention relates to the determination of the previously unpublished high-resolution structure of the *E. coli* SSB bound to a target protein, Exonuclease I (Exo I) from *Escherichia coli*. The *E. coli* Exonuclease I was described by Lehman, 1960, *J. Biol. Chem.* 235: 1479-1487. Exonucleases, which can be found as individual enzymes, or as parts of larger enzyme complexes, are enzymes that cleave nucleotides one at a time from an end of a polynucleotide chain. The *E. coli* Exonuclease I has the nucleotide sequence of SEQ ID NO:3, and it has the amino acid sequence of SEQ ID NO:4. The atomic coordinates of the crystal structure of the *E. coli* Exonuclease I have been deposited in the Protein Data Bank under the accession code 3C95. The present invention contemplates the use of other prokaryotic exonucleases, and in particular the use of other prokaryotic homologs of the *E. coli* Exonuclease I.

Prokaryotic exonucleases of the present invention include polypeptides that are polymorphic variants, mutants, and interspecies homologs of SEQ ID NO:4. Prokaryotic exonucleases of the present invention also include functional equivalents or fragments of SEQ ID NO:4.

Methods are provided for assaying binding of a prokaryotic SSB to a "SSB-binding protein" (also referred to herein as a "target protein"). An SSB-binding protein is a protein that binds to SSB. The SSB may be a prokaryotic SSB, for example the SSB may be an *E. coli* SSB. The SSB-binding protein may be a prokaryotic SSB-binding protein, for example the SSB-binding protein may be Exonuclease. The Exonuclease may be prokaryotic Exonuclease, and in particular it may be Exonuclease I. The Exonuclease I may be an *E. coli* Exonuclease I.

Also provided are rapid fluorescence polarization methods for measuring the binding of SSB to Exonuclease I in solution. Fluorescence polarization (FP) is a technique that can measure the binding of a tagged molecule to a target molecule using polarized light and a fluorescent tracer. When excited with polarized light, tracers attached to molecules emit high levels of polarized fluorescence. Tracers attached to larger molecules are slower in rotations compared to tracers attached to smaller molecules. For example, fluorescein-labeled peptides can be used to detect specific binding of the peptides to a variety of molecules, since the fluorescein-labeled peptides are depolarized more slowly when bound to targets due to their slower tumbling rates relative to their free tumbling rates. In chemistry, fluorescence anisotropy assays the rotational diffusion of a molecule from the decorrelation of polarization in fluorescence, i.e., between the exciting and emitted (fluorescent) photons. From the rotational diffusion constants, one can estimate the shape of a macromolecule and use that information to design other molecules that may be drug candidates.

Given (1) the importance of protein interactions with SSBs, (2) the broad conservation of SSB protein-binding sequences across bacterial species, and (3) the apparent absence of SSB protein-binding sequences from eukaryotic (human) systems, these assays can be specific for the identification of compounds that selectively inhibit prokaryotic growth. Small molecules that selectively inhibit interaction between SSB and its target proteins are thus attractive, novel, broad-spectrum antibiotics. The present invention contemplates the use of the methods described herein for a high-throughput screen for small-molecule inhibitors of this interaction. Such inhibitors can serve as lead compounds for future biochemical and anti-microbial studies.

The methods of the present invention may be practiced in solution, i.e., in vitro. Thus, by conducting in vitro assays, it is possible to identify novel antimicrobial compounds according to the present invention. In another example, the methods of the present invention may be practiced in silico, i.e. through simulations using computer programs. Thus, using information on the crystal structures of the present invention, it is possible to design and/or to identify structures of novel antimicrobial compounds that can then be chemically synthesized using methods known in the art.

Examples of libraries of compounds that can be screened used in the practice of this invention include a variety of screening libraries that can be obtained from Maybridge (e.g., the HitFinder collection of 14,400 compounds); the 16,000 compound DIVERSet library from ChemBridge; the Chemdiversity library, Chemical Diversity Labs, Inc., etc. Any other candidate compounds can be used in the assays according to this invention. Candidate compounds do not have to be obtained from libraries in order to be screened. Candidate compounds can be synthesized using methods known in the art, and can then be used in the assays of the present invention. For example, candidate compounds can be designed in silico, using data on the crystal structures of the interacting proteins (e.g. SSB and Exonuclease). Once candidate compounds are designed in silico, these candidate compounds can be synthesized using known methods of synthetic chemistry, and can then be tested for their efficacy to inhibit or influence the interaction between the interacting proteins (e.g. SSB and Exonuclease).

In one example, the identification of compounds that inhibit SSB C-terminal tail mediated protein/protein interactions is assayed using a high throughput fluorescence polarization (FP) based screen. The inventors used an FP screen to identify compounds that inhibit binding of ExoI to the C-terminal tail of *E. coli* SSB. The use of ExoI-SSB C-terminal tail binding as a reporter for the high throughput screen has several advantages. First, binding between ExoI and SSB's C-terminal tail is quite strong in comparison to other known binding events allowing determination of an accurate $K_d$ using FP and allowing screening of significant populations of ExoI-SSB-Ct complexes since complex formation can be saturated. Second, FP is very amenable to a high throughput platform, thus allowing for screening large numbers of compounds quickly. Third, the inventors' recent discovery of the crystal structures of Exonuclease I bound to the C-terminal tail of SSB has provided the first known high-resolution picture of the SSB C-terminal tail bound to a functional partner. The crystal structure suggests that the final amino acids of the C-terminal tail play vital roles in binding. These findings are supported by FP data indicating that mutation of the penultimate Pro residue of SSB to Ser eliminates the ability of the ExoI to bind the C-terminal tail of SSB. Not wanting to be bound by the following theory, it is possible that, given the extremely high conservation between the final four amino acids of SSB among disparate bacterial SSB homologs, this mode of protein binding may be a conserved mechanism of recruitment for proteins vital for genome maintenance.

By finding small molecules that inhibit these binding events, it is possible to disrupt the SSB-Exonuclease I interactions thus slowing bacterial growth or killing the bacteria. Furthermore, small molecules that inhibit binding may also inhibit binding between SSB C-terminal tail and other binding partners.

In one example, high throughput screens could be done looking for molecules that disrupt the interaction between SSB's C-terminal tail and other known SSB binding partners. For example, over a dozen SSB-interacting proteins have been already identified in *E. coli* (Butland et al., 2005, *Nature* 433: 531-537). Many of these interactions are mediated by contacts between the C-terminal tail of SSB and its heterotypic binding partners, e.g. ExoI (Sandigursky et al., 1996, *Radiation Research* 145: 619-623; Genschel et al., 2000, *Biol. Chem.* 381: 183-192), the χψ subunit of DNA polymerase III (Yuzhakov et al., 1999, *Cell* 96: 153-163; Witte et al., 2003, *Nucleic Acids Res.* 31: 4434-4440), uracil DNA glycosylase (Hanada et al., 2001, *J. Biol. Chem.* 276: 16992-16997), PriA DNA helicase (Cadman and McGlynn, 2004, *Nucleic Acids Res.* 32:6378-6387), and RecQ DNA helicase (Shereda et al., 2007, *J. Biol. Chem.* 282: 19247-19258).

Since bacterial SSB proteins are predominantly homotetrameric (with four C-termini that can act as protein binding sites) and multiple SSB tetramers can bind to a single extended ssDNA region (Lohman and Ferrari, 1994, *Annu. Rev. Biochem.* 66: 527-570), utilization of SSB as a common target for many genome maintenance enzymes fosters efficient targeting and coordination of several DNA metabolic activities.

Order of Addition of Assay Components when Performing the Screen for Antimicrobial Compounds The present invention contemplates variations of the screens for antimicrobial compounds described herein. As shown below, it is possible to screen libraries of compounds, to identify a number of hits that as candidate antimicrobial compounds. These candidate compounds can be mapped to a peptide-binding site in a crystal structure that represents the C-terminus of SSB bound to a SSB-binding protein (e.g. ExoI). In one example, it is possible to make a screen using a solution of fluorescently labeled C-terminal SSB peptide pre-bound to ExoI and titrate in compounds. Alternatively, it would be possible to conduct a screen by adding Exonuclease I (e.g. to 384 well plates), and then adding a single (e.g. different) candidate compound to each well. This would allow the compound some time to bind to the binding pocket is of ExoI. Fluorescently labeled peptide of the present invention can then be added. This fluorescently labeled peptide would compete for any compounds that were bound to the pocket/s. Not wanting to be bound by the following theory, it is possible that the latter would be a more physiologically relevant screen, since a drug in vivo would likely see its target before the target saw the SSB tail. While in the examples below the screen was conducted using ExoI and the peptide tail, there are numerous variations on this theme that could potentially be useful. The screen can also be performed using other targets from *E. coli*, e.g. Topoisomerase III, the Chi subunit of DNA polymerase, Gyrase, mixtures of these or other targets, etc. Furthermore, this screen could be done using proteins from another bacterium, including but not limited to *Staphylococcus, Bacillus, Enterococcus*, etc. These assays can be done using the entire protein or the C-terminal tail from the species that is being tested.

Using Docking Computer Programs to Identify and Improve Binding of Compounds

Computer modeling and docking procedures can be used to examine and improve the hits from small molecule screening libraries by analyzing the docking modes of known small molecules in the binding pocket. Docking starts with a crystal structure of the small molecule in the receptor pocket. It may happen that an initial hit from a database may not be an optimal structure for a drug. This can be tested by modeling the hit in the active site, then docking other molecules. A binding energy is calculated and compared to the known hits. Conformational fit is also an important part of the docking results and is usually examined by modeling.

After the initial crystal structure is determined for a bound small molecule, computational screening and docking programs such as AutoDock (Scripps research Institute, La Jolla, Calif.), FlexX (BioSolveIT GmbH, Sankt Augustin, Germany), and SLIDE (Michigan State University, East Lansing, Mich.) can be used to screen thousands of compounds from known databases. In this example, each molecule is allowed conformational flexibility to fit in the receptor site and scored on binding ability. In most cases, the receptor is also allowed flexibility. The top compounds from the databases are scored and ranked and the binding modes and binding energies are compared to actual hits from the small molecule assays. This ranks the reliability of both the chemical assay and the docking modes. This procedure leads to a group of molecules that can serve as starting molecules for optimizing the binding pocket with atom by atom de novo or by similar drug binding computer programs.

The methods described herein are amenable to this type of procedure. Indeed, the inventors of the present application have solved a number of crystal structures in which inhibitors are bound to the binding pocket. Using these tools, it is possible to search in silico (i.e., using computer programs) for molecules that bind as well or perhaps even better than the ones that have already been identified herein. In essence, appropriate computer software might be used to help identify the structure of a compound that will optimally inhibit peptide binding. The advantage of using the in silico techniques is the rapidity with which the potential candidate compounds can be screened, since this is a much faster way than doing thousands of binding assays in solution, i.e. in vitro.

Pharmaceutical Compositions that Include Identified Compounds

Pharmaceutical compositions are also provided, which include as active agents the antimicrobial compounds that are identified according to the present invention. The pharmaceutical compositions may be liquid or solid. The liquid composition may, for example, be an aqueous solution comprising one or more antimicrobial compounds. The solid composition may, for example, be a solid preparation obtainable by freeze-drying or spray-drying the above aqueous solution. In one embodiment the solid preparation is a lyophilizate. The aqueous preparation mentioned above includes an aqueous solution of such solid preparation. Still, the above solid composition may be in the form of a kit wherein the solid preparation and an infusion are formulated into separate preparations.

An example of the technology for producing the pharmaceutical compositions of this invention is described below. An aqueous solution can be produced by dissolving the antimicrobial compound in a conventional manner, in a solvent of choice. This aqueous solution may be alkaline, neutral, or basic; it is just sufficient that the antimicrobial compound is dissolved in the aqueous solution. The concentration of the antimicrobial compound in such an aqueous solution may for example be at concentrations consistent with measured minimal inhibitory concentrations (Table 3). In some embodiments, the concentration is chosen so that it permits successful lyophilization in a subsequent procedure. Referring to the manufacture of a solid pharmaceutical composition, a lyophilizate, for instance, can be produced by freeze-drying an aqueous solution that includes one or more antimicrobial compounds of the present invention. An exemplary procedure comprises freezing the aqueous solution at about −25° C. and, with the internal negative pressure of the freeze-dryer being maintained at about 0.1 Torr or less, increasing the plate temperature at a rate of about 5° C. to 20° C./hour to an ultimate temperature of about 25° C. to 40° C. Where lyophilization is carried out, a form regulator may be added to an aqueous solution of the antimicrobial compound for the purpose of improving the morphology of the lyophilizate. The form regulator may include various sugars (e.g. sugar alcohols such as mannitol, xylitol, inositol, sorbitol, etc., hexose-based disaccharides such as maltose, sucrose, lactose, etc., and monosaccharides such as glucose), neutral amino acids (e.g. glycine, alanine, proline, valine, methionine, etc.) and alkali metal salts of succinic acid (e.g. sodium succinate, etc.). Where a spray-dried preparation is the desired product, the aqueous solution described above is spray-dried by a per se known technique. An exemplary procedure comprises ejecting the aqueous solution in mist form from a spray dryer nozzle (e.g. a twin nozzle, a pressure nozzle, etc.) or rotary disk into its drying chamber at a flow rate of about 5-20 ml/minute (e.g. drying chamber inlet and out temperatures: about 80° C. to 120° C. and about 30° C. to 50° C., respectively; air flow rate about 70-100 kg/hour).

For insuring a further increase in drug absorption, a surfactant can be used concomitantly in the pharmaceutical compositions of this invention. Examples of suitable surfactants include nonionic surfactants such as sorbitan fatty acid esters (e.g. sorbitan monopalmitate, sorbitan sesquistearate, etc.), glycerin fatty acid esters (e.g. glyceryl monostearate, etc.), propylene glycol fatty acid esters (e.g. propylene glycol monostearate), polyoxyethylene glycerin fatty acid esters (e.g. polyoxyethylene glyceryl monostearate, etc.), polyethylene glycol fatty acid esters (e.g. polyoxyethylene monostearate, PEG distearate, etc.), polyoxyethylene alkyl ethers (e.g. polyoxyethylene lauryl ether, polyoxyethylene stearyl ether, etc.), polyoxyethylene hydrogenated castor oil, polyoxyethylene sorbitol beeswax derivatives, polyoxyethylene lanolin alcohol, polyoxyethylene sorbitol fatty acid esters, Pluronic series surfactants, anionic surfactants such as alkali metal dodecyl sulfates, alkali metal stearates, alkali metal palmitates, and liquid surfactants such as Tween 20 and Tween 80, among others. These surfactants can be used singly or plurally in a suitable ratio.

For improving the solubility or stability of the antimicrobial compound, a variety of salts (e.g. salts of organic acids such as sodium citrate, sodium tartrate, sodium benzoate, etc.) and/or stabilizers (e.g. basic inorganic salts such as magnesium carbonate, calcium carbonate, magnesium hydrogen carbonate, calcium hydrogen carbonate, etc.) may be incorporated or added to the compositions of this invention. If necessary, an isotonizing agent (e.g. sodium chloride) for osmotic pressure adjustment and/or a soothing or local anesthetic agent (e.g. glucose, sorbitol, mannitol, benzyl alcohol, mepivacaine hydrochloride, xylocaine hydrochloride, etc.) can also be employed.

A preservative and a pH control agent can be added in small amounts as required. The preservative includes parabens such as methyl p-hydroxybenzoate, propyl p-hydroxybenzoates, etc., alcohols such as chlorobutanol, quaternary ammonium salts such as benzalkonium chloride, benzethonium chloride, cetrimide, etc., sorbic acid, chlorhexidines, thimerosal and so on. The pH control agent includes various acids, e.g. inorganic acids such as hydrochloric acid, boric acid, phosphoric acid, carbonic acid, hydrogen carbonic acid, etc., organic acids such as mono- or polycarboxylic acids, amino acids, etc., and various bases, e.g. alkali metal hydroxides such as sodium hydroxide, potassium hydroxide, etc. and alkali metal (hydrogen) carbonates such as sodium hydrogen carbonate, sodium carbonate and so on. These additives can be used alone or in combination and can be added in a proportion of about 0.001-10 mg, preferably about 0.01-5 mg, per milligram of the antimicrobial compound.

The pharmaceutical compositions of this invention are generally administered orally or parenterally in a dosage form manufactured by formulating such an active ingredient with a pharmacologically acceptable carrier or excipient. The pharmaceutical composition of this invention can be put to use in the following manner. Taking a solid composition as an example, it can be extemporaneously dissolved in sterile distilled water or an infusion fluid (e.g. physiological saline, glucose infusion, etc.) and used as, for example, an intravenous, subcutaneous, intramuscular or intravenous drip injection or as an ophthalmic solution. Preparation of such an injection is preferably carried out by known aseptic procedures.

The dosage of the pharmaceutical composition of this invention is dependent on dosage form, therapeutic regimen, species of active compound and other factors. In some embodiments, the pharmaceutical composition may be administered once or divided into 2 to 3 times a day.

EXAMPLES

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

Structures of Compounds

Shown below are examples of compounds that were identified in the screens for compounds that inhibit SSB-Exonuclease I binding, according to this invention. For each of the compounds, the name of the compound, the chemical formula of the compound, the molecular weight of the compound (MW), and the chemical structure of the compound are shown. Also shown are the name of the company that provided the library from which the compound was identified, and the product code for the specific compound in the library. The $K_i$ value is dissociation constant used to describe the affinity between a ligand (such as a drug, in the present case the tested inhibitory compound) and a peptide or a protein, i.e. how tightly a ligand (i.e., the tested inhibitory compound) binds to a particular peptide or protein. The $IC_{50}$ value refers to the half maximal inhibitory concentration, i.e. the concentration of an inhibitory compound that is required for 50% inhibition of its target in vitro. It measures how much of a particular substance/molecule is needed to inhibit some biological process (e.g., bacterial growth in LB) by 50%.

Compound 3

Name: 2-[5-(3-bromobenzylidene)-4-oxo-2-thioxo-1,3-thiazolidin-3-yl]-3-phenylpropanoic acid. Formula: $C_{19}H_{14}BrNO_3S_2$. MW: 448.36. Company: ChemBridge. Product Code: 6044448. $K_i$=~2.5 µM. $IC_{50}$ E. coli 4213=5.5 µM. $IC_{50}$ Staphylococcus aureus=10 µM.

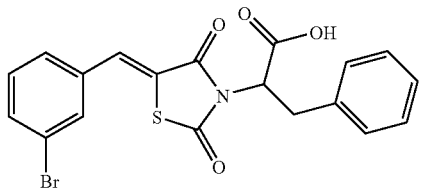 [SMILES: O=C(O)C(Cc1ccccc1)N1C(=O)S/C(=C\c2cccc(Br)c2)C1=O]

Compound 8

Name: [5-(2-methyl-3-phenyl-2-propen-1-ylidene)-4-oxo-2-thioxo-1,3-thiazolidin-3-yl](phenyl)acetic acid. Formula: $C_{21}H_{17}NO_3S_2$. MW: 395.5. Company: ChemBridge. Product Code: 5767720. $K_i$=~4 µM. $IC_{50}$ E. coli 4213=11 µM. $IC_{50}$ Staphylococcus aureus=29 µM.

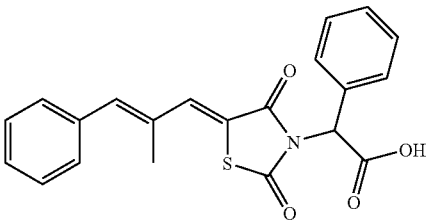 [SMILES: CC(/C=C1\SC(=O)N(C(C(=O)O)c2ccccc2)C1=O)=C\c1ccccc1]

Compound 9

Name: 3-(tert-butyl)-1-(6-chloro-1,3-benzothiazol-2-yl)-4,5-dihydro-1H-pyrazol-5-one. Formula: $C_{14}H_{14}ClN_3OS$. MW: 307.79766. Company: Maybridge. Product Code: SEW01297. $K_i$=~773 nM. $IC_{50}$ E. coli 4213=6 µM. $IC_{50}$ Staphylococcus aureus=5.5 µM.

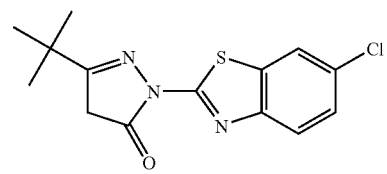 [SMILES: CC(C)(C)C1=NN(c2nc3ccc(Cl)cc3s2)C(=O)C1]

Compound 10

Name: 2-[2-chloro-5-(trifluoromethyl)anilino]-5-methoxybenzoic acid. ACD Code: MFCD00175807. Formula: $C_{15}H_{11}ClF_3NO_3$. MW: 345.705449. Company: Maybridge. Product Code: S07197. $K_i$=~124.7 nM. $IC_{50}$ E. coli 4213=30 µM. $IC_{50}$ Staphylococcus aureus=18 µM.

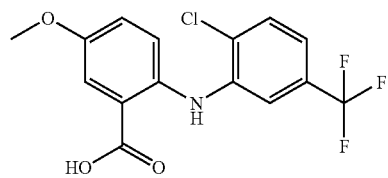 [SMILES: COc1ccc(Nc2cc(C(F)(F)F)ccc2Cl)c(C(=O)O)c1]

Compound 28

Name: 1-(1,3-benzothiazol-2-yl)-3,4-dimethyl-1H-pyrazol-5-ol. Formula: $C_{12}H_{11}N_3OS$. MW: 245.3. Company: Chembridge. Product Code: 9040944.

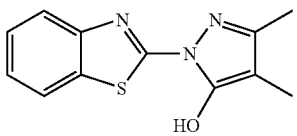 [SMILES: Cc1nn(-c2nc3ccccc3s2)c(O)c1C]

Compound 29

Name: 1-(1,3-benzothiazol-2-yl)-3-isopropyl-1H-pyrazol-5-ol. Formula: $C_{13}H_{13}N_3OS$. MW: 259.33. Company: ChemBridge. Product Code: 9036389.

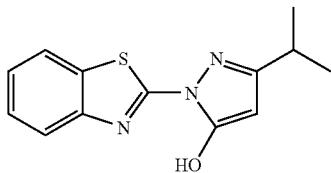 [SMILES: CC(C)c1cc(O)n(-c2nc3ccccc3s2)n1]

Compound 31

Name: 2-(1,3-benzothiazol-2-yl)-5-methyl-2,4-dihydro-3H-pyrazol-3-one. Formula: $C_{11}H_9N_3OS$. MW: 231.27. Company: Chembridge. Product Code: 5108305.

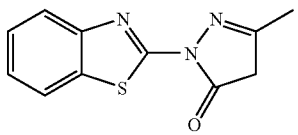 [SMILES: CC1=NN(c2nc3ccccc3s2)C(=O)C1]

Compound 32

Name: 2-[3-(trifluoromethyl)anilino]benzoic acid. Formula: $C_{14}H_{10}F_3NO_2$. MW: 281.234109. Company: Maybridge. Product Code: RJC02179.

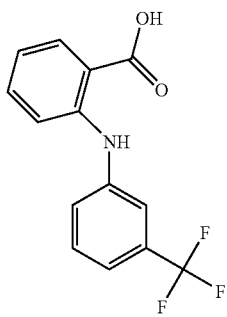 [SMILES: O=C(O)c1ccccc1Nc1cccc(C(F)(F)F)c1]

Compound 37

Name: 5-[2-chloro-5-(trifluoromethyl)phenoxy]-2-nitrophenol. Formula: $C_{13}H_7ClF_3NO_4$. MW: 333.64. Company: ChemBridge. Product Code: 5524827.

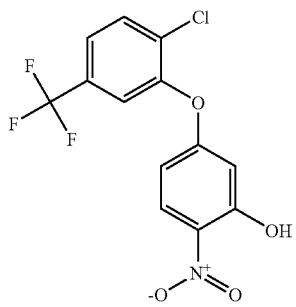

Compound 42

Name: N-(6-chloro-1,3-benzothiazol-2-yl)-3,5-dimethyl-4-isoxazolecarboxamide. Formula: $C_{13}H_{10}ClN_3OS$. MW: 307.7543. Company: Maybridge. Product Code: HTS08909.

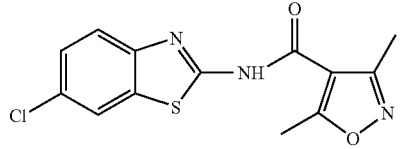 [SMILES: Cc1noc(C)c1C(=O)Nc1nc2ccc(Cl)cc2s1]

Compound 46

Name: 1-(6-chloro-1,3-benzothiazol-2-yl)-3-methyl-4,5-dihydro-1H-pyrazol-5-one. Formula: $C_{11}H_8ClN_3OS$. MW: 265.71702. Company: Maybridge. Product Code: SEW01296.

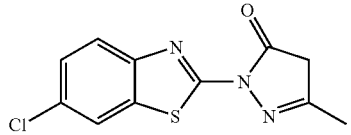 [SMILES: CC1=NN(c2nc3ccc(Cl)cc3s2)C(=O)C1]

Peptides Corresponding to the C-Terminal Tail of SSB

Peptides corresponding to the C-terminal tail of SSB or variants thereof were synthesized and purified by the University of Wisconsin-Madison Biotechnology Center. "WT" peptide comprises an added N-terminal Trp (W) residue for quantification followed by the 9 C-terminal-most residues from E. coli SSB: Trp-Met-Asp-Phe-Asp-Asp-Asp-Ile-Pro-Phe (SEQ ID NO:6). Thus, the synthesized peptide was fluorescein-WMDFDDDIPF (i.e., fluorescein-SEQ ID NO:6). The Trp residue absorbs at 280 nm thus allowing accurate quantification of the peptide concentration. Alternatively, other residues or tags could be used for practicing the invention, so long as they can be used to accurately quantify the peptide concentration. In competitive binding experiments, the peptide WMDFDDDIPF (SEQ ID NO:6) was used without a fluorescent moiety.

A second peptide that was used, "F-WT", comprises the same sequence but adds an N-terminal fluorescein moiety. Two additional peptides that alter the F-WT sequence were also synthesized: the first, "F-P176S", substitutes a Ser residue for the penultimate Pro in the WT sequence, and the second, "F-mixed", is a randomly-chosen sequence of the SSB-derived portion of the F-WT peptide sequence Trp-Asp-Phe-Met-Asp-Asp-Pro-Phe-Ile-Asp (SEQ ID NO:8). Other peptides that were used in the experiments described below were WDDIPF (SEQ ID NO:7) and WMDFDDDIPF (SEQ ID NO:6). Neither of these peptides was fluorescently labeled.

Peptide Binding Assay

Peptide binding assays were performed in solution, using the peptides from above, and Exonuclease I, in the absence or presence of various compounds. Different amounts of Exonuclease I (ExoI) were used in the peptide binding assays. Typically, 0.1-10,000 nM E. coli ExoI (or a variant) was incubated with 10 nM F-WT, F-P176S, or F-mixed peptide in 20 mM Tris-HCl, pH 8.0, 100 mM NaCl, 1 mM $MgCl_2$, 4% (v/v) glycerol, 1 mM 2-mercaptoethanol, and 0.1 mg/ml bovine serum albumin (BSA) at room temperature for 10 minutes. Fluorescence polarization (FP) was measured at 25°

C. in triplicate; the average FP value was plotted with standard deviation of the mean shown as error.

Figure 6:
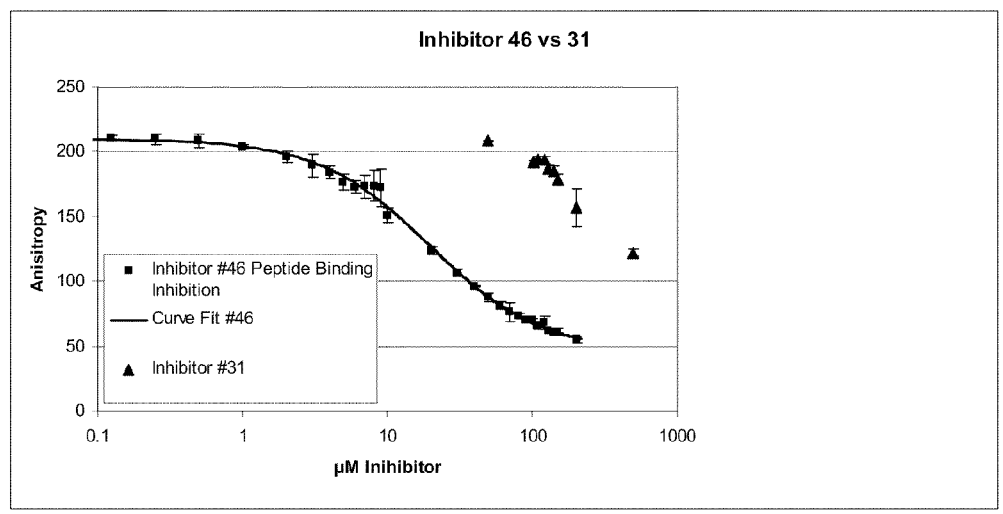
FIG. 6 is a graph showing peptide binding inhibition by inhibitor 46 vs. peptide binding inhibition by inhibitor 31.
Figure 7:
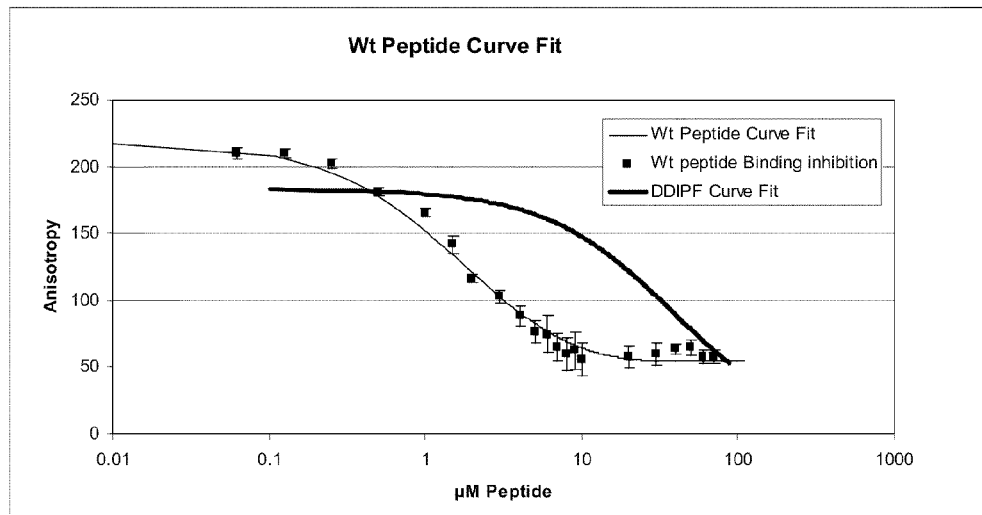
FIG. 7 is a graph showing peptide binding inhibition by the WT peptide.
Figure 8:
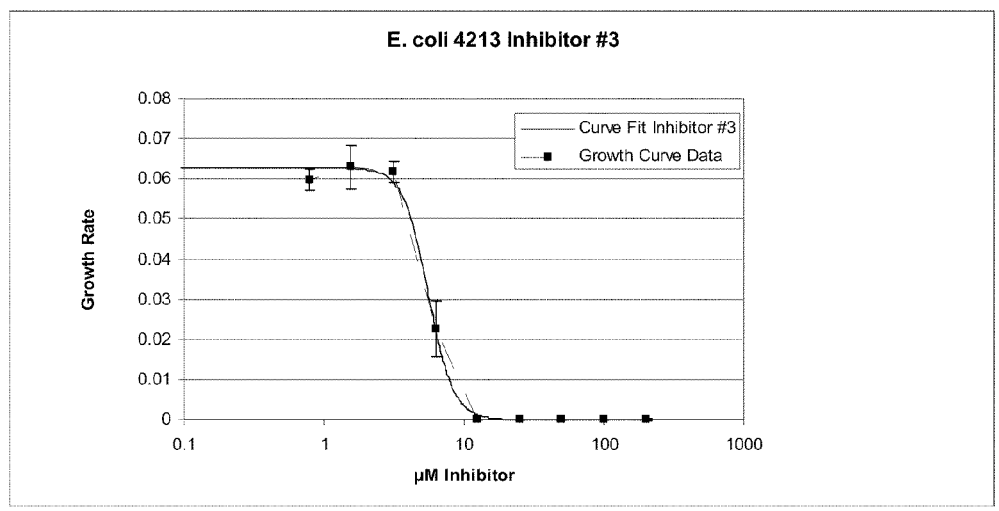
FIG. 8 is a graph showing the inhibition of *Escherichia coli* 4213 growth by inhibitor 3.
Figure 9:
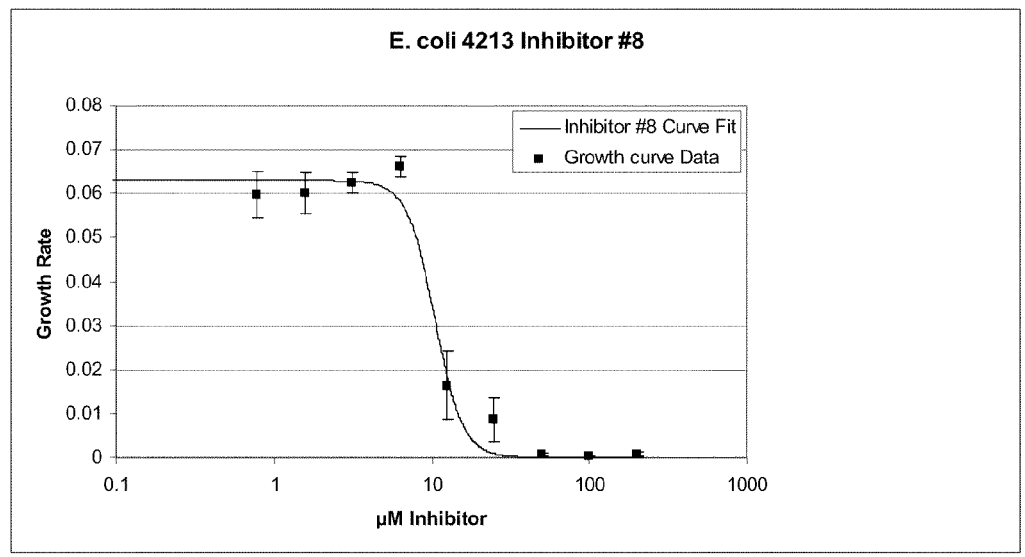
FIG. 9 is a graph showing the inhibition of *Escherichia coli* 4213 growth by inhibitor 8.
Figure 10:
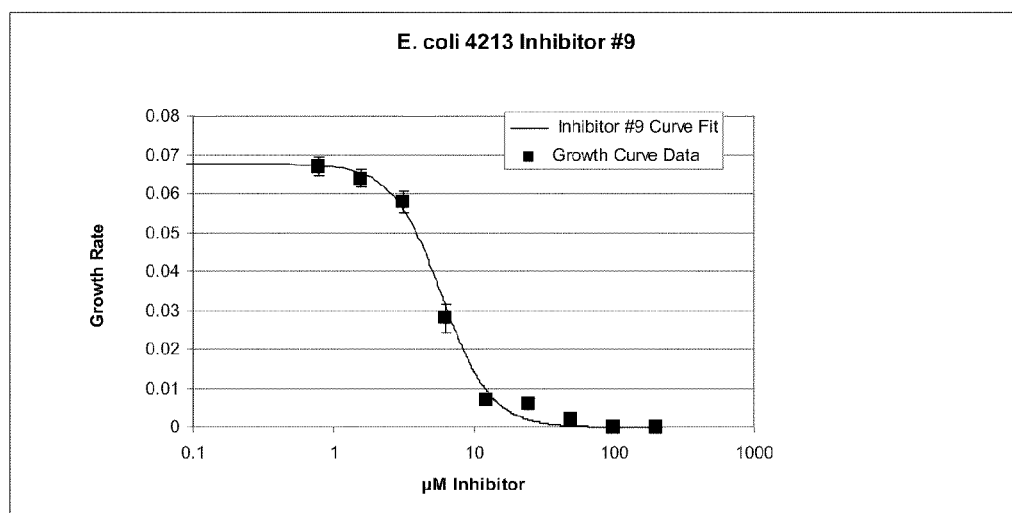
FIG. 10 is a graph showing the inhibition of *Escherichia coli* 4213 growth by inhibitor 9.
Figure 11:
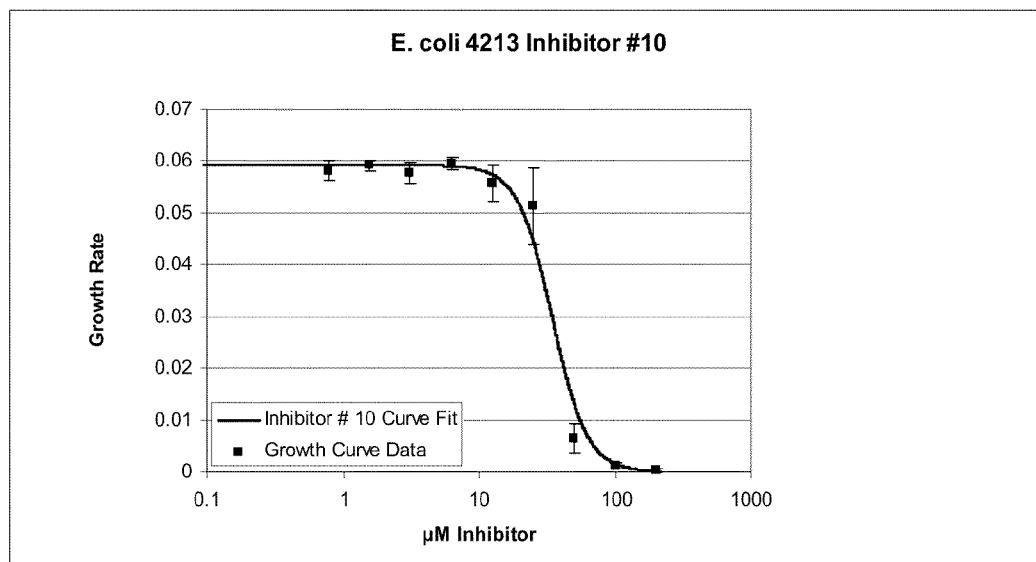
FIG. 11 is a graph showing the inhibition of *Escherichia coli* 4213 growth by inhibitor 10.
Figure 12:
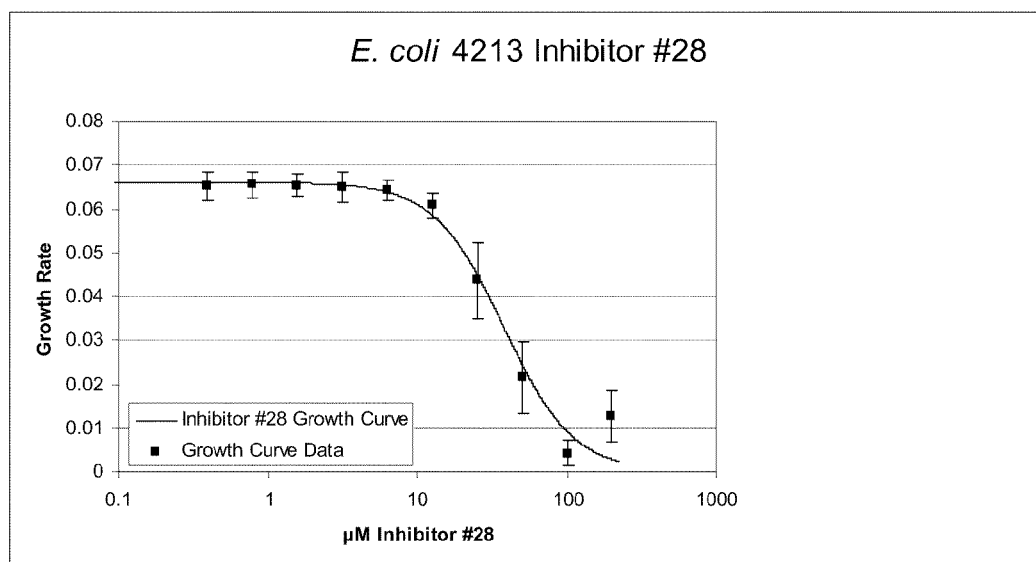
FIG. 12 is a graph showing the inhibition of *Escherichia coli* 4213 growth by inhibitor 28.
Figure 13:
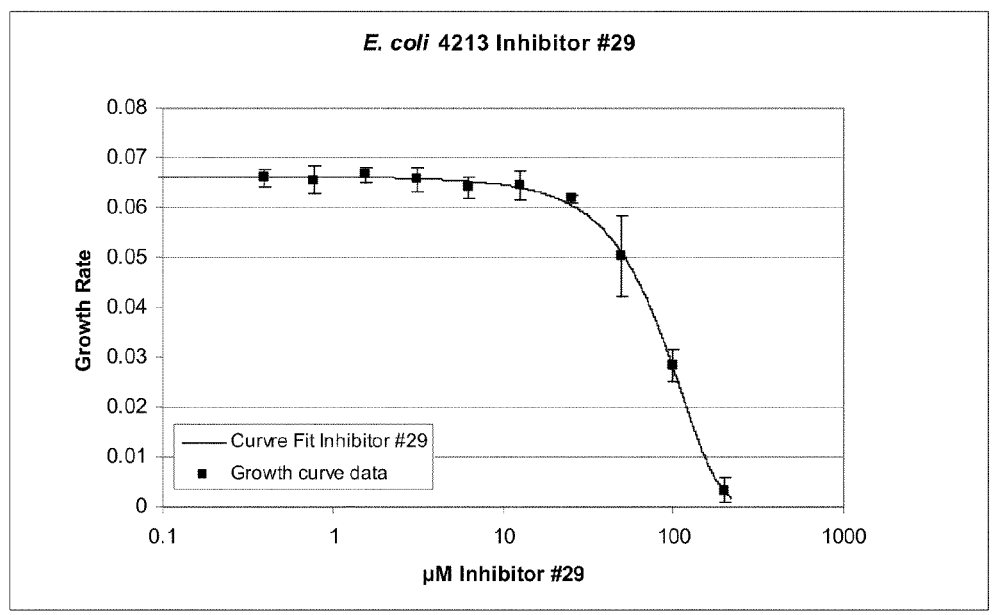
FIG. 13 is a graph showing the inhibition of *Escherichia coli* 4213 growth by inhibitor 29.
Figure 14:
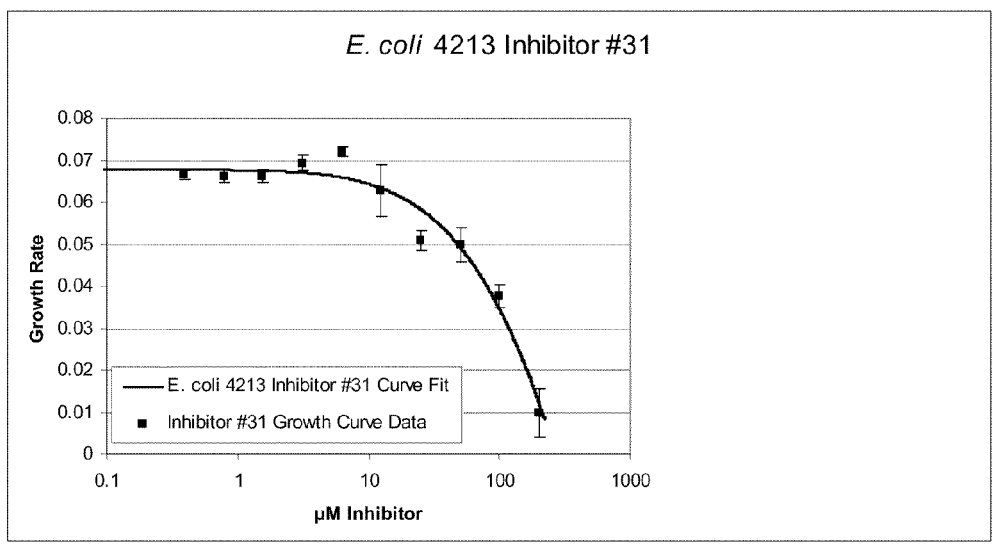
FIG. 14 is a graph showing the inhibition of *Escherichia coli* 4213 growth by inhibitor 31.
Figure 15:
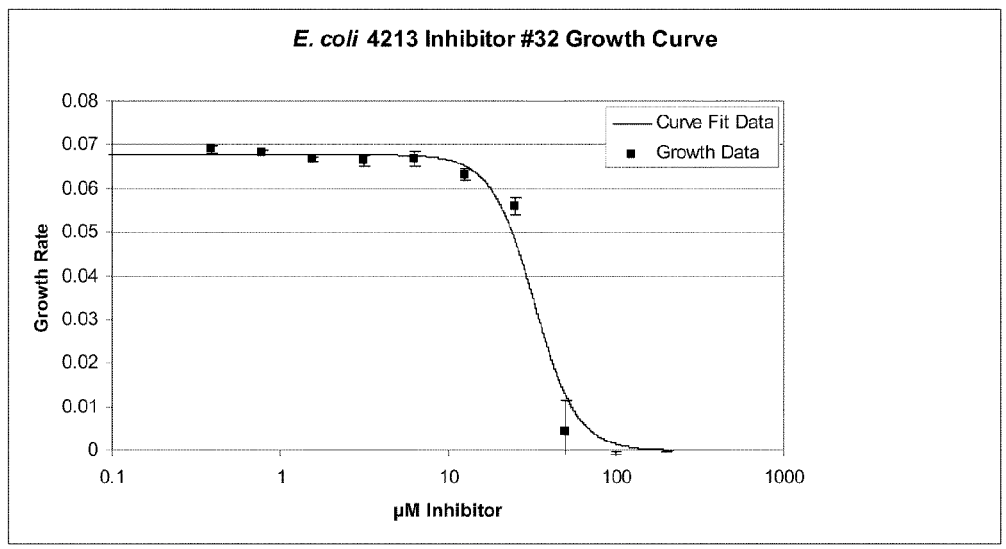
FIG. 15 is a graph showing the inhibition of *Escherichia coli* 4213 growth by inhibitor 32.
Figure 16:
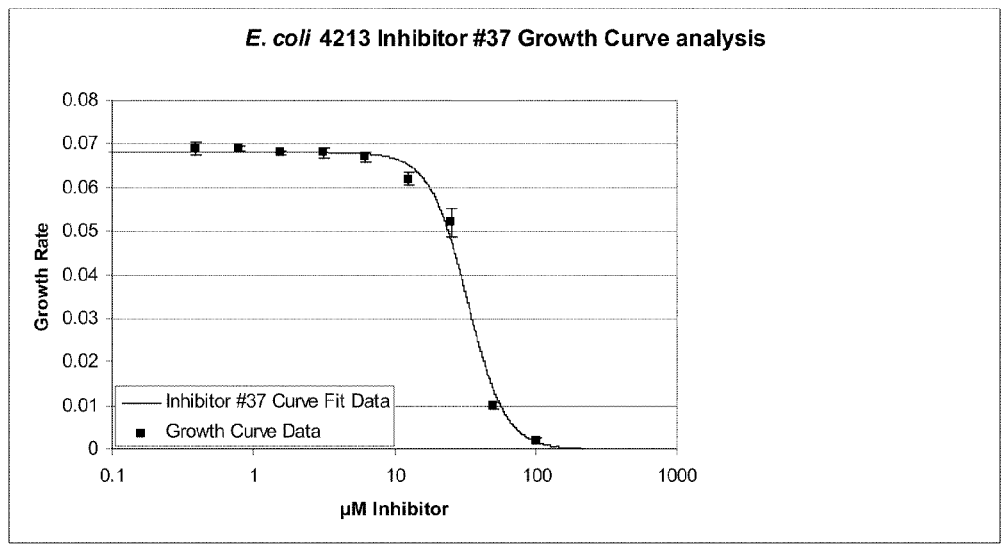
FIG. 16 is a graph showing the inhibition of *Escherichia coli* 4213 growth by inhibitor 37.
Figure 17:
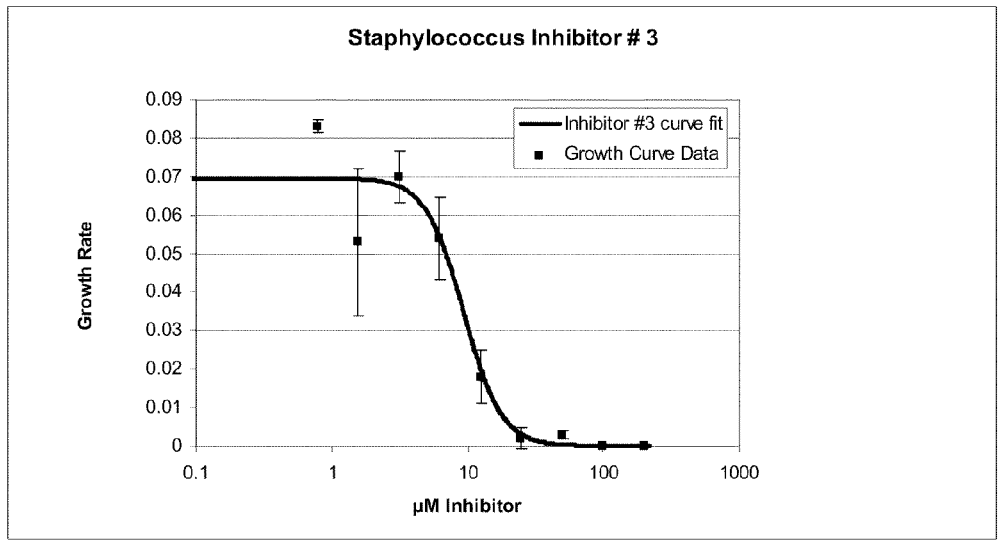
FIG. 17 is a graph showing the inhibition of *Staphylococcus aureus* growth by inhibitor 3.
Figure 18:
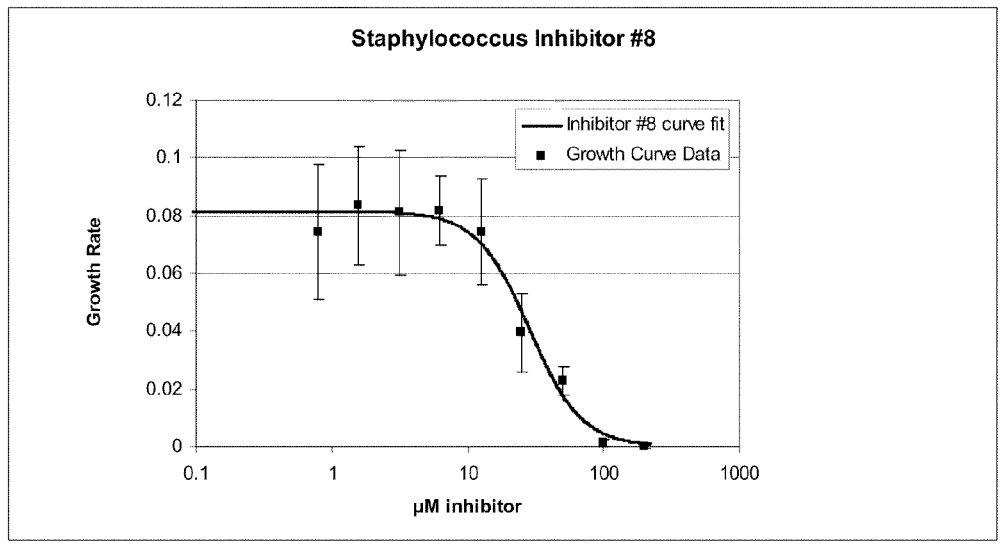
FIG. 18 is a graph showing the inhibition of *Staphylococcus aureus* growth by inhibitor 8.
Figure 19:
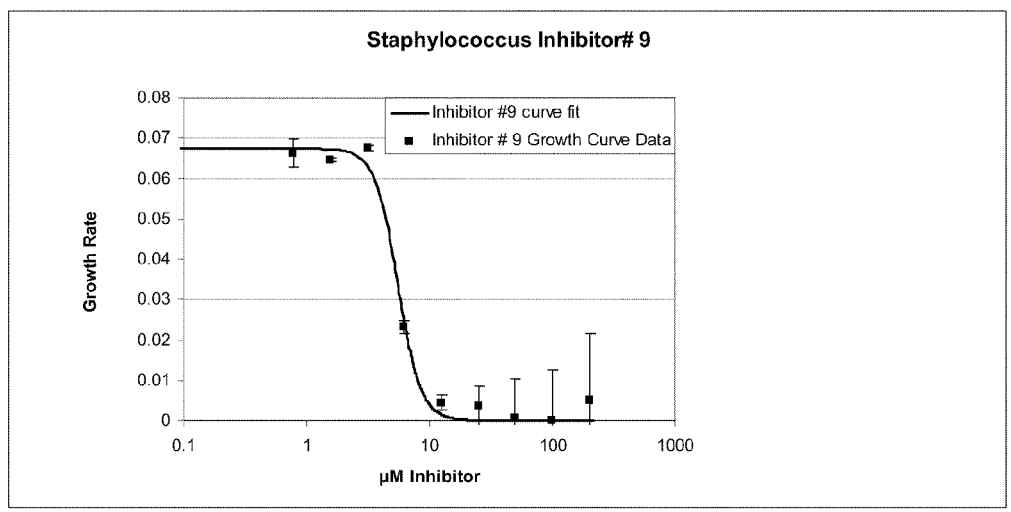
FIG. 19 is a graph showing the inhibition of *Staphylococcus aureus* growth by inhibitor 9.
Figure 20:
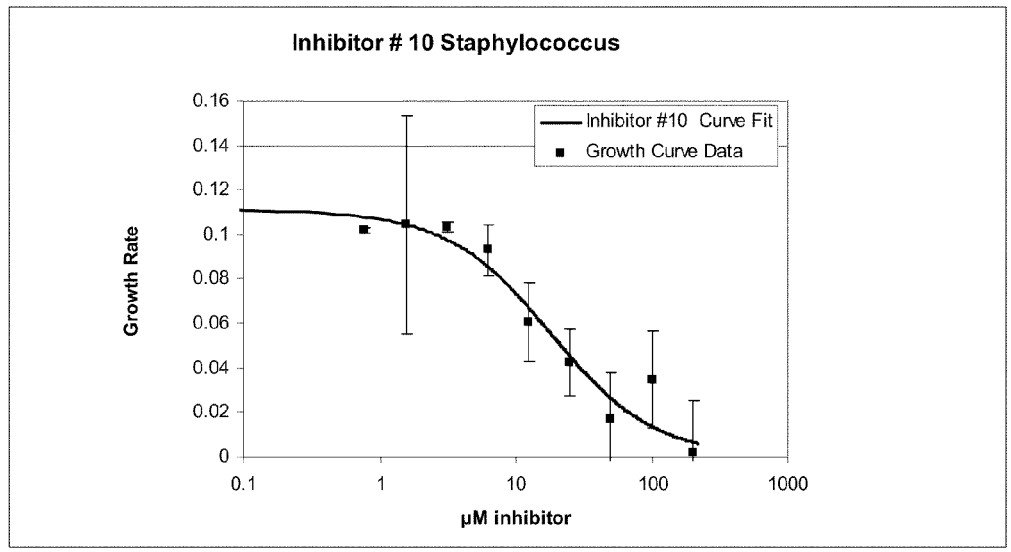
FIG. 20 is a graph showing the inhibition of *Staphylococcus aureus* growth by inhibitor 10.
Figure 21:
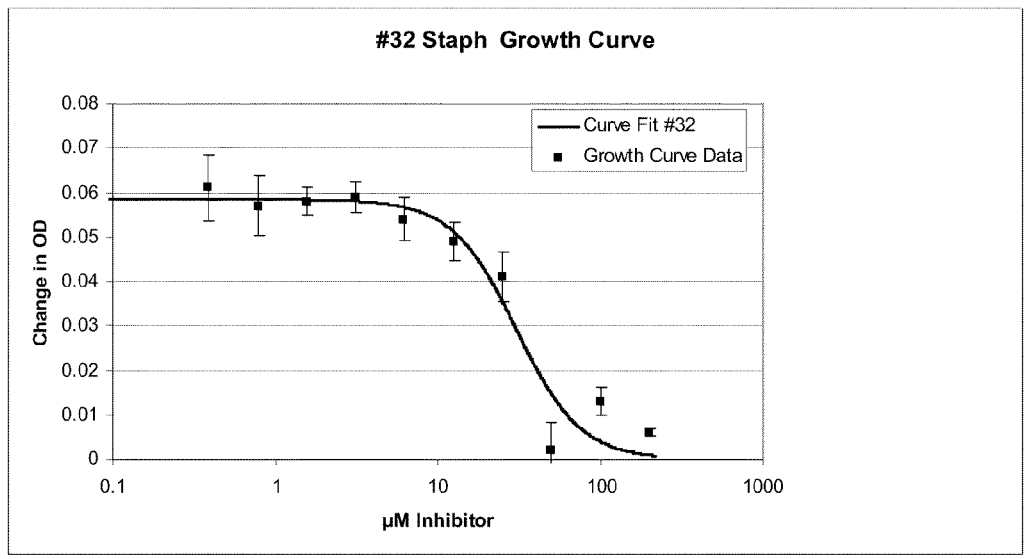
FIG. 21 is a graph showing the inhibition of *Staphylococcus aureus* growth by inhibitor 32.
Figure 22:
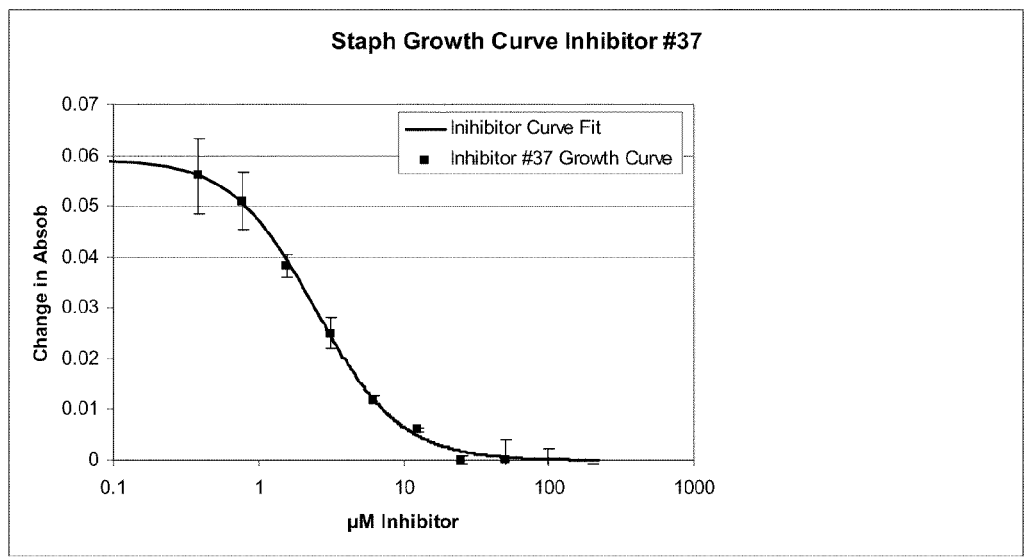
FIG. 22 is a graph showing the inhibition of *Staphylococcus aureus* growth by inhibitor 37.
Figure 23:
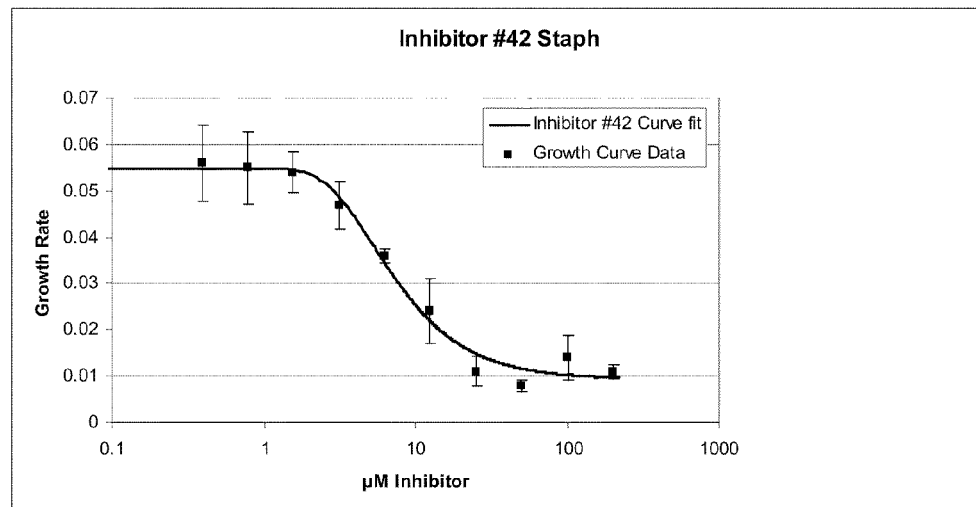
FIG. 23 is a graph showing the inhibition of *Staphylococcus aureus* growth by inhibitor 42.

The data in Table 2 summarize the values of the dissociation constants ($K_i$) for several candidate compounds tested. Graphs showing peptide binding data for individual compounds (i.e., inhibitors) are shown in FIGS. 1-6. The data for the WT peptide control are shown in FIG. 7.

TABLE 2

Dissociation constant ($K_i$) estimates

| Compound | $K_i$ estimates |
|---|---|
| 3 | 2.5 µM |
| 8 | 4 µM |
| 9 | 2.2 µM |
| 10 | 350 nM |
| 32 | 1.5 µM |
| 37 | 700 nM |
| 46 | 1.5 µM |
| WT peptide | 53 nM |

In one example, it was noteworthy that the only difference between compounds (inhibitors) 46 and 31 was the presence of a Cl atom in the former. To examine the significance of one atom substitution, the peptide binding inhibition values of inhibitor 46 were plotted against the peptide binding inhibition values of inhibitor 31 (FIG. 6). Absence of the Cl atom resulted in much weaker binding (Table 3).

FIG. 7 shows which portions of the C-terminal peptide are important for binding to Exonuclease I. The principle of the experiment shown in FIG. 7 is very similar to the experiments performed with the inhibitors (FIGS. 1-6), but instead of titrating different inhibitors into a solution that has fluorescently tagged SSB C-terminal tail peptide bound to Exonuclease I, an unlabeled peptide, or an unlabeled peptide DDDIPF (SEQ ID NO:7) that has three amino acids residues (MDF) missing from the N-terminus was titrated. It should be again pointed out that the W is there only for quantitative purposes. If the missing residues play important roles in peptide binding then the truncated version of the peptide should compete more poorly than the full-length peptide. This is precisely what is seen in FIG. 7; it takes ten-fold more of the truncated peptide than the full-length peptide to titrate away the fluorescent peptide already bound to the protein. The fact that it is possible to titrate away the protein suggests that while those N-terminal three residues play a role in binding they are not the vital for binding since the truncated peptide competes, but does so more poorly.

The compounds 28, 29, and 31 did not inhibit binding (Table 3).

High Throughput Screen to Find Molecules that Inhibit SSB/Exonuclease I Interaction Concentrated Exonuclease I was dialyzed overnight into 2 liters dilution buffer (DB) (20 mM Tris pH 8.0 HCl, 100 mM NaCl, 1 mM MgCl$_2$, and 1 mM Beta-Mercaptoethanol). After dialysis, Exonuclease I was mixed with fluorescently labeled SSB C-terminal peptide, amino acid sequence (N-terminus) Fluorescein-WMDFDDDIPF, i.e. fluorescein-SEQ ID NO:6 (C-terminus), also previously diluted in DB. The final concentrations of the components of the Exonuclease I/SSB C-terminal peptide mixture after-adjustment with DB were 1 µM Exonuclease I, 10 nM fluorescently labeled SSB C-terminal peptide with 20 mM Tris pH 8.0 HCl, 100 mM NaCl, 1 mM MgCl$_2$, and 1 mM Beta-Mercaptoethanol. After sitting at room temperature for 5 min, a liquid handling system was used to aliquot this solution into 384 well plates providing 30 microliters/well. One microliter of 1 mM compound was then added. The screened compounds were obtained from the ChemBridge DIVERSet library (ChemBridge Corporation, San Diego, Calif.), from the Maybridge HitFinder library (Thermo Fisher Scientific, Waltham, Mass.), from the ChemDiv library (Chemical Diversity Labs, San Diego, Calif.), or from the Known Bioactive Library—KBA01.

The FP (fluorescence polarization) values for each well were read using a (plate reader) 5 minutes after compound addition. Compounds that lowered the FP values were identified. This was typically done using three standard deviations. Compounds that were fluorescent or caused excessive precipitation were eliminated from consideration. Roughly 20 compounds that met these criteria were isolated and more stringently tested using a PanVera Beacon 2000 FP (PanVera Corp., Madison, Wis.). From these experiments 5 compounds were identified that were able to lower the FP values to a degree that suggested a complete inhibition of peptide binding thus allowing the determination of $K_i$.

To determine the $K_i$, a master mix was prepared similar to what was previously described above, using 1 µM Exonuclease I, 10 nM fluorescently labeled SSB C-terminal peptide with 20 mM Tris pH 8.0 HCl, 100 mM NaCl, 1 mM MgCl$_2$, and 1 mM Beta-Mercaptoethanol. Increasing amounts of compound were titrated into peptide protein mixture until FP values were lowered to values given by only fluorescently labeled peptide alone. $K_i$ values were determined using the $K_i$ calculator for fluorescence-based competitive binding assays of Prof. Shaomeng Wang, University of Michigan (Nikolovska-Coleska et al., 2004, *Anal. Biochem.* 332: 261-273).

Bacterial Growth Assays

The candidate compounds were tested for their ability to inhibit bacterial growth, as shown in FIGS. 8-23 and in Table 3. For example, in FIGS. 8-16, the growth curves for *E. coli* 4213, a Gram-negative bacterium that has a compromised cell wall, are shown. FIGS. 8-16 show how individual candidate inhibitory compounds inhibit the growth of *E. coli* 4213. The compromised cell wall allows the chemicals to pass through it more readily. As well, FIGS. 17-23 show how individual candidate inhibitory compounds inhibit the growth of *Staphylococcus aureus* 12598, a Gram-positive bacterium.

100 µL of LB containing *E. coli* 1655, *E. coli* 4213, or *S. aureus* at A ~0.05 OD 600 was aliquoted in 96 well plates. One µL of compound in DMSO was added to final concentrations given. Plates were incubated at 37° C. with shaking at 250 RPM. Rate of growth was calculated by determining the average change in OD/hour that took place between hours 3 and 7 (log growth phase). The graphs shown herein are plots of this bacterial growth rate (change in OD/h) against inhibitor concentration in µM.

The data in Table 3 summarize the concentrations of selected compounds according to the present invention, which are necessary to reduce bacterial growth by 50% in liquid media.

TABLE 3

Concentrations of selected compounds necessary to reduce bacterial growth 50% in liquid media

| Compound structure | Ki[a] (μM) | IC(50) E. coli imp4213 | IC(50) S. aureus | IC(50) Human cell line | Hemolysis [b](μM) | MIC[c] (μg/ml) | Compound name/info |
|---|---|---|---|---|---|---|---|
| 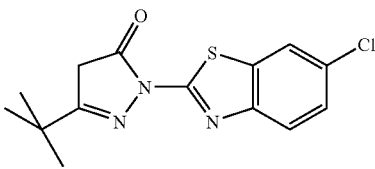 [SMILES: CC(C)(C)C1=NN(c2nc3ccc(Cl)cc3s2)C(=O)C1] | 0.8 | 6 | 6 | >100 | >800 | 9.0 (E. coli) 6.2 (B. subtilis) | Compound 9; also called BCBP. Came from original Maybridge HTS collection. |
| 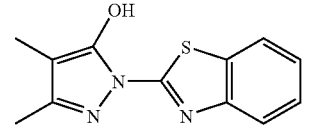 [SMILES: Cc1nn(-c2nc3ccccc3s2)c(O)c1C] | ND[d] | 38 | TBD[e] | TBD | >800 | TBD | Compound 28. Derivative of compound 9. |
| 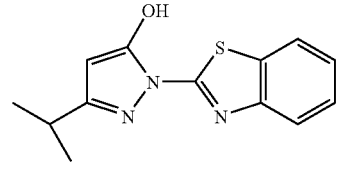 [SMILES: CC(C)c1cc(O)n(-c2nc3ccccc3s2)n1] | ND | 88 | TBD | TBD | >800 | TBD | Compound 29. Derivative of compound 9. |
| 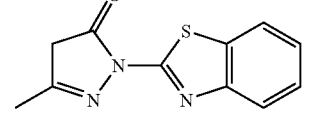 | ND | 50-100 | TBD | TBD | >800 | TBD | Compound 31. Derivative of compound 9. |
| 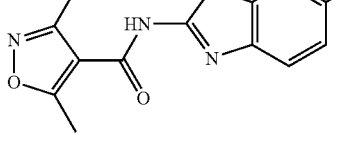 | TBD | TBD | 9 | TBD | >800 | TBD | Compound 42. Derivative of compound 9. |
| 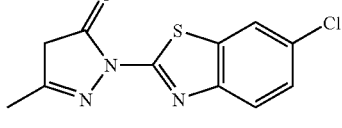 | 1.5 | TBD | TBD | TBD | >800 | TBD | Compound 46. Derivative of compound 9. |
| 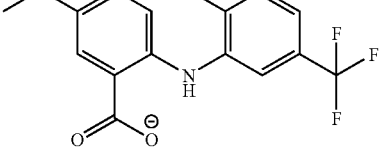 | 0.1 | 30 | 20 | >100 | ~800 | 12.3 (E. coli) 11.1 (B. subtilis) | Compound 10; also called CFAM. Came from original Maybridge HTS collection. |
| 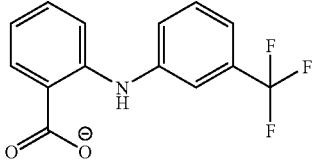 [SMILES: O=C([O-])c1ccccc1Nc1cccc(C(F)(F)F)c1] | 1.5 | 33 | 30 | TBD | >800 | TBD | Compound 32. Derivative of compound 10. |

TABLE 3-continued

Concentrations of selected compounds necessary to reduce bacterial growth 50% in liquid media

| Compound structure | Ki[a] (μM) | IC(50) E. coli imp4213 | IC(50) S. aureus | IC(50) Human cell line | Hemolysis [b](μM) | MIC[c] (μg/ml) | Compound name/info |
|---|---|---|---|---|---|---|---|
| (structure) | 0.7 | 33 | 2.5 | TBD | >800 | TBD | Compound 37. Derivative of compound 10. |
| (structure) | 2.5 | 6 | 9 | 12 | ~100 | 3.6 (E. coli) 3.6 (B. subtilis.) | Compound 3; also called BOTP. Came from original Maybridge HTS collection. Bactericidal for B. subtilis |
| (structure) | 4 | 11 | 29 | >100 | ~200 | 4.0 (E.coli) 6.3 (B. subtilis) | Compound 8; also called MPTA. Came from original Maybridge HTS collection. Bactericidal for B. subtilis |

[a]Ki is the amount of compound needed to dissociate 50% of Exonuclease I/SSB-Ct complexes in vitro.
[b]Hemolysis is the minimum concentration of compounded necessary to lyse red blood cells.
[c]MIC is the minimal concentration necessary to inhibit growth of E. coli (imp4213) or B. subtilis cells on solid media. Data are the same for either bacterial strain.
[d]Not detected; no dissociation of the Exonuclease I/SSB-Ct complex was observed even in the highest concentrations tested.
[e]To be determined.

Data from the *Escherichia coli* inhibition experiments are summarized in Table 4.

TABLE 4

Inhibition of *E. coli* growth

| Inhibitor | $IC_{50}$ μM inhibitor |
|---|---|
| 3 | 6 |
| 8 | 11 |
| 9 | 6 |
| 10 | 30 |
| 32 | 33 |
| 37 | 33 |
| 28 | 38 |
| 29 | 88 |
| 31 | 50-100 |
| 46 | |

Data from the *Staphylococcus aureus* inhibition experiments are summarized in Table 5.

TABLE 5

Inhibition of *S. aureus* growth

| Inhibitor | $IC_{50}$ μM inhibitor |
|---|---|
| 3 | 9 |
| 8 | 30 |
| 9 | 6 |

TABLE 5-continued

Inhibition of *S. aureus* growth

| Inhibitor | $IC_{50}$ μM inhibitor |
|---|---|
| 10 | 20 |
| 32 | 30 |
| 37 | 2.5 |
| 42 | 9 |

A number of the tested candidate compounds had profound inhibitory effects on bacterial growth. In addition, it was discovered that the identified drug compounds can slow the growth of a number of other Gram-positive bacterial species. For example, the growth of *Bacillus subtilis* and *Enterococcus faecalis* was inhibited when these bacteria were grown on agar plates containing 100 μM of either compound 9 or compound 10. Growth of *Deinococcus radiodurans* was also inhibited when tested in a similar manner.

Crystal Structures

Exonuclease I crystals were transferred to a soak solution containing 12% PEG 4000, 1 mM $MgCl_2$, 20 mM Tris pH 8.0, and 5 mM compound. These solutions were allowed to soak in watch glasses for 5 days at which point the crystals were transferred to a cryo solution containing 12% PEG 4000, 1 mM $MgCl_2$, 20 mM Tris pH 8.0, 5 mM compound, and 25% glycerol. Crystals were then flash frozen in liquid Nitrogen.

In spite of the noted importance of SSB interactions with heterologous proteins in cells, a structural and mechanistic understanding of interactions between SSB and its partner proteins has remained unclear. In one aspect, the present invention provides elucidation of the high-resolution structure of E. coli ExoI bound to the C-terminus of its cognate SSB. The crystal structures of apo and SSB peptide-bound forms of E. coli ExoI were determined, as were candidate compounds that bind in one of the binding pockets previously occupied by the C-terminal peptide tail of SSB in the crystal structure (Lu and Keck, 2008, Proc. Natl. Acad. Sci. USA, in press).

The crystal structure of E. coli ExoI bound to a peptide comprising the SSB-Ct element was determined. ExoI/SSB-Ct protein crystals diffracted to 2.7-Å resolution and the structure of the complex was determined by molecular replacement using the apo ExoI structure (Breyer and Matthews, 2000, Nat. Struct Biol. 7: 1125-1128) as a search model (Table 9). In addition, the 1.7-Å-resolution structure of E. coli ExoI crystallized in the absence of the SSB-Ct peptide (but otherwise under the same crystallization conditions as the peptide-bound form) was determined, for comparative structural analysis. As was described for the initial apo-ExoI structure, ExoI in both crystal forms is comprised of exonuclease (residues 1-201), SH3-like (residues 202-352), and helical (residues 360-476) domains (FIGS. 25A and 25B).

Figure 28:
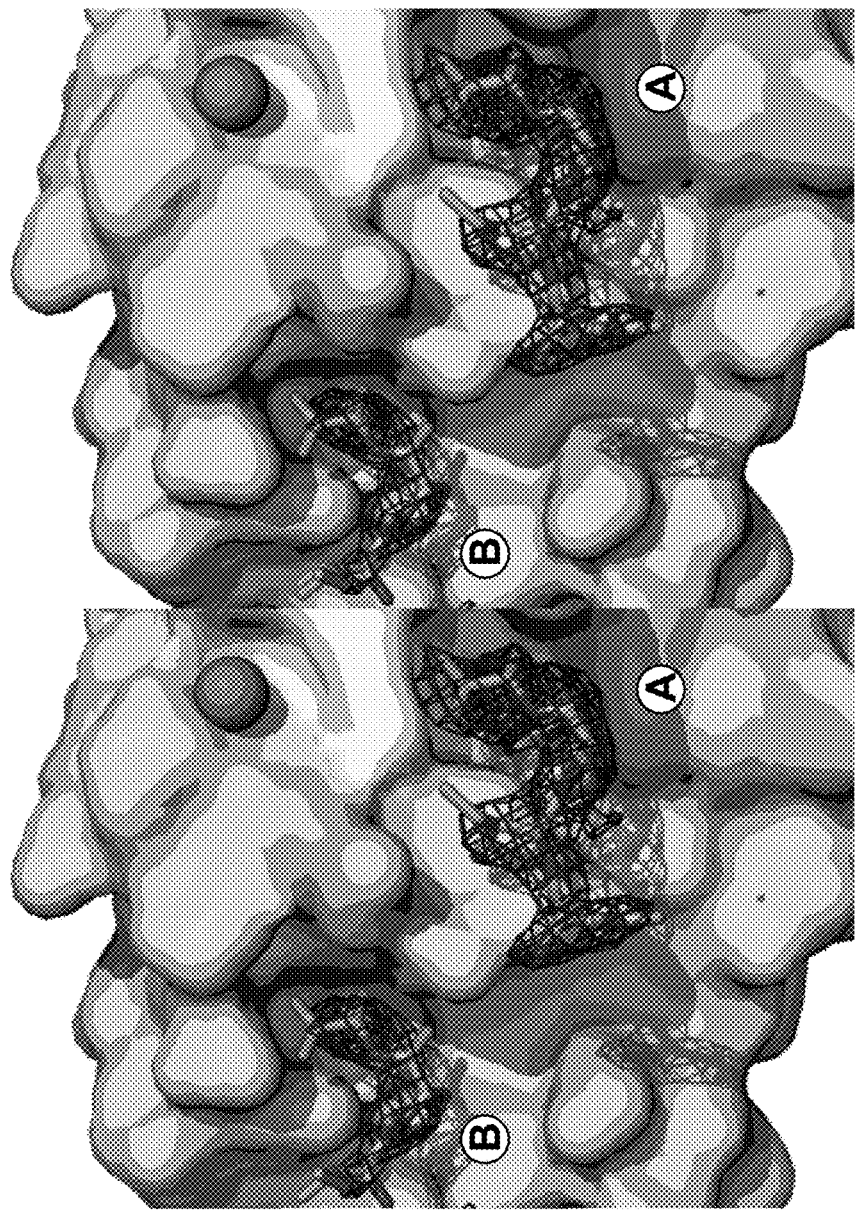
FIG. 28 is a stereo diagram displaying Fo-Fc omit electron-density map for SSB-Ct peptides A and B.
Figure 29:
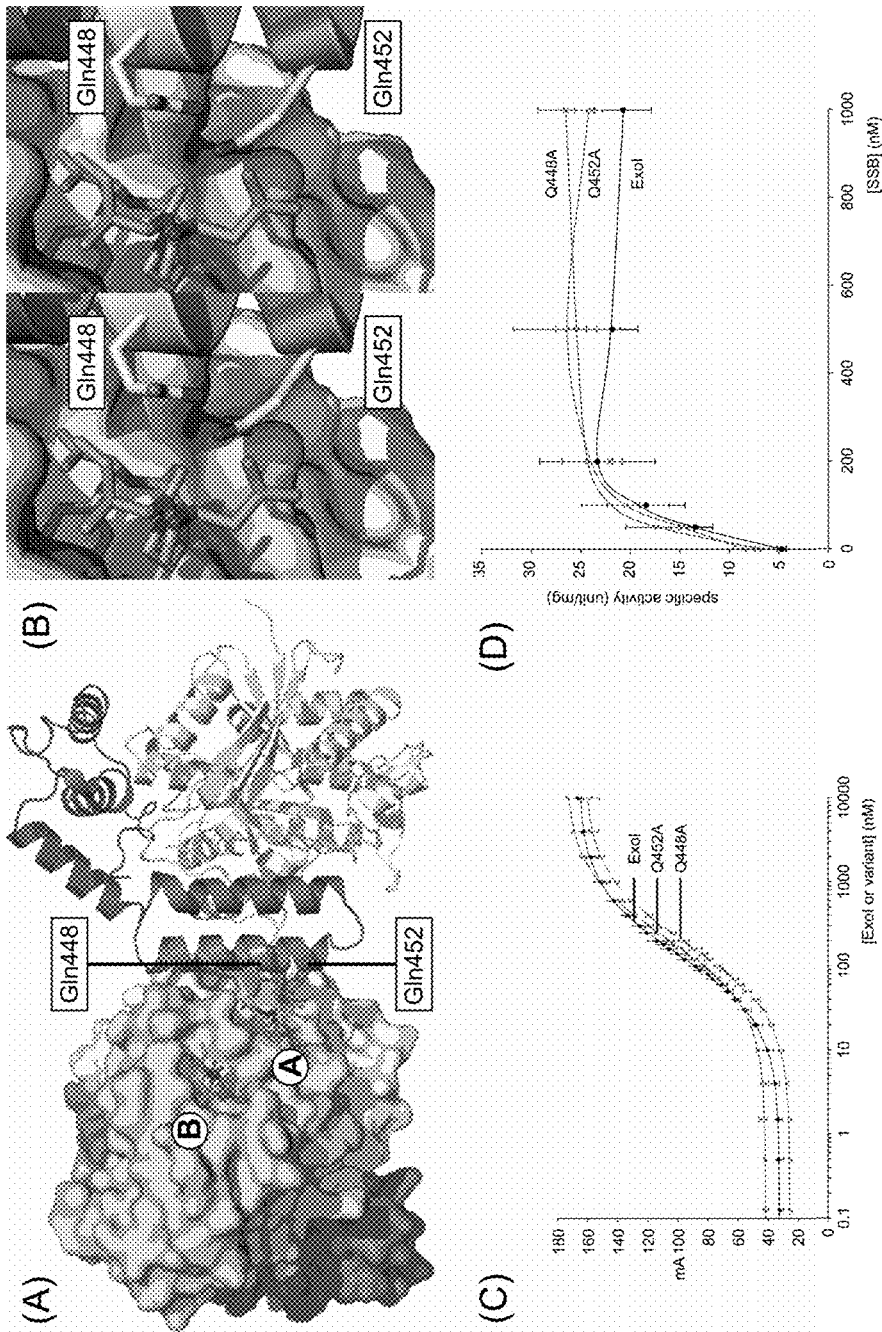
FIG. 29 illustrates the crystallographic association of two glutamine residues from the ExoI helical domain associate with the SSB-Ct peptide A.

Inspection of difference electron-density maps from the SSB-Ct-bound ExoI crystals revealed features corresponding to the C-termini from two SSB-Ct peptides associated with the ExoI surface, as shown in FIGS. 25C, 25D, and FIG. 28. Both peptides bind at sites that are >20 Å from the active site. The first peptide ("peptide A") binds between the exonuclease and SH3-like domains of ExoI (FIGS. 25C and 25E). Electron density is apparent for the C-terminal-most SSB residues of peptide A (174-177), but is missing for residues 169-173, consistent with the N-terminus being dynamic or disordered. The peptide-A binding site anchors the C-terminal-most SSB-Ct residue (Phe177) in a deep pocket comprised of evolutionarily conserved residues from ExoI. In this interaction, the hydrophobic Phe side chain is packed against Leu147, Leu204, and Tyr207 side chains from ExoI and its α-carboxyl oxygens form apparent ionic bonds with the Arg148 side chain. The more N-terminal region of peptide A packs against Ala310, Gln311, and Thr314 from ExoI with the exception of Asp174, which contacts ExoI residues Gln448 and Gln452 in an adjacent ExoI molecule within the crystal lattice (FIG. 29). SSB-Ct binding to site A is coincident with rearrangement of the ExoI Arg316 side chain, which orients toward the path of peptide A (FIG. 25E). This Arg316 rotamer position allows a non-active site $Mg^{2+}$ ion to bind to an acidic pocket formed by Glu150, Glu318, and Asp319. In addition to these elements, a "basic ridge" formed by the Arg338 and Lys227 ExoI side chains presents a prominent electropositive patch near the N-terminus of peptide A (FIG. 25D). Given the presence of additional unresolved Asp residues on the SSB-Ct, this ridge could play a role in SSB-Ct binding that is not accounted for in the structure. This possibility was also tested.

Electron density for the second peptide, "peptide B", includes SSB residues 175-177, which are bound entirely by the ExoI SH3-like domain (FIG. 25F). As with the peptide-A site, the peptide-B site binds primarily to Phe177 from the SSB-Ct, anchoring its side chain in a hydrophobic pocket (comprised of residues Trp245, Leu264, and Cys330) and binding its α-carboxyl oxygens in apparent ionic bonds formed with Arg327 from ExoI. ExoI residues Leu331, Leu334, and Pro338 contact more N-terminal regions of peptide B. Since prior solution studies indicated that ExoI/SSB complexes are stoichiometric (Genschel et al., 2000, Biol. Chem. 381: 183-192), finding two peptides bound to the surface of a single ExoI monomer was unexpected. Moreover, since peptide A is positioned between symmetrically-related ExoI molecules in the crystal lattice, there was a strong possibility that crystal packing could have influenced the structure of the complex. This structure was therefore used as a starting point to design experiments that evaluated the roles of ExoI residues in each site for SSB binding and enzymatic stimulation.

Solution SSB-Ct Binding Studies Define Important Features of the ExoI/SSB Complex To examine ExoI/SSB-Ct complex formation in solution, an equilibrium fluorescence-anisotropy assay that measures ExoI binding to a fluorescein-labeled SSB-Ct peptide (F-SSB-Ct) was developed. ExoI binds F-SSB-Ct with an apparent equilibrium dissociation constant ($K_{d,\ app}$) of 136+/−11 nM in this assay (FIG. 26A). This binding is higher affinity than that observed for SSB-Ct peptide binding by PriA and RecQ, which associate with respective $K_{d,app}$ values of 2 and 6 μM. To test whether this interaction was specific, ExoI binding to two control peptides was examined. The first, "F-P176S", changes the penultimate Pro residue in the F-SSB-Ct sequence to Ser, which mimics the well studied ssb113 mutation that causes impaired cell growth due to defects in its interactions with cellular DNA replication machinery. The second control peptide, "F-mixed", randomly mixes the arrangement of the residues in F-SSB-Ct. ExoI binding to both control peptides was minimal relative to the F-SSB-Ct peptide (FIG. 26A). Analogous specificities were observed for SSB-Ct peptide binding by PriA and RecQ. These results indicate that ExoI specifically interacts with the F-SSB-Ct peptide in solution, which is consistent with a previous study that examined ExoI binding to SSB-derived peptides in competition experiments (Lecointe et al., 2007, EMBO J. 26: 4239-4251).

A panel of ExoI variants was created in which surface-exposed residues forming the peptide-A (Arg148, Tyr207, Gln311 and Arg316) or peptide-B (Arg327 and Leu331) binding sites were individually mutated to alanine to assess the contributions of the two sites to SSB-Ct binding. Additional Ala variants were made to test whether the prominent "basic ridge" on ExoI (Lys227 and Arg338) and ExoI residues that bind $Mg^{2+}$ in the presence of the SSB-Ct peptide (Glu150, Glu318 and Asp319) have roles in F-SSB-Ct binding. Finally, Ala variants altering residues from the helical domain (Gln448 and Gln452) that mediate inter-protein contacts with peptide A in the crystal structure were also created. Each ExoI variant was purified and tested for binding to the F-SSB-Ct peptide. Far UV circular dichroic spectra of the variants were indistinguishable from wild type ExoI, indicating that the mutations did not alter the secondary structure of the variants significantly.

Three of the peptide-A-site variants displayed dramatically reduced F-SSB-Ct binding (FIG. 26B and Table 10). Arg148, Tyr207, and Arg316 Ala variants bound the peptide ~10- to 100-fold more weakly than wild-type ExoI, with the Arg148 variant exhibiting the poorest binding. $K_{d,\ app}$ values could not be derived for these variants since peptide binding was not saturated at the highest enzyme concentrations tested (10 μM). The Gln311 variant led to a more modest 2-fold binding defect relative to wild-type ExoI. In contrast to the peptide-A-site variants, neither of the peptide-B-site variants had measurable F-SSB-Ct binding defects (FIG. 26C). This was surprising given their direct contacts with Phe177 from peptide B and the strong defects displayed by analogous mutations in the peptide-A binding site.

Additional variants were used to test the roles of basic ridge, $Mg^{2+}$-binding and helical domain surfaces in binding the F-SSB-Ct peptide in solution (FIG. 26D). The basic ridge variants had dramatic defects in peptide binding. ExoI Lys227 and Arg338 variants had 7- and 3-fold binding defects, respectively. These results indicate a significant role for the ExoI basic ridge in SSB-Ct binding. Two of the $Mg^{2+}$-binding variants had ~2-fold enhanced binding relative to wild-type ExoI (Glu150 and Glu318), whereas the Asp319 variant had a 2-fold binding defect. Not wanting to be bound by the following theory, these modest effects suggested that $Mg^{2+}$ binding observed in the crystal structure could be a consequence of the high concentration of the metal in the crystallization conditions rather than reflecting a major role for $Mg^{2+}$ in SSB/ExoI complex formation. F-SSB-Ct binding by the Gln448 and Gln452 variants was indistinguishable from that of wild-type ExoI, suggesting that their association with the SSB-Ct peptide in the crystal structure was due to their proximity to the peptide through crystal packing but that they do not play a role in SSB-Ct binding in solution (FIG. 29).

ExoI/SSB Complex Formation is Essential for SSB stimulation of ExoI Activity

Early studies showed that *E. coli* SSB stimulates ExoI nuclease activity and that the two proteins physically interact. However, whether ExoI/SSB complex formation is required for this stimulation has not been tested. To examine this, a nuclease assay in which hydrolysis of a radiolabeled ssDNA substrate is catalyzed by ExoI in a reaction that can be stimulated ~4-fold with the addition of SSB was developed (FIG. 27A). SSB stimulation plateaus at 200 nM SSB, which is the concentration necessary to saturate the ssDNA with SSB.

To assess whether association with SSB is necessary for ExoI stimulation, two SSB variants wee substituted into the assay. The first, SSB113, is a well-characterized *E. coli* SSB variant with dramatically reduced ExoI binding affinity but wild type ssDNA binding attributes, and the second, SSB-mixed, is a variant with a mixed C-terminal sequence that matches the sequence used in the F-mixed peptide. SSB113 provided greatly reduced stimulation (<2-fold) compared to wild type SSB, whereas SSB-mixed entirely failed to stimulate ExoI activity (FIG. 27A). These results support the idea that ExoI/SSB interaction is critical for SSB stimulation. To test whether binding to the SSB-Ct element alone is sufficient to stimulate ExoI activity, the SSB-Ct peptide was titrated into the ExoI assay. The peptide had no apparent effect on ExoI nuclease activity even at concentrations well above the $K_{d, app}$ for binding the enzyme (FIG. 27A). Together, these data are consistent with SSB-Ct/ExoI complex formation being necessary, but not sufficient, for SSB stimulation of ExoI activity.

The effects of Ala substitutions on SSB-stimulated ExoI nuclease activity were also tested. If SSB stimulates ExoI by recruiting the enzyme to its substrate, then ExoI variants that are defective for binding the SSB-Ct peptide would have parallel defects in SSB-stimulated activity. The peptide-A- and peptide-B-site variants matched this prediction remarkably well. Two of the peptide-A-site variants (Arg148 and Tyr207) appeared to be unaffected by the addition of SSB, maintaining wild-type levels of nuclease activity at all SSB concentrations tested (FIG. 27B); these variants also had the weakest F-SSB-Ct binding among the panel of ExoI mutant proteins (FIG. 26B). A third peptide-A-site variant, Arg316, had dramatically reduced SSB-dependent activity (<2-fold enhancement by SSB) relative to wild-type ExoI. As with the Arg148 and Tyr207 variants, the Arg316 variant also had impaired F-SSB-Ct binding affinity, although it appeared to bind with higher affinity than the former variants (FIG. 26B). Finally, the Gln311 variant had only a mildly reduced SSB-stimulation relative to wild-type ExoI, which paralleled its modest reduction in affinity for the F-SSB-Ct peptide. As would be predicted from these findings, the peptide-B-site and helical domain variants, which did not alter F-SSB-Ct binding in solution, also had wild-type SSB-dependent nuclease activity (FIG. 27C and FIG. 29).

The basic ridge and $Mg^{2+}$-binding ExoI variants were also tested for SSB-dependent nuclease activities. The basic ridge variants (Lys227 and Arg338), which had defects in F-SSB-Ct binding, similarly had reduced stimulation by SSB (FIG. 27D). These results confirmed the importance of the basic ridge for coordinated activity with SSB. Two of the $Mg^{2+}$-binding variants (Glu318 and Asp319) had wild-type levels of SSB-stimulated nuclease activity whereas the third (Glu150) had moderately elevated levels of both intrinsic (SSB-independent) and SSB-dependent activity. Although the maximal SSB-stimulated activity of the Glu150 variant exceeded that of wild-type ExoI, the fold stimulation by SSB was the same as with the wild-type enzyme. Thus the ~2-fold higher F-SSB-Ct binding affinity of the Glu150 and Glu318 variants did not result in enhanced SSB-stimulation of nuclease activity.

The atomic coordinates of the crystal structure of *Escherichia coli* Exonuclease I bound to the C-terminal peptide from *E. coli* SSB have been deposited in the Protein Data Bank under the accession code 3C94. Prokaryotic exonucleases that bind to SSBs and that upon binding have crystal structures whose models substantially represent the atomic coordinates specified in the model deposited in the Protein Data Bank under the accession code 3C94, can be used for practicing the present invention. As well, SSBs that bind to prokaryotic exonculeases and that upon binding have crystal structures whose models substantially represent the atomic coordinates specified in the model deposited in the Protein Data Bank under the accession code 3C94, can be used for practicing the present invention.

Figure 25:
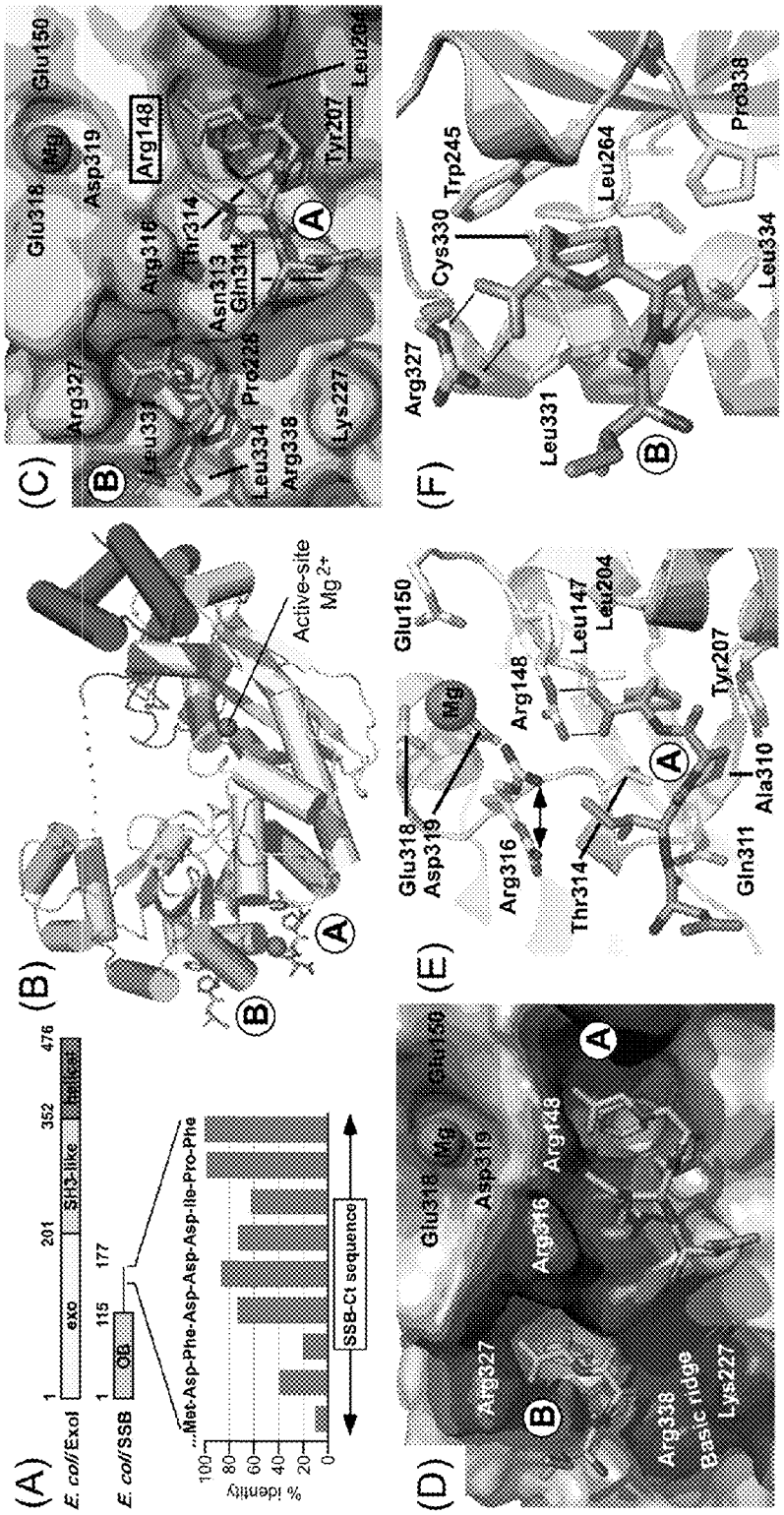
FIG. 25 illustrates the structure of the *E. coli* ExoI/SSB-Ct complex.

FIG. 25 illustrates the structure of the *E. coli* ExoI/SSB-Ct complex. FIG. 25(A): schematic diagram of *E. coli* ExoI and SSB's structural features (ExoI: Exonuclease domain; SH3-like domain, and helical domain; SSB: oligonucleotide-binding (OB) domain followed by ~60 disordered C-terminal residues). The bar graph depicts evolutionary conservation of the SSB C-terminus (SSB-Ct) sequence among 284 bacterial SSB proteins as percent identity. FIG. 25(B): ribbon diagram of ExoI bound to two SSB-Ct peptides. Dotted lines represent segments for which electron density was not observed. FIG. 25(C): surface representation depicting the binding sites for two SSB-Ct peptides (A and B) bound to ExoI. Selected ExoI residues are labeled. FIG. 25(D): surface representation as in (C) that models electropositive and electronegative potential. FIG. 25 (E and F): detailed views of the peptide-A and peptide-B sites. The Arg316 side chain from apo ExoI is superimposed.

Figure 26:
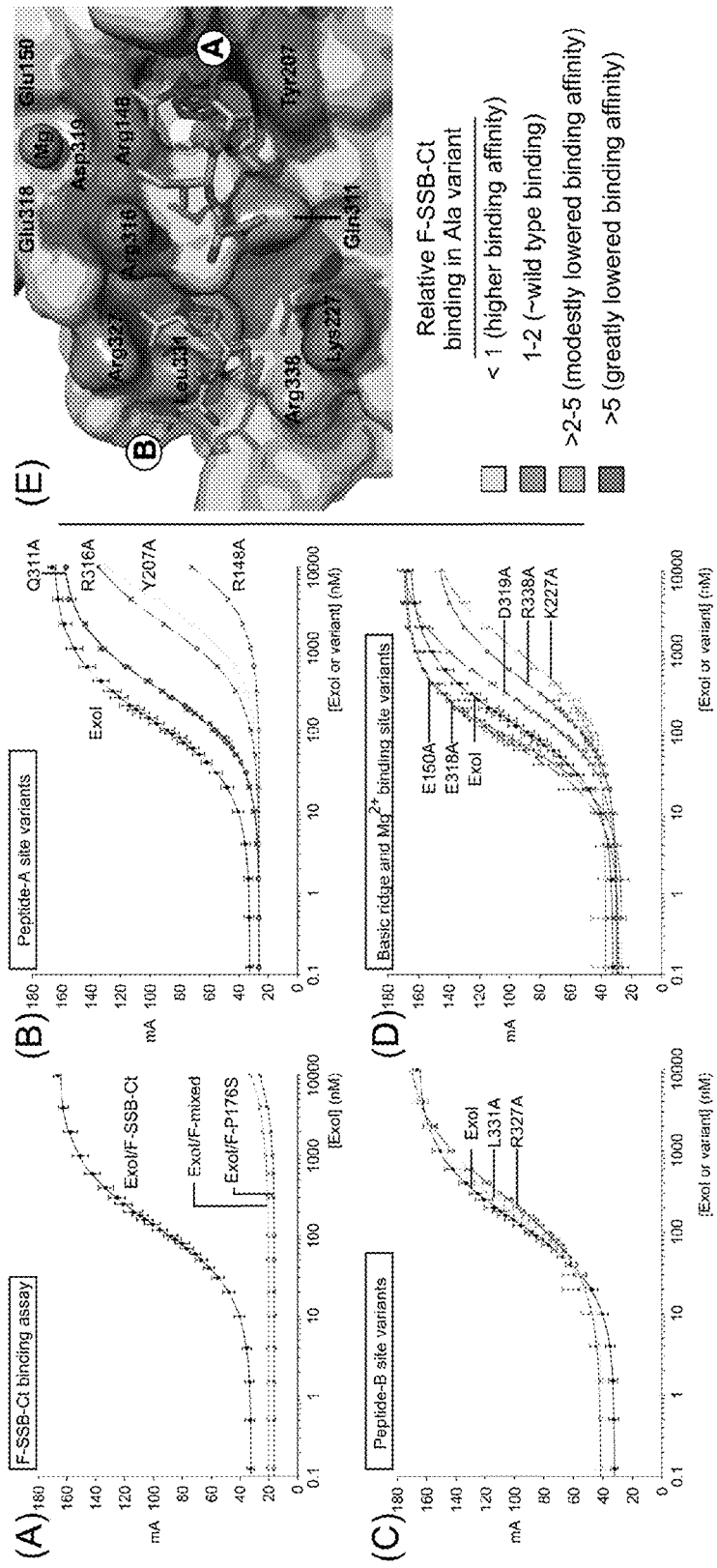
FIG. 26 illustrates equilibrium binding highlights the roles of the peptide-A-binding site and the basic ridge in SSB-Ct binding.

FIG. 26 illustrates equilibrium binding highlights the roles of the peptide-A-binding site and the basic ridge in SSB-Ct binding. FIG. 26(A-D): equilibrium binding isotherms of F-SSB-Ct (or peptide variant) association with ExoI (or Ala variant) as monitored by fluorescence anisotropy. All data points are the average of three experiments. Error bars are one standard deviation from the mean. FIG. 26(A): F-SSB-Ct, F-P176S, and F-mixed ExoI binding isotherms. FIG. 26(B): F-SSB-Ct binding by peptide-A-site ExoI variants (R148A, Y207A, Q311A, and R316A). FIG. 26(C): F-SSB-Ct binding by peptide-B-site ExoI variants (L331A, R327A). FIG. 26(D): F-SSB-Ct binding by basic ridge (K227A, R338A) and Mg2+ binding site (E150A, E318A, D319A) ExoI variants. (E) Summary of ExoI variant F-SSB-Ct binding. The fold-change observed in F-SSB-Ct binding affinity relative to wild-type ExoI was: <1-fold binding changes (higher affinity), 1-2 fold, >2-5 fold, and >5 fold.

Figure 27:
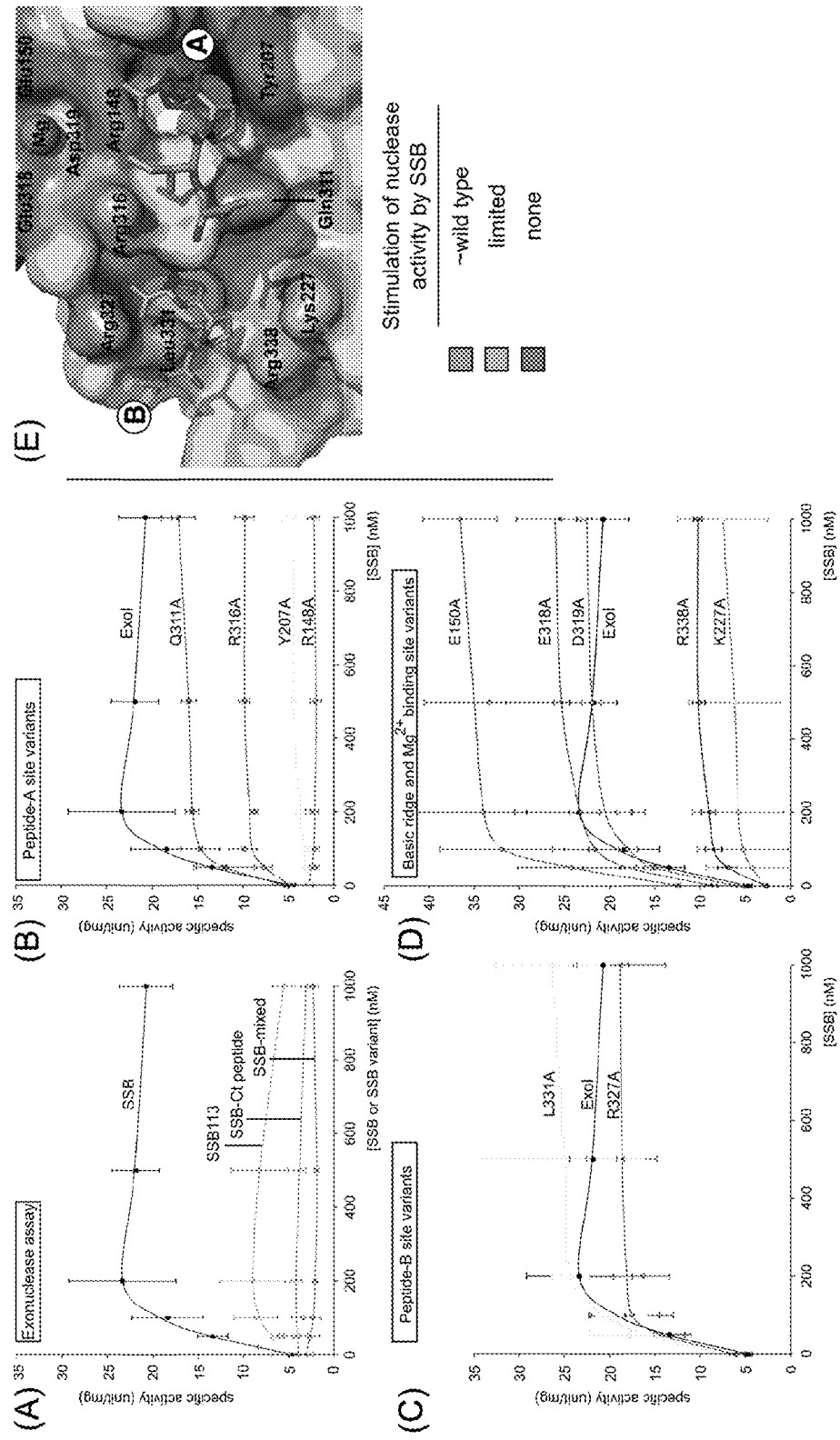
FIG. 27 illustrates how ExoI/SSB physical interaction is essential for SSB stimulation of ExoI activity.

FIG. 27 illustrates how ExoI/SSB physical interaction is essential for SSB stimulation of ExoI activity. FIG. 27(A-D): ExoI specific activity is plotted as a function of SSB (or SSB variant). Data points are the mean of three experiments. Error bars are one standard deviation from the mean. Trend lines are shown for clarity. FIG. 27(A): ExoI activity on ssDNA is stimulated ~4 fold by the addition of SSB but not the SSB-Ct peptide alone. SSB-Ct peptide variants modestly stimulate (SSB113) or have no effect on (SSB-mixed) ExoI activity. FIG. 27(B): SSB-dependence of Peptide-A-site ExoI variant nuclease activities (R148A, Y207A, Q311A, and R316A). FIG. 27(C): SSB-dependence of Peptide-B-site ExoI variant nuclease activities (L331A, R327A). FIG. 27(D): SSB-dependence of basic ridge ($K_{227}$A, R338A) and Mg2+-binding site (E150A, E318A, D319A) ExoI variants nuclease activity. FIG. 27(E): summary of the SSB dependence of ExoI variants nuclease activity.

FIG. 28 is a stereo diagram displaying Fo-Fc omit electron-density map (contoured at 2.8σ) for SSB-Ct peptides A and B.

FIG. 29 illustrates the crystallographic association of two glutamine residues from the ExoI helical domain associate with the SSB-Ct peptide A. FIG. 29(A): SSB-Ct peptide A associates with a symmetrically-related ExoI molecule (shown in ribbon form) in the crystal lattice via two Gln residues from the ExoI helical domain (Gln448 and Gln452. FIG. 29(B): close-up stereo diagram of the Gln-mediated interaction in the crystal lattice. FIG. 29(C): Gln448 and Gln452 Ala variants have no apparent F-SSB-Ct binding defects (Q448A, Q452A). FIG. 29(D): Gln448 and Gln452 Ala variants have wild-type SSB-dependent nuclease activities (Q448A, Q452A).

Figure 30:
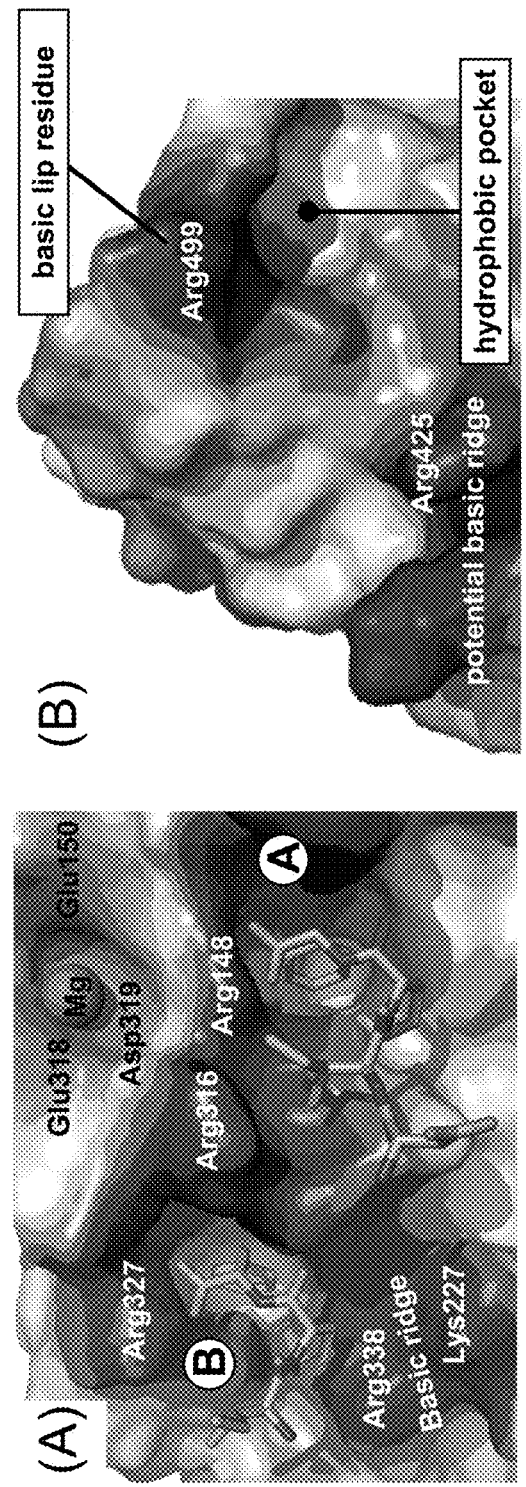
FIG. 30 illustrates the similarity of the ExoI SSB-Ct binding site (A) and a site on the surface of the *E. coli* RecQ winged-helix domain (B).

FIG. 30 illustrates the similarity of the ExoI SSB-Ct binding site (A) and a site on the surface of the *E. coli* RecQ winged-helix domain (B). The RecQ winged-helix domain binds the SSB-Ct element but the binding site has not been described. Regions on the RecQ domain with similar electrostatic features to those involved in ExoI/SSB-Ct binding are highlighted in (B).

Table 6 shows the coordinates of the crystal structure of *E. coli* ExoI bound to compound 9 that was identified in a screen according to the present invention. Compounds that bind prokaryotic exonucleases and that have crystal structures whose models substantially represent the atomic coordinates specified in Table 6, can be used for practicing the present invention.

TABLE 6

Coordinates of the crystal structure of *E. coli* ExoI bound to compound 9

```
HEADER    ----                                              XX-XXX-XX    xxxx
COMPND    ---
REMARK 3
REMARK 3    REFINEMENT.
REMARK 3       PROGRAM          : REFMAC 5.2.0019
REMARK 3       AUTHORS          : MURSHUDOV, VAGIN, DODSON
REMARK 3
REMARK 3       REFINEMENT TARGET : MAXIMUM LIKELIHOOD
REMARK 3
REMARK 3    DATA USED IN REFINEMENT.
REMARK 3       RESOLUTION RANGE HIGH        (ANGSTROMS) :    1.55
REMARK 3       RESOLUTION RANGE LOW         (ANGSTROMS) :   19.87
REMARK 3       DATA CUTOFF                  (SIGMA(F))  : NONE
REMARK 3       COMPLETENESS FOR RANGE             (%)  :   92.76
REMARK 3       NUMBER OF REFLECTIONS              :    68041
REMARK 3
REMARK 3    FIT TO DATA USED IN REFINEMENT.
REMARK 3       CROSS-VALIDATION METHOD              : THROUGHOUT
REMARK 3       FREE R VALUE TEST SET SELECTION      : RANDOM
REMARK 3       R VALUE            (WORKING + TEST SET) : 0.21370
REMARK 3       R VALUE              (WORKING SET)  :  0.21267
REMARK 3       FREE R VALUE                        :  0.23374
REMARK 3       FREE R VALUE TEST SET SIZE      (%) :    5.0
REMARK 3       FREE R VALUE TEST SET COUNT         :   3592
REMARK 3
REMARK 3    FIT IN THE HIGHEST RESOLUTION BIN.
REMARK 3       TOTAL NUMBER OF BINS USED            :      20
REMARK 3       BIN RESOLUTION RANGE HIGH            :   1.550
REMARK 3       BIN RESOLUTION RANGE LOW             :   1.590
REMARK 3       REFLECTION IN BIN         (WORKING SET) :    4542
REMARK 3       BIN COMPLETENESS     (WORKING + TEST) (%) :   85.08
REMARK 3       BIN R VALUE             (WORKING SET) :   0.268
REMARK 3       BIN FREE R VALUE SET COUNT           :     253
REMARK 3       BIN FREE R VALUE                     :   0.320
REMARK 3
REMARK 3    NUMBER OF NON-HYDROGEN ATOMS USED IN REFINEMENT.
REMARK 3       ALL ATOMS                      :    4220
REMARK 3
REMARK 3    B VALUES.
REMARK 3       FROM WILSON PLOT          (A**2) : NULL
REMARK 3       MEAN B VALUE      (OVERALL, A**2) :  24.107
REMARK 3       OVERALL ANISOTROPIC B VALUE.
REMARK 3          B11 (A**2) :    0.01
REMARK 3          B22 (A**2) :    0.00
REMARK 3          B33 (A**2) :    0.00
```

TABLE 6-continued

Coordinates of the crystal structure of *E. coli* ExoI bound to compound 9

| | | | | | |
|---|---|---|---|---|---|
| REMARK 3 | B12 (A**2): | 0.00 | | | |
| REMARK 3 | B13 (A**2): | 0.00 | | | |
| REMARK 3 | B23 (A**2): | 0.00 | | | |
| REMARK 3 | | | | | |
| REMARK 3 | ESTIMATED OVERALL COORDINATE ERROR. | | | | |
| REMARK 3 | ESU BASED ON R VALUE | | (A): | 0.099 | |
| REMARK 3 | ESU BASED ON FREE R VALUE | | (A): | 0.094 | |
| REMARK 3 | ESU BASED ON MAXIMUM LIKELIHOOD | | (A): | 0.059 | |
| REMARK 3 | ESU FOR B VALUES BASED ON MAXIMUM LIKELIHOOD | | (A**2): | 3.239 | |
| REMARK 3 | | | | | |
| REMARK 3 | CORRELATION COEFFICIENTS. | | | | |
| REMARK 3 | CORRELATION COEFFICIENT FO-FC | : | 0.954 | | |
| REMARK 3 | CORRELATION COEFFICIENT FO-FC FREE | : | 0.935 | | |
| REMARK 3 | | | | | |
| REMARK 3 | RMS DEVIATIONS FROM IDEAL VALUES | | COUNT | RMS | WEIGHT |
| REMARK 3 | BOND LENGTHS REFINED ATOMS | (A): | 3737; | 0.008; | 0.022 |
| REMARK 3 | BOND ANGLES REFINED ATOMS | (DEGREES): | 5084; | 1.038; | 1.951 |
| REMARK 3 | TORSION ANGLES, PERIOD 1 | (DEGREES): | 442; | 5.149; | 5.000 |
| REMARK 3 | TORSION ANGLES, PERIOD 2 | (DEGREES): | 197; | 32.714; | 23.858 |
| REMARK 3 | TORSION ANGLES, PERIOD 3 | (DEGREES): | 606; | 11.915; | 15.000 |
| REMARK 3 | TORSION ANGLES, PERIOD 4 | (DEGREES): | 30; | 12.440; | 15.000 |
| REMARK 3 | CHIRAL-CENTER RESTRAINTS | (A**3): | 545; | 0.057; | 0.200 |
| REMARK 3 | GENERAL PLANES REFINED ATOMS | (A): | 2920; | 0.003; | 0.020 |
| REMARK 3 | NON-BONDED CONTACTS REFINED ATOMS | (A): | 1836; | 0.196; | 0.200 |
| REMARK 3 | NON-BONDED TORSION REFINED ATOMS | (A): | 2568; | 0.303; | 0.200 |
| REMARK 3 | H-BOND (X . . . Y) REFINED ATOMS | (A): | 468; | 0.136; | 0.200 |
| REMARK 3 | POTENTIAL METAL-ION REFINED ATOMS | (A): | 2; | 0.017; | 0.200 |
| REMARK 3 | SYMMETRY VDW REFINED ATOMS | (A): | 39; | 0.225; | 0.200 |
| REMARK 3 | SYMMETRY H-BOND REFINED ATOMS | (A): | 27; | 0.225; | 0.200 |
| REMARK 3 | | | | | |
| REMARK 3 | ISOTROPIC THERMAL FACTOR RESTRAINTS. | | COUNT | RMS | WEIGHT |
| REMARK 3 | MAIN-CHAIN BOND REFINED ATOMS | (A**2): | 2305; | 0.433; | 1.500 |
| REMARK 3 | MAIN-CHAIN ANGLE REFINED ATOMS | (A**2): | 3608; | 0.664; | 2.000 |
| REMARK 3 | SIDE-CHAIN BOND REFINED ATOMS | (A**2): | 1709; | 1.021; | 3.000 |
| REMARK 3 | SIDE-CHAIN ANGLE REFINED ATOMS | (A**2): | 1476; | 1.651; | 4.500 |
| REMARK 3 | | | | | |
| REMARK 3 | NCS RESTRAINTS STATISTICS | | | | |
| REMARK 3 | NUMBER OF NCS GROUPS : NULL | | | | |
| REMARK 3 | | | | | |
| REMARK 3 | | | | | |
| REMARK 3 | TLS DETAILS | | | | |
| REMARK 3 | NUMBER OF TLS GROUPS : 3 | | | | |
| REMARK 3 | ATOM RECORD CONTAINS RESIDUAL B FACTORS ONLY | | | | |
| REMARK 3 | | | | | |
| REMARK 3 | TLS GROUP : 1 | | | | |
| REMARK 3 | NUMBER OF COMPONENTS GROUP : 1 | | | | |
| REMARK 3 | COMPONENTS C SSSEQI TO C SSSEQI | | | | |
| REMARK 3 | RESIDUE RANGE: A 1 A 201 | | | | |
| REMARK 3 | ORIGIN FOR THE GROUP (A): 30.6117 26.4458 31.1155 | | | | |
| REMARK 3 | T TENSOR | | | | |
| REMARK 3 | T11: −0.0145 T22: −0.0126 | | | | |
| REMARK 3 | T33: 0.0000 T12: −0.0097 | | | | |
| REMARK 3 | T13: 0.0041 T23: −0.0023 | | | | |
| REMARK 3 | L TENSOR | | | | |
| REMARK 3 | L11: 0.1747 L22: 0.2763 | | | | |
| REMARK 3 | L33: 0.5243 L12: −0.0803 | | | | |
| REMARK 3 | L13: 0.1528 L23: −0.2242 | | | | |
| REMARK 3 | S TENSOR | | | | |
| REMARK 3 | S11: 0.0196 S12: 0.0055 S13: 0.0154 | | | | |
| REMARK 3 | S21: −0.0690 S22: 0.0139 S23: −0.0222 | | | | |
| REMARK 3 | S31: −0.0123 S32: 0.0319 S33: −0.0335 | | | | |
| REMARK 3 | | | | | |
| REMARK 3 | TLS GROUP : 2 | | | | |
| REMARK 3 | NUMBER OF COMPONENTS GROUP : 1 | | | | |
| REMARK 3 | COMPONENTS C SSSEQI TO C SSSEQI | | | | |
| REMARK 3 | RESIDUE RANGE: A 202 A 354 | | | | |
| REMARK 3 | ORIGIN FOR THE GROUP (A): 25.1747 4.7360 46.6329 | | | | |
| REMARK 3 | T TENSOR | | | | |
| REMARK 3 | T11: −0.0578 T22: −0.0315 | | | | |
| REMARK 3 | T33: −0.0114 T12: −0.0002 | | | | |
| REMARK 3 | T13: 0.0088 T23: 0.0016 | | | | |
| REMARK 3 | L TENSOR | | | | |
| REMARK 3 | L11: 0.6486 L22: 1.1345 | | | | |
| REMARK 3 | L33: 0.9027 L12: 0.2886 | | | | |
| REMARK 3 | L13: −0.1969 L23: −0.1079 | | | | |
| REMARK 3 | S TENSOR | | | | |
| REMARK 3 | S11: −0.0401 S12: 0.0041 S13: −0.0065 | | | | |
| REMARK 3 | S21: −0.0122 S22: 0.0400 S23: 0.1062 | | | | |

TABLE 6-continued

Coordinates of the crystal structure of *E. coli* ExoI bound to compound 9

| | | | | | | | | | | | |
|---|---|---|---|---|---|---|---|---|---|---|---|
| REMARK | 3 | | S31: | 0.0979 S32: | −0.0452 S33: | 0.0001 | | | | | |
| REMARK | 3 | | | | | | | | | | |
| REMARK | 3 | | TLS GROUP : | 3 | | | | | | | |
| REMARK | 3 | | NUMBER OF COMPONENTS GROUP : | | | 1 | | | | | |
| REMARK | 3 | | COMPONENTS | | C | SSSEQI | TO | C | SSSEQI | | |
| REMARK | 3 | | RESIDUE RANGE: | | A | 355 | | A | 477 | | |
| REMARK | 3 | | ORIGIN FOR THE GROUP (A): | | | 12.6823 | 27.6878 | 16.5653 | | | |
| REMARK | 3 | | T TENSOR | | | | | | | | |
| REMARK | 3 | | T11: | −0.0330 T22: | −0.0129 | | | | | | |
| REMARK | 3 | | T33: | −0.0882 T12: | −0.0147 | | | | | | |
| REMARK | 3 | | T13: | −0.0325 T23: | 0.0227 | | | | | | |
| REMARK | 3 | | L TENSOR | | | | | | | | |
| REMARK | 3 | | L11: | 0.5669 L22: | 1.2815 | | | | | | |
| REMARK | 3 | | L33: | 1.0851 L12: | 0.0040 | | | | | | |
| REMARK | 3 | | L13: | −0.1252 L23: | 0.5280 | | | | | | |
| REMARK | 3 | | S TENSOR | | | | | | | | |
| REMARK | 3 | | S11: | 0.0297 S12: | 0.0777 S13: | −0.0305 | | | | | |
| REMARK | 3 | | S21: | −0.1022 S22: | −0.0153 S23: | 0.1608 | | | | | |
| REMARK | 3 | | S31: | −0.0144 S32: | −0.1499 S33: | −0.0145 | | | | | |
| REMARK | 3 | | | | | | | | | | |
| REMARK | 3 | | | | | | | | | | |
| REMARK | 3 | | BULK SOLVENT MODELLING. | | | | | | | | |
| REMARK | 3 | | METHOD USED: BABINET MODEL WITH MASK | | | | | | | | |
| REMARK | 3 | | PARAMETERS FOR MASK CALCULATION | | | | | | | | |
| REMARK | 3 | | VDW PROBE RADIUS | | : | 1.20 | | | | | |
| REMARK | 3 | | ION PROBE RADIUS | | : | 0.80 | | | | | |
| REMARK | 3 | | SHRINKAGE RADIUS | | : | 0.80 | | | | | |
| REMARK | 3 | | | | | | | | | | |
| REMARK | 3 | | OTHER REFINEMENT REMARKS: NULL | | | | | | | | |
| REMARK | 3 | | | | | | | | | | |
| CISPEP | 1 | | HIS A | 177 | SER A | 178 | | | 0.00 | | |
| LINK | | | | SER A 178 | | | | | ASP A 182 | gap | |
| LINK | | | | ARG A 280 | | | | | ALA A 295 | gap | |
| LINK | | | | GLU A 353 | | | | | SER A 360 | gap | |
| CRYST 1 | | | 53.823 | 91.966 | 106.280 | 90.00 | 90.00 | 90.00 P 21 21 21 | | | |
| SCALE 1 | | | 0.018579 | | 0.000000 | 0.000000 | | 0.00000 | | | |
| SCALE 2 | | | 0.000000 | | 0.010874 | 0.000000 | | 0.00000 | | | |
| SCALE 3 | | | 0.000000 | | 0.000000 | 0.009409 | | 0.00000 | | | |
| ATOM | 1 | N | GLN | A | 7 | 50.557 | 15.759 | 20.315 | 1.00 | 27.46 | N |
| ATOM | 2 | CA | GLN | A | 7 | 49.450 | 16.551 | 20.924 | 1.00 | 27.31 | C |
| ATOM | 3 | CB | GLN | A | 7 | 48.092 | 15.990 | 20.489 | 1.00 | 27.52 | C |
| ATOM | 4 | CG | GLN | A | 7 | 46.884 | 16.848 | 20.888 | 1.00 | 28.40 | C |
| ATOM | 5 | CD | GLN | A | 7 | 46.601 | 17.984 | 19.911 | 1.00 | 29.59 | C |
| ATOM | 6 | OE1 | GLN | A | 7 | 47.389 | 18.258 | 19.002 | 1.00 | 30.56 | O |
| ATOM | 7 | NE2 | GLN | A | 7 | 45.467 | 18.649 | 20.098 | 1.00 | 29.83 | N |
| ATOM | 8 | C | GLN | A | 7 | 49.558 | 16.553 | 22.448 | 1.00 | 26.84 | C |
| ATOM | 9 | O | GLN | A | 7 | 49.743 | 15.503 | 23.070 | 1.00 | 27.02 | O |
| ATOM | 10 | N | GLN | A | 8 | 49.450 | 17.739 | 23.041 | 1.00 | 26.18 | N |
| ATOM | 11 | CA | GLN | A | 8 | 49.483 | 17.879 | 24.495 | 1.00 | 25.51 | C |
| ATOM | 12 | CB | GLN | A | 8 | 50.193 | 19.175 | 24.902 | 1.00 | 25.77 | C |
| ATOM | 13 | CG | GLN | A | 8 | 49.479 | 20.452 | 24.463 | 1.00 | 26.77 | C |
| ATOM | 14 | CD | GLN | A | 8 | 50.023 | 21.697 | 25.134 | 1.00 | 27.43 | C |
| ATOM | 15 | OE1 | GLN | A | 8 | 50.793 | 21.618 | 26.097 | 1.00 | 29.46 | O |
| ATOM | 16 | NE2 | GLN | A | 8 | 49.616 | 22.862 | 24.633 | 1.00 | 29.00 | N |
| ATOM | 17 | C | GLN | A | 8 | 48.076 | 17.845 | 25.081 | 1.00 | 24.47 | C |
| ATOM | 18 | O | GLN | A | 8 | 47.104 | 18.220 | 24.416 | 1.00 | 24.29 | O |
| ATOM | 19 | N | SER | A | 9 | 47.974 | 17.390 | 26.327 | 1.00 | 23.25 | N |
| ATOM | 20 | CA | SER | A | 9 | 46.708 | 17.409 | 27.051 | 1.00 | 22.05 | C |
| ATOM | 21 | CB | SER | A | 9 | 46.786 | 16.528 | 28.299 | 1.00 | 22.13 | C |
| ATOM | 22 | OG | SER | A | 9 | 47.031 | 15.175 | 27.953 | 1.00 | 22.89 | O |
| ATOM | 23 | C | SER | A | 9 | 46.355 | 18.841 | 27.436 | 1.00 | 21.07 | C |
| ATOM | 24 | O | SER | A | 9 | 47.194 | 19.580 | 27.961 | 1.00 | 20.89 | O |
| ATOM | 25 | N | THR | A | 10 | 45.118 | 19.238 | 27.151 | 1.00 | 19.73 | N |
| ATOM | 26 | CA | THR | A | 10 | 44.658 | 20.583 | 27.480 | 1.00 | 18.69 | C |
| ATOM | 27 | CB | THR | A | 10 | 44.569 | 21.493 | 26.224 | 1.00 | 18.74 | C |
| ATOM | 28 | OG1 | THR | A | 10 | 43.608 | 20.962 | 25.305 | 1.00 | 18.51 | O |
| ATOM | 29 | CG2 | THR | A | 10 | 45.929 | 21.613 | 25.533 | 1.00 | 18.94 | C |
| ATOM | 30 | C | THR | A | 10 | 43.300 | 20.557 | 28.168 | 1.00 | 17.97 | C |
| ATOM | 31 | O | THR | A | 10 | 42.583 | 19.557 | 28.111 | 1.00 | 17.87 | O |
| ATOM | 32 | N | PHE | A | 11 | 42.973 | 21.660 | 28.836 | 1.00 | 16.92 | N |
| ATOM | 33 | CA | PHE | A | 11 | 41.638 | 21.890 | 29.371 | 1.00 | 16.34 | C |
| ATOM | 34 | CB | PHE | A | 11 | 41.716 | 22.339 | 30.830 | 1.00 | 16.30 | C |
| ATOM | 35 | CG | PHE | A | 11 | 42.156 | 21.265 | 31.777 | 1.00 | 16.20 | C |
| ATOM | 36 | CD1 | PHE | A | 11 | 41.221 | 20.426 | 32.376 | 1.00 | 16.26 | C |
| ATOM | 37 | CE1 | PHE | A | 11 | 41.619 | 19.431 | 33.261 | 1.00 | 16.26 | C |
| ATOM | 38 | CZ | PHE | A | 11 | 42.965 | 19.266 | 33.561 | 1.00 | 17.12 | C |
| ATOM | 39 | CE2 | PHE | A | 11 | 43.911 | 20.101 | 32.973 | 1.00 | 17.27 | C |
| ATOM | 40 | CD2 | PHE | A | 11 | 43.503 | 21.097 | 32.088 | 1.00 | 17.00 | C |

TABLE 6-continued

Coordinates of the crystal structure of *E. coli* ExoI bound to compound 9

| ATOM | 41 | C | PHE | A | 11 | 40.959 | 22.974 | 28.559 | 1.00 | 15.81 | C |
|---|---|---|---|---|---|---|---|---|---|---|---|
| ATOM | 42 | O | PHE | A | 11 | 41.581 | 23.978 | 28.209 | 1.00 | 15.67 | O |
| ATOM | 43 | N | LEU | A | 12 | 39.684 | 22.775 | 28.255 | 1.00 | 15.13 | N |
| ATOM | 44 | CA | LEU | A | 12 | 38.883 | 23.837 | 27.673 | 1.00 | 14.78 | C |
| ATOM | 45 | CB | LEU | A | 12 | 38.307 | 23.429 | 26.315 | 1.00 | 14.84 | C |
| ATOM | 46 | CG | LEU | A | 12 | 37.592 | 24.535 | 25.525 | 1.00 | 15.52 | C |
| ATOM | 47 | CD1 | LEU | A | 12 | 38.567 | 25.629 | 25.082 | 1.00 | 16.05 | C |
| ATOM | 48 | CD2 | LEU | A | 12 | 36.863 | 23.962 | 24.333 | 1.00 | 15.62 | C |
| ATOM | 49 | C | LEU | A | 12 | 37.778 | 24.221 | 28.637 | 1.00 | 14.29 | C |
| ATOM | 50 | O | LEU | A | 12 | 36.763 | 23.530 | 28.743 | 1.00 | 14.07 | O |
| ATOM | 51 | N | PHE | A | 13 | 38.013 | 25.304 | 29.369 | 1.00 | 14.01 | N |
| ATOM | 52 | CA | PHE | A | 13 | 37.022 | 25.869 | 30.270 | 1.00 | 13.80 | C |
| ATOM | 53 | CB | PHE | A | 13 | 37.694 | 26.807 | 31.274 | 1.00 | 13.63 | C |
| ATOM | 54 | CG | PHE | A | 13 | 38.570 | 26.104 | 32.283 | 1.00 | 13.27 | C |
| ATOM | 55 | CD1 | PHE | A | 13 | 38.078 | 25.784 | 33.548 | 1.00 | 13.35 | C |
| ATOM | 56 | CE1 | PHE | A | 13 | 38.885 | 25.144 | 34.489 | 1.00 | 12.71 | C |
| ATOM | 57 | CZ | PHE | A | 13 | 40.204 | 24.820 | 34.166 | 1.00 | 12.95 | C |
| ATOM | 58 | CE2 | PHE | A | 13 | 40.708 | 25.140 | 32.911 | 1.00 | 12.37 | C |
| ATOM | 59 | CD2 | PHE | A | 13 | 39.892 | 25.777 | 31.975 | 1.00 | 12.95 | C |
| ATOM | 60 | C | PHE | A | 13 | 36.013 | 26.644 | 29.443 | 1.00 | 13.88 | C |
| ATOM | 61 | O | PHE | A | 13 | 36.391 | 27.396 | 28.548 | 1.00 | 14.05 | O |
| ATOM | 62 | N | HIS | A | 14 | 34.729 | 26.456 | 29.734 | 1.00 | 13.87 | N |
| ATOM | 63 | CA | HIS | A | 14 | 33.678 | 27.117 | 28.965 | 1.00 | 13.75 | C |
| ATOM | 64 | CB | HIS | A | 14 | 33.269 | 26.257 | 27.767 | 1.00 | 14.02 | C |
| ATOM | 65 | CG | HIS | A | 14 | 32.455 | 25.062 | 28.145 | 1.00 | 14.10 | C |
| ATOM | 66 | ND1 | HIS | A | 14 | 31.105 | 24.968 | 27.888 | 1.00 | 15.76 | N |
| ATOM | 67 | CE1 | HIS | A | 14 | 30.651 | 23.818 | 28.350 | 1.00 | 14.67 | C |
| ATOM | 68 | NE2 | HIS | A | 14 | 31.656 | 23.167 | 28.907 | 1.00 | 16.74 | N |
| ATOM | 69 | CD2 | HIS | A | 14 | 32.795 | 23.926 | 28.796 | 1.00 | 14.51 | C |
| ATOM | 70 | C | HIS | A | 14 | 32.451 | 27.420 | 29.816 | 1.00 | 13.65 | C |
| ATOM | 71 | O | HIS | A | 14 | 32.282 | 26.866 | 30.908 | 1.00 | 13.85 | O |
| ATOM | 72 | N | ASP | A | 15 | 31.593 | 28.290 | 29.290 | 1.00 | 13.54 | N |
| ATOM | 73 | CA | ASP | A | 15 | 30.356 | 28.674 | 29.952 | 1.00 | 13.85 | C |
| ATOM | 74 | CB | ASP | A | 15 | 30.640 | 29.713 | 31.042 | 1.00 | 13.93 | C |
| ATOM | 75 | CG | ASP | A | 15 | 29.424 | 30.009 | 31.900 | 1.00 | 15.01 | C |
| ATOM | 76 | OD1 | ASP | A | 15 | 28.825 | 29.055 | 32.454 | 1.00 | 15.75 | O |
| ATOM | 77 | OD2 | ASP | A | 15 | 29.073 | 31.198 | 32.039 | 1.00 | 17.02 | O |
| ATOM | 78 | C | ASP | A | 15 | 29.382 | 29.250 | 28.932 | 1.00 | 13.67 | C |
| ATOM | 79 | O | ASP | A | 15 | 29.786 | 29.996 | 28.039 | 1.00 | 13.73 | O |
| ATOM | 80 | N | TYR | A | 16 | 28.107 | 28.891 | 29.062 | 1.00 | 14.02 | N |
| ATOM | 81 | CA | TYR | A | 16 | 27.046 | 29.511 | 28.272 | 1.00 | 14.37 | C |
| ATOM | 82 | CB | TYR | A | 16 | 26.015 | 28.476 | 27.820 | 1.00 | 14.27 | C |
| ATOM | 83 | CG | TYR | A | 16 | 26.457 | 27.486 | 26.771 | 1.00 | 14.10 | C |
| ATOM | 84 | CD1 | TYR | A | 16 | 26.364 | 27.788 | 25.409 | 1.00 | 14.43 | C |
| ATOM | 85 | CE1 | TYR | A | 16 | 26.736 | 26.857 | 24.439 | 1.00 | 14.31 | C |
| ATOM | 86 | CZ | TYR | A | 16 | 27.183 | 25.603 | 24.832 | 1.00 | 14.50 | C |
| ATOM | 87 | OH | TYR | A | 16 | 27.547 | 24.671 | 23.889 | 1.00 | 14.16 | O |
| ATOM | 88 | CE2 | TYR | A | 16 | 27.261 | 25.277 | 26.175 | 1.00 | 13.93 | C |
| ATOM | 89 | CD2 | TYR | A | 16 | 26.889 | 26.212 | 27.134 | 1.00 | 14.54 | C |
| ATOM | 90 | C | TYR | A | 16 | 26.291 | 30.548 | 29.085 | 1.00 | 14.77 | C |
| ATOM | 91 | O | TYR | A | 16 | 26.019 | 30.347 | 30.275 | 1.00 | 14.91 | O |
| ATOM | 92 | N | GLU | A | 17 | 25.928 | 31.644 | 28.430 | 1.00 | 15.18 | N |
| ATOM | 93 | CA | GLU | A | 17 | 24.799 | 32.445 | 28.872 | 1.00 | 15.82 | C |
| ATOM | 94 | CB | GLU | A | 17 | 25.115 | 33.944 | 28.803 | 1.00 | 16.31 | C |
| ATOM | 95 | CG | GLU | A | 17 | 26.328 | 34.386 | 29.633 | 1.00 | 18.97 | C |
| ATOM | 96 | CD | GLU | A | 17 | 26.115 | 34.275 | 31.147 | 1.00 | 22.44 | C |
| ATOM | 97 | OE1 | GLU | A | 17 | 24.980 | 34.008 | 31.591 | 1.00 | 24.46 | O |
| ATOM | 98 | OE2 | GLU | A | 17 | 27.096 | 34.461 | 31.898 | 1.00 | 25.38 | O |
| ATOM | 99 | C | GLU | A | 17 | 23.646 | 32.098 | 27.949 | 1.00 | 15.59 | C |
| ATOM | 100 | O | GLU | A | 17 | 23.821 | 32.041 | 26.731 | 1.00 | 15.67 | O |
| ATOM | 101 | N | THR | A | 18 | 22.482 | 31.813 | 28.526 | 1.00 | 15.43 | N |
| ATOM | 102 | CA | THR | A | 18 | 21.321 | 31.413 | 27.731 | 1.00 | 15.37 | C |
| ATOM | 103 | CB | THR | A | 18 | 20.904 | 29.946 | 27.999 | 1.00 | 15.55 | C |
| ATOM | 104 | OG1 | THR | A | 18 | 20.307 | 29.844 | 29.295 | 1.00 | 16.45 | O |
| ATOM | 105 | CG2 | THR | A | 18 | 22.107 | 29.007 | 27.908 | 1.00 | 15.79 | C |
| ATOM | 106 | C | THR | A | 18 | 20.125 | 32.326 | 27.978 | 1.00 | 15.23 | C |
| ATOM | 107 | O | THR | A | 18 | 20.159 | 33.187 | 28.861 | 1.00 | 15.56 | O |
| ATOM | 108 | N | PHE | A | 19 | 19.070 | 32.129 | 27.193 | 1.00 | 15.09 | N |
| ATOM | 109 | CA | PHE | A | 19 | 17.858 | 32.930 | 27.312 | 1.00 | 14.91 | C |
| ATOM | 110 | CB | PHE | A | 19 | 17.279 | 33.237 | 25.928 | 1.00 | 14.79 | C |
| ATOM | 111 | CG | PHE | A | 19 | 18.037 | 34.296 | 25.175 | 1.00 | 14.13 | C |
| ATOM | 112 | CD1 | PHE | A | 19 | 18.182 | 35.577 | 25.705 | 1.00 | 14.77 | C |
| ATOM | 113 | CE1 | PHE | A | 19 | 18.878 | 36.565 | 25.009 | 1.00 | 14.06 | C |
| ATOM | 114 | CZ | PHE | A | 19 | 19.429 | 36.278 | 23.770 | 1.00 | 14.30 | C |
| ATOM | 115 | CE2 | PHE | A | 19 | 19.286 | 35.008 | 23.223 | 1.00 | 14.16 | C |
| ATOM | 116 | CD2 | PHE | A | 19 | 18.588 | 34.021 | 23.929 | 1.00 | 14.19 | C |
| ATOM | 117 | C | PHE | A | 19 | 16.805 | 32.262 | 28.196 | 1.00 | 15.28 | C |
| ATOM | 118 | O | PHE | A | 19 | 15.666 | 32.721 | 28.271 | 1.00 | 15.20 | O |

TABLE 6-continued

Coordinates of the crystal structure of *E. coli* ExoI bound to compound 9

| ATOM | 119 | N | GLY | A | 20 | 17.197 | 31.189 | 28.877 | 1.00 | 15.71 | N |
|---|---|---|---|---|---|---|---|---|---|---|---|
| ATOM | 120 | CA | GLY | A | 20 | 16.289 | 30.508 | 29.789 | 1.00 | 16.41 | C |
| ATOM | 121 | C | GLY | A | 20 | 16.873 | 29.276 | 30.441 | 1.00 | 16.87 | C |
| ATOM | 122 | O | GLY | A | 20 | 17.980 | 28.849 | 30.113 | 1.00 | 16.68 | O |
| ATOM | 123 | N | THR | A | 21 | 16.096 | 28.690 | 31.347 | 1.00 | 17.63 | N |
| ATOM | 124 | CA | THR | A | 21 | 16.571 | 27.616 | 32.219 | 1.00 | 18.54 | C |
| ATOM | 125 | CB | THR | A | 21 | 15.754 | 27.555 | 33.532 | 1.00 | 18.77 | C |
| ATOM | 126 | OG1 | THR | A | 21 | 14.374 | 27.333 | 33.227 | 1.00 | 20.19 | O |
| ATOM | 127 | CG2 | THR | A | 21 | 15.892 | 28.859 | 34.318 | 1.00 | 19.50 | C |
| ATOM | 128 | C | THR | A | 21 | 16.543 | 26.234 | 31.559 | 1.00 | 18.69 | C |
| ATOM | 129 | O | THR | A | 21 | 17.235 | 25.315 | 32.007 | 1.00 | 18.83 | O |
| ATOM | 130 | N | HIS | A | 22 | 15.736 | 26.084 | 30.510 | 1.00 | 18.75 | N |
| ATOM | 131 | CA | HIS | A | 22 | 15.606 | 24.792 | 29.837 | 1.00 | 19.27 | C |
| ATOM | 132 | CB | HIS | A | 22 | 14.208 | 24.621 | 29.241 | 1.00 | 19.39 | C |
| ATOM | 133 | CG | HIS | A | 22 | 13.843 | 23.195 | 28.974 | 1.00 | 20.16 | C |
| ATOM | 134 | ND1 | HIS | A | 22 | 12.795 | 22.562 | 29.608 | 1.00 | 21.93 | N |
| ATOM | 135 | CE1 | HIS | A | 22 | 12.721 | 21.312 | 29.187 | 1.00 | 21.83 | C |
| ATOM | 136 | NE2 | HIS | A | 22 | 13.689 | 21.108 | 28.312 | 1.00 | 22.15 | N |
| ATOM | 137 | CD2 | HIS | A | 22 | 14.408 | 22.269 | 28.164 | 1.00 | 20.52 | C |
| ATOM | 138 | C | HIS | A | 22 | 16.676 | 24.606 | 28.756 | 1.00 | 19.53 | C |
| ATOM | 139 | O | HIS | A | 22 | 16.705 | 25.354 | 27.777 | 1.00 | 19.17 | O |
| ATOM | 140 | N | PRO | A | 23 | 17.546 | 23.588 | 28.921 | 1.00 | 19.58 | N |
| ATOM | 141 | CA | PRO | A | 23 | 18.676 | 23.383 | 28.003 | 1.00 | 19.95 | C |
| ATOM | 142 | CB | PRO | A | 23 | 19.424 | 22.192 | 28.616 | 1.00 | 20.08 | C |
| ATOM | 143 | CG | PRO | A | 23 | 18.910 | 22.066 | 30.005 | 1.00 | 20.23 | C |
| ATOM | 144 | CD | PRO | A | 23 | 17.515 | 22.569 | 29.985 | 1.00 | 19.70 | C |
| ATOM | 145 | C | PRO | A | 23 | 18.257 | 23.052 | 26.569 | 1.00 | 19.96 | C |
| ATOM | 146 | O | PRO | A | 23 | 19.047 | 23.243 | 25.641 | 1.00 | 20.25 | O |
| ATOM | 147 | N | ALA | A | 24 | 17.027 | 22.567 | 26.396 | 1.00 | 19.92 | N |
| ATOM | 148 | CA | ALA | A | 24 | 16.505 | 22.202 | 25.079 | 1.00 | 19.89 | C |
| ATOM | 149 | CB | ALA | A | 24 | 15.819 | 20.842 | 25.137 | 1.00 | 20.01 | C |
| ATOM | 150 | C | ALA | A | 24 | 15.551 | 23.252 | 24.511 | 1.00 | 19.82 | C |
| ATOM | 151 | O | ALA | A | 24 | 15.642 | 23.607 | 23.333 | 1.00 | 20.09 | O |
| ATOM | 152 | N | LEU | A | 25 | 14.644 | 23.745 | 25.354 | 1.00 | 19.43 | N |
| ATOM | 153 | CA | LEU | A | 25 | 13.538 | 24.597 | 24.900 | 1.00 | 19.28 | C |
| ATOM | 154 | CB | LEU | A | 25 | 12.261 | 24.295 | 25.690 | 1.00 | 19.47 | C |
| ATOM | 155 | CG | LEU | A | 25 | 11.674 | 22.888 | 25.528 | 1.00 | 20.18 | C |
| ATOM | 156 | CD1 | LEU | A | 25 | 10.377 | 22.760 | 26.309 | 1.00 | 20.77 | C |
| ATOM | 157 | CD2 | LEU | A | 25 | 11.457 | 22.536 | 24.060 | 1.00 | 21.08 | C |
| ATOM | 158 | C | LEU | A | 25 | 13.850 | 26.089 | 24.944 | 1.00 | 18.94 | C |
| ATOM | 159 | O | LEU | A | 25 | 13.148 | 26.895 | 24.326 | 1.00 | 19.13 | O |
| ATOM | 160 | N | ASP | A | 26 | 14.896 | 26.456 | 25.677 | 1.00 | 18.37 | N |
| ATOM | 161 | CA | ASP | A | 26 | 15.397 | 27.823 | 25.650 | 1.00 | 17.98 | C |
| ATOM | 162 | CB | ASP | A | 26 | 15.625 | 28.343 | 27.071 | 1.00 | 17.69 | C |
| ATOM | 163 | CG | ASP | A | 26 | 14.321 | 28.595 | 27.815 | 1.00 | 18.14 | C |
| ATOM | 164 | OD1 | ASP | A | 26 | 13.507 | 29.412 | 27.334 | 1.00 | 17.60 | O |
| ATOM | 165 | OD2 | ASP | A | 26 | 14.115 | 27.987 | 28.888 | 1.00 | 18.41 | O |
| ATOM | 166 | C | ASP | A | 26 | 16.678 | 27.896 | 24.825 | 1.00 | 17.72 | C |
| ATOM | 167 | O | ASP | A | 26 | 17.450 | 26.938 | 24.775 | 1.00 | 18.49 | O |
| ATOM | 168 | N | ARG | A | 27 | 16.894 | 29.031 | 24.168 | 1.00 | 16.86 | N |
| ATOM | 169 | CA | ARG | A | 27 | 18.006 | 29.167 | 23.228 | 1.00 | 16.22 | C |
| ATOM | 170 | CB | ARG | A | 27 | 17.592 | 30.017 | 22.019 | 1.00 | 16.09 | C |
| ATOM | 171 | CG | ARG | A | 27 | 16.238 | 29.659 | 21.425 | 1.00 | 16.52 | C |
| ATOM | 172 | CD | ARG | A | 27 | 16.260 | 28.368 | 20.612 | 1.00 | 16.60 | C |
| ATOM | 173 | NE | ARG | A | 27 | 14.902 | 27.860 | 20.429 | 1.00 | 17.60 | N |
| ATOM | 174 | CZ | ARG | A | 27 | 14.077 | 28.230 | 19.452 | 1.00 | 17.84 | C |
| ATOM | 175 | NH1 | ARG | A | 27 | 14.468 | 29.105 | 18.525 | 1.00 | 17.82 | N |
| ATOM | 176 | NH2 | ARG | A | 27 | 12.856 | 27.715 | 19.395 | 1.00 | 18.04 | N |
| ATOM | 177 | C | ARG | A | 27 | 19.239 | 29.772 | 23.894 | 1.00 | 15.87 | C |
| ATOM | 178 | O | ARG | A | 27 | 19.115 | 30.575 | 24.826 | 1.00 | 15.56 | O |
| ATOM | 179 | N | PRO | A | 28 | 20.440 | 29.389 | 23.417 | 1.00 | 15.52 | N |
| ATOM | 180 | CA | PRO | A | 28 | 21.668 | 29.978 | 23.942 | 1.00 | 15.49 | C |
| ATOM | 181 | CB | PRO | A | 28 | 22.764 | 29.122 | 23.307 | 1.00 | 15.36 | C |
| ATOM | 182 | CG | PRO | A | 28 | 22.155 | 28.610 | 22.047 | 1.00 | 15.52 | C |
| ATOM | 183 | CD | PRO | A | 28 | 20.712 | 28.388 | 22.365 | 1.00 | 15.47 | C |
| ATOM | 184 | C | PRO | A | 28 | 21.803 | 31.429 | 23.494 | 1.00 | 15.32 | C |
| ATOM | 185 | O | PRO | A | 28 | 21.260 | 31.807 | 22.450 | 1.00 | 15.54 | O |
| ATOM | 186 | N | ALA | A | 29 | 22.508 | 32.230 | 24.285 | 1.00 | 14.92 | N |
| ATOM | 187 | CA | ALA | A | 29 | 22.746 | 33.633 | 23.952 | 1.00 | 15.06 | C |
| ATOM | 188 | CB | ALA | A | 29 | 22.303 | 34.528 | 25.094 | 1.00 | 14.98 | C |
| ATOM | 189 | C | ALA | A | 29 | 24.215 | 33.876 | 23.634 | 1.00 | 14.92 | C |
| ATOM | 190 | O | ALA | A | 29 | 24.547 | 34.556 | 22.658 | 1.00 | 14.81 | O |
| ATOM | 191 | N | GLN | A | 30 | 25.093 | 33.312 | 24.462 | 1.00 | 14.93 | N |
| ATOM | 192 | CA | GLN | A | 30 | 26.525 | 33.567 | 24.368 | 1.00 | 15.30 | C |
| ATOM | 193 | CB | GLN | A | 30 | 26.892 | 34.783 | 25.227 | 1.00 | 15.18 | C |
| ATOM | 194 | CG | GLN | A | 30 | 28.320 | 35.283 | 25.073 | 1.00 | 16.92 | C |
| ATOM | 195 | CD | GLN | A | 30 | 28.708 | 36.258 | 26.167 | 1.00 | 17.27 | C |
| ATOM | 196 | OE1 | GLN | A | 30 | 28.784 | 35.893 | 27.343 | 1.00 | 21.13 | O |

TABLE 6-continued

Coordinates of the crystal structure of *E. coli* ExoI bound to compound 9

| ATOM | 197 | NE2 | GLN | A | 30 | 28.960 | 37.508 | 25.787 | 1.00 | 20.44 | N |
|------|-----|-----|-----|---|----|--------|--------|--------|------|-------|---|
| ATOM | 198 | C | GLN | A | 30 | 27.324 | 32.349 | 24.820 | 1.00 | 14.87 | C |
| ATOM | 199 | O | GLN | A | 30 | 26.937 | 31.660 | 25.763 | 1.00 | 15.19 | O |
| ATOM | 200 | N | PHE | A | 31 | 28.433 | 32.093 | 24.130 | 1.00 | 14.51 | N |
| ATOM | 201 | CA | PHE | A | 31 | 29.388 | 31.056 | 24.513 | 1.00 | 14.29 | C |
| ATOM | 202 | CB | PHE | A | 31 | 29.530 | 30.030 | 23.383 | 1.00 | 14.25 | C |
| ATOM | 203 | CG | PHE | A | 31 | 30.586 | 28.974 | 23.625 | 1.00 | 14.20 | C |
| ATOM | 204 | CD1 | PHE | A | 31 | 30.260 | 27.765 | 24.239 | 1.00 | 14.04 | C |
| ATOM | 205 | CE1 | PHE | A | 31 | 31.232 | 26.779 | 24.438 | 1.00 | 13.99 | C |
| ATOM | 206 | CZ | PHE | A | 31 | 32.537 | 26.995 | 24.002 | 1.00 | 13.88 | C |
| ATOM | 207 | CE2 | PHE | A | 31 | 32.868 | 28.190 | 23.376 | 1.00 | 14.18 | C |
| ATOM | 208 | CD2 | PHE | A | 31 | 31.895 | 29.169 | 23.188 | 1.00 | 13.96 | C |
| ATOM | 209 | C | PHE | A | 31 | 30.729 | 31.719 | 24.804 | 1.00 | 14.32 | C |
| ATOM | 210 | O | PHE | A | 31 | 31.167 | 32.598 | 24.064 | 1.00 | 14.16 | O |
| ATOM | 211 | N | ALA | A | 32 | 31.363 | 31.306 | 25.897 | 1.00 | 14.37 | N |
| ATOM | 212 | CA | ALA | A | 32 | 32.673 | 31.822 | 26.271 | 1.00 | 14.83 | C |
| ATOM | 213 | CB | ALA | A | 32 | 32.552 | 32.794 | 27.429 | 1.00 | 14.68 | C |
| ATOM | 214 | C | ALA | A | 32 | 33.569 | 30.661 | 26.645 | 1.00 | 14.99 | C |
| ATOM | 215 | O | ALA | A | 32 | 33.130 | 29.733 | 27.322 | 1.00 | 15.38 | O |
| ATOM | 216 | N | ALA | A | 33 | 34.819 | 30.705 | 26.194 | 1.00 | 15.45 | N |
| ATOM | 217 | CA | ALA | A | 33 | 35.768 | 29.635 | 26.482 | 1.00 | 15.71 | C |
| ATOM | 218 | CB | ALA | A | 33 | 35.554 | 28.458 | 25.536 | 1.00 | 15.98 | C |
| ATOM | 219 | C | ALA | A | 33 | 37.206 | 30.109 | 26.411 | 1.00 | 16.12 | C |
| ATOM | 220 | O | ALA | A | 33 | 37.517 | 31.089 | 25.730 | 1.00 | 16.43 | O |
| ATOM | 221 | N | ILE | A | 34 | 38.079 | 29.410 | 27.128 | 1.00 | 16.39 | N |
| ATOM | 222 | CA | ILE | A | 34 | 39.519 | 29.580 | 26.971 | 1.00 | 16.74 | C |
| ATOM | 223 | CB | ILE | A | 34 | 40.071 | 30.740 | 27.850 | 1.00 | 17.07 | C |
| ATOM | 224 | CG1 | ILE | A | 34 | 41.369 | 31.304 | 27.257 | 1.00 | 17.60 | C |
| ATOM | 225 | CD1 | ILE | A | 34 | 41.647 | 32.748 | 27.650 | 1.00 | 18.75 | C |
| ATOM | 226 | CG2 | ILE | A | 34 | 40.241 | 30.302 | 29.298 | 1.00 | 16.97 | C |
| ATOM | 227 | C | ILE | A | 34 | 40.236 | 28.261 | 27.254 | 1.00 | 16.68 | C |
| ATOM | 228 | O | ILE | A | 34 | 39.808 | 27.477 | 28.108 | 1.00 | 16.42 | O |
| ATOM | 229 | N | ARG | A | 35 | 41.306 | 28.013 | 26.507 | 1.00 | 16.69 | N |
| ATOM | 230 | CA | ARG | A | 35 | 42.080 | 26.789 | 26.647 | 1.00 | 16.85 | C |
| ATOM | 231 | CB | ARG | A | 35 | 42.550 | 26.303 | 25.271 | 1.00 | 16.75 | C |
| ATOM | 232 | CG | ARG | A | 35 | 43.051 | 24.867 | 25.249 | 1.00 | 17.00 | C |
| ATOM | 233 | CD | ARG | A | 35 | 43.346 | 24.394 | 23.830 | 1.00 | 17.03 | C |
| ATOM | 234 | NE | ARG | A | 35 | 42.146 | 24.346 | 22.992 | 1.00 | 17.29 | N |
| ATOM | 235 | CZ | ARG | A | 35 | 41.310 | 23.311 | 22.921 | 1.00 | 17.56 | C |
| ATOM | 236 | NH1 | ARG | A | 35 | 41.523 | 22.219 | 23.646 | 1.00 | 17.86 | N |
| ATOM | 237 | NH2 | ARG | A | 35 | 40.255 | 23.370 | 22.121 | 1.00 | 17.90 | N |
| ATOM | 238 | C | ARG | A | 35 | 43.272 | 27.017 | 27.573 | 1.00 | 17.06 | C |
| ATOM | 239 | O | ARG | A | 35 | 43.894 | 28.085 | 27.546 | 1.00 | 17.08 | O |
| ATOM | 240 | N | THR | A | 36 | 43.564 | 26.022 | 28.413 | 1.00 | 17.31 | N |
| ATOM | 241 | CA | THR | A | 36 | 44.743 | 26.052 | 29.282 | 1.00 | 17.83 | C |
| ATOM | 242 | CB | THR | A | 36 | 44.370 | 26.175 | 30.793 | 1.00 | 18.01 | C |
| ATOM | 243 | OG1 | THR | A | 36 | 43.932 | 24.906 | 31.296 | 1.00 | 18.26 | O |
| ATOM | 244 | CG2 | THR | A | 36 | 43.289 | 27.226 | 31.025 | 1.00 | 17.90 | C |
| ATOM | 245 | C | THR | A | 36 | 45.570 | 24.783 | 29.100 | 1.00 | 18.08 | C |
| ATOM | 246 | O | THR | A | 36 | 45.066 | 23.775 | 28.599 | 1.00 | 17.81 | O |
| ATOM | 247 | N | ASP | A | 37 | 46.834 | 24.830 | 29.517 | 1.00 | 18.48 | N |
| ATOM | 248 | CA | ASP | A | 37 | 47.650 | 23.621 | 29.582 | 1.00 | 19.18 | C |
| ATOM | 249 | CB | ASP | A | 37 | 49.158 | 23.952 | 29.575 | 1.00 | 19.15 | C |
| ATOM | 250 | CG | ASP | A | 37 | 49.610 | 24.746 | 30.798 | 1.00 | 19.92 | C |
| ATOM | 251 | OD1 | ASP | A | 37 | 48.833 | 24.894 | 31.765 | 1.00 | 20.67 | O |
| ATOM | 252 | OD2 | ASP | A | 37 | 50.771 | 25.219 | 30.787 | 1.00 | 20.60 | O |
| ATOM | 253 | C | ASP | A | 37 | 47.257 | 22.774 | 30.797 | 1.00 | 19.55 | C |
| ATOM | 254 | O | ASP | A | 37 | 46.341 | 23.136 | 31.547 | 1.00 | 19.64 | O |
| ATOM | 255 | N | SER | A | 38 | 47.947 | 21.653 | 30.988 | 1.00 | 20.21 | N |
| ATOM | 256 | CA | SER | A | 38 | 47.623 | 20.716 | 32.066 | 1.00 | 20.94 | C |
| ATOM | 257 | CB | SER | A | 38 | 48.441 | 19.432 | 31.917 | 1.00 | 20.98 | C |
| ATOM | 258 | OG | SER | A | 38 | 49.829 | 19.713 | 31.908 | 1.00 | 21.79 | O |
| ATOM | 259 | C | SER | A | 38 | 47.824 | 21.313 | 33.462 | 1.00 | 21.25 | C |
| ATOM | 260 | O | SER | A | 38 | 47.371 | 20.741 | 34.457 | 1.00 | 21.58 | O |
| ATOM | 261 | N | GLU | A | 39 | 48.494 | 22.466 | 33.522 | 1.00 | 21.48 | N |
| ATOM | 262 | CA | GLU | A | 39 | 48.767 | 23.153 | 34.789 | 1.00 | 21.82 | C |
| ATOM | 263 | CB | GLU | A | 39 | 50.256 | 23.507 | 34.896 | 1.00 | 22.13 | C |
| ATOM | 264 | CG | GLU | A | 39 | 51.180 | 22.296 | 35.015 | 1.00 | 23.91 | C |
| ATOM | 265 | CD | GLU | A | 39 | 50.916 | 21.476 | 36.267 | 1.00 | 26.19 | C |
| ATOM | 266 | OE1 | GLU | A | 39 | 50.905 | 22.057 | 37.373 | 1.00 | 27.78 | O |
| ATOM | 267 | OE2 | GLU | A | 39 | 50.718 | 20.248 | 36.143 | 1.00 | 27.92 | O |
| ATOM | 268 | C | GLU | A | 39 | 47.901 | 24.405 | 34.972 | 1.00 | 21.65 | C |
| ATOM | 269 | O | GLU | A | 39 | 48.106 | 25.183 | 35.909 | 1.00 | 21.67 | O |
| ATOM | 270 | N | PHE | A | 40 | 46.930 | 24.576 | 34.072 | 1.00 | 21.49 | N |
| ATOM | 271 | CA | PHE | A | 40 | 45.956 | 25.683 | 34.112 | 1.00 | 21.58 | C |
| ATOM | 272 | CB | PHE | A | 40 | 45.230 | 25.759 | 35.469 | 1.00 | 21.41 | C |
| ATOM | 273 | CG | PHE | A | 40 | 44.506 | 24.493 | 35.841 | 1.00 | 21.31 | C |
| ATOM | 274 | CD1 | PHE | A | 40 | 43.623 | 23.889 | 34.948 | 1.00 | 21.03 | C |

TABLE 6-continued

Coordinates of the crystal structure of *E. coli* ExoI bound to compound 9

| ATOM | 275 | CE1 | PHE | A | 40 | 42.954 | 22.716 | 35.289 | 1.00 | 20.68 | C |
|------|-----|-----|-----|---|----|--------|--------|--------|------|-------|---|
| ATOM | 276 | CZ | PHE | A | 40 | 43.160 | 22.140 | 36.536 | 1.00 | 21.44 | C |
| ATOM | 277 | CE2 | PHE | A | 40 | 44.032 | 22.736 | 37.438 | 1.00 | 21.87 | C |
| ATOM | 278 | CD2 | PHE | A | 40 | 44.701 | 23.908 | 37.089 | 1.00 | 21.78 | C |
| ATOM | 279 | C | PHE | A | 40 | 46.511 | 27.052 | 33.698 | 1.00 | 21.77 | C |
| ATOM | 280 | O | PHE | A | 40 | 45.916 | 28.089 | 34.008 | 1.00 | 21.87 | O |
| ATOM | 281 | N | ASN | A | 41 | 47.641 | 27.045 | 32.992 | 1.00 | 22.05 | N |
| ATOM | 282 | CA | ASN | A | 41 | 48.137 | 28.245 | 32.320 | 1.00 | 22.27 | C |
| ATOM | 283 | CB | ASN | A | 41 | 49.645 | 28.150 | 32.056 | 1.00 | 22.41 | C |
| ATOM | 284 | CG | ASN | A | 41 | 50.438 | 27.769 | 33.292 | 1.00 | 22.55 | C |
| ATOM | 285 | OD1 | ASN | A | 41 | 51.112 | 26.738 | 33.314 | 1.00 | 23.79 | O |
| ATOM | 286 | ND2 | ASN | A | 41 | 50.363 | 28.596 | 34.327 | 1.00 | 23.32 | N |
| ATOM | 287 | C | ASN | A | 41 | 47.401 | 28.432 | 31.003 | 1.00 | 22.47 | C |
| ATOM | 288 | O | ASN | A | 41 | 47.337 | 27.510 | 30.188 | 1.00 | 22.33 | O |
| ATOM | 289 | N | VAL | A | 42 | 46.845 | 29.625 | 30.802 | 1.00 | 22.96 | N |
| ATOM | 290 | CA | VAL | A | 42 | 46.115 | 29.951 | 29.574 | 1.00 | 23.38 | C |
| ATOM | 291 | CB | VAL | A | 42 | 45.518 | 31.385 | 29.639 | 1.00 | 23.30 | C |
| ATOM | 292 | CG1 | VAL | A | 42 | 44.983 | 31.817 | 28.284 | 1.00 | 23.40 | C |
| ATOM | 293 | CG2 | VAL | A | 42 | 44.424 | 31.462 | 30.698 | 1.00 | 23.15 | C |
| ATOM | 294 | C | VAL | A | 42 | 47.030 | 29.815 | 28.356 | 1.00 | 23.84 | C |
| ATOM | 295 | O | VAL | A | 42 | 48.157 | 30.317 | 28.362 | 1.00 | 23.83 | O |
| ATOM | 296 | N | ILE | A | 43 | 46.556 | 29.115 | 27.326 | 1.00 | 24.38 | N |
| ATOM | 297 | CA | ILE | A | 43 | 47.357 | 28.921 | 26.108 | 1.00 | 25.12 | C |
| ATOM | 298 | CB | ILE | A | 43 | 47.824 | 27.443 | 25.918 | 1.00 | 25.11 | C |
| ATOM | 299 | CG1 | ILE | A | 43 | 46.631 | 26.485 | 25.871 | 1.00 | 25.16 | C |
| ATOM | 300 | CD1 | ILE | A | 43 | 47.007 | 25.063 | 25.503 | 1.00 | 25.21 | C |
| ATOM | 301 | CG2 | ILE | A | 43 | 48.812 | 27.044 | 27.017 | 1.00 | 25.45 | C |
| ATOM | 302 | C | ILE | A | 43 | 46.712 | 29.462 | 24.825 | 1.00 | 25.54 | C |
| ATOM | 303 | O | ILE | A | 43 | 47.378 | 29.587 | 23.795 | 1.00 | 25.90 | O |
| ATOM | 304 | N | GLY | A | 44 | 45.425 | 29.786 | 24.889 | 1.00 | 25.87 | N |
| ATOM | 305 | CA | GLY | A | 44 | 44.735 | 30.348 | 23.733 | 1.00 | 26.38 | C |
| ATOM | 306 | C | GLY | A | 44 | 44.261 | 31.774 | 23.945 | 1.00 | 26.59 | C |
| ATOM | 307 | O | GLY | A | 44 | 44.393 | 32.332 | 25.039 | 1.00 | 26.91 | O |
| ATOM | 308 | N | GLU | A | 45 | 43.730 | 32.372 | 22.882 | 1.00 | 26.48 | N |
| ATOM | 309 | CA | GLU | A | 45 | 42.979 | 33.615 | 22.993 | 1.00 | 26.37 | C |
| ATOM | 310 | CB | GLU | A | 45 | 42.892 | 34.320 | 21.633 | 1.00 | 26.59 | C |
| ATOM | 311 | CG | GLU | A | 45 | 44.230 | 34.835 | 21.095 | 1.00 | 27.78 | C |
| ATOM | 312 | CD | GLU | A | 45 | 44.871 | 35.883 | 21.994 | 1.00 | 29.22 | C |
| ATOM | 313 | OE1 | GLU | A | 45 | 44.152 | 36.792 | 22.468 | 1.00 | 30.39 | O |
| ATOM | 314 | OE2 | GLU | A | 45 | 46.097 | 35.799 | 22.219 | 1.00 | 30.40 | O |
| ATOM | 315 | C | GLU | A | 45 | 41.577 | 33.286 | 23.501 | 1.00 | 25.89 | C |
| ATOM | 316 | O | GLU | A | 45 | 41.081 | 32.181 | 23.260 | 1.00 | 25.87 | O |
| ATOM | 317 | N | PRO | A | 46 | 40.936 | 34.235 | 24.216 | 1.00 | 25.47 | N |
| ATOM | 318 | CA | PRO | A | 46 | 39.554 | 34.018 | 24.645 | 1.00 | 25.05 | C |
| ATOM | 319 | CB | PRO | A | 46 | 39.207 | 35.315 | 25.390 | 1.00 | 25.19 | C |
| ATOM | 320 | CG | PRO | A | 46 | 40.521 | 35.900 | 25.775 | 1.00 | 25.39 | C |
| ATOM | 321 | CD | PRO | A | 46 | 41.454 | 35.537 | 24.673 | 1.00 | 25.43 | C |
| ATOM | 322 | C | PRO | A | 46 | 38.619 | 33.829 | 23.452 | 1.00 | 24.60 | C |
| ATOM | 323 | O | PRO | A | 46 | 38.751 | 34.527 | 22.440 | 1.00 | 24.34 | O |
| ATOM | 324 | N | GLU | A | 47 | 37.705 | 32.871 | 23.567 | 1.00 | 23.93 | N |
| ATOM | 325 | CA | GLU | A | 47 | 36.691 | 32.636 | 22.546 | 1.00 | 23.56 | C |
| ATOM | 326 | CB | GLU | A | 47 | 36.653 | 31.152 | 22.154 | 1.00 | 23.73 | C |
| ATOM | 327 | CG | GLU | A | 47 | 37.983 | 30.581 | 21.659 | 1.00 | 25.05 | C |
| ATOM | 328 | CD | GLU | A | 47 | 38.238 | 30.848 | 20.184 | 1.00 | 26.33 | C |
| ATOM | 329 | OE1 | GLU | A | 47 | 37.274 | 31.162 | 19.448 | 1.00 | 27.07 | O |
| ATOM | 330 | OE2 | GLU | A | 47 | 39.407 | 30.731 | 19.758 | 1.00 | 27.50 | O |
| ATOM | 331 | C | GLU | A | 47 | 35.331 | 33.059 | 23.086 | 1.00 | 22.90 | C |
| ATOM | 332 | O | GLU | A | 47 | 34.768 | 32.393 | 23.951 | 1.00 | 22.80 | O |
| ATOM | 333 | N | VAL | A | 48 | 34.818 | 34.183 | 22.590 | 1.00 | 22.04 | N |
| ATOM | 334 | CA | VAL | A | 48 | 33.505 | 34.686 | 23.005 | 1.00 | 21.35 | C |
| ATOM | 335 | CB | VAL | A | 48 | 33.618 | 35.928 | 23.945 | 1.00 | 21.57 | C |
| ATOM | 336 | CG1 | VAL | A | 48 | 32.234 | 36.405 | 24.380 | 1.00 | 21.71 | C |
| ATOM | 337 | CG2 | VAL | A | 48 | 34.471 | 35.613 | 25.167 | 1.00 | 21.88 | C |
| ATOM | 338 | C | VAL | A | 48 | 32.676 | 35.054 | 21.780 | 1.00 | 20.67 | C |
| ATOM | 339 | O | VAL | A | 48 | 33.097 | 35.879 | 20.964 | 1.00 | 20.73 | O |
| ATOM | 340 | N | PHE | A | 49 | 31.501 | 34.440 | 21.653 | 1.00 | 19.66 | N |
| ATOM | 341 | CA | PHE | A | 49 | 30.592 | 34.741 | 20.540 | 1.00 | 18.82 | C |
| ATOM | 342 | CB | PHE | A | 49 | 30.970 | 33.953 | 19.274 | 1.00 | 18.80 | C |
| ATOM | 343 | CG | PHE | A | 49 | 31.245 | 32.492 | 19.515 | 1.00 | 18.76 | C |
| ATOM | 344 | CD1 | PHE | A | 49 | 30.229 | 31.553 | 19.400 | 1.00 | 18.52 | C |
| ATOM | 345 | CE1 | PHE | A | 49 | 30.482 | 30.198 | 19.615 | 1.00 | 18.18 | C |
| ATOM | 346 | CZ | PHE | A | 49 | 31.769 | 29.776 | 19.935 | 1.00 | 18.18 | C |
| ATOM | 347 | CE2 | PHE | A | 49 | 32.794 | 30.705 | 20.046 | 1.00 | 18.51 | C |
| ATOM | 348 | CD2 | PHE | A | 49 | 32.531 | 32.056 | 19.834 | 1.00 | 19.00 | C |
| ATOM | 349 | C | PHE | A | 49 | 29.117 | 34.544 | 20.892 | 1.00 | 18.46 | C |
| ATOM | 350 | O | PHE | A | 49 | 28.780 | 33.815 | 21.828 | 1.00 | 17.58 | O |
| ATOM | 351 | N | TYR | A | 50 | 28.250 | 35.212 | 20.135 | 1.00 | 18.22 | N |
| ATOM | 352 | CA | TYR | A | 50 | 26.816 | 35.216 | 20.398 | 1.00 | 18.09 | C |

TABLE 6-continued

Coordinates of the crystal structure of *E. coli* ExoI bound to compound 9

| ATOM | 353 | CB | TYR | A | 50 | 26.254 | 36.637 | 20.273 | 1.00 | 18.60 | C |
|---|---|---|---|---|---|---|---|---|---|---|---|
| ATOM | 354 | CG | TYR | A | 50 | 26.723 | 37.606 | 21.337 | 1.00 | 19.37 | C |
| ATOM | 355 | CD1 | TYR | A | 50 | 26.026 | 37.742 | 22.536 | 1.00 | 20.46 | C |
| ATOM | 356 | CE1 | TYR | A | 50 | 26.444 | 38.637 | 23.515 | 1.00 | 21.26 | C |
| ATOM | 357 | CZ | TYR | A | 50 | 27.567 | 39.415 | 23.296 | 1.00 | 21.36 | C |
| ATOM | 358 | OH | TYR | A | 50 | 27.978 | 40.303 | 24.269 | 1.00 | 22.46 | O |
| ATOM | 359 | CE2 | TYR | A | 50 | 28.276 | 39.306 | 22.110 | 1.00 | 21.29 | C |
| ATOM | 360 | CD2 | TYR | A | 50 | 27.849 | 38.405 | 21.135 | 1.00 | 20.77 | C |
| ATOM | 361 | C | TYR | A | 50 | 26.063 | 34.294 | 19.444 | 1.00 | 17.58 | C |
| ATOM | 362 | O | TYR | A | 50 | 26.562 | 33.948 | 18.364 | 1.00 | 17.36 | O |
| ATOM | 363 | N | CYS | A | 51 | 24.856 | 33.904 | 19.849 | 1.00 | 17.04 | N |
| ATOM | 364 | CA | CYS | A | 51 | 23.968 | 33.130 | 18.995 | 1.00 | 16.99 | C |
| ATOM | 365 | CB | CYS | A | 51 | 23.567 | 31.818 | 19.673 | 1.00 | 16.78 | C |
| ATOM | 366 | SG | CYS | A | 51 | 22.709 | 30.666 | 18.576 | 1.00 | 16.89 | S |
| ATOM | 367 | C | CYS | A | 51 | 22.722 | 33.933 | 18.664 | 1.00 | 17.11 | C |
| ATOM | 368 | O | CYS | A | 51 | 22.016 | 34.396 | 19.563 | 1.00 | 16.98 | O |
| ATOM | 369 | N | LYS | A | 52 | 22.463 | 34.103 | 17.370 | 1.00 | 17.43 | N |
| ATOM | 370 | CA | LYS | A | 52 | 21.241 | 34.744 | 16.906 | 1.00 | 18.04 | C |
| ATOM | 371 | CB | LYS | A | 52 | 21.341 | 35.057 | 15.409 | 1.00 | 18.17 | C |
| ATOM | 372 | CG | LYS | A | 52 | 20.124 | 35.756 | 14.829 | 1.00 | 19.34 | C |
| ATOM | 373 | CD | LYS | A | 52 | 20.271 | 35.964 | 13.328 | 1.00 | 20.17 | C |
| ATOM | 374 | CE | LYS | A | 52 | 19.036 | 36.630 | 12.746 | 1.00 | 22.70 | C |
| ATOM | 375 | NZ | LYS | A | 52 | 19.139 | 36.808 | 11.270 | 1.00 | 24.68 | N |
| ATOM | 376 | C | LYS | A | 52 | 20.040 | 33.836 | 17.189 | 1.00 | 17.92 | C |
| ATOM | 377 | O | LYS | A | 52 | 20.015 | 32.684 | 16.745 | 1.00 | 18.27 | O |
| ATOM | 378 | N | PRO | A | 53 | 19.055 | 34.341 | 17.956 | 1.00 | 18.06 | N |
| ATOM | 379 | CA | PRO | A | 53 | 17.838 | 33.564 | 18.180 | 1.00 | 18.09 | C |
| ATOM | 380 | CB | PRO | A | 53 | 17.218 | 34.233 | 19.408 | 1.00 | 18.04 | C |
| ATOM | 381 | CG | PRO | A | 53 | 17.685 | 35.652 | 19.343 | 1.00 | 18.12 | C |
| ATOM | 382 | CD | PRO | A | 53 | 19.032 | 35.636 | 18.667 | 1.00 | 18.06 | C |
| ATOM | 383 | C | PRO | A | 53 | 16.887 | 33.637 | 16.986 | 1.00 | 18.25 | C |
| ATOM | 384 | O | PRO | A | 53 | 16.646 | 34.723 | 16.450 | 1.00 | 18.68 | O |
| ATOM | 385 | N | ALA | A | 54 | 16.357 | 32.484 | 16.579 | 1.00 | 18.31 | N |
| ATOM | 386 | CA | ALA | A | 54 | 15.371 | 32.417 | 15.501 | 1.00 | 18.29 | C |
| ATOM | 387 | CB | ALA | A | 54 | 15.082 | 30.978 | 15.145 | 1.00 | 18.39 | C |
| ATOM | 388 | C | ALA | A | 54 | 14.078 | 33.142 | 15.882 | 1.00 | 18.36 | C |
| ATOM | 389 | O | ALA | A | 54 | 13.818 | 33.383 | 17.062 | 1.00 | 18.35 | O |
| ATOM | 390 | N | ASP | A | 55 | 13.265 | 33.475 | 14.882 | 1.00 | 18.43 | N |
| ATOM | 391 | CA | ASP | A | 55 | 12.073 | 34.295 | 15.110 | 1.00 | 18.66 | C |
| ATOM | 392 | CB | ASP | A | 55 | 11.730 | 35.128 | 13.861 | 1.00 | 19.05 | C |
| ATOM | 393 | CG | ASP | A | 55 | 11.266 | 34.278 | 12.683 | 1.00 | 20.25 | C |
| ATOM | 394 | OD1 | ASP | A | 55 | 11.256 | 33.029 | 12.783 | 1.00 | 21.62 | O |
| ATOM | 395 | OD2 | ASP | A | 55 | 10.908 | 34.873 | 11.646 | 1.00 | 22.14 | O |
| ATOM | 396 | C | ASP | A | 55 | 10.840 | 33.525 | 15.620 | 1.00 | 18.39 | C |
| ATOM | 397 | O | ASP | A | 55 | 9.716 | 34.029 | 15.555 | 1.00 | 18.35 | O |
| ATOM | 398 | N | ASP | A | 56 | 11.060 | 32.317 | 16.139 | 1.00 | 18.02 | N |
| ATOM | 399 | CA | ASP | A | 56 | 9.980 | 31.526 | 16.731 | 1.00 | 17.85 | C |
| ATOM | 400 | CB | ASP | A | 56 | 9.946 | 30.112 | 16.127 | 1.00 | 17.87 | C |
| ATOM | 401 | CG | ASP | A | 56 | 11.154 | 29.263 | 16.527 | 1.00 | 18.36 | C |
| ATOM | 402 | OD1 | ASP | A | 56 | 12.229 | 29.830 | 16.825 | 1.00 | 18.82 | O |
| ATOM | 403 | OD2 | ASP | A | 56 | 11.024 | 28.021 | 16.537 | 1.00 | 19.81 | O |
| ATOM | 404 | C | ASP | A | 56 | 10.100 | 31.458 | 18.256 | 1.00 | 17.49 | C |
| ATOM | 405 | O | ASP | A | 56 | 9.523 | 30.577 | 18.894 | 1.00 | 17.77 | O |
| ATOM | 406 | N | TYR | A | 57 | 10.831 | 32.407 | 18.834 | 1.00 | 17.09 | N |
| ATOM | 407 | CA | TYR | A | 57 | 11.226 | 32.310 | 20.234 | 1.00 | 16.68 | C |
| ATOM | 408 | CB | TYR | A | 57 | 12.593 | 31.619 | 20.334 | 1.00 | 16.45 | C |
| ATOM | 409 | CG | TYR | A | 57 | 13.141 | 31.500 | 21.741 | 1.00 | 16.16 | C |
| ATOM | 410 | CD1 | TYR | A | 57 | 12.652 | 30.533 | 22.623 | 1.00 | 15.88 | C |
| ATOM | 411 | CE1 | TYR | A | 57 | 13.156 | 30.419 | 23.916 | 1.00 | 16.09 | C |
| ATOM | 412 | CZ | TYR | A | 57 | 14.166 | 31.272 | 24.335 | 1.00 | 16.18 | C |
| ATOM | 413 | OH | TYR | A | 57 | 14.666 | 31.160 | 25.611 | 1.00 | 16.26 | O |
| ATOM | 414 | CE2 | TYR | A | 57 | 14.673 | 32.236 | 23.475 | 1.00 | 15.81 | C |
| ATOM | 415 | CD2 | TYR | A | 57 | 14.158 | 32.346 | 22.186 | 1.00 | 15.91 | C |
| ATOM | 416 | C | TYR | A | 57 | 11.273 | 33.658 | 20.939 | 1.00 | 16.54 | C |
| ATOM | 417 | O | TYR | A | 57 | 11.759 | 34.645 | 20.383 | 1.00 | 16.53 | O |
| ATOM | 418 | N | LEU | A | 58 | 10.761 | 33.686 | 22.169 | 1.00 | 16.33 | N |
| ATOM | 419 | CA | LEU | A | 58 | 10.957 | 34.815 | 23.072 | 1.00 | 16.43 | C |
| ATOM | 420 | CB | LEU | A | 58 | 9.616 | 35.427 | 23.489 | 1.00 | 16.46 | C |
| ATOM | 421 | CG | LEU | A | 58 | 8.817 | 36.202 | 22.440 | 1.00 | 16.58 | C |
| ATOM | 422 | CD1 | LEU | A | 58 | 7.510 | 36.695 | 23.041 | 1.00 | 17.29 | C |
| ATOM | 423 | CD2 | LEU | A | 58 | 9.622 | 37.367 | 21.896 | 1.00 | 17.31 | C |
| ATOM | 424 | C | LEU | A | 58 | 11.725 | 34.358 | 24.308 | 1.00 | 16.45 | C |
| ATOM | 425 | O | LEU | A | 58 | 11.401 | 33.318 | 24.890 | 1.00 | 16.17 | O |
| ATOM | 426 | N | PRO | A | 59 | 12.759 | 35.123 | 24.705 | 1.00 | 16.50 | N |
| ATOM | 427 | CA | PRO | A | 59 | 13.555 | 34.769 | 25.886 | 1.00 | 16.57 | C |
| ATOM | 428 | CB | PRO | A | 59 | 14.676 | 35.815 | 25.881 | 1.00 | 16.63 | C |
| ATOM | 429 | CG | PRO | A | 59 | 14.144 | 36.948 | 25.089 | 1.00 | 16.92 | C |
| ATOM | 430 | CD | PRO | A | 59 | 13.250 | 36.352 | 24.056 | 1.00 | 16.58 | C |

TABLE 6-continued

Coordinates of the crystal structure of *E. coli* ExoI bound to compound 9

| ATOM | 431 | C | PRO | A | 59 | 12.768 | 34.872 | 27.186 | 1.00 | 16.86 | C |
| ATOM | 432 | O | PRO | A | 59 | 11.827 | 35.660 | 27.281 | 1.00 | 16.89 | O |
| ATOM | 433 | N | GLN | A | 60 | 13.153 | 34.074 | 28.178 | 1.00 | 16.97 | N |
| ATOM | 434 | CA | GLN | A | 60 | 12.611 | 34.229 | 29.523 | 1.00 | 17.66 | C |
| ATOM | 435 | CB | GLN | A | 60 | 13.008 | 33.048 | 30.410 | 1.00 | 17.54 | C |
| ATOM | 436 | CG | GLN | A | 60 | 12.432 | 31.705 | 29.978 | 1.00 | 18.84 | C |
| ATOM | 437 | CD | GLN | A | 60 | 12.727 | 30.588 | 30.973 | 1.00 | 19.43 | C |
| ATOM | 438 | OE1 | GLN | A | 60 | 13.691 | 30.656 | 31.742 | 1.00 | 21.53 | O |
| ATOM | 439 | NE2 | GLN | A | 60 | 11.897 | 29.549 | 30.957 | 1.00 | 21.90 | N |
| ATOM | 440 | C | GLN | A | 60 | 13.150 | 35.528 | 30.116 | 1.00 | 17.55 | C |
| ATOM | 441 | O | GLN | A | 60 | 14.365 | 35.718 | 30.178 | 1.00 | 17.29 | O |
| ATOM | 442 | N | PRO | A | 61 | 12.247 | 36.437 | 30.537 | 1.00 | 17.70 | N |
| ATOM | 443 | CA | PRO | A | 61 | 12.679 | 37.711 | 31.118 | 1.00 | 17.82 | C |
| ATOM | 444 | CB | PRO | A | 61 | 11.366 | 38.338 | 31.598 | 1.00 | 17.83 | C |
| ATOM | 445 | CG | PRO | A | 61 | 10.328 | 37.751 | 30.706 | 1.00 | 17.88 | C |
| ATOM | 446 | CD | PRO | A | 61 | 10.776 | 36.337 | 30.469 | 1.00 | 17.59 | C |
| ATOM | 447 | C | PRO | A | 61 | 13.670 | 37.547 | 32.281 | 1.00 | 17.86 | C |
| ATOM | 448 | O | PRO | A | 61 | 14.646 | 38.295 | 32.369 | 1.00 | 18.00 | O |
| ATOM | 449 | N | GLY | A | 62 | 13.434 | 36.562 | 33.147 | 1.00 | 18.02 | N |
| ATOM | 450 | CA | GLY | A | 62 | 14.322 | 36.305 | 34.282 | 1.00 | 18.01 | C |
| ATOM | 451 | C | GLY | A | 62 | 15.761 | 36.037 | 33.878 | 1.00 | 18.02 | C |
| ATOM | 452 | O | GLY | A | 62 | 16.700 | 36.513 | 34.528 | 1.00 | 18.40 | O |
| ATOM | 453 | N | ALA | A | 63 | 15.936 | 35.281 | 32.796 | 1.00 | 17.90 | N |
| ATOM | 454 | CA | ALA | A | 63 | 17.265 | 34.950 | 32.289 | 1.00 | 17.51 | C |
| ATOM | 455 | CB | ALA | A | 63 | 17.169 | 33.921 | 31.177 | 1.00 | 17.69 | C |
| ATOM | 456 | C | ALA | A | 63 | 18.011 | 36.190 | 31.808 | 1.00 | 17.37 | C |
| ATOM | 457 | O | ALA | A | 63 | 19.200 | 36.348 | 32.079 | 1.00 | 17.33 | O |
| ATOM | 458 | N | VAL | A | 64 | 17.301 | 37.064 | 31.097 | 1.00 | 17.23 | N |
| ATOM | 459 | CA | VAL | A | 64 | 17.880 | 38.305 | 30.577 | 1.00 | 17.18 | C |
| ATOM | 460 | CB | VAL | A | 64 | 16.917 | 39.010 | 29.582 | 1.00 | 17.00 | C |
| ATOM | 461 | CG1 | VAL | A | 64 | 17.491 | 40.346 | 29.104 | 1.00 | 17.01 | C |
| ATOM | 462 | CG2 | VAL | A | 64 | 16.627 | 38.096 | 28.394 | 1.00 | 17.42 | C |
| ATOM | 463 | C | VAL | A | 64 | 18.282 | 39.249 | 31.714 | 1.00 | 17.28 | C |
| ATOM | 464 | O | VAL | A | 64 | 19.290 | 39.942 | 31.621 | 1.00 | 17.15 | O |
| ATOM | 465 | N | LEU | A | 65 | 17.505 | 39.251 | 32.796 | 1.00 | 17.61 | N |
| ATOM | 466 | CA | LEU | A | 65 | 17.850 | 40.051 | 33.973 | 1.00 | 18.18 | C |
| ATOM | 467 | CB | LEU | A | 65 | 16.699 | 40.071 | 34.984 | 1.00 | 18.22 | C |
| ATOM | 468 | CG | LEU | A | 65 | 15.440 | 40.838 | 34.569 | 1.00 | 18.35 | C |
| ATOM | 469 | CD1 | LEU | A | 65 | 14.403 | 40.795 | 35.680 | 1.00 | 19.16 | C |
| ATOM | 470 | CD2 | LEU | A | 65 | 15.769 | 42.282 | 34.197 | 1.00 | 19.05 | C |
| ATOM | 471 | C | LEU | A | 65 | 19.141 | 39.570 | 34.638 | 1.00 | 18.47 | C |
| ATOM | 472 | O | LEU | A | 65 | 19.884 | 40.366 | 35.216 | 1.00 | 18.98 | O |
| ATOM | 473 | N | ILE | A | 66 | 19.399 | 38.268 | 34.547 | 1.00 | 18.79 | N |
| ATOM | 474 | CA | ILE | A | 66 | 20.634 | 37.682 | 35.064 | 1.00 | 19.06 | C |
| ATOM | 475 | CB | ILE | A | 66 | 20.492 | 36.143 | 35.271 | 1.00 | 19.18 | C |
| ATOM | 476 | CG1 | ILE | A | 66 | 19.574 | 35.852 | 36.463 | 1.00 | 19.58 | C |
| ATOM | 477 | CD1 | ILE | A | 66 | 19.065 | 34.424 | 36.520 | 1.00 | 20.67 | C |
| ATOM | 478 | CG2 | ILE | A | 66 | 21.859 | 35.487 | 35.478 | 1.00 | 19.53 | C |
| ATOM | 479 | C | ILE | A | 66 | 21.832 | 37.997 | 34.158 | 1.00 | 19.02 | C |
| ATOM | 480 | O | ILE | A | 66 | 22.865 | 38.473 | 34.633 | 1.00 | 19.54 | O |
| ATOM | 481 | N | THR | A | 67 | 21.674 | 37.753 | 32.855 | 1.00 | 18.77 | N |
| ATOM | 482 | CA | THR | A | 67 | 22.793 | 37.823 | 31.905 | 1.00 | 18.49 | C |
| ATOM | 483 | CB | THR | A | 67 | 22.530 | 36.957 | 30.655 | 1.00 | 18.46 | C |
| ATOM | 484 | OG1 | THR | A | 67 | 21.456 | 37.528 | 29.899 | 1.00 | 18.33 | O |
| ATOM | 485 | CG2 | THR | A | 67 | 22.173 | 35.529 | 31.045 | 1.00 | 18.45 | C |
| ATOM | 486 | C | THR | A | 67 | 23.083 | 39.242 | 31.427 | 1.00 | 18.41 | C |
| ATOM | 487 | O | THR | A | 67 | 24.235 | 39.584 | 31.137 | 1.00 | 18.90 | O |
| ATOM | 488 | N | GLY | A | 68 | 22.034 | 40.053 | 31.314 | 1.00 | 18.06 | N |
| ATOM | 489 | CA | GLY | A | 68 | 22.158 | 41.394 | 30.748 | 1.00 | 17.48 | C |
| ATOM | 490 | C | GLY | A | 68 | 22.275 | 41.401 | 29.230 | 1.00 | 17.28 | C |
| ATOM | 491 | O | GLY | A | 68 | 22.572 | 42.438 | 28.630 | 1.00 | 17.58 | O |
| ATOM | 492 | N | ILE | A | 69 | 22.044 | 40.244 | 28.609 | 1.00 | 16.85 | N |
| ATOM | 493 | CA | ILE | A | 69 | 22.078 | 40.125 | 27.150 | 1.00 | 16.50 | C |
| ATOM | 494 | CB | ILE | A | 69 | 22.809 | 38.837 | 26.680 | 1.00 | 16.56 | C |
| ATOM | 495 | CG1 | ILE | A | 69 | 24.216 | 38.750 | 27.280 | 1.00 | 16.54 | C |
| ATOM | 496 | CD1 | ILE | A | 69 | 24.861 | 37.363 | 27.157 | 1.00 | 17.06 | C |
| ATOM | 497 | CG2 | ILE | A | 69 | 22.872 | 38.785 | 25.145 | 1.00 | 16.48 | C |
| ATOM | 498 | C | ILE | A | 69 | 20.660 | 40.120 | 26.590 | 1.00 | 16.10 | C |
| ATOM | 499 | O | ILE | A | 69 | 19.892 | 39.184 | 26.826 | 1.00 | 16.02 | O |
| ATOM | 500 | N | THR | A | 70 | 20.321 | 41.173 | 25.853 | 1.00 | 15.70 | N |
| ATOM | 501 | CA | THR | A | 70 | 19.012 | 41.286 | 25.215 | 1.00 | 15.32 | C |
| ATOM | 502 | CB | THR | A | 70 | 18.698 | 42.744 | 24.825 | 1.00 | 15.31 | C |
| ATOM | 503 | OG1 | THR | A | 70 | 19.668 | 43.208 | 23.876 | 1.00 | 15.64 | O |
| ATOM | 504 | CG2 | THR | A | 70 | 18.711 | 43.648 | 26.050 | 1.00 | 15.43 | C |
| ATOM | 505 | C | THR | A | 70 | 18.971 | 40.425 | 23.954 | 1.00 | 15.06 | C |
| ATOM | 506 | O | THR | A | 70 | 20.015 | 40.135 | 23.371 | 1.00 | 14.70 | O |
| ATOM | 507 | N | PRO | A | 71 | 17.761 | 40.007 | 23.529 | 1.00 | 14.88 | N |
| ATOM | 508 | CA | PRO | A | 71 | 17.639 | 39.311 | 22.246 | 1.00 | 14.75 | C |

TABLE 6-continued

Coordinates of the crystal structure of *E. coli* ExoI bound to compound 9

| ATOM | 509 | CB | PRO | A | 71 | 16.137 | 39.025 | 22.136 | 1.00 | 14.86 | C |
|------|-----|-----|-----|---|----|--------|--------|--------|------|-------|---|
| ATOM | 510 | CG | PRO | A | 71 | 15.486 | 39.960 | 23.119 | 1.00 | 14.89 | C |
| ATOM | 511 | CD | PRO | A | 71 | 16.464 | 40.138 | 24.217 | 1.00 | 14.80 | C |
| ATOM | 512 | C | PRO | A | 71 | 18.119 | 40.173 | 21.070 | 1.00 | 14.66 | C |
| ATOM | 513 | O | PRO | A | 71 | 18.645 | 39.638 | 20.094 | 1.00 | 14.71 | O |
| ATOM | 514 | N | GLN | A | 72 | 17.956 | 41.493 | 21.182 | 1.00 | 14.69 | N |
| ATOM | 515 | CA | GLN | A | 72 | 18.452 | 42.428 | 20.165 | 1.00 | 14.86 | C |
| ATOM | 516 | CB | GLN | A | 72 | 18.028 | 43.867 | 20.479 | 1.00 | 14.82 | C |
| ATOM | 517 | CG | GLN | A | 72 | 16.529 | 44.127 | 20.387 | 1.00 | 14.90 | C |
| ATOM | 518 | CD | GLN | A | 72 | 15.826 | 44.050 | 21.731 | 1.00 | 15.27 | C |
| ATOM | 519 | OE1 | GLN | A | 72 | 16.242 | 43.314 | 22.625 | 1.00 | 15.46 | O |
| ATOM | 520 | NE2 | GLN | A | 72 | 14.752 | 44.818 | 21.877 | 1.00 | 15.57 | N |
| ATOM | 521 | C | GLN | A | 72 | 19.973 | 42.359 | 20.013 | 1.00 | 14.93 | C |
| ATOM | 522 | O | GLN | A | 72 | 20.492 | 42.350 | 18.892 | 1.00 | 14.77 | O |
| ATOM | 523 | N | GLU | A | 73 | 20.682 | 42.327 | 21.140 | 1.00 | 15.09 | N |
| ATOM | 524 | CA | GLU | A | 73 | 22.139 | 42.233 | 21.113 | 1.00 | 15.36 | C |
| ATOM | 525 | CB | GLU | A | 73 | 22.739 | 42.416 | 22.508 | 1.00 | 15.71 | C |
| ATOM | 526 | CG | GLU | A | 73 | 24.267 | 42.367 | 22.512 | 1.00 | 17.54 | C |
| ATOM | 527 | CD | GLU | A | 73 | 24.883 | 42.870 | 23.799 | 1.00 | 20.20 | C |
| ATOM | 528 | OE1 | GLU | A | 73 | 24.331 | 42.579 | 24.883 | 1.00 | 21.84 | O |
| ATOM | 529 | OE2 | GLU | A | 73 | 25.933 | 43.545 | 23.724 | 1.00 | 21.38 | O |
| ATOM | 530 | C | GLU | A | 73 | 22.607 | 40.915 | 20.496 | 1.00 | 15.01 | C |
| ATOM | 531 | O | GLU | A | 73 | 23.488 | 40.910 | 19.636 | 1.00 | 14.92 | O |
| ATOM | 532 | N | ALA | A | 74 | 22.011 | 39.803 | 20.927 | 1.00 | 14.76 | N |
| ATOM | 533 | CA | ALA | A | 74 | 22.388 | 38.488 | 20.400 | 1.00 | 14.83 | C |
| ATOM | 534 | CB | ALA | A | 74 | 21.705 | 37.381 | 21.180 | 1.00 | 14.82 | C |
| ATOM | 535 | C | ALA | A | 74 | 22.073 | 38.377 | 18.908 | 1.00 | 14.98 | C |
| ATOM | 536 | O | ALA | A | 74 | 22.842 | 37.791 | 18.145 | 1.00 | 14.87 | O |
| ATOM | 537 | N | ARG | A | 75 | 20.946 | 38.957 | 18.498 | 1.00 | 15.07 | N |
| ATOM | 538 | CA | ARG | A | 75 | 20.556 | 38.966 | 17.091 | 1.00 | 15.58 | C |
| ATOM | 539 | CB | ARG | A | 75 | 19.128 | 39.494 | 16.930 | 1.00 | 15.60 | C |
| ATOM | 540 | CG | ARG | A | 75 | 18.630 | 39.522 | 15.492 | 1.00 | 17.28 | C |
| ATOM | 541 | CD | ARG | A | 75 | 17.152 | 39.856 | 15.424 | 1.00 | 18.48 | C |
| ATOM | 542 | NE | ARG | A | 75 | 16.876 | 41.253 | 15.761 | 1.00 | 19.56 | N |
| ATOM | 543 | CZ | ARG | A | 75 | 15.672 | 41.818 | 15.690 | 1.00 | 20.65 | C |
| ATOM | 544 | NH1 | ARG | A | 75 | 14.619 | 41.110 | 15.292 | 1.00 | 20.90 | N |
| ATOM | 545 | NH2 | ARG | A | 75 | 15.518 | 43.095 | 16.015 | 1.00 | 21.36 | N |
| ATOM | 546 | C | ARG | A | 75 | 21.523 | 39.791 | 16.243 | 1.00 | 15.50 | C |
| ATOM | 547 | O | ARG | A | 75 | 21.913 | 39.372 | 15.152 | 1.00 | 15.79 | O |
| ATOM | 548 | N | ALA | A | 76 | 21.907 | 40.959 | 16.754 | 1.00 | 15.45 | N |
| ATOM | 549 | CA | ALA | A | 76 | 22.773 | 41.881 | 16.014 | 1.00 | 15.48 | C |
| ATOM | 550 | CB | ALA | A | 76 | 22.683 | 43.280 | 16.607 | 1.00 | 15.48 | C |
| ATOM | 551 | C | ALA | A | 76 | 24.229 | 41.417 | 15.961 | 1.00 | 15.72 | C |
| ATOM | 552 | O | ALA | A | 76 | 24.929 | 41.673 | 14.982 | 1.00 | 15.53 | O |
| ATOM | 553 | N | LYS | A | 77 | 24.678 | 40.733 | 17.011 | 1.00 | 16.04 | N |
| ATOM | 554 | CA | LYS | A | 77 | 26.091 | 40.375 | 17.147 | 1.00 | 16.47 | C |
| ATOM | 555 | CB | LYS | A | 77 | 26.616 | 40.787 | 18.521 | 1.00 | 16.57 | C |
| ATOM | 556 | CG | LYS | A | 77 | 26.624 | 42.278 | 18.746 | 1.00 | 17.11 | C |
| ATOM | 557 | CD | LYS | A | 77 | 27.172 | 42.613 | 20.106 | 1.00 | 18.65 | C |
| ATOM | 558 | CE | LYS | A | 77 | 27.189 | 44.108 | 20.327 | 1.00 | 19.06 | C |
| ATOM | 559 | NZ | LYS | A | 77 | 27.605 | 44.437 | 21.711 | 1.00 | 20.55 | N |
| ATOM | 560 | C | LYS | A | 77 | 26.391 | 38.902 | 16.905 | 1.00 | 16.78 | C |
| ATOM | 561 | O | LYS | A | 77 | 27.555 | 38.514 | 16.794 | 1.00 | 17.20 | O |
| ATOM | 562 | N | GLY | A | 78 | 25.348 | 38.084 | 16.825 | 1.00 | 16.93 | N |
| ATOM | 563 | CA | GLY | A | 78 | 25.529 | 36.645 | 16.717 | 1.00 | 17.28 | C |
| ATOM | 564 | C | GLY | A | 78 | 25.499 | 36.118 | 15.302 | 1.00 | 17.69 | C |
| ATOM | 565 | O | GLY | A | 78 | 25.157 | 36.834 | 14.361 | 1.00 | 17.94 | O |
| ATOM | 566 | N | GLU | A | 79 | 25.890 | 34.860 | 15.157 | 1.00 | 17.81 | N |
| ATOM | 567 | CA | GLU | A | 79 | 25.646 | 34.114 | 13.935 | 1.00 | 18.20 | C |
| ATOM | 568 | CB | GLU | A | 79 | 26.906 | 33.356 | 13.516 | 1.00 | 18.44 | C |
| ATOM | 569 | CG | GLU | A | 79 | 28.098 | 34.270 | 13.222 | 1.00 | 20.04 | C |
| ATOM | 570 | CD | GLU | A | 79 | 29.401 | 33.516 | 13.049 | 1.00 | 20.79 | C |
| ATOM | 571 | OE1 | GLU | A | 79 | 29.618 | 32.516 | 13.770 | 1.00 | 24.47 | O |
| ATOM | 572 | OE2 | GLU | A | 79 | 30.222 | 33.938 | 12.207 | 1.00 | 24.43 | O |
| ATOM | 573 | C | GLU | A | 79 | 24.502 | 33.152 | 14.215 | 1.00 | 17.52 | C |
| ATOM | 574 | O | GLU | A | 79 | 24.133 | 32.952 | 15.379 | 1.00 | 17.07 | O |
| ATOM | 575 | N | ASN | A | 80 | 23.920 | 32.573 | 13.167 | 1.00 | 16.85 | N |
| ATOM | 576 | CA | ASN | A | 80 | 22.838 | 31.612 | 13.367 | 1.00 | 16.48 | C |
| ATOM | 577 | CB | ASN | A | 80 | 22.139 | 31.235 | 12.040 | 1.00 | 16.69 | C |
| ATOM | 578 | CG | ASN | A | 80 | 23.062 | 30.534 | 11.041 | 1.00 | 17.13 | C |
| ATOM | 579 | OD1 | ASN | A | 80 | 24.055 | 29.907 | 11.409 | 1.00 | 18.22 | O |
| ATOM | 580 | ND2 | ASN | A | 80 | 22.710 | 30.623 | 9.762 | 1.00 | 17.57 | N |
| ATOM | 581 | C | ASN | A | 80 | 23.317 | 30.388 | 14.152 | 1.00 | 16.15 | C |
| ATOM | 582 | O | ASN | A | 80 | 24.523 | 30.170 | 14.296 | 1.00 | 15.83 | O |
| ATOM | 583 | N | GLU | A | 81 | 22.379 | 29.612 | 14.686 | 1.00 | 15.75 | N |
| ATOM | 584 | CA | GLU | A | 81 | 22.740 | 28.501 | 15.571 | 1.00 | 15.64 | C |
| ATOM | 585 | CB | GLU | A | 81 | 21.499 | 27.873 | 16.201 | 1.00 | 15.52 | C |
| ATOM | 586 | CG | GLU | A | 81 | 21.777 | 27.155 | 17.520 | 1.00 | 16.22 | C |

TABLE 6-continued

Coordinates of the crystal structure of *E. coli* ExoI bound to compound 9

| ATOM | 587 | CD | GLU | A | 81 | 20.525 | 26.599 | 18.155 | 1.00 | 17.76 | C |
|---|---|---|---|---|---|---|---|---|---|---|---|
| ATOM | 588 | OE1 | GLU | A | 81 | 19.950 | 25.640 | 17.595 | 1.00 | 18.33 | O |
| ATOM | 589 | OE2 | GLU | A | 81 | 20.121 | 27.113 | 19.221 | 1.00 | 18.67 | O |
| ATOM | 590 | C | GLU | A | 81 | 23.602 | 27.441 | 14.876 | 1.00 | 15.66 | C |
| ATOM | 591 | O | GLU | A | 81 | 24.438 | 26.806 | 15.513 | 1.00 | 15.63 | O |
| ATOM | 592 | N | ALA | A | 82 | 23.408 | 27.274 | 13.567 | 1.00 | 15.63 | N |
| ATOM | 593 | CA | ALA | A | 82 | 24.240 | 26.370 | 12.771 | 1.00 | 15.67 | C |
| ATOM | 594 | CB | ALA | A | 82 | 23.764 | 26.343 | 11.314 | 1.00 | 15.81 | C |
| ATOM | 595 | C | ALA | A | 82 | 25.721 | 26.749 | 12.846 | 1.00 | 15.71 | C |
| ATOM | 596 | O | ALA | A | 82 | 26.580 | 25.891 | 13.062 | 1.00 | 15.65 | O |
| ATOM | 597 | N | ALA | A | 83 | 26.010 | 28.039 | 12.675 | 1.00 | 15.61 | N |
| ATOM | 598 | CA | ALA | A | 83 | 27.381 | 28.544 | 12.743 | 1.00 | 15.64 | C |
| ATOM | 599 | CB | ALA | A | 83 | 27.468 | 29.925 | 12.116 | 1.00 | 15.69 | C |
| ATOM | 600 | C | ALA | A | 83 | 27.898 | 28.569 | 14.182 | 1.00 | 15.62 | C |
| ATOM | 601 | O | ALA | A | 83 | 29.073 | 28.289 | 14.436 | 1.00 | 15.68 | O |
| ATOM | 602 | N | PHE | A | 84 | 27.005 | 28.915 | 15.109 | 1.00 | 15.41 | N |
| ATOM | 603 | CA | PHE | A | 84 | 27.264 | 28.854 | 16.548 | 1.00 | 15.46 | C |
| ATOM | 604 | CB | PHE | A | 84 | 25.981 | 29.252 | 17.298 | 1.00 | 15.20 | C |
| ATOM | 605 | CG | PHE | A | 84 | 26.163 | 29.489 | 18.777 | 1.00 | 14.93 | C |
| ATOM | 606 | CD1 | PHE | A | 84 | 26.849 | 30.611 | 19.247 | 1.00 | 14.78 | C |
| ATOM | 607 | CE1 | PHE | A | 84 | 26.986 | 30.842 | 20.619 | 1.00 | 14.63 | C |
| ATOM | 608 | CZ | PHE | A | 84 | 26.419 | 29.955 | 21.529 | 1.00 | 14.87 | C |
| ATOM | 609 | CE2 | PHE | A | 84 | 25.718 | 28.843 | 21.071 | 1.00 | 14.51 | C |
| ATOM | 610 | CD2 | PHE | A | 84 | 25.589 | 28.619 | 19.702 | 1.00 | 14.96 | C |
| ATOM | 611 | C | PHE | A | 84 | 27.712 | 27.433 | 16.932 | 1.00 | 15.58 | C |
| ATOM | 612 | O | PHE | A | 84 | 28.769 | 27.249 | 17.540 | 1.00 | 15.73 | O |
| ATOM | 613 | N | ALA | A | 85 | 26.917 | 26.439 | 16.532 | 1.00 | 15.68 | N |
| ATOM | 614 | CA | ALA | A | 85 | 27.236 | 25.025 | 16.760 | 1.00 | 15.90 | C |
| ATOM | 615 | CB | ALA | A | 85 | 26.117 | 24.137 | 16.228 | 1.00 | 15.88 | C |
| ATOM | 616 | C | ALA | A | 85 | 28.578 | 24.611 | 16.146 | 1.00 | 15.99 | C |
| ATOM | 617 | O | ALA | A | 85 | 29.346 | 23.871 | 16.764 | 1.00 | 16.13 | O |
| ATOM | 618 | N | ALA | A | 86 | 28.845 | 25.085 | 14.928 | 1.00 | 16.07 | N |
| ATOM | 619 | CA | ALA | A | 86 | 30.085 | 24.762 | 14.219 | 1.00 | 16.15 | C |
| ATOM | 620 | CB | ALA | A | 86 | 30.079 | 25.377 | 12.820 | 1.00 | 16.23 | C |
| ATOM | 621 | C | ALA | A | 86 | 31.329 | 25.202 | 14.988 | 1.00 | 16.20 | C |
| ATOM | 622 | O | ALA | A | 86 | 32.297 | 24.444 | 15.104 | 1.00 | 16.18 | O |
| ATOM | 623 | N | ARG | A | 87 | 31.294 | 26.426 | 15.513 | 1.00 | 16.27 | N |
| ATOM | 624 | CA | ARG | A | 87 | 32.424 | 26.986 | 16.250 | 1.00 | 16.59 | C |
| ATOM | 625 | CB | ARG | A | 87 | 32.181 | 28.460 | 16.578 | 1.00 | 16.76 | C |
| ATOM | 626 | CG | ARG | A | 87 | 32.208 | 29.388 | 15.378 | 1.00 | 18.66 | C |
| ATOM | 627 | CD | ARG | A | 87 | 32.229 | 30.846 | 15.817 | 1.00 | 21.18 | C |
| ATOM | 628 | NE | ARG | A | 87 | 33.477 | 31.203 | 16.493 | 1.00 | 23.62 | N |
| ATOM | 629 | CZ | ARG | A | 87 | 33.784 | 32.427 | 16.922 | 1.00 | 24.97 | C |
| ATOM | 630 | NH1 | ARG | A | 87 | 32.934 | 33.431 | 16.757 | 1.00 | 26.02 | N |
| ATOM | 631 | NH2 | ARG | A | 87 | 34.943 | 32.646 | 17.527 | 1.00 | 25.78 | N |
| ATOM | 632 | C | ARG | A | 87 | 32.695 | 26.210 | 17.533 | 1.00 | 16.14 | C |
| ATOM | 633 | O | ARG | A | 87 | 33.846 | 25.925 | 17.862 | 1.00 | 16.38 | O |
| ATOM | 634 | N | ILE | A | 88 | 31.629 | 25.879 | 18.256 | 1.00 | 15.87 | N |
| ATOM | 635 | CA | ILE | A | 88 | 31.746 | 25.122 | 19.501 | 1.00 | 15.59 | C |
| ATOM | 636 | CB | ILE | A | 88 | 30.402 | 25.109 | 20.285 | 1.00 | 15.46 | C |
| ATOM | 637 | CG1 | ILE | A | 88 | 30.001 | 26.546 | 20.656 | 1.00 | 15.32 | C |
| ATOM | 638 | CD1 | ILE | A | 88 | 28.570 | 26.697 | 21.133 | 1.00 | 15.40 | C |
| ATOM | 639 | CG2 | ILE | A | 88 | 30.503 | 24.230 | 21.538 | 1.00 | 15.30 | C |
| ATOM | 640 | C | ILE | A | 88 | 32.256 | 23.701 | 19.234 | 1.00 | 15.79 | C |
| ATOM | 641 | O | ILE | A | 88 | 33.183 | 23.231 | 19.902 | 1.00 | 15.48 | O |
| ATOM | 642 | N | HIS | A | 89 | 31.674 | 23.042 | 18.232 | 1.00 | 16.14 | N |
| ATOM | 643 | CA | HIS | A | 89 | 32.102 | 21.700 | 17.837 | 1.00 | 16.63 | C |
| ATOM | 644 | CB | HIS | A | 89 | 31.258 | 21.181 | 16.667 | 1.00 | 16.67 | C |
| ATOM | 645 | CG | HIS | A | 89 | 31.509 | 19.745 | 16.332 | 1.00 | 17.60 | C |
| ATOM | 646 | ND1 | HIS | A | 89 | 32.333 | 19.356 | 15.298 | 1.00 | 18.72 | N |
| ATOM | 647 | CE1 | HIS | A | 89 | 32.367 | 18.037 | 15.237 | 1.00 | 18.96 | C |
| ATOM | 648 | NE2 | HIS | A | 89 | 31.596 | 17.555 | 16.195 | 1.00 | 18.90 | N |
| ATOM | 649 | CD2 | HIS | A | 89 | 31.048 | 18.602 | 16.895 | 1.00 | 18.05 | C |
| ATOM | 650 | C | HIS | A | 89 | 33.588 | 21.651 | 17.477 | 1.00 | 16.83 | C |
| ATOM | 651 | O | HIS | A | 89 | 34.284 | 20.703 | 17.840 | 1.00 | 16.85 | O |
| ATOM | 652 | N | SER | A | 90 | 34.071 | 22.679 | 16.777 | 1.00 | 17.23 | N |
| ATOM | 653 | CA | SER | A | 90 | 35.478 | 22.745 | 16.383 | 1.00 | 17.67 | C |
| ATOM | 654 | CB | SER | A | 90 | 35.727 | 23.927 | 15.442 | 1.00 | 17.88 | C |
| ATOM | 655 | OG | SER | A | 90 | 35.515 | 25.162 | 16.103 | 1.00 | 20.31 | O |
| ATOM | 656 | C | SER | A | 90 | 36.400 | 22.830 | 17.602 | 1.00 | 17.56 | C |
| ATOM | 657 | O | SER | A | 90 | 37.474 | 22.234 | 17.620 | 1.00 | 17.93 | O |
| ATOM | 658 | N | LEU | A | 91 | 35.967 | 23.571 | 18.620 | 1.00 | 17.26 | N |
| ATOM | 659 | CA | LEU | A | 91 | 36.736 | 23.710 | 19.854 | 1.00 | 17.08 | C |
| ATOM | 660 | CB | LEU | A | 91 | 36.204 | 24.883 | 20.684 | 1.00 | 17.15 | C |
| ATOM | 661 | CG | LEU | A | 91 | 36.336 | 26.291 | 20.095 | 1.00 | 17.75 | C |
| ATOM | 662 | CD1 | LEU | A | 91 | 35.471 | 27.272 | 20.872 | 1.00 | 18.55 | C |
| ATOM | 663 | CD2 | LEU | A | 91 | 37.793 | 26.750 | 20.075 | 1.00 | 18.09 | C |
| ATOM | 664 | C | LEU | A | 91 | 36.714 | 22.428 | 20.686 | 1.00 | 16.87 | C |

TABLE 6-continued

Coordinates of the crystal structure of *E. coli* ExoI bound to compound 9

| ATOM | 665 | O   | LEU | A | 91  | 37.739 | 22.015 | 21.238 | 1.00 | 16.55 | O |
|------|-----|-----|-----|---|-----|--------|--------|--------|------|-------|---|
| ATOM | 666 | N   | PHE | A | 92  | 35.542 | 21.803 | 20.760 | 1.00 | 16.59 | N |
| ATOM | 667 | CA  | PHE | A | 92  | 35.324 | 20.638 | 21.622 | 1.00 | 16.54 | C |
| ATOM | 668 | CB  | PHE | A | 92  | 33.818 | 20.399 | 21.821 | 1.00 | 16.11 | C |
| ATOM | 669 | CG  | PHE | A | 92  | 33.177 | 21.289 | 22.872 | 1.00 | 15.40 | C |
| ATOM | 670 | CD1 | PHE | A | 92  | 33.810 | 22.446 | 23.330 | 1.00 | 15.34 | C |
| ATOM | 671 | CE1 | PHE | A | 92  | 33.206 | 23.260 | 24.293 | 1.00 | 15.03 | C |
| ATOM | 672 | CZ  | PHE | A | 92  | 31.955 | 22.928 | 24.795 | 1.00 | 15.29 | C |
| ATOM | 673 | CE2 | PHE | A | 92  | 31.307 | 21.786 | 24.338 | 1.00 | 15.17 | C |
| ATOM | 674 | CD2 | PHE | A | 92  | 31.917 | 20.975 | 23.378 | 1.00 | 14.73 | C |
| ATOM | 675 | C   | PHE | A | 92  | 35.983 | 19.360 | 21.088 | 1.00 | 16.84 | C |
| ATOM | 676 | O   | PHE | A | 92  | 36.227 | 18.421 | 21.851 | 1.00 | 17.26 | O |
| ATOM | 677 | N   | THR | A | 93  | 36.258 | 19.322 | 19.783 | 1.00 | 16.91 | N |
| ATOM | 678 | CA  | THR | A | 93  | 36.775 | 18.103 | 19.143 | 1.00 | 17.06 | C |
| ATOM | 679 | CB  | THR | A | 93  | 36.017 | 17.764 | 17.833 | 1.00 | 16.85 | C |
| ATOM | 680 | OG1 | THR | A | 93  | 36.057 | 18.885 | 16.946 | 1.00 | 17.15 | O |
| ATOM | 681 | CG2 | THR | A | 93  | 34.565 | 17.401 | 18.127 | 1.00 | 17.01 | C |
| ATOM | 682 | C   | THR | A | 93  | 38.287 | 18.128 | 18.887 | 1.00 | 17.14 | C |
| ATOM | 683 | O   | THR | A | 93  | 38.833 | 17.217 | 18.249 | 1.00 | 17.47 | O |
| ATOM | 684 | N   | VAL | A | 94  | 38.957 | 19.171 | 19.377 | 1.00 | 17.23 | N |
| ATOM | 685 | CA  | VAL | A | 94  | 40.419 | 19.189 | 19.420 | 1.00 | 17.22 | C |
| ATOM | 686 | CB  | VAL | A | 94  | 40.962 | 20.533 | 19.984 | 1.00 | 17.18 | C |
| ATOM | 687 | CG1 | VAL | A | 94  | 42.476 | 20.470 | 20.210 | 1.00 | 17.25 | C |
| ATOM | 688 | CG2 | VAL | A | 94  | 40.605 | 21.691 | 19.053 | 1.00 | 17.24 | C |
| ATOM | 689 | C   | VAL | A | 94  | 40.880 | 18.017 | 20.294 | 1.00 | 17.23 | C |
| ATOM | 690 | O   | VAL | A | 94  | 40.401 | 17.860 | 21.417 | 1.00 | 17.19 | O |
| ATOM | 691 | N   | PRO | A | 95  | 41.773 | 17.160 | 19.760 | 1.00 | 17.25 | N |
| ATOM | 692 | CA  | PRO | A | 95  | 42.222 | 15.975 | 20.497 | 1.00 | 17.20 | C |
| ATOM | 693 | CB  | PRO | A | 95  | 43.290 | 15.376 | 19.576 | 1.00 | 17.22 | C |
| ATOM | 694 | CG  | PRO | A | 95  | 42.906 | 15.838 | 18.221 | 1.00 | 17.29 | C |
| ATOM | 695 | CD  | PRO | A | 95  | 42.381 | 17.227 | 18.418 | 1.00 | 17.27 | C |
| ATOM | 696 | C   | PRO | A | 95  | 42.825 | 16.286 | 21.864 | 1.00 | 17.13 | C |
| ATOM | 697 | O   | PRO | A | 95  | 43.418 | 17.353 | 22.057 | 1.00 | 17.08 | O |
| ATOM | 698 | N   | LYS | A | 96  | 42.657 | 15.345 | 22.796 | 1.00 | 17.07 | N |
| ATOM | 699 | CA  | LYS | A | 96  | 43.241 | 15.413 | 24.143 | 1.00 | 17.36 | C |
| ATOM | 700 | CB  | LYS | A | 96  | 44.775 | 15.388 | 24.081 | 1.00 | 17.39 | C |
| ATOM | 701 | CG  | LYS | A | 96  | 45.343 | 14.098 | 23.498 | 1.00 | 18.57 | C |
| ATOM | 702 | CD  | LYS | A | 96  | 46.865 | 14.097 | 23.506 | 1.00 | 19.11 | C |
| ATOM | 703 | CE  | LYS | A | 96  | 47.430 | 13.683 | 24.861 | 1.00 | 21.71 | C |
| ATOM | 704 | NZ  | LYS | A | 96  | 47.230 | 12.228 | 25.141 | 1.00 | 23.87 | N |
| ATOM | 705 | C   | LYS | A | 96  | 42.736 | 16.599 | 24.966 | 1.00 | 16.80 | C |
| ATOM | 706 | O   | LYS | A | 96  | 43.462 | 17.148 | 25.800 | 1.00 | 17.10 | O |
| ATOM | 707 | N   | THR | A | 97  | 41.482 | 16.976 | 24.728 | 1.00 | 16.26 | N |
| ATOM | 708 | CA  | THR | A | 97  | 40.844 | 18.070 | 25.454 | 1.00 | 15.70 | C |
| ATOM | 709 | CB  | THR | A | 97  | 39.980 | 18.941 | 24.507 | 1.00 | 15.74 | C |
| ATOM | 710 | OG1 | THR | A | 97  | 40.801 | 19.500 | 23.476 | 1.00 | 16.12 | O |
| ATOM | 711 | CG2 | THR | A | 97  | 39.297 | 20.072 | 25.273 | 1.00 | 15.72 | C |
| ATOM | 712 | C   | THR | A | 97  | 39.949 | 17.535 | 26.570 | 1.00 | 15.33 | C |
| ATOM | 713 | O   | THR | A | 97  | 39.110 | 16.664 | 26.340 | 1.00 | 15.17 | O |
| ATOM | 714 | N   | CYS | A | 98  | 40.135 | 18.065 | 27.777 | 1.00 | 14.66 | N |
| ATOM | 715 | CA  | CYS | A | 98  | 39.153 | 17.901 | 28.842 | 1.00 | 14.18 | C |
| ATOM | 716 | CB  | CYS | A | 98  | 39.840 | 17.730 | 30.198 | 1.00 | 14.26 | C |
| ATOM | 717 | SG  | CYS | A | 98  | 38.690 | 17.667 | 31.598 | 1.00 | 14.39 | S |
| ATOM | 718 | C   | CYS | A | 98  | 38.244 | 19.124 | 28.852 | 1.00 | 13.77 | C |
| ATOM | 719 | O   | CYS | A | 98  | 38.679 | 20.227 | 29.197 | 1.00 | 13.75 | O |
| ATOM | 720 | N   | ILE | A | 99  | 36.994 | 18.934 | 28.430 | 1.00 | 13.80 | N |
| ATOM | 721 | CA  | ILE | A | 99  | 36.020 | 20.022 | 28.392 | 1.00 | 13.84 | C |
| ATOM | 722 | CB  | ILE | A | 99  | 34.928 | 19.802 | 27.299 | 1.00 | 13.91 | C |
| ATOM | 723 | CG1 | ILE | A | 99  | 35.551 | 19.716 | 25.897 | 1.00 | 15.01 | C |
| ATOM | 724 | CD1 | ILE | A | 99  | 35.910 | 18.306 | 25.454 | 1.00 | 15.61 | C |
| ATOM | 725 | CG2 | ILE | A | 99  | 33.891 | 20.923 | 27.337 | 1.00 | 14.48 | C |
| ATOM | 726 | C   | ILE | A | 99  | 35.354 | 20.140 | 29.753 | 1.00 | 13.65 | C |
| ATOM | 727 | O   | ILE | A | 99  | 34.733 | 19.193 | 30.231 | 1.00 | 14.01 | O |
| ATOM | 728 | N   | LEU | A | 100 | 35.491 | 21.299 | 30.384 | 1.00 | 13.55 | N |
| ATOM | 729 | CA  | LEU | A | 100 | 34.952 | 21.477 | 31.729 | 1.00 | 13.40 | C |
| ATOM | 730 | CB  | LEU | A | 100 | 36.007 | 21.129 | 32.792 | 1.00 | 13.38 | C |
| ATOM | 731 | CG  | LEU | A | 100 | 37.158 | 22.096 | 33.102 | 1.00 | 13.15 | C |
| ATOM | 732 | CD1 | LEU | A | 100 | 38.076 | 21.464 | 34.131 | 1.00 | 13.55 | C |
| ATOM | 733 | CD2 | LEU | A | 100 | 37.954 | 22.486 | 31.850 | 1.00 | 12.90 | C |
| ATOM | 734 | C   | LEU | A | 100 | 34.388 | 22.862 | 31.969 | 1.00 | 13.55 | C |
| ATOM | 735 | O   | LEU | A | 100 | 34.626 | 23.792 | 31.198 | 1.00 | 13.66 | O |
| ATOM | 736 | N   | GLY | A | 101 | 33.630 | 22.988 | 33.049 | 1.00 | 13.29 | N |
| ATOM | 737 | CA  | GLY | A | 101 | 33.082 | 24.266 | 33.452 | 1.00 | 13.04 | C |
| ATOM | 738 | C   | GLY | A | 101 | 32.659 | 24.216 | 34.894 | 1.00 | 12.69 | C |
| ATOM | 739 | O   | GLY | A | 101 | 33.262 | 23.504 | 35.707 | 1.00 | 12.81 | O |
| ATOM | 740 | N   | TYR | A | 102 | 31.619 | 24.978 | 35.212 | 1.00 | 12.78 | N |
| ATOM | 741 | CA  | TYR | A | 102 | 31.070 | 25.006 | 36.552 | 1.00 | 12.71 | C |
| ATOM | 742 | CB  | TYR | A | 102 | 31.383 | 26.341 | 37.239 | 1.00 | 12.74 | C |

TABLE 6-continued

Coordinates of the crystal structure of *E. coli* ExoI bound to compound 9

| ATOM | 743 | CG | TYR | A | 102 | 31.322 | 26.247 | 38.739 | 1.00 | 12.16 | C |
|---|---|---|---|---|---|---|---|---|---|---|---|
| ATOM | 744 | CD1 | TYR | A | 102 | 32.384 | 25.708 | 39.463 | 1.00 | 11.94 | C |
| ATOM | 745 | CE1 | TYR | A | 102 | 32.332 | 25.601 | 40.850 | 1.00 | 11.78 | C |
| ATOM | 746 | CZ | TYR | A | 102 | 31.206 | 26.031 | 41.525 | 1.00 | 12.47 | C |
| ATOM | 747 | OH | TYR | A | 102 | 31.161 | 25.919 | 42.893 | 1.00 | 12.70 | O |
| ATOM | 748 | CE2 | TYR | A | 102 | 30.131 | 26.572 | 40.829 | 1.00 | 12.43 | C |
| ATOM | 749 | CD2 | TYR | A | 102 | 30.194 | 26.673 | 39.438 | 1.00 | 12.41 | C |
| ATOM | 750 | C | TYR | A | 102 | 29.570 | 24.773 | 36.470 | 1.00 | 13.14 | C |
| ATOM | 751 | O | TYR | A | 102 | 28.823 | 25.648 | 36.030 | 1.00 | 13.68 | O |
| ATOM | 752 | N | ASN | A | 103 | 29.150 | 23.580 | 36.891 | 1.00 | 13.63 | N |
| ATOM | 753 | CA | ASN | A | 103 | 27.786 | 23.075 | 36.677 | 1.00 | 13.94 | C |
| ATOM | 754 | CB | ASN | A | 103 | 26.720 | 24.047 | 37.212 | 1.00 | 14.21 | C |
| ATOM | 755 | CG | ASN | A | 103 | 25.376 | 23.369 | 37.445 | 1.00 | 14.49 | C |
| ATOM | 756 | OD1 | ASN | A | 103 | 25.316 | 22.188 | 37.794 | 1.00 | 15.72 | O |
| ATOM | 757 | ND2 | ASN | A | 103 | 24.291 | 24.110 | 37.234 | 1.00 | 16.28 | N |
| ATOM | 758 | C | ASN | A | 103 | 27.510 | 22.692 | 35.213 | 1.00 | 14.23 | C |
| ATOM | 759 | O | ASN | A | 103 | 26.349 | 22.617 | 34.784 | 1.00 | 14.23 | O |
| ATOM | 760 | N | ASN | A | 104 | 28.571 | 22.429 | 34.455 | 1.00 | 14.30 | N |
| ATOM | 761 | CA | ASN | A | 104 | 28.410 | 22.044 | 33.052 | 1.00 | 14.80 | C |
| ATOM | 762 | CB | ASN | A | 104 | 29.736 | 22.111 | 32.287 | 1.00 | 14.66 | C |
| ATOM | 763 | CG | ASN | A | 104 | 30.822 | 21.269 | 32.921 | 1.00 | 14.18 | C |
| ATOM | 764 | OD1 | ASN | A | 104 | 31.268 | 21.551 | 34.029 | 1.00 | 13.93 | O |
| ATOM | 765 | ND2 | ASN | A | 104 | 31.259 | 20.230 | 32.213 | 1.00 | 15.36 | N |
| ATOM | 766 | C | ASN | A | 104 | 27.747 | 20.687 | 32.859 | 1.00 | 15.56 | C |
| ATOM | 767 | O | ASN | A | 104 | 26.975 | 20.509 | 31.931 | 1.00 | 15.61 | O |
| ATOM | 768 | N | VAL | A | 105 | 28.034 | 19.736 | 33.744 | 1.00 | 16.33 | N |
| ATOM | 769 | CA | VAL | A | 105 | 27.477 | 18.388 | 33.598 | 1.00 | 17.10 | C |
| ATOM | 770 | CB | VAL | A | 105 | 28.037 | 17.411 | 34.666 | 1.00 | 17.09 | C |
| ATOM | 771 | CG1 | VAL | A | 105 | 27.206 | 16.134 | 34.730 | 1.00 | 18.11 | C |
| ATOM | 772 | CG2 | VAL | A | 105 | 29.482 | 17.077 | 34.354 | 1.00 | 17.71 | C |
| ATOM | 773 | C | VAL | A | 105 | 25.942 | 18.398 | 33.600 | 1.00 | 17.34 | C |
| ATOM | 774 | O | VAL | A | 105 | 25.310 | 17.712 | 32.787 | 1.00 | 17.57 | O |
| ATOM | 775 | N | ARG | A | 106 | 25.351 | 19.203 | 34.480 | 1.00 | 17.58 | N |
| ATOM | 776 | CA | ARG | A | 106 | 23.892 | 19.264 | 34.594 | 1.00 | 18.16 | C |
| ATOM | 777 | CB | ARG | A | 106 | 23.459 | 19.472 | 36.052 | 1.00 | 18.90 | C |
| ATOM | 778 | CG | ARG | A | 106 | 23.844 | 18.333 | 37.005 | 1.00 | 21.54 | C |
| ATOM | 779 | CD | ARG | A | 106 | 23.032 | 17.072 | 36.757 | 1.00 | 25.71 | C |
| ATOM | 780 | NE | ARG | A | 106 | 23.392 | 16.007 | 37.690 | 1.00 | 28.42 | N |
| ATOM | 781 | CZ | ARG | A | 106 | 22.921 | 14.762 | 37.635 | 1.00 | 30.09 | C |
| ATOM | 782 | NH1 | ARG | A | 106 | 22.062 | 14.407 | 36.687 | 1.00 | 31.00 | N |
| ATOM | 783 | NH2 | ARG | A | 106 | 23.316 | 13.868 | 38.534 | 1.00 | 30.81 | N |
| ATOM | 784 | C | ARG | A | 106 | 23.251 | 20.323 | 33.697 | 1.00 | 17.67 | C |
| ATOM | 785 | O | ARG | A | 106 | 22.075 | 20.203 | 33.343 | 1.00 | 17.93 | O |
| ATOM | 786 | N | PHE | A | 107 | 24.014 | 21.351 | 33.326 | 1.00 | 16.77 | N |
| ATOM | 787 | CA | PHE | A | 107 | 23.470 | 22.431 | 32.500 | 1.00 | 16.20 | C |
| ATOM | 788 | CB | PHE | A | 107 | 23.423 | 23.761 | 33.266 | 1.00 | 16.14 | C |
| ATOM | 789 | CG | PHE | A | 107 | 22.750 | 24.871 | 32.501 | 1.00 | 16.18 | C |
| ATOM | 790 | CD1 | PHE | A | 107 | 21.374 | 24.845 | 32.280 | 1.00 | 16.71 | C |
| ATOM | 791 | CE1 | PHE | A | 107 | 20.746 | 25.866 | 31.561 | 1.00 | 16.35 | C |
| ATOM | 792 | CZ | PHE | A | 107 | 21.499 | 26.926 | 31.064 | 1.00 | 16.54 | C |
| ATOM | 793 | CE2 | PHE | A | 107 | 22.875 | 26.961 | 31.284 | 1.00 | 16.03 | C |
| ATOM | 794 | CD2 | PHE | A | 107 | 23.492 | 25.934 | 31.997 | 1.00 | 16.50 | C |
| ATOM | 795 | C | PHE | A | 107 | 24.146 | 22.608 | 31.136 | 1.00 | 15.99 | C |
| ATOM | 796 | O | PHE | A | 107 | 23.547 | 22.303 | 30.109 | 1.00 | 16.02 | O |
| ATOM | 797 | N | ASP | A | 108 | 25.380 | 23.113 | 31.126 | 1.00 | 15.37 | N |
| ATOM | 798 | CA | ASP | A | 108 | 26.031 | 23.500 | 29.869 | 1.00 | 15.64 | C |
| ATOM | 799 | CB | ASP | A | 108 | 27.380 | 24.175 | 30.131 | 1.00 | 15.39 | C |
| ATOM | 800 | CG | ASP | A | 108 | 27.262 | 25.356 | 31.076 | 1.00 | 15.55 | C |
| ATOM | 801 | OD1 | ASP | A | 108 | 27.311 | 26.515 | 30.604 | 1.00 | 14.99 | O |
| ATOM | 802 | OD2 | ASP | A | 108 | 27.094 | 25.125 | 32.295 | 1.00 | 15.85 | O |
| ATOM | 803 | C | ASP | A | 108 | 26.180 | 22.338 | 28.884 | 1.00 | 15.81 | C |
| ATOM | 804 | O | ASP | A | 108 | 25.989 | 22.515 | 27.681 | 1.00 | 15.93 | O |
| ATOM | 805 | N | ASP | A | 109 | 26.505 | 21.153 | 29.397 | 1.00 | 16.16 | N |
| ATOM | 806 | CA | ASP | A | 109 | 26.644 | 19.971 | 28.545 | 1.00 | 16.50 | C |
| ATOM | 807 | CB | ASP | A | 109 | 27.241 | 18.793 | 29.322 | 1.00 | 17.00 | C |
| ATOM | 808 | CG | ASP | A | 109 | 28.701 | 19.018 | 29.711 | 1.00 | 18.58 | C |
| ATOM | 809 | OD1 | ASP | A | 109 | 29.306 | 20.032 | 29.294 | 1.00 | 21.14 | O |
| ATOM | 810 | OD2 | ASP | A | 109 | 29.245 | 18.170 | 30.448 | 1.00 | 21.53 | O |
| ATOM | 811 | C | ASP | A | 109 | 25.315 | 19.565 | 27.914 | 1.00 | 16.46 | C |
| ATOM | 812 | O | ASP | A | 109 | 25.291 | 19.043 | 26.802 | 1.00 | 16.35 | O |
| ATOM | 813 | N | GLU | A | 110 | 24.216 | 19.805 | 28.628 | 1.00 | 16.19 | N |
| ATOM | 814 | CA | GLU | A | 110 | 22.880 | 19.560 | 28.080 | 1.00 | 16.39 | C |
| ATOM | 815 | CB | GLU | A | 110 | 21.820 | 19.573 | 29.185 | 1.00 | 16.49 | C |
| ATOM | 816 | CG | GLU | A | 110 | 21.933 | 18.413 | 30.176 | 1.00 | 18.63 | C |
| ATOM | 817 | CD | GLU | A | 110 | 21.863 | 17.046 | 29.505 | 1.00 | 20.67 | C |
| ATOM | 818 | OE1 | GLU | A | 110 | 20.972 | 16.839 | 28.653 | 1.00 | 22.32 | O |
| ATOM | 819 | OE2 | GLU | A | 110 | 22.702 | 16.179 | 29.835 | 1.00 | 23.12 | O |
| ATOM | 820 | C | GLU | A | 110 | 22.536 | 20.572 | 26.987 | 1.00 | 15.99 | C |

TABLE 6-continued

Coordinates of the crystal structure of *E. coli* ExoI bound to compound 9

| ATOM | 821 | O | GLU | A | 110 | 21.935 | 20.217 | 25.972 | 1.00 | 15.80 | O |
|---|---|---|---|---|---|---|---|---|---|---|---|
| ATOM | 822 | N | VAL | A | 111 | 22.934 | 21.826 | 27.192 | 1.00 | 15.23 | N |
| ATOM | 823 | CA | VAL | A | 111 | 22.814 | 22.855 | 26.156 | 1.00 | 14.93 | C |
| ATOM | 824 | CB | VAL | A | 111 | 23.297 | 24.244 | 26.668 | 1.00 | 14.62 | C |
| ATOM | 825 | CG1 | VAL | A | 111 | 23.269 | 25.272 | 25.551 | 1.00 | 14.55 | C |
| ATOM | 826 | CG2 | VAL | A | 111 | 22.433 | 24.710 | 27.835 | 1.00 | 15.01 | C |
| ATOM | 827 | C | VAL | A | 111 | 23.591 | 22.437 | 24.899 | 1.00 | 14.95 | C |
| ATOM | 828 | O | VAL | A | 111 | 23.049 | 22.465 | 23.788 | 1.00 | 15.06 | O |
| ATOM | 829 | N | THR | A | 112 | 24.847 | 22.026 | 25.092 | 1.00 | 14.81 | N |
| ATOM | 830 | CA | THR | A | 112 | 25.710 | 21.546 | 24.003 | 1.00 | 14.98 | C |
| ATOM | 831 | CB | THR | A | 112 | 27.100 | 21.109 | 24.540 | 1.00 | 14.98 | C |
| ATOM | 832 | OG1 | THR | A | 112 | 27.763 | 22.234 | 25.132 | 1.00 | 14.96 | O |
| ATOM | 833 | CG2 | THR | A | 112 | 27.973 | 20.546 | 23.421 | 1.00 | 15.49 | C |
| ATOM | 834 | C | THR | A | 112 | 25.077 | 20.382 | 23.239 | 1.00 | 15.13 | C |
| ATOM | 835 | O | THR | A | 112 | 25.028 | 20.394 | 22.006 | 1.00 | 14.99 | O |
| ATOM | 836 | N | ARG | A | 113 | 24.594 | 19.381 | 23.975 | 1.00 | 15.15 | N |
| ATOM | 837 | CA | ARG | A | 113 | 23.950 | 18.219 | 23.359 | 1.00 | 15.42 | C |
| ATOM | 838 | CB | ARG | A | 113 | 23.494 | 17.219 | 24.422 | 1.00 | 15.69 | C |
| ATOM | 839 | CG | ARG | A | 113 | 24.631 | 16.460 | 25.071 | 1.00 | 17.33 | C |
| ATOM | 840 | CD | ARG | A | 113 | 24.121 | 15.427 | 26.053 | 1.00 | 21.07 | C |
| ATOM | 841 | NE | ARG | A | 113 | 25.214 | 14.812 | 26.801 | 1.00 | 24.39 | N |
| ATOM | 842 | CZ | ARG | A | 113 | 25.055 | 13.882 | 27.739 | 1.00 | 25.95 | C |
| ATOM | 843 | NH1 | ARG | A | 113 | 23.840 | 13.447 | 28.055 | 1.00 | 26.90 | N |
| ATOM | 844 | NH2 | ARG | A | 113 | 26.115 | 13.385 | 28.361 | 1.00 | 27.24 | N |
| ATOM | 845 | C | ARG | A | 113 | 22.771 | 18.639 | 22.496 | 1.00 | 15.07 | C |
| ATOM | 846 | O | ARG | A | 113 | 22.596 | 18.134 | 21.383 | 1.00 | 15.01 | O |
| ATOM | 847 | N | ASN | A | 114 | 21.977 | 19.574 | 23.007 | 1.00 | 14.95 | N |
| ATOM | 848 | CA | ASN | A | 114 | 20.795 | 20.050 | 22.296 | 1.00 | 15.03 | C |
| ATOM | 849 | CB | ASN | A | 114 | 19.845 | 20.762 | 23.251 | 1.00 | 14.99 | C |
| ATOM | 850 | CG | ASN | A | 114 | 18.980 | 19.793 | 24.026 | 1.00 | 15.70 | C |
| ATOM | 851 | OD1 | ASN | A | 114 | 19.190 | 19.563 | 25.221 | 1.00 | 17.72 | O |
| ATOM | 852 | ND2 | ASN | A | 114 | 18.017 | 19.196 | 23.343 | 1.00 | 15.14 | N |
| ATOM | 853 | C | ASN | A | 114 | 21.111 | 20.916 | 21.079 | 1.00 | 15.03 | C |
| ATOM | 854 | O | ASN | A | 114 | 20.445 | 20.810 | 20.052 | 1.00 | 14.98 | O |
| ATOM | 855 | N | ILE | A | 115 | 22.132 | 21.763 | 21.198 | 1.00 | 15.18 | N |
| ATOM | 856 | CA | ILE | A | 115 | 22.614 | 22.559 | 20.064 | 1.00 | 15.62 | C |
| ATOM | 857 | CB | ILE | A | 115 | 23.729 | 23.557 | 20.494 | 1.00 | 15.76 | C |
| ATOM | 858 | CG1 | ILE | A | 115 | 23.169 | 24.613 | 21.454 | 1.00 | 15.99 | C |
| ATOM | 859 | CD1 | ILE | A | 115 | 24.231 | 25.510 | 22.069 | 1.00 | 16.53 | C |
| ATOM | 860 | CG2 | ILE | A | 115 | 24.355 | 24.233 | 19.278 | 1.00 | 16.50 | C |
| ATOM | 861 | C | ILE | A | 115 | 23.127 | 21.648 | 18.940 | 1.00 | 15.53 | C |
| ATOM | 862 | O | ILE | A | 115 | 22.801 | 21.848 | 17.769 | 1.00 | 15.53 | O |
| ATOM | 863 | N | PHE | A | 116 | 23.915 | 20.640 | 19.308 | 1.00 | 15.29 | N |
| ATOM | 864 | CA | PHE | A | 116 | 24.461 | 19.691 | 18.337 | 1.00 | 15.31 | C |
| ATOM | 865 | CB | PHE | A | 116 | 25.482 | 18.770 | 19.012 | 1.00 | 15.21 | C |
| ATOM | 866 | CG | PHE | A | 116 | 26.809 | 19.439 | 19.317 | 1.00 | 15.36 | C |
| ATOM | 867 | CD1 | PHE | A | 116 | 27.034 | 20.780 | 18.994 | 1.00 | 15.37 | C |
| ATOM | 868 | CE1 | PHE | A | 116 | 28.256 | 21.394 | 19.285 | 1.00 | 15.42 | C |
| ATOM | 869 | CZ | PHE | A | 116 | 29.264 | 20.671 | 19.915 | 1.00 | 15.69 | C |
| ATOM | 870 | CE2 | PHE | A | 116 | 29.051 | 19.339 | 20.248 | 1.00 | 15.68 | C |
| ATOM | 871 | CD2 | PHE | A | 116 | 27.826 | 18.730 | 19.952 | 1.00 | 15.54 | C |
| ATOM | 872 | C | PHE | A | 116 | 23.336 | 18.880 | 17.687 | 1.00 | 15.22 | C |
| ATOM | 873 | O | PHE | A | 116 | 23.307 | 18.706 | 16.466 | 1.00 | 15.41 | O |
| ATOM | 874 | N | TYR | A | 117 | 22.405 | 18.418 | 18.521 | 1.00 | 15.26 | N |
| ATOM | 875 | CA | TYR | A | 117 | 21.207 | 17.687 | 18.093 | 1.00 | 15.33 | C |
| ATOM | 876 | CB | TYR | A | 117 | 20.373 | 17.345 | 19.337 | 1.00 | 15.37 | C |
| ATOM | 877 | CG | TYR | A | 117 | 18.947 | 16.891 | 19.109 | 1.00 | 15.35 | C |
| ATOM | 878 | CD1 | TYR | A | 117 | 18.664 | 15.604 | 18.641 | 1.00 | 15.45 | C |
| ATOM | 879 | CE1 | TYR | A | 117 | 17.349 | 15.177 | 18.468 | 1.00 | 15.76 | C |
| ATOM | 880 | CZ | TYR | A | 117 | 16.303 | 16.033 | 18.786 | 1.00 | 15.83 | C |
| ATOM | 881 | OH | TYR | A | 117 | 15.001 | 15.618 | 18.621 | 1.00 | 16.23 | O |
| ATOM | 882 | CE2 | TYR | A | 117 | 16.560 | 17.306 | 19.274 | 1.00 | 15.24 | C |
| ATOM | 883 | CD2 | TYR | A | 117 | 17.876 | 17.721 | 19.444 | 1.00 | 15.21 | C |
| ATOM | 884 | C | TYR | A | 117 | 20.379 | 18.463 | 17.060 | 1.00 | 15.39 | C |
| ATOM | 885 | O | TYR | A | 117 | 20.011 | 17.919 | 16.013 | 1.00 | 15.53 | O |
| ATOM | 886 | N | ARG | A | 118 | 20.111 | 19.736 | 17.345 | 1.00 | 15.21 | N |
| ATOM | 887 | CA | ARG | A | 118 | 19.320 | 20.583 | 16.443 | 1.00 | 15.27 | C |
| ATOM | 888 | CB | ARG | A | 118 | 18.921 | 21.890 | 17.131 | 1.00 | 15.22 | C |
| ATOM | 889 | CG | ARG | A | 118 | 17.867 | 21.730 | 18.209 | 1.00 | 15.72 | C |
| ATOM | 890 | CD | ARG | A | 118 | 17.214 | 23.058 | 18.554 | 1.00 | 16.48 | C |
| ATOM | 891 | NE | ARG | A | 118 | 18.135 | 24.014 | 19.176 | 1.00 | 16.31 | N |
| ATOM | 892 | CZ | ARG | A | 118 | 18.316 | 24.146 | 20.489 | 1.00 | 16.23 | C |
| ATOM | 893 | NH1 | ARG | A | 118 | 17.664 | 23.363 | 21.341 | 1.00 | 16.71 | N |
| ATOM | 894 | NH2 | ARG | A | 118 | 19.163 | 25.057 | 20.954 | 1.00 | 17.02 | N |
| ATOM | 895 | C | ARG | A | 118 | 20.029 | 20.898 | 15.127 | 1.00 | 15.44 | C |
| ATOM | 896 | O | ARG | A | 118 | 19.378 | 21.164 | 14.115 | 1.00 | 15.21 | O |
| ATOM | 897 | N | ASN | A | 119 | 21.358 | 20.870 | 15.141 | 1.00 | 15.55 | N |
| ATOM | 898 | CA | ASN | A | 119 | 22.140 | 21.345 | 13.997 | 1.00 | 15.92 | C |

TABLE 6-continued

Coordinates of the crystal structure of *E. coli* ExoI bound to compound 9

| ATOM | 899 | CB | ASN | A | 119 | 22.957 | 22.572 | 14.395 | 1.00 | 15.86 | C |
|---|---|---|---|---|---|---|---|---|---|---|---|
| ATOM | 900 | CG | ASN | A | 119 | 22.080 | 23.719 | 14.834 | 1.00 | 15.91 | C |
| ATOM | 901 | OD1 | ASN | A | 119 | 21.464 | 24.395 | 14.008 | 1.00 | 16.05 | O |
| ATOM | 902 | ND2 | ASN | A | 119 | 21.986 | 23.925 | 16.143 | 1.00 | 15.71 | N |
| ATOM | 903 | C | ASN | A | 119 | 23.003 | 20.275 | 13.323 | 1.00 | 16.10 | C |
| ATOM | 904 | O | ASN | A | 119 | 24.002 | 20.585 | 12.656 | 1.00 | 16.16 | O |
| ATOM | 905 | N | PHE | A | 120 | 22.592 | 19.019 | 13.499 | 1.00 | 16.42 | N |
| ATOM | 906 | CA | PHE | A | 120 | 23.129 | 17.875 | 12.744 | 1.00 | 16.83 | C |
| ATOM | 907 | CB | PHE | A | 120 | 22.908 | 18.058 | 11.231 | 1.00 | 16.95 | C |
| ATOM | 908 | CG | PHE | A | 120 | 21.468 | 17.968 | 10.827 | 1.00 | 17.27 | C |
| ATOM | 909 | CD1 | PHE | A | 120 | 20.961 | 16.793 | 10.285 | 1.00 | 17.40 | C |
| ATOM | 910 | CE1 | PHE | A | 120 | 19.619 | 16.695 | 9.925 | 1.00 | 18.11 | C |
| ATOM | 911 | CZ | PHE | A | 120 | 18.770 | 17.775 | 10.115 | 1.00 | 18.05 | C |
| ATOM | 912 | CE2 | PHE | A | 120 | 19.260 | 18.952 | 10.661 | 1.00 | 18.03 | C |
| ATOM | 913 | CD2 | PHE | A | 120 | 20.605 | 19.045 | 11.016 | 1.00 | 17.09 | C |
| ATOM | 914 | C | PHE | A | 120 | 24.578 | 17.516 | 13.082 | 1.00 | 17.08 | C |
| ATOM | 915 | O | PHE | A | 120 | 25.327 | 17.000 | 12.239 | 1.00 | 17.37 | O |
| ATOM | 916 | N | TYR | A | 121 | 24.954 | 17.782 | 14.331 | 1.00 | 17.18 | N |
| ATOM | 917 | CA | TYR | A | 121 | 26.191 | 17.268 | 14.894 | 1.00 | 17.43 | C |
| ATOM | 918 | CB | TYR | A | 121 | 26.953 | 18.371 | 15.633 | 1.00 | 17.20 | C |
| ATOM | 919 | CG | TYR | A | 121 | 27.571 | 19.403 | 14.725 | 1.00 | 17.07 | C |
| ATOM | 920 | CD1 | TYR | A | 121 | 28.815 | 19.181 | 14.133 | 1.00 | 16.79 | C |
| ATOM | 921 | CE1 | TYR | A | 121 | 29.392 | 20.129 | 13.294 | 1.00 | 17.16 | C |
| ATOM | 922 | CZ | TYR | A | 121 | 28.723 | 21.315 | 13.042 | 1.00 | 16.99 | C |
| ATOM | 923 | OH | TYR | A | 121 | 29.289 | 22.253 | 12.206 | 1.00 | 17.30 | O |
| ATOM | 924 | CE2 | TYR | A | 121 | 27.484 | 21.562 | 13.621 | 1.00 | 16.88 | C |
| ATOM | 925 | CD2 | TYR | A | 121 | 26.918 | 20.606 | 14.461 | 1.00 | 16.73 | C |
| ATOM | 926 | C | TYR | A | 121 | 25.886 | 16.129 | 15.854 | 1.00 | 17.80 | C |
| ATOM | 927 | O | TYR | A | 121 | 24.825 | 16.107 | 16.488 | 1.00 | 17.95 | O |
| ATOM | 928 | N | ASP | A | 122 | 26.813 | 15.181 | 15.951 | 1.00 | 17.97 | N |
| ATOM | 929 | CA | ASP | A | 122 | 26.726 | 14.121 | 16.945 | 1.00 | 18.33 | C |
| ATOM | 930 | CB | ASP | A | 122 | 27.917 | 13.170 | 16.807 | 1.00 | 18.50 | C |
| ATOM | 931 | CG | ASP | A | 122 | 27.710 | 11.865 | 17.545 | 1.00 | 19.19 | C |
| ATOM | 932 | OD1 | ASP | A | 122 | 27.535 | 11.891 | 18.784 | 1.00 | 19.38 | O |
| ATOM | 933 | OD2 | ASP | A | 122 | 27.734 | 10.806 | 16.886 | 1.00 | 21.11 | O |
| ATOM | 934 | C | ASP | A | 122 | 26.699 | 14.752 | 18.340 | 1.00 | 18.48 | C |
| ATOM | 935 | O | ASP | A | 122 | 27.630 | 15.464 | 18.710 | 1.00 | 18.47 | O |
| ATOM | 936 | N | PRO | A | 123 | 25.610 | 14.519 | 19.105 | 1.00 | 18.60 | N |
| ATOM | 937 | CA | PRO | A | 123 | 25.468 | 15.160 | 20.418 | 1.00 | 18.98 | C |
| ATOM | 938 | CB | PRO | A | 123 | 24.016 | 14.837 | 20.816 | 1.00 | 18.96 | C |
| ATOM | 939 | CG | PRO | A | 123 | 23.350 | 14.360 | 19.550 | 1.00 | 18.81 | C |
| ATOM | 940 | CD | PRO | A | 123 | 24.437 | 13.692 | 18.779 | 1.00 | 18.92 | C |
| ATOM | 941 | C | PRO | A | 123 | 26.432 | 14.639 | 21.488 | 1.00 | 19.31 | C |
| ATOM | 942 | O | PRO | A | 123 | 26.592 | 15.287 | 22.526 | 1.00 | 19.38 | O |
| ATOM | 943 | N | TYR | A | 124 | 27.071 | 13.495 | 21.233 | 1.00 | 19.63 | N |
| ATOM | 944 | CA | TYR | A | 124 | 27.844 | 12.795 | 22.272 | 1.00 | 20.03 | C |
| ATOM | 945 | CB | TYR | A | 124 | 27.228 | 11.424 | 22.566 | 1.00 | 20.41 | C |
| ATOM | 946 | CG | TYR | A | 124 | 25.769 | 11.469 | 22.953 | 1.00 | 20.97 | C |
| ATOM | 947 | CD1 | TYR | A | 124 | 25.380 | 11.821 | 24.249 | 1.00 | 21.42 | C |
| ATOM | 948 | CE1 | TYR | A | 124 | 24.036 | 11.862 | 24.610 | 1.00 | 22.00 | C |
| ATOM | 949 | CZ | TYR | A | 124 | 23.066 | 11.547 | 23.669 | 1.00 | 21.78 | C |
| ATOM | 950 | OH | TYR | A | 124 | 21.737 | 11.584 | 24.019 | 1.00 | 22.38 | O |
| ATOM | 951 | CE2 | TYR | A | 124 | 23.427 | 11.192 | 22.377 | 1.00 | 21.45 | C |
| ATOM | 952 | CD2 | TYR | A | 124 | 24.774 | 11.153 | 22.028 | 1.00 | 21.08 | C |
| ATOM | 953 | C | TYR | A | 124 | 29.336 | 12.623 | 21.972 | 1.00 | 20.06 | C |
| ATOM | 954 | O | TYR | A | 124 | 30.164 | 12.689 | 22.885 | 1.00 | 20.26 | O |
| ATOM | 955 | N | ALA | A | 125 | 29.670 | 12.394 | 20.702 | 1.00 | 19.90 | N |
| ATOM | 956 | CA | ALA | A | 125 | 31.029 | 11.993 | 20.304 | 1.00 | 19.83 | C |
| ATOM | 957 | CB | ALA | A | 125 | 31.114 | 11.831 | 18.791 | 1.00 | 19.95 | C |
| ATOM | 958 | C | ALA | A | 125 | 32.136 | 12.925 | 20.804 | 1.00 | 19.78 | C |
| ATOM | 959 | O | ALA | A | 125 | 33.220 | 12.468 | 21.168 | 1.00 | 19.65 | O |
| ATOM | 960 | N | TRP | A | 126 | 31.849 | 14.226 | 20.828 | 1.00 | 19.70 | N |
| ATOM | 961 | CA | TRP | A | 126 | 32.829 | 15.250 | 21.210 | 1.00 | 19.77 | C |
| ATOM | 962 | CB | TRP | A | 126 | 32.169 | 16.634 | 21.238 | 1.00 | 19.66 | C |
| ATOM | 963 | CG | TRP | A | 126 | 31.005 | 16.736 | 22.195 | 1.00 | 19.81 | C |
| ATOM | 964 | CD1 | TRP | A | 126 | 29.701 | 16.421 | 21.937 | 1.00 | 19.67 | C |
| ATOM | 965 | NE1 | TRP | A | 126 | 28.928 | 16.644 | 23.051 | 1.00 | 19.31 | N |
| ATOM | 966 | CE2 | TRP | A | 126 | 29.728 | 17.109 | 24.062 | 1.00 | 19.57 | C |
| ATOM | 967 | CD2 | TRP | A | 126 | 31.047 | 17.180 | 23.559 | 1.00 | 19.35 | C |
| ATOM | 968 | CE3 | TRP | A | 126 | 32.071 | 17.632 | 24.405 | 1.00 | 20.15 | C |
| ATOM | 969 | CZ3 | TRP | A | 126 | 31.747 | 17.992 | 25.711 | 1.00 | 19.88 | C |
| ATOM | 970 | CH2 | TRP | A | 126 | 30.423 | 17.910 | 26.182 | 1.00 | 19.60 | C |
| ATOM | 971 | CZ2 | TRP | A | 126 | 29.403 | 17.473 | 25.375 | 1.00 | 19.46 | C |
| ATOM | 972 | C | TRP | A | 126 | 33.524 | 14.982 | 22.552 | 1.00 | 19.88 | C |
| ATOM | 973 | O | TRP | A | 126 | 34.700 | 15.320 | 22.725 | 1.00 | 19.92 | O |
| ATOM | 974 | N | SER | A | 127 | 32.799 | 14.364 | 23.485 | 1.00 | 19.81 | N |
| ATOM | 975 | CA | SER | A | 127 | 33.263 | 14.246 | 24.868 | 1.00 | 19.97 | C |
| ATOM | 976 | CB | SER | A | 127 | 32.073 | 14.181 | 25.834 | 1.00 | 20.00 | C |

TABLE 6-continued

Coordinates of the crystal structure of *E. coli* ExoI bound to compound 9

| ATOM | 977 | OG | SER | A | 127 | 31.327 | 12.993 | 25.648 | 1.00 | 21.41 | O |
|---|---|---|---|---|---|---|---|---|---|---|---|
| ATOM | 978 | C | SER | A | 127 | 34.212 | 13.077 | 25.121 | 1.00 | 19.75 | C |
| ATOM | 979 | O | SER | A | 127 | 34.825 | 13.002 | 26.185 | 1.00 | 19.96 | O |
| ATOM | 980 | N | TRP | A | 128 | 34.334 | 12.164 | 24.156 | 1.00 | 19.47 | N |
| ATOM | 981 | CA | TRP | A | 128 | 35.167 | 10.972 | 24.356 | 1.00 | 19.35 | C |
| ATOM | 982 | CB | TRP | A | 128 | 34.308 | 9.748 | 24.711 | 1.00 | 19.21 | C |
| ATOM | 983 | CG | TRP | A | 128 | 33.365 | 9.314 | 23.628 | 1.00 | 19.16 | C |
| ATOM | 984 | CD1 | TRP | A | 128 | 32.055 | 9.666 | 23.496 | 1.00 | 19.24 | C |
| ATOM | 985 | NE1 | TRP | A | 128 | 31.512 | 9.065 | 22.386 | 1.00 | 19.59 | N |
| ATOM | 986 | CE2 | TRP | A | 128 | 32.474 | 8.304 | 21.775 | 1.00 | 19.07 | C |
| ATOM | 987 | CD2 | TRP | A | 128 | 33.658 | 8.432 | 22.533 | 1.00 | 19.12 | C |
| ATOM | 988 | CE3 | TRP | A | 128 | 34.806 | 7.740 | 22.119 | 1.00 | 19.01 | C |
| ATOM | 989 | CZ3 | TRP | A | 128 | 34.735 | 6.953 | 20.970 | 1.00 | 19.33 | C |
| ATOM | 990 | CH2 | TRP | A | 128 | 33.541 | 6.847 | 20.238 | 1.00 | 19.10 | C |
| ATOM | 991 | CZ2 | TRP | A | 128 | 32.403 | 7.512 | 20.622 | 1.00 | 19.29 | C |
| ATOM | 992 | C | TRP | A | 128 | 36.121 | 10.650 | 23.204 | 1.00 | 19.50 | C |
| ATOM | 993 | O | TRP | A | 128 | 37.146 | 9.998 | 23.412 | 1.00 | 19.27 | O |
| ATOM | 994 | N | GLN | A | 129 | 35.784 | 11.096 | 21.997 | 1.00 | 19.58 | N |
| ATOM | 995 | CA | GLN | A | 129 | 36.633 | 10.837 | 20.831 | 1.00 | 20.12 | C |
| ATOM | 996 | CB | GLN | A | 129 | 35.897 | 11.173 | 19.534 | 1.00 | 20.10 | C |
| ATOM | 997 | CG | GLN | A | 129 | 34.776 | 10.203 | 19.195 | 1.00 | 20.80 | C |
| ATOM | 998 | CD | GLN | A | 129 | 34.276 | 10.349 | 17.768 | 1.00 | 21.42 | C |
| ATOM | 999 | OE1 | GLN | A | 129 | 34.455 | 11.392 | 17.131 | 1.00 | 21.82 | O |
| ATOM | 1000 | NE2 | GLN | A | 129 | 33.638 | 9.301 | 17.261 | 1.00 | 21.57 | N |
| ATOM | 1001 | C | GLN | A | 129 | 37.941 | 11.615 | 20.915 | 1.00 | 20.31 | C |
| ATOM | 1002 | O | GLN | A | 129 | 37.989 | 12.694 | 21.504 | 1.00 | 20.52 | O |
| ATOM | 1003 | N | HIS | A | 130 | 38.997 | 11.053 | 20.322 | 1.00 | 20.55 | N |
| ATOM | 1004 | CA | HIS | A | 130 | 40.331 | 11.676 | 20.300 | 1.00 | 20.90 | C |
| ATOM | 1005 | CB | HIS | A | 130 | 40.314 | 13.008 | 19.527 | 1.00 | 21.05 | C |
| ATOM | 1006 | CG | HIS | A | 130 | 39.495 | 12.977 | 18.274 | 1.00 | 22.25 | C |
| ATOM | 1007 | ND1 | HIS | A | 130 | 39.876 | 12.275 | 17.151 | 1.00 | 23.43 | N |
| ATOM | 1008 | CE1 | HIS | A | 130 | 38.968 | 12.435 | 16.205 | 1.00 | 23.56 | C |
| ATOM | 1009 | NE2 | HIS | A | 130 | 38.015 | 13.222 | 16.671 | 1.00 | 23.82 | N |
| ATOM | 1010 | CD2 | HIS | A | 130 | 38.321 | 13.577 | 17.962 | 1.00 | 23.28 | C |
| ATOM | 1011 | C | HIS | A | 130 | 40.906 | 11.879 | 21.711 | 1.00 | 20.64 | C |
| ATOM | 1012 | O | HIS | A | 130 | 41.578 | 12.879 | 21.978 | 1.00 | 20.82 | O |
| ATOM | 1013 | N | ASP | A | 131 | 40.636 | 10.919 | 22.599 | 1.00 | 20.55 | N |
| ATOM | 1014 | CA | ASP | A | 131 | 41.098 | 10.949 | 24.000 | 1.00 | 20.38 | C |
| ATOM | 1015 | CB | ASP | A | 131 | 42.634 | 10.926 | 24.085 | 1.00 | 20.89 | C |
| ATOM | 1016 | CG | ASP | A | 131 | 43.219 | 9.581 | 23.704 | 1.00 | 22.29 | C |
| ATOM | 1017 | OD1 | ASP | A | 131 | 42.707 | 8.546 | 24.183 | 1.00 | 24.53 | O |
| ATOM | 1018 | OD2 | ASP | A | 131 | 44.200 | 9.560 | 22.930 | 1.00 | 24.56 | O |
| ATOM | 1019 | C | ASP | A | 131 | 40.526 | 12.110 | 24.819 | 1.00 | 19.67 | C |
| ATOM | 1020 | O | ASP | A | 131 | 41.102 | 12.514 | 25.835 | 1.00 | 19.86 | O |
| ATOM | 1021 | N | ASN | A | 132 | 39.385 | 12.635 | 24.386 | 1.00 | 18.50 | N |
| ATOM | 1022 | CA | ASN | A | 132 | 38.737 | 13.716 | 25.113 | 1.00 | 17.51 | C |
| ATOM | 1023 | CB | ASN | A | 132 | 37.792 | 14.506 | 24.196 | 1.00 | 17.56 | C |
| ATOM | 1024 | CG | ASN | A | 132 | 38.542 | 15.427 | 23.244 | 1.00 | 17.41 | C |
| ATOM | 1025 | OD1 | ASN | A | 132 | 39.764 | 15.349 | 23.120 | 1.00 | 17.71 | O |
| ATOM | 1026 | ND2 | ASN | A | 132 | 37.810 | 16.308 | 22.573 | 1.00 | 17.89 | N |
| ATOM | 1027 | C | ASN | A | 132 | 38.013 | 13.223 | 26.357 | 1.00 | 16.95 | C |
| ATOM | 1028 | O | ASN | A | 132 | 37.799 | 12.023 | 26.534 | 1.00 | 16.55 | O |
| ATOM | 1029 | N | SER | A | 133 | 37.665 | 14.158 | 27.233 | 1.00 | 16.16 | N |
| ATOM | 1030 | CA | SER | A | 133 | 36.934 | 13.843 | 28.451 | 1.00 | 15.87 | C |
| ATOM | 1031 | CB | SER | A | 133 | 37.890 | 13.362 | 29.550 | 1.00 | 15.85 | C |
| ATOM | 1032 | OG | SER | A | 133 | 38.746 | 14.409 | 29.982 | 1.00 | 15.85 | O |
| ATOM | 1033 | C | SER | A | 133 | 36.188 | 15.080 | 28.903 | 1.00 | 15.63 | C |
| ATOM | 1034 | O | SER | A | 133 | 36.307 | 16.146 | 28.293 | 1.00 | 15.32 | O |
| ATOM | 1035 | N | ARG | A | 134 | 35.402 | 14.935 | 29.960 | 1.00 | 15.54 | N |
| ATOM | 1036 | CA | ARG | A | 134 | 34.783 | 16.088 | 30.586 | 1.00 | 15.77 | C |
| ATOM | 1037 | CB | ARG | A | 134 | 33.298 | 16.205 | 30.209 | 1.00 | 16.43 | C |
| ATOM | 1038 | CG | ARG | A | 134 | 32.408 | 15.083 | 30.703 | 1.00 | 18.91 | C |
| ATOM | 1039 | CD | ARG | A | 134 | 30.954 | 15.464 | 30.493 | 1.00 | 22.85 | C |
| ATOM | 1040 | NE | ARG | A | 134 | 30.038 | 14.349 | 30.692 | 1.00 | 25.21 | N |
| ATOM | 1041 | CZ | ARG | A | 134 | 28.712 | 14.457 | 30.661 | 1.00 | 26.15 | C |
| ATOM | 1042 | NH1 | ARG | A | 134 | 28.140 | 15.635 | 30.441 | 1.00 | 26.76 | N |
| ATOM | 1043 | NH2 | ARG | A | 134 | 27.954 | 13.386 | 30.850 | 1.00 | 26.51 | N |
| ATOM | 1044 | C | ARG | A | 134 | 34.982 | 16.087 | 32.095 | 1.00 | 14.98 | C |
| ATOM | 1045 | O | ARG | A | 134 | 35.337 | 15.069 | 32.684 | 1.00 | 14.98 | O |
| ATOM | 1046 | N | TRP | A | 135 | 34.773 | 17.248 | 32.703 | 1.00 | 14.31 | N |
| ATOM | 1047 | CA | TRP | A | 135 | 34.861 | 17.401 | 34.144 | 1.00 | 13.77 | C |
| ATOM | 1048 | CB | TRP | A | 135 | 36.321 | 17.620 | 34.566 | 1.00 | 13.68 | C |
| ATOM | 1049 | CG | TRP | A | 135 | 36.644 | 17.220 | 35.998 | 1.00 | 13.12 | C |
| ATOM | 1050 | CD1 | TRP | A | 135 | 35.948 | 16.345 | 36.795 | 1.00 | 12.79 | C |
| ATOM | 1051 | NE1 | TRP | A | 135 | 36.560 | 16.230 | 38.021 | 1.00 | 13.20 | N |
| ATOM | 1052 | CE2 | TRP | A | 135 | 37.683 | 17.017 | 38.032 | 1.00 | 13.03 | C |
| ATOM | 1053 | CD2 | TRP | A | 135 | 37.770 | 17.650 | 36.768 | 1.00 | 13.01 | C |
| ATOM | 1054 | CE3 | TRP | A | 135 | 38.842 | 18.521 | 36.520 | 1.00 | 13.64 | C |

TABLE 6-continued

Coordinates of the crystal structure of *E. coli* ExoI bound to compound 9

| ATOM | 1055 | CZ3 | TRP | A | 135 | 39.782 | 18.727 | 37.525 | 1.00 | 13.26 | C |
|---|---|---|---|---|---|---|---|---|---|---|---|
| ATOM | 1056 | CH2 | TRP | A | 135 | 39.666 | 18.083 | 38.772 | 1.00 | 13.14 | C |
| ATOM | 1057 | CZ2 | TRP | A | 135 | 38.629 | 17.228 | 39.043 | 1.00 | 13.19 | C |
| ATOM | 1058 | C | TRP | A | 135 | 33.986 | 18.580 | 34.551 | 1.00 | 13.57 | C |
| ATOM | 1059 | O | TRP | A | 135 | 33.445 | 19.284 | 33.697 | 1.00 | 13.88 | O |
| ATOM | 1060 | N | ASP | A | 136 | 33.829 | 18.783 | 35.851 | 1.00 | 13.21 | N |
| ATOM | 1061 | CA | ASP | A | 136 | 32.950 | 19.823 | 36.363 | 1.00 | 12.93 | C |
| ATOM | 1062 | CB | ASP | A | 136 | 31.514 | 19.290 | 36.458 | 1.00 | 13.00 | C |
| ATOM | 1063 | CG | ASP | A | 136 | 30.491 | 20.374 | 36.776 | 1.00 | 13.03 | C |
| ATOM | 1064 | OD1 | ASP | A | 136 | 30.856 | 21.429 | 37.347 | 1.00 | 12.52 | O |
| ATOM | 1065 | OD2 | ASP | A | 136 | 29.305 | 20.147 | 36.460 | 1.00 | 13.16 | O |
| ATOM | 1066 | C | ASP | A | 136 | 33.450 | 20.240 | 37.726 | 1.00 | 12.96 | C |
| ATOM | 1067 | O | ASP | A | 136 | 33.517 | 19.424 | 38.643 | 1.00 | 13.44 | O |
| ATOM | 1068 | N | LEU | A | 137 | 33.811 | 21.511 | 37.856 | 1.00 | 12.52 | N |
| ATOM | 1069 | CA | LEU | A | 137 | 34.396 | 22.004 | 39.100 | 1.00 | 12.63 | C |
| ATOM | 1070 | CB | LEU | A | 137 | 35.151 | 23.323 | 38.877 | 1.00 | 12.90 | C |
| ATOM | 1071 | CG | LEU | A | 137 | 36.644 | 23.259 | 38.514 | 1.00 | 14.10 | C |
| ATOM | 1072 | CD1 | LEU | A | 137 | 37.468 | 22.555 | 39.600 | 1.00 | 14.95 | C |
| ATOM | 1073 | CD2 | LEU | A | 137 | 36.854 | 22.598 | 37.169 | 1.00 | 15.29 | C |
| ATOM | 1074 | C | LEU | A | 137 | 33.388 | 22.158 | 40.230 | 1.00 | 12.44 | C |
| ATOM | 1075 | O | LEU | A | 137 | 33.778 | 22.284 | 41.390 | 1.00 | 12.54 | O |
| ATOM | 1076 | N | LEU | A | 138 | 32.096 | 22.141 | 39.906 | 1.00 | 12.19 | N |
| ATOM | 1077 | CA | LEU | A | 138 | 31.072 | 22.276 | 40.948 | 1.00 | 12.28 | C |
| ATOM | 1078 | CB | LEU | A | 138 | 29.664 | 22.381 | 40.349 | 1.00 | 12.13 | C |
| ATOM | 1079 | CG | LEU | A | 138 | 28.495 | 22.312 | 41.350 | 1.00 | 12.30 | C |
| ATOM | 1080 | CD1 | LEU | A | 138 | 28.574 | 23.424 | 42.411 | 1.00 | 12.88 | C |
| ATOM | 1081 | CD2 | LEU | A | 138 | 27.154 | 22.352 | 40.623 | 1.00 | 12.55 | C |
| ATOM | 1082 | C | LEU | A | 138 | 31.141 | 21.146 | 41.974 | 1.00 | 12.43 | C |
| ATOM | 1083 | O | LEU | A | 138 | 31.223 | 21.399 | 43.175 | 1.00 | 12.66 | O |
| ATOM | 1084 | N | ASP | A | 139 | 31.109 | 19.899 | 41.508 | 1.00 | 13.18 | N |
| ATOM | 1085 | CA | ASP | A | 139 | 31.163 | 18.776 | 42.440 | 1.00 | 13.57 | C |
| ATOM | 1086 | CB | ASP | A | 139 | 30.648 | 17.477 | 41.799 | 1.00 | 14.45 | C |
| ATOM | 1087 | CG | ASP | A | 139 | 29.116 | 17.383 | 41.805 | 1.00 | 16.60 | C |
| ATOM | 1088 | OD1 | ASP | A | 139 | 28.452 | 18.247 | 42.419 | 1.00 | 17.94 | O |
| ATOM | 1089 | OD2 | ASP | A | 139 | 28.574 | 16.435 | 41.194 | 1.00 | 19.38 | O |
| ATOM | 1090 | C | ASP | A | 139 | 32.560 | 18.604 | 43.051 | 1.00 | 13.11 | C |
| ATOM | 1091 | O | ASP | A | 139 | 32.698 | 18.002 | 44.112 | 1.00 | 13.17 | O |
| ATOM | 1092 | N | VAL | A | 140 | 33.580 | 19.156 | 42.390 | 1.00 | 12.51 | N |
| ATOM | 1093 | CA | VAL | A | 140 | 34.915 | 19.255 | 42.988 | 1.00 | 12.14 | C |
| ATOM | 1094 | CB | VAL | A | 140 | 35.972 | 19.774 | 41.980 | 1.00 | 12.06 | C |
| ATOM | 1095 | CG1 | VAL | A | 140 | 37.318 | 19.996 | 42.673 | 1.00 | 12.35 | C |
| ATOM | 1096 | CG2 | VAL | A | 140 | 36.119 | 18.793 | 40.816 | 1.00 | 12.44 | C |
| ATOM | 1097 | C | VAL | A | 140 | 34.880 | 20.141 | 44.236 | 1.00 | 12.04 | C |
| ATOM | 1098 | O | VAL | A | 140 | 35.380 | 19.748 | 45.294 | 1.00 | 11.91 | O |
| ATOM | 1099 | N | MET | A | 141 | 34.273 | 21.324 | 44.117 | 1.00 | 11.56 | N |
| ATOM | 1100 | CA | MET | A | 141 | 34.141 | 22.222 | 45.263 | 1.00 | 11.62 | C |
| ATOM | 1101 | CB | MET | A | 141 | 33.517 | 23.562 | 44.859 | 1.00 | 11.79 | C |
| ATOM | 1102 | CG | MET | A | 141 | 34.314 | 24.368 | 43.826 | 1.00 | 13.16 | C |
| ATOM | 1103 | SD | MET | A | 141 | 36.091 | 24.433 | 44.145 | 1.00 | 15.72 | S |
| ATOM | 1104 | CE | MET | A | 141 | 36.152 | 25.429 | 45.636 | 1.00 | 16.58 | C |
| ATOM | 1105 | C | MET | A | 141 | 33.313 | 21.573 | 46.364 | 1.00 | 11.24 | C |
| ATOM | 1106 | O | MET | A | 141 | 33.659 | 21.654 | 47.537 | 1.00 | 10.96 | O |
| ATOM | 1107 | N | ARG | A | 142 | 32.223 | 20.918 | 45.977 | 1.00 | 11.10 | N |
| ATOM | 1108 | CA | ARG | A | 142 | 31.383 | 20.214 | 46.944 | 1.00 | 11.33 | C |
| ATOM | 1109 | CB | ARG | A | 142 | 30.146 | 19.639 | 46.261 | 1.00 | 11.37 | C |
| ATOM | 1110 | CG | ARG | A | 142 | 29.109 | 20.676 | 45.894 | 1.00 | 11.94 | C |
| ATOM | 1111 | CD | ARG | A | 142 | 27.941 | 20.018 | 45.198 | 1.00 | 13.07 | C |
| ATOM | 1112 | NE | ARG | A | 142 | 26.823 | 20.935 | 45.001 | 1.00 | 15.27 | N |
| ATOM | 1113 | CZ | ARG | A | 142 | 25.991 | 20.880 | 43.965 | 1.00 | 15.36 | C |
| ATOM | 1114 | NH1 | ARG | A | 142 | 26.170 | 19.973 | 43.012 | 1.00 | 15.39 | N |
| ATOM | 1115 | NH2 | ARG | A | 142 | 24.988 | 21.740 | 43.873 | 1.00 | 17.10 | N |
| ATOM | 1116 | C | ARG | A | 142 | 32.146 | 19.105 | 47.661 | 1.00 | 11.50 | C |
| ATOM | 1117 | O | ARG | A | 142 | 32.022 | 18.947 | 48.883 | 1.00 | 11.32 | O |
| ATOM | 1118 | N | ALA | A | 143 | 32.941 | 18.350 | 46.901 | 1.00 | 11.95 | N |
| ATOM | 1119 | CA | ALA | A | 143 | 33.734 | 17.256 | 47.457 | 1.00 | 12.40 | C |
| ATOM | 1120 | CB | ALA | A | 143 | 34.379 | 16.440 | 46.345 | 1.00 | 12.65 | C |
| ATOM | 1121 | C | ALA | A | 143 | 34.792 | 17.781 | 48.421 | 1.00 | 12.80 | C |
| ATOM | 1122 | O | ALA | A | 143 | 35.046 | 17.180 | 49.466 | 1.00 | 12.91 | O |
| ATOM | 1123 | N | CYS | A | 144 | 35.397 | 18.912 | 48.067 | 1.00 | 13.36 | N |
| ATOM | 1124 | CA | CYS | A | 144 | 36.400 | 19.543 | 48.917 | 1.00 | 13.71 | C |
| ATOM | 1125 | CB | CYS | A | 144 | 37.023 | 20.748 | 48.216 | 1.00 | 13.89 | C |
| ATOM | 1126 | SG | CYS | A | 144 | 38.648 | 21.205 | 48.871 | 1.00 | 17.63 | S |
| ATOM | 1127 | C | CYS | A | 144 | 35.789 | 19.964 | 50.248 | 1.00 | 13.15 | C |
| ATOM | 1128 | O | CYS | A | 144 | 36.337 | 19.680 | 51.306 | 1.00 | 13.26 | O |
| ATOM | 1129 | N | TYR | A | 145 | 34.639 | 20.628 | 50.193 | 1.00 | 12.80 | N |
| ATOM | 1130 | CA | TYR | A | 145 | 33.959 | 21.037 | 51.417 | 1.00 | 12.99 | C |
| ATOM | 1131 | CB | TYR | A | 145 | 32.681 | 21.806 | 51.095 | 1.00 | 13.37 | C |
| ATOM | 1132 | CG | TYR | A | 145 | 31.838 | 22.082 | 52.318 | 1.00 | 13.87 | C |

TABLE 6-continued

Coordinates of the crystal structure of *E. coli* ExoI bound to compound 9

| ATOM | 1133 | CD1 | TYR | A | 145 | 32.068 | 23.212 | 53.108 | 1.00 | 16.64 | C |
|------|------|-----|-----|---|-----|--------|--------|--------|------|-------|---|
| ATOM | 1134 | CE1 | TYR | A | 145 | 31.302 | 23.456 | 54.248 | 1.00 | 14.79 | C |
| ATOM | 1135 | CZ  | TYR | A | 145 | 30.296 | 22.563 | 54.598 | 1.00 | 15.17 | C |
| ATOM | 1136 | OH  | TYR | A | 145 | 29.528 | 22.788 | 55.719 | 1.00 | 16.31 | O |
| ATOM | 1137 | CE2 | TYR | A | 145 | 30.060 | 21.435 | 53.834 | 1.00 | 14.86 | C |
| ATOM | 1138 | CD2 | TYR | A | 145 | 30.826 | 21.199 | 52.703 | 1.00 | 14.64 | C |
| ATOM | 1139 | C   | TYR | A | 145 | 33.635 | 19.831 | 52.297 | 1.00 | 13.03 | C |
| ATOM | 1140 | O   | TYR | A | 145 | 33.856 | 19.857 | 53.510 | 1.00 | 12.68 | O |
| ATOM | 1141 | N   | ALA | A | 146 | 33.113 | 18.779 | 51.676 | 1.00 | 13.12 | N |
| ATOM | 1142 | CA  | ALA | A | 146 | 32.661 | 17.602 | 52.406 | 1.00 | 13.42 | C |
| ATOM | 1143 | CB  | ALA | A | 146 | 31.823 | 16.723 | 51.504 | 1.00 | 13.40 | C |
| ATOM | 1144 | C   | ALA | A | 146 | 33.814 | 16.799 | 53.006 | 1.00 | 13.87 | C |
| ATOM | 1145 | O   | ALA | A | 146 | 33.752 | 16.381 | 54.165 | 1.00 | 14.10 | O |
| ATOM | 1146 | N   | LEU | A | 147 | 34.862 | 16.586 | 52.212 | 1.00 | 14.03 | N |
| ATOM | 1147 | CA  | LEU | A | 147 | 35.916 | 15.630 | 52.567 | 1.00 | 14.65 | C |
| ATOM | 1148 | CB  | LEU | A | 147 | 36.277 | 14.751 | 51.361 | 1.00 | 14.66 | C |
| ATOM | 1149 | CG  | LEU | A | 147 | 35.145 | 13.997 | 50.651 | 1.00 | 15.56 | C |
| ATOM | 1150 | CD1 | LEU | A | 147 | 35.665 | 13.307 | 49.401 | 1.00 | 16.43 | C |
| ATOM | 1151 | CD2 | LEU | A | 147 | 34.482 | 12.991 | 51.584 | 1.00 | 16.71 | C |
| ATOM | 1152 | C   | LEU | A | 147 | 37.182 | 16.266 | 53.146 | 1.00 | 14.97 | C |
| ATOM | 1153 | O   | LEU | A | 147 | 37.757 | 15.738 | 54.099 | 1.00 | 15.49 | O |
| ATOM | 1154 | N   | ARG | A | 148 | 37.622 | 17.380 | 52.557 | 1.00 | 14.86 | N |
| ATOM | 1155 | CA  | ARG | A | 148 | 38.887 | 18.026 | 52.944 | 1.00 | 15.33 | C |
| ATOM | 1156 | CB  | ARG | A | 148 | 40.035 | 17.566 | 52.025 | 1.00 | 15.51 | C |
| ATOM | 1157 | CG  | ARG | A | 148 | 40.272 | 16.060 | 51.962 | 1.00 | 17.75 | C |
| ATOM | 1158 | CD  | ARG | A | 148 | 40.914 | 15.529 | 53.236 | 1.00 | 20.53 | C |
| ATOM | 1159 | NE  | ARG | A | 148 | 41.300 | 14.123 | 53.108 | 1.00 | 22.94 | N |
| ATOM | 1160 | CZ  | ARG | A | 148 | 40.481 | 13.090 | 53.303 | 1.00 | 23.76 | C |
| ATOM | 1161 | NH1 | ARG | A | 148 | 39.214 | 13.288 | 53.646 | 1.00 | 23.96 | N |
| ATOM | 1162 | NH2 | ARG | A | 148 | 40.934 | 11.851 | 53.162 | 1.00 | 25.04 | N |
| ATOM | 1163 | C   | ARG | A | 148 | 38.770 | 19.559 | 52.900 | 1.00 | 15.14 | C |
| ATOM | 1164 | O   | ARG | A | 148 | 39.365 | 20.202 | 52.036 | 1.00 | 14.77 | O |
| ATOM | 1165 | N   | PRO | A | 149 | 37.991 | 20.146 | 53.830 | 1.00 | 15.28 | N |
| ATOM | 1166 | CA  | PRO | A | 149 | 37.684 | 21.584 | 53.790 | 1.00 | 15.60 | C |
| ATOM | 1167 | CB  | PRO | A | 149 | 36.543 | 21.720 | 54.798 | 1.00 | 15.72 | C |
| ATOM | 1168 | CG  | PRO | A | 149 | 36.776 | 20.609 | 55.772 | 1.00 | 15.40 | C |
| ATOM | 1169 | CD  | PRO | A | 149 | 37.320 | 19.471 | 54.962 | 1.00 | 15.43 | C |
| ATOM | 1170 | C   | PRO | A | 149 | 38.837 | 22.510 | 54.189 | 1.00 | 15.79 | C |
| ATOM | 1171 | O   | PRO | A | 149 | 38.791 | 23.706 | 53.897 | 1.00 | 15.37 | O |
| ATOM | 1172 | N   | GLU | A | 150 | 39.852 | 21.960 | 54.847 | 1.00 | 16.45 | N |
| ATOM | 1173 | CA  | GLU | A | 150 | 40.928 | 22.762 | 55.427 | 1.00 | 17.32 | C |
| ATOM | 1174 | CB  | GLU | A | 150 | 41.921 | 21.852 | 56.169 | 1.00 | 17.80 | C |
| ATOM | 1175 | CG  | GLU | A | 150 | 41.278 | 20.923 | 57.233 | 1.00 | 20.75 | C |
| ATOM | 1176 | CD  | GLU | A | 150 | 40.737 | 19.591 | 56.666 | 1.00 | 23.67 | C |
| ATOM | 1177 | OE1 | GLU | A | 150 | 40.847 | 19.342 | 55.442 | 1.00 | 23.65 | O |
| ATOM | 1178 | OE2 | GLU | A | 150 | 40.200 | 18.783 | 57.462 | 1.00 | 27.09 | O |
| ATOM | 1179 | C   | GLU | A | 150 | 41.655 | 23.596 | 54.362 | 1.00 | 16.95 | C |
| ATOM | 1180 | O   | GLU | A | 150 | 42.038 | 23.077 | 53.318 | 1.00 | 18.07 | O |
| ATOM | 1181 | N   | GLY | A | 151 | 41.818 | 24.893 | 54.622 | 1.00 | 16.58 | N |
| ATOM | 1182 | CA  | GLY | A | 151 | 42.584 | 25.766 | 53.725 | 1.00 | 16.00 | C |
| ATOM | 1183 | C   | GLY | A | 151 | 41.763 | 26.676 | 52.826 | 1.00 | 15.79 | C |
| ATOM | 1184 | O   | GLY | A | 151 | 42.275 | 27.665 | 52.305 | 1.00 | 15.47 | O |
| ATOM | 1185 | N   | ILE | A | 152 | 40.491 | 26.333 | 52.630 | 1.00 | 15.42 | N |
| ATOM | 1186 | CA  | ILE | A | 152 | 39.581 | 27.139 | 51.815 | 1.00 | 15.31 | C |
| ATOM | 1187 | CB  | ILE | A | 152 | 38.966 | 26.301 | 50.651 | 1.00 | 15.16 | C |
| ATOM | 1188 | CG1 | ILE | A | 152 | 40.059 | 25.904 | 49.652 | 1.00 | 15.23 | C |
| ATOM | 1189 | CD1 | ILE | A | 152 | 39.622 | 24.895 | 48.608 | 1.00 | 15.70 | C |
| ATOM | 1190 | CG2 | ILE | A | 152 | 37.843 | 27.076 | 49.936 | 1.00 | 14.93 | C |
| ATOM | 1191 | C   | ILE | A | 152 | 38.482 | 27.728 | 52.698 | 1.00 | 15.20 | C |
| ATOM | 1192 | O   | ILE | A | 152 | 38.013 | 27.074 | 53.629 | 1.00 | 15.54 | O |
| ATOM | 1193 | N   | ASN | A | 153 | 38.100 | 28.971 | 52.417 | 1.00 | 15.16 | N |
| ATOM | 1194 | CA  | ASN | A | 153 | 36.988 | 29.617 | 53.112 | 1.00 | 15.40 | C |
| ATOM | 1195 | CB  | ASN | A | 153 | 37.163 | 31.134 | 53.115 | 1.00 | 15.88 | C |
| ATOM | 1196 | CG  | ASN | A | 153 | 38.372 | 31.585 | 53.916 | 1.00 | 17.59 | C |
| ATOM | 1197 | OD1 | ASN | A | 153 | 39.108 | 32.478 | 53.492 | 1.00 | 20.14 | O |
| ATOM | 1198 | ND2 | ASN | A | 153 | 38.580 | 30.974 | 55.078 | 1.00 | 19.62 | N |
| ATOM | 1199 | C   | ASN | A | 153 | 35.667 | 29.250 | 52.455 | 1.00 | 15.02 | C |
| ATOM | 1200 | O   | ASN | A | 153 | 35.488 | 29.440 | 51.251 | 1.00 | 15.24 | O |
| ATOM | 1201 | N   | TRP | A | 154 | 34.745 | 28.724 | 53.254 | 1.00 | 14.59 | N |
| ATOM | 1202 | CA  | TRP | A | 154 | 33.486 | 28.207 | 52.731 | 1.00 | 14.62 | C |
| ATOM | 1203 | CB  | TRP | A | 154 | 33.253 | 26.778 | 53.227 | 1.00 | 14.06 | C |
| ATOM | 1204 | CG  | TRP | A | 154 | 34.336 | 25.853 | 52.791 | 1.00 | 13.57 | C |
| ATOM | 1205 | CD1 | TRP | A | 154 | 35.358 | 25.368 | 53.556 | 1.00 | 13.37 | C |
| ATOM | 1206 | NE1 | TRP | A | 154 | 36.180 | 24.567 | 52.797 | 1.00 | 14.01 | N |
| ATOM | 1207 | CE2 | TRP | A | 154 | 35.701 | 24.530 | 51.513 | 1.00 | 12.87 | C |
| ATOM | 1208 | CD2 | TRP | A | 154 | 34.540 | 25.335 | 51.471 | 1.00 | 13.08 | C |
| ATOM | 1209 | CE3 | TRP | A | 154 | 33.851 | 25.465 | 50.257 | 1.00 | 12.93 | C |
| ATOM | 1210 | CZ3 | TRP | A | 154 | 34.336 | 24.794 | 49.138 | 1.00 | 13.25 | C |

TABLE 6-continued

Coordinates of the crystal structure of *E. coli* ExoI bound to compound 9

| ATOM | 1211 | CH2 | TRP | A | 154 | 35.494 | 23.999 | 49.213 | 1.00 | 13.53 | C |
|---|---|---|---|---|---|---|---|---|---|---|---|
| ATOM | 1212 | CZ2 | TRP | A | 154 | 36.188 | 23.856 | 50.388 | 1.00 | 13.49 | C |
| ATOM | 1213 | C | TRP | A | 154 | 32.323 | 29.117 | 53.100 | 1.00 | 14.88 | C |
| ATOM | 1214 | O | TRP | A | 154 | 31.899 | 29.146 | 54.260 | 1.00 | 15.50 | O |
| ATOM | 1215 | N | PRO | A | 155 | 31.802 | 29.869 | 52.108 | 1.00 | 15.42 | N |
| ATOM | 1216 | CA | PRO | A | 155 | 30.760 | 30.856 | 52.371 | 1.00 | 15.76 | C |
| ATOM | 1217 | CB | PRO | A | 155 | 30.678 | 31.637 | 51.054 | 1.00 | 15.95 | C |
| ATOM | 1218 | CG | PRO | A | 155 | 31.111 | 30.678 | 50.020 | 1.00 | 15.67 | C |
| ATOM | 1219 | CD | PRO | A | 155 | 32.164 | 29.819 | 50.678 | 1.00 | 15.41 | C |
| ATOM | 1220 | C | PRO | A | 155 | 29.418 | 30.209 | 52.679 | 1.00 | 16.21 | C |
| ATOM | 1221 | O | PRO | A | 155 | 29.143 | 29.100 | 52.218 | 1.00 | 15.87 | O |
| ATOM | 1222 | N | GLU | A | 156 | 28.608 | 30.900 | 53.476 | 1.00 | 17.18 | N |
| ATOM | 1223 | CA | GLU | A | 156 | 27.227 | 30.506 | 53.717 | 1.00 | 18.23 | C |
| ATOM | 1224 | CB | GLU | A | 156 | 26.864 | 30.676 | 55.196 | 1.00 | 18.44 | C |
| ATOM | 1225 | CG | GLU | A | 156 | 27.301 | 29.525 | 56.100 | 1.00 | 20.25 | C |
| ATOM | 1226 | CD | GLU | A | 156 | 26.828 | 29.690 | 57.544 | 1.00 | 20.90 | C |
| ATOM | 1227 | OE1 | GLU | A | 156 | 26.141 | 30.693 | 57.851 | 1.00 | 24.13 | O |
| ATOM | 1228 | OE2 | GLU | A | 156 | 27.140 | 28.811 | 58.374 | 1.00 | 24.81 | O |
| ATOM | 1229 | C | GLU | A | 156 | 26.303 | 31.366 | 52.869 | 1.00 | 18.22 | C |
| ATOM | 1230 | O | GLU | A | 156 | 26.566 | 32.553 | 52.664 | 1.00 | 18.66 | O |
| ATOM | 1231 | N | ASN | A | 157 | 25.223 | 30.772 | 52.371 | 1.00 | 17.87 | N |
| ATOM | 1232 | CA | ASN | A | 157 | 24.185 | 31.550 | 51.697 | 1.00 | 17.84 | C |
| ATOM | 1233 | CB | ASN | A | 157 | 23.411 | 30.694 | 50.682 | 1.00 | 17.67 | C |
| ATOM | 1234 | CG | ASN | A | 157 | 22.704 | 29.503 | 51.321 | 1.00 | 17.25 | C |
| ATOM | 1235 | OD1 | ASN | A | 157 | 22.250 | 29.566 | 52.464 | 1.00 | 16.01 | O |
| ATOM | 1236 | ND2 | ASN | A | 157 | 22.594 | 28.415 | 50.569 | 1.00 | 17.91 | N |
| ATOM | 1237 | C | ASN | A | 157 | 23.250 | 32.207 | 52.720 | 1.00 | 17.99 | C |
| ATOM | 1238 | O | ASN | A | 157 | 23.451 | 32.066 | 53.928 | 1.00 | 17.66 | O |
| ATOM | 1239 | N | ASP | A | 158 | 22.237 | 32.921 | 52.233 | 1.00 | 18.57 | N |
| ATOM | 1240 | CA | ASP | A | 158 | 21.319 | 33.659 | 53.109 | 1.00 | 19.21 | C |
| ATOM | 1241 | CB | ASP | A | 158 | 20.445 | 34.617 | 52.295 | 1.00 | 19.80 | C |
| ATOM | 1242 | CG | ASP | A | 158 | 21.207 | 35.839 | 51.816 | 1.00 | 22.26 | C |
| ATOM | 1243 | OD1 | ASP | A | 158 | 22.238 | 36.190 | 52.433 | 1.00 | 24.52 | O |
| ATOM | 1244 | OD2 | ASP | A | 158 | 20.768 | 36.452 | 50.821 | 1.00 | 25.31 | O |
| ATOM | 1245 | C | ASP | A | 158 | 20.444 | 32.764 | 53.992 | 1.00 | 18.79 | C |
| ATOM | 1246 | O | ASP | A | 158 | 19.833 | 33.238 | 54.955 | 1.00 | 19.15 | O |
| ATOM | 1247 | N | ASP | A | 159 | 20.390 | 31.475 | 53.669 | 1.00 | 18.01 | N |
| ATOM | 1248 | CA | ASP | A | 159 | 19.648 | 30.521 | 54.490 | 1.00 | 17.50 | C |
| ATOM | 1249 | CB | ASP | A | 159 | 18.976 | 29.454 | 53.616 | 1.00 | 17.76 | C |
| ATOM | 1250 | CG | ASP | A | 159 | 17.894 | 30.034 | 52.712 | 1.00 | 18.58 | C |
| ATOM | 1251 | OD1 | ASP | A | 159 | 17.319 | 31.091 | 53.059 | 1.00 | 20.34 | O |
| ATOM | 1252 | OD2 | ASP | A | 159 | 17.621 | 29.437 | 51.651 | 1.00 | 21.00 | O |
| ATOM | 1253 | C | ASP | A | 159 | 20.526 | 29.881 | 55.573 | 1.00 | 16.64 | C |
| ATOM | 1254 | O | ASP | A | 159 | 20.024 | 29.171 | 56.453 | 1.00 | 16.38 | O |
| ATOM | 1255 | N | GLY | A | 160 | 21.834 | 30.149 | 55.511 | 1.00 | 16.05 | N |
| ATOM | 1256 | CA | GLY | A | 160 | 22.780 | 29.689 | 56.534 | 1.00 | 15.43 | C |
| ATOM | 1257 | C | GLY | A | 160 | 23.413 | 28.348 | 56.220 | 1.00 | 15.36 | C |
| ATOM | 1258 | O | GLY | A | 160 | 23.950 | 27.679 | 57.107 | 1.00 | 15.56 | O |
| ATOM | 1259 | N | LEU | A | 161 | 23.353 | 27.967 | 54.948 | 1.00 | 15.03 | N |
| ATOM | 1260 | CA | LEU | A | 161 | 23.889 | 26.699 | 54.482 | 1.00 | 15.00 | C |
| ATOM | 1261 | CB | LEU | A | 161 | 22.816 | 25.938 | 53.694 | 1.00 | 15.45 | C |
| ATOM | 1262 | CG | LEU | A | 161 | 21.535 | 25.575 | 54.454 | 1.00 | 16.60 | C |
| ATOM | 1263 | CD1 | LEU | A | 161 | 20.364 | 25.424 | 53.500 | 1.00 | 18.75 | C |
| ATOM | 1264 | CD2 | LEU | A | 161 | 21.727 | 24.324 | 55.291 | 1.00 | 18.16 | C |
| ATOM | 1265 | C | LEU | A | 161 | 25.099 | 26.966 | 53.596 | 1.00 | 14.52 | C |
| ATOM | 1266 | O | LEU | A | 161 | 25.221 | 28.051 | 53.041 | 1.00 | 14.06 | O |
| ATOM | 1267 | N | PRO | A | 162 | 26.001 | 25.973 | 53.460 | 1.00 | 14.21 | N |
| ATOM | 1268 | CA | PRO | A | 162 | 27.166 | 26.179 | 52.598 | 1.00 | 14.32 | C |
| ATOM | 1269 | CB | PRO | A | 162 | 27.914 | 24.840 | 52.681 | 1.00 | 14.58 | C |
| ATOM | 1270 | CG | PRO | A | 162 | 26.929 | 23.867 | 53.205 | 1.00 | 15.14 | C |
| ATOM | 1271 | CD | PRO | A | 162 | 25.998 | 24.636 | 54.077 | 1.00 | 14.33 | C |
| ATOM | 1272 | C | PRO | A | 162 | 26.751 | 26.477 | 51.161 | 1.00 | 14.27 | C |
| ATOM | 1273 | O | PRO | A | 162 | 25.892 | 25.786 | 50.602 | 1.00 | 14.48 | O |
| ATOM | 1274 | N | SER | A | 163 | 27.337 | 27.525 | 50.593 | 1.00 | 14.20 | N |
| ATOM | 1275 | CA | SER | A | 163 | 27.048 | 27.935 | 49.230 | 1.00 | 14.41 | C |
| ATOM | 1276 | CB | SER | A | 163 | 26.849 | 29.445 | 49.159 | 1.00 | 14.49 | C |
| ATOM | 1277 | OG | SER | A | 163 | 26.619 | 29.860 | 47.824 | 1.00 | 15.65 | O |
| ATOM | 1278 | C | SER | A | 163 | 28.167 | 27.534 | 48.291 | 1.00 | 14.45 | C |
| ATOM | 1279 | O | SER | A | 163 | 29.350 | 27.640 | 48.632 | 1.00 | 14.57 | O |
| ATOM | 1280 | N | PHE | A | 164 | 27.787 | 27.094 | 47.097 | 1.00 | 14.45 | N |
| ATOM | 1281 | CA | PHE | A | 164 | 28.752 | 26.719 | 46.073 | 1.00 | 14.94 | C |
| ATOM | 1282 | CB | PHE | A | 164 | 28.697 | 25.212 | 45.826 | 1.00 | 14.65 | C |
| ATOM | 1283 | CG | PHE | A | 164 | 29.047 | 24.414 | 47.039 | 1.00 | 13.63 | C |
| ATOM | 1284 | CD1 | PHE | A | 164 | 30.375 | 24.163 | 47.360 | 1.00 | 12.83 | C |
| ATOM | 1285 | CE1 | PHE | A | 164 | 30.707 | 23.459 | 48.507 | 1.00 | 12.89 | C |
| ATOM | 1286 | CZ | PHE | A | 164 | 29.702 | 23.012 | 49.364 | 1.00 | 13.46 | C |
| ATOM | 1287 | CE2 | PHE | A | 164 | 28.375 | 23.277 | 49.065 | 1.00 | 13.92 | C |
| ATOM | 1288 | CD2 | PHE | A | 164 | 28.053 | 23.983 | 47.914 | 1.00 | 13.57 | C |

TABLE 6-continued

Coordinates of the crystal structure of *E. coli* ExoI bound to compound 9

| ATOM | 1289 | C | PHE | A | 164 | 28.539 | 27.528 | 44.808 | 1.00 | 15.50 | C |
|---|---|---|---|---|---|---|---|---|---|---|---|
| ATOM | 1290 | O | PHE | A | 164 | 28.995 | 27.156 | 43.731 | 1.00 | 16.05 | O |
| ATOM | 1291 | N | ARG | A | 165 | 27.860 | 28.659 | 44.961 | 1.00 | 15.92 | N |
| ATOM | 1292 | CA | ARG | A | 165 | 27.745 | 29.631 | 43.888 | 1.00 | 16.71 | C |
| ATOM | 1293 | CB | ARG | A | 165 | 26.738 | 30.720 | 44.251 | 1.00 | 17.04 | C |
| ATOM | 1294 | CG | ARG | A | 165 | 25.309 | 30.216 | 44.320 | 1.00 | 19.09 | C |
| ATOM | 1295 | CD | ARG | A | 165 | 24.369 | 31.278 | 44.841 | 1.00 | 23.00 | C |
| ATOM | 1296 | NE | ARG | A | 165 | 24.014 | 32.257 | 43.818 | 1.00 | 26.05 | N |
| ATOM | 1297 | CZ | ARG | A | 165 | 23.240 | 33.321 | 44.032 | 1.00 | 27.94 | C |
| ATOM | 1298 | NH1 | ARG | A | 165 | 22.737 | 33.557 | 45.240 | 1.00 | 28.81 | N |
| ATOM | 1299 | NH2 | ARG | A | 165 | 22.970 | 34.153 | 43.034 | 1.00 | 29.25 | N |
| ATOM | 1300 | C | ARG | A | 165 | 29.111 | 30.230 | 43.618 | 1.00 | 16.87 | C |
| ATOM | 1301 | O | ARG | A | 165 | 29.832 | 30.614 | 44.545 | 1.00 | 16.55 | O |
| ATOM | 1302 | N | LEU | A | 166 | 29.464 | 30.287 | 42.340 | 1.00 | 17.35 | N |
| ATOM | 1303 | CA | LEU | A | 166 | 30.783 | 30.719 | 41.906 | 1.00 | 18.02 | C |
| ATOM | 1304 | CB | LEU | A | 166 | 30.850 | 30.695 | 40.376 | 1.00 | 18.00 | C |
| ATOM | 1305 | CG | LEU | A | 166 | 32.209 | 30.730 | 39.680 | 1.00 | 18.31 | C |
| ATOM | 1306 | CD1 | LEU | A | 166 | 33.115 | 29.605 | 40.159 | 1.00 | 17.97 | C |
| ATOM | 1307 | CD2 | LEU | A | 166 | 32.012 | 30.656 | 38.174 | 1.00 | 18.48 | C |
| ATOM | 1308 | C | LEU | A | 166 | 31.145 | 32.106 | 42.442 | 1.00 | 18.36 | C |
| ATOM | 1309 | O | LEU | A | 166 | 32.273 | 32.331 | 42.884 | 1.00 | 18.87 | O |
| ATOM | 1310 | N | GLU | A | 167 | 30.175 | 33.020 | 42.422 | 1.00 | 18.91 | N |
| ATOM | 1311 | CA | GLU | A | 167 | 30.379 | 34.383 | 42.919 | 1.00 | 19.19 | C |
| ATOM | 1312 | CB | GLU | A | 167 | 29.210 | 35.300 | 42.521 | 1.00 | 19.83 | C |
| ATOM | 1313 | CG | GLU | A | 167 | 27.842 | 34.875 | 43.061 | 1.00 | 21.88 | C |
| ATOM | 1314 | CD | GLU | A | 167 | 27.043 | 34.025 | 42.078 | 1.00 | 24.40 | C |
| ATOM | 1315 | OE1 | GLU | A | 167 | 27.652 | 33.280 | 41.276 | 1.00 | 25.54 | O |
| ATOM | 1316 | OE2 | GLU | A | 167 | 25.794 | 34.102 | 42.113 | 1.00 | 26.68 | O |
| ATOM | 1317 | C | GLU | A | 167 | 30.624 | 34.450 | 44.434 | 1.00 | 18.64 | C |
| ATOM | 1318 | O | GLU | A | 167 | 31.309 | 35.351 | 44.914 | 1.00 | 18.90 | O |
| ATOM | 1319 | N | HIS | A | 168 | 30.060 | 33.498 | 45.178 | 1.00 | 17.92 | N |
| ATOM | 1320 | CA | HIS | A | 168 | 30.275 | 33.437 | 46.623 | 1.00 | 17.49 | C |
| ATOM | 1321 | CB | HIS | A | 168 | 29.190 | 32.603 | 47.309 | 1.00 | 17.52 | C |
| ATOM | 1322 | CG | HIS | A | 168 | 27.830 | 33.231 | 47.280 | 1.00 | 18.42 | C |
| ATOM | 1323 | ND1 | HIS | A | 168 | 26.679 | 32.524 | 47.554 | 1.00 | 18.79 | N |
| ATOM | 1324 | CE1 | HIS | A | 168 | 25.635 | 33.328 | 47.452 | 1.00 | 19.62 | C |
| ATOM | 1325 | NE2 | HIS | A | 168 | 26.067 | 34.530 | 47.116 | 1.00 | 19.64 | N |
| ATOM | 1326 | CD2 | HIS | A | 168 | 27.436 | 34.497 | 47.002 | 1.00 | 19.62 | C |
| ATOM | 1327 | C | HIS | A | 168 | 31.646 | 32.871 | 46.957 | 1.00 | 16.82 | C |
| ATOM | 1328 | O | HIS | A | 168 | 32.319 | 33.354 | 47.870 | 1.00 | 17.05 | O |
| ATOM | 1329 | N | LEU | A | 169 | 32.053 | 31.844 | 46.216 | 1.00 | 16.25 | N |
| ATOM | 1330 | CA | LEU | A | 169 | 33.329 | 31.168 | 46.470 | 1.00 | 15.90 | C |
| ATOM | 1331 | CB | LEU | A | 169 | 33.408 | 29.849 | 45.700 | 1.00 | 15.86 | C |
| ATOM | 1332 | CG | LEU | A | 169 | 32.510 | 28.717 | 46.207 | 1.00 | 15.38 | C |
| ATOM | 1333 | CD1 | LEU | A | 169 | 32.431 | 27.620 | 45.169 | 1.00 | 16.14 | C |
| ATOM | 1334 | CD2 | LEU | A | 169 | 33.002 | 28.160 | 47.534 | 1.00 | 16.14 | C |
| ATOM | 1335 | C | LEU | A | 169 | 34.524 | 32.045 | 46.131 | 1.00 | 16.11 | C |
| ATOM | 1336 | O | LEU | A | 169 | 35.533 | 32.020 | 46.834 | 1.00 | 15.79 | O |
| ATOM | 1337 | N | THR | A | 170 | 34.413 | 32.806 | 45.045 | 1.00 | 16.60 | N |
| ATOM | 1338 | CA | THR | A | 170 | 35.469 | 33.746 | 44.667 | 1.00 | 17.15 | C |
| ATOM | 1339 | CB | THR | A | 170 | 35.226 | 34.372 | 43.271 | 1.00 | 17.17 | C |
| ATOM | 1340 | OG1 | THR | A | 170 | 33.912 | 34.939 | 43.221 | 1.00 | 17.26 | O |
| ATOM | 1341 | CG2 | THR | A | 170 | 35.370 | 33.325 | 42.175 | 1.00 | 17.25 | C |
| ATOM | 1342 | C | THR | A | 170 | 35.622 | 34.848 | 45.718 | 1.00 | 17.59 | C |
| ATOM | 1343 | O | THR | A | 170 | 36.724 | 35.089 | 46.218 | 1.00 | 17.52 | O |
| ATOM | 1344 | N | LYS | A | 171 | 34.507 | 35.488 | 46.073 | 1.00 | 18.04 | N |
| ATOM | 1345 | CA | LYS | A | 171 | 34.510 | 36.555 | 47.079 | 1.00 | 18.75 | C |
| ATOM | 1346 | CB | LYS | A | 171 | 33.093 | 37.113 | 47.275 | 1.00 | 19.02 | C |
| ATOM | 1347 | CG | LYS | A | 171 | 33.020 | 38.386 | 48.124 | 1.00 | 20.90 | C |
| ATOM | 1348 | CD | LYS | A | 171 | 33.512 | 39.597 | 47.345 | 1.00 | 23.93 | C |
| ATOM | 1349 | CE | LYS | A | 171 | 33.163 | 40.895 | 48.049 | 1.00 | 25.78 | C |
| ATOM | 1350 | NZ | LYS | A | 171 | 33.372 | 42.069 | 47.156 | 1.00 | 27.44 | N |
| ATOM | 1351 | C | LYS | A | 171 | 35.088 | 36.085 | 48.417 | 1.00 | 18.65 | C |
| ATOM | 1352 | O | LYS | A | 171 | 35.912 | 36.775 | 49.026 | 1.00 | 18.96 | O |
| ATOM | 1353 | N | ALA | A | 172 | 34.670 | 34.900 | 48.858 | 1.00 | 18.51 | N |
| ATOM | 1354 | CA | ALA | A | 172 | 35.088 | 34.367 | 50.156 | 1.00 | 18.61 | C |
| ATOM | 1355 | CB | ALA | A | 172 | 34.268 | 33.139 | 50.515 | 1.00 | 18.48 | C |
| ATOM | 1356 | C | ALA | A | 172 | 36.580 | 34.043 | 50.211 | 1.00 | 18.66 | C |
| ATOM | 1357 | O | ALA | A | 172 | 37.160 | 33.945 | 51.297 | 1.00 | 18.46 | O |
| ATOM | 1358 | N | ASN | A | 173 | 37.194 | 33.884 | 49.040 | 1.00 | 19.01 | N |
| ATOM | 1359 | CA | ASN | A | 173 | 38.591 | 33.465 | 48.953 | 1.00 | 19.64 | C |
| ATOM | 1360 | CB | ASN | A | 173 | 38.691 | 32.101 | 48.264 | 1.00 | 19.21 | C |
| ATOM | 1361 | CG | ASN | A | 173 | 38.117 | 30.987 | 49.112 | 1.00 | 18.39 | C |
| ATOM | 1362 | OD1 | ASN | A | 173 | 36.981 | 30.543 | 48.899 | 1.00 | 18.47 | O |
| ATOM | 1363 | ND2 | ASN | A | 173 | 38.882 | 30.549 | 50.103 | 1.00 | 15.58 | N |
| ATOM | 1364 | C | ASN | A | 173 | 39.516 | 34.494 | 48.293 | 1.00 | 20.56 | C |
| ATOM | 1365 | O | ASN | A | 173 | 40.628 | 34.165 | 47.879 | 1.00 | 20.71 | O |
| ATOM | 1366 | N | GLY | A | 174 | 39.047 | 35.737 | 48.207 | 1.00 | 21.57 | N |

TABLE 6-continued

Coordinates of the crystal structure of *E. coli* ExoI bound to compound 9

| | | | | | | | | | | | |
|---|---|---|---|---|---|---|---|---|---|---|---|
| ATOM | 1367 | CA | GLY | A | 174 | 39.877 | 36.856 | 47.744 | 1.00 | 22.98 | C |
| ATOM | 1368 | C | GLY | A | 174 | 40.171 | 36.846 | 46.255 | 1.00 | 24.05 | C |
| ATOM | 1369 | O | GLY | A | 174 | 41.061 | 37.558 | 45.785 | 1.00 | 23.97 | O |
| ATOM | 1370 | N | ILE | A | 175 | 39.421 | 36.037 | 45.514 | 1.00 | 25.09 | N |
| ATOM | 1371 | CA | ILE | A | 175 | 39.580 | 35.944 | 44.070 | 1.00 | 26.48 | C |
| ATOM | 1372 | CB | ILE | A | 175 | 39.225 | 34.529 | 43.558 | 1.00 | 26.28 | C |
| ATOM | 1373 | CG1 | ILE | A | 175 | 40.236 | 33.511 | 44.095 | 1.00 | 26.32 | C |
| ATOM | 1374 | CD1 | ILE | A | 175 | 39.730 | 32.087 | 44.126 | 1.00 | 26.16 | C |
| ATOM | 1375 | CG2 | ILE | A | 175 | 39.181 | 34.498 | 42.026 | 1.00 | 26.36 | C |
| ATOM | 1376 | C | ILE | A | 175 | 38.702 | 36.989 | 43.401 | 1.00 | 27.60 | C |
| ATOM | 1377 | O | ILE | A | 175 | 37.510 | 37.097 | 43.704 | 1.00 | 27.64 | O |
| ATOM | 1378 | N | GLU | A | 176 | 39.397 | 37.862 | 42.287 | 1.00 | 29.15 | N |
| ATOM | 1379 | CA | GLU | A | 176 | 38.476 | 38.953 | 41.895 | 1.00 | 30.68 | C |
| ATOM | 1380 | CB | GLU | A | 176 | 39.215 | 40.293 | 41.691 | 1.00 | 30.87 | C |
| ATOM | 1381 | CG | GLU | A | 176 | 38.779 | 41.134 | 40.550 | 1.00 | 32.20 | C |
| ATOM | 1382 | CD | GLU | A | 176 | 38.556 | 42.478 | 41.248 | 1.00 | 33.78 | C |
| ATOM | 1383 | OE1 | GLU | A | 176 | 38.910 | 42.595 | 42.451 | 1.00 | 34.69 | O |
| ATOM | 1384 | OE2 | GLU | A | 176 | 38.016 | 43.409 | 40.607 | 1.00 | 34.97 | O |
| ATOM | 1385 | C | GLU | A | 176 | 37.596 | 38.571 | 40.703 | 1.00 | 31.35 | C |
| ATOM | 1386 | O | GLU | A | 176 | 38.115 | 38.207 | 39.640 | 1.00 | 31.77 | O |
| ATOM | 1387 | N | HIS | A | 177 | 36.287 | 38.658 | 40.904 | 1.00 | 32.22 | N |
| ATOM | 1388 | CA | HIS | A | 177 | 35.315 | 38.246 | 39.895 | 1.00 | 33.00 | C |
| ATOM | 1389 | CB | HIS | A | 177 | 34.908 | 36.786 | 40.195 | 1.00 | 32.93 | C |
| ATOM | 1390 | CG | HIS | A | 177 | 33.778 | 36.229 | 39.513 | 1.00 | 33.16 | C |
| ATOM | 1391 | ND1 | HIS | A | 177 | 32.675 | 35.626 | 40.082 | 1.00 | 33.42 | N |
| ATOM | 1392 | CE1 | HIS | A | 177 | 31.884 | 35.168 | 39.127 | 1.00 | 33.35 | C |
| ATOM | 1393 | NE2 | HIS | A | 177 | 32.436 | 35.447 | 37.960 | 1.00 | 33.29 | N |
| ATOM | 1394 | CD2 | HIS | A | 177 | 33.626 | 36.105 | 38.173 | 1.00 | 33.10 | C |
| ATOM | 1395 | C | HIS | A | 177 | 34.114 | 39.189 | 39.917 | 1.00 | 33.51 | C |
| ATOM | 1396 | O | HIS | A | 177 | 33.329 | 39.184 | 40.876 | 1.00 | 33.83 | O |
| ATOM | 1397 | N | SER | A | 178 | 33.945 | 40.014 | 38.881 | 1.00 | 34.07 | N |
| ATOM | 1398 | CA | SER | A | 178 | 34.891 | 40.153 | 37.766 | 1.00 | 34.50 | C |
| ATOM | 1399 | CB | SER | A | 178 | 34.173 | 40.915 | 36.639 | 1.00 | 34.57 | C |
| ATOM | 1400 | OG | SER | A | 178 | 34.771 | 40.576 | 35.349 | 1.00 | 35.10 | O |
| ATOM | 1401 | C | SER | A | 178 | 36.178 | 40.871 | 38.165 | 1.00 | 34.67 | C |
| ATOM | 1402 | O | SER | A | 178 | 36.201 | 41.617 | 39.159 | 1.00 | 34.97 | O |
| ATOM | 1403 | N | ASP | A | 182 | 34.971 | 40.128 | 31.700 | 0.50 | 19.78 | N |
| ATOM | 1404 | CA | ASP | A | 182 | 33.575 | 40.540 | 31.602 | 0.50 | 19.66 | C |
| ATOM | 1405 | CB | ASP | A | 182 | 33.433 | 41.725 | 30.642 | 0.50 | 19.93 | C |
| ATOM | 1406 | CG | ASP | A | 182 | 32.169 | 42.540 | 30.893 | 0.50 | 20.54 | C |
| ATOM | 1407 | OD1 | ASP | A | 182 | 31.159 | 41.971 | 31.364 | 0.50 | 21.52 | O |
| ATOM | 1408 | OD2 | ASP | A | 182 | 32.186 | 43.757 | 30.611 | 0.50 | 21.53 | O |
| ATOM | 1409 | C | ASP | A | 182 | 32.701 | 39.375 | 31.141 | 0.50 | 19.23 | C |
| ATOM | 1410 | O | ASP | A | 182 | 32.099 | 38.679 | 31.958 | 0.50 | 19.38 | O |
| ATOM | 1411 | N | ALA | A | 183 | 32.625 | 39.176 | 29.829 | 0.50 | 18.71 | N |
| ATOM | 1412 | CA | ALA | A | 183 | 31.960 | 38.003 | 29.280 | 0.50 | 17.98 | C |
| ATOM | 1413 | CB | ALA | A | 183 | 31.836 | 38.121 | 27.771 | 0.50 | 18.08 | C |
| ATOM | 1414 | C | ALA | A | 183 | 32.758 | 36.761 | 29.656 | 0.50 | 17.41 | C |
| ATOM | 1415 | O | ALA | A | 183 | 32.250 | 35.640 | 29.618 | 0.50 | 17.33 | O |
| ATOM | 1416 | N | MET | A | 184 | 34.013 | 36.978 | 30.031 | 0.50 | 16.71 | N |
| ATOM | 1417 | CA | MET | A | 184 | 34.914 | 35.895 | 30.398 | 0.50 | 16.03 | C |
| ATOM | 1418 | CB | MET | A | 184 | 36.326 | 36.197 | 29.894 | 0.50 | 15.98 | C |
| ATOM | 1419 | CG | MET | A | 184 | 36.524 | 35.986 | 28.403 | 0.50 | 15.42 | C |
| ATOM | 1420 | SD | MET | A | 184 | 36.354 | 34.259 | 27.917 | 0.50 | 15.06 | S |
| ATOM | 1421 | CE | MET | A | 184 | 37.746 | 33.519 | 28.762 | 0.50 | 15.02 | C |
| ATOM | 1422 | C | MET | A | 184 | 34.941 | 35.669 | 31.908 | 0.50 | 15.85 | C |
| ATOM | 1423 | O | MET | A | 184 | 35.606 | 34.754 | 32.396 | 0.50 | 15.18 | O |
| ATOM | 1424 | N | ALA | A | 185 | 34.209 | 36.500 | 32.640 | 0.50 | 15.71 | N |
| ATOM | 1425 | CA | ALA | A | 185 | 34.250 | 36.487 | 34.103 | 0.50 | 16.04 | C |
| ATOM | 1426 | CB | ALA | A | 185 | 33.205 | 37.441 | 34.674 | 0.50 | 16.01 | C |
| ATOM | 1427 | C | ALA | A | 185 | 34.090 | 35.093 | 34.708 | 0.50 | 16.19 | C |
| ATOM | 1428 | O | ALA | A | 185 | 34.898 | 34.679 | 35.543 | 0.50 | 15.99 | O |
| ATOM | 1429 | N | ASP | A | 186 | 33.047 | 34.376 | 34.295 | 1.00 | 16.76 | N |
| ATOM | 1430 | CA | ASP | A | 186 | 32.747 | 33.065 | 34.871 | 1.00 | 17.17 | C |
| ATOM | 1431 | CB | ASP | A | 186 | 31.333 | 32.617 | 34.495 | 1.00 | 18.01 | C |
| ATOM | 1432 | CG | ASP | A | 186 | 30.253 | 33.385 | 35.250 | 1.00 | 20.53 | C |
| ATOM | 1433 | OD1 | ASP | A | 186 | 29.093 | 33.383 | 34.788 | 1.00 | 24.87 | O |
| ATOM | 1434 | OD2 | ASP | A | 186 | 30.558 | 33.984 | 36.304 | 1.00 | 22.76 | O |
| ATOM | 1435 | C | ASP | A | 186 | 33.776 | 31.999 | 34.489 | 1.00 | 16.71 | C |
| ATOM | 1436 | O | ASP | A | 186 | 34.112 | 31.135 | 35.300 | 1.00 | 16.63 | O |
| ATOM | 1437 | N | VAL | A | 187 | 34.277 | 32.069 | 33.258 | 1.00 | 16.07 | N |
| ATOM | 1438 | CA | VAL | A | 187 | 35.321 | 31.155 | 32.801 | 1.00 | 15.75 | C |
| ATOM | 1439 | CB | VAL | A | 187 | 35.603 | 31.314 | 31.281 | 1.00 | 15.57 | C |
| ATOM | 1440 | CG1 | VAL | A | 187 | 36.850 | 30.536 | 30.876 | 1.00 | 15.34 | C |
| ATOM | 1441 | CG2 | VAL | A | 187 | 34.399 | 30.850 | 30.466 | 1.00 | 16.27 | C |
| ATOM | 1442 | C | VAL | A | 187 | 36.607 | 31.338 | 33.620 | 1.00 | 15.65 | C |
| ATOM | 1443 | O | VAL | A | 187 | 37.185 | 30.361 | 34.109 | 1.00 | 15.26 | O |
| ATOM | 1444 | N | TYR | A | 188 | 37.039 | 32.588 | 33.782 | 1.00 | 15.72 | N |

TABLE 6-continued

Coordinates of the crystal structure of *E. coli* ExoI bound to compound 9

| ATOM | 1445 | CA | TYR | A | 188 | 38.225 | 32.880 | 34.592 | 1.00 | 15.94 | C |
|---|---|---|---|---|---|---|---|---|---|---|---|
| ATOM | 1446 | CB | TYR | A | 188 | 38.624 | 34.355 | 34.486 | 1.00 | 16.66 | C |
| ATOM | 1447 | CG | TYR | A | 188 | 39.255 | 34.736 | 33.161 | 1.00 | 17.87 | C |
| ATOM | 1448 | CD1 | TYR | A | 188 | 40.247 | 33.941 | 32.578 | 1.00 | 19.04 | C |
| ATOM | 1449 | CE1 | TYR | A | 188 | 40.832 | 34.295 | 31.361 | 1.00 | 19.69 | C |
| ATOM | 1450 | CZ | TYR | A | 188 | 40.431 | 35.462 | 30.724 | 1.00 | 19.07 | C |
| ATOM | 1451 | OH | TYR | A | 188 | 41.004 | 35.821 | 29.528 | 1.00 | 19.55 | O |
| ATOM | 1452 | CE2 | TYR | A | 188 | 39.463 | 36.273 | 31.291 | 1.00 | 19.42 | C |
| ATOM | 1453 | CD2 | TYR | A | 188 | 38.879 | 35.907 | 32.503 | 1.00 | 18.86 | C |
| ATOM | 1454 | C | TYR | A | 188 | 38.043 | 32.478 | 36.055 | 1.00 | 15.58 | C |
| ATOM | 1455 | O | TYR | A | 188 | 38.977 | 31.979 | 36.684 | 1.00 | 15.53 | O |
| ATOM | 1456 | N | ALA | A | 189 | 36.840 | 32.684 | 36.588 | 1.00 | 15.26 | N |
| ATOM | 1457 | CA | ALA | A | 189 | 36.532 | 32.286 | 37.966 | 1.00 | 15.06 | C |
| ATOM | 1458 | CB | ALA | A | 189 | 35.171 | 32.818 | 38.389 | 1.00 | 15.29 | C |
| ATOM | 1459 | C | ALA | A | 189 | 36.597 | 30.770 | 38.149 | 1.00 | 15.16 | C |
| ATOM | 1460 | O | ALA | A | 189 | 37.005 | 30.284 | 39.203 | 1.00 | 15.23 | O |
| ATOM | 1461 | N | THR | A | 190 | 36.192 | 30.032 | 37.118 | 1.00 | 14.75 | N |
| ATOM | 1462 | CA | THR | A | 190 | 36.226 | 28.572 | 37.156 | 1.00 | 14.73 | C |
| ATOM | 1463 | CB | THR | A | 190 | 35.431 | 27.959 | 35.974 | 1.00 | 14.76 | C |
| ATOM | 1464 | OG1 | THR | A | 190 | 34.093 | 28.472 | 35.985 | 1.00 | 15.21 | O |
| ATOM | 1465 | CG2 | THR | A | 190 | 35.382 | 26.447 | 36.076 | 1.00 | 14.43 | C |
| ATOM | 1466 | C | THR | A | 190 | 37.671 | 28.064 | 37.173 | 1.00 | 14.68 | C |
| ATOM | 1467 | O | THR | A | 190 | 38.000 | 27.133 | 37.913 | 1.00 | 14.85 | O |
| ATOM | 1468 | N | ILE | A | 191 | 38.529 | 28.692 | 36.367 | 1.00 | 14.61 | N |
| ATOM | 1469 | CA | ILE | A | 191 | 39.963 | 28.389 | 36.376 | 1.00 | 14.67 | C |
| ATOM | 1470 | CB | ILE | A | 191 | 40.730 | 29.209 | 35.304 | 1.00 | 14.63 | C |
| ATOM | 1471 | CG1 | ILE | A | 191 | 40.224 | 28.860 | 33.900 | 1.00 | 14.62 | C |
| ATOM | 1472 | CD1 | ILE | A | 191 | 40.755 | 29.772 | 32.801 | 1.00 | 14.39 | C |
| ATOM | 1473 | CG2 | ILE | A | 191 | 42.247 | 28.965 | 35.409 | 1.00 | 14.95 | C |
| ATOM | 1474 | C | ILE | A | 191 | 40.552 | 28.650 | 37.771 | 1.00 | 14.94 | C |
| ATOM | 1475 | O | ILE | A | 191 | 41.341 | 27.844 | 38.282 | 1.00 | 14.89 | O |
| ATOM | 1476 | N | ALA | A | 192 | 40.143 | 29.762 | 38.384 | 1.00 | 15.33 | N |
| ATOM | 1477 | CA | ALA | A | 192 | 40.577 | 30.112 | 39.740 | 1.00 | 15.80 | C |
| ATOM | 1478 | CB | ALA | A | 192 | 40.033 | 31.480 | 40.139 | 1.00 | 15.69 | C |
| ATOM | 1479 | C | ALA | A | 192 | 40.169 | 29.053 | 40.764 | 1.00 | 15.95 | C |
| ATOM | 1480 | O | ALA | A | 192 | 40.933 | 28.743 | 41.679 | 1.00 | 16.20 | O |
| ATOM | 1481 | N | MET | A | 193 | 38.968 | 28.498 | 40.607 | 1.00 | 15.93 | N |
| ATOM | 1482 | CA | MET | A | 193 | 38.505 | 27.406 | 41.471 | 1.00 | 16.48 | C |
| ATOM | 1483 | CB | MET | A | 193 | 37.054 | 27.034 | 41.155 | 1.00 | 16.66 | C |
| ATOM | 1484 | CG | MET | A | 193 | 36.047 | 28.132 | 41.420 | 1.00 | 19.01 | C |
| ATOM | 1485 | SD | MET | A | 193 | 35.912 | 28.590 | 43.159 | 1.00 | 23.55 | S |
| ATOM | 1486 | CE | MET | A | 193 | 37.193 | 29.824 | 43.319 | 1.00 | 22.77 | C |
| ATOM | 1487 | C | MET | A | 193 | 39.389 | 26.177 | 41.331 | 1.00 | 16.02 | C |
| ATOM | 1488 | O | MET | A | 193 | 39.757 | 25.552 | 42.326 | 1.00 | 15.82 | O |
| ATOM | 1489 | N | ALA | A | 194 | 39.727 | 25.836 | 40.089 | 1.00 | 15.74 | N |
| ATOM | 1490 | CA | ALA | A | 194 | 40.583 | 24.690 | 39.815 | 1.00 | 15.59 | C |
| ATOM | 1491 | CB | ALA | A | 194 | 40.731 | 24.480 | 38.310 | 1.00 | 15.59 | C |
| ATOM | 1492 | C | ALA | A | 194 | 41.948 | 24.851 | 40.479 | 1.00 | 15.77 | C |
| ATOM | 1493 | O | ALA | A | 194 | 42.438 | 23.928 | 41.130 | 1.00 | 15.72 | O |
| ATOM | 1494 | N | LYS | A | 195 | 42.545 | 26.032 | 40.324 | 1.00 | 15.85 | N |
| ATOM | 1495 | CA | LYS | A | 195 | 43.837 | 26.332 | 40.940 | 1.00 | 16.01 | C |
| ATOM | 1496 | CB | LYS | A | 195 | 44.345 | 27.700 | 40.487 | 1.00 | 16.03 | C |
| ATOM | 1497 | CG | LYS | A | 195 | 44.771 | 27.760 | 39.038 | 1.00 | 17.42 | C |
| ATOM | 1498 | CD | LYS | A | 195 | 45.332 | 29.132 | 38.706 | 1.00 | 19.39 | C |
| ATOM | 1499 | CE | LYS | A | 195 | 45.617 | 29.280 | 37.228 | 1.00 | 20.86 | C |
| ATOM | 1500 | NZ | LYS | A | 195 | 46.055 | 30.666 | 36.909 | 1.00 | 22.55 | N |
| ATOM | 1501 | C | LYS | A | 195 | 43.746 | 26.291 | 42.461 | 1.00 | 15.97 | C |
| ATOM | 1502 | O | LYS | A | 195 | 44.650 | 25.789 | 43.131 | 1.00 | 16.10 | O |
| ATOM | 1503 | N | LEU | A | 196 | 42.645 | 26.815 | 42.996 | 1.00 | 15.90 | N |
| ATOM | 1504 | CA | LEU | A | 196 | 42.406 | 26.842 | 44.437 | 1.00 | 15.96 | C |
| ATOM | 1505 | CB | LEU | A | 196 | 41.049 | 27.494 | 44.731 | 1.00 | 16.10 | C |
| ATOM | 1506 | CG | LEU | A | 196 | 40.684 | 27.857 | 46.170 | 1.00 | 16.88 | C |
| ATOM | 1507 | CD1 | LEU | A | 196 | 41.606 | 28.941 | 46.710 | 1.00 | 17.76 | C |
| ATOM | 1508 | CD2 | LEU | A | 196 | 39.243 | 28.314 | 46.223 | 1.00 | 16.73 | C |
| ATOM | 1509 | C | LEU | A | 196 | 42.476 | 25.440 | 45.045 | 1.00 | 15.73 | C |
| ATOM | 1510 | O | LEU | A | 196 | 43.244 | 25.198 | 45.973 | 1.00 | 15.76 | O |
| ATOM | 1511 | N | VAL | A | 197 | 41.692 | 24.514 | 44.502 | 1.00 | 15.45 | N |
| ATOM | 1512 | CA | VAL | A | 197 | 41.652 | 23.152 | 45.030 | 1.00 | 15.55 | C |
| ATOM | 1513 | CB | VAL | A | 197 | 40.411 | 22.373 | 44.524 | 1.00 | 15.51 | C |
| ATOM | 1514 | CG1 | VAL | A | 197 | 40.378 | 20.971 | 45.110 | 1.00 | 16.33 | C |
| ATOM | 1515 | CG2 | VAL | A | 197 | 39.141 | 23.114 | 44.899 | 1.00 | 16.27 | C |
| ATOM | 1516 | C | VAL | A | 197 | 42.950 | 22.383 | 44.746 | 1.00 | 15.19 | C |
| ATOM | 1517 | O | VAL | A | 197 | 43.438 | 21.648 | 45.606 | 1.00 | 14.93 | O |
| ATOM | 1518 | N | LYS | A | 198 | 43.515 | 22.566 | 43.553 | 1.00 | 15.09 | N |
| ATOM | 1519 | CA | LYS | A | 198 | 44.767 | 21.893 | 43.197 | 1.00 | 15.16 | C |
| ATOM | 1520 | CB | LYS | A | 198 | 45.174 | 22.220 | 41.757 | 1.00 | 15.27 | C |
| ATOM | 1521 | CG | LYS | A | 198 | 46.399 | 21.453 | 41.257 | 1.00 | 16.41 | C |
| ATOM | 1522 | CD | LYS | A | 198 | 46.867 | 21.994 | 39.921 | 1.00 | 18.29 | C |

TABLE 6-continued

Coordinates of the crystal structure of *E. coli* ExoI bound to compound 9

| ATOM | 1523 | CE | LYS | A | 198 | 48.222 | 21.425 | 39.524 | 1.00 | 20.44 | C |
|------|------|-----|-----|---|-----|--------|--------|--------|------|-------|---|
| ATOM | 1524 | NZ | LYS | A | 198 | 48.095 | 20.129 | 38.812 | 1.00 | 21.73 | N |
| ATOM | 1525 | C | LYS | A | 198 | 45.887 | 22.275 | 44.163 | 1.00 | 15.12 | C |
| ATOM | 1526 | O | LYS | A | 198 | 46.683 | 21.427 | 44.567 | 1.00 | 15.32 | O |
| ATOM | 1527 | N | THR | A | 199 | 45.928 | 23.551 | 44.535 | 1.00 | 15.06 | N |
| ATOM | 1528 | CA | THR | A | 199 | 46.977 | 24.077 | 45.414 | 1.00 | 15.20 | C |
| ATOM | 1529 | CB | THR | A | 199 | 47.052 | 25.628 | 45.323 | 1.00 | 15.37 | C |
| ATOM | 1530 | OG1 | THR | A | 199 | 47.456 | 26.006 | 44.004 | 1.00 | 16.96 | O |
| ATOM | 1531 | CG2 | THR | A | 199 | 48.045 | 26.197 | 46.330 | 1.00 | 16.37 | C |
| ATOM | 1532 | C | THR | A | 199 | 46.775 | 23.653 | 46.868 | 1.00 | 14.86 | C |
| ATOM | 1533 | O | THR | A | 199 | 47.733 | 23.306 | 47.562 | 1.00 | 14.71 | O |
| ATOM | 1534 | N | ARG | A | 200 | 45.528 | 23.679 | 47.324 | 1.00 | 14.28 | N |
| ATOM | 1535 | CA | ARG | A | 200 | 45.245 | 23.538 | 48.748 | 1.00 | 13.96 | C |
| ATOM | 1536 | CB | ARG | A | 200 | 44.224 | 24.592 | 49.191 | 1.00 | 14.35 | C |
| ATOM | 1537 | CG | ARG | A | 200 | 44.701 | 26.007 | 48.849 | 1.00 | 15.23 | C |
| ATOM | 1538 | CD | ARG | A | 200 | 43.936 | 27.087 | 49.560 | 1.00 | 16.46 | C |
| ATOM | 1539 | NE | ARG | A | 200 | 44.247 | 28.395 | 48.988 | 1.00 | 16.30 | N |
| ATOM | 1540 | CZ | ARG | A | 200 | 43.671 | 29.538 | 49.352 | 1.00 | 16.74 | C |
| ATOM | 1541 | NH1 | ARG | A | 200 | 42.748 | 29.555 | 50.307 | 1.00 | 16.92 | N |
| ATOM | 1542 | NH2 | ARG | A | 200 | 44.017 | 30.666 | 48.751 | 1.00 | 16.62 | N |
| ATOM | 1543 | C | ARG | A | 200 | 44.847 | 22.131 | 49.164 | 1.00 | 13.42 | C |
| ATOM | 1544 | O | ARG | A | 200 | 45.007 | 21.751 | 50.326 | 1.00 | 13.05 | O |
| ATOM | 1545 | N | GLN | A | 201 | 44.353 | 21.345 | 48.208 | 1.00 | 12.67 | N |
| ATOM | 1546 | CA | GLN | A | 201 | 44.092 | 19.924 | 48.447 | 1.00 | 12.15 | C |
| ATOM | 1547 | CB | GLN | A | 201 | 42.595 | 19.676 | 48.711 | 1.00 | 12.05 | C |
| ATOM | 1548 | CG | GLN | A | 201 | 42.079 | 20.263 | 50.033 | 1.00 | 12.51 | C |
| ATOM | 1549 | CD | GLN | A | 201 | 42.724 | 19.632 | 51.272 | 1.00 | 12.82 | C |
| ATOM | 1550 | OE1 | GLN | A | 201 | 43.303 | 18.548 | 51.203 | 1.00 | 12.32 | O |
| ATOM | 1551 | NE2 | GLN | A | 201 | 42.595 | 20.303 | 52.415 | 1.00 | 13.25 | N |
| ATOM | 1552 | C | GLN | A | 201 | 44.600 | 19.071 | 47.279 | 1.00 | 12.14 | C |
| ATOM | 1553 | O | GLN | A | 201 | 43.805 | 18.482 | 46.544 | 1.00 | 11.55 | O |
| ATOM | 1554 | N | PRO | A | 202 | 45.938 | 19.003 | 47.109 | 1.00 | 11.99 | N |
| ATOM | 1555 | CA | PRO | A | 202 | 46.554 | 18.376 | 45.931 | 1.00 | 12.33 | C |
| ATOM | 1556 | CB | PRO | A | 202 | 48.054 | 18.436 | 46.240 | 1.00 | 12.38 | C |
| ATOM | 1557 | CG | PRO | A | 202 | 48.201 | 19.521 | 47.228 | 1.00 | 12.21 | C |
| ATOM | 1558 | CD | PRO | A | 202 | 46.955 | 19.536 | 48.039 | 1.00 | 12.19 | C |
| ATOM | 1559 | C | PRO | A | 202 | 46.130 | 16.930 | 45.685 | 1.00 | 12.58 | C |
| ATOM | 1560 | O | PRO | A | 202 | 45.815 | 16.572 | 44.549 | 1.00 | 12.77 | O |
| ATOM | 1561 | N | ARG | A | 203 | 46.136 | 16.107 | 46.731 | 1.00 | 12.83 | N |
| ATOM | 1562 | CA | ARG | A | 203 | 45.833 | 14.681 | 46.579 | 1.00 | 13.37 | C |
| ATOM | 1563 | CB | ARG | A | 203 | 46.199 | 13.898 | 47.842 | 1.00 | 13.92 | C |
| ATOM | 1564 | CG | ARG | A | 203 | 47.676 | 13.923 | 48.189 | 1.00 | 17.16 | C |
| ATOM | 1565 | CD | ARG | A | 203 | 48.511 | 13.059 | 47.262 | 1.00 | 21.11 | C |
| ATOM | 1566 | NE | ARG | A | 203 | 49.938 | 13.210 | 47.546 | 1.00 | 23.96 | N |
| ATOM | 1567 | CZ | ARG | A | 203 | 50.915 | 12.664 | 46.827 | 1.00 | 25.59 | C |
| ATOM | 1568 | NH1 | ARG | A | 203 | 50.630 | 11.920 | 45.764 | 1.00 | 26.84 | N |
| ATOM | 1569 | NH2 | ARG | A | 203 | 52.180 | 12.865 | 47.171 | 1.00 | 26.99 | N |
| ATOM | 1570 | C | ARG | A | 203 | 44.368 | 14.452 | 46.221 | 1.00 | 13.27 | C |
| ATOM | 1571 | O | ARG | A | 203 | 44.057 | 13.613 | 45.379 | 1.00 | 13.36 | O |
| ATOM | 1572 | N | LEU | A | 204 | 43.474 | 15.200 | 46.863 | 1.00 | 12.94 | N |
| ATOM | 1573 | CA | LEU | A | 204 | 42.053 | 15.104 | 46.545 | 1.00 | 13.16 | C |
| ATOM | 1574 | CB | LEU | A | 204 | 41.206 | 15.907 | 47.539 | 1.00 | 13.02 | C |
| ATOM | 1575 | CG | LEU | A | 204 | 39.684 | 15.861 | 47.322 | 1.00 | 13.22 | C |
| ATOM | 1576 | CD1 | LEU | A | 204 | 39.150 | 14.431 | 47.418 | 1.00 | 14.13 | C |
| ATOM | 1577 | CD2 | LEU | A | 204 | 38.967 | 16.775 | 48.301 | 1.00 | 13.97 | C |
| ATOM | 1578 | C | LEU | A | 204 | 41.780 | 15.558 | 45.114 | 1.00 | 13.30 | C |
| ATOM | 1579 | O | LEU | A | 204 | 41.032 | 14.907 | 44.387 | 1.00 | 13.36 | O |
| ATOM | 1580 | N | PHE | A | 205 | 42.398 | 16.667 | 44.712 | 1.00 | 13.44 | N |
| ATOM | 1581 | CA | PHE | A | 205 | 42.255 | 17.170 | 43.347 | 1.00 | 13.82 | C |
| ATOM | 1582 | CB | PHE | A | 205 | 43.074 | 18.448 | 43.147 | 1.00 | 14.20 | C |
| ATOM | 1583 | CG | PHE | A | 205 | 42.727 | 19.198 | 41.889 | 1.00 | 15.23 | C |
| ATOM | 1584 | CD1 | PHE | A | 205 | 41.625 | 20.046 | 41.852 | 1.00 | 16.70 | C |
| ATOM | 1585 | CE1 | PHE | A | 205 | 41.296 | 20.743 | 40.692 | 1.00 | 16.75 | C |
| ATOM | 1586 | CZ | PHE | A | 205 | 42.076 | 20.599 | 39.558 | 1.00 | 16.27 | C |
| ATOM | 1587 | CE2 | PHE | A | 205 | 43.178 | 19.755 | 39.577 | 1.00 | 16.65 | C |
| ATOM | 1588 | CD2 | PHE | A | 205 | 43.501 | 19.059 | 40.744 | 1.00 | 16.46 | C |
| ATOM | 1589 | C | PHE | A | 205 | 42.656 | 16.110 | 42.320 | 1.00 | 13.90 | C |
| ATOM | 1590 | O | PHE | A | 205 | 41.916 | 15.846 | 41.368 | 1.00 | 13.72 | O |
| ATOM | 1591 | N | ASP | A | 206 | 43.820 | 15.497 | 42.532 | 1.00 | 14.18 | N |
| ATOM | 1592 | CA | ASP | A | 206 | 44.323 | 14.446 | 41.649 | 1.00 | 14.63 | C |
| ATOM | 1593 | CB | ASP | A | 206 | 45.718 | 14.002 | 42.094 | 1.00 | 15.26 | C |
| ATOM | 1594 | CG | ASP | A | 206 | 46.789 | 15.031 | 41.776 | 1.00 | 18.22 | C |
| ATOM | 1595 | OD1 | ASP | A | 206 | 46.544 | 15.915 | 40.924 | 1.00 | 21.73 | O |
| ATOM | 1596 | OD2 | ASP | A | 206 | 47.885 | 14.954 | 42.374 | 1.00 | 21.57 | O |
| ATOM | 1597 | C | ASP | A | 206 | 43.379 | 13.251 | 41.618 | 1.00 | 14.13 | C |
| ATOM | 1598 | O | ASP | A | 206 | 43.085 | 12.708 | 40.548 | 1.00 | 13.94 | O |
| ATOM | 1599 | N | TYR | A | 207 | 42.901 | 12.847 | 42.792 | 1.00 | 13.73 | N |
| ATOM | 1600 | CA | TYR | A | 207 | 41.947 | 11.746 | 42.885 | 1.00 | 13.33 | C |

TABLE 6-continued

Coordinates of the crystal structure of *E. coli* ExoI bound to compound 9

| ATOM | 1601 | CB | TYR | A | 207 | 41.555 | 11.457 | 44.343 | 1.00 | 13.56 | C |
|---|---|---|---|---|---|---|---|---|---|---|---|
| ATOM | 1602 | CG | TYR | A | 207 | 40.488 | 10.390 | 44.448 | 1.00 | 13.43 | C |
| ATOM | 1603 | CD1 | TYR | A | 207 | 40.832 | 9.040 | 44.508 | 1.00 | 13.64 | C |
| ATOM | 1604 | CE1 | TYR | A | 207 | 39.857 | 8.055 | 44.583 | 1.00 | 13.66 | C |
| ATOM | 1605 | CZ | TYR | A | 207 | 38.516 | 8.418 | 44.586 | 1.00 | 14.26 | C |
| ATOM | 1606 | OH | TYR | A | 207 | 37.547 | 7.444 | 44.649 | 1.00 | 14.50 | O |
| ATOM | 1607 | CE2 | TYR | A | 207 | 38.147 | 9.748 | 44.520 | 1.00 | 14.19 | C |
| ATOM | 1608 | CD2 | TYR | A | 207 | 39.131 | 10.727 | 44.448 | 1.00 | 13.84 | C |
| ATOM | 1609 | C | TYR | A | 207 | 40.696 | 12.032 | 42.055 | 1.00 | 13.31 | C |
| ATOM | 1610 | O | TYR | A | 207 | 40.268 | 11.200 | 41.249 | 1.00 | 13.40 | O |
| ATOM | 1611 | N | LEU | A | 208 | 40.117 | 13.211 | 42.253 | 1.00 | 13.17 | N |
| ATOM | 1612 | CA | LEU | A | 208 | 38.884 | 13.572 | 41.557 | 1.00 | 13.25 | C |
| ATOM | 1613 | CB | LEU | A | 208 | 38.303 | 14.876 | 42.113 | 1.00 | 13.08 | C |
| ATOM | 1614 | CG | LEU | A | 208 | 37.833 | 14.811 | 43.573 | 1.00 | 13.39 | C |
| ATOM | 1615 | CD1 | LEU | A | 208 | 37.542 | 16.202 | 44.101 | 1.00 | 13.36 | C |
| ATOM | 1616 | CD2 | LEU | A | 208 | 36.609 | 13.903 | 43.745 | 1.00 | 14.58 | C |
| ATOM | 1617 | C | LEU | A | 208 | 39.081 | 13.647 | 40.043 | 1.00 | 13.37 | C |
| ATOM | 1618 | O | LEU | A | 208 | 38.236 | 13.172 | 39.276 | 1.00 | 13.64 | O |
| ATOM | 1619 | N | PHE | A | 209 | 40.206 | 14.218 | 39.615 | 1.00 | 13.50 | N |
| ATOM | 1620 | CA | PHE | A | 209 | 40.514 | 14.309 | 38.193 | 1.00 | 13.83 | C |
| ATOM | 1621 | CB | PHE | A | 209 | 41.785 | 15.131 | 37.964 | 1.00 | 13.80 | C |
| ATOM | 1622 | CG | PHE | A | 209 | 42.194 | 15.220 | 36.520 | 1.00 | 14.14 | C |
| ATOM | 1623 | CD1 | PHE | A | 209 | 41.404 | 15.907 | 35.598 | 1.00 | 15.00 | C |
| ATOM | 1624 | CE1 | PHE | A | 209 | 41.774 | 15.987 | 34.259 | 1.00 | 14.80 | C |
| ATOM | 1625 | CZ | PHE | A | 209 | 42.953 | 15.382 | 33.829 | 1.00 | 14.59 | C |
| ATOM | 1626 | CE2 | PHE | A | 209 | 43.750 | 14.691 | 34.740 | 1.00 | 14.91 | C |
| ATOM | 1627 | CD2 | PHE | A | 209 | 43.367 | 14.615 | 36.078 | 1.00 | 15.39 | C |
| ATOM | 1628 | C | PHE | A | 209 | 40.652 | 12.923 | 37.573 | 1.00 | 14.10 | C |
| ATOM | 1629 | O | PHE | A | 209 | 40.062 | 12.641 | 36.533 | 1.00 | 14.03 | O |
| ATOM | 1630 | N | THR | A | 210 | 41.409 | 12.053 | 38.232 | 1.00 | 14.49 | N |
| ATOM | 1631 | CA | THR | A | 210 | 41.620 | 10.698 | 37.732 | 1.00 | 15.15 | C |
| ATOM | 1632 | CB | THR | A | 210 | 42.648 | 9.940 | 38.602 | 1.00 | 15.28 | C |
| ATOM | 1633 | OG1 | THR | A | 210 | 43.931 | 10.570 | 38.471 | 1.00 | 17.01 | O |
| ATOM | 1634 | CG2 | THR | A | 210 | 42.763 | 8.480 | 38.173 | 1.00 | 16.94 | C |
| ATOM | 1635 | C | THR | A | 210 | 40.296 | 9.930 | 37.641 | 1.00 | 14.95 | C |
| ATOM | 1636 | O | THR | A | 210 | 40.066 | 9.175 | 36.692 | 1.00 | 15.26 | O |
| ATOM | 1637 | N | HIS | A | 211 | 39.411 | 10.164 | 38.601 | 1.00 | 14.91 | N |
| ATOM | 1638 | CA | HIS | A | 211 | 38.152 | 9.430 | 38.653 | 1.00 | 15.03 | C |
| ATOM | 1639 | CB | HIS | A | 211 | 37.768 | 9.130 | 40.101 | 1.00 | 15.04 | C |
| ATOM | 1640 | CG | HIS | A | 211 | 38.663 | 8.123 | 40.743 | 1.00 | 15.65 | C |
| ATOM | 1641 | ND1 | HIS | A | 211 | 38.294 | 6.807 | 40.926 | 1.00 | 17.36 | N |
| ATOM | 1642 | CE1 | HIS | A | 211 | 39.297 | 6.146 | 41.478 | 1.00 | 16.04 | C |
| ATOM | 1643 | NE2 | HIS | A | 211 | 40.308 | 6.980 | 41.637 | 1.00 | 17.36 | N |
| ATOM | 1644 | CD2 | HIS | A | 211 | 39.941 | 8.220 | 41.177 | 1.00 | 15.45 | C |
| ATOM | 1645 | C | HIS | A | 211 | 37.004 | 10.059 | 37.861 | 1.00 | 15.16 | C |
| ATOM | 1646 | O | HIS | A | 211 | 35.855 | 9.646 | 37.995 | 1.00 | 15.16 | O |
| ATOM | 1647 | N | ARG | A | 212 | 37.325 | 11.029 | 37.004 | 1.00 | 15.47 | N |
| ATOM | 1648 | CA | ARG | A | 212 | 36.362 | 11.500 | 36.010 | 1.00 | 15.93 | C |
| ATOM | 1649 | CB | ARG | A | 212 | 36.861 | 12.781 | 35.318 | 1.00 | 15.83 | C |
| ATOM | 1650 | CG | ARG | A | 212 | 37.836 | 12.560 | 34.167 | 1.00 | 15.45 | C |
| ATOM | 1651 | CD | ARG | A | 212 | 38.585 | 13.851 | 33.815 | 1.00 | 15.16 | C |
| ATOM | 1652 | NE | ARG | A | 212 | 39.478 | 13.685 | 32.666 | 1.00 | 14.75 | N |
| ATOM | 1653 | CZ | ARG | A | 212 | 40.663 | 13.076 | 32.709 | 1.00 | 14.33 | C |
| ATOM | 1654 | NH1 | ARG | A | 212 | 41.115 | 12.555 | 33.845 | 1.00 | 13.79 | N |
| ATOM | 1655 | NH2 | ARG | A | 212 | 41.398 | 12.981 | 31.608 | 1.00 | 14.22 | N |
| ATOM | 1656 | C | ARG | A | 212 | 36.105 | 10.381 | 34.990 | 1.00 | 16.76 | C |
| ATOM | 1657 | O | ARG | A | 212 | 35.056 | 10.340 | 34.343 | 1.00 | 17.51 | O |
| ATOM | 1658 | N | ASN | A | 213 | 37.075 | 9.473 | 34.883 | 1.00 | 17.38 | N |
| ATOM | 1659 | CA | ASN | A | 213 | 37.057 | 8.362 | 33.930 | 1.00 | 17.71 | C |
| ATOM | 1660 | CB | ASN | A | 213 | 38.497 | 7.850 | 33.736 | 1.00 | 18.26 | C |
| ATOM | 1661 | CG | ASN | A | 213 | 38.573 | 6.562 | 32.938 | 1.00 | 19.19 | C |
| ATOM | 1662 | OD1 | ASN | A | 213 | 38.395 | 5.475 | 33.482 | 1.00 | 21.02 | O |
| ATOM | 1663 | ND2 | ASN | A | 213 | 38.886 | 6.678 | 31.651 | 1.00 | 21.22 | N |
| ATOM | 1664 | C | ASN | A | 213 | 36.120 | 7.252 | 34.416 | 1.00 | 17.64 | C |
| ATOM | 1665 | O | ASN | A | 213 | 36.207 | 6.821 | 35.568 | 1.00 | 17.23 | O |
| ATOM | 1666 | N | LYS | A | 214 | 35.220 | 6.804 | 33.538 | 1.00 | 17.63 | N |
| ATOM | 1667 | CA | LYS | A | 214 | 34.179 | 5.837 | 33.922 | 1.00 | 17.91 | C |
| ATOM | 1668 | CB | LYS | A | 214 | 33.157 | 5.628 | 32.791 | 1.00 | 17.94 | C |
| ATOM | 1669 | CG | LYS | A | 214 | 33.705 | 4.960 | 31.533 | 1.00 | 19.15 | C |
| ATOM | 1670 | CD | LYS | A | 214 | 32.607 | 4.750 | 30.501 | 1.00 | 19.48 | C |
| ATOM | 1671 | CE | LYS | A | 214 | 33.054 | 3.808 | 29.394 | 1.00 | 21.33 | C |
| ATOM | 1672 | NZ | LYS | A | 214 | 32.047 | 3.736 | 28.295 | 1.00 | 22.45 | N |
| ATOM | 1673 | C | LYS | A | 214 | 34.728 | 4.496 | 34.411 | 1.00 | 17.51 | C |
| ATOM | 1674 | O | LYS | A | 214 | 34.127 | 3.865 | 35.272 | 1.00 | 17.26 | O |
| ATOM | 1675 | N | HIS | A | 215 | 35.869 | 4.071 | 33.869 | 1.00 | 17.45 | N |
| ATOM | 1676 | CA | HIS | A | 215 | 36.464 | 2.785 | 34.256 | 1.00 | 17.45 | C |
| ATOM | 1677 | CB | HIS | A | 215 | 37.553 | 2.353 | 33.266 | 1.00 | 17.81 | C |
| ATOM | 1678 | CG | HIS | A | 215 | 37.045 | 2.105 | 31.881 | 1.00 | 18.53 | C |

TABLE 6-continued

Coordinates of the crystal structure of *E. coli* ExoI bound to compound 9

| ATOM | 1679 | ND1 | HIS | A | 215 | 35.844 | 1.476 | 31.629 | 1.00 | 19.42 | N |
|---|---|---|---|---|---|---|---|---|---|---|---|
| ATOM | 1680 | CE1 | HIS | A | 215 | 35.661 | 1.391 | 30.323 | 1.00 | 19.31 | C |
| ATOM | 1681 | NE2 | HIS | A | 215 | 36.700 | 1.938 | 29.720 | 1.00 | 19.79 | N |
| ATOM | 1682 | CD2 | HIS | A | 215 | 37.582 | 2.388 | 30.672 | 1.00 | 18.99 | C |
| ATOM | 1683 | C | HIS | A | 215 | 37.013 | 2.810 | 35.675 | 1.00 | 17.43 | C |
| ATOM | 1684 | O | HIS | A | 215 | 36.917 | 1.819 | 36.403 | 1.00 | 17.34 | O |
| ATOM | 1685 | N | LYS | A | 216 | 37.586 | 3.947 | 36.064 | 1.00 | 17.36 | N |
| ATOM | 1686 | CA | LYS | A | 216 | 38.030 | 4.154 | 37.436 | 1.00 | 17.25 | C |
| ATOM | 1687 | CB | LYS | A | 216 | 38.781 | 5.484 | 37.568 | 1.00 | 17.50 | C |
| ATOM | 1688 | CG | LYS | A | 216 | 40.127 | 5.528 | 36.831 | 1.00 | 18.65 | C |
| ATOM | 1689 | CD | LYS | A | 216 | 41.132 | 4.512 | 37.383 | 1.00 | 21.49 | C |
| ATOM | 1690 | CE | LYS | A | 216 | 41.701 | 4.939 | 38.732 | 1.00 | 23.17 | C |
| ATOM | 1691 | NZ | LYS | A | 216 | 42.760 | 4.001 | 39.210 | 1.00 | 24.87 | N |
| ATOM | 1692 | C | LYS | A | 216 | 36.842 | 4.117 | 38.393 | 1.00 | 16.90 | C |
| ATOM | 1693 | O | LYS | A | 216 | 36.931 | 3.551 | 39.480 | 1.00 | 16.78 | O |
| ATOM | 1694 | N | LEU | A | 217 | 35.728 | 4.712 | 37.975 | 1.00 | 16.80 | N |
| ATOM | 1695 | CA | LEU | A | 217 | 34.510 | 4.706 | 38.783 | 1.00 | 16.79 | C |
| ATOM | 1696 | CB | LEU | A | 217 | 33.483 | 5.698 | 38.233 | 1.00 | 16.55 | C |
| ATOM | 1697 | CG | LEU | A | 217 | 33.850 | 7.182 | 38.326 | 1.00 | 16.10 | C |
| ATOM | 1698 | CD1 | LEU | A | 217 | 32.929 | 8.007 | 37.441 | 1.00 | 16.48 | C |
| ATOM | 1699 | CD2 | LEU | A | 217 | 33.820 | 7.691 | 39.773 | 1.00 | 14.81 | C |
| ATOM | 1700 | C | LEU | A | 217 | 33.899 | 3.314 | 38.890 | 1.00 | 17.13 | C |
| ATOM | 1701 | O | LEU | A | 217 | 33.500 | 2.894 | 39.973 | 1.00 | 17.09 | O |
| ATOM | 1702 | N | MET | A | 218 | 33.844 | 2.598 | 37.766 | 1.00 | 17.56 | N |
| ATOM | 1703 | CA | MET | A | 218 | 33.296 | 1.236 | 37.740 | 1.00 | 18.68 | C |
| ATOM | 1704 | CB | MET | A | 218 | 33.277 | 0.687 | 36.314 | 1.00 | 18.70 | C |
| ATOM | 1705 | CG | MET | A | 218 | 32.299 | 1.386 | 35.385 | 1.00 | 20.24 | C |
| ATOM | 1706 | SD | MET | A | 218 | 32.570 | 0.886 | 33.679 | 1.00 | 23.07 | S |
| ATOM | 1707 | CE | MET | A | 218 | 31.807 | 2.211 | 32.778 | 1.00 | 23.31 | C |
| ATOM | 1708 | C | MET | A | 218 | 34.065 | 0.282 | 38.655 | 1.00 | 18.02 | C |
| ATOM | 1709 | O | MET | A | 218 | 33.477 | −0.620 | 39.253 | 1.00 | 17.65 | O |
| ATOM | 1710 | N | ALA | A | 219 | 35.376 | 0.492 | 38.764 | 1.00 | 17.87 | N |
| ATOM | 1711 | CA | ALA | A | 219 | 36.224 | −0.330 | 39.630 | 1.00 | 17.92 | C |
| ATOM | 1712 | CB | ALA | A | 219 | 37.687 | 0.064 | 39.471 | 1.00 | 18.12 | C |
| ATOM | 1713 | C | ALA | A | 219 | 35.800 | −0.247 | 41.099 | 1.00 | 18.18 | C |
| ATOM | 1714 | O | ALA | A | 219 | 36.009 | −1.191 | 41.865 | 1.00 | 18.31 | O |
| ATOM | 1715 | N | LEU | A | 220 | 35.189 | 0.879 | 41.472 | 1.00 | 18.33 | N |
| ATOM | 1716 | CA | LEU | A | 220 | 34.705 | 1.098 | 42.842 | 1.00 | 18.72 | C |
| ATOM | 1717 | CB | LEU | A | 220 | 34.525 | 2.596 | 43.117 | 1.00 | 18.59 | C |
| ATOM | 1718 | CG | LEU | A | 220 | 35.749 | 3.514 | 43.031 | 1.00 | 18.98 | C |
| ATOM | 1719 | CD1 | LEU | A | 220 | 35.319 | 4.975 | 43.049 | 1.00 | 19.06 | C |
| ATOM | 1720 | CD2 | LEU | A | 220 | 36.728 | 3.229 | 44.160 | 1.00 | 20.15 | C |
| ATOM | 1721 | C | LEU | A | 220 | 33.384 | 0.391 | 43.107 | 1.00 | 18.96 | C |
| ATOM | 1722 | O | LEU | A | 220 | 32.982 | 0.228 | 44.260 | 1.00 | 18.98 | O |
| ATOM | 1723 | N | ILE | A | 221 | 32.705 | −0.009 | 42.037 | 1.00 | 19.39 | N |
| ATOM | 1724 | CA | ILE | A | 221 | 31.353 | −0.547 | 42.137 | 1.00 | 20.11 | C |
| ATOM | 1725 | CB | ILE | A | 221 | 30.476 | −0.093 | 40.936 | 1.00 | 20.08 | C |
| ATOM | 1726 | CG1 | ILE | A | 221 | 30.308 | 1.435 | 40.957 | 1.00 | 20.97 | C |
| ATOM | 1727 | CD1 | ILE | A | 221 | 29.762 | 2.031 | 39.673 | 1.00 | 21.54 | C |
| ATOM | 1728 | CG2 | ILE | A | 221 | 29.116 | −0.807 | 40.952 | 1.00 | 20.68 | C |
| ATOM | 1729 | C | ILE | A | 221 | 31.370 | −2.069 | 42.267 | 1.00 | 20.09 | C |
| ATOM | 1730 | O | ILE | A | 221 | 31.838 | −2.776 | 41.369 | 1.00 | 20.23 | O |
| ATOM | 1731 | N | ASP | A | 222 | 30.878 | −2.557 | 43.406 | 1.00 | 20.05 | N |
| ATOM | 1732 | CA | ASP | A | 222 | 30.749 | −3.989 | 43.658 | 1.00 | 20.18 | C |
| ATOM | 1733 | CB | ASP | A | 222 | 31.731 | −4.444 | 44.746 | 1.00 | 20.32 | C |
| ATOM | 1734 | CG | ASP | A | 222 | 31.927 | −5.958 | 44.775 | 1.00 | 21.08 | C |
| ATOM | 1735 | OD1 | ASP | A | 222 | 30.973 | −6.705 | 44.465 | 1.00 | 21.43 | O |
| ATOM | 1736 | OD2 | ASP | A | 222 | 33.042 | −6.403 | 45.120 | 1.00 | 22.80 | O |
| ATOM | 1737 | C | ASP | A | 222 | 29.311 | −4.309 | 44.058 | 1.00 | 19.87 | C |
| ATOM | 1738 | O | ASP | A | 222 | 28.956 | −4.281 | 45.241 | 1.00 | 19.86 | O |
| ATOM | 1739 | N | VAL | A | 223 | 28.493 | −4.608 | 43.055 | 1.00 | 19.69 | N |
| ATOM | 1740 | CA | VAL | A | 223 | 27.071 | −4.882 | 43.244 | 1.00 | 19.55 | C |
| ATOM | 1741 | CB | VAL | A | 223 | 26.315 | −4.935 | 41.877 | 1.00 | 19.60 | C |
| ATOM | 1742 | CG1 | VAL | A | 223 | 24.889 | −5.412 | 42.055 | 1.00 | 19.80 | C |
| ATOM | 1743 | CG2 | VAL | A | 223 | 26.338 | −3.565 | 41.200 | 1.00 | 20.04 | C |
| ATOM | 1744 | C | VAL | A | 223 | 26.795 | −6.145 | 44.093 | 1.00 | 19.53 | C |
| ATOM | 1745 | O | VAL | A | 223 | 25.989 | −6.090 | 45.025 | 1.00 | 19.19 | O |
| ATOM | 1746 | N | PRO | A | 224 | 27.456 | −7.285 | 43.773 | 1.00 | 19.47 | N |
| ATOM | 1747 | CA | PRO | A | 224 | 27.243 | −8.494 | 44.579 | 1.00 | 19.68 | C |
| ATOM | 1748 | CB | PRO | A | 224 | 28.238 | −9.496 | 43.977 | 1.00 | 19.61 | C |
| ATOM | 1749 | CG | PRO | A | 224 | 28.419 | −9.038 | 42.578 | 1.00 | 19.85 | C |
| ATOM | 1750 | CD | PRO | A | 224 | 28.388 | −7.542 | 42.656 | 1.00 | 19.51 | C |
| ATOM | 1751 | C | PRO | A | 224 | 27.514 | −8.307 | 46.078 | 1.00 | 19.80 | C |
| ATOM | 1752 | O | PRO | A | 224 | 26.817 | −8.900 | 46.904 | 1.00 | 19.94 | O |
| ATOM | 1753 | N | GLN | A | 225 | 28.507 | −7.485 | 46.419 | 1.00 | 20.05 | N |
| ATOM | 1754 | CA | GLN | A | 225 | 28.867 | −7.249 | 47.822 | 1.00 | 20.44 | C |
| ATOM | 1755 | CB | GLN | A | 225 | 30.376 | −7.006 | 47.964 | 1.00 | 20.89 | C |
| ATOM | 1756 | CG | GLN | A | 225 | 31.263 | −8.152 | 47.475 | 1.00 | 22.94 | C |

TABLE 6-continued

Coordinates of the crystal structure of *E. coli* ExoI bound to compound 9

| ATOM | 1757 | CD | GLN | A | 225 | 31.117 | −9.417 | 48.299 | 1.00 | 25.44 | C |
|---|---|---|---|---|---|---|---|---|---|---|---|
| ATOM | 1758 | OE1 | GLN | A | 225 | 31.025 | −9.369 | 49.527 | 1.00 | 27.59 | O |
| ATOM | 1759 | NE2 | GLN | A | 225 | 31.107 | −10.560 | 47.625 | 1.00 | 26.94 | N |
| ATOM | 1760 | C | GLN | A | 225 | 28.102 | −6.073 | 48.431 | 1.00 | 20.09 | C |
| ATOM | 1761 | O | GLN | A | 225 | 28.182 | −5.836 | 49.641 | 1.00 | 20.00 | O |
| ATOM | 1762 | N | MET | A | 226 | 27.363 | −5.341 | 47.591 | 1.00 | 19.78 | N |
| ATOM | 1763 | CA | MET | A | 226 | 26.747 | −4.065 | 47.985 | 1.00 | 19.76 | C |
| ATOM | 1764 | CB | MET | A | 226 | 25.530 | −4.287 | 48.901 | 1.00 | 19.68 | C |
| ATOM | 1765 | CG | MET | A | 226 | 24.396 | −5.089 | 48.282 | 1.00 | 20.20 | C |
| ATOM | 1766 | SD | MET | A | 226 | 22.960 | −5.112 | 49.374 | 1.00 | 20.94 | S |
| ATOM | 1767 | CE | MET | A | 226 | 21.951 | −6.384 | 48.614 | 1.00 | 20.50 | C |
| ATOM | 1768 | C | MET | A | 226 | 27.778 | −3.165 | 48.675 | 1.00 | 19.40 | C |
| ATOM | 1769 | O | MET | A | 226 | 27.476 | −2.506 | 49.672 | 1.00 | 19.22 | O |
| ATOM | 1770 | N | LYS | A | 227 | 28.997 | −3.151 | 48.138 | 1.00 | 18.93 | N |
| ATOM | 1771 | CA | LYS | A | 227 | 30.110 | −2.439 | 48.762 | 1.00 | 18.82 | C |
| ATOM | 1772 | CB | LYS | A | 227 | 31.404 | −2.649 | 47.971 | 1.00 | 18.94 | C |
| ATOM | 1773 | CG | LYS | A | 227 | 32.648 | −2.094 | 48.662 | 1.00 | 20.38 | C |
| ATOM | 1774 | CD | LYS | A | 227 | 33.930 | −2.458 | 47.921 | 1.00 | 21.14 | C |
| ATOM | 1775 | CE | LYS | A | 227 | 34.078 | −1.661 | 46.636 | 1.00 | 23.75 | C |
| ATOM | 1776 | NZ | LYS | A | 227 | 35.444 | −1.783 | 46.052 | 1.00 | 26.02 | N |
| ATOM | 1777 | C | LYS | A | 227 | 29.804 | −0.948 | 48.910 | 1.00 | 17.87 | C |
| ATOM | 1778 | O | LYS | A | 227 | 29.510 | −0.271 | 47.920 | 1.00 | 17.45 | O |
| ATOM | 1779 | N | PRO | A | 228 | 29.854 | −0.436 | 50.155 | 1.00 | 17.28 | N |
| ATOM | 1780 | CA | PRO | A | 228 | 29.503 | 0.957 | 50.416 | 1.00 | 16.78 | C |
| ATOM | 1781 | CB | PRO | A | 228 | 29.447 | 1.025 | 51.946 | 1.00 | 16.72 | C |
| ATOM | 1782 | CG | PRO | A | 228 | 30.361 | −0.052 | 52.400 | 1.00 | 17.10 | C |
| ATOM | 1783 | CD | PRO | A | 228 | 30.227 | −1.152 | 51.392 | 1.00 | 17.20 | C |
| ATOM | 1784 | C | PRO | A | 228 | 30.537 | 1.942 | 49.879 | 1.00 | 16.33 | C |
| ATOM | 1785 | O | PRO | A | 228 | 31.733 | 1.643 | 49.853 | 1.00 | 16.46 | O |
| ATOM | 1786 | N | LEU | A | 229 | 30.059 | 3.103 | 49.446 | 1.00 | 16.00 | N |
| ATOM | 1787 | CA | LEU | A | 229 | 30.916 | 4.159 | 48.934 | 1.00 | 15.53 | C |
| ATOM | 1788 | CB | LEU | A | 229 | 30.811 | 4.231 | 47.406 | 1.00 | 15.51 | C |
| ATOM | 1789 | CG | LEU | A | 229 | 31.265 | 3.017 | 46.589 | 1.00 | 15.86 | C |
| ATOM | 1790 | CD1 | LEU | A | 229 | 30.859 | 3.189 | 45.132 | 1.00 | 16.73 | C |
| ATOM | 1791 | CD2 | LEU | A | 229 | 32.774 | 2.795 | 46.707 | 1.00 | 16.88 | C |
| ATOM | 1792 | C | LEU | A | 229 | 30.475 | 5.485 | 49.516 | 1.00 | 15.49 | C |
| ATOM | 1793 | O | LEU | A | 229 | 29.295 | 5.673 | 49.813 | 1.00 | 15.72 | O |
| ATOM | 1794 | N | VAL | A | 230 | 31.413 | 6.413 | 49.671 | 1.00 | 15.38 | N |
| ATOM | 1795 | CA | VAL | A | 230 | 31.034 | 7.805 | 49.887 | 1.00 | 15.35 | C |
| ATOM | 1796 | CB | VAL | A | 230 | 32.135 | 8.633 | 50.627 | 1.00 | 15.63 | C |
| ATOM | 1797 | CG1 | VAL | A | 230 | 33.421 | 8.670 | 49.846 | 1.00 | 17.35 | C |
| ATOM | 1798 | CG2 | VAL | A | 230 | 31.642 | 10.049 | 50.913 | 1.00 | 16.44 | C |
| ATOM | 1799 | C | VAL | A | 230 | 30.663 | 8.431 | 48.541 | 1.00 | 14.90 | C |
| ATOM | 1800 | O | VAL | A | 230 | 31.346 | 8.221 | 47.535 | 1.00 | 14.97 | O |
| ATOM | 1801 | N | HIS | A | 231 | 29.556 | 9.164 | 48.528 | 1.00 | 14.44 | N |
| ATOM | 1802 | CA | HIS | A | 231 | 29.072 | 9.820 | 47.328 | 1.00 | 14.40 | C |
| ATOM | 1803 | CB | HIS | A | 231 | 27.843 | 9.064 | 46.785 | 1.00 | 14.52 | C |
| ATOM | 1804 | CG | HIS | A | 231 | 27.247 | 9.652 | 45.538 | 1.00 | 14.60 | C |
| ATOM | 1805 | ND1 | HIS | A | 231 | 28.008 | 10.151 | 44.501 | 1.00 | 15.15 | N |
| ATOM | 1806 | CE1 | HIS | A | 231 | 27.209 | 10.578 | 43.537 | 1.00 | 16.20 | C |
| ATOM | 1807 | NE2 | HIS | A | 231 | 25.960 | 10.352 | 43.900 | 1.00 | 15.71 | N |
| ATOM | 1808 | CD2 | HIS | A | 231 | 25.955 | 9.766 | 45.142 | 1.00 | 15.21 | C |
| ATOM | 1809 | C | HIS | A | 231 | 28.731 | 11.259 | 47.671 | 1.00 | 14.29 | C |
| ATOM | 1810 | O | HIS | A | 231 | 27.999 | 11.521 | 48.625 | 1.00 | 14.26 | O |
| ATOM | 1811 | N | VAL | A | 232 | 29.310 | 12.190 | 46.920 | 1.00 | 14.20 | N |
| ATOM | 1812 | CA | VAL | A | 232 | 28.996 | 13.606 | 47.060 | 1.00 | 14.34 | C |
| ATOM | 1813 | CB | VAL | A | 232 | 30.282 | 14.474 | 47.166 | 1.00 | 14.14 | C |
| ATOM | 1814 | CG1 | VAL | A | 232 | 29.929 | 15.952 | 47.329 | 1.00 | 15.14 | C |
| ATOM | 1815 | CG2 | VAL | A | 232 | 31.150 | 14.000 | 48.332 | 1.00 | 13.76 | C |
| ATOM | 1816 | C | VAL | A | 232 | 28.171 | 14.037 | 45.862 | 1.00 | 14.70 | C |
| ATOM | 1817 | O | VAL | A | 232 | 28.595 | 13.880 | 44.716 | 1.00 | 14.68 | O |
| ATOM | 1818 | N | SER | A | 233 | 26.984 | 14.571 | 46.133 | 1.00 | 15.02 | N |
| ATOM | 1819 | CA | SER | A | 233 | 26.034 | 14.910 | 45.086 | 1.00 | 15.78 | C |
| ATOM | 1820 | CB | SER | A | 233 | 25.188 | 13.685 | 44.730 | 1.00 | 16.03 | C |
| ATOM | 1821 | OG | SER | A | 233 | 24.145 | 14.023 | 43.831 | 1.00 | 17.78 | O |
| ATOM | 1822 | C | SER | A | 233 | 25.132 | 16.042 | 45.541 | 1.00 | 15.96 | C |
| ATOM | 1823 | O | SER | A | 233 | 24.666 | 16.051 | 46.683 | 1.00 | 15.66 | O |
| ATOM | 1824 | N | GLY | A | 234 | 24.879 | 16.989 | 44.639 | 1.00 | 16.47 | N |
| ATOM | 1825 | CA | GLY | A | 234 | 23.979 | 18.109 | 44.920 | 1.00 | 17.13 | C |
| ATOM | 1826 | C | GLY | A | 234 | 22.589 | 17.671 | 45.352 | 1.00 | 17.83 | C |
| ATOM | 1827 | O | GLY | A | 234 | 21.904 | 18.394 | 46.076 | 1.00 | 17.68 | O |
| ATOM | 1828 | N | MET | A | 235 | 22.184 | 16.477 | 44.917 | 1.00 | 18.31 | N |
| ATOM | 1829 | CA | MET | A | 235 | 20.874 | 15.916 | 45.270 | 1.00 | 19.90 | C |
| ATOM | 1830 | CB | MET | A | 235 | 20.604 | 14.633 | 44.479 | 1.00 | 19.87 | C |
| ATOM | 1831 | CG | MET | A | 235 | 20.636 | 14.806 | 42.971 | 1.00 | 22.46 | C |
| ATOM | 1832 | SD | MET | A | 235 | 19.943 | 13.392 | 42.091 | 1.00 | 26.93 | S |
| ATOM | 1833 | CE | MET | A | 235 | 18.184 | 13.616 | 42.377 | 1.00 | 27.02 | C |
| ATOM | 1834 | C | MET | A | 235 | 20.729 | 15.626 | 46.767 | 1.00 | 18.55 | C |

TABLE 6-continued

Coordinates of the crystal structure of *E. coli* ExoI bound to compound 9

| ATOM | 1835 | O | MET | A | 235 | 19.607 | 15.581 | 47.289 | 1.00 | 18.66 | O |
|---|---|---|---|---|---|---|---|---|---|---|---|
| ATOM | 1836 | N | PHE | A | 236 | 21.853 | 15.425 | 47.456 | 1.00 | 17.54 | N |
| ATOM | 1837 | CA | PHE | A | 236 | 21.819 | 15.129 | 48.888 | 1.00 | 16.56 | C |
| ATOM | 1838 | CB | PHE | A | 236 | 23.113 | 14.448 | 49.355 | 1.00 | 16.45 | C |
| ATOM | 1839 | CG | PHE | A | 236 | 23.252 | 13.015 | 48.900 | 1.00 | 16.34 | C |
| ATOM | 1840 | CD1 | PHE | A | 236 | 22.138 | 12.181 | 48.799 | 1.00 | 16.76 | C |
| ATOM | 1841 | CE1 | PHE | A | 236 | 22.271 | 10.851 | 48.382 | 1.00 | 17.06 | C |
| ATOM | 1842 | CZ | PHE | A | 236 | 23.530 | 10.341 | 48.084 | 1.00 | 16.76 | C |
| ATOM | 1843 | CE2 | PHE | A | 236 | 24.645 | 11.158 | 48.191 | 1.00 | 16.13 | C |
| ATOM | 1844 | CD2 | PHE | A | 236 | 24.505 | 12.488 | 48.605 | 1.00 | 15.86 | C |
| ATOM | 1845 | C | PHE | A | 236 | 21.511 | 16.358 | 49.743 | 1.00 | 16.31 | C |
| ATOM | 1846 | O | PHE | A | 236 | 20.946 | 16.232 | 50.830 | 1.00 | 16.55 | O |
| ATOM | 1847 | N | GLY | A | 237 | 21.877 | 17.539 | 49.248 | 1.00 | 15.77 | N |
| ATOM | 1848 | CA | GLY | A | 237 | 21.524 | 18.796 | 49.915 | 1.00 | 15.30 | C |
| ATOM | 1849 | C | GLY | A | 237 | 22.636 | 19.375 | 50.771 | 1.00 | 15.02 | C |
| ATOM | 1850 | O | GLY | A | 237 | 23.373 | 18.641 | 51.438 | 1.00 | 15.15 | O |
| ATOM | 1851 | N | ALA | A | 238 | 22.737 | 20.702 | 50.762 | 1.00 | 14.97 | N |
| ATOM | 1852 | CA | ALA | A | 238 | 23.798 | 21.415 | 51.475 | 1.00 | 14.74 | C |
| ATOM | 1853 | CB | ALA | A | 238 | 23.750 | 22.907 | 51.144 | 1.00 | 15.08 | C |
| ATOM | 1854 | C | ALA | A | 238 | 23.756 | 21.201 | 52.990 | 1.00 | 14.89 | C |
| ATOM | 1855 | O | ALA | A | 238 | 24.783 | 21.301 | 53.663 | 1.00 | 14.56 | O |
| ATOM | 1856 | N | TRP | A | 239 | 22.573 | 20.882 | 53.513 | 1.00 | 14.88 | N |
| ATOM | 1857 | CA | TRP | A | 239 | 22.390 | 20.696 | 54.952 | 1.00 | 15.05 | C |
| ATOM | 1858 | CB | TRP | A | 239 | 20.907 | 20.551 | 55.297 | 1.00 | 15.08 | C |
| ATOM | 1859 | CG | TRP | A | 239 | 20.225 | 19.398 | 54.617 | 1.00 | 15.39 | C |
| ATOM | 1860 | CD1 | TRP | A | 239 | 19.536 | 19.433 | 53.439 | 1.00 | 15.59 | C |
| ATOM | 1861 | NE1 | TRP | A | 239 | 19.039 | 18.190 | 53.141 | 1.00 | 16.02 | N |
| ATOM | 1862 | CE2 | TRP | A | 239 | 19.400 | 17.316 | 54.133 | 1.00 | 15.28 | C |
| ATOM | 1863 | CD2 | TRP | A | 239 | 20.145 | 18.045 | 55.086 | 1.00 | 15.37 | C |
| ATOM | 1864 | CE3 | TRP | A | 239 | 20.638 | 17.375 | 56.216 | 1.00 | 15.47 | C |
| ATOM | 1865 | CZ3 | TRP | A | 239 | 20.365 | 16.014 | 56.359 | 1.00 | 16.08 | C |
| ATOM | 1866 | CH2 | TRP | A | 239 | 19.620 | 15.319 | 55.390 | 1.00 | 16.34 | C |
| ATOM | 1867 | CZ2 | TRP | A | 239 | 19.128 | 15.950 | 54.275 | 1.00 | 16.37 | C |
| ATOM | 1868 | C | TRP | A | 239 | 23.190 | 19.524 | 55.517 | 1.00 | 15.04 | C |
| ATOM | 1869 | O | TRP | A | 239 | 23.469 | 19.481 | 56.721 | 1.00 | 15.45 | O |
| ATOM | 1870 | N | ARG | A | 240 | 23.543 | 18.575 | 54.649 | 1.00 | 14.96 | N |
| ATOM | 1871 | CA | ARG | A | 240 | 24.451 | 17.484 | 55.016 | 1.00 | 14.68 | C |
| ATOM | 1872 | CB | ARG | A | 240 | 23.758 | 16.113 | 54.916 | 1.00 | 14.96 | C |
| ATOM | 1873 | CG | ARG | A | 240 | 22.962 | 15.873 | 53.638 | 1.00 | 14.45 | C |
| ATOM | 1874 | CD | ARG | A | 240 | 22.520 | 14.422 | 53.553 | 1.00 | 15.27 | C |
| ATOM | 1875 | NE | ARG | A | 240 | 21.453 | 14.221 | 52.579 | 1.00 | 16.23 | N |
| ATOM | 1876 | CZ | ARG | A | 240 | 20.980 | 13.030 | 52.222 | 1.00 | 16.62 | C |
| ATOM | 1877 | NH1 | ARG | A | 240 | 21.486 | 11.923 | 52.753 | 1.00 | 16.98 | N |
| ATOM | 1878 | NH2 | ARG | A | 240 | 20.004 | 12.945 | 51.328 | 1.00 | 17.49 | N |
| ATOM | 1879 | C | ARG | A | 240 | 25.728 | 17.510 | 54.173 | 1.00 | 14.43 | C |
| ATOM | 1880 | O | ARG | A | 240 | 26.334 | 16.470 | 53.909 | 1.00 | 14.51 | O |
| ATOM | 1881 | N | GLY | A | 241 | 26.128 | 18.708 | 53.750 | 1.00 | 14.21 | N |
| ATOM | 1882 | CA | GLY | A | 241 | 27.324 | 18.872 | 52.928 | 1.00 | 14.05 | C |
| ATOM | 1883 | C | GLY | A | 241 | 27.291 | 18.029 | 51.666 | 1.00 | 14.02 | C |
| ATOM | 1884 | O | GLY | A | 241 | 28.332 | 17.576 | 51.188 | 1.00 | 14.10 | O |
| ATOM | 1885 | N | ASN | A | 242 | 26.085 | 17.809 | 51.134 | 1.00 | 13.71 | N |
| ATOM | 1886 | CA | ASN | A | 242 | 25.901 | 17.098 | 49.863 | 1.00 | 13.99 | C |
| ATOM | 1887 | CB | ASN | A | 242 | 26.517 | 17.905 | 48.710 | 1.00 | 13.75 | C |
| ATOM | 1888 | CG | ASN | A | 242 | 25.844 | 19.247 | 48.515 | 1.00 | 14.13 | C |
| ATOM | 1889 | OD1 | ASN | A | 242 | 24.635 | 19.323 | 48.312 | 1.00 | 14.64 | O |
| ATOM | 1890 | ND2 | ASN | A | 242 | 26.630 | 20.315 | 48.568 | 1.00 | 14.19 | N |
| ATOM | 1891 | C | ASN | A | 242 | 26.455 | 15.674 | 49.866 | 1.00 | 14.06 | C |
| ATOM | 1892 | O | ASN | A | 242 | 26.785 | 15.128 | 48.813 | 1.00 | 14.29 | O |
| ATOM | 1893 | N | THR | A | 243 | 26.518 | 15.062 | 51.045 | 1.00 | 14.19 | N |
| ATOM | 1894 | CA | THR | A | 243 | 27.267 | 13.822 | 51.217 | 1.00 | 14.72 | C |
| ATOM | 1895 | CB | THR | A | 243 | 28.577 | 14.090 | 51.989 | 1.00 | 14.75 | C |
| ATOM | 1896 | OG1 | THR | A | 243 | 29.384 | 14.993 | 51.229 | 1.00 | 15.13 | O |
| ATOM | 1897 | CG2 | THR | A | 243 | 29.361 | 12.801 | 52.229 | 1.00 | 15.83 | C |
| ATOM | 1898 | C | THR | A | 243 | 26.470 | 12.722 | 51.905 | 1.00 | 14.74 | C |
| ATOM | 1899 | O | THR | A | 243 | 25.675 | 12.984 | 52.812 | 1.00 | 14.79 | O |
| ATOM | 1900 | N | SER | A | 244 | 26.684 | 11.488 | 51.457 | 1.00 | 14.75 | N |
| ATOM | 1901 | CA | SER | A | 244 | 26.176 | 10.317 | 52.158 | 1.00 | 15.02 | C |
| ATOM | 1902 | CB | SER | A | 244 | 24.695 | 10.092 | 51.840 | 1.00 | 15.21 | C |
| ATOM | 1903 | OG | SER | A | 244 | 24.100 | 9.263 | 52.825 | 1.00 | 15.64 | O |
| ATOM | 1904 | C | SER | A | 244 | 26.977 | 9.076 | 51.801 | 1.00 | 15.30 | C |
| ATOM | 1905 | O | SER | A | 244 | 27.822 | 9.102 | 50.899 | 1.00 | 15.29 | O |
| ATOM | 1906 | N | TRP | A | 245 | 26.724 | 7.996 | 52.531 | 1.00 | 15.34 | N |
| ATOM | 1907 | CA | TRP | A | 245 | 27.194 | 6.682 | 52.135 | 1.00 | 15.69 | C |
| ATOM | 1908 | CB | TRP | A | 245 | 27.535 | 5.833 | 53.358 | 1.00 | 16.05 | C |
| ATOM | 1909 | CG | TRP | A | 245 | 28.886 | 6.120 | 53.943 | 1.00 | 16.43 | C |
| ATOM | 1910 | CD1 | TRP | A | 245 | 30.100 | 5.796 | 53.402 | 1.00 | 17.01 | C |
| ATOM | 1911 | NE1 | TRP | A | 245 | 31.113 | 6.212 | 54.229 | 1.00 | 17.52 | N |
| ATOM | 1912 | CE2 | TRP | A | 245 | 30.566 | 6.812 | 55.334 | 1.00 | 17.00 | C |

TABLE 6-continued

Coordinates of the crystal structure of *E. coli* ExoI bound to compound 9

| ATOM | 1913 | CD2 | TRP | A | 245 | 29.162 | 6.771 | 55.186 | 1.00 | 16.88 | C |
|---|---|---|---|---|---|---|---|---|---|---|---|
| ATOM | 1914 | CE3 | TRP | A | 245 | 28.359 | 7.325 | 56.193 | 1.00 | 17.00 | C |
| ATOM | 1915 | CZ3 | TRP | A | 245 | 28.977 | 7.895 | 57.301 | 1.00 | 16.84 | C |
| ATOM | 1916 | CH2 | TRP | A | 245 | 30.379 | 7.918 | 57.420 | 1.00 | 16.85 | C |
| ATOM | 1917 | CZ2 | TRP | A | 245 | 31.188 | 7.385 | 56.451 | 1.00 | 16.77 | C |
| ATOM | 1918 | C | TRP | A | 245 | 26.113 | 6.002 | 51.309 | 1.00 | 15.83 | C |
| ATOM | 1919 | O | TRP | A | 245 | 24.929 | 6.039 | 51.666 | 1.00 | 16.01 | O |
| ATOM | 1920 | N | VAL | A | 246 | 26.522 | 5.404 | 50.194 | 1.00 | 15.86 | N |
| ATOM | 1921 | CA | VAL | A | 246 | 25.600 | 4.704 | 49.302 | 1.00 | 16.17 | C |
| ATOM | 1922 | CB | VAL | A | 246 | 25.447 | 5.433 | 47.936 | 1.00 | 16.13 | C |
| ATOM | 1923 | CG1 | VAL | A | 246 | 24.817 | 6.804 | 48.123 | 1.00 | 15.98 | C |
| ATOM | 1924 | CG2 | VAL | A | 246 | 26.798 | 5.546 | 47.215 | 1.00 | 15.47 | C |
| ATOM | 1925 | C | VAL | A | 246 | 26.046 | 3.263 | 49.059 | 1.00 | 16.48 | C |
| ATOM | 1926 | O | VAL | A | 246 | 27.220 | 2.930 | 49.232 | 1.00 | 16.67 | O |
| ATOM | 1927 | N | ALA | A | 247 | 25.101 | 2.414 | 48.665 | 1.00 | 16.71 | N |
| ATOM | 1928 | CA | ALA | A | 247 | 25.421 | 1.048 | 48.251 | 1.00 | 17.14 | C |
| ATOM | 1929 | CB | ALA | A | 247 | 25.017 | 0.049 | 49.329 | 1.00 | 17.29 | C |
| ATOM | 1930 | C | ALA | A | 247 | 24.733 | 0.722 | 46.930 | 1.00 | 17.43 | C |
| ATOM | 1931 | O | ALA | A | 247 | 23.554 | 1.041 | 46.752 | 1.00 | 17.42 | O |
| ATOM | 1932 | N | PRO | A | 248 | 25.475 | 0.103 | 45.987 | 1.00 | 17.73 | N |
| ATOM | 1933 | CA | PRO | A | 248 | 24.898 | −0.307 | 44.708 | 1.00 | 18.09 | C |
| ATOM | 1934 | CB | PRO | A | 248 | 26.130 | −0.540 | 43.828 | 1.00 | 18.22 | C |
| ATOM | 1935 | CG | PRO | A | 248 | 27.192 | −0.942 | 44.776 | 1.00 | 17.84 | C |
| ATOM | 1936 | CD | PRO | A | 248 | 26.914 | −0.217 | 46.071 | 1.00 | 17.92 | C |
| ATOM | 1937 | C | PRO | A | 248 | 24.073 | −1.586 | 44.833 | 1.00 | 18.53 | C |
| ATOM | 1938 | O | PRO | A | 248 | 24.560 | −2.594 | 45.357 | 1.00 | 18.97 | O |
| ATOM | 1939 | N | LEU | A | 249 | 22.830 | −1.531 | 44.366 | 1.00 | 18.90 | N |
| ATOM | 1940 | CA | LEU | A | 249 | 21.934 | −2.687 | 44.412 | 1.00 | 19.29 | C |
| ATOM | 1941 | CB | LEU | A | 249 | 20.519 | −2.261 | 44.806 | 1.00 | 19.62 | C |
| ATOM | 1942 | CG | LEU | A | 249 | 20.209 | −1.960 | 46.272 | 1.00 | 20.98 | C |
| ATOM | 1943 | CD1 | LEU | A | 249 | 18.718 | −1.733 | 46.428 | 1.00 | 22.37 | C |
| ATOM | 1944 | CD2 | LEU | A | 249 | 20.668 | −3.086 | 47.186 | 1.00 | 22.46 | C |
| ATOM | 1945 | C | LEU | A | 249 | 21.883 | −3.426 | 43.082 | 1.00 | 19.13 | C |
| ATOM | 1946 | O | LEU | A | 249 | 21.780 | −4.654 | 43.048 | 1.00 | 19.16 | O |
| ATOM | 1947 | N | ALA | A | 250 | 21.926 | −2.666 | 41.990 | 1.00 | 19.03 | N |
| ATOM | 1948 | CA | ALA | A | 250 | 21.832 | −3.222 | 40.643 | 1.00 | 18.99 | C |
| ATOM | 1949 | CB | ALA | A | 250 | 20.463 | −3.856 | 40.423 | 1.00 | 19.20 | C |
| ATOM | 1950 | C | ALA | A | 250 | 22.073 | −2.134 | 39.613 | 1.00 | 18.99 | C |
| ATOM | 1951 | O | ALA | A | 250 | 22.049 | −0.949 | 39.935 | 1.00 | 19.17 | O |
| ATOM | 1952 | N | TRP | A | 251 | 22.300 | −2.545 | 38.372 | 1.00 | 18.96 | N |
| ATOM | 1953 | CA | TRP | A | 251 | 22.410 | −1.611 | 37.267 | 1.00 | 19.14 | C |
| ATOM | 1954 | CB | TRP | A | 251 | 23.402 | −2.133 | 36.232 | 1.00 | 19.09 | C |
| ATOM | 1955 | CG | TRP | A | 251 | 24.804 | −2.019 | 36.701 | 1.00 | 19.05 | C |
| ATOM | 1956 | CD1 | TRP | A | 251 | 25.477 | −2.896 | 37.504 | 1.00 | 18.96 | C |
| ATOM | 1957 | NE1 | TRP | A | 251 | 26.754 | −2.441 | 37.735 | 1.00 | 18.93 | N |
| ATOM | 1958 | CE2 | TRP | A | 251 | 26.923 | −1.246 | 37.085 | 1.00 | 19.18 | C |
| ATOM | 1959 | CD2 | TRP | A | 251 | 25.710 | −0.948 | 36.426 | 1.00 | 18.63 | C |
| ATOM | 1960 | CE3 | TRP | A | 251 | 25.618 | 0.234 | 35.677 | 1.00 | 18.82 | C |
| ATOM | 1961 | CZ3 | TRP | A | 251 | 26.727 | 1.071 | 35.616 | 1.00 | 19.08 | C |
| ATOM | 1962 | CH2 | TRP | A | 251 | 27.919 | 0.747 | 36.282 | 1.00 | 19.76 | C |
| ATOM | 1963 | CZ2 | TRP | A | 251 | 28.037 | −0.403 | 37.021 | 1.00 | 19.19 | C |
| ATOM | 1964 | C | TRP | A | 251 | 21.051 | −1.348 | 36.636 | 1.00 | 19.55 | C |
| ATOM | 1965 | O | TRP | A | 251 | 20.180 | −2.223 | 36.630 | 1.00 | 19.41 | O |
| ATOM | 1966 | N | HIS | A | 252 | 20.872 | −0.131 | 36.128 | 1.00 | 20.04 | N |
| ATOM | 1967 | CA | HIS | A | 252 | 19.635 | 0.275 | 35.463 | 1.00 | 20.98 | C |
| ATOM | 1968 | CB | HIS | A | 252 | 19.780 | 1.705 | 34.934 | 1.00 | 20.99 | C |
| ATOM | 1969 | CG | HIS | A | 252 | 18.480 | 2.369 | 34.601 | 1.00 | 21.68 | C |
| ATOM | 1970 | ND1 | HIS | A | 252 | 17.736 | 2.037 | 33.489 | 1.00 | 22.07 | N |
| ATOM | 1971 | CE1 | HIS | A | 252 | 16.654 | 2.793 | 33.444 | 1.00 | 22.45 | C |
| ATOM | 1972 | NE2 | HIS | A | 252 | 16.672 | 3.609 | 34.482 | 1.00 | 22.56 | N |
| ATOM | 1973 | CD2 | HIS | A | 252 | 17.806 | 3.367 | 35.220 | 1.00 | 22.29 | C |
| ATOM | 1974 | C | HIS | A | 252 | 19.309 | −0.689 | 34.315 | 1.00 | 21.35 | C |
| ATOM | 1975 | O | HIS | A | 252 | 20.181 | −0.999 | 33.501 | 1.00 | 21.32 | O |
| ATOM | 1976 | N | PRO | A | 253 | 18.052 | −1.178 | 34.256 | 1.00 | 21.99 | N |
| ATOM | 1977 | CA | PRO | A | 253 | 17.661 | −2.187 | 33.259 | 1.00 | 22.43 | C |
| ATOM | 1978 | CB | PRO | A | 253 | 16.200 | −2.493 | 33.621 | 1.00 | 22.38 | C |
| ATOM | 1979 | CG | PRO | A | 253 | 15.736 | −1.308 | 34.390 | 1.00 | 22.25 | C |
| ATOM | 1980 | CD | PRO | A | 253 | 16.930 | −0.822 | 35.144 | 1.00 | 21.98 | C |
| ATOM | 1981 | C | PRO | A | 253 | 17.764 | −1.720 | 31.801 | 1.00 | 22.95 | C |
| ATOM | 1982 | O | PRO | A | 253 | 17.895 | −2.554 | 30.900 | 1.00 | 23.24 | O |
| ATOM | 1983 | N | GLU | A | 254 | 17.706 | −0.408 | 31.575 | 1.00 | 23.34 | N |
| ATOM | 1984 | CA | GLU | A | 254 | 17.765 | 0.139 | 30.216 | 1.00 | 23.86 | C |
| ATOM | 1985 | CB | GLU | A | 254 | 16.459 | 0.862 | 29.855 | 1.00 | 24.08 | C |
| ATOM | 1986 | CG | GLU | A | 254 | 15.205 | −0.028 | 29.874 | 1.00 | 25.50 | C |
| ATOM | 1987 | CD | GLU | A | 254 | 15.238 | −1.156 | 28.844 | 1.00 | 27.12 | C |
| ATOM | 1988 | OE1 | GLU | A | 254 | 15.884 | −0.994 | 27.784 | 1.00 | 28.18 | O |
| ATOM | 1989 | OE2 | GLU | A | 254 | 14.602 | −2.204 | 29.092 | 1.00 | 28.43 | O |
| ATOM | 1990 | C | GLU | A | 254 | 18.970 | 1.050 | 29.985 | 1.00 | 23.73 | C |

TABLE 6-continued

Coordinates of the crystal structure of *E. coli* ExoI bound to compound 9

| ATOM | 1991 | O | GLU | A | 254 | 19.635 | 0.958 | 28.949 | 1.00 | 24.16 | O |
|---|---|---|---|---|---|---|---|---|---|---|---|
| ATOM | 1992 | N | ASN | A | 255 | 19.245 | 1.929 | 30.948 | 1.00 | 23.41 | N |
| ATOM | 1993 | CA | ASN | A | 255 | 20.369 | 2.857 | 30.849 | 1.00 | 22.98 | C |
| ATOM | 1994 | CB | ASN | A | 255 | 20.151 | 4.075 | 31.760 | 1.00 | 23.09 | C |
| ATOM | 1995 | CG | ASN | A | 255 | 21.168 | 5.193 | 31.514 | 1.00 | 23.12 | C |
| ATOM | 1996 | OD1 | ASN | A | 255 | 22.264 | 4.960 | 31.004 | 1.00 | 23.00 | O |
| ATOM | 1997 | ND2 | ASN | A | 255 | 20.801 | 6.413 | 31.890 | 1.00 | 23.76 | N |
| ATOM | 1998 | C | ASN | A | 255 | 21.691 | 2.164 | 31.174 | 1.00 | 22.78 | C |
| ATOM | 1999 | O | ASN | A | 255 | 21.954 | 1.813 | 32.324 | 1.00 | 22.55 | O |
| ATOM | 2000 | N | ARG | A | 256 | 22.517 | 1.989 | 30.146 | 1.00 | 22.49 | N |
| ATOM | 2001 | CA | ARG | A | 256 | 23.775 | 1.244 | 30.245 | 1.00 | 22.40 | C |
| ATOM | 2002 | CB | ARG | A | 256 | 24.401 | 1.101 | 28.849 | 1.00 | 22.38 | C |
| ATOM | 2003 | CG | ARG | A | 256 | 25.431 | −0.013 | 28.718 | 1.00 | 23.43 | C |
| ATOM | 2004 | CD | ARG | A | 256 | 25.793 | −0.267 | 27.258 | 1.00 | 23.57 | C |
| ATOM | 2005 | NE | ARG | A | 256 | 26.850 | −1.270 | 27.121 | 1.00 | 25.65 | N |
| ATOM | 2006 | CZ | ARG | A | 256 | 27.287 | −1.755 | 25.960 | 1.00 | 26.46 | C |
| ATOM | 2007 | NH1 | ARG | A | 256 | 26.761 | −1.339 | 24.814 | 1.00 | 26.98 | N |
| ATOM | 2008 | NH2 | ARG | A | 256 | 28.252 | −2.666 | 25.945 | 1.00 | 27.03 | N |
| ATOM | 2009 | C | ARG | A | 256 | 24.780 | 1.883 | 31.214 | 1.00 | 21.84 | C |
| ATOM | 2010 | O | ARG | A | 256 | 25.665 | 1.204 | 31.739 | 1.00 | 21.63 | O |
| ATOM | 2011 | N | ASN | A | 257 | 24.632 | 3.185 | 31.452 | 1.00 | 21.28 | N |
| ATOM | 2012 | CA | ASN | A | 257 | 25.610 | 3.941 | 32.237 | 1.00 | 20.85 | C |
| ATOM | 2013 | CB | ASN | A | 257 | 26.105 | 5.155 | 31.439 | 1.00 | 21.32 | C |
| ATOM | 2014 | CG | ASN | A | 257 | 26.792 | 4.761 | 30.144 | 1.00 | 22.40 | C |
| ATOM | 2015 | OD1 | ASN | A | 257 | 26.311 | 5.074 | 29.051 | 1.00 | 24.76 | O |
| ATOM | 2016 | ND2 | ASN | A | 257 | 27.915 | 4.058 | 30.258 | 1.00 | 24.27 | N |
| ATOM | 2017 | C | ASN | A | 257 | 25.123 | 4.374 | 33.624 | 1.00 | 20.06 | C |
| ATOM | 2018 | O | ASN | A | 257 | 25.797 | 5.140 | 34.312 | 1.00 | 20.29 | O |
| ATOM | 2019 | N | ALA | A | 258 | 23.962 | 3.874 | 34.038 | 1.00 | 19.22 | N |
| ATOM | 2020 | CA | ALA | A | 258 | 23.401 | 4.233 | 35.338 | 1.00 | 18.54 | C |
| ATOM | 2021 | CB | ALA | A | 258 | 22.021 | 4.865 | 35.172 | 1.00 | 18.61 | C |
| ATOM | 2022 | C | ALA | A | 258 | 23.333 | 3.044 | 36.288 | 1.00 | 18.22 | C |
| ATOM | 2023 | O | ALA | A | 258 | 22.813 | 1.983 | 35.936 | 1.00 | 17.88 | O |
| ATOM | 2024 | N | VAL | A | 259 | 23.873 | 3.230 | 37.489 | 1.00 | 17.80 | N |
| ATOM | 2025 | CA | VAL | A | 259 | 23.763 | 2.235 | 38.551 | 1.00 | 18.02 | C |
| ATOM | 2026 | CB | VAL | A | 259 | 25.159 | 1.904 | 39.190 | 1.00 | 18.16 | C |
| ATOM | 2027 | CG1 | VAL | A | 259 | 25.795 | 3.136 | 39.817 | 1.00 | 19.20 | C |
| ATOM | 2028 | CG2 | VAL | A | 259 | 25.051 | 0.765 | 40.199 | 1.00 | 18.50 | C |
| ATOM | 2029 | C | VAL | A | 259 | 22.742 | 2.701 | 39.597 | 1.00 | 17.69 | C |
| ATOM | 2030 | O | VAL | A | 259 | 22.644 | 3.896 | 39.894 | 1.00 | 17.39 | O |
| ATOM | 2031 | N | ILE | A | 260 | 21.958 | 1.759 | 40.115 | 1.00 | 17.65 | N |
| ATOM | 2032 | CA | ILE | A | 260 | 20.954 | 2.071 | 41.124 | 1.00 | 17.83 | C |
| ATOM | 2033 | CB | ILE | A | 260 | 19.723 | 1.133 | 41.033 | 1.00 | 17.76 | C |
| ATOM | 2034 | CG1 | ILE | A | 260 | 19.160 | 1.117 | 39.607 | 1.00 | 17.88 | C |
| ATOM | 2035 | CD1 | ILE | A | 260 | 18.193 | −0.030 | 39.331 | 1.00 | 17.61 | C |
| ATOM | 2036 | CG2 | ILE | A | 260 | 18.659 | 1.560 | 42.039 | 1.00 | 17.70 | C |
| ATOM | 2037 | C | ILE | A | 260 | 21.567 | 1.974 | 42.514 | 1.00 | 18.01 | C |
| ATOM | 2038 | O | ILE | A | 260 | 21.998 | 0.897 | 42.942 | 1.00 | 18.20 | O |
| ATOM | 2039 | N | MET | A | 261 | 21.614 | 3.111 | 43.206 | 1.00 | 18.18 | N |
| ATOM | 2040 | CA | MET | A | 261 | 22.194 | 3.198 | 44.541 | 1.00 | 18.49 | C |
| ATOM | 2041 | CB | MET | A | 261 | 23.139 | 4.397 | 44.629 | 1.00 | 18.95 | C |
| ATOM | 2042 | CG | MET | A | 261 | 24.328 | 4.323 | 43.705 | 1.00 | 20.24 | C |
| ATOM | 2043 | SD | MET | A | 261 | 25.596 | 3.232 | 44.346 | 1.00 | 21.93 | S |
| ATOM | 2044 | CE | MET | A | 261 | 27.037 | 3.847 | 43.478 | 1.00 | 21.25 | C |
| ATOM | 2045 | C | MET | A | 261 | 21.114 | 3.355 | 45.594 | 1.00 | 18.31 | C |
| ATOM | 2046 | O | MET | A | 261 | 20.047 | 3.901 | 45.320 | 1.00 | 18.35 | O |
| ATOM | 2047 | N | VAL | A | 262 | 21.403 | 2.881 | 46.802 | 1.00 | 17.89 | N |
| ATOM | 2048 | CA | VAL | A | 262 | 20.582 | 3.200 | 47.962 | 1.00 | 17.97 | C |
| ATOM | 2049 | CB | VAL | A | 262 | 20.172 | 1.927 | 48.753 | 1.00 | 18.03 | C |
| ATOM | 2050 | CG1 | VAL | A | 262 | 19.474 | 2.297 | 50.057 | 1.00 | 18.35 | C |
| ATOM | 2051 | CG2 | VAL | A | 262 | 19.270 | 1.062 | 47.916 | 1.00 | 19.01 | C |
| ATOM | 2052 | C | VAL | A | 262 | 21.349 | 4.161 | 48.862 | 1.00 | 17.61 | C |
| ATOM | 2053 | O | VAL | A | 262 | 22.535 | 3.955 | 49.138 | 1.00 | 17.21 | O |
| ATOM | 2054 | N | ASP | A | 263 | 20.679 | 5.232 | 49.279 | 1.00 | 17.43 | N |
| ATOM | 2055 | CA | ASP | A | 263 | 21.227 | 6.142 | 50.271 | 1.00 | 17.72 | C |
| ATOM | 2056 | CB | ASP | A | 263 | 20.490 | 7.487 | 50.231 | 1.00 | 17.57 | C |
| ATOM | 2057 | CG | ASP | A | 263 | 21.002 | 8.471 | 51.272 | 1.00 | 18.01 | C |
| ATOM | 2058 | OD1 | ASP | A | 263 | 21.948 | 8.134 | 52.014 | 1.00 | 16.76 | O |
| ATOM | 2059 | OD2 | ASP | A | 263 | 20.446 | 9.586 | 51.355 | 1.00 | 19.03 | O |
| ATOM | 2060 | C | ASP | A | 263 | 21.107 | 5.492 | 51.643 | 1.00 | 17.65 | C |
| ATOM | 2061 | O | ASP | A | 263 | 20.004 | 5.350 | 52.185 | 1.00 | 17.86 | O |
| ATOM | 2062 | N | LEU | A | 264 | 22.248 | 5.093 | 52.199 | 1.00 | 17.66 | N |
| ATOM | 2063 | CA | LEU | A | 264 | 22.268 | 4.346 | 53.458 | 1.00 | 17.44 | C |
| ATOM | 2064 | CB | LEU | A | 264 | 23.637 | 3.693 | 53.687 | 1.00 | 17.50 | C |
| ATOM | 2065 | CG | LEU | A | 264 | 24.048 | 2.611 | 52.682 | 1.00 | 17.27 | C |
| ATOM | 2066 | CD1 | LEU | A | 264 | 25.487 | 2.196 | 52.905 | 1.00 | 17.83 | C |
| ATOM | 2067 | CD2 | LEU | A | 264 | 23.124 | 1.399 | 52.756 | 1.00 | 17.33 | C |
| ATOM | 2068 | C | LEU | A | 264 | 21.857 | 5.179 | 54.672 | 1.00 | 17.58 | C |

TABLE 6-continued

Coordinates of the crystal structure of *E. coli* ExoI bound to compound 9

| ATOM | 2069 | O | LEU | A | 264 | 21.546 | 4.628 | 55.726 | 1.00 | 17.30 | O |
|---|---|---|---|---|---|---|---|---|---|---|---|
| ATOM | 2070 | N | ALA | A | 265 | 21.850 | 6.503 | 54.513 | 1.00 | 17.57 | N |
| ATOM | 2071 | CA | ALA | A | 265 | 21.405 | 7.407 | 55.578 | 1.00 | 17.94 | C |
| ATOM | 2072 | CB | ALA | A | 265 | 22.032 | 8.785 | 55.404 | 1.00 | 17.98 | C |
| ATOM | 2073 | C | ALA | A | 265 | 19.884 | 7.514 | 55.629 | 1.00 | 18.21 | C |
| ATOM | 2074 | O | ALA | A | 265 | 19.325 | 8.098 | 56.560 | 1.00 | 18.28 | O |
| ATOM | 2075 | N | GLY | A | 266 | 19.218 | 6.943 | 54.628 | 1.00 | 18.49 | N |
| ATOM | 2076 | CA | GLY | A | 266 | 17.768 | 7.041 | 54.522 | 1.00 | 19.08 | C |
| ATOM | 2077 | C | GLY | A | 266 | 17.018 | 5.995 | 55.324 | 1.00 | 19.56 | C |
| ATOM | 2078 | O | GLY | A | 266 | 17.594 | 5.298 | 56.167 | 1.00 | 19.16 | O |
| ATOM | 2079 | N | ASP | A | 267 | 15.718 | 5.906 | 55.061 | 1.00 | 20.17 | N |
| ATOM | 2080 | CA | ASP | A | 267 | 14.847 | 4.907 | 55.668 | 1.00 | 20.83 | C |
| ATOM | 2081 | CB | ASP | A | 267 | 13.535 | 5.568 | 56.130 | 1.00 | 21.05 | C |
| ATOM | 2082 | CG | ASP | A | 267 | 12.546 | 4.575 | 56.749 | 1.00 | 21.59 | C |
| ATOM | 2083 | OD1 | ASP | A | 267 | 12.894 | 3.388 | 56.934 | 1.00 | 22.94 | O |
| ATOM | 2084 | OD2 | ASP | A | 267 | 11.409 | 4.995 | 57.057 | 1.00 | 22.79 | O |
| ATOM | 2085 | C | ASP | A | 267 | 14.571 | 3.829 | 54.627 | 1.00 | 21.36 | C |
| ATOM | 2086 | O | ASP | A | 267 | 13.876 | 4.075 | 53.639 | 1.00 | 21.41 | O |
| ATOM | 2087 | N | ILE | A | 268 | 15.130 | 2.640 | 54.843 | 1.00 | 21.86 | N |
| ATOM | 2088 | CA | ILE | A | 268 | 15.031 | 1.559 | 53.855 | 1.00 | 22.65 | C |
| ATOM | 2089 | CB | ILE | A | 268 | 16.318 | 0.686 | 53.801 | 1.00 | 22.62 | C |
| ATOM | 2090 | CG1 | ILE | A | 268 | 16.551 | −0.033 | 55.135 | 1.00 | 23.00 | C |
| ATOM | 2091 | CD1 | ILE | A | 268 | 17.500 | −1.215 | 55.041 | 1.00 | 23.11 | C |
| ATOM | 2092 | CG2 | ILE | A | 268 | 17.532 | 1.535 | 53.390 | 1.00 | 22.46 | C |
| ATOM | 2093 | C | ILE | A | 268 | 13.797 | 0.673 | 54.041 | 1.00 | 23.23 | C |
| ATOM | 2094 | O | ILE | A | 268 | 13.590 | −0.274 | 53.281 | 1.00 | 23.41 | O |
| ATOM | 2095 | N | SER | A | 269 | 12.978 | 0.995 | 55.042 | 1.00 | 24.01 | N |
| ATOM | 2096 | CA | SER | A | 269 | 11.737 | 0.253 | 55.306 | 1.00 | 24.89 | C |
| ATOM | 2097 | CB | SER | A | 269 | 10.979 | 0.848 | 56.499 | 1.00 | 24.91 | C |
| ATOM | 2098 | OG | SER | A | 269 | 11.690 | 0.640 | 57.706 | 1.00 | 25.77 | O |
| ATOM | 2099 | C | SER | A | 269 | 10.813 | 0.131 | 54.079 | 1.00 | 25.39 | C |
| ATOM | 2100 | O | SER | A | 269 | 10.347 | −0.968 | 53.779 | 1.00 | 25.49 | O |
| ATOM | 2101 | N | PRO | A | 270 | 10.549 | 1.255 | 53.364 | 1.00 | 25.94 | N |
| ATOM | 2102 | CA | PRO | A | 270 | 9.733 | 1.173 | 52.143 | 1.00 | 26.40 | C |
| ATOM | 2103 | CB | PRO | A | 270 | 9.838 | 2.585 | 51.556 | 1.00 | 26.42 | C |
| ATOM | 2104 | CG | PRO | A | 270 | 10.100 | 3.454 | 52.721 | 1.00 | 26.43 | C |
| ATOM | 2105 | CD | PRO | A | 270 | 10.957 | 2.647 | 53.649 | 1.00 | 26.03 | C |
| ATOM | 2106 | C | PRO | A | 270 | 10.259 | 0.146 | 51.136 | 1.00 | 26.83 | C |
| ATOM | 2107 | O | PRO | A | 270 | 9.468 | −0.534 | 50.483 | 1.00 | 26.72 | O |
| ATOM | 2108 | N | LEU | A | 271 | 11.584 | 0.037 | 51.024 | 1.00 | 27.26 | N |
| ATOM | 2109 | CA | LEU | A | 271 | 12.214 | −0.914 | 50.104 | 1.00 | 27.95 | C |
| ATOM | 2110 | CB | LEU | A | 271 | 13.722 | −0.649 | 50.000 | 1.00 | 27.98 | C |
| ATOM | 2111 | CG | LEU | A | 271 | 14.191 | 0.629 | 49.299 | 1.00 | 28.13 | C |
| ATOM | 2112 | CD1 | LEU | A | 271 | 15.702 | 0.766 | 49.423 | 1.00 | 28.43 | C |
| ATOM | 2113 | CD2 | LEU | A | 271 | 13.770 | 0.639 | 47.833 | 1.00 | 28.30 | C |
| ATOM | 2114 | C | LEU | A | 271 | 11.972 | −2.366 | 50.508 | 1.00 | 28.41 | C |
| ATOM | 2115 | O | LEU | A | 271 | 11.920 | −3.253 | 49.656 | 1.00 | 28.42 | O |
| ATOM | 2116 | N | LEU | A | 272 | 11.826 | −2.600 | 51.809 | 1.00 | 29.14 | N |
| ATOM | 2117 | CA | LEU | A | 272 | 11.621 | −3.948 | 52.330 | 1.00 | 30.02 | C |
| ATOM | 2118 | CB | LEU | A | 272 | 12.144 | −4.058 | 53.769 | 1.00 | 29.91 | C |
| ATOM | 2119 | CG | LEU | A | 272 | 13.614 | −3.712 | 54.045 | 1.00 | 30.10 | C |
| ATOM | 2120 | CD1 | LEU | A | 272 | 13.877 | −3.670 | 55.543 | 1.00 | 30.43 | C |
| ATOM | 2121 | CD2 | LEU | A | 272 | 14.559 | −4.690 | 53.361 | 1.00 | 30.27 | C |
| ATOM | 2122 | C | LEU | A | 272 | 10.153 | −4.382 | 52.269 | 1.00 | 30.64 | C |
| ATOM | 2123 | O | LEU | A | 272 | 9.851 | −5.516 | 51.888 | 1.00 | 30.75 | O |
| ATOM | 2124 | N | GLU | A | 273 | 9.248 | −3.473 | 52.628 | 1.00 | 31.44 | N |
| ATOM | 2125 | CA | GLU | A | 273 | 7.847 | −3.834 | 52.879 | 1.00 | 32.20 | C |
| ATOM | 2126 | CB | GLU | A | 273 | 7.392 | −3.290 | 54.243 | 1.00 | 32.28 | C |
| ATOM | 2127 | CG | GLU | A | 273 | 7.360 | −1.766 | 54.343 | 1.00 | 32.84 | C |
| ATOM | 2128 | CD | GLU | A | 273 | 7.446 | −1.263 | 55.777 | 1.00 | 33.54 | C |
| ATOM | 2129 | OE1 | GLU | A | 273 | 6.807 | −0.235 | 56.084 | 1.00 | 34.30 | O |
| ATOM | 2130 | OE2 | GLU | A | 273 | 8.153 | −1.891 | 56.595 | 1.00 | 33.75 | O |
| ATOM | 2131 | C | GLU | A | 273 | 6.855 | −3.426 | 51.776 | 1.00 | 32.67 | C |
| ATOM | 2132 | O | GLU | A | 273 | 5.672 | −3.775 | 51.844 | 1.00 | 32.65 | O |
| ATOM | 2133 | N | LEU | A | 274 | 7.333 | −2.701 | 50.767 | 1.00 | 33.22 | N |
| ATOM | 2134 | CA | LEU | A | 274 | 6.458 | −2.236 | 49.684 | 1.00 | 33.80 | C |
| ATOM | 2135 | CB | LEU | A | 274 | 6.450 | −0.704 | 49.606 | 1.00 | 33.74 | C |
| ATOM | 2136 | CG | LEU | A | 274 | 6.027 | 0.069 | 50.860 | 1.00 | 33.91 | C |
| ATOM | 2137 | CD1 | LEU | A | 274 | 6.216 | 1.564 | 50.664 | 1.00 | 33.94 | C |
| ATOM | 2138 | CD2 | LEU | A | 274 | 4.591 | −0.249 | 51.259 | 1.00 | 33.97 | C |
| ATOM | 2139 | C | LEU | A | 274 | 6.834 | −2.835 | 48.328 | 1.00 | 34.16 | C |
| ATOM | 2140 | O | LEU | A | 274 | 8.009 | −3.087 | 48.054 | 1.00 | 34.25 | O |
| ATOM | 2141 | N | ASP | A | 275 | 5.825 | −3.056 | 47.486 | 1.00 | 34.65 | N |
| ATOM | 2142 | CA | ASP | A | 275 | 6.033 | −3.615 | 46.148 | 1.00 | 35.13 | C |
| ATOM | 2143 | CB | ASP | A | 275 | 4.726 | −4.203 | 45.588 | 1.00 | 35.16 | C |
| ATOM | 2144 | CG | ASP | A | 275 | 3.606 | −3.175 | 45.493 | 1.00 | 35.50 | C |
| ATOM | 2145 | OD1 | ASP | A | 275 | 2.593 | −3.335 | 46.206 | 1.00 | 35.93 | O |
| ATOM | 2146 | OD2 | ASP | A | 275 | 3.732 | −2.213 | 44.703 | 1.00 | 35.74 | O |

TABLE 6-continued

Coordinates of the crystal structure of *E. coli* ExoI bound to compound 9

| ATOM | 2147 | C   | ASP | A | 275 | 6.622  | −2.586 | 45.182 | 1.00 | 35.37 | C |
|------|------|-----|-----|---|-----|--------|--------|--------|------|-------|---|
| ATOM | 2148 | O   | ASP | A | 275 | 6.596  | −1.381 | 45.450 | 1.00 | 35.41 | O |
| ATOM | 2149 | N   | SER | A | 276 | 7.138  | −3.072 | 44.054 | 1.00 | 35.74 | N |
| ATOM | 2150 | CA  | SER | A | 276 | 7.849  | −2.233 | 43.084 | 1.00 | 36.09 | C |
| ATOM | 2151 | CB  | SER | A | 276 | 8.480  | −3.098 | 41.991 | 1.00 | 36.12 | C |
| ATOM | 2152 | OG  | SER | A | 276 | 7.507  | −3.905 | 41.348 | 1.00 | 36.24 | O |
| ATOM | 2153 | C   | SER | A | 276 | 6.981  | −1.136 | 42.456 | 1.00 | 36.27 | C |
| ATOM | 2154 | O   | SER | A | 276 | 7.476  | −0.050 | 42.147 | 1.00 | 36.29 | O |
| ATOM | 2155 | N   | ASP | A | 277 | 5.694  | −1.427 | 42.271 | 1.00 | 36.57 | N |
| ATOM | 2156 | CA  | ASP | A | 277 | 4.758  | −0.464 | 41.685 | 1.00 | 36.83 | C |
| ATOM | 2157 | CB  | ASP | A | 277 | 3.431  | −1.144 | 41.325 | 1.00 | 36.90 | C |
| ATOM | 2158 | CG  | ASP | A | 277 | 3.539  | −2.030 | 40.089 | 1.00 | 37.18 | C |
| ATOM | 2159 | OD1 | ASP | A | 277 | 4.198  | −1.621 | 39.107 | 1.00 | 37.30 | O |
| ATOM | 2160 | OD2 | ASP | A | 277 | 2.950  | −3.132 | 40.095 | 1.00 | 37.67 | O |
| ATOM | 2161 | C   | ASP | A | 277 | 4.509  | 0.738  | 42.600 | 1.00 | 36.93 | C |
| ATOM | 2162 | O   | ASP | A | 277 | 4.449  | 1.878  | 42.133 | 1.00 | 36.95 | O |
| ATOM | 2163 | N   | THR | A | 278 | 4.373  | 0.475  | 43.900 | 1.00 | 37.08 | N |
| ATOM | 2164 | CA  | THR | A | 278 | 4.133  | 1.527  | 44.893 | 1.00 | 37.21 | C |
| ATOM | 2165 | CB  | THR | A | 278 | 3.707  | 0.934  | 46.260 | 1.00 | 37.24 | C |
| ATOM | 2166 | OG1 | THR | A | 278 | 2.723  | −0.090 | 46.057 | 1.00 | 37.26 | O |
| ATOM | 2167 | CG2 | THR | A | 278 | 3.123  | 2.017  | 47.164 | 1.00 | 37.32 | C |
| ATOM | 2168 | C   | THR | A | 278 | 5.365  | 2.420  | 45.080 | 1.00 | 37.33 | C |
| ATOM | 2169 | O   | THR | A | 278 | 5.240  | 3.638  | 45.234 | 1.00 | 37.33 | O |
| ATOM | 2170 | N   | LEU | A | 279 | 6.548  | 1.805  | 45.056 | 1.00 | 37.41 | N |
| ATOM | 2171 | CA  | LEU | A | 279 | 7.813  | 2.532  | 45.199 | 1.00 | 37.52 | C |
| ATOM | 2172 | CB  | LEU | A | 279 | 8.986  | 1.552  | 45.327 | 1.00 | 37.54 | C |
| ATOM | 2173 | CG  | LEU | A | 279 | 9.101  | 0.718  | 46.608 | 1.00 | 37.62 | C |
| ATOM | 2174 | CD1 | LEU | A | 279 | 9.966  | −0.510 | 46.371 | 1.00 | 37.83 | C |
| ATOM | 2175 | CD2 | LEU | A | 279 | 9.646  | 1.548  | 47.764 | 1.00 | 37.83 | C |
| ATOM | 2176 | C   | LEU | A | 279 | 8.058  | 3.492  | 44.033 | 1.00 | 37.57 | C |
| ATOM | 2177 | O   | LEU | A | 279 | 8.646  | 4.561  | 44.213 | 1.00 | 37.61 | O |
| ATOM | 2178 | N   | ARG | A | 280 | 7.602  | 3.099  | 42.845 | 1.00 | 37.64 | N |
| ATOM | 2179 | CA  | ARG | A | 280 | 7.757  | 3.904  | 41.634 | 1.00 | 37.73 | C |
| ATOM | 2180 | CB  | ARG | A | 280 | 7.426  | 3.064  | 40.400 | 1.00 | 37.74 | C |
| ATOM | 2181 | CG  | ARG | A | 280 | 7.876  | 3.676  | 39.078 | 1.00 | 37.84 | C |
| ATOM | 2182 | CD  | ARG | A | 280 | 7.328  | 2.898  | 37.883 | 1.00 | 37.88 | C |
| ATOM | 2183 | NE  | ARG | A | 280 | 7.781  | 1.505  | 37.868 | 1.00 | 38.18 | N |
| ATOM | 2184 | CZ  | ARG | A | 280 | 7.022  | 0.460  | 38.195 | 1.00 | 38.31 | C |
| ATOM | 2185 | NH1 | ARG | A | 280 | 5.755  | 0.636  | 38.553 | 1.00 | 38.32 | N |
| ATOM | 2186 | NH2 | ARG | A | 280 | 7.526  | −0.765 | 38.146 | 1.00 | 38.33 | N |
| ATOM | 2187 | C   | ARG | A | 280 | 6.867  | 5.143  | 41.671 | 1.00 | 37.74 | C |
| ATOM | 2188 | O   | ARG | A | 280 | 7.336  | 6.246  | 41.971 | 1.00 | 37.72 | O |
| ATOM | 2189 | N   | ALA | A | 295 | 9.877  | 8.433  | 52.274 | 1.00 | 25.76 | N |
| ATOM | 2190 | CA  | ALA | A | 295 | 10.781 | 8.783  | 51.185 | 1.00 | 25.58 | C |
| ATOM | 2191 | CB  | ALA | A | 295 | 11.658 | 9.962  | 51.581 | 1.00 | 25.68 | C |
| ATOM | 2192 | C   | ALA | A | 295 | 11.638 | 7.584  | 50.782 | 1.00 | 25.50 | C |
| ATOM | 2193 | O   | ALA | A | 295 | 12.276 | 6.951  | 51.629 | 1.00 | 25.66 | O |
| ATOM | 2194 | N   | VAL | A | 296 | 11.640 | 7.274  | 49.486 | 1.00 | 25.14 | N |
| ATOM | 2195 | CA  | VAL | A | 296 | 12.369 | 6.119  | 48.966 | 1.00 | 24.66 | C |
| ATOM | 2196 | CB  | VAL | A | 296 | 11.730 | 5.567  | 47.661 | 1.00 | 24.71 | C |
| ATOM | 2197 | CG1 | VAL | A | 296 | 12.414 | 4.275  | 47.230 | 1.00 | 24.78 | C |
| ATOM | 2198 | CG2 | VAL | A | 296 | 10.232 | 5.334  | 47.851 | 1.00 | 24.58 | C |
| ATOM | 2199 | C   | VAL | A | 296 | 13.836 | 6.491  | 48.722 | 1.00 | 24.36 | C |
| ATOM | 2200 | O   | VAL | A | 296 | 14.134 | 7.288  | 47.829 | 1.00 | 24.46 | O |
| ATOM | 2201 | M   | PRO | A | 297 | 14.756 | 5.908  | 49.516 | 1.00 | 23.99 | N |
| ATOM | 2202 | CA  | PRO | A | 297 | 16.163 | 6.305  | 49.483 | 1.00 | 23.74 | C |
| ATOM | 2203 | CB  | PRO | A | 297 | 16.692 | 5.798  | 50.824 | 1.00 | 23.69 | C |
| ATOM | 2204 | CG  | PRO | A | 297 | 15.882 | 4.580  | 51.099 | 1.00 | 23.75 | C |
| ATOM | 2205 | CD  | PRO | A | 297 | 14.515 | 4.822  | 50.488 | 1.00 | 23.89 | C |
| ATOM | 2206 | C   | PRO | A | 297 | 16.920 | 5.658  | 48.320 | 1.00 | 23.66 | C |
| ATOM | 2207 | O   | PRO | A | 297 | 17.931 | 4.981  | 48.528 | 1.00 | 23.48 | O |
| ATOM | 2208 | N   | VAL | A | 298 | 16.421 | 5.873  | 47.108 | 1.00 | 23.57 | N |
| ATOM | 2209 | CA  | VAL | A | 298 | 17.029 | 5.322  | 45.905 | 1.00 | 23.75 | C |
| ATOM | 2210 | CB  | VAL | A | 298 | 16.066 | 4.327  | 45.196 | 1.00 | 23.90 | C |
| ATOM | 2211 | CG1 | VAL | A | 298 | 16.452 | 4.122  | 43.731 | 1.00 | 24.23 | C |
| ATOM | 2212 | CG2 | VAL | A | 298 | 16.040 | 2.996  | 45.937 | 1.00 | 24.33 | C |
| ATOM | 2213 | C   | VAL | A | 298 | 17.419 | 6.453  | 44.960 | 1.00 | 23.70 | C |
| ATOM | 2214 | O   | VAL | A | 298 | 16.653 | 7.396  | 44.757 | 1.00 | 23.73 | O |
| ATOM | 2215 | N   | LYS | A | 299 | 18.622 | 6.363  | 44.402 | 1.00 | 23.47 | N |
| ATOM | 2216 | CA  | LYS | A | 299 | 19.066 | 7.326  | 43.406 | 1.00 | 23.55 | C |
| ATOM | 2217 | CB  | LYS | A | 299 | 19.792 | 8.504  | 44.067 | 1.00 | 24.04 | C |
| ATOM | 2218 | CG  | LYS | A | 299 | 21.161 | 8.167  | 44.649 | 1.00 | 25.38 | C |
| ATOM | 2219 | CD  | LYS | A | 299 | 22.096 | 9.375  | 44.600 | 1.00 | 27.13 | C |
| ATOM | 2220 | CE  | LYS | A | 299 | 22.269 | 9.881  | 43.168 | 1.00 | 28.37 | C |
| ATOM | 2221 | NZ  | LYS | A | 299 | 23.271 | 10.975 | 43.052 | 1.00 | 28.89 | N |
| ATOM | 2222 | C   | LYS | A | 299 | 19.947 | 6.678  | 42.346 | 1.00 | 22.95 | C |
| ATOM | 2223 | O   | LYS | A | 299 | 20.664 | 5.711  | 42.623 | 1.00 | 23.10 | O |
| ATOM | 2224 | N   | LEU | A | 300 | 19.879 | 7.210  | 41.132 | 1.00 | 22.36 | N |

TABLE 6-continued

Coordinates of the crystal structure of *E. coli* ExoI bound to compound 9

| ATOM | 2225 | CA | LEU | A | 300 | 20.734 | 6.753 | 40.051 | 1.00 | 21.72 | C |
|---|---|---|---|---|---|---|---|---|---|---|---|
| ATOM | 2226 | CB | LEU | A | 300 | 20.057 | 6.963 | 38.695 | 1.00 | 21.88 | C |
| ATOM | 2227 | CG | LEU | A | 300 | 18.787 | 6.160 | 38.393 | 1.00 | 22.24 | C |
| ATOM | 2228 | CD1 | LEU | A | 300 | 18.215 | 6.566 | 37.046 | 1.00 | 22.48 | C |
| ATOM | 2229 | CD2 | LEU | A | 300 | 19.056 | 4.657 | 38.431 | 1.00 | 22.49 | C |
| ATOM | 2230 | C | LEU | A | 300 | 22.058 | 7.494 | 40.085 | 1.00 | 21.20 | C |
| ATOM | 2231 | O | LEU | A | 300 | 22.100 | 8.703 | 40.311 | 1.00 | 21.28 | O |
| ATOM | 2232 | N | VAL | A | 301 | 23.138 | 6.753 | 39.876 | 1.00 | 20.12 | N |
| ATOM | 2233 | CA | VAL | A | 301 | 24.452 | 7.345 | 39.673 | 1.00 | 19.53 | C |
| ATOM | 2234 | CB | VAL | A | 301 | 25.492 | 6.776 | 40.664 | 1.00 | 19.49 | C |
| ATOM | 2235 | CG1 | VAL | A | 301 | 26.910 | 7.165 | 40.255 | 1.00 | 20.01 | C |
| ATOM | 2236 | CG2 | VAL | A | 301 | 25.190 | 7.266 | 42.074 | 1.00 | 19.25 | C |
| ATOM | 2237 | C | VAL | A | 301 | 24.868 | 7.082 | 38.236 | 1.00 | 19.22 | C |
| ATOM | 2238 | O | VAL | A | 301 | 24.911 | 5.933 | 37.794 | 1.00 | 18.96 | O |
| ATOM | 2239 | N | HIS | A | 302 | 25.143 | 8.158 | 37.505 | 1.00 | 18.78 | N |
| ATOM | 2240 | CA | HIS | A | 302 | 25.494 | 8.069 | 36.096 | 1.00 | 18.73 | C |
| ATOM | 2241 | CB | HIS | A | 302 | 24.820 | 9.192 | 35.309 | 1.00 | 19.01 | C |
| ATOM | 2242 | CG | HIS | A | 302 | 23.327 | 9.161 | 35.380 | 1.00 | 19.89 | C |
| ATOM | 2243 | ND1 | HIS | A | 302 | 22.623 | 9.658 | 36.455 | 1.00 | 21.67 | N |
| ATOM | 2244 | CE1 | HIS | A | 302 | 21.329 | 9.490 | 36.245 | 1.00 | 21.22 | C |
| ATOM | 2245 | NE2 | HIS | A | 302 | 21.170 | 8.897 | 35.077 | 1.00 | 22.02 | N |
| ATOM | 2246 | CD2 | HIS | A | 302 | 22.404 | 8.678 | 34.516 | 1.00 | 20.67 | C |
| ATOM | 2247 | C | HIS | A | 302 | 27.000 | 8.143 | 35.939 | 1.00 | 18.54 | C |
| ATOM | 2248 | O | HIS | A | 302 | 27.601 | 9.195 | 36.155 | 1.00 | 17.95 | O |
| ATOM | 2249 | N | ILE | A | 303 | 27.605 | 7.021 | 35.556 | 1.00 | 18.41 | N |
| ATOM | 2250 | CA | ILE | A | 303 | 29.068 | 6.897 | 35.544 | 1.00 | 18.75 | C |
| ATOM | 2251 | CB | ILE | A | 303 | 29.530 | 5.425 | 35.403 | 1.00 | 18.89 | C |
| ATOM | 2252 | CG1 | ILE | A | 303 | 28.977 | 4.810 | 34.111 | 1.00 | 19.75 | C |
| ATOM | 2253 | CD1 | ILE | A | 303 | 29.151 | 3.324 | 34.014 | 1.00 | 20.54 | C |
| ATOM | 2254 | CG2 | ILE | A | 303 | 29.151 | 4.617 | 36.658 | 1.00 | 19.75 | C |
| ATOM | 2255 | C | ILE | A | 303 | 29.745 | 7.757 | 34.477 | 1.00 | 18.39 | C |
| ATOM | 2256 | O | ILE | A | 303 | 30.956 | 7.964 | 34.521 | 1.00 | 17.99 | O |
| ATOM | 2257 | N | ASN | A | 304 | 28.959 | 8.251 | 33.523 | 1.00 | 18.32 | N |
| ATOM | 2258 | CA | ASN | A | 304 | 29.475 | 9.162 | 32.501 | 1.00 | 18.64 | C |
| ATOM | 2259 | CB | ASN | A | 304 | 28.827 | 8.880 | 31.129 | 1.00 | 19.11 | C |
| ATOM | 2260 | CG | ASN | A | 304 | 27.296 | 8.814 | 31.186 | 1.00 | 20.53 | C |
| ATOM | 2261 | OD1 | ASN | A | 304 | 26.697 | 8.625 | 32.246 | 1.00 | 22.87 | O |
| ATOM | 2262 | ND2 | ASN | A | 304 | 26.665 | 8.954 | 30.026 | 1.00 | 22.68 | N |
| ATOM | 2263 | C | ASN | A | 304 | 29.335 | 10.641 | 32.872 | 1.00 | 18.43 | C |
| ATOM | 2264 | O | ASN | A | 304 | 29.711 | 11.517 | 32.095 | 1.00 | 18.48 | O |
| ATOM | 2265 | N | LYS | A | 305 | 28.819 | 10.909 | 34.070 | 1.00 | 17.99 | N |
| ATOM | 2266 | CA | LYS | A | 305 | 28.513 | 12.280 | 34.490 | 1.00 | 17.91 | C |
| ATOM | 2267 | CB | LYS | A | 305 | 27.030 | 12.405 | 34.858 | 1.00 | 18.35 | C |
| ATOM | 2268 | CG | LYS | A | 305 | 26.094 | 12.276 | 33.669 | 1.00 | 19.69 | C |
| ATOM | 2269 | CD | LYS | A | 305 | 24.672 | 12.655 | 34.031 | 1.00 | 22.17 | C |
| ATOM | 2270 | CE | LYS | A | 305 | 23.787 | 12.684 | 32.791 | 1.00 | 24.13 | C |
| ATOM | 2271 | NZ | LYS | A | 305 | 22.386 | 13.066 | 33.110 | 1.00 | 26.24 | N |
| ATOM | 2272 | C | LYS | A | 305 | 29.401 | 12.774 | 35.638 | 1.00 | 17.56 | C |
| ATOM | 2273 | O | LYS | A | 305 | 28.974 | 13.593 | 36.453 | 1.00 | 17.40 | O |
| ATOM | 2274 | N | CYS | A | 306 | 30.638 | 12.277 | 35.681 | 1.00 | 17.12 | N |
| ATOM | 2275 | CA | CYS | A | 306 | 31.616 | 12.647 | 36.721 | 1.00 | 16.92 | C |
| ATOM | 2276 | CB | CYS | A | 306 | 32.221 | 14.029 | 36.441 | 1.00 | 17.16 | C |
| ATOM | 2277 | SG | CYS | A | 306 | 32.868 | 14.228 | 34.799 | 1.00 | 19.64 | S |
| ATOM | 2278 | C | CYS | A | 306 | 31.050 | 12.618 | 38.144 | 1.00 | 16.23 | C |
| ATOM | 2279 | O | CYS | A | 306 | 31.200 | 13.589 | 38.891 | 1.00 | 16.57 | O |
| ATOM | 2280 | N | PRO | A | 307 | 30.407 | 11.503 | 38.536 | 1.00 | 15.55 | N |
| ATOM | 2281 | CA | PRO | A | 307 | 29.928 | 11.435 | 39.913 | 1.00 | 15.21 | C |
| ATOM | 2282 | CB | PRO | A | 307 | 29.089 | 10.156 | 39.929 | 1.00 | 15.16 | C |
| ATOM | 2283 | CG | PRO | A | 307 | 29.690 | 9.305 | 38.854 | 1.00 | 14.99 | C |
| ATOM | 2284 | CD | PRO | A | 307 | 30.122 | 10.266 | 37.785 | 1.00 | 15.31 | C |
| ATOM | 2285 | C | PRO | A | 307 | 31.101 | 11.315 | 40.875 | 1.00 | 14.94 | C |
| ATOM | 2286 | O | PRO | A | 307 | 32.095 | 10.653 | 40.558 | 1.00 | 14.73 | O |
| ATOM | 2287 | N | VAL | A | 308 | 31.007 | 11.987 | 42.020 | 1.00 | 14.58 | N |
| ATOM | 2288 | CA | VAL | A | 308 | 32.041 | 11.880 | 43.039 | 1.00 | 14.38 | C |
| ATOM | 2289 | CB | VAL | A | 308 | 32.095 | 13.128 | 43.950 | 1.00 | 14.27 | C |
| ATOM | 2290 | CG1 | VAL | A | 308 | 33.123 | 12.930 | 45.059 | 1.00 | 14.53 | C |
| ATOM | 2291 | CG2 | VAL | A | 308 | 32.424 | 14.374 | 43.129 | 1.00 | 15.01 | C |
| ATOM | 2292 | C | VAL | A | 308 | 31.799 | 10.629 | 43.866 | 1.00 | 14.31 | C |
| ATOM | 2293 | O | VAL | A | 308 | 30.786 | 10.524 | 44.565 | 1.00 | 14.45 | O |
| ATOM | 2294 | N | LEU | A | 309 | 32.721 | 9.675 | 43.760 | 1.00 | 14.25 | N |
| ATOM | 2295 | CA | LEU | A | 309 | 32.628 | 8.408 | 44.485 | 1.00 | 14.24 | C |
| ATOM | 2296 | CB | LEU | A | 309 | 32.162 | 7.282 | 43.556 | 1.00 | 14.13 | C |
| ATOM | 2297 | CG | LEU | A | 309 | 30.734 | 7.295 | 43.002 | 1.00 | 14.20 | C |
| ATOM | 2298 | CD1 | LEU | A | 309 | 30.584 | 6.216 | 41.932 | 1.00 | 14.78 | C |
| ATOM | 2299 | CD2 | LEU | A | 309 | 29.696 | 7.108 | 44.103 | 1.00 | 15.11 | C |
| ATOM | 2300 | C | LEU | A | 309 | 33.983 | 8.037 | 45.045 | 1.00 | 14.61 | C |
| ATOM | 2301 | O | LEU | A | 309 | 35.007 | 8.228 | 44.385 | 1.00 | 14.41 | O |
| ATOM | 2302 | N | ALA | A | 310 | 33.986 | 7.488 | 46.253 | 1.00 | 15.14 | N |

TABLE 6-continued

Coordinates of the crystal structure of *E. coli* ExoI bound to compound 9

| ATOM | 2303 | CA | ALA | A | 310 | 35.217 | 6.987 | 46.865 | 1.00 | 15.91 | C |
|---|---|---|---|---|---|---|---|---|---|---|---|
| ATOM | 2304 | CB | ALA | A | 310 | 35.956 | 8.114 | 47.581 | 1.00 | 16.02 | C |
| ATOM | 2305 | C | ALA | A | 310 | 34.916 | 5.850 | 47.829 | 1.00 | 16.86 | C |
| ATOM | 2306 | O | ALA | A | 310 | 33.774 | 5.678 | 48.258 | 1.00 | 16.58 | O |
| ATOM | 2307 | N | GLN | A | 311 | 35.945 | 5.075 | 48.169 | 1.00 | 17.85 | N |
| ATOM | 2308 | CA | GLN | A | 311 | 35.812 | 4.009 | 49.164 | 1.00 | 19.42 | C |
| ATOM | 2309 | CB | GLN | A | 311 | 37.169 | 3.342 | 49.436 | 1.00 | 19.58 | C |
| ATOM | 2310 | CG | GLN | A | 311 | 38.293 | 4.306 | 49.805 | 1.00 | 21.33 | C |
| ATOM | 2311 | CD | GLN | A | 311 | 39.614 | 3.605 | 50.088 | 1.00 | 22.30 | C |
| ATOM | 2312 | OE1 | GLN | A | 311 | 39.776 | 2.414 | 49.816 | 1.00 | 26.55 | O |
| ATOM | 2313 | NE2 | GLN | A | 311 | 40.571 | 4.350 | 50.638 | 1.00 | 25.81 | N |
| ATOM | 2314 | C | GLN | A | 311 | 35.210 | 4.558 | 50.457 | 1.00 | 19.41 | C |
| ATOM | 2315 | O | GLN | A | 311 | 35.450 | 5.710 | 50.819 | 1.00 | 18.91 | O |
| ATOM | 2316 | N | ALA | A | 312 | 34.418 | 3.730 | 51.136 | 1.00 | 20.15 | N |
| ATOM | 2317 | CA | ALA | A | 312 | 33.643 | 4.165 | 52.305 | 1.00 | 20.85 | C |
| ATOM | 2318 | CB | ALA | A | 312 | 32.865 | 2.994 | 52.894 | 1.00 | 20.99 | C |
| ATOM | 2319 | C | ALA | A | 312 | 34.478 | 4.857 | 53.389 | 1.00 | 21.47 | C |
| ATOM | 2320 | O | ALA | A | 312 | 34.021 | 5.821 | 54.003 | 1.00 | 21.38 | O |
| ATOM | 2321 | N | ASN | A | 313 | 35.700 | 4.372 | 53.612 | 1.00 | 22.21 | N |
| ATOM | 2322 | CA | ASN | A | 313 | 36.552 | 4.913 | 54.678 | 1.00 | 22.99 | C |
| ATOM | 2323 | CB | ASN | A | 313 | 37.631 | 3.898 | 55.097 | 1.00 | 23.35 | C |
| ATOM | 2324 | CG | ASN | A | 313 | 38.760 | 3.767 | 54.077 | 1.00 | 24.25 | C |
| ATOM | 2325 | OD1 | ASN | A | 313 | 38.743 | 4.394 | 53.018 | 1.00 | 25.71 | O |
| ATOM | 2326 | ND2 | ASN | A | 313 | 39.754 | 2.946 | 54.406 | 1.00 | 26.19 | N |
| ATOM | 2327 | C | ASN | A | 313 | 37.165 | 6.295 | 54.397 | 1.00 | 23.17 | C |
| ATOM | 2328 | O | ASN | A | 313 | 37.811 | 6.879 | 55.273 | 1.00 | 23.31 | O |
| ATOM | 2329 | N | THR | A | 314 | 36.956 | 6.813 | 53.184 | 1.00 | 23.21 | N |
| ATOM | 2330 | CA | THR | A | 314 | 37.395 | 8.169 | 52.819 | 1.00 | 23.60 | C |
| ATOM | 2331 | CB | THR | A | 314 | 37.095 | 8.484 | 51.333 | 1.00 | 23.64 | C |
| ATOM | 2332 | OG1 | THR | A | 314 | 37.724 | 7.506 | 50.501 | 1.00 | 24.38 | O |
| ATOM | 2333 | CG2 | THR | A | 314 | 37.609 | 9.873 | 50.947 | 1.00 | 23.80 | C |
| ATOM | 2334 | C | THR | A | 314 | 36.729 | 9.223 | 53.708 | 1.00 | 23.64 | C |
| ATOM | 2335 | O | THR | A | 314 | 37.332 | 10.253 | 54.029 | 1.00 | 23.91 | O |
| ATOM | 2336 | N | LEU | A | 315 | 35.481 | 8.960 | 54.086 | 1.00 | 23.65 | N |
| ATOM | 2337 | CA | LEU | A | 315 | 34.779 | 9.782 | 55.056 | 1.00 | 23.66 | C |
| ATOM | 2338 | CB | LEU | A | 315 | 33.293 | 9.902 | 54.689 | 1.00 | 23.52 | C |
| ATOM | 2339 | CG | LEU | A | 315 | 32.476 | 11.001 | 55.375 | 1.00 | 23.24 | C |
| ATOM | 2340 | CD1 | LEU | A | 315 | 32.862 | 12.374 | 54.850 | 1.00 | 23.13 | C |
| ATOM | 2341 | CD2 | LEU | A | 315 | 30.993 | 10.754 | 55.170 | 1.00 | 23.20 | C |
| ATOM | 2342 | C | LEU | A | 315 | 34.953 | 9.160 | 56.438 | 1.00 | 23.89 | C |
| ATOM | 2343 | O | LEU | A | 315 | 34.350 | 8.133 | 56.753 | 1.00 | 23.82 | O |
| ATOM | 2344 | N | ARG | A | 316 | 35.805 | 9.780 | 57.246 | 1.00 | 24.44 | N |
| ATOM | 2345 | CA | ARG | A | 316 | 36.149 | 9.256 | 58.563 | 1.00 | 24.97 | C |
| ATOM | 2346 | CB | ARG | A | 316 | 37.540 | 9.749 | 58.974 | 1.00 | 25.29 | C |
| ATOM | 2347 | CG | ARG | A | 316 | 38.667 | 9.171 | 58.119 | 1.00 | 26.77 | C |
| ATOM | 2348 | CD | ARG | A | 316 | 39.928 | 10.021 | 58.179 | 1.00 | 29.89 | C |
| ATOM | 2349 | NE | ARG | A | 316 | 39.798 | 11.261 | 57.409 | 1.00 | 31.75 | N |
| ATOM | 2350 | CZ | ARG | A | 316 | 40.818 | 12.042 | 57.063 | 1.00 | 33.02 | C |
| ATOM | 2351 | NH1 | ARG | A | 316 | 42.060 | 11.720 | 57.409 | 1.00 | 33.79 | N |
| ATOM | 2352 | NH2 | ARG | A | 316 | 40.598 | 13.149 | 56.370 | 1.00 | 34.00 | N |
| ATOM | 2353 | C | ARG | A | 316 | 35.088 | 9.652 | 59.594 | 1.00 | 24.93 | C |
| ATOM | 2354 | O | ARG | A | 316 | 34.334 | 10.598 | 59.366 | 1.00 | 24.77 | O |
| ATOM | 2355 | N | PRO | A | 317 | 34.997 | 8.903 | 60.716 | 1.00 | 25.05 | N |
| ATOM | 2356 | CA | PRO | A | 317 | 34.018 | 9.216 | 61.766 | 1.00 | 24.98 | C |
| ATOM | 2357 | CB | PRO | A | 317 | 34.500 | 8.386 | 62.971 | 1.00 | 24.96 | C |
| ATOM | 2358 | CG | PRO | A | 317 | 35.734 | 7.656 | 62.514 | 1.00 | 25.21 | C |
| ATOM | 2359 | CD | PRO | A | 317 | 35.768 | 7.691 | 61.037 | 1.00 | 25.07 | C |
| ATOM | 2360 | C | PRO | A | 317 | 33.944 | 10.703 | 62.130 | 1.00 | 25.00 | C |
| ATOM | 2361 | O | PRO | A | 317 | 32.847 | 11.229 | 62.331 | 1.00 | 24.83 | O |
| ATOM | 2362 | N | GLU | A | 318 | 35.097 | 11.370 | 62.200 | 1.00 | 25.02 | N |
| ATOM | 2363 | CA | GLU | A | 318 | 35.146 | 12.800 | 62.528 | 1.00 | 25.13 | C |
| ATOM | 2364 | CB | GLU | A | 318 | 36.572 | 13.235 | 62.918 | 1.00 | 25.38 | C |
| ATOM | 2365 | CG | GLU | A | 318 | 37.633 | 13.054 | 61.823 | 1.00 | 26.70 | C |
| ATOM | 2366 | CD | GLU | A | 318 | 38.376 | 11.722 | 61.909 | 1.00 | 28.26 | C |
| ATOM | 2367 | OE1 | GLU | A | 318 | 37.827 | 10.748 | 62.472 | 1.00 | 28.57 | O |
| ATOM | 2368 | OE2 | GLU | A | 318 | 39.518 | 11.654 | 61.403 | 1.00 | 29.44 | O |
| ATOM | 2369 | C | GLU | A | 318 | 34.589 | 13.684 | 61.403 | 1.00 | 24.84 | C |
| ATOM | 2370 | O | GLU | A | 318 | 34.036 | 14.755 | 61.664 | 1.00 | 24.73 | O |
| ATOM | 2371 | N | ASP | A | 319 | 34.736 | 13.225 | 60.159 | 1.00 | 24.57 | N |
| ATOM | 2372 | CA | ASP | A | 319 | 34.174 | 13.920 | 58.998 | 1.00 | 24.36 | C |
| ATOM | 2373 | CB | ASP | A | 319 | 34.741 | 13.345 | 57.695 | 1.00 | 24.59 | C |
| ATOM | 2374 | CG | ASP | A | 319 | 36.246 | 13.517 | 57.575 | 1.00 | 25.22 | C |
| ATOM | 2375 | OD1 | ASP | A | 319 | 36.766 | 14.586 | 57.963 | 1.00 | 26.23 | O |
| ATOM | 2376 | OD2 | ASP | A | 319 | 36.909 | 12.584 | 57.068 | 1.00 | 26.18 | O |
| ATOM | 2377 | C | ASP | A | 319 | 32.650 | 13.809 | 58.989 | 1.00 | 23.92 | C |
| ATOM | 2378 | O | ASP | A | 319 | 31.948 | 14.788 | 58.725 | 1.00 | 23.64 | O |
| ATOM | 2379 | N | ALA | A | 320 | 32.150 | 12.608 | 59.279 | 1.00 | 23.57 | N |
| ATOM | 2380 | CA | ALA | A | 320 | 30.710 | 12.362 | 59.358 | 1.00 | 23.46 | C |

TABLE 6-continued

Coordinates of the crystal structure of *E. coli* ExoI bound to compound 9

| ATOM | 2381 | CB | ALA | A | 320 | 30.436 | 10.881 | 59.579 | 1.00 | 23.46 | C |
|------|------|-----|-----|---|-----|--------|--------|--------|------|-------|---|
| ATOM | 2382 | C | ALA | A | 320 | 30.060 | 13.201 | 60.459 | 1.00 | 23.35 | C |
| ATOM | 2383 | O | ALA | A | 320 | 28.975 | 13.752 | 60.268 | 1.00 | 23.22 | O |
| ATOM | 2384 | N | ASP | A | 321 | 30.739 | 13.301 | 61.604 | 1.00 | 23.33 | N |
| ATOM | 2385 | CA | ASP | A | 321 | 30.255 | 14.106 | 62.729 | 1.00 | 23.33 | C |
| ATOM | 2386 | CB | ASP | A | 321 | 31.190 | 13.966 | 63.938 | 1.00 | 23.72 | C |
| ATOM | 2387 | CG | ASP | A | 321 | 31.140 | 12.578 | 64.564 | 1.00 | 25.17 | C |
| ATOM | 2388 | OD1 | ASP | A | 321 | 30.175 | 11.828 | 64.300 | 1.00 | 27.19 | O |
| ATOM | 2389 | OD2 | ASP | A | 321 | 32.072 | 12.238 | 65.324 | 1.00 | 27.12 | O |
| ATOM | 2390 | C | ASP | A | 321 | 30.115 | 15.575 | 62.341 | 1.00 | 22.91 | C |
| ATOM | 2391 | O | ASP | A | 321 | 29.114 | 16.217 | 62.666 | 1.00 | 22.72 | O |
| ATOM | 2392 | N | ARG | A | 322 | 31.120 | 16.091 | 61.634 | 1.00 | 22.49 | N |
| ATOM | 2393 | CA | ARG | A | 322 | 31.113 | 17.471 | 61.143 | 1.00 | 22.19 | C |
| ATOM | 2394 | CB | ARG | A | 322 | 32.437 | 17.792 | 60.432 | 1.00 | 22.22 | C |
| ATOM | 2395 | CG | ARG | A | 322 | 32.479 | 19.161 | 59.769 | 1.00 | 22.55 | C |
| ATOM | 2396 | CD | ARG | A | 322 | 33.768 | 19.378 | 58.999 | 1.00 | 23.30 | C |
| ATOM | 2397 | NE | ARG | A | 322 | 33.646 | 20.499 | 58.069 | 1.00 | 24.98 | N |
| ATOM | 2398 | CZ | ARG | A | 322 | 33.445 | 20.373 | 56.759 | 1.00 | 24.81 | C |
| ATOM | 2399 | NH1 | ARG | A | 322 | 33.359 | 19.168 | 56.206 | 1.00 | 24.90 | N |
| ATOM | 2400 | NH2 | ARG | A | 322 | 33.341 | 21.454 | 55.997 | 1.00 | 25.12 | N |
| ATOM | 2401 | C | ARG | A | 322 | 29.926 | 17.737 | 60.210 | 1.00 | 21.78 | C |
| ATOM | 2402 | O | ARG | A | 322 | 29.302 | 18.798 | 60.276 | 1.00 | 21.78 | O |
| ATOM | 2403 | N | LEU | A | 323 | 29.617 | 16.766 | 59.353 | 1.00 | 21.10 | N |
| ATOM | 2404 | CA | LEU | A | 323 | 28.533 | 16.906 | 58.378 | 1.00 | 20.82 | C |
| ATOM | 2405 | CB | LEU | A | 323 | 28.845 | 16.102 | 57.110 | 1.00 | 20.56 | C |
| ATOM | 2406 | CG | LEU | A | 323 | 30.109 | 16.485 | 56.333 | 1.00 | 20.41 | C |
| ATOM | 2407 | CD1 | LEU | A | 323 | 30.343 | 15.517 | 55.188 | 1.00 | 20.38 | C |
| ATOM | 2408 | CD2 | LEU | A | 323 | 30.032 | 17.921 | 55.819 | 1.00 | 20.70 | C |
| ATOM | 2409 | C | LEU | A | 323 | 27.171 | 16.494 | 58.942 | 1.00 | 20.63 | C |
| ATOM | 2410 | O | LEU | A | 323 | 26.145 | 16.640 | 58.273 | 1.00 | 20.55 | O |
| ATOM | 2411 | N | GLY | A | 324 | 27.171 | 15.977 | 60.169 | 1.00 | 20.56 | N |
| ATOM | 2412 | CA | GLY | A | 324 | 25.936 | 15.567 | 60.844 | 1.00 | 20.54 | C |
| ATOM | 2413 | C | GLY | A | 324 | 25.360 | 14.254 | 60.341 | 1.00 | 20.62 | C |
| ATOM | 2414 | O | GLY | A | 324 | 24.167 | 13.989 | 60.507 | 1.00 | 20.98 | O |
| ATOM | 2415 | N | ILE | A | 325 | 26.213 | 13.429 | 59.737 | 1.00 | 20.56 | N |
| ATOM | 2416 | CA | ILE | A | 325 | 25.791 | 12.143 | 59.180 | 1.00 | 20.60 | C |
| ATOM | 2417 | CB | ILE | A | 325 | 26.606 | 11.784 | 57.904 | 1.00 | 20.53 | C |
| ATOM | 2418 | CG1 | ILE | A | 325 | 26.419 | 12.867 | 56.836 | 1.00 | 20.70 | C |
| ATOM | 2419 | CD1 | ILE | A | 325 | 27.453 | 12.836 | 55.723 | 1.00 | 20.37 | C |
| ATOM | 2420 | CG2 | ILE | A | 325 | 26.202 | 10.401 | 57.362 | 1.00 | 21.15 | C |
| ATOM | 2421 | C | ILE | A | 325 | 25.919 | 11.033 | 60.226 | 1.00 | 20.62 | C |
| ATOM | 2422 | O | ILE | A | 325 | 26.963 | 10.888 | 60.863 | 1.00 | 20.83 | O |
| ATOM | 2423 | N | ASN | A | 326 | 24.844 | 10.263 | 60.395 | 1.00 | 20.58 | N |
| ATOM | 2424 | CA | ASN | A | 326 | 24.817 | 9.141 | 61.335 | 1.00 | 20.69 | C |
| ATOM | 2425 | CB | ASN | A | 326 | 23.369 | 8.831 | 61.745 | 1.00 | 20.79 | C |
| ATOM | 2426 | CG | ASN | A | 326 | 23.274 | 7.952 | 62.997 | 1.00 | 21.31 | C |
| ATOM | 2427 | OD1 | ASN | A | 326 | 22.289 | 8.023 | 63.735 | 1.00 | 23.24 | O |
| ATOM | 2428 | ND2 | ASN | A | 326 | 24.284 | 7.120 | 63.230 | 1.00 | 21.17 | N |
| ATOM | 2429 | C | ASN | A | 326 | 25.486 | 7.904 | 60.733 | 1.00 | 20.40 | C |
| ATOM | 2430 | O | ASN | A | 326 | 24.861 | 7.143 | 59.989 | 1.00 | 20.45 | O |
| ATOM | 2431 | N | ARG | A | 327 | 26.761 | 7.716 | 61.070 | 1.00 | 20.25 | N |
| ATOM | 2432 | CA | ARG | A | 327 | 27.580 | 6.629 | 60.530 | 1.00 | 20.22 | C |
| ATOM | 2433 | CB | ARG | A | 327 | 29.027 | 6.775 | 61.017 | 1.00 | 20.28 | C |
| ATOM | 2434 | CG | ARG | A | 327 | 30.025 | 5.801 | 60.404 | 1.00 | 20.65 | C |
| ATOM | 2435 | CD | ARG | A | 327 | 31.431 | 6.110 | 60.896 | 1.00 | 20.96 | C |
| ATOM | 2436 | NE | ARG | A | 327 | 32.417 | 5.128 | 60.449 | 1.00 | 22.26 | N |
| ATOM | 2437 | CZ | ARG | A | 327 | 32.745 | 4.028 | 61.125 | 1.00 | 23.08 | C |
| ATOM | 2438 | NH1 | ARG | A | 327 | 32.159 | 3.753 | 62.283 | 1.00 | 23.38 | N |
| ATOM | 2439 | NH2 | ARG | A | 327 | 33.661 | 3.200 | 60.638 | 1.00 | 23.92 | N |
| ATOM | 2440 | C | ARG | A | 327 | 27.029 | 5.237 | 60.875 | 1.00 | 19.92 | C |
| ATOM | 2441 | O | ARG | A | 327 | 26.925 | 4.374 | 60.001 | 1.00 | 20.03 | O |
| ATOM | 2442 | N | GLN | A | 328 | 26.673 | 5.029 | 62.143 | 1.00 | 19.65 | N |
| ATOM | 2443 | CA | GLN | A | 328 | 26.159 | 3.732 | 62.587 | 1.00 | 19.32 | C |
| ATOM | 2444 | CB | GLN | A | 328 | 26.042 | 3.677 | 64.117 | 1.00 | 19.35 | C |
| ATOM | 2445 | CG | GLN | A | 328 | 25.840 | 2.263 | 64.677 | 1.00 | 19.94 | C |
| ATOM | 2446 | CD | GLN | A | 328 | 26.906 | 1.281 | 64.201 | 1.00 | 20.35 | C |
| ATOM | 2447 | OE1 | GLN | A | 328 | 28.099 | 1.478 | 64.435 | 1.00 | 21.19 | O |
| ATOM | 2448 | NE2 | GLN | A | 328 | 26.475 | 0.219 | 63.528 | 1.00 | 21.05 | N |
| ATOM | 2449 | C | GLN | A | 328 | 24.824 | 3.370 | 61.928 | 1.00 | 18.99 | C |
| ATOM | 2450 | O | GLN | A | 328 | 24.573 | 2.202 | 61.633 | 1.00 | 19.16 | O |
| ATOM | 2451 | N | HIS | A | 329 | 23.974 | 4.371 | 61.698 | 1.00 | 18.85 | N |
| ATOM | 2452 | CA | HIS | A | 329 | 22.712 | 4.150 | 60.991 | 1.00 | 18.74 | C |
| ATOM | 2453 | CB | HIS | A | 329 | 21.884 | 5.436 | 60.942 | 1.00 | 18.98 | C |
| ATOM | 2454 | CG | HIS | A | 329 | 20.599 | 5.299 | 60.184 | 1.00 | 19.79 | C |
| ATOM | 2455 | ND1 | HIS | A | 329 | 19.485 | 4.682 | 60.712 | 1.00 | 21.92 | N |
| ATOM | 2456 | CE1 | HIS | A | 329 | 18.506 | 4.711 | 59.824 | 1.00 | 22.02 | C |
| ATOM | 2457 | NE2 | HIS | A | 329 | 18.945 | 5.326 | 58.740 | 1.00 | 21.91 | N |
| ATOM | 2458 | CD2 | HIS | A | 329 | 20.250 | 5.704 | 58.940 | 1.00 | 21.39 | C |

TABLE 6-continued

Coordinates of the crystal structure of *E. coli* ExoI bound to compound 9

| ATOM | 2459 | C | HIS | A | 329 | 22.960 | 3.619 | 59.578 | 1.00 | 18.57 | C |
|---|---|---|---|---|---|---|---|---|---|---|---|
| ATOM | 2460 | O | HIS | A | 329 | 22.260 | 2.717 | 59.114 | 1.00 | 18.41 | O |
| ATOM | 2461 | N | CYS | A | 330 | 23.962 | 4.184 | 58.904 | 1.00 | 18.22 | N |
| ATOM | 2462 | CA | CYS | A | 330 | 24.350 | 3.734 | 57.567 | 1.00 | 18.07 | C |
| ATOM | 2463 | CB | CYS | A | 330 | 25.386 | 4.681 | 56.959 | 1.00 | 18.07 | C |
| ATOM | 2464 | SG | CYS | A | 330 | 24.742 | 6.328 | 56.591 | 1.00 | 18.74 | S |
| ATOM | 2465 | C | CYS | A | 330 | 24.875 | 2.299 | 57.585 | 1.00 | 18.02 | C |
| ATOM | 2466 | O | CYS | A | 330 | 24.528 | 1.495 | 56.716 | 1.00 | 17.98 | O |
| ATOM | 2467 | N | LEU | A | 331 | 25.707 | 1.986 | 58.580 | 1.00 | 17.89 | N |
| ATOM | 2468 | CA | LEU | A | 331 | 26.221 | 0.626 | 58.766 | 1.00 | 18.11 | C |
| ATOM | 2469 | CB | LEU | A | 331 | 27.266 | 0.590 | 59.885 | 1.00 | 18.15 | C |
| ATOM | 2470 | CG | LEU | A | 331 | 28.644 | 1.179 | 59.568 | 1.00 | 18.84 | C |
| ATOM | 2471 | CD1 | LEU | A | 331 | 29.422 | 1.432 | 60.849 | 1.00 | 19.51 | C |
| ATOM | 2472 | CD2 | LEU | A | 331 | 29.428 | 0.257 | 58.639 | 1.00 | 18.77 | C |
| ATOM | 2473 | C | LEU | A | 331 | 25.100 | −0.370 | 59.060 | 1.00 | 18.08 | C |
| ATOM | 2474 | O | LEU | A | 331 | 25.104 | −1.491 | 58.543 | 1.00 | 18.15 | O |
| ATOM | 2475 | N | ASP | A | 332 | 24.144 | 0.049 | 59.888 | 1.00 | 18.23 | N |
| ATOM | 2476 | CA | ASP | A | 332 | 22.983 | −0.778 | 60.221 | 1.00 | 18.36 | C |
| ATOM | 2477 | CB | ASP | A | 332 | 22.136 | −0.109 | 61.307 | 1.00 | 18.62 | C |
| ATOM | 2478 | CG | ASP | A | 332 | 22.808 | −0.123 | 62.670 | 1.00 | 19.73 | C |
| ATOM | 2479 | OD1 | ASP | A | 332 | 23.821 | −0.840 | 62.842 | 1.00 | 21.29 | O |
| ATOM | 2480 | OD2 | ASP | A | 332 | 22.318 | 0.584 | 63.576 | 1.00 | 21.64 | O |
| ATOM | 2481 | C | ASP | A | 332 | 22.131 | −1.068 | 58.992 | 1.00 | 18.13 | C |
| ATOM | 2482 | O | ASP | A | 332 | 21.719 | −2.207 | 58.772 | 1.00 | 18.22 | O |
| ATOM | 2483 | N | ASN | A | 333 | 21.875 | −0.034 | 58.191 | 1.00 | 18.07 | N |
| ATOM | 2484 | CA | ASN | A | 333 | 21.117 | −0.187 | 56.950 | 1.00 | 18.06 | C |
| ATOM | 2485 | CB | ASN | A | 333 | 20.853 | 1.176 | 56.302 | 1.00 | 17.93 | C |
| ATOM | 2486 | CG | ASN | A | 333 | 19.598 | 1.853 | 56.836 | 1.00 | 18.32 | C |
| ATOM | 2487 | OD1 | ASN | A | 333 | 19.377 | 3.038 | 56.592 | 1.00 | 19.16 | O |
| ATOM | 2488 | ND2 | ASN | A | 333 | 18.766 | 1.101 | 57.549 | 1.00 | 17.36 | N |
| ATOM | 2489 | C | ASN | A | 333 | 21.811 | −1.104 | 55.951 | 1.00 | 17.99 | C |
| ATOM | 2490 | O | ASN | A | 333 | 21.160 | −1.894 | 55.270 | 1.00 | 18.27 | O |
| ATOM | 2491 | N | LEU | A | 334 | 23.135 | −0.989 | 55.864 | 1.00 | 17.99 | N |
| ATOM | 2492 | CA | LEU | A | 334 | 23.922 | −1.826 | 54.961 | 1.00 | 18.04 | C |
| ATOM | 2493 | CB | LEU | A | 334 | 25.395 | −1.400 | 54.971 | 1.00 | 17.91 | C |
| ATOM | 2494 | CG | LEU | A | 334 | 26.366 | −2.220 | 54.112 | 1.00 | 17.45 | C |
| ATOM | 2495 | CD1 | LEU | A | 334 | 26.037 | −2.092 | 52.631 | 1.00 | 18.05 | C |
| ATOM | 2496 | CD2 | LEU | A | 334 | 27.801 | −1.805 | 54.389 | 1.00 | 17.93 | C |
| ATOM | 2497 | C | LEU | A | 334 | 23.787 | −3.305 | 55.320 | 1.00 | 18.45 | C |
| ATOM | 2498 | O | LEU | A | 334 | 23.619 | −4.148 | 54.436 | 1.00 | 18.51 | O |
| ATOM | 2499 | N | LYS | A | 335 | 23.854 | −3.608 | 56.617 | 1.00 | 18.96 | N |
| ATOM | 2500 | CA | LYS | A | 335 | 23.696 | −4.981 | 57.098 | 1.00 | 19.62 | C |
| ATOM | 2501 | CB | LYS | A | 335 | 23.904 | −5.056 | 58.615 | 1.00 | 19.51 | C |
| ATOM | 2502 | CG | LYS | A | 335 | 23.936 | −6.478 | 59.166 | 1.00 | 20.07 | C |
| ATOM | 2503 | CD | LYS | A | 335 | 24.222 | −6.492 | 60.659 | 1.00 | 20.67 | C |
| ATOM | 2504 | CE | LYS | A | 335 | 24.105 | −7.901 | 61.234 | 1.00 | 22.00 | C |
| ATOM | 2505 | NZ | LYS | A | 335 | 22.687 | −8.367 | 61.300 | 1.00 | 23.40 | N |
| ATOM | 2506 | C | LYS | A | 335 | 22.328 | −5.545 | 56.713 | 1.00 | 19.76 | C |
| ATOM | 2507 | O | LYS | A | 3352 | 2.234 | −6.662 | 56.204 | 1.00 | 20.11 | O |
| ATOM | 2508 | N | ILE | A | 336 | 21.275 | −4.759 | 56.941 | 1.00 | 20.17 | N |
| ATOM | 2509 | CA | ILE | A | 336 | 19.912 | −5.176 | 56.605 | 1.00 | 20.40 | C |
| ATOM | 2510 | CB | ILE | A | 336 | 18.852 | −4.163 | 57.114 | 1.00 | 20.54 | C |
| ATOM | 2511 | CG1 | ILE | A | 336 | 18.868 | −4.102 | 58.645 | 1.00 | 20.57 | C |
| ATOM | 2512 | CD1 | ILE | A | 336 | 18.142 | −2.899 | 59.228 | 1.00 | 21.67 | C |
| ATOM | 2513 | CG2 | ILE | A | 336 | 17.454 | −4.540 | 56.609 | 1.00 | 20.44 | C |
| ATOM | 2514 | C | ILE | A | 336 | 19.750 | −5.410 | 55.101 | 1.00 | 20.50 | C |
| ATOM | 2515 | O | ILE | A | 336 | 19.191 | −6.425 | 54.685 | 1.00 | 20.70 | O |
| ATOM | 2516 | N | LEU | A | 337 | 20.259 | −4.481 | 54.291 | 1.00 | 20.64 | N |
| ATOM | 2517 | CA | LEU | A | 337 | 20.169 | −4.609 | 52.837 | 1.00 | 20.89 | C |
| ATOM | 2518 | CB | LEU | A | 337 | 20.764 | −3.380 | 52.138 | 1.00 | 20.92 | C |
| ATOM | 2519 | CG | LEU | A | 337 | 19.896 | −2.119 | 52.114 | 1.00 | 21.61 | C |
| ATOM | 2520 | CD1 | LEU | A | 337 | 20.722 | −0.928 | 51.680 | 1.00 | 22.45 | C |
| ATOM | 2521 | CD2 | LEU | A | 337 | 18.680 | −2.292 | 51.201 | 1.00 | 22.27 | C |
| ATOM | 2522 | C | LEU | A | 337 | 20.841 | −5.885 | 52.338 | 1.00 | 20.93 | C |
| ATOM | 2523 | O | LEU | A | 337 | 20.287 | −6.596 | 51.499 | 1.00 | 21.08 | O |
| ATOM | 2524 | N | ARG | A | 338 | 22.026 | −6.176 | 52.875 | 1.00 | 21.06 | N |
| ATOM | 2525 | CA | ARG | A | 338 | 22.789 | −7.369 | 52.498 | 1.00 | 21.19 | C |
| ATOM | 2526 | CB | ARG | A | 338 | 24.178 | −7.334 | 53.132 | 1.00 | 20.97 | C |
| ATOM | 2527 | CG | ARG | A | 338 | 25.153 | −6.431 | 52.402 | 1.00 | 20.33 | C |
| ATOM | 2528 | CD | ARG | A | 338 | 26.404 | −6.179 | 53.220 | 1.00 | 19.44 | C |
| ATOM | 2529 | NE | ARG | A | 338 | 27.484 | −5.639 | 52.395 | 1.00 | 18.52 | N |
| ATOM | 2530 | CZ | ARG | A | 338 | 28.638 | −5.179 | 52.870 | 1.00 | 17.85 | C |
| ATOM | 2531 | NH1 | ARG | A | 338 | 28.869 | −5.173 | 54.179 | 1.00 | 18.83 | N |
| ATOM | 2532 | NH2 | ARG | A | 338 | 29.562 | −4.716 | 52.033 | 1.00 | 18.24 | N |
| ATOM | 2533 | C | ARG | A | 338 | 22.069 | −8.663 | 52.868 | 1.00 | 21.66 | C |
| ATOM | 2534 | O | ARG | A | 338 | 22.253 | −9.692 | 52.217 | 1.00 | 21.74 | O |
| ATOM | 2535 | N | GLU | A | 339 | 21.249 | −8.600 | 53.912 | 1.00 | 22.15 | N |
| ATOM | 2536 | CA | GLU | A | 339 | 20.464 | −9.750 | 54.352 | 1.00 | 22.84 | C |

TABLE 6-continued

Coordinates of the crystal structure of *E. coli* ExoI bound to compound 9

| ATOM | 2537 | CB | GLU | A | 339 | 20.252 | −9.699 | 55.868 | 1.00 | 22.87 | C |
|---|---|---|---|---|---|---|---|---|---|---|---|
| ATOM | 2538 | CG | GLU | A | 339 | 21.530 | −9.890 | 56.681 | 1.00 | 23.77 | C |
| ATOM | 2539 | CD | GLU | A | 339 | 21.344 | −9.598 | 58.163 | 1.00 | 24.29 | C |
| ATOM | 2540 | OE1 | GLU | A | 339 | 20.214 | −9.255 | 58.576 | 1.00 | 25.96 | O |
| ATOM | 2541 | OE2 | GLU | A | 339 | 22.335 | −9.711 | 58.916 | 1.00 | 26.34 | O |
| ATOM | 2542 | C | GLU | A | 339 | 19.121 | −9.827 | 53.623 | 1.00 | 22.88 | C |
| ATOM | 2543 | O | GLU | A | 339 | 18.331 | −10.747 | 53.853 | 1.00 | 22.86 | O |
| ATOM | 2544 | N | ASN | A | 340 | 18.874 | −8.863 | 52.737 | 1.00 | 23.02 | N |
| ATOM | 2545 | CA | ASN | A | 340 | 17.625 | −8.805 | 51.981 | 1.00 | 23.34 | C |
| ATOM | 2546 | CB | ASN | A | 340 | 16.726 | −7.697 | 52.534 | 1.00 | 23.20 | C |
| ATOM | 2547 | CG | ASN | A | 340 | 16.119 | −8.058 | 53.871 | 1.00 | 23.34 | C |
| ATOM | 2548 | OD1 | ASN | A | 340 | 15.099 | −8.743 | 53.937 | 1.00 | 23.26 | O |
| ATOM | 2549 | ND2 | ASN | A | 340 | 16.740 | −7.592 | 54.947 | 1.00 | 23.23 | N |
| ATOM | 2550 | C | ASN | A | 340 | 17.848 | −8.609 | 50.476 | 1.00 | 23.61 | C |
| ATOM | 2551 | O | ASN | A | 340 | 17.505 | −7.561 | 49.932 | 1.00 | 23.68 | O |
| ATOM | 2552 | N | PRO | A | 341 | 18.393 | −9.638 | 49.793 | 1.00 | 23.96 | N |
| ATOM | 2553 | CA | PRO | A | 341 | 18.789 | −9.499 | 48.385 | 1.00 | 24.26 | C |
| ATOM | 2554 | CB | PRO | A | 341 | 19.495 | −10.831 | 48.079 | 1.00 | 24.37 | C |
| ATOM | 2555 | CG | PRO | A | 341 | 19.729 | −11.481 | 49.405 | 1.00 | 24.14 | C |
| ATOM | 2556 | CD | PRO | A | 341 | 18.644 | −11.000 | 50.293 | 1.00 | 24.07 | C |
| ATOM | 2557 | C | PRO | A | 341 | 17.606 | −9.303 | 47.434 | 1.00 | 24.55 | C |
| ATOM | 2558 | O | PRO | A | 341 | 17.805 | −8.904 | 46.285 | 1.00 | 24.53 | O |
| ATOM | 2559 | N | GLN | A | 342 | 16.391 | −9.579 | 47.908 | 1.00 | 24.80 | N |
| ATOM | 2560 | CA | GLN | A | 342 | 15.183 | −9.423 | 47.088 | 1.00 | 25.20 | C |
| ATOM | 2561 | CB | GLN | A | 342 | 13.965 | −10.078 | 47.765 | 1.00 | 25.05 | C |
| ATOM | 2562 | CG | GLN | A | 342 | 13.384 | −9.299 | 48.951 | 1.00 | 24.88 | C |
| ATOM | 2563 | CD | GLN | A | 342 | 14.148 | −9.518 | 50.249 | 1.00 | 24.52 | C |
| ATOM | 2564 | OE1 | GLN | A | 342 | 15.103 | −10.293 | 50.303 | 1.00 | 24.25 | O |
| ATOM | 2565 | NE2 | GLN | A | 342 | 13.721 | −8.834 | 51.305 | 1.00 | 24.79 | N |
| ATOM | 2566 | C | GLN | A | 342 | 14.890 | −7.956 | 46.744 | 1.00 | 25.48 | C |
| ATOM | 2567 | O | GLN | A | 342 | 14.076 | −7.667 | 45.863 | 1.00 | 25.68 | O |
| ATOM | 2568 | N | VAL | A | 343 | 15.562 | −7.041 | 47.443 | 1.00 | 25.92 | N |
| ATOM | 2569 | CA | VAL | A | 343 | 15.441 | −5.609 | 47.168 | 1.00 | 26.34 | C |
| ATOM | 2570 | CB | VAL | A | 343 | 16.042 | −4.745 | 48.326 | 1.00 | 26.42 | C |
| ATOM | 2571 | CG1 | VAL | A | 343 | 17.565 | −4.833 | 48.350 | 1.00 | 26.98 | C |
| ATOM | 2572 | CG2 | VAL | A | 343 | 15.586 | −3.295 | 48.215 | 1.00 | 27.06 | C |
| ATOM | 2573 | C | VAL | A | 343 | 16.067 | −5.234 | 45.812 | 1.00 | 26.36 | C |
| ATOM | 2574 | O | VAL | A | 343 | 15.667 | −4.247 | 45.190 | 1.00 | 26.27 | O |
| ATOM | 2575 | N | ARG | A | 344 | 17.033 | −6.039 | 45.359 | 1.00 | 26.53 | N |
| ATOM | 2576 | CA | ARG | A | 344 | 17.685 | −5.828 | 44.061 | 1.00 | 26.68 | C |
| ATOM | 2577 | CB | ARG | A | 344 | 18.747 | −6.898 | 43.799 | 1.00 | 26.58 | C |
| ATOM | 2578 | CG | ARG | A | 344 | 19.907 | −6.937 | 44.775 | 1.00 | 25.81 | C |
| ATOM | 2579 | CD | ARG | A | 344 | 20.955 | −7.901 | 44.248 | 1.00 | 25.10 | C |
| ATOM | 2580 | NE | ARG | A | 344 | 22.003 | −8.234 | 45.211 | 1.00 | 24.01 | N |
| ATOM | 2581 | CZ | ARG | A | 344 | 23.089 | −7.498 | 45.430 | 1.00 | 23.61 | C |
| ATOM | 2582 | NH1 | ARG | A | 344 | 23.266 | −6.349 | 44.788 | 1.00 | 22.91 | N |
| ATOM | 2583 | NH2 | ARG | A | 344 | 23.992 | −7.903 | 46.309 | 1.00 | 23.37 | N |
| ATOM | 2584 | C | ARG | A | 344 | 16.669 | −5.855 | 42.925 | 1.00 | 27.18 | C |
| ATOM | 2585 | O | ARG | A | 344 | 16.601 | −4.925 | 42.124 | 1.00 | 27.16 | O |
| ATOM | 2586 | N | GLU | A | 345 | 15.885 | −6.932 | 42.865 | 1.00 | 27.64 | N |
| ATOM | 2587 | CA | GLU | A | 345 | 14.881 | −7.112 | 41.816 | 1.00 | 28.28 | C |
| ATOM | 2588 | CB | GLU | A | 345 | 14.278 | −8.520 | 41.888 | 1.00 | 28.23 | C |
| ATOM | 2589 | CG | GLU | A | 345 | 13.704 | −9.028 | 40.566 | 1.00 | 29.12 | C |
| ATOM | 2590 | CD | GLU | A | 345 | 13.217 | −10.468 | 40.644 | 1.00 | 29.33 | C |
| ATOM | 2591 | OE1 | GLU | A | 345 | 12.445 | −10.795 | 41.572 | 1.00 | 30.44 | O |
| ATOM | 2592 | OE2 | GLU | A | 345 | 13.597 | −11.272 | 39.764 | 1.00 | 30.80 | O |
| ATOM | 2593 | C | GLU | A | 345 | 13.782 | −6.053 | 41.912 | 1.00 | 28.27 | C |
| ATOM | 2594 | O | GLU | A | 345 | 13.224 | −5.633 | 40.895 | 1.00 | 28.35 | O |
| ATOM | 2595 | N | LYS | A | 346 | 13.487 | −5.625 | 43.139 | 1.00 | 28.49 | N |
| ATOM | 2596 | CA | LYS | A | 346 | 12.507 | −4.567 | 43.389 | 1.00 | 28.78 | C |
| ATOM | 2597 | CB | LYS | A | 346 | 12.329 | −4.339 | 44.889 | 1.00 | 28.82 | C |
| ATOM | 2598 | CG | LYS | A | 346 | 11.361 | −5.282 | 45.567 | 1.00 | 29.10 | C |
| ATOM | 2599 | CD | LYS | A | 346 | 10.968 | −4.726 | 46.923 | 1.00 | 29.38 | C |
| ATOM | 2600 | CE | LYS | A | 346 | 10.105 | −5.689 | 47.705 | 1.00 | 29.35 | C |
| ATOM | 2601 | NZ | LYS | A | 346 | 9.740 | −5.118 | 49.030 | 1.00 | 29.35 | N |
| ATOM | 2602 | C | LYS | A | 346 | 12.885 | −3.248 | 42.714 | 1.00 | 28.92 | C |
| ATOM | 2603 | O | LYS | A | 346 | 12.077 | −2.669 | 41.983 | 1.00 | 29.04 | O |
| ATOM | 2604 | N | VAL | A | 347 | 14.109 | −2.777 | 42.963 | 1.00 | 29.06 | N |
| ATOM | 2605 | CA | VAL | A | 347 | 14.558 | −1.482 | 42.429 | 1.00 | 29.09 | C |
| ATOM | 2606 | CB | VAL | A | 347 | 15.819 | −0.919 | 43.164 | 1.00 | 29.02 | C |
| ATOM | 2607 | CG1 | VAL | A | 347 | 15.500 | −0.610 | 44.622 | 1.00 | 28.88 | C |
| ATOM | 2608 | CG2 | VAL | A | 347 | 17.006 | −1.876 | 43.051 | 1.00 | 28.85 | C |
| ATOM | 2609 | C | VAL | A | 347 | 14.777 | −1.497 | 40.913 | 1.00 | 29.27 | C |
| ATOM | 2610 | O | VAL | A | 347 | 14.626 | −0.468 | 40.254 | 1.00 | 29.25 | O |
| ATOM | 2611 | N | VAL | A | 348 | 15.125 | −2.665 | 40.371 | 1.00 | 29.53 | N |
| ATOM | 2612 | CA | VAL | A | 348 | 15.235 | −2.845 | 38.921 | 1.00 | 29.89 | C |
| ATOM | 2613 | CB | VAL | A | 348 | 15.838 | −4.232 | 38.549 | 1.00 | 29.85 | C |
| ATOM | 2614 | CG1 | VAL | A | 348 | 15.738 | −4.489 | 37.046 | 1.00 | 29.65 | C |

TABLE 6-continued

Coordinates of the crystal structure of *E. coli* ExoI bound to compound 9

| ATOM | 2615 | CG2 | VAL | A | 348 | 17.282 | −4.322 | 38.996 | 1.00 | 29.77 | C |
|---|---|---|---|---|---|---|---|---|---|---|---|
| ATOM | 2616 | C | VAL | A | 348 | 13.860 | −2.688 | 38.277 | 1.00 | 30.26 | C |
| ATOM | 2617 | O | VAL | A | 348 | 13.722 | −2.039 | 37.236 | 1.00 | 30.33 | O |
| ATOM | 2618 | N | ALA | A | 349 | 12.846 | −3.266 | 38.921 | 1.00 | 30.72 | N |
| ATOM | 2619 | CA | ALA | A | 349 | 11.467 | −3.192 | 38.442 | 1.00 | 31.16 | C |
| ATOM | 2620 | CB | ALA | A | 349 | 10.576 | −4.123 | 39.247 | 1.00 | 31.09 | C |
| ATOM | 2621 | C | ALA | A | 349 | 10.915 | −1.763 | 38.462 | 1.00 | 31.47 | C |
| ATOM | 2622 | O | ALA | A | 349 | 10.070 | −1.413 | 37.637 | 1.00 | 31.59 | O |
| ATOM | 2623 | N | ILE | A | 350 | 11.398 | −0.946 | 39.401 | 1.00 | 31.91 | N |
| ATOM | 2624 | CA | ILE | A | 350 | 11.031 | 0.475 | 39.466 | 1.00 | 32.31 | C |
| ATOM | 2625 | CB | ILE | A | 350 | 11.716 | 1.201 | 40.665 | 1.00 | 32.32 | C |
| ATOM | 2626 | CG1 | ILE | A | 350 | 11.229 | 0.628 | 42.001 | 1.00 | 32.31 | C |
| ATOM | 2627 | CD1 | ILE | A | 350 | 12.027 | 1.107 | 43.213 | 1.00 | 32.35 | C |
| ATOM | 2628 | CG2 | ILE | A | 350 | 11.467 | 2.715 | 40.602 | 1.00 | 32.24 | C |
| ATOM | 2629 | C | ILE | A | 350 | 11.390 | 1.191 | 38.159 | 1.00 | 32.67 | C |
| ATOM | 2630 | O | ILE | A | 350 | 10.551 | 1.871 | 37.564 | 1.00 | 32.75 | O |
| ATOM | 2631 | N | PHE | A | 351 | 12.632 | 1.012 | 37.714 | 1.00 | 33.03 | N |
| ATOM | 2632 | CA | PHE | A | 351 | 13.145 | 1.701 | 36.531 | 1.00 | 33.41 | C |
| ATOM | 2633 | CB | PHE | A | 351 | 14.626 | 2.051 | 36.719 | 1.00 | 33.32 | C |
| ATOM | 2634 | CG | PHE | A | 351 | 14.895 | 2.945 | 37.899 | 1.00 | 33.07 | C |
| ATOM | 2635 | CD1 | PHE | A | 351 | 15.278 | 2.406 | 39.124 | 1.00 | 32.93 | C |
| ATOM | 2636 | CE1 | PHE | A | 351 | 15.528 | 3.228 | 40.220 | 1.00 | 32.82 | C |
| ATOM | 2637 | CZ | PHE | A | 351 | 15.400 | 4.608 | 40.095 | 1.00 | 32.92 | C |
| ATOM | 2638 | CE2 | PHE | A | 351 | 15.020 | 5.159 | 38.875 | 1.00 | 32.86 | C |
| ATOM | 2639 | CD2 | PHE | A | 351 | 14.771 | 4.328 | 37.785 | 1.00 | 32.98 | C |
| ATOM | 2640 | C | PHE | A | 351 | 12.950 | 0.893 | 35.243 | 1.00 | 33.83 | C |
| ATOM | 2641 | O | PHE | A | 351 | 13.425 | 1.293 | 34.174 | 1.00 | 33.89 | O |
| ATOM | 2642 | N | ALA | A | 352 | 12.246 | −0.234 | 35.350 | 1.00 | 34.24 | N |
| ATOM | 2643 | CA | ALA | A | 352 | 12.010 | −1.121 | 34.207 | 1.00 | 34.71 | C |
| ATOM | 2644 | CB | ALA | A | 352 | 11.557 | −2.494 | 34.683 | 1.00 | 34.69 | C |
| ATOM | 2645 | C | ALA | A | 352 | 11.006 | −0.542 | 33.210 | 1.00 | 35.05 | C |
| ATOM | 2646 | O | ALA | A | 352 | 11.147 | −0.731 | 31.999 | 1.00 | 35.20 | O |
| ATOM | 2647 | N | GLU | A | 353 | 9.995 | 0.158 | 33.723 | 1.00 | 35.41 | N |
| ATOM | 2648 | CA | GLU | A | 353 | 8.970 | 0.771 | 32.874 | 1.00 | 35.75 | C |
| ATOM | 2649 | CB | GLU | A | 353 | 7.565 | 0.356 | 33.328 | 1.00 | 35.76 | C |
| ATOM | 2650 | CG | GLU | A | 353 | 7.194 | 0.809 | 34.737 | 1.00 | 36.09 | C |
| ATOM | 2651 | CD | GLU | A | 353 | 5.802 | 0.359 | 35.162 | 1.00 | 36.25 | C |
| ATOM | 2652 | OE1 | GLU | A | 353 | 5.350 | −0.716 | 34.706 | 1.00 | 36.77 | O |
| ATOM | 2653 | OE2 | GLU | A | 353 | 5.162 | 1.081 | 35.962 | 1.00 | 36.88 | O |
| ATOM | 2654 | C | GLU | A | 353 | 9.094 | 2.295 | 32.836 | 1.00 | 35.78 | C |
| ATOM | 2655 | O | GLU | A | 353 | 9.601 | 2.914 | 33.774 | 1.00 | 35.89 | O |
| ATOM | 2656 | N | SER | A | 360 | 6.060 | 15.154 | 24.340 | 1.00 | 32.56 | N |
| ATOM | 2657 | CA | SER | A | 360 | 5.465 | 16.221 | 23.542 | 1.00 | 32.43 | C |
| ATOM | 2658 | CB | SER | A | 360 | 5.969 | 17.591 | 24.014 | 1.00 | 32.58 | C |
| ATOM | 2659 | OG | SER | A | 360 | 7.353 | 17.758 | 23.745 | 1.00 | 33.06 | O |
| ATOM | 2660 | C | SER | A | 360 | 5.759 | 16.028 | 22.054 | 1.00 | 32.11 | C |
| ATOM | 2661 | O | SER | A | 360 | 6.662 | 15.270 | 21.687 | 1.00 | 32.26 | O |
| ATOM | 2662 | N | ASP | A | 361 | 4.994 | 16.716 | 21.205 | 1.00 | 31.62 | N |
| ATOM | 2663 | CA | ASP | A | 361 | 5.202 | 16.656 | 19.754 | 1.00 | 31.02 | C |
| ATOM | 2664 | CB | ASP | A | 361 | 3.885 | 16.912 | 18.991 | 1.00 | 31.38 | C |
| ATOM | 2665 | CG | ASP | A | 361 | 3.271 | 18.285 | 19.292 | 1.00 | 32.23 | C |
| ATOM | 2666 | OD1 | ASP | A | 361 | 3.942 | 19.142 | 19.908 | 1.00 | 33.51 | O |
| ATOM | 2667 | OD2 | ASP | A | 361 | 2.104 | 18.504 | 18.900 | 1.00 | 33.69 | O |
| ATOM | 2668 | C | ASP | A | 361 | 6.313 | 17.603 | 19.279 | 1.00 | 30.18 | C |
| ATOM | 2669 | O | ASP | A | 361 | 6.628 | 17.658 | 18.087 | 1.00 | 30.33 | O |
| ATOM | 2670 | N | ASN | A | 362 | 6.897 | 18.341 | 20.222 | 1.00 | 28.99 | N |
| ATOM | 2671 | CA | ASN | A | 362 | 8.000 | 19.251 | 19.932 | 1.00 | 27.83 | C |
| ATOM | 2672 | CB | ASN | A | 362 | 8.117 | 20.313 | 21.037 | 1.00 | 27.87 | C |
| ATOM | 2673 | CG | ASN | A | 362 | 9.012 | 21.489 | 20.644 | 1.00 | 27.95 | C |
| ATOM | 2674 | OD1 | ASN | A | 362 | 9.058 | 22.502 | 21.346 | 1.00 | 28.45 | O |
| ATOM | 2675 | ND2 | ASN | A | 362 | 9.725 | 21.359 | 19.531 | 1.00 | 27.22 | N |
| ATOM | 2676 | C | ASN | A | 362 | 9.314 | 18.488 | 19.779 | 1.00 | 26.96 | C |
| ATOM | 2677 | O | ASN | A | 362 | 9.862 | 17.972 | 20.759 | 1.00 | 26.68 | O |
| ATOM | 2678 | N | VAL | A | 363 | 9.813 | 18.424 | 18.544 | 1.00 | 26.03 | N |
| ATOM | 2679 | CA | VAL | A | 363 | 11.051 | 17.701 | 18.236 | 1.00 | 25.16 | C |
| ATOM | 2680 | CB | VAL | A | 363 | 11.306 | 17.615 | 16.695 | 1.00 | 25.24 | C |
| ATOM | 2681 | CG1 | VAL | A | 363 | 11.676 | 18.981 | 16.113 | 1.00 | 25.06 | C |
| ATOM | 2682 | CG2 | VAL | A | 363 | 12.374 | 16.570 | 16.373 | 1.00 | 25.10 | C |
| ATOM | 2683 | C | VAL | A | 363 | 12.275 | 18.267 | 18.987 | 1.00 | 24.68 | C |
| ATOM | 2684 | O | VAL | A | 363 | 13.224 | 17.534 | 19.273 | 1.00 | 24.22 | O |
| ATOM | 2685 | N | ASP | A | 364 | 12.231 | 19.560 | 19.322 | 1.00 | 24.39 | N |
| ATOM | 2686 | CA | ASP | A | 364 | 13.261 | 20.185 | 20.171 | 1.00 | 24.11 | C |
| ATOM | 2687 | CB | ASP | A | 364 | 12.939 | 21.664 | 20.431 | 1.00 | 24.20 | C |
| ATOM | 2688 | CG | ASP | A | 364 | 13.269 | 22.568 | 19.244 | 1.00 | 24.94 | C |
| ATOM | 2689 | OD1 | ASP | A | 364 | 13.819 | 22.081 | 18.234 | 1.00 | 25.45 | O |
| ATOM | 2690 | OD2 | ASP | A | 364 | 12.974 | 23.781 | 19.334 | 1.00 | 26.26 | O |
| ATOM | 2691 | C | ASP | A | 364 | 13.417 | 19.465 | 21.515 | 1.00 | 23.85 | C |
| ATOM | 2692 | O | ASP | A | 364 | 14.499 | 19.465 | 22.103 | 1.00 | 23.56 | O |

TABLE 6-continued

Coordinates of the crystal structure of *E. coli* ExoI bound to compound 9

| ATOM | 2693 | N | ALA | A | 365 | 12.330 | 18.860 | 21.994 | 1.00 | 23.43 | N |
|---|---|---|---|---|---|---|---|---|---|---|---|
| ATOM | 2694 | CA | ALA | A | 365 | 12.309 | 18.225 | 23.315 | 1.00 | 23.50 | C |
| ATOM | 2695 | CB | ALA | A | 365 | 10.956 | 18.461 | 23.987 | 1.00 | 23.51 | C |
| ATOM | 2696 | C | ALA | A | 365 | 12.628 | 16.726 | 23.266 | 1.00 | 23.38 | C |
| ATOM | 2697 | O | ALA | A | 365 | 12.537 | 16.032 | 24.285 | 1.00 | 23.47 | O |
| ATOM | 2698 | N | GLN | A | 366 | 13.032 | 16.240 | 22.096 | 1.00 | 23.35 | N |
| ATOM | 2699 | CA | GLN | A | 366 | 13.083 | 14.797 | 21.843 | 1.00 | 23.43 | C |
| ATOM | 2700 | CB | GLN | A | 366 | 12.219 | 14.445 | 20.627 | 1.00 | 23.36 | C |
| ATOM | 2701 | CG | GLN | A | 366 | 10.728 | 14.667 | 20.850 | 1.00 | 23.86 | C |
| ATOM | 2702 | CD | GLN | A | 366 | 9.879 | 14.294 | 19.645 | 1.00 | 24.06 | C |
| ATOM | 2703 | OE1 | GLN | A | 366 | 10.393 | 13.879 | 18.606 | 1.00 | 25.85 | O |
| ATOM | 2704 | NE2 | GLN | A | 366 | 8.569 | 14.444 | 19.783 | 1.00 | 25.43 | N |
| ATOM | 2705 | C | GLN | A | 366 | 14.491 | 14.206 | 21.688 | 1.00 | 23.42 | C |
| ATOM | 2706 | O | GLN | A | 366 | 14.654 | 13.128 | 21.113 | 1.00 | 23.21 | O |
| ATOM | 2707 | N | LEU | A | 367 | 15.498 | 14.895 | 22.222 | 1.00 | 23.58 | N |
| ATOM | 2708 | CA | LEU | A | 367 | 16.881 | 14.404 | 22.166 | 1.00 | 24.10 | C |
| ATOM | 2709 | CB | LEU | A | 367 | 17.829 | 15.346 | 22.931 | 1.00 | 23.96 | C |
| ATOM | 2710 | CG | LEU | A | 367 | 19.261 | 14.883 | 23.241 | 1.00 | 24.42 | C |
| ATOM | 2711 | CD1 | LEU | A | 367 | 20.063 | 14.620 | 21.968 | 1.00 | 24.95 | C |
| ATOM | 2712 | CD2 | LEU | A | 367 | 19.966 | 15.906 | 24.117 | 1.00 | 24.42 | C |
| ATOM | 2713 | C | LEU | A | 367 | 17.017 | 12.970 | 22.687 | 1.00 | 24.30 | C |
| ATOM | 2714 | O | LEU | A | 367 | 17.688 | 12.141 | 22.071 | 1.00 | 24.28 | O |
| ATOM | 2715 | N | TYR | A | 368 | 16.368 | 12.680 | 23.811 | 1.00 | 24.76 | N |
| ATOM | 2716 | CA | TYR | A | 368 | 16.534 | 11.386 | 24.473 | 1.00 | 25.35 | C |
| ATOM | 2717 | CB | TYR | A | 368 | 16.648 | 11.566 | 25.992 | 1.00 | 25.31 | C |
| ATOM | 2718 | CG | TYR | A | 368 | 17.858 | 12.381 | 26.399 | 1.00 | 25.37 | C |
| ATOM | 2719 | CD1 | TYR | A | 368 | 19.149 | 11.891 | 26.200 | 1.00 | 25.28 | C |
| ATOM | 2720 | CE1 | TYR | A | 368 | 20.265 | 12.635 | 26.558 | 1.00 | 25.61 | C |
| ATOM | 2721 | CZ | TYR | A | 368 | 20.101 | 13.885 | 27.122 | 1.00 | 25.52 | C |
| ATOM | 2722 | OH | TYR | A | 368 | 21.213 | 14.612 | 27.471 | 1.00 | 25.76 | O |
| ATOM | 2723 | CE2 | TYR | A | 368 | 18.832 | 14.403 | 27.329 | 1.00 | 25.45 | C |
| ATOM | 2724 | CD2 | TYR | A | 368 | 17.715 | 13.648 | 26.965 | 1.00 | 25.44 | C |
| ATOM | 2725 | C | TYR | A | 368 | 15.460 | 10.358 | 24.099 | 1.00 | 25.91 | C |
| ATOM | 2726 | O | TYR | A | 368 | 15.259 | 9.367 | 24.810 | 1.00 | 25.82 | O |
| ATOM | 2727 | N | ASN | A | 369 | 14.798 | 10.586 | 22.964 | 1.00 | 26.66 | N |
| ATOM | 2728 | CA | ASN | A | 369 | 13.861 | 9.611 | 22.401 | 1.00 | 27.46 | C |
| ATOM | 2729 | CB | ASN | A | 369 | 12.909 | 10.286 | 21.407 | 1.00 | 27.69 | C |
| ATOM | 2730 | CG | ASN | A | 369 | 11.733 | 10.963 | 22.086 | 1.00 | 28.32 | C |
| ATOM | 2731 | OD1 | ASN | A | 369 | 11.880 | 11.608 | 23.126 | 1.00 | 29.94 | O |
| ATOM | 2732 | ND2 | ASN | A | 369 | 10.553 | 10.826 | 21.491 | 1.00 | 29.53 | N |
| ATOM | 2733 | C | ASN | A | 369 | 14.573 | 8.433 | 21.731 | 1.00 | 27.79 | C |
| ATOM | 2734 | O | ASN | A | 369 | 13.940 | 7.614 | 21.058 | 1.00 | 28.22 | O |
| ATOM | 2735 | N | GLY | A | 370 | 15.889 | 8.356 | 21.918 | 1.00 | 28.11 | N |
| ATOM | 2736 | CA | GLY | A | 370 | 16.687 | 7.257 | 21.384 | 1.00 | 28.39 | C |
| ATOM | 2737 | C | GLY | A | 370 | 17.938 | 7.717 | 20.663 | 1.00 | 28.56 | C |
| ATOM | 2738 | O | GLY | A | 370 | 18.032 | 8.869 | 20.223 | 1.00 | 28.71 | O |
| ATOM | 2739 | N | PHE | A | 371 | 18.907 | 6.812 | 20.546 | 1.00 | 28.68 | N |
| ATOM | 2740 | CA | PHE | A | 371 | 20.119 | 7.072 | 19.777 | 1.00 | 28.78 | C |
| ATOM | 2741 | CB | PHE | A | 371 | 21.259 | 6.156 | 20.236 | 1.00 | 28.92 | C |
| ATOM | 2742 | CG | PHE | A | 371 | 21.633 | 6.323 | 21.683 | 1.00 | 29.24 | C |
| ATOM | 2743 | CD1 | PHE | A | 371 | 22.419 | 7.398 | 22.095 | 1.00 | 29.38 | C |
| ATOM | 2744 | CE1 | PHE | A | 371 | 22.773 | 7.552 | 23.437 | 1.00 | 29.62 | C |
| ATOM | 2745 | CZ | PHE | A | 371 | 22.344 | 6.621 | 24.380 | 1.00 | 29.79 | C |
| ATOM | 2746 | CE2 | PHE | A | 371 | 21.563 | 5.540 | 23.979 | 1.00 | 29.99 | C |
| ATOM | 2747 | CD2 | PHE | A | 371 | 21.214 | 5.395 | 22.634 | 1.00 | 29.62 | C |
| ATOM | 2748 | C | PHE | A | 371 | 19.860 | 6.860 | 18.292 | 1.00 | 28.64 | C |
| ATOM | 2749 | O | PHE | A | 371 | 19.043 | 6.018 | 17.907 | 1.00 | 28.78 | O |
| ATOM | 2750 | N | PHE | A | 372 | 20.557 | 7.628 | 17.460 | 1.00 | 28.49 | N |
| ATOM | 2751 | CA | PHE | A | 372 | 20.476 | 7.460 | 16.012 | 1.00 | 28.23 | C |
| ATOM | 2752 | CB | PHE | A | 372 | 20.894 | 8.745 | 15.292 | 1.00 | 28.15 | C |
| ATOM | 2753 | CG | PHE | A | 372 | 19.963 | 9.902 | 15.523 | 1.00 | 28.16 | C |
| ATOM | 2754 | CD1 | PHE | A | 372 | 18.734 | 9.968 | 14.869 | 1.00 | 28.01 | C |
| ATOM | 2755 | CE1 | PHE | A | 372 | 17.868 | 11.042 | 15.082 | 1.00 | 28.19 | C |
| ATOM | 2756 | CZ | PHE | A | 372 | 18.234 | 12.065 | 15.948 | 1.00 | 27.90 | C |
| ATOM | 2757 | CE2 | PHE | A | 372 | 19.458 | 12.013 | 16.600 | 1.00 | 28.03 | C |
| ATOM | 2758 | CD2 | PHE | A | 372 | 20.317 | 10.934 | 16.385 | 1.00 | 28.06 | C |
| ATOM | 2759 | C | PHE | A | 372 | 21.348 | 6.295 | 15.556 | 1.00 | 28.16 | C |
| ATOM | 2760 | O | PHE | A | 372 | 22.398 | 6.024 | 16.144 | 1.00 | 28.05 | O |
| ATOM | 2761 | N | SER | A | 373 | 20.905 | 5.608 | 14.506 | 1.00 | 28.17 | N |
| ATOM | 2762 | CA | SER | A | 373 | 21.667 | 4.503 | 13.928 | 1.00 | 28.13 | C |
| ATOM | 2763 | CB | SER | A | 373 | 20.780 | 3.672 | 12.995 | 1.00 | 28.09 | C |
| ATOM | 2764 | OG | SER | A | 373 | 20.357 | 4.433 | 11.876 | 1.00 | 28.16 | O |
| ATOM | 2765 | C | SER | A | 373 | 22.893 | 5.018 | 13.175 | 1.00 | 28.18 | C |
| ATOM | 2766 | O | SER | A | 373 | 23.011 | 6.218 | 12.908 | 1.00 | 28.07 | O |
| ATOM | 2767 | N | ASP | A | 374 | 23.804 | 4.105 | 12.841 | 1.00 | 28.21 | N |
| ATOM | 2768 | CA | ASP | A | 374 | 24.992 | 4.435 | 12.051 | 1.00 | 28.34 | C |
| ATOM | 2769 | CB | ASP | A | 374 | 25.867 | 3.192 | 11.847 | 1.00 | 28.51 | C |
| ATOM | 2770 | CG | ASP | A | 374 | 26.381 | 2.607 | 13.158 | 1.00 | 29.17 | C |

TABLE 6-continued

Coordinates of the crystal structure of *E. coli* ExoI bound to compound 9

| | | | | | | | | | | | |
|---|---|---|---|---|---|---|---|---|---|---|---|
| ATOM | 2771 | OD1 | ASP | A | 374 | 26.168 | 3.223 | 14.225 | 1.00 | 30.24 | O |
| ATOM | 2772 | OD2 | ASP | A | 374 | 27.004 | 1.525 | 13.115 | 1.00 | 30.06 | O |
| ATOM | 2773 | C | ASP | A | 374 | 24.610 | 5.026 | 10.694 | 1.00 | 28.13 | C |
| ATOM | 2774 | O | ASP | A | 374 | 25.230 | 5.986 | 10.229 | 1.00 | 28.04 | O |
| ATOM | 2775 | N | ALA | A | 375 | 23.584 | 4.446 | 10.072 | 1.00 | 28.00 | N |
| ATOM | 2776 | CA | ALA | A | 375 | 23.096 | 4.903 | 8.771 | 1.00 | 27.78 | C |
| ATOM | 2777 | CB | ALA | A | 375 | 22.075 | 3.923 | 8.211 | 1.00 | 27.83 | C |
| ATOM | 2778 | C | ALA | A | 375 | 22.504 | 6.308 | 8.852 | 1.00 | 27.63 | C |
| ATOM | 2779 | O | ALA | A | 375 | 22.754 | 7.144 | 7.980 | 1.00 | 27.65 | O |
| ATOM | 2780 | N | ASP | A | 376 | 21.724 | 6.562 | 9.902 | 1.00 | 27.44 | N |
| ATOM | 2781 | CA | ASP | A | 376 | 21.133 | 7.883 | 10.122 | 1.00 | 27.26 | C |
| ATOM | 2782 | CB | ASP | A | 376 | 20.071 | 7.834 | 11.225 | 1.00 | 27.23 | C |
| ATOM | 2783 | CG | ASP | A | 376 | 18.683 | 7.504 | 10.691 | 1.00 | 27.44 | C |
| ATOM | 2784 | OD1 | ASP | A | 376 | 18.487 | 7.517 | 9.454 | 1.00 | 27.54 | O |
| ATOM | 2785 | OD2 | ASP | A | 376 | 17.781 | 7.242 | 11.512 | 1.00 | 27.38 | O |
| ATOM | 2786 | C | ASP | A | 376 | 22.182 | 8.946 | 10.436 | 1.00 | 27.06 | C |
| ATOM | 2787 | O | ASP | A | 376 | 22.063 | 10.086 | 9.989 | 1.00 | 26.87 | O |
| ATOM | 2788 | N | ARG | A | 377 | 23.205 | 8.567 | 11.202 | 1.00 | 26.93 | N |
| ATOM | 2789 | CA | ARG | A | 377 | 24.315 | 9.473 | 11.508 | 1.00 | 26.92 | C |
| ATOM | 2790 | CB | ARG | A | 377 | 25.228 | 8.878 | 12.592 | 1.00 | 27.11 | C |
| ATOM | 2791 | CG | ARG | A | 377 | 26.452 | 9.740 | 12.973 | 1.00 | 28.22 | C |
| ATOM | 2792 | CD | ARG | A | 377 | 26.082 | 11.190 | 13.314 | 1.00 | 29.90 | C |
| ATOM | 2793 | NE | ARG | A | 377 | 25.125 | 11.283 | 14.417 | 1.00 | 30.87 | N |
| ATOM | 2794 | CZ | ARG | A | 377 | 24.338 | 12.332 | 14.641 | 1.00 | 31.14 | C |
| ATOM | 2795 | NH1 | ARG | A | 377 | 24.377 | 13.386 | 13.835 | 1.00 | 31.29 | N |
| ATOM | 2796 | NH2 | ARG | A | 377 | 23.499 | 12.323 | 15.668 | 1.00 | 31.65 | N |
| ATOM | 2797 | C | ARG | A | 377 | 25.110 | 9.827 | 10.250 | 1.00 | 26.68 | C |
| ATOM | 2798 | O | ARG | A | 377 | 25.522 | 10.975 | 10.072 | 1.00 | 26.61 | O |
| ATOM | 2799 | N | ALA | A | 378 | 25.308 | 8.838 | 9.378 | 1.00 | 26.43 | N |
| ATOM | 2800 | CA | ALA | A | 378 | 25.990 | 9.052 | 8.103 | 1.00 | 26.33 | C |
| ATOM | 2801 | CB | ALA | A | 378 | 26.243 | 7.722 | 7.404 | 1.00 | 26.28 | C |
| ATOM | 2802 | C | ALA | A | 378 | 25.193 | 9.993 | 7.198 | 1.00 | 26.17 | C |
| ATOM | 2803 | O | ALA | A | 378 | 25.769 | 10.840 | 6.511 | 1.00 | 26.13 | O |
| ATOM | 2804 | N | ALA | A | 379 | 23.870 | 9.842 | 7.213 | 1.00 | 26.16 | N |
| ATOM | 2805 | CA | ALA | A | 379 | 22.975 | 10.688 | 6.422 | 1.00 | 26.13 | C |
| ATOM | 2806 | CB | ALA | A | 379 | 21.573 | 10.093 | 6.386 | 1.00 | 26.10 | C |
| ATOM | 2807 | C | ALA | A | 379 | 22.935 | 12.126 | 6.943 | 1.00 | 26.24 | C |
| ATOM | 2808 | O | ALA | A | 379 | 22.894 | 13.074 | 6.158 | 1.00 | 26.21 | O |
| ATOM | 2809 | N | MET | A | 380 | 22.945 | 12.280 | 8.267 | 1.00 | 26.32 | N |
| ATOM | 2810 | CA | MET | A | 380 | 22.957 | 13.608 | 8.888 | 1.00 | 26.67 | C |
| ATOM | 2811 | CB | MET | A | 380 | 22.642 | 13.516 | 10.389 | 1.00 | 26.57 | C |
| ATOM | 2812 | CG | MET | A | 380 | 21.196 | 13.107 | 10.693 | 1.00 | 26.96 | C |
| ATOM | 2813 | SD | MET | A | 380 | 20.810 | 13.016 | 12.455 | 1.00 | 28.29 | S |
| ATOM | 2814 | CE | MET | A | 380 | 19.994 | 14.578 | 12.728 | 1.00 | 29.37 | C |
| ATOM | 2815 | C | MET | A | 380 | 24.284 | 14.333 | 8.642 | 1.00 | 26.42 | C |
| ATOM | 2816 | O | MET | A | 380 | 24.323 | 15.562 | 8.570 | 1.00 | 26.41 | O |
| ATOM | 2817 | N | LYS | A | 381 | 25.362 | 13.561 | 8.498 | 1.00 | 26.41 | N |
| ATOM | 2818 | CA | LYS | A | 381 | 26.673 | 14.107 | 8.142 | 1.00 | 26.43 | C |
| ATOM | 2819 | CB | LYS | A | 381 | 27.755 | 13.027 | 8.263 | 1.00 | 26.44 | C |
| ATOM | 2820 | CG | LYS | A | 381 | 29.185 | 13.553 | 8.174 | 1.00 | 27.08 | C |
| ATOM | 2821 | CD | LYS | A | 381 | 30.198 | 12.449 | 8.439 | 1.00 | 27.35 | C |
| ATOM | 2822 | CE | LYS | A | 381 | 31.625 | 12.978 | 8.351 | 1.00 | 28.65 | C |
| ATOM | 2823 | NZ | LYS | A | 381 | 32.635 | 11.905 | 8.573 | 1.00 | 29.41 | N |
| ATOM | 2824 | C | LYS | A | 381 | 26.667 | 14.704 | 6.729 | 1.00 | 26.17 | C |
| ATOM | 2825 | O | LYS | A | 381 | 27.337 | 15.706 | 6.470 | 1.00 | 26.12 | O |
| ATOM | 2826 | N | ILE | A | 382 | 25.911 | 14.080 | 5.825 | 1.00 | 26.08 | N |
| ATOM | 2827 | CA | ILE | A | 382 | 25.738 | 14.606 | 4.468 | 1.00 | 26.02 | C |
| ATOM | 2828 | CB | ILE | A | 382 | 25.044 | 13.578 | 3.525 | 1.00 | 26.02 | C |
| ATOM | 2829 | CG1 | ILE | A | 382 | 25.999 | 12.416 | 3.220 | 1.00 | 26.09 | C |
| ATOM | 2830 | CD1 | ILE | A | 382 | 25.344 | 11.225 | 2.537 | 1.00 | 26.16 | C |
| ATOM | 2831 | CG2 | ILE | A | 382 | 24.586 | 14.249 | 2.222 | 1.00 | 25.83 | C |
| ATOM | 2832 | C | ILE | A | 382 | 24.985 | 15.942 | 4.494 | 1.00 | 26.09 | C |
| ATOM | 2833 | O | ILE | A | 382 | 25.379 | 16.892 | 3.817 | 1.00 | 25.99 | O |
| ATOM | 2834 | N | VAL | A | 383 | 23.925 | 16.015 | 5.300 | 1.00 | 26.28 | N |
| ATOM | 2835 | CA | VAL | A | 383 | 23.202 | 17.275 | 5.526 | 1.00 | 26.60 | C |
| ATOM | 2836 | CB | VAL | A | 383 | 22.060 | 17.108 | 6.570 | 1.00 | 26.55 | C |
| ATOM | 2837 | CG1 | VAL | A | 383 | 21.445 | 18.462 | 6.929 | 1.00 | 26.59 | C |
| ATOM | 2838 | CG2 | VAL | A | 383 | 20.995 | 16.158 | 6.056 | 1.00 | 26.50 | C |
| ATOM | 2839 | C | VAL | A | 383 | 24.167 | 18.364 | 5.995 | 1.00 | 26.80 | C |
| ATOM | 2840 | O | VAL | A | 383 | 24.144 | 19.492 | 5.496 | 1.00 | 26.60 | O |
| ATOM | 2841 | N | LEU | A | 384 | 25.025 | 18.004 | 6.946 | 1.00 | 27.39 | N |
| ATOM | 2842 | CA | LEU | A | 384 | 25.989 | 18.927 | 7.528 | 1.00 | 28.05 | C |
| ATOM | 2843 | CB | LEU | A | 384 | 26.726 | 18.244 | 8.684 | 1.00 | 28.00 | C |
| ATOM | 2844 | CG | LEU | A | 384 | 27.578 | 19.102 | 9.615 | 1.00 | 28.19 | C |
| ATOM | 2845 | CD1 | LEU | A | 384 | 26.710 | 20.077 | 10.398 | 1.00 | 28.31 | C |
| ATOM | 2846 | CD2 | LEU | A | 384 | 28.363 | 18.202 | 10.553 | 1.00 | 28.11 | C |
| ATOM | 2847 | C | LEU | A | 384 | 26.993 | 19.447 | 6.496 | 1.00 | 28.58 | C |
| ATOM | 2848 | O | LEU | A | 384 | 27.352 | 20.628 | 6.509 | 1.00 | 28.62 | O |

TABLE 6-continued

Coordinates of the crystal structure of *E. coli* ExoI bound to compound 9

| ATOM | 2849 | N | GLU | A | 385 | 27.434 | 18.564 | 5.601 | 1.00 | 29.30 | N |
|---|---|---|---|---|---|---|---|---|---|---|---|
| ATOM | 2850 | CA | GLU | A | 385 | 28.472 | 18.907 | 4.628 | 1.00 | 30.11 | C |
| ATOM | 2851 | CB | GLU | A | 385 | 29.430 | 17.726 | 4.424 | 1.00 | 30.16 | C |
| ATOM | 2852 | CG | GLU | A | 385 | 30.447 | 17.571 | 5.557 | 1.00 | 31.29 | C |
| ATOM | 2853 | CD | GLU | A | 385 | 31.052 | 16.177 | 5.644 | 1.00 | 32.28 | C |
| ATOM | 2854 | OE1 | GLU | A | 385 | 31.035 | 15.441 | 4.636 | 1.00 | 33.18 | O |
| ATOM | 2855 | OE2 | GLU | A | 385 | 31.554 | 15.820 | 6.728 | 1.00 | 33.47 | O |
| ATOM | 2856 | C | GLU | A | 385 | 27.913 | 19.419 | 3.291 | 1.00 | 30.40 | C |
| ATOM | 2857 | O | GLU | A | 385 | 28.671 | 19.840 | 2.415 | 1.00 | 30.53 | O |
| ATOM | 2858 | N | THR | A | 386 | 26.588 | 19.386 | 3.150 | 1.00 | 30.93 | N |
| ATOM | 2859 | CA | THR | A | 386 | 25.912 | 19.960 | 1.983 | 1.00 | 31.39 | C |
| ATOM | 2860 | CB | THR | A | 386 | 24.553 | 19.257 | 1.713 | 1.00 | 31.34 | C |
| ATOM | 2861 | OG1 | THR | A | 386 | 24.767 | 17.853 | 1.523 | 1.00 | 30.95 | O |
| ATOM | 2862 | CG2 | THR | A | 386 | 23.871 | 19.827 | 0.473 | 1.00 | 31.35 | C |
| ATOM | 2863 | C | THR | A | 386 | 25.686 | 21.461 | 2.183 | 1.00 | 31.90 | C |
| ATOM | 2864 | O | THR | A | 386 | 25.335 | 21.903 | 3.277 | 1.00 | 31.98 | O |
| ATOM | 2865 | N | GLU | A | 387 | 25.899 | 22.239 | 1.123 | 1.00 | 32.53 | N |
| ATOM | 2866 | CA | GLU | A | 387 | 25.625 | 23.676 | 1.154 | 1.00 | 33.12 | C |
| ATOM | 2867 | CB | GLU | A | 387 | 26.139 | 24.359 | −0.122 | 1.00 | 33.31 | C |
| ATOM | 2868 | CG | GLU | A | 387 | 27.530 | 23.891 | −0.565 | 1.00 | 34.06 | C |
| ATOM | 2869 | CD | GLU | A | 387 | 28.424 | 25.032 | −1.013 | 1.00 | 35.29 | C |
| ATOM | 2870 | OE1 | GLU | A | 387 | 28.701 | 25.933 | −0.189 | 1.00 | 36.16 | O |
| ATOM | 2871 | OE2 | GLU | A | 387 | 28.866 | 25.017 | −2.181 | 1.00 | 35.88 | O |
| ATOM | 2872 | C | GLU | A | 387 | 24.121 | 23.918 | 1.333 | 1.00 | 33.40 | C |
| ATOM | 2873 | O | GLU | A | 387 | 23.308 | 23.226 | 0.720 | 1.00 | 33.41 | O |
| ATOM | 2874 | N | PRO | A | 388 | 23.749 | 24.890 | 2.197 | 1.00 | 33.68 | N |
| ATOM | 2875 | CA | PRO | A | 388 | 22.342 | 25.161 | 2.542 | 1.00 | 33.85 | C |
| ATOM | 2876 | CB | PRO | A | 388 | 22.424 | 26.474 | 3.325 | 1.00 | 33.91 | C |
| ATOM | 2877 | CG | PRO | A | 388 | 23.777 | 26.456 | 3.930 | 1.00 | 33.88 | C |
| ATOM | 2878 | CD | PRO | A | 388 | 24.668 | 25.791 | 2.920 | 1.00 | 33.73 | C |
| ATOM | 2879 | C | PRO | A | 388 | 21.412 | 25.318 | 1.333 | 1.00 | 34.05 | C |
| ATOM | 2880 | O | PRO | A | 388 | 20.248 | 24.918 | 1.399 | 1.00 | 34.14 | O |
| ATOM | 2881 | N | ARG | A | 389 | 21.926 | 25.890 | 0.243 | 1.00 | 34.14 | N |
| ATOM | 2882 | CA | ARG | A | 389 | 21.137 | 26.091 | −0.979 | 1.00 | 34.28 | C |
| ATOM | 2883 | CB | ARG | A | 389 | 21.838 | 27.078 | −1.926 | 1.00 | 34.29 | C |
| ATOM | 2884 | CG | ARG | A | 389 | 23.278 | 26.709 | −2.278 | 1.00 | 34.69 | C |
| ATOM | 2885 | CD | ARG | A | 389 | 23.950 | 27.808 | −3.086 | 1.00 | 35.21 | C |
| ATOM | 2886 | NE | ARG | A | 389 | 25.405 | 27.655 | −3.111 | 1.00 | 36.56 | N |
| ATOM | 2887 | CZ | ARG | A | 389 | 26.075 | 26.948 | −4.018 | 1.00 | 37.03 | C |
| ATOM | 2888 | NH1 | ARG | A | 389 | 25.430 | 26.318 | −4.994 | 1.00 | 37.57 | N |
| ATOM | 2889 | NH2 | ARG | A | 389 | 27.398 | 26.873 | −3.951 | 1.00 | 37.60 | N |
| ATOM | 2890 | C | ARG | A | 389 | 20.826 | 24.781 | −1.712 | 1.00 | 34.05 | C |
| ATOM | 2891 | O | ARG | A | 389 | 19.870 | 24.711 | −2.488 | 1.00 | 34.09 | O |
| ATOM | 2892 | N | ASN | A | 390 | 21.633 | 23.752 | −1.458 | 1.00 | 33.80 | N |
| ATOM | 2893 | CA | ASN | A | 390 | 21.483 | 22.460 | −2.133 | 1.00 | 33.57 | C |
| ATOM | 2894 | CB | ASN | A | 390 | 22.855 | 21.906 | −2.541 | 1.00 | 33.55 | C |
| ATOM | 2895 | CG | ASN | A | 390 | 23.555 | 22.771 | −3.582 | 1.00 | 33.68 | C |
| ATOM | 2896 | OD1 | ASN | A | 390 | 22.913 | 23.505 | −4.336 | 1.00 | 33.81 | O |
| ATOM | 2897 | ND2 | ASN | A | 390 | 24.879 | 22.680 | −3.630 | 1.00 | 33.82 | N |
| ATOM | 2898 | C | ASN | A | 390 | 20.704 | 21.420 | −1.317 | 1.00 | 33.42 | C |
| ATOM | 2899 | O | ASN | A | 390 | 20.555 | 20.273 | −1.743 | 1.00 | 33.34 | O |
| ATOM | 2900 | N | LEU | A | 391 | 20.200 | 21.831 | −0.153 | 1.00 | 33.26 | N |
| ATOM | 2901 | CA | LEU | A | 391 | 19.431 | 20.936 | 0.719 | 1.00 | 33.09 | C |
| ATOM | 2902 | CB | LEU | A | 391 | 19.284 | 21.525 | 2.131 | 1.00 | 33.00 | C |
| ATOM | 2903 | CG | LEU | A | 391 | 20.515 | 21.489 | 3.045 | 1.00 | 32.79 | C |
| ATOM | 2904 | CD1 | LEU | A | 391 | 20.262 | 22.291 | 4.313 | 1.00 | 32.24 | C |
| ATOM | 2905 | CD2 | LEU | A | 391 | 20.921 | 20.054 | 3.387 | 1.00 | 32.47 | C |
| ATOM | 2906 | C | LEU | A | 391 | 18.056 | 20.514 | 0.160 | 1.00 | 33.13 | C |
| ATOM | 2907 | O | LEU | A | 391 | 17.671 | 19.353 | 0.308 | 1.00 | 33.18 | O |
| ATOM | 2908 | N | PRO | A | 392 | 17.311 | 21.450 | −0.482 | 1.00 | 33.13 | N |
| ATOM | 2909 | CA | PRO | A | 392 | 15.982 | 21.081 | −0.995 | 1.00 | 33.14 | C |
| ATOM | 2910 | CB | PRO | A | 392 | 15.471 | 22.386 | −1.622 | 1.00 | 33.17 | C |
| ATOM | 2911 | CG | PRO | A | 392 | 16.277 | 23.460 | −0.991 | 1.00 | 33.16 | C |
| ATOM | 2912 | CD | PRO | A | 392 | 17.620 | 22.865 | −0.756 | 1.00 | 33.14 | C |
| ATOM | 2913 | C | PRO | A | 392 | 16.019 | 19.971 | −2.050 | 1.00 | 33.14 | C |
| ATOM | 2914 | O | PRO | A | 392 | 15.075 | 19.185 | −2.148 | 1.00 | 33.25 | O |
| ATOM | 2915 | N | ALA | A | 393 | 17.103 | 19.912 | −2.824 | 1.00 | 33.05 | N |
| ATOM | 2916 | CA | ALA | A | 393 | 17.242 | 18.926 | −3.897 | 1.00 | 33.01 | C |
| ATOM | 2917 | CB | ALA | A | 393 | 17.900 | 19.561 | −5.117 | 1.00 | 33.04 | C |
| ATOM | 2918 | C | ALA | A | 393 | 18.017 | 17.679 | −3.456 | 1.00 | 32.98 | C |
| ATOM | 2919 | O | ALA | A | 393 | 18.218 | 16.752 | −4.247 | 1.00 | 33.01 | O |
| ATOM | 2920 | N | LEU | A | 394 | 18.439 | 17.658 | −2.193 | 1.00 | 32.89 | N |
| ATOM | 2921 | CA | LEU | A | 394 | 19.246 | 16.561 | −1.662 | 1.00 | 32.88 | C |
| ATOM | 2922 | CB | LEU | A | 394 | 19.795 | 16.922 | −0.275 | 1.00 | 32.89 | C |
| ATOM | 2923 | CG | LEU | A | 394 | 20.937 | 16.084 | 0.309 | 1.00 | 32.90 | C |
| ATOM | 2924 | CD1 | LEU | A | 394 | 22.191 | 16.156 | −0.562 | 1.00 | 32.67 | C |
| ATOM | 2925 | CD2 | LEU | A | 394 | 21.242 | 16.546 | 1.723 | 1.00 | 32.84 | C |
| ATOM | 2926 | C | LEU | A | 394 | 18.454 | 15.256 | −1.607 | 1.00 | 32.91 | C |

TABLE 6-continued

Coordinates of the crystal structure of *E. coli* ExoI bound to compound 9

| ATOM | 2927 | O | LEU | A | 394 | 17.362 | 15.200 | −1.036 | 1.00 | 32.97 | O |
|---|---|---|---|---|---|---|---|---|---|---|---|
| ATOM | 2928 | N | ASP | A | 395 | 19.015 | 14.213 | −2.213 | 1.00 | 32.90 | N |
| ATOM | 2929 | CA | ASP | A | 395 | 18.352 | 12.914 | −2.305 | 1.00 | 32.91 | C |
| ATOM | 2930 | CB | ASP | A | 395 | 18.449 | 12.350 | −3.736 | 1.00 | 33.07 | C |
| ATOM | 2931 | CG | ASP | A | 395 | 19.863 | 12.420 | −4.311 | 1.00 | 33.85 | C |
| ATOM | 2932 | OD1 | ASP | A | 395 | 20.491 | 13.503 | −4.250 | 1.00 | 34.69 | O |
| ATOM | 2933 | OD2 | ASP | A | 395 | 20.339 | 11.393 | −4.844 | 1.00 | 34.84 | O |
| ATOM | 2934 | C | ASP | A | 395 | 18.890 | 11.914 | −1.275 | 1.00 | 32.64 | C |
| ATOM | 2935 | O | ASP | A | 395 | 19.734 | 11.069 | −1.588 | 1.00 | 32.73 | O |
| ATOM | 2936 | N | ILE | A | 396 | 18.402 | 12.031 | −0.040 | 1.00 | 32.27 | N |
| ATOM | 2937 | CA | ILE | A | 396 | 18.761 | 11.101 | 1.039 | 1.00 | 31.92 | C |
| ATOM | 2938 | CB | ILE | A | 396 | 19.888 | 11.661 | 1.960 | 1.00 | 32.03 | C |
| ATOM | 2939 | CG1 | ILE | A | 396 | 19.510 | 13.035 | 2.524 | 1.00 | 32.11 | C |
| ATOM | 2940 | CD1 | ILE | A | 396 | 20.424 | 13.511 | 3.639 | 1.00 | 32.20 | C |
| ATOM | 2941 | CG2 | ILE | A | 396 | 21.233 | 11.698 | 1.223 | 1.00 | 32.30 | C |
| ATOM | 2942 | C | ILE | A | 396 | 17.539 | 10.719 | 1.879 | 1.00 | 31.46 | C |
| ATOM | 2943 | O | ILE | A | 396 | 16.529 | 11.428 | 1.882 | 1.00 | 31.44 | O |
| ATOM | 2944 | N | THR | A | 397 | 17.641 | 9.595 | 2.586 | 1.00 | 30.85 | N |
| ATOM | 2945 | CA | THR | A | 397 | 16.527 | 9.057 | 3.365 | 1.00 | 30.33 | C |
| ATOM | 2946 | CB | THR | A | 397 | 16.032 | 7.708 | 2.771 | 1.00 | 30.35 | C |
| ATOM | 2947 | OG1 | THR | A | 397 | 15.662 | 7.898 | 1.400 | 1.00 | 30.75 | O |
| ATOM | 2948 | CG2 | THR | A | 397 | 14.826 | 7.170 | 3.541 | 1.00 | 30.65 | C |
| ATOM | 2949 | C | THR | A | 397 | 16.918 | 8.875 | 4.832 | 1.00 | 29.83 | C |
| ATOM | 2950 | O | THR | A | 397 | 18.070 | 8.559 | 5.144 | 1.00 | 29.69 | O |
| ATOM | 2951 | N | PHE | A | 398 | 15.953 | 9.093 | 5.724 | 1.00 | 29.24 | N |
| ATOM | 2952 | CA | PHE | A | 398 | 16.152 | 8.890 | 7.156 | 1.00 | 28.80 | C |
| ATOM | 2953 | CB | PHE | A | 398 | 15.952 | 10.202 | 7.920 | 1.00 | 28.77 | C |
| ATOM | 2954 | CG | PHE | A | 398 | 16.728 | 11.362 | 7.359 | 1.00 | 28.68 | C |
| ATOM | 2955 | CD1 | PHE | A | 398 | 18.116 | 11.419 | 7.482 | 1.00 | 28.66 | C |
| ATOM | 2956 | CE1 | PHE | A | 398 | 18.834 | 12.499 | 6.970 | 1.00 | 28.53 | C |
| ATOM | 2957 | CZ | PHE | A | 398 | 18.161 | 13.537 | 6.333 | 1.00 | 28.54 | C |
| ATOM | 2958 | CE2 | PHE | A | 398 | 16.778 | 13.492 | 6.207 | 1.00 | 28.52 | C |
| ATOM | 2959 | CD2 | PHE | A | 398 | 16.068 | 12.410 | 6.722 | 1.00 | 28.73 | C |
| ATOM | 2960 | C | PHE | A | 398 | 15.189 | 7.836 | 7.692 | 1.00 | 28.43 | C |
| ATOM | 2961 | O | PHE | A | 398 | 14.060 | 7.713 | 7.212 | 1.00 | 28.51 | O |
| ATOM | 2962 | N | VAL | A | 399 | 15.639 | 7.081 | 8.691 | 1.00 | 27.93 | N |
| ATOM | 2963 | CA | VAL | A | 399 | 14.789 | 6.095 | 9.356 | 1.00 | 27.51 | C |
| ATOM | 2964 | CB | VAL | A | 399 | 15.594 | 4.836 | 9.790 | 1.00 | 27.56 | C |
| ATOM | 2965 | CG1 | VAL | A | 399 | 14.694 | 3.837 | 10.510 | 1.00 | 27.48 | C |
| ATOM | 2966 | CG2 | VAL | A | 399 | 16.256 | 4.180 | 8.579 | 1.00 | 27.62 | C |
| ATOM | 2967 | C | VAL | A | 399 | 14.085 | 6.725 | 10.562 | 1.00 | 27.14 | C |
| ATOM | 2968 | O | VAL | A | 399 | 12.860 | 6.643 | 10.687 | 1.00 | 27.16 | O |
| ATOM | 2969 | N | ASP | A | 400 | 14.869 | 7.362 | 11.434 | 1.00 | 26.60 | N |
| ATOM | 2970 | CA | ASP | A | 400 | 14.344 | 8.027 | 12.627 | 1.00 | 26.12 | C |
| ATOM | 2971 | CB | ASP | A | 400 | 15.499 | 8.546 | 13.494 | 1.00 | 26.07 | C |
| ATOM | 2972 | CG | ASP | A | 400 | 15.071 | 8.866 | 14.916 | 1.00 | 25.68 | C |
| ATOM | 2973 | OD1 | ASP | A | 400 | 14.322 | 9.844 | 15.111 | 1.00 | 24.98 | O |
| ATOM | 2974 | OD2 | ASP | A | 400 | 15.504 | 8.150 | 15.845 | 1.00 | 25.50 | O |
| ATOM | 2975 | C | ASP | A | 400 | 13.403 | 9.173 | 12.249 | 1.00 | 25.99 | C |
| ATOM | 2976 | O | ASP | A | 400 | 13.758 | 10.043 | 11.449 | 1.00 | 25.75 | O |
| ATOM | 2977 | N | LYS | A | 401 | 12.209 | 9.166 | 12.842 | 1.00 | 25.84 | N |
| ATOM | 2978 | CA | LYS | A | 401 | 11.140 | 10.111 | 12.494 | 1.00 | 25.89 | C |
| ATOM | 2979 | CB | LYS | A | 401 | 9.806 | 9.650 | 13.094 | 1.00 | 26.10 | C |
| ATOM | 2980 | CG | LYS | A | 401 | 9.119 | 8.529 | 12.318 | 1.00 | 27.10 | C |
| ATOM | 2981 | CD | LYS | A | 401 | 8.119 | 9.070 | 11.296 | 1.00 | 28.84 | C |
| ATOM | 2982 | CE | LYS | A | 401 | 6.795 | 9.460 | 11.957 | 1.00 | 29.73 | C |
| ATOM | 2983 | NZ | LYS | A | 401 | 5.721 | 9.739 | 10.960 | 1.00 | 30.42 | N |
| ATOM | 2984 | C | LYS | A | 401 | 11.425 | 11.556 | 12.912 | 1.00 | 25.59 | C |
| ATOM | 2985 | O | LYS | A | 401 | 10.795 | 12.488 | 12.406 | 1.00 | 25.69 | O |
| ATOM | 2986 | N | ARG | A | 402 | 12.369 | 11.735 | 13.833 | 1.00 | 25.23 | N |
| ATOM | 2987 | CA | ARG | A | 402 | 12.731 | 13.070 | 14.322 | 1.00 | 24.90 | C |
| ATOM | 2988 | CB | ARG | A | 402 | 13.626 | 12.967 | 15.559 | 1.00 | 24.85 | C |
| ATOM | 2989 | CG | ARG | A | 402 | 12.933 | 12.426 | 16.804 | 1.00 | 24.34 | C |
| ATOM | 2990 | CD | ARG | A | 402 | 13.935 | 12.169 | 17.923 | 1.00 | 24.35 | C |
| ATOM | 2991 | NE | ARG | A | 402 | 14.868 | 11.091 | 17.593 | 1.00 | 23.14 | N |
| ATOM | 2992 | CZ | ARG | A | 402 | 15.897 | 10.724 | 18.355 | 1.00 | 23.18 | C |
| ATOM | 2993 | NH1 | ARG | A | 402 | 16.144 | 11.350 | 19.500 | 1.00 | 22.48 | N |
| ATOM | 2994 | NH2 | ARG | A | 402 | 16.686 | 9.732 | 17.968 | 1.00 | 23.20 | N |
| ATOM | 2995 | C | ARG | A | 402 | 13.434 | 13.914 | 13.261 | 1.00 | 25.03 | C |
| ATOM | 2996 | O | ARG | A | 402 | 13.277 | 15.138 | 13.233 | 1.00 | 25.02 | O |
| ATOM | 2997 | N | ILE | A | 403 | 14.202 | 13.257 | 12.392 | 1.00 | 25.12 | N |
| ATOM | 2998 | CA | ILE | A | 403 | 15.139 | 13.957 | 11.504 | 1.00 | 25.22 | C |
| ATOM | 2999 | CB | ILE | A | 403 | 16.121 | 12.984 | 10.796 | 1.00 | 25.16 | C |
| ATOM | 3000 | CG1 | ILE | A | 403 | 16.822 | 12.092 | 11.829 | 1.00 | 25.47 | C |
| ATOM | 3001 | CD1 | ILE | A | 403 | 17.636 | 10.951 | 11.234 | 1.00 | 25.14 | C |
| ATOM | 3002 | CG2 | ILE | A | 403 | 17.151 | 13.773 | 9.983 | 1.00 | 25.08 | C |
| ATOM | 3003 | C | ILE | A | 403 | 14.448 | 14.878 | 10.487 | 1.00 | 25.43 | C |
| ATOM | 3004 | O | ILE | A | 403 | 14.899 | 16.003 | 10.262 | 1.00 | 25.44 | O |

TABLE 6-continued

Coordinates of the crystal structure of *E. coli* ExoI bound to compound 9

| ATOM | 3005 | N | GLU | A | 404 | 13.358 | 14.400 | 9.889 | 1.00 | 25.70 | N |
|------|------|------|-----|---|-----|--------|--------|--------|------|-------|---|
| ATOM | 3006 | CA | GLU | A | 404 | 12.561 | 15.211 | 8.964 | 1.00 | 26.04 | C |
| ATOM | 3007 | CB | GLU | A | 404 | 11.339 | 14.430 | 8.465 | 1.00 | 26.36 | C |
| ATOM | 3008 | CG | GLU | A | 404 | 11.668 | 13.186 | 7.636 | 1.00 | 28.24 | C |
| ATOM | 3009 | CD | GLU | A | 404 | 11.785 | 11.916 | 8.472 | 1.00 | 30.17 | C |
| ATOM | 3010 | OE1 | GLU | A | 404 | 11.889 | 12.014 | 9.716 | 1.00 | 31.41 | O |
| ATOM | 3011 | OE2 | GLU | A | 404 | 11.766 | 10.812 | 7.879 | 1.00 | 31.34 | O |
| ATOM | 3012 | C | GLU | A | 404 | 12.114 | 16.519 | 9.623 | 1.00 | 25.73 | C |
| ATOM | 3013 | O | GLU | A | 404 | 12.182 | 17.587 | 9.012 | 1.00 | 25.68 | O |
| ATOM | 3014 | N | LYS | A | 405 | 11.667 | 16.418 | 10.874 | 1.00 | 25.31 | N |
| ATOM | 3015 | CA | LYS | A | 405 | 11.236 | 17.579 | 11.649 | 1.00 | 25.09 | C |
| ATOM | 3016 | CB | LYS | A | 405 | 10.519 | 17.138 | 12.927 | 1.00 | 25.34 | C |
| ATOM | 3017 | CG | LYS | A | 405 | 9.289 | 16.282 | 12.693 | 1.00 | 25.92 | C |
| ATOM | 3018 | CD | LYS | A | 405 | 8.734 | 15.764 | 14.007 | 1.00 | 26.97 | C |
| ATOM | 3019 | CE | LYS | A | 405 | 7.549 | 14.846 | 13.777 | 1.00 | 27.76 | C |
| ATOM | 3020 | NZ | LYS | A | 405 | 6.963 | 14.382 | 15.063 | 1.00 | 28.66 | N |
| ATOM | 3021 | C | LYS | A | 405 | 12.425 | 18.467 | 12.001 | 1.00 | 24.63 | C |
| ATOM | 3022 | O | LYS | A | 405 | 12.345 | 19.693 | 11.895 | 1.00 | 24.35 | O |
| ATOM | 3023 | N | LEU | A | 406 | 13.523 | 17.840 | 12.424 | 1.00 | 24.20 | N |
| ATOM | 3024 | CA | LEU | A | 406 | 14.759 | 18.561 | 12.725 | 1.00 | 23.99 | C |
| ATOM | 3025 | CB | LEU | A | 406 | 15.847 | 17.603 | 13.221 | 1.00 | 24.04 | C |
| ATOM | 3026 | CG | LEU | A | 406 | 15.716 | 17.022 | 14.633 | 1.00 | 24.13 | C |
| ATOM | 3027 | CD1 | LEU | A | 406 | 16.721 | 15.897 | 14.837 | 1.00 | 24.41 | C |
| ATOM | 3028 | CD2 | LEU | A | 406 | 15.891 | 18.097 | 15.701 | 1.00 | 24.39 | C |
| ATOM | 3029 | C | LEU | A | 406 | 15.265 | 19.323 | 11.508 | 1.00 | 23.82 | C |
| ATOM | 3030 | O | LEU | A | 406 | 15.735 | 20.452 | 11.631 | 1.00 | 23.88 | O |
| ATOM | 3031 | N | LEU | A | 407 | 15.151 | 18.702 | 10.334 | 1.00 | 23.66 | N |
| ATOM | 3032 | CA | LEU | A | 407 | 15.665 | 19.285 | 9.098 | 1.00 | 23.48 | C |
| ATOM | 3033 | CB | LEU | A | 407 | 15.693 | 18.244 | 7.970 | 1.00 | 23.48 | C |
| ATOM | 3034 | CG | LEU | A | 407 | 16.245 | 18.652 | 6.597 | 1.00 | 23.44 | C |
| ATOM | 3035 | CD1 | LEU | A | 407 | 17.680 | 19.174 | 6.678 | 1.00 | 23.69 | C |
| ATOM | 3036 | CD2 | LEU | A | 407 | 16.151 | 17.483 | 5.626 | 1.00 | 23.72 | C |
| ATOM | 3037 | C | LEU | A | 407 | 14.883 | 20.528 | 8.676 | 1.00 | 23.45 | C |
| ATOM | 3038 | O | LEU | A | 407 | 15.483 | 21.534 | 8.295 | 1.00 | 23.32 | O |
| ATOM | 3039 | N | PHE | A | 408 | 13.552 | 20.463 | 8.754 | 1.00 | 23.44 | N |
| ATOM | 3040 | CA | PHE | A | 408 | 12.722 | 21.625 | 8.428 | 1.00 | 23.61 | C |
| ATOM | 3041 | CB | PHE | A | 408 | 11.227 | 21.299 | 8.459 | 1.00 | 23.79 | C |
| ATOM | 3042 | CG | PHE | A | 408 | 10.351 | 22.500 | 8.213 | 1.00 | 24.34 | C |
| ATOM | 3043 | CD1 | PHE | A | 408 | 10.211 | 23.024 | 6.926 | 1.00 | 24.69 | C |
| ATOM | 3044 | CE1 | PHE | A | 408 | 9.421 | 24.146 | 6.695 | 1.00 | 25.46 | C |
| ATOM | 3045 | CZ | PHE | A | 408 | 8.768 | 24.764 | 7.755 | 1.00 | 25.45 | C |
| ATOM | 3046 | CE2 | PHE | A | 408 | 8.904 | 24.259 | 9.042 | 1.00 | 25.49 | C |
| ATOM | 3047 | CD2 | PHE | A | 408 | 9.698 | 23.133 | 9.267 | 1.00 | 24.99 | C |
| ATOM | 3048 | C | PHE | A | 408 | 13.015 | 22.808 | 9.348 | 1.00 | 23.50 | C |
| ATOM | 3049 | O | PHE | A | 408 | 13.247 | 23.921 | 8.873 | 1.00 | 23.58 | O |
| ATOM | 3050 | N | ASN | A | 409 | 12.996 | 22.561 | 10.659 | 1.00 | 23.47 | N |
| ATOM | 3051 | CA | ASN | A | 409 | 13.348 | 23.579 | 11.649 | 1.00 | 23.38 | C |
| ATOM | 3052 | CB | ASN | A | 409 | 13.283 | 23.000 | 13.065 | 1.00 | 23.45 | C |
| ATOM | 3053 | CG | ASN | A | 409 | 11.863 | 22.829 | 13.568 | 1.00 | 24.08 | C |
| ATOM | 3054 | OD1 | ASN | A | 409 | 10.902 | 23.264 | 12.930 | 1.00 | 25.17 | O |
| ATOM | 3055 | ND2 | ASN | A | 409 | 11.724 | 22.193 | 14.727 | 1.00 | 25.11 | N |
| ATOM | 3056 | C | ASN | A | 409 | 14.735 | 24.161 | 11.398 | 1.00 | 23.17 | C |
| ATOM | 3057 | O | ASN | A | 409 | 14.922 | 25.376 | 11.451 | 1.00 | 23.25 | O |
| ATOM | 3058 | N | TYR | A | 410 | 15.694 | 23.280 | 11.115 | 1.00 | 22.82 | N |
| ATOM | 3059 | CA | TYR | A | 410 | 17.077 | 23.666 | 10.825 | 1.00 | 22.69 | C |
| ATOM | 3060 | CB | TYR | A | 410 | 17.911 | 22.414 | 10.521 | 1.00 | 22.72 | C |
| ATOM | 3061 | CG | TYR | A | 410 | 19.363 | 22.658 | 10.155 | 1.00 | 22.89 | C |
| ATOM | 3062 | CD1 | TYR | A | 410 | 20.302 | 23.008 | 11.129 | 1.00 | 22.39 | C |
| ATOM | 3063 | CE1 | TYR | A | 410 | 21.641 | 23.214 | 10.798 | 1.00 | 22.91 | C |
| ATOM | 3064 | CZ | TYR | A | 410 | 22.057 | 23.053 | 9.485 | 1.00 | 22.99 | C |
| ATOM | 3065 | OH | TYR | A | 410 | 23.382 | 23.253 | 9.157 | 1.00 | 24.19 | O |
| ATOM | 3066 | CE2 | TYR | A | 410 | 21.147 | 22.698 | 8.499 | 1.00 | 22.91 | C |
| ATOM | 3067 | CD2 | TYR | A | 410 | 19.807 | 22.497 | 8.840 | 1.00 | 22.68 | C |
| ATOM | 3068 | C | TYR | A | 410 | 17.133 | 24.646 | 9.658 | 1.00 | 22.61 | C |
| ATOM | 3069 | O | TYR | A | 410 | 17.747 | 25.705 | 9.756 | 1.00 | 22.20 | O |
| ATOM | 3070 | N | ARG | A | 411 | 16.455 | 24.298 | 8.568 | 1.00 | 22.67 | N |
| ATOM | 3071 | CA | ARG | A | 411 | 16.416 | 25.144 | 7.381 | 1.00 | 22.90 | C |
| ATOM | 3072 | CB | ARG | A | 411 | 15.814 | 24.381 | 6.197 | 1.00 | 22.87 | C |
| ATOM | 3073 | CG | ARG | A | 411 | 16.669 | 23.217 | 5.711 | 1.00 | 23.06 | C |
| ATOM | 3074 | CD | ARG | A | 411 | 16.050 | 22.526 | 4.501 | 1.00 | 23.74 | C |
| ATOM | 3075 | NE | ARG | A | 411 | 15.922 | 23.438 | 3.365 | 1.00 | 25.83 | N |
| ATOM | 3076 | CZ | ARG | A | 411 | 14.769 | 23.784 | 2.797 | 1.00 | 27.04 | C |
| ATOM | 3077 | NH1 | ARG | A | 411 | 13.621 | 23.281 | 3.234 | 1.00 | 27.76 | N |
| ATOM | 3078 | NH2 | ARG | A | 411 | 14.766 | 24.631 | 1.779 | 1.00 | 27.44 | N |
| ATOM | 3079 | C | ARG | A | 411 | 15.650 | 26.445 | 7.623 | 1.00 | 22.98 | C |
| ATOM | 3080 | O | ARG | A | 411 | 16.107 | 27.516 | 7.236 | 1.00 | 23.23 | O |
| ATOM | 3081 | N | ALA | A | 412 | 14.493 | 26.344 | 8.274 | 1.00 | 23.00 | N |
| ATOM | 3082 | CA | ALA | A | 412 | 13.624 | 27.503 | 8.493 | 1.00 | 23.20 | C |

TABLE 6-continued

Coordinates of the crystal structure of *E. coli* ExoI bound to compound 9

| ATOM | 3083 | CB | ALA | A | 412 | 12.244 | 27.056 | 8.938 | 1.00 | 23.26 | C |
|------|------|-----|-----|---|-----|--------|--------|-------|------|-------|---|
| ATOM | 3084 | C | ALA | A | 412 | 14.206 | 28.520 | 9.481 | 1.00 | 23.39 | C |
| ATOM | 3085 | O | ALA | A | 412 | 14.024 | 29.725 | 9.312 | 1.00 | 23.34 | O |
| ATOM | 3086 | N | ARG | A | 413 | 14.901 | 28.027 | 10.506 | 1.00 | 23.67 | N |
| ATOM | 3087 | CA | ARG | A | 413 | 15.495 | 28.893 | 11.531 | 1.00 | 24.15 | C |
| ATOM | 3088 | CB | ARG | A | 413 | 15.727 | 28.111 | 12.826 | 1.00 | 23.96 | C |
| ATOM | 3089 | CG | ARG | A | 413 | 14.469 | 27.811 | 13.607 | 1.00 | 24.04 | C |
| ATOM | 3090 | CD | ARG | A | 413 | 14.776 | 26.932 | 14.804 | 1.00 | 23.45 | C |
| ATOM | 3091 | NE | ARG | A | 413 | 13.580 | 26.661 | 15.597 | 1.00 | 23.29 | N |
| ATOM | 3092 | CZ | ARG | A | 413 | 13.402 | 25.574 | 16.342 | 1.00 | 23.80 | C |
| ATOM | 3093 | NH1 | ARG | A | 413 | 14.340 | 24.635 | 16.393 | 1.00 | 24.34 | N |
| ATOM | 3094 | NH2 | ARG | A | 413 | 12.277 | 25.421 | 17.030 | 1.00 | 23.75 | N |
| ATOM | 3095 | C | ARG | A | 413 | 16.806 | 29.530 | 11.079 | 1.00 | 24.55 | C |
| ATOM | 3096 | O | ARG | A | 413 | 17.068 | 30.700 | 11.375 | 1.00 | 24.94 | O |
| ATOM | 3097 | N | ASN | A | 414 | 17.628 | 28.754 | 10.375 | 1.00 | 24.94 | N |
| ATOM | 3098 | CA | ASN | A | 414 | 18.976 | 29.187 | 10.003 | 1.00 | 25.44 | C |
| ATOM | 3099 | CB | ASN | A | 414 | 19.959 | 28.020 | 10.101 | 1.00 | 25.34 | C |
| ATOM | 3100 | CG | ASN | A | 414 | 20.127 | 27.520 | 11.518 | 1.00 | 25.48 | C |
| ATOM | 3101 | OD1 | ASN | A | 414 | 19.707 | 26.415 | 11.851 | 1.00 | 26.75 | O |
| ATOM | 3102 | ND2 | ASN | A | 414 | 20.735 | 28.335 | 12.363 | 1.00 | 24.95 | N |
| ATOM | 3103 | C | ASN | A | 414 | 19.060 | 29.806 | 8.617 | 1.00 | 25.77 | C |
| ATOM | 3104 | O | ASN | A | 414 | 19.779 | 30.787 | 8.414 | 1.00 | 25.93 | O |
| ATOM | 3105 | N | PHE | A | 415 | 18.334 | 29.223 | 7.664 | 1.00 | 26.20 | N |
| ATOM | 3106 | CA | PHE | A | 415 | 18.420 | 29.643 | 6.264 | 1.00 | 26.54 | C |
| ATOM | 3107 | CB | PHE | A | 415 | 19.195 | 28.600 | 5.444 | 1.00 | 26.66 | C |
| ATOM | 3108 | CG | PHE | A | 415 | 20.414 | 28.057 | 6.144 | 1.00 | 27.00 | C |
| ATOM | 3109 | CD1 | PHE | A | 415 | 21.548 | 28.850 | 6.315 | 1.00 | 27.23 | C |
| ATOM | 3110 | CE1 | PHE | A | 415 | 22.675 | 28.353 | 6.967 | 1.00 | 27.54 | C |
| ATOM | 3111 | CZ | PHE | A | 415 | 22.678 | 27.046 | 7.455 | 1.00 | 27.40 | C |
| ATOM | 3112 | CE2 | PHE | A | 415 | 21.554 | 26.244 | 7.289 | 1.00 | 27.59 | C |
| ATOM | 3113 | CD2 | PHE | A | 415 | 20.427 | 26.752 | 6.636 | 1.00 | 27.40 | C |
| ATOM | 3114 | C | PHE | A | 415 | 17.029 | 29.883 | 5.656 | 1.00 | 26.71 | C |
| ATOM | 3115 | O | PHE | A | 415 | 16.632 | 29.182 | 4.717 | 1.00 | 26.60 | O |
| ATOM | 3116 | N | PRO | A | 416 | 16.290 | 30.887 | 6.181 | 1.00 | 26.91 | N |
| ATOM | 3117 | CA | PRO | A | 416 | 14.900 | 31.119 | 5.761 | 1.00 | 26.95 | C |
| ATOM | 3118 | CB | PRO | A | 416 | 14.446 | 32.269 | 6.669 | 1.00 | 26.99 | C |
| ATOM | 3119 | CG | PRO | A | 416 | 15.701 | 32.954 | 7.068 | 1.00 | 27.10 | C |
| ATOM | 3120 | CD | PRO | A | 416 | 16.722 | 31.872 | 7.190 | 1.00 | 27.01 | C |
| ATOM | 3121 | C | PRO | A | 416 | 14.754 | 31.516 | 4.287 | 1.00 | 27.01 | C |
| ATOM | 3122 | O | PRO | A | 416 | 13.674 | 31.363 | 3.716 | 1.00 | 27.07 | O |
| ATOM | 3123 | N | GLY | A | 417 | 15.835 | 32.010 | 3.686 | 1.00 | 27.03 | N |
| ATOM | 3124 | CA | GLY | A | 417 | 15.832 | 32.404 | 2.275 | 1.00 | 26.99 | C |
| ATOM | 3125 | C | GLY | A | 417 | 15.814 | 31.232 | 1.307 | 1.00 | 26.96 | C |
| ATOM | 3126 | O | GLY | A | 417 | 15.642 | 31.419 | 0.097 | 1.00 | 27.15 | O |
| ATOM | 3127 | N | THR | A | 418 | 15.993 | 30.022 | 1.839 | 1.00 | 26.93 | N |
| ATOM | 3128 | CA | THR | A | 418 | 15.991 | 28.800 | 1.029 | 1.00 | 26.91 | C |
| ATOM | 3129 | CB | THR | A | 418 | 17.091 | 27.807 | 1.484 | 1.00 | 26.93 | C |
| ATOM | 3130 | OG1 | THR | A | 418 | 16.789 | 27.320 | 2.797 | 1.00 | 26.88 | O |
| ATOM | 3131 | CG2 | THR | A | 418 | 18.463 | 28.475 | 1.489 | 1.00 | 26.87 | C |
| ATOM | 3132 | C | THR | A | 418 | 14.631 | 28.089 | 1.046 | 1.00 | 26.81 | C |
| ATOM | 3133 | O | THR | A | 418 | 14.461 | 27.046 | 0.409 | 1.00 | 27.05 | O |
| ATOM | 3134 | N | LEU | A | 419 | 13.671 | 28.655 | 1.775 | 1.00 | 26.77 | N |
| ATOM | 3135 | CA | LEU | A | 419 | 12.323 | 28.090 | 1.856 | 1.00 | 26.69 | C |
| ATOM | 3136 | CB | LEU | A | 419 | 11.638 | 28.501 | 3.165 | 1.00 | 26.73 | C |
| ATOM | 3137 | CG | LEU | A | 419 | 12.333 | 28.262 | 4.510 | 1.00 | 26.68 | C |
| ATOM | 3138 | CD1 | LEU | A | 419 | 11.499 | 28.866 | 5.626 | 1.00 | 27.10 | C |
| ATOM | 3139 | CD2 | LEU | A | 419 | 12.585 | 26.779 | 4.767 | 1.00 | 26.83 | C |
| ATOM | 3140 | C | LEU | A | 419 | 11.463 | 28.543 | 0.682 | 1.00 | 26.67 | C |
| ATOM | 3141 | O | LEU | A | 419 | 11.508 | 29.712 | 0.289 | 1.00 | 26.75 | O |
| ATOM | 3142 | N | ASP | A | 420 | 10.675 | 27.621 | 0.129 | 1.00 | 26.66 | N |
| ATOM | 3143 | CA | ASP | A | 420 | 9.688 | 27.977 | −0.897 | 1.00 | 26.64 | C |
| ATOM | 3144 | CB | ASP | A | 420 | 9.446 | 26.812 | −1.880 | 1.00 | 26.99 | C |
| ATOM | 3145 | CG | ASP | A | 420 | 8.792 | 25.592 | −1.226 | 1.00 | 27.60 | C |
| ATOM | 3146 | OD1 | ASP | A | 420 | 8.213 | 25.714 | −0.127 | 1.00 | 28.34 | O |
| ATOM | 3147 | OD2 | ASP | A | 420 | 8.844 | 24.503 | −1.838 | 1.00 | 29.00 | O |
| ATOM | 3148 | C | ASP | A | 420 | 8.386 | 28.468 | −0.250 | 1.00 | 26.44 | C |
| ATOM | 3149 | O | ASP | A | 420 | 8.278 | 28.497 | 0.977 | 1.00 | 26.23 | O |
| ATOM | 3150 | N | TYR | A | 421 | 7.407 | 28.854 | −1.069 | 1.00 | 26.26 | N |
| ATOM | 3151 | CA | TYR | A | 421 | 6.157 | 29.424 | −0.552 | 1.00 | 26.15 | C |
| ATOM | 3152 | CB | TYR | A | 421 | 5.205 | 29.814 | −1.690 | 1.00 | 26.02 | C |
| ATOM | 3153 | CG | TYR | A | 421 | 3.926 | 30.468 | −1.203 | 1.00 | 26.01 | C |
| ATOM | 3154 | CD1 | TYR | A | 421 | 3.890 | 31.828 | −0.887 | 1.00 | 25.95 | C |
| ATOM | 3155 | CE1 | TYR | A | 421 | 2.721 | 32.430 | −0.429 | 1.00 | 25.88 | C |
| ATOM | 3156 | CZ | TYR | A | 421 | 1.571 | 31.668 | −0.278 | 1.00 | 25.96 | C |
| ATOM | 3157 | OH | TYR | A | 421 | 0.410 | 32.256 | 0.173 | 1.00 | 26.24 | O |
| ATOM | 3158 | CE2 | TYR | A | 421 | 1.581 | 30.316 | −0.584 | 1.00 | 25.71 | C |
| ATOM | 3159 | CD2 | TYR | A | 421 | 2.756 | 29.723 | −1.041 | 1.00 | 25.85 | C |
| ATOM | 3160 | C | TYR | A | 421 | 5.448 | 28.501 | 0.441 | 1.00 | 26.30 | C |

TABLE 6-continued

Coordinates of the crystal structure of *E. coli* ExoI bound to compound 9

| ATOM | 3161 | O | TYR | A | 421 | 5.021 | 28.944 | 1.511 | 1.00 | 26.11 | O |
|---|---|---|---|---|---|---|---|---|---|---|---|
| ATOM | 3162 | N | ALA | A | 422 | 5.328 | 27.223 | 0.081 | 1.00 | 26.38 | N |
| ATOM | 3163 | CA | ALA | A | 422 | 4.668 | 26.230 | 0.929 | 1.00 | 26.50 | C |
| ATOM | 3164 | CB | ALA | A | 422 | 4.560 | 24.895 | 0.204 | 1.00 | 26.50 | C |
| ATOM | 3165 | C | ALA | A | 422 | 5.387 | 26.060 | 2.268 | 1.00 | 26.59 | C |
| ATOM | 3166 | O | ALA | A | 422 | 4.743 | 25.950 | 3.313 | 1.00 | 26.66 | O |
| ATOM | 3167 | N | GLU | A | 423 | 6.720 | 26.047 | 2.225 | 1.00 | 26.74 | N |
| ATOM | 3168 | CA | GLU | A | 423 | 7.543 | 25.948 | 3.440 | 1.00 | 26.96 | C |
| ATOM | 3169 | CB | GLU | A | 423 | 9.001 | 25.635 | 3.086 | 1.00 | 27.01 | C |
| ATOM | 3170 | CG | GLU | A | 423 | 9.244 | 24.190 | 2.643 | 1.00 | 27.20 | C |
| ATOM | 3171 | CD | GLU | A | 423 | 10.597 | 23.988 | 1.970 | 1.00 | 27.41 | C |
| ATOM | 3172 | OE1 | GLU | A | 423 | 11.132 | 24.955 | 1.388 | 1.00 | 27.82 | O |
| ATOM | 3173 | OE2 | GLU | A | 423 | 11.118 | 22.853 | 2.012 | 1.00 | 27.85 | O |
| ATOM | 3174 | C | GLU | A | 423 | 7.462 | 27.219 | 4.286 | 1.00 | 27.00 | C |
| ATOM | 3175 | O | GLU | A | 423 | 7.503 | 27.156 | 5.520 | 1.00 | 26.93 | O |
| ATOM | 3176 | N | GLN | A | 424 | 7.346 | 28.367 | 3.618 | 1.00 | 27.08 | N |
| ATOM | 3177 | CA | GLN | A | 424 | 7.159 | 29.652 | 4.296 | 1.00 | 27.28 | C |
| ATOM | 3178 | CB | GLN | A | 424 | 7.221 | 30.808 | 3.291 | 1.00 | 27.26 | C |
| ATOM | 3179 | CG | GLN | A | 424 | 8.634 | 31.194 | 2.862 | 1.00 | 27.48 | C |
| ATOM | 3180 | CD | GLN | A | 424 | 8.654 | 32.162 | 1.686 | 1.00 | 28.08 | C |
| ATOM | 3181 | OE1 | GLN | A | 424 | 7.618 | 32.692 | 1.279 | 1.00 | 28.92 | O |
| ATOM | 3182 | NE2 | GLN | A | 424 | 9.839 | 32.390 | 1.131 | 1.00 | 29.26 | N |
| ATOM | 3183 | C | GLN | A | 424 | 5.839 | 29.696 | 5.066 | 1.00 | 27.30 | C |
| ATOM | 3184 | O | GLN | A | 424 | 5.775 | 30.247 | 6.166 | 1.00 | 27.24 | O |
| ATOM | 3185 | N | GLN | A | 425 | 4.793 | 29.114 | 4.481 | 1.00 | 27.36 | N |
| ATOM | 3186 | CA | GLN | A | 425 | 3.481 | 29.048 | 5.128 | 1.00 | 27.44 | C |
| ATOM | 3187 | CB | GLN | A | 425 | 2.389 | 28.685 | 4.116 | 1.00 | 27.51 | C |
| ATOM | 3188 | CG | GLN | A | 425 | 2.139 | 29.753 | 3.051 | 1.00 | 27.94 | C |
| ATOM | 3189 | CD | GLN | A | 425 | 1.797 | 31.113 | 3.642 | 1.00 | 28.66 | C |
| ATOM | 3190 | OE1 | GLN | A | 425 | 2.521 | 32.087 | 3.442 | 1.00 | 29.19 | O |
| ATOM | 3191 | NE2 | GLN | A | 425 | 0.692 | 31.181 | 4.379 | 1.00 | 29.28 | N |
| ATOM | 3192 | C | GLN | A | 425 | 3.475 | 28.067 | 6.298 | 1.00 | 27.51 | C |
| ATOM | 3193 | O | GLN | A | 425 | 2.792 | 28.293 | 7.299 | 1.00 | 27.41 | O |
| ATOM | 3194 | N | ARG | A | 426 | 4.239 | 26.983 | 6.164 | 1.00 | 27.53 | N |
| ATOM | 3195 | CA | ARG | A | 426 | 4.408 | 26.014 | 7.246 | 1.00 | 27.80 | C |
| ATOM | 3196 | CB | ARG | A | 426 | 5.198 | 24.790 | 6.763 | 1.00 | 27.86 | C |
| ATOM | 3197 | CG | ARG | A | 426 | 5.292 | 23.655 | 7.784 | 1.00 | 28.29 | C |
| ATOM | 3198 | CD | ARG | A | 426 | 6.118 | 22.486 | 7.259 | 1.00 | 28.56 | C |
| ATOM | 3199 | NE | ARG | A | 426 | 6.593 | 21.624 | 8.345 | 1.00 | 29.94 | N |
| ATOM | 3200 | CZ | ARG | A | 426 | 7.375 | 20.559 | 8.178 | 1.00 | 30.12 | C |
| ATOM | 3201 | NH1 | ARG | A | 426 | 7.782 | 20.205 | 6.963 | 1.00 | 30.30 | N |
| ATOM | 3202 | NH2 | ARG | A | 426 | 7.751 | 19.843 | 9.230 | 1.00 | 30.61 | N |
| ATOM | 3203 | C | ARG | A | 426 | 5.099 | 26.669 | 8.444 | 1.00 | 27.71 | C |
| ATOM | 3204 | O | ARG | A | 426 | 4.740 | 26.411 | 9.595 | 1.00 | 27.67 | O |
| ATOM | 3205 | N | TRP | A | 427 | 6.075 | 27.531 | 8.162 | 1.00 | 27.67 | N |
| ATOM | 3206 | CA | TRP | A | 427 | 6.793 | 28.248 | 9.213 | 1.00 | 27.78 | C |
| ATOM | 3207 | CB | TRP | A | 427 | 8.091 | 28.854 | 8.680 | 1.00 | 27.72 | C |
| ATOM | 3208 | CG | TRP | A | 427 | 8.970 | 29.396 | 9.767 | 1.00 | 27.64 | C |
| ATOM | 3209 | CD1 | TRP | A | 427 | 9.319 | 30.700 | 9.965 | 1.00 | 27.83 | C |
| ATOM | 3210 | NE1 | TRP | A | 427 | 10.131 | 30.811 | 11.070 | 1.00 | 27.75 | N |
| ATOM | 3211 | CE2 | TRP | A | 427 | 10.313 | 29.568 | 11.615 | 1.00 | 27.64 | C |
| ATOM | 3212 | CD2 | TRP | A | 427 | 9.591 | 28.649 | 10.821 | 1.00 | 27.94 | C |
| ATOM | 3213 | CE3 | TRP | A | 427 | 9.610 | 27.291 | 11.169 | 1.00 | 27.75 | C |
| ATOM | 3214 | CZ3 | TRP | A | 427 | 10.347 | 26.898 | 12.282 | 1.00 | 27.78 | C |
| ATOM | 3215 | CH2 | TRP | A | 427 | 11.053 | 27.839 | 13.053 | 1.00 | 27.62 | C |
| ATOM | 3216 | CZ2 | TRP | A | 427 | 11.050 | 29.173 | 12.735 | 1.00 | 27.48 | C |
| ATOM | 3217 | C | TRP | A | 427 | 5.936 | 29.325 | 9.875 | 1.00 | 28.06 | C |
| ATOM | 3218 | O | TRP | A | 427 | 6.022 | 29.531 | 11.086 | 1.00 | 27.94 | O |
| ATOM | 3219 | N | LEU | A | 428 | 5.117 | 30.011 | 9.078 | 1.00 | 28.34 | N |
| ATOM | 3220 | CA | LEU | A | 428 | 4.186 | 31.007 | 9.609 | 1.00 | 28.82 | C |
| ATOM | 3221 | CB | LEU | A | 428 | 3.427 | 31.708 | 8.477 | 1.00 | 28.88 | C |
| ATOM | 3222 | CG | LEU | A | 428 | 4.144 | 32.848 | 7.744 | 1.00 | 29.44 | C |
| ATOM | 3223 | CD1 | LEU | A | 428 | 3.336 | 33.277 | 6.527 | 1.00 | 29.77 | C |
| ATOM | 3224 | CD2 | LEU | A | 428 | 4.389 | 34.040 | 8.673 | 1.00 | 29.87 | C |
| ATOM | 3225 | C | LEU | A | 428 | 3.205 | 30.380 | 10.595 | 1.00 | 29.04 | C |
| ATOM | 3226 | O | LEU | A | 428 | 2.918 | 30.958 | 11.647 | 1.00 | 29.04 | O |
| ATOM | 3227 | N | GLU | A | 429 | 2.706 | 29.192 | 10.252 | 1.00 | 29.33 | N |
| ATOM | 3228 | CA | GLU | A | 429 | 1.798 | 28.447 | 11.123 | 1.00 | 29.77 | C |
| ATOM | 3229 | CB | GLU | A | 429 | 1.199 | 27.247 | 10.380 | 1.00 | 29.95 | C |
| ATOM | 3230 | CG | GLU | A | 429 | 0.032 | 26.575 | 11.106 | 1.00 | 31.05 | C |
| ATOM | 3231 | CD | GLU | A | 429 | −1.092 | 27.545 | 11.440 | 1.00 | 32.27 | C |
| ATOM | 3232 | OE1 | GLU | A | 429 | −1.690 | 28.116 | 10.502 | 1.00 | 33.20 | O |
| ATOM | 3233 | OE2 | GLU | A | 429 | −1.377 | 27.732 | 12.642 | 1.00 | 33.24 | O |
| ATOM | 3234 | C | GLU | A | 429 | 2.505 | 27.987 | 12.399 | 1.00 | 29.75 | C |
| ATOM | 3235 | O | GLU | A | 429 | 1.921 | 28.020 | 13.484 | 1.00 | 29.78 | O |
| ATOM | 3236 | N | HIS | A | 430 | 3.760 | 27.562 | 12.255 | 1.00 | 29.80 | N |
| ATOM | 3237 | CA | HIS | A | 430 | 4.600 | 27.188 | 13.395 | 1.00 | 29.92 | C |
| ATOM | 3238 | CB | HIS | A | 430 | 5.984 | 26.734 | 12.910 | 1.00 | 29.82 | C |

TABLE 6-continued

Coordinates of the crystal structure of *E. coli* ExoI bound to compound 9

| ATOM | 3239 | CG | HIS | A | 430 | 7.002 | 26.607 | 14.003 | 1.00 | 29.75 | C |
|------|------|------|-----|---|-----|--------|--------|--------|------|-------|---|
| ATOM | 3240 | ND1 | HIS | A | 430 | 7.202 | 25.437 | 14.702 | 1.00 | 29.97 | N |
| ATOM | 3241 | CE1 | HIS | A | 430 | 8.160 | 25.617 | 15.594 | 1.00 | 30.02 | C |
| ATOM | 3242 | NE2 | HIS | A | 430 | 8.591 | 26.862 | 15.497 | 1.00 | 29.87 | N |
| ATOM | 3243 | CD2 | HIS | A | 430 | 7.884 | 27.502 | 14.508 | 1.00 | 30.04 | C |
| ATOM | 3244 | C | HIS | A | 430 | 4.731 | 28.346 | 14.383 | 1.00 | 30.18 | C |
| ATOM | 3245 | O | HIS | A | 430 | 4.585 | 28.157 | 15.595 | 1.00 | 30.08 | O |
| ATOM | 3246 | N | ARG | A | 431 | 5.000 | 29.541 | 13.857 | 1.00 | 30.45 | N |
| ATOM | 3247 | CA | ARG | A | 431 | 5.151 | 30.740 | 14.685 | 1.00 | 30.84 | C |
| ATOM | 3248 | CB | ARG | A | 431 | 5.711 | 31.905 | 13.862 | 1.00 | 30.80 | C |
| ATOM | 3249 | CG | ARG | A | 431 | 7.134 | 31.681 | 13.364 | 1.00 | 31.07 | C |
| ATOM | 3250 | CD | ARG | A | 431 | 7.624 | 32.838 | 12.509 | 1.00 | 31.47 | C |
| ATOM | 3251 | NE | ARG | A | 431 | 8.098 | 33.960 | 13.317 | 1.00 | 32.66 | N |
| ATOM | 3252 | CZ | ARG | A | 431 | 7.475 | 35.132 | 13.427 | 1.00 | 33.11 | C |
| ATOM | 3253 | NH1 | ARG | A | 431 | 6.340 | 35.357 | 12.774 | 1.00 | 33.51 | N |
| ATOM | 3254 | NH2 | ARG | A | 431 | 7.994 | 36.085 | 14.188 | 1.00 | 33.18 | N |
| ATOM | 3255 | C | ARG | A | 431 | 3.838 | 31.139 | 15.355 | 1.00 | 30.98 | C |
| ATOM | 3256 | O | ARG | A | 431 | 3.833 | 31.576 | 16.505 | 1.00 | 30.90 | O |
| ATOM | 3257 | N | ARG | A | 432 | 2.729 | 30.976 | 14.631 | 1.00 | 31.21 | N |
| ATOM | 3258 | CA | ARG | A | 432 | 1.395 | 31.258 | 15.172 | 1.00 | 31.58 | C |
| ATOM | 3259 | CB | ARG | A | 432 | 0.334 | 31.187 | 14.067 | 1.00 | 31.56 | C |
| ATOM | 3260 | CG | ARG | A | 432 | 0.323 | 32.391 | 13.133 | 1.00 | 32.02 | C |
| ATOM | 3261 | CD | ARG | A | 432 | −0.734 | 32.245 | 12.046 | 1.00 | 32.35 | C |
| ATOM | 3262 | NE | ARG | A | 432 | −0.628 | 33.299 | 11.037 | 1.00 | 33.80 | N |
| ATOM | 3263 | CZ | ARG | A | 432 | −1.452 | 33.439 | 10.001 | 1.00 | 34.49 | C |
| ATOM | 3264 | NH1 | ARG | A | 432 | −2.460 | 32.592 | 9.822 | 1.00 | 34.96 | N |
| ATOM | 3265 | NH2 | ARG | A | 432 | −1.270 | 34.431 | 9.139 | 1.00 | 35.02 | N |
| ATOM | 3266 | C | ARG | A | 432 | 1.025 | 30.315 | 16.321 | 1.00 | 31.58 | C |
| ATOM | 3267 | O | ARG | A | 432 | 0.307 | 30.705 | 17.244 | 1.00 | 31.53 | O |
| ATOM | 3268 | N | GLN | A | 433 | 1.520 | 29.079 | 16.256 | 1.00 | 31.63 | N |
| ATOM | 3269 | CA | GLN | A | 433 | 1.252 | 28.077 | 17.292 | 1.00 | 31.83 | C |
| ATOM | 3270 | CB | GLN | A | 433 | 1.495 | 26.663 | 16.752 | 1.00 | 31.81 | C |
| ATOM | 3271 | CG | GLN | A | 433 | 0.379 | 26.154 | 15.836 | 1.00 | 32.28 | C |
| ATOM | 3272 | CD | GLN | A | 433 | 0.749 | 24.880 | 15.085 | 1.00 | 32.55 | C |
| ATOM | 3273 | OE1 | GLN | A | 433 | 1.763 | 24.240 | 15.373 | 1.00 | 33.88 | O |
| ATOM | 3274 | NE2 | GLN | A | 433 | −0.078 | 24.509 | 14.115 | 1.00 | 33.03 | N |
| ATOM | 3275 | C | GLN | A | 433 | 2.076 | 28.322 | 18.558 | 1.00 | 31.71 | C |
| ATOM | 3276 | O | GLN | A | 433 | 1.646 | 27.982 | 19.663 | 1.00 | 31.67 | O |
| ATOM | 3277 | N | VAL | A | 434 | 3.257 | 28.913 | 18.387 | 1.00 | 31.60 | N |
| ATOM | 3278 | CA | VAL | A | 434 | 4.078 | 29.346 | 19.519 | 1.00 | 31.59 | C |
| ATOM | 3279 | CB | VAL | A | 434 | 5.565 | 29.564 | 19.107 | 1.00 | 31.49 | C |
| ATOM | 3280 | CG1 | VAL | A | 434 | 6.374 | 30.132 | 20.270 | 1.00 | 31.66 | C |
| ATOM | 3281 | CG2 | VAL | A | 434 | 6.181 | 28.265 | 18.616 | 1.00 | 31.59 | C |
| ATOM | 3282 | C | VAL | A | 434 | 3.511 | 30.639 | 20.107 | 1.00 | 31.57 | C |
| ATOM | 3283 | O | VAL | A | 434 | 3.282 | 30.735 | 21.317 | 1.00 | 31.59 | O |
| ATOM | 3284 | N | PHE | A | 435 | 3.270 | 31.621 | 19.240 | 1.00 | 31.62 | N |
| ATOM | 3285 | CA | PHE | A | 435 | 2.837 | 32.944 | 19.674 | 1.00 | 31.68 | C |
| ATOM | 3286 | CB | PHE | A | 435 | 3.458 | 34.034 | 18.795 | 1.00 | 31.57 | C |
| ATOM | 3287 | CG | PHE | A | 435 | 4.960 | 33.977 | 18.730 | 1.00 | 31.44 | C |
| ATOM | 3288 | CD1 | PHE | A | 435 | 5.718 | 33.801 | 19.890 | 1.00 | 31.49 | C |
| ATOM | 3289 | CE1 | PHE | A | 435 | 7.109 | 33.748 | 19.832 | 1.00 | 31.29 | C |
| ATOM | 3290 | CZ | PHE | A | 435 | 7.755 | 33.882 | 18.609 | 1.00 | 31.33 | C |
| ATOM | 3291 | CE2 | PHE | A | 435 | 7.012 | 34.061 | 17.447 | 1.00 | 31.39 | C |
| ATOM | 3292 | CD2 | PHE | A | 435 | 5.621 | 34.110 | 17.513 | 1.00 | 31.62 | C |
| ATOM | 3293 | C | PHE | A | 435 | 1.317 | 33.075 | 19.723 | 1.00 | 31.86 | C |
| ATOM | 3294 | O | PHE | A | 435 | 0.689 | 33.627 | 18.810 | 1.00 | 31.90 | O |
| ATOM | 3295 | N | THR | A | 436 | 0.700 | 32.611 | 20.811 | 1.00 | 32.09 | N |
| ATOM | 3296 | CA | THR | A | 436 | −0.744 | 32.538 | 20.995 | 1.00 | 32.28 | C |
| ATOM | 3297 | CB | THR | A | 436 | −1.159 | 31.204 | 21.667 | 1.00 | 32.28 | C |
| ATOM | 3298 | OG1 | THR | A | 436 | −0.358 | 30.984 | 22.838 | 1.00 | 32.26 | O |
| ATOM | 3299 | CG2 | THR | A | 436 | −0.973 | 30.035 | 20.707 | 1.00 | 32.38 | C |
| ATOM | 3300 | C | THR | A | 436 | −1.160 | 33.696 | 21.892 | 1.00 | 32.48 | C |
| ATOM | 3301 | O | THR | A | 436 | −0.354 | 34.219 | 22.669 | 1.00 | 32.58 | O |
| ATOM | 3302 | N | PRO | A | 437 | −2.343 | 34.199 | 21.692 | 1.00 | 32.62 | N |
| ATOM | 3303 | CA | PRO | A | 437 | −2.854 | 35.312 | 22.499 | 1.00 | 32.65 | C |
| ATOM | 3304 | CB | PRO | A | 437 | −4.369 | 35.295 | 22.216 | 1.00 | 32.69 | C |
| ATOM | 3305 | CG | PRO | A | 437 | −4.623 | 34.009 | 21.452 | 1.00 | 32.68 | C |
| ATOM | 3306 | CD | PRO | A | 437 | −3.353 | 33.708 | 20.741 | 1.00 | 32.65 | C |
| ATOM | 3307 | C | PRO | A | 437 | −2.587 | 35.106 | 23.993 | 1.00 | 32.64 | C |
| ATOM | 3308 | O | PRO | A | 437 | −2.222 | 36.053 | 24.690 | 1.00 | 32.71 | O |
| ATOM | 3309 | N | GLU | A | 438 | −2.733 | 33.802 | 24.450 | 1.00 | 32.58 | N |
| ATOM | 3310 | CA | GLU | A | 438 | −2.477 | 33.443 | 25.848 | 1.00 | 32.57 | C |
| ATOM | 3311 | CB | GLU | A | 438 | −2.982 | 32.028 | 26.136 | 1.00 | 32.61 | C |
| ATOM | 3312 | CG | GLU | A | 438 | −2.649 | 31.018 | 25.043 | 1.00 | 33.20 | C |
| ATOM | 3313 | CD | GLU | A | 438 | −3.124 | 29.618 | 25.366 | 1.00 | 33.53 | C |
| ATOM | 3314 | OE1 | GLU | A | 438 | −3.471 | 29.361 | 26.543 | 1.00 | 34.34 | O |
| ATOM | 3315 | OE2 | GLU | A | 438 | −3.147 | 28.774 | 24.443 | 1.00 | 34.01 | O |
| ATOM | 3316 | C | GLU | A | 438 | −1.000 | 33.554 | 26.226 | 1.00 | 32.24 | C |

TABLE 6-continued

Coordinates of the crystal structure of *E. coli* ExoI bound to compound 9

| ATOM | 3317 | O | GLU | A | 438 | −0.668 | 34.011 | 27.322 | 1.00 | 32.33 | O |
|---|---|---|---|---|---|---|---|---|---|---|---|
| ATOM | 3318 | N | PHE | A | 439 | −0.109 | 33.131 | 25.363 | 1.00 | 31.85 | N |
| ATOM | 3319 | CA | PHE | A | 439 | 1.328 | 33.215 | 25.600 | 1.00 | 31.35 | C |
| ATOM | 3320 | CB | PHE | A | 439 | 2.105 | 32.373 | 24.581 | 1.00 | 31.40 | C |
| ATOM | 3321 | CG | PHE | A | 439 | 3.600 | 32.534 | 24.673 | 1.00 | 31.40 | C |
| ATOM | 3322 | CD1 | PHE | A | 439 | 4.317 | 31.947 | 25.716 | 1.00 | 31.59 | C |
| ATOM | 3323 | CE1 | PHE | A | 439 | 5.699 | 32.096 | 25.805 | 1.00 | 31.55 | C |
| ATOM | 3324 | CZ | PHE | A | 439 | 6.379 | 32.836 | 24.843 | 1.00 | 31.46 | C |
| ATOM | 3325 | CE2 | PHE | A | 439 | 5.677 | 33.425 | 23.798 | 1.00 | 31.37 | C |
| ATOM | 3326 | CD2 | PHE | A | 439 | 4.293 | 33.272 | 23.717 | 1.00 | 31.61 | C |
| ATOM | 3327 | C | PHE | A | 439 | 1.801 | 34.666 | 25.571 | 1.00 | 31.05 | C |
| ATOM | 3328 | O | PHE | A | 439 | 2.592 | 35.082 | 26.419 | 1.00 | 30.99 | O |
| ATOM | 3329 | N | LEU | A | 440 | 1.301 | 35.429 | 24.600 | 1.00 | 30.61 | N |
| ATOM | 3330 | CA | LEU | A | 440 | 1.692 | 36.828 | 24.435 | 1.00 | 30.26 | C |
| ATOM | 3331 | CB | LEU | A | 440 | 1.212 | 37.380 | 23.084 | 1.00 | 30.43 | C |
| ATOM | 3332 | CG | LEU | A | 440 | 1.605 | 36.629 | 21.804 | 1.00 | 30.59 | C |
| ATOM | 3333 | CD1 | LEU | A | 440 | 1.288 | 37.462 | 20.571 | 1.00 | 31.06 | C |
| ATOM | 3334 | CD2 | LEU | A | 440 | 3.069 | 36.214 | 21.810 | 1.00 | 31.06 | C |
| ATOM | 3335 | C | LEU | A | 440 | 1.179 | 37.697 | 25.580 | 1.00 | 29.92 | C |
| ATOM | 3336 | O | LEU | A | 440 | 1.871 | 38.614 | 26.028 | 1.00 | 29.84 | O |
| ATOM | 3337 | N | GLN | A | 441 | −0.034 | 37.400 | 26.049 | 1.00 | 29.49 | N |
| ATOM | 3338 | CA | GLN | A | 441 | −0.615 | 38.099 | 27.194 | 1.00 | 29.07 | C |
| ATOM | 3339 | CB | GLN | A | 441 | −2.102 | 37.753 | 27.351 | 1.00 | 29.18 | C |
| ATOM | 3340 | CG | GLN | A | 441 | −2.841 | 38.606 | 28.383 | 1.00 | 29.75 | C |
| ATOM | 3341 | CD | GLN | A | 441 | −2.852 | 40.081 | 28.024 | 1.00 | 30.43 | C |
| ATOM | 3342 | OE1 | GLN | A | 441 | −3.384 | 40.476 | 26.986 | 1.00 | 31.08 | O |
| ATOM | 3343 | NE2 | GLN | A | 441 | −2.266 | 40.904 | 28.885 | 1.00 | 30.79 | N |
| ATOM | 3344 | C | GLN | A | 441 | 0.144 | 37.765 | 28.474 | 1.00 | 28.58 | C |
| ATOM | 3345 | O | GLN | A | 441 | 0.458 | 38.655 | 29.265 | 1.00 | 28.65 | O |
| ATOM | 3346 | N | GLY | A | 442 | 0.439 | 36.479 | 28.666 | 1.00 | 27.94 | N |
| ATOM | 3347 | CA | GLY | A | 442 | 1.241 | 36.022 | 29.800 | 1.00 | 27.15 | C |
| ATOM | 3348 | C | GLY | A | 442 | 2.633 | 36.628 | 29.795 | 1.00 | 26.49 | C |
| ATOM | 3349 | O | GLY | A | 442 | 3.180 | 36.958 | 30.849 | 1.00 | 26.50 | O |
| ATOM | 3350 | N | TYR | A | 443 | 3.200 | 36.781 | 28.599 | 1.00 | 25.80 | N |
| ATOM | 3351 | CA | TYR | A | 443 | 4.506 | 37.409 | 28.434 | 1.00 | 25.26 | C |
| ATOM | 3352 | CB | TYR | A | 443 | 5.005 | 37.245 | 26.994 | 1.00 | 24.62 | C |
| ATOM | 3353 | CG | TYR | A | 443 | 6.499 | 37.411 | 26.843 | 1.00 | 23.83 | C |
| ATOM | 3354 | CD1 | TYR | A | 443 | 7.366 | 36.341 | 27.081 | 1.00 | 23.37 | C |
| ATOM | 3355 | CE1 | TYR | A | 443 | 8.742 | 36.487 | 26.946 | 1.00 | 22.61 | C |
| ATOM | 3356 | CZ | TYR | A | 443 | 9.266 | 37.715 | 26.568 | 1.00 | 22.69 | C |
| ATOM | 3357 | OH | TYR | A | 443 | 10.626 | 37.863 | 26.431 | 1.00 | 22.52 | O |
| ATOM | 3358 | CE2 | TYR | A | 443 | 8.428 | 38.792 | 26.325 | 1.00 | 22.51 | C |
| ATOM | 3359 | CD2 | TYR | A | 443 | 7.051 | 38.635 | 26.465 | 1.00 | 22.79 | C |
| ATOM | 3360 | C | TYR | A | 443 | 4.459 | 38.888 | 28.819 | 1.00 | 25.28 | C |
| ATOM | 3361 | O | TYR | A | 443 | 5.304 | 39.363 | 29.580 | 1.00 | 25.21 | O |
| ATOM | 3362 | N | ALA | A | 444 | 3.462 | 39.604 | 28.297 | 1.00 | 25.48 | N |
| ATOM | 3363 | CA | ALA | A | 444 | 3.257 | 41.016 | 28.626 | 1.00 | 25.81 | C |
| ATOM | 3364 | CB | ALA | A | 444 | 2.107 | 41.593 | 27.806 | 1.00 | 25.81 | C |
| ATOM | 3365 | C | ALA | A | 444 | 3.001 | 41.213 | 30.120 | 1.00 | 26.01 | C |
| ATOM | 3366 | O | ALA | A | 444 | 3.508 | 42.162 | 30.724 | 1.00 | 26.04 | O |
| ATOM | 3367 | N | ASP | A | 445 | 2.220 | 40.307 | 30.708 | 1.00 | 26.34 | N |
| ATOM | 3368 | CA | ASP | A | 445 | 1.905 | 40.350 | 32.137 | 1.00 | 26.71 | C |
| ATOM | 3369 | CB | ASP | A | 445 | 0.853 | 39.293 | 32.497 | 1.00 | 26.87 | C |
| ATOM | 3370 | CG | ASP | A | 445 | −0.544 | 39.660 | 32.012 | 1.00 | 27.59 | C |
| ATOM | 3371 | OD1 | ASP | A | 445 | −0.797 | 40.852 | 31.730 | 1.00 | 28.24 | O |
| ATOM | 3372 | OD2 | ASP | A | 445 | −1.395 | 38.749 | 31.919 | 1.00 | 28.77 | O |
| ATOM | 3373 | C | ASP | A | 445 | 3.144 | 40.169 | 33.010 | 1.00 | 26.77 | C |
| ATOM | 3374 | O | ASP | A | 445 | 3.273 | 40.815 | 34.050 | 1.00 | 26.68 | O |
| ATOM | 3375 | N | GLU | A | 446 | 4.047 | 39.285 | 32.587 | 1.00 | 26.79 | N |
| ATOM | 3376 | CA | GLU | A | 446 | 5.284 | 39.045 | 33.327 | 1.00 | 27.17 | C |
| ATOM | 3377 | CB | GLU | A | 446 | 6.018 | 37.808 | 32.799 | 1.00 | 27.24 | C |
| ATOM | 3378 | CG | GLU | A | 446 | 7.149 | 37.340 | 33.717 | 1.00 | 28.26 | C |
| ATOM | 3379 | CD | GLU | A | 446 | 7.944 | 36.169 | 33.159 | 1.00 | 28.85 | C |
| ATOM | 3380 | OE1 | GLU | A | 446 | 7.471 | 35.503 | 32.211 | 1.00 | 31.26 | O |
| ATOM | 3381 | OE2 | GLU | A | 446 | 9.050 | 35.912 | 33.682 | 1.00 | 30.75 | O |
| ATOM | 3382 | C | GLU | A | 446 | 6.202 | 40.265 | 33.290 | 1.00 | 26.78 | C |
| ATOM | 3383 | O | GLU | A | 446 | 6.779 | 40.644 | 34.310 | 1.00 | 26.64 | O |
| ATOM | 3384 | N | LEU | A | 447 | 6.325 | 40.876 | 32.112 | 1.00 | 26.64 | N |
| ATOM | 3385 | CA | LEU | A | 447 | 7.156 | 42.070 | 31.941 | 1.00 | 26.52 | C |
| ATOM | 3386 | CB | LEU | A | 447 | 7.206 | 42.491 | 30.468 | 1.00 | 26.40 | C |
| ATOM | 3387 | CG | LEU | A | 447 | 7.883 | 41.528 | 29.485 | 1.00 | 26.07 | C |
| ATOM | 3388 | CD1 | LEU | A | 447 | 7.698 | 42.008 | 28.056 | 1.00 | 25.63 | C |
| ATOM | 3389 | CD2 | LEU | A | 447 | 9.364 | 41.353 | 29.809 | 1.00 | 26.15 | C |
| ATOM | 3390 | C | LEU | A | 447 | 6.668 | 43.231 | 32.805 | 1.00 | 26.64 | C |
| ATOM | 3391 | O | LEU | A | 447 | 7.468 | 43.905 | 33.458 | 1.00 | 26.39 | O |
| ATOM | 3392 | N | GLN | A | 448 | 5.354 | 43.449 | 32.806 | 1.00 | 26.82 | N |
| ATOM | 3393 | CA | GLN | A | 448 | 4.740 | 44.508 | 33.607 | 1.00 | 27.29 | C |
| ATOM | 3394 | CB | GLN | A | 448 | 3.264 | 44.676 | 33.232 | 1.00 | 27.26 | C |

TABLE 6-continued

Coordinates of the crystal structure of *E. coli* ExoI bound to compound 9

| ATOM | 3395 | CG  | GLN | A | 448 | 3.053  | 45.288 | 31.847 | 1.00 | 28.22 | C |
| ---- | ---- | --- | --- | - | --- | ------ | ------ | ------ | ---- | ----- | - |
| ATOM | 3396 | CD  | GLN | A | 448 | 1.613  | 45.199 | 31.366 | 1.00 | 28.41 | C |
| ATOM | 3397 | OE1 | GLN | A | 448 | 1.048  | 44.108 | 31.250 | 1.00 | 29.89 | O |
| ATOM | 3398 | NE2 | GLN | A | 448 | 1.019  | 46.349 | 31.064 | 1.00 | 29.54 | N |
| ATOM | 3399 | C   | GLN | A | 448 | 4.892  | 44.239 | 35.104 | 1.00 | 27.18 | C |
| ATOM | 3400 | O   | GLN | A | 448 | 5.084  | 45.164 | 35.893 | 1.00 | 27.10 | O |
| ATOM | 3401 | N   | MET | A | 449 | 4.820  | 42.965 | 35.482 | 1.00 | 27.21 | N |
| ATOM | 3402 | CA  | MET | A | 449 | 5.036  | 42.551 | 36.864 | 1.00 | 27.66 | C |
| ATOM | 3403 | CB  | MET | A | 449 | 4.669  | 41.077 | 37.034 | 1.00 | 27.54 | C |
| ATOM | 3404 | CG  | MET | A | 449 | 4.509  | 40.630 | 38.473 | 1.00 | 28.84 | C |
| ATOM | 3405 | SD  | MET | A | 449 | 4.974  | 38.903 | 38.692 | 1.00 | 30.54 | S |
| ATOM | 3406 | CE  | MET | A | 449 | 6.764  | 39.033 | 38.635 | 1.00 | 29.99 | C |
| ATOM | 3407 | C   | MET | A | 449 | 6.487  | 42.788 | 37.301 | 1.00 | 27.01 | C |
| ATOM | 3408 | O   | MET | A | 449 | 6.740  | 43.274 | 38.404 | 1.00 | 27.03 | O |
| ATOM | 3409 | N   | LEU | A | 450 | 7.431  | 42.447 | 36.426 | 1.00 | 26.53 | N |
| ATOM | 3410 | CA  | LEU | A | 450 | 8.854  | 42.574 | 36.741 | 1.00 | 26.09 | C |
| ATOM | 3411 | CB  | LEU | A | 450 | 9.703  | 41.746 | 35.769 | 1.00 | 25.90 | C |
| ATOM | 3412 | CG  | LEU | A | 450 | 9.678  | 40.224 | 35.953 | 1.00 | 25.59 | C |
| ATOM | 3413 | CD1 | LEU | A | 450 | 10.228 | 39.533 | 34.720 | 1.00 | 24.88 | C |
| ATOM | 3414 | CD2 | LEU | A | 450 | 10.451 | 39.794 | 37.202 | 1.00 | 25.33 | C |
| ATOM | 3415 | C   | LEU | A | 450 | 9.333  | 44.024 | 36.767 | 1.00 | 26.10 | C |
| ATOM | 3416 | O   | LEU | A | 450 | 10.233 | 44.367 | 37.533 | 1.00 | 25.89 | O |
| ATOM | 3417 | N   | VAL | A | 451 | 8.734  | 44.872 | 35.931 | 1.00 | 26.34 | N |
| ATOM | 3418 | CA  | VAL | A | 451 | 9.092  | 46.294 | 35.903 | 1.00 | 26.66 | C |
| ATOM | 3419 | CB  | VAL | A | 451 | 8.560  | 47.024 | 34.623 | 1.00 | 26.83 | C |
| ATOM | 3420 | CG1 | VAL | A | 451 | 7.083  | 47.377 | 34.750 | 1.00 | 27.07 | C |
| ATOM | 3421 | CG2 | VAL | A | 451 | 9.385  | 48.271 | 34.333 | 1.00 | 27.23 | C |
| ATOM | 3422 | C   | VAL | A | 451 | 8.653  | 47.005 | 37.191 | 1.00 | 26.75 | C |
| ATOM | 3423 | O   | VAL | A | 451 | 9.318  | 47.932 | 37.652 | 1.00 | 26.68 | O |
| ATOM | 3424 | N   | GLN | A | 452 | 7.546  | 46.544 | 37.774 | 1.00 | 26.84 | N |
| ATOM | 3425 | CA  | GLN | A | 452 | 7.090  | 47.040 | 39.071 | 1.00 | 27.12 | C |
| ATOM | 3426 | CB  | GLN | A | 452 | 5.642  | 46.614 | 39.341 | 1.00 | 27.08 | C |
| ATOM | 3427 | CG  | GLN | A | 452 | 4.604  | 47.333 | 38.478 | 1.00 | 27.73 | C |
| ATOM | 3428 | CD  | GLN | A | 452 | 3.169  | 46.990 | 38.861 | 1.00 | 27.95 | C |
| ATOM | 3429 | OE1 | GLN | A | 452 | 2.812  | 46.980 | 40.039 | 1.00 | 28.85 | O |
| ATOM | 3430 | NE2 | GLN | A | 452 | 2.339  | 46.720 | 37.858 | 1.00 | 28.80 | N |
| ATOM | 3431 | C   | GLN | A | 452 | 8.007  | 46.545 | 40.189 | 1.00 | 27.01 | C |
| ATOM | 3432 | O   | GLN | A | 452 | 8.342  | 47.297 | 41.106 | 1.00 | 27.00 | O |
| ATOM | 3433 | N   | GLN | A | 453 | 8.416  | 45.280 | 40.093 | 1.00 | 27.00 | N |
| ATOM | 3434 | CA  | GLN | A | 453 | 9.306  | 44.660 | 41.077 | 1.00 | 27.00 | C |
| ATOM | 3435 | CB  | GLN | A | 453 | 9.433  | 43.155 | 40.805 | 1.00 | 26.93 | C |
| ATOM | 3436 | CG  | GLN | A | 453 | 10.280 | 42.392 | 41.825 | 1.00 | 27.10 | C |
| ATOM | 3437 | CD  | GLN | A | 453 | 10.320 | 40.894 | 41.566 | 1.00 | 26.88 | C |
| ATOM | 3438 | OE1 | GLN | A | 453 | 9.389  | 40.321 | 40.994 | 1.00 | 26.80 | O |
| ATOM | 3439 | NE2 | GLN | A | 453 | 11.396 | 40.250 | 42.003 | 1.00 | 27.08 | N |
| ATOM | 3440 | C   | GLN | A | 453 | 10.690 | 45.314 | 41.092 | 1.00 | 27.13 | C |
| ATOM | 3441 | O   | GLN | A | 453 | 11.277 | 45.519 | 42.156 | 1.00 | 27.04 | O |
| ATOM | 3442 | N   | TYR | A | 454 | 11.199 | 45.644 | 39.906 | 1.00 | 27.29 | N |
| ATOM | 3443 | CA  | TYR | A | 454 | 12.549 | 46.189 | 39.767 | 1.00 | 27.53 | C |
| ATOM | 3444 | CB  | TYR | A | 454 | 13.356 | 45.361 | 38.756 | 1.00 | 27.69 | C |
| ATOM | 3445 | CG  | TYR | A | 454 | 13.641 | 43.947 | 39.214 | 1.00 | 28.08 | C |
| ATOM | 3446 | CD1 | TYR | A | 454 | 14.590 | 43.694 | 40.207 | 1.00 | 28.54 | C |
| ATOM | 3447 | CE1 | TYR | A | 454 | 14.858 | 42.397 | 40.635 | 1.00 | 28.98 | C |
| ATOM | 3448 | CZ  | TYR | A | 454 | 14.172 | 41.334 | 40.071 | 1.00 | 28.56 | C |
| ATOM | 3449 | OH  | TYR | A | 454 | 14.436 | 40.052 | 40.498 | 1.00 | 29.25 | O |
| ATOM | 3450 | CE2 | TYR | A | 454 | 13.222 | 41.556 | 39.085 | 1.00 | 28.18 | C |
| ATOM | 3451 | CD2 | TYR | A | 454 | 12.962 | 42.861 | 38.661 | 1.00 | 27.92 | C |
| ATOM | 3452 | C   | TYR | A | 454 | 12.552 | 47.670 | 39.376 | 1.00 | 27.57 | C |
| ATOM | 3453 | O   | TYR | A | 454 | 13.510 | 48.157 | 38.771 | 1.00 | 27.50 | O |
| ATOM | 3454 | N   | ALA | A | 455 | 11.491 | 48.384 | 39.758 | 1.00 | 27.70 | N |
| ATOM | 3455 | CA  | ALA | A | 455 | 11.306 | 49.795 | 39.386 | 1.00 | 27.84 | C |
| ATOM | 3456 | CB  | ALA | A | 455 | 10.013 | 50.338 | 39.989 | 1.00 | 27.78 | C |
| ATOM | 3457 | C   | ALA | A | 455 | 12.487 | 50.693 | 39.759 | 1.00 | 27.96 | C |
| ATOM | 3458 | O   | ALA | A | 455 | 12.766 | 51.679 | 39.072 | 1.00 | 28.01 | O |
| ATOM | 3459 | N   | ASP | A | 456 | 13.178 | 50.345 | 40.842 | 1.00 | 28.07 | N |
| ATOM | 3460 | CA  | ASP | A | 456 | 14.289 | 51.152 | 41.341 | 1.00 | 28.26 | C |
| ATOM | 3461 | CB  | ASP | A | 456 | 14.261 | 51.210 | 42.874 | 1.00 | 28.51 | C |
| ATOM | 3462 | CG  | ASP | A | 456 | 13.053 | 51.974 | 43.408 | 1.00 | 29.33 | C |
| ATOM | 3463 | OD1 | ASP | A | 456 | 12.679 | 53.008 | 42.807 | 1.00 | 30.45 | O |
| ATOM | 3464 | OD2 | ASP | A | 456 | 12.480 | 51.544 | 44.432 | 1.00 | 30.63 | O |
| ATOM | 3465 | C   | ASP | A | 456 | 15.659 | 50.689 | 40.823 | 1.00 | 28.05 | C |
| ATOM | 3466 | O   | ASP | A | 456 | 16.692 | 51.271 | 41.167 | 1.00 | 28.26 | O |
| ATOM | 3467 | N   | ASP | A | 457 | 15.657 | 49.649 | 39.990 | 1.00 | 27.64 | N |
| ATOM | 3468 | CA  | ASP | A | 457 | 16.862 | 49.221 | 39.279 | 1.00 | 27.20 | C |
| ATOM | 3469 | CB  | ASP | A | 457 | 17.069 | 47.706 | 39.413 | 1.00 | 27.37 | C |
| ATOM | 3470 | CG  | ASP | A | 457 | 18.442 | 47.250 | 38.921 | 1.00 | 27.99 | C |
| ATOM | 3471 | OD1 | ASP | A | 457 | 18.876 | 47.687 | 37.831 | 1.00 | 28.65 | O |
| ATOM | 3472 | OD2 | ASP | A | 457 | 19.082 | 46.438 | 39.620 | 1.00 | 29.17 | O |

TABLE 6-continued

Coordinates of the crystal structure of *E. coli* ExoI bound to compound 9

| ATOM | 3473 | C | ASP | A | 457 | 16.745 | 49.622 | 37.811 | 1.00 | 26.82 | C |
| --- | --- | --- | --- | --- | --- | --- | --- | --- | --- | --- | --- |
| ATOM | 3474 | O | ASP | A | 457 | 16.171 | 48.891 | 36.999 | 1.00 | 26.61 | O |
| ATOM | 3475 | N | LYS | A | 458 | 17.301 | 50.784 | 37.479 | 1.00 | 26.34 | N |
| ATOM | 3476 | CA | LYS | A | 458 | 17.100 | 51.393 | 36.162 | 1.00 | 26.00 | C |
| ATOM | 3477 | CB | LYS | A | 458 | 17.657 | 52.822 | 36.132 | 1.00 | 26.17 | C |
| ATOM | 3478 | CG | LYS | A | 458 | 17.052 | 53.764 | 37.189 | 1.00 | 26.56 | C |
| ATOM | 3479 | CD | LYS | A | 458 | 15.520 | 53.792 | 37.126 | 1.00 | 27.36 | C |
| ATOM | 3480 | CE | LYS | A | 458 | 14.930 | 54.831 | 38.072 | 1.00 | 27.51 | C |
| ATOM | 3481 | NZ | LYS | A | 458 | 15.049 | 54.436 | 39.504 | 1.00 | 28.15 | N |
| ATOM | 3482 | C | LYS | A | 458 | 17.673 | 50.558 | 35.013 | 1.00 | 25.67 | C |
| ATOM | 3483 | O | LYS | A | 458 | 17.127 | 50.564 | 33.908 | 1.00 | 25.29 | O |
| ATOM | 3484 | N | GLU | A | 459 | 18.764 | 49.841 | 35.282 | 1.00 | 25.32 | N |
| ATOM | 3485 | CA | GLU | A | 459 | 19.354 | 48.927 | 34.298 | 1.00 | 25.35 | C |
| ATOM | 3486 | CB | GLU | A | 459 | 20.676 | 48.358 | 34.809 | 1.00 | 25.44 | C |
| ATOM | 3487 | CG | GLU | A | 459 | 21.861 | 49.300 | 34.695 | 1.00 | 26.84 | C |
| ATOM | 3488 | CD | GLU | A | 459 | 23.128 | 48.722 | 35.309 | 1.00 | 27.47 | C |
| ATOM | 3489 | OE1 | GLU | A | 459 | 23.124 | 47.527 | 35.692 | 1.00 | 30.55 | O |
| ATOM | 3490 | OE2 | GLU | A | 459 | 24.130 | 49.463 | 35.411 | 1.00 | 30.02 | O |
| ATOM | 3491 | C | GLU | A | 459 | 18.403 | 47.784 | 33.962 | 1.00 | 24.66 | C |
| ATOM | 3492 | O | GLU | A | 459 | 18.244 | 47.422 | 32.796 | 1.00 | 24.46 | O |
| ATOM | 3493 | N | LYS | A | 460 | 17.779 | 47.213 | 34.991 | 1.00 | 24.09 | N |
| ATOM | 3494 | CA | LYS | A | 460 | 16.840 | 46.111 | 34.797 | 1.00 | 23.81 | C |
| ATOM | 3495 | CB | LYS | A | 460 | 16.492 | 45.445 | 36.130 | 1.00 | 23.95 | C |
| ATOM | 3496 | CG | LYS | A | 460 | 17.641 | 44.658 | 36.743 | 1.00 | 25.13 | C |
| ATOM | 3497 | CD | LYS | A | 460 | 17.149 | 43.729 | 37.839 | 1.00 | 27.43 | C |
| ATOM | 3498 | CE | LYS | A | 460 | 18.271 | 43.332 | 38.789 | 1.00 | 29.03 | C |
| ATOM | 3499 | NZ | LYS | A | 460 | 19.314 | 42.499 | 38.132 | 1.00 | 30.46 | N |
| ATOM | 3500 | C | LYS | A | 460 | 15.577 | 46.581 | 34.086 | 1.00 | 23.30 | C |
| ATOM | 3501 | O | LYS | A | 460 | 15.050 | 45.880 | 33.220 | 1.00 | 23.33 | O |
| ATOM | 3502 | N | VAL | A | 461 | 15.106 | 47.776 | 34.443 | 1.00 | 22.87 | N |
| ATOM | 3503 | CA | VAL | A | 461 | 13.964 | 48.386 | 33.761 | 1.00 | 22.45 | C |
| ATOM | 3504 | CB | VAL | A | 461 | 13.576 | 49.758 | 34.386 | 1.00 | 22.49 | C |
| ATOM | 3505 | CG1 | VAL | A | 461 | 12.444 | 50.413 | 33.600 | 1.00 | 22.59 | C |
| ATOM | 3506 | CG2 | VAL | A | 461 | 13.164 | 49.578 | 35.836 | 1.00 | 22.25 | C |
| ATOM | 3507 | C | VAL | A | 461 | 14.247 | 48.521 | 32.260 | 1.00 | 22.27 | C |
| ATOM | 3508 | O | VAL | A | 461 | 13.397 | 48.187 | 31.433 | 1.00 | 22.30 | O |
| ATOM | 3509 | N | ALA | A | 462 | 15.456 | 48.975 | 31.922 | 1.00 | 21.99 | N |
| ATOM | 3510 | CA | ALA | A | 462 | 15.887 | 49.092 | 30.524 | 1.00 | 21.82 | C |
| ATOM | 3511 | CB | ALA | A | 462 | 17.259 | 49.763 | 30.436 | 1.00 | 21.80 | C |
| ATOM | 3512 | C | ALA | A | 462 | 15.900 | 47.739 | 29.810 | 1.00 | 21.74 | C |
| ATOM | 3513 | O | ALA | A | 462 | 15.493 | 47.642 | 28.652 | 1.00 | 21.87 | O |
| ATOM | 3514 | N | LEU | A | 463 | 16.354 | 46.696 | 30.506 | 1.00 | 21.41 | N |
| ATOM | 3515 | CA | LEU | A | 463 | 16.355 | 45.344 | 29.938 | 1.00 | 21.23 | C |
| ATOM | 3516 | CB | LEU | A | 463 | 17.094 | 44.356 | 30.851 | 1.00 | 21.10 | C |
| ATOM | 3517 | CG | LEU | A | 463 | 18.619 | 44.467 | 30.963 | 1.00 | 20.92 | C |
| ATOM | 3518 | CD1 | LEU | A | 463 | 19.140 | 43.560 | 32.069 | 1.00 | 20.25 | C |
| ATOM | 3519 | CD2 | LEU | A | 463 | 19.305 | 44.144 | 29.639 | 1.00 | 21.03 | C |
| ATOM | 3520 | C | LEU | A | 463 | 14.934 | 44.856 | 29.668 | 1.00 | 21.23 | C |
| ATOM | 3521 | O | LEU | A | 463 | 14.666 | 44.253 | 28.630 | 1.00 | 21.26 | O |
| ATOM | 3522 | N | LEU | A | 464 | 14.022 | 45.136 | 30.600 | 1.00 | 21.24 | N |
| ATOM | 3523 | CA | LEU | A | 464 | 12.627 | 44.719 | 30.456 | 1.00 | 21.40 | C |
| ATOM | 3524 | CB | LEU | A | 464 | 11.875 | 44.873 | 31.781 | 1.00 | 21.24 | C |
| ATOM | 3525 | CG | LEU | A | 464 | 12.291 | 43.886 | 32.877 | 1.00 | 21.17 | C |
| ATOM | 3526 | CD1 | LEU | A | 464 | 11.930 | 44.413 | 34.255 | 1.00 | 20.85 | C |
| ATOM | 3527 | CD2 | LEU | A | 464 | 11.686 | 42.498 | 32.642 | 1.00 | 21.02 | C |
| ATOM | 3528 | C | LEU | A | 464 | 11.913 | 45.466 | 29.329 | 1.00 | 21.60 | C |
| ATOM | 3529 | O | LEU | A | 464 | 11.088 | 44.887 | 28.618 | 1.00 | 21.79 | O |
| ATOM | 3530 | N | LYS | A | 465 | 12.248 | 46.745 | 29.165 | 1.00 | 21.83 | N |
| ATOM | 3531 | CA | LYS | A | 465 | 11.737 | 47.548 | 28.050 | 1.00 | 22.23 | C |
| ATOM | 3532 | CB | LYS | A | 465 | 12.151 | 49.016 | 28.202 | 1.00 | 22.41 | C |
| ATOM | 3533 | CG | LYS | A | 465 | 11.571 | 49.718 | 29.424 | 1.00 | 24.11 | C |
| ATOM | 3534 | CD | LYS | A | 465 | 10.082 | 49.995 | 29.275 | 1.00 | 26.38 | C |
| ATOM | 3535 | CE | LYS | A | 465 | 9.534 | 50.732 | 30.492 | 1.00 | 27.88 | C |
| ATOM | 3536 | NZ | LYS | A | 465 | 10.156 | 52.079 | 30.662 | 1.00 | 28.79 | N |
| ATOM | 3537 | C | LYS | A | 465 | 12.216 | 47.005 | 26.705 | 1.00 | 22.14 | C |
| ATOM | 3538 | O | LYS | A | 465 | 11.464 | 47.001 | 25.727 | 1.00 | 22.11 | O |
| ATOM | 3539 | N | ALA | A | 466 | 13.468 | 46.548 | 26.668 | 1.00 | 22.09 | N |
| ATOM | 3540 | CA | ALA | A | 466 | 14.036 | 45.922 | 25.475 | 1.00 | 22.14 | C |
| ATOM | 3541 | CB | ALA | A | 466 | 15.519 | 45.646 | 25.673 | 1.00 | 22.15 | C |
| ATOM | 3542 | C | ALA | A | 466 | 13.290 | 44.635 | 25.119 | 1.00 | 22.22 | C |
| ATOM | 3543 | O | ALA | A | 466 | 13.030 | 44.364 | 23.948 | 1.00 | 22.19 | O |
| ATOM | 3544 | N | LEU | A | 467 | 12.934 | 43.855 | 26.138 | 1.00 | 22.40 | N |
| ATOM | 3545 | CA | LEU | A | 467 | 12.176 | 42.620 | 25.935 | 1.00 | 22.71 | C |
| ATOM | 3546 | CB | LEU | A | 467 | 12.093 | 41.818 | 27.235 | 1.00 | 22.59 | C |
| ATOM | 3547 | CG | LEU | A | 467 | 13.403 | 41.213 | 27.742 | 1.00 | 22.58 | C |
| ATOM | 3548 | CD1 | LEU | A | 467 | 13.219 | 40.659 | 29.131 | 1.00 | 22.56 | C |
| ATOM | 3549 | CD2 | LEU | A | 467 | 13.895 | 40.132 | 26.801 | 1.00 | 23.61 | C |
| ATOM | 3550 | C | LEU | A | 467 | 10.777 | 42.879 | 25.387 | 1.00 | 23.12 | C |

TABLE 6-continued

Coordinates of the crystal structure of *E. coli* ExoI bound to compound 9

| ATOM | 3551 | O | LEU | A | 467 | 10.274 | 42.107 | 24.566 | 1.00 | 23.16 | O |
|---|---|---|---|---|---|---|---|---|---|---|---|
| ATOM | 3552 | N | TRP | A | 468 | 10.151 | 43.960 | 25.853 | 1.00 | 23.80 | N |
| ATOM | 3553 | CA | TRP | A | 468 | 8.846 | 44.383 | 25.346 | 1.00 | 24.42 | C |
| ATOM | 3554 | CB | TRP | A | 468 | 8.316 | 45.569 | 26.160 | 1.00 | 24.94 | C |
| ATOM | 3555 | CG | TRP | A | 468 | 6.899 | 45.965 | 25.820 | 1.00 | 25.60 | C |
| ATOM | 3556 | CD1 | TRP | A | 468 | 6.488 | 46.704 | 24.745 | 1.00 | 26.31 | C |
| ATOM | 3557 | NE1 | TRP | A | 468 | 5.124 | 46.863 | 24.772 | 1.00 | 26.64 | N |
| ATOM | 3558 | CE2 | TRP | A | 468 | 4.623 | 46.228 | 25.878 | 1.00 | 26.57 | C |
| ATOM | 3559 | CD2 | TRP | A | 468 | 5.715 | 45.651 | 26.566 | 1.00 | 26.41 | C |
| ATOM | 3560 | CE3 | TRP | A | 468 | 5.469 | 44.935 | 27.748 | 1.00 | 26.50 | C |
| ATOM | 3561 | CZ3 | TRP | A | 468 | 4.157 | 44.821 | 28.200 | 1.00 | 26.33 | C |
| ATOM | 3562 | CH2 | TRP | A | 468 | 3.090 | 45.408 | 27.491 | 1.00 | 26.30 | C |
| ATOM | 3563 | CZ2 | TRP | A | 468 | 3.303 | 46.113 | 26.332 | 1.00 | 26.49 | C |
| ATOM | 3564 | C | TRP | A | 468 | 8.946 | 44.757 | 23.869 | 1.00 | 24.63 | C |
| ATOM | 3565 | O | TRP | A | 468 | 8.140 | 44.310 | 23.052 | 1.00 | 24.46 | O |
| ATOM | 3566 | N | GLN | A | 469 | 9.954 | 45.562 | 23.540 | 1.00 | 24.89 | N |
| ATOM | 3567 | CA | GLN | A | 469 | 10.174 | 46.033 | 22.171 | 1.00 | 25.51 | C |
| ATOM | 3568 | CB | GLN | A | 469 | 11.314 | 47.053 | 22.137 | 1.00 | 25.53 | C |
| ATOM | 3569 | CG | GLN | A | 469 | 10.941 | 48.414 | 22.717 | 1.00 | 27.45 | C |
| ATOM | 3570 | CD | GLN | A | 469 | 12.153 | 49.242 | 23.113 | 1.00 | 29.02 | C |
| ATOM | 3571 | OE1 | GLN | A | 469 | 13.108 | 49.379 | 22.347 | 1.00 | 30.62 | O |
| ATOM | 3572 | NE2 | GLN | A | 469 | 12.113 | 49.807 | 24.316 | 1.00 | 30.06 | N |
| ATOM | 3573 | C | GLN | A | 469 | 10.457 | 44.884 | 21.205 | 1.00 | 25.42 | C |
| ATOM | 3574 | O | GLN | A | 469 | 9.975 | 44.887 | 20.070 | 1.00 | 25.46 | O |
| ATOM | 3575 | N | TYR | A | 470 | 11.234 | 43.903 | 21.662 | 1.00 | 25.53 | N |
| ATOM | 3576 | CA | TYR | A | 470 | 11.524 | 42.716 | 20.861 | 1.00 | 25.75 | C |
| ATOM | 3577 | CB | TYR | A | 470 | 12.596 | 41.853 | 21.533 | 1.00 | 25.15 | C |
| ATOM | 3578 | CG | TYR | A | 470 | 13.091 | 40.704 | 20.677 | 1.00 | 24.30 | C |
| ATOM | 3579 | CD1 | TYR | A | 470 | 13.969 | 40.928 | 19.613 | 1.00 | 23.47 | C |
| ATOM | 3580 | CE1 | TYR | A | 470 | 14.427 | 39.875 | 18.825 | 1.00 | 23.13 | C |
| ATOM | 3581 | CZ | TYR | A | 470 | 14.015 | 38.581 | 19.105 | 1.00 | 23.70 | C |
| ATOM | 3582 | OH | TYR | A | 470 | 14.467 | 37.537 | 18.333 | 1.00 | 23.91 | O |
| ATOM | 3583 | CE2 | TYR | A | 470 | 13.148 | 38.333 | 20.161 | 1.00 | 23.33 | C |
| ATOM | 3584 | CD2 | TYR | A | 470 | 12.694 | 39.392 | 20.939 | 1.00 | 23.86 | C |
| ATOM | 3585 | C | TYR | A | 470 | 10.257 | 41.903 | 20.612 | 1.00 | 26.49 | C |
| ATOM | 3586 | O | TYR | A | 470 | 10.011 | 41.463 | 19.490 | 1.00 | 26.47 | O |
| ATOM | 3587 | N | ALA | A | 471 | 9.455 | 41.721 | 21.663 | 1.00 | 27.50 | N |
| ATOM | 3588 | CA | ALA | A | 471 | 8.171 | 41.021 | 21.555 | 1.00 | 28.58 | C |
| ATOM | 3589 | CB | ALA | A | 471 | 7.530 | 40.861 | 22.930 | 1.00 | 28.43 | C |
| ATOM | 3590 | C | ALA | A | 471 | 7.215 | 41.731 | 20.593 | 1.00 | 29.45 | C |
| ATOM | 3591 | O | ALA | A | 471 | 6.536 | 41.083 | 19.799 | 1.00 | 29.58 | O |
| ATOM | 3592 | N | ASP | A | 472 | 7.181 | 43.062 | 20.662 | 1.00 | 30.53 | N |
| ATOM | 3593 | CA | ASP | A | 472 | 6.341 | 43.870 | 19.771 | 1.00 | 31.75 | C |
| ATOM | 3594 | CB | ASP | A | 472 | 6.453 | 45.358 | 20.127 | 1.00 | 31.91 | C |
| ATOM | 3595 | CG | ASP | A | 472 | 5.566 | 45.753 | 21.301 | 1.00 | 32.76 | C |
| ATOM | 3596 | OD1 | ASP | A | 472 | 5.383 | 44.931 | 22.227 | 1.00 | 34.40 | O |
| ATOM | 3597 | OD2 | ASP | A | 472 | 5.054 | 46.894 | 21.299 | 1.00 | 33.98 | O |
| ATOM | 3598 | C | ASP | A | 472 | 6.682 | 43.655 | 18.294 | 1.00 | 32.42 | C |
| ATOM | 3599 | O | ASP | A | 472 | 5.791 | 43.617 | 17.444 | 1.00 | 32.58 | O |
| ATOM | 3600 | N | GLU | A | 473 | 7.973 | 43.511 | 18.003 | 1.00 | 33.28 | N |
| ATOM | 3601 | CA | GLU | A | 473 | 8.454 | 43.315 | 16.636 | 1.00 | 34.24 | C |
| ATOM | 3602 | CB | GLU | A | 473 | 9.949 | 43.648 | 16.548 | 1.00 | 34.18 | C |
| ATOM | 3603 | CG | GLU | A | 473 | 10.546 | 43.519 | 15.144 | 1.00 | 34.99 | C |
| ATOM | 3604 | CD | GLU | A | 473 | 12.049 | 43.275 | 15.158 | 1.00 | 35.74 | C |
| ATOM | 3605 | OE1 | GLU | A | 473 | 12.739 | 43.808 | 16.052 | 1.00 | 36.34 | O |
| ATOM | 3606 | OE2 | GLU | A | 473 | 12.540 | 42.551 | 14.265 | 1.00 | 35.99 | O |
| ATOM | 3607 | C | GLU | A | 473 | 8.209 | 41.884 | 16.155 | 1.00 | 34.75 | C |
| ATOM | 3608 | O | GLU | A | 473 | 7.581 | 41.664 | 15.116 | 1.00 | 34.89 | O |
| ATOM | 3609 | N | ILE | A | 474 | 8.711 | 40.922 | 16.924 | 1.00 | 35.46 | N |
| ATOM | 3610 | CA | ILE | A | 474 | 8.707 | 39.513 | 16.535 | 1.00 | 36.13 | C |
| ATOM | 3611 | CB | ILE | A | 474 | 9.763 | 38.704 | 17.357 | 1.00 | 36.14 | C |
| ATOM | 3612 | CG1 | ILE | A | 474 | 9.876 | 37.258 | 16.866 | 1.00 | 36.42 | C |
| ATOM | 3613 | CD1 | ILE | A | 474 | 10.902 | 36.441 | 17.628 | 1.00 | 36.28 | C |
| ATOM | 3614 | CG2 | ILE | A | 474 | 9.463 | 38.763 | 18.844 | 1.00 | 36.45 | C |
| ATOM | 3615 | C | ILE | A | 474 | 7.314 | 38.867 | 16.638 | 1.00 | 36.47 | C |
| ATOM | 3616 | O | ILE | A | 474 | 6.959 | 38.014 | 15.821 | 1.00 | 36.61 | O |
| ATOM | 3617 | N | VAL | A | 475 | 6.529 | 39.287 | 17.632 | 1.00 | 36.88 | N |
| ATOM | 3618 | CA | VAL | A | 475 | 5.220 | 38.674 | 17.889 | 1.00 | 37.23 | C |
| ATOM | 3619 | CB | VAL | A | 475 | 5.204 | 37.867 | 19.233 | 1.00 | 37.27 | C |
| ATOM | 3620 | CG1 | VAL | A | 475 | 6.525 | 37.148 | 19.438 | 1.00 | 37.47 | C |
| ATOM | 3621 | CG2 | VAL | A | 475 | 4.923 | 38.779 | 20.425 | 1.00 | 37.50 | C |
| ATOM | 3622 | C | VAL | A | 475 | 4.078 | 39.695 | 17.880 | 1.00 | 37.42 | C |
| ATOM | 3623 | O | VAL | A | 475 | 2.906 | 39.327 | 17.759 | 1.00 | 37.62 | O |
| ATOM | 3624 | MG | MG | I | 1 | 27.308 | 28.832 | 33.737 | 1.00 | 14.76 | MG |
| ATOM | 3625 | CL1 | YYY | B | 1 | 28.094 | 2.115 | 55.180 | 1.00 | 22.85 | CL |
| ATOM | 3626 | C4 | YYY | B | 1 | 29.678 | 2.529 | 55.906 | 1.00 | 23.32 | C |
| ATOM | 3627 | C3 | YYY | B | 1 | 29.790 | 3.717 | 56.615 | 1.00 | 23.46 | C |
| ATOM | 3628 | C2 | YYY | B | 1 | 31.000 | 4.068 | 57.200 | 1.00 | 23.50 | C |

TABLE 6-continued

Coordinates of the crystal structure of *E. coli* ExoI bound to compound 9

| ATOM | 3629 | C5 | YYY | B | 1 | 30.782 | 1.678 | 55.779 | 1.00 | 23.55 | C |
|------|------|------|-----|---|---|--------|--------|--------|------|-------|---|
| ATOM | 3630 | C6 | YYY | B | 1 | 32.000 | 2.034 | 56.372 | 1.00 | 23.45 | C |
| ATOM | 3631 | S1 | YYY | B | 1 | 33.362 | 1.030 | 56.240 | 1.00 | 23.51 | S |
| ATOM | 3632 | C7 | YYY | B | 1 | 32.103 | 3.231 | 57.079 | 1.00 | 23.62 | C |
| ATOM | 3633 | N1 | YYY | B | 1 | 33.360 | 3.359 | 57.554 | 1.00 | 23.68 | N |
| ATOM | 3634 | C1 | YYY | B | 1 | 34.103 | 2.293 | 57.193 | 1.00 | 23.69 | C |
| ATOM | 3635 | N2 | YYY | B | 1 | 35.395 | 2.252 | 57.583 | 1.00 | 23.73 | N |
| ATOM | 3636 | C8 | YYY | B | 1 | 36.295 | 1.293 | 57.331 | 1.00 | 23.94 | C |
| ATOM | 3637 | O1 | YYY | B | 1 | 36.002 | 0.242 | 56.648 | 1.00 | 24.30 | O |
| ATOM | 3638 | N3 | YYY | B | 1 | 35.995 | 3.280 | 58.357 | 1.00 | 23.88 | N |
| ATOM | 3639 | C10 | YYY | B | 1 | 37.266 | 2.782 | 58.479 | 1.00 | 24.22 | C |
| ATOM | 3640 | C9 | YYY | B | 1 | 37.674 | 1.458 | 57.871 | 1.00 | 24.01 | C |
| ATOM | 3641 | C11 | YYY | B | 1 | 38.279 | 3.589 | 59.263 | 1.00 | 24.41 | C |
| ATOM | 3642 | C12 | YYY | B | 1 | 38.106 | 3.275 | 60.744 | 1.00 | 25.86 | C |
| ATOM | 3643 | C13 | YYY | B | 1 | 39.701 | 3.239 | 58.833 | 1.00 | 25.35 | C |
| ATOM | 3644 | C14 | YYY | B | 1 | 38.042 | 5.078 | 59.026 | 1.00 | 25.63 | C |
| ATOM | 3645 | OW0 | HOH | Z | 1 | 30.735 | 26.960 | 51.029 | 1.00 | 16.15 | O |
| ATOM | 3646 | OW0 | HOH | Z | 2 | 44.217 | 16.660 | 49.450 | 1.00 | 14.33 | O |
| ATOM | 3647 | OW0 | HOH | Z | 3 | 24.975 | 26.526 | 46.160 | 1.00 | 16.01 | O |
| ATOM | 3648 | OW0 | HOH | Z | 4 | 29.478 | 19.724 | 49.693 | 1.00 | 15.11 | O |
| ATOM | 3649 | OW0 | HOH | Z | 5 | 30.447 | −0.495 | 45.382 | 1.00 | 19.69 | O |
| ATOM | 3650 | OW0 | HOH | Z | 6 | 25.382 | 10.988 | 38.994 | 1.00 | 17.43 | O |
| ATOM | 3651 | OW0 | HOH | Z | 7 | 44.837 | 23.107 | 52.651 | 1.00 | 20.53 | O |
| ATOM | 3652 | OW0 | HOH | Z | 8 | 33.925 | 11.386 | 38.637 | 1.00 | 15.24 | O |
| ATOM | 3653 | OW0 | HOH | Z | 9 | 38.427 | 5.626 | 46.633 | 1.00 | 16.61 | O |
| ATOM | 3654 | OW0 | HOH | Z | 10 | 23.944 | 11.578 | 54.516 | 1.00 | 16.09 | O |
| ATOM | 3655 | OW0 | HOH | Z | 11 | 28.525 | 13.633 | 42.165 | 1.00 | 17.08 | O |
| ATOM | 3656 | OW0 | HOH | Z | 12 | 25.033 | 22.532 | 47.158 | 1.00 | 17.75 | O |
| ATOM | 3657 | OW0 | HOH | Z | 13 | 27.496 | 29.414 | 40.232 | 1.00 | 20.32 | O |
| ATOM | 3658 | OW0 | HOH | Z | 14 | 29.182 | 21.762 | 27.282 | 1.00 | 19.96 | O |
| ATOM | 3659 | OW0 | HOH | Z | 15 | 32.302 | 10.304 | 34.313 | 1.00 | 17.52 | O |
| ATOM | 3660 | OW0 | HOH | Z | 16 | 35.189 | 10.612 | 42.318 | 1.00 | 16.35 | O |
| ATOM | 3661 | OW0 | HOH | Z | 17 | 35.725 | 12.468 | 40.290 | 1.00 | 15.12 | O |
| ATOM | 3662 | OW0 | HOH | Z | 18 | 30.672 | 26.650 | 33.045 | 1.00 | 14.54 | O |
| ATOM | 3663 | OW0 | HOH | Z | 19 | 24.951 | 22.872 | 11.339 | 1.00 | 22.33 | O |
| ATOM | 3664 | OW0 | HOH | Z | 20 | 24.568 | 25.015 | 48.441 | 1.00 | 19.23 | O |
| ATOM | 3665 | OW0 | HOH | Z | 21 | 19.932 | 32.297 | 20.323 | 1.00 | 19.71 | O |
| ATOM | 3666 | OW0 | HOH | Z | 22 | 41.852 | 29.558 | 24.116 | 1.00 | 25.68 | O |
| ATOM | 3667 | OW0 | HOH | Z | 23 | 18.984 | 43.268 | 16.674 | 1.00 | 17.99 | O |
| ATOM | 3668 | OW0 | HOH | Z | 24 | 15.754 | 17.610 | 23.551 | 1.00 | 19.61 | O |
| ATOM | 3669 | OW0 | HOH | Z | 25 | 19.703 | 30.937 | 14.675 | 1.00 | 21.60 | O |
| ATOM | 3670 | OW0 | HOH | Z | 26 | 30.149 | 15.360 | 18.800 | 1.00 | 23.55 | O |
| ATOM | 3671 | OW0 | HOH | Z | 27 | 16.476 | 31.681 | 55.796 | 1.00 | 21.45 | O |
| ATOM | 3672 | OW0 | HOH | Z | 28 | 31.461 | 28.841 | 34.678 | 1.00 | 20.46 | O |
| ATOM | 3673 | OW0 | HOH | Z | 29 | 26.682 | 19.963 | 37.147 | 1.00 | 18.83 | O |
| ATOM | 3674 | OW0 | HOH | Z | 30 | 36.742 | −0.870 | 35.859 | 1.00 | 19.22 | O |
| ATOM | 3675 | OW0 | HOH | Z | 31 | 41.694 | 32.798 | 36.364 | 1.00 | 22.28 | O |
| ATOM | 3676 | OW0 | HOH | Z | 32 | 13.964 | 35.164 | 19.055 | 1.00 | 23.29 | O |
| ATOM | 3677 | OW0 | HOH | Z | 33 | 44.687 | 19.290 | 23.496 | 1.00 | 24.75 | O |
| ATOM | 3678 | OW0 | HOH | Z | 34 | 11.439 | 39.520 | 24.163 | 1.00 | 20.33 | O |
| ATOM | 3679 | OW0 | HOH | Z | 35 | 23.843 | 29.049 | 47.659 | 1.00 | 22.99 | O |
| ATOM | 3680 | OW0 | HOH | Z | 36 | 22.474 | 12.245 | 56.697 | 1.00 | 19.77 | O |
| ATOM | 3681 | OW0 | HOH | Z | 37 | 22.608 | 21.073 | 46.779 | 1.00 | 23.31 | O |
| ATOM | 3682 | OW0 | HOH | Z | 38 | 22.463 | 10.731 | 58.957 | 1.00 | 22.59 | O |
| ATOM | 3683 | OW0 | HOH | Z | 39 | 19.336 | 29.785 | 19.101 | 1.00 | 21.51 | O |
| ATOM | 3684 | OW0 | HOH | Z | 41 | 14.440 | 21.298 | 15.751 | 1.00 | 20.75 | O |
| ATOM | 3685 | OW0 | HOH | Z | 42 | 33.650 | −3.329 | 39.080 | 1.00 | 24.45 | O |
| ATOM | 3686 | OW0 | HOH | Z | 43 | 16.722 | 21.450 | 14.026 | 1.00 | 19.23 | O |
| ATOM | 3687 | OW0 | HOH | Z | 44 | 39.081 | 3.110 | 40.982 | 1.00 | 24.16 | O |
| ATOM | 3688 | OW0 | HOH | Z | 45 | 34.278 | 0.969 | 50.266 | 1.00 | 24.59 | O |
| ATOM | 3689 | OW0 | HOH | Z | 46 | 14.349 | 14.267 | 25.329 | 1.00 | 25.77 | O |
| ATOM | 3690 | OW0 | HOH | Z | 47 | 16.681 | 24.131 | 14.691 | 1.00 | 21.03 | O |
| ATOM | 3691 | OW0 | HOH | Z | 48 | 46.024 | 29.060 | 46.493 | 1.00 | 26.02 | O |
| ATOM | 3692 | OW0 | HOH | Z | 49 | 17.127 | 29.764 | 17.587 | 1.00 | 20.93 | O |
| ATOM | 3693 | OW0 | HOH | Z | 50 | 43.551 | 11.011 | 34.180 | 1.00 | 24.73 | O |
| ATOM | 3694 | OW0 | HOH | Z | 51 | 19.008 | 32.280 | 4.186 | 1.00 | 30.73 | O |
| ATOM | 3695 | OW0 | HOH | Z | 52 | 34.412 | 6.047 | 58.495 | 1.00 | 22.05 | O |
| ATOM | 3696 | OW0 | HOH | Z | 53 | 34.329 | 27.513 | 32.898 | 1.00 | 20.20 | O |
| ATOM | 3697 | OW0 | HOH | Z | 54 | 19.084 | 25.572 | 14.852 | 1.00 | 20.40 | O |
| ATOM | 3698 | OW0 | HOH | Z | 55 | 22.745 | −0.549 | 33.308 | 1.00 | 26.43 | O |
| ATOM | 3699 | OW0 | HOH | Z | 56 | 35.422 | 28.058 | 56.081 | 1.00 | 24.58 | O |
| ATOM | 3700 | OW0 | HOH | Z | 57 | 22.195 | 43.452 | 25.965 | 1.00 | 27.10 | O |
| ATOM | 3701 | OW0 | HOH | Z | 58 | 45.427 | 30.869 | 34.212 | 1.00 | 26.35 | O |
| ATOM | 3702 | OW0 | HOH | Z | 59 | 21.828 | 24.908 | 48.645 | 1.00 | 24.91 | O |
| ATOM | 3703 | OW0 | HOH | Z | 60 | 30.837 | 28.719 | 12.210 | 1.00 | 25.43 | O |
| ATOM | 3704 | OW0 | HOH | Z | 61 | 17.828 | 17.925 | 50.430 | 1.00 | 27.79 | O |
| ATOM | 3705 | OW0 | HOH | Z | 62 | 20.320 | 35.970 | 28.204 | 1.00 | 27.42 | O |
| ATOM | 3706 | OW0 | HOH | Z | 63 | 35.174 | 15.298 | 40.368 | 1.00 | 20.63 | O |

TABLE 6-continued

Coordinates of the crystal structure of *E. coli* ExoI bound to compound 9

| ATOM | 3707 | OW0 | HOH | Z | 64 | 16.178 | 2.221 | 57.687 | 1.00 | 25.09 | O |
|---|---|---|---|---|---|---|---|---|---|---|---|
| ATOM | 3708 | OW0 | HOH | Z | 65 | 19.078 | 25.252 | 23.832 | 1.00 | 21.17 | O |
| ATOM | 3709 | OW0 | HOH | Z | 66 | 26.215 | 28.413 | 32.156 | 1.00 | 16.27 | O |
| ATOM | 3710 | OW0 | HOH | Z | 67 | 25.853 | 16.573 | 41.891 | 1.00 | 23.07 | O |
| ATOM | 3711 | OW0 | HOH | Z | 68 | 35.020 | 12.399 | 31.602 | 1.00 | 22.28 | O |
| ATOM | 3712 | OW0 | HOH | Z | 69 | 21.269 | 22.265 | 48.825 | 1.00 | 24.30 | O |
| ATOM | 3713 | OW0 | HOH | Z | 70 | 16.855 | 20.587 | 21.270 | 1.00 | 20.31 | O |
| ATOM | 3714 | OW0 | HOH | Z | 71 | 29.288 | 15.327 | 14.200 | 1.00 | 30.70 | O |
| ATOM | 3715 | OW0 | HOH | Z | 72 | 18.064 | 9.522 | 40.926 | 1.00 | 32.63 | O |
| ATOM | 3716 | OW0 | HOH | Z | 73 | 18.792 | 32.399 | 12.581 | 1.00 | 24.74 | O |
| ATOM | 3717 | OW0 | HOH | Z | 74 | 41.991 | 8.585 | 34.749 | 1.00 | 27.73 | O |
| ATOM | 3718 | OW0 | HOH | Z | 75 | 19.048 | 27.076 | 27.917 | 1.00 | 24.01 | O |
| ATOM | 3719 | OW0 | HOH | Z | 76 | 23.777 | 17.792 | 58.709 | 1.00 | 25.91 | O |
| ATOM | 3720 | OW0 | HOH | Z | 77 | 29.374 | 36.692 | 17.816 | 1.00 | 24.49 | O |
| ATOM | 3721 | OW0 | HOH | Z | 78 | 19.918 | 10.676 | 22.406 | 1.00 | 28.68 | O |
| ATOM | 3722 | OW0 | HOH | Z | 79 | 27.313 | −3.150 | 58.251 | 1.00 | 24.72 | O |
| ATOM | 3723 | OW0 | HOH | Z | 80 | 42.835 | 30.604 | 42.664 | 1.00 | 26.43 | O |
| ATOM | 3724 | OW0 | HOH | Z | 81 | 16.601 | 27.062 | 51.347 | 1.00 | 26.54 | O |
| ATOM | 3725 | OW0 | HOH | Z | 82 | 36.122 | 14.693 | 20.290 | 1.00 | 24.81 | O |
| ATOM | 3726 | OW0 | HOH | Z | 83 | 16.776 | 8.608 | 57.609 | 1.00 | 27.55 | O |
| ATOM | 3727 | OW0 | HOH | Z | 84 | 49.363 | 21.380 | 43.879 | 1.00 | 26.69 | O |
| ATOM | 3728 | OW0 | HOH | Z | 85 | 18.125 | 28.617 | 15.154 | 1.00 | 24.57 | O |
| ATOM | 3729 | OW0 | HOH | Z | 86 | 23.381 | 9.809 | 18.221 | 1.00 | 24.73 | O |
| ATOM | 3730 | OW0 | HOH | Z | 87 | 27.366 | 23.751 | 10.836 | 1.00 | 27.27 | O |
| ATOM | 3731 | OW0 | HOH | Z | 88 | 18.276 | 5.937 | 13.820 | 1.00 | 31.75 | O |
| ATOM | 3732 | OW0 | HOH | Z | 89 | 9.076 | 31.346 | 23.118 | 1.00 | 27.61 | O |
| ATOM | 3733 | OW0 | HOH | Z | 90 | 12.198 | 18.017 | 6.329 | 1.00 | 24.92 | O |
| ATOM | 3734 | OW0 | HOH | Z | 91 | 34.770 | 14.038 | 17.854 | 1.00 | 25.97 | O |
| ATOM | 3735 | OW0 | HOH | Z | 92 | 20.353 | 45.797 | 23.808 | 1.00 | 24.47 | O |
| ATOM | 3736 | OW0 | HOH | Z | 93 | 5.383 | 26.022 | −2.819 | 1.00 | 37.33 | O |
| ATOM | 3737 | OW0 | HOH | Z | 94 | 30.003 | 27.609 | 9.860 | 1.00 | 29.09 | O |
| ATOM | 3738 | OW0 | HOH | Z | 95 | 22.149 | 32.114 | 31.499 | 1.00 | 30.63 | O |
| ATOM | 3739 | OW0 | HOH | Z | 96 | 49.452 | 20.738 | 28.598 | 1.00 | 32.06 | O |
| ATOM | 3740 | OW0 | HOH | Z | 97 | 24.888 | 33.333 | 10.620 | 1.00 | 26.86 | O |
| ATOM | 3741 | OW0 | HOH | Z | 98 | 32.635 | 11.157 | 31.563 | 1.00 | 23.89 | O |
| ATOM | 3742 | OW0 | HOH | Z | 99 | 47.392 | 31.855 | 32.606 | 1.00 | 28.44 | O |
| ATOM | 3743 | OW0 | HOH | Z | 100 | 39.099 | 8.373 | 19.132 | 1.00 | 22.62 | O |
| ATOM | 3744 | OW0 | HOH | Z | 101 | 29.416 | 18.809 | 39.094 | 1.00 | 28.00 | O |
| ATOM | 3745 | OW0 | HOH | Z | 102 | 36.628 | 10.364 | 30.797 | 1.00 | 27.51 | O |
| ATOM | 3746 | OW0 | HOH | Z | 103 | 33.009 | 16.670 | 38.915 | 1.00 | 29.71 | O |
| ATOM | 3747 | OW0 | HOH | Z | 104 | 24.149 | 40.802 | 12.562 | 1.00 | 27.28 | O |
| ATOM | 3748 | OW0 | HOH | Z | 105 | 30.877 | 9.387 | 62.920 | 1.00 | 28.76 | O |
| ATOM | 3749 | OW0 | HOH | Z | 106 | 22.434 | 33.698 | 49.336 | 1.00 | 30.13 | O |
| ATOM | 3750 | OW0 | HOH | Z | 107 | 42.970 | 15.955 | 28.432 | 1.00 | 29.47 | O |
| ATOM | 3751 | OW0 | HOH | Z | 108 | 14.375 | 25.132 | 21.428 | 1.00 | 27.34 | O |
| ATOM | 3752 | OW0 | HOH | Z | 109 | 11.291 | 34.633 | 33.574 | 1.00 | 30.36 | O |
| ATOM | 3753 | OW0 | HOH | Z | 110 | 16.154 | 37.037 | 37.132 | 1.00 | 27.33 | O |
| ATOM | 3754 | OW0 | HOH | Z | 111 | 50.368 | 22.690 | 46.917 | 1.00 | 30.48 | O |
| ATOM | 3755 | OW0 | HOH | Z | 112 | 12.996 | 20.132 | 5.018 | 1.00 | 31.98 | O |
| ATOM | 3756 | OW0 | HOH | Z | 113 | 45.519 | 11.333 | 44.780 | 1.00 | 25.99 | O |
| ATOM | 3757 | OW0 | HOH | Z | 114 | 18.149 | 24.934 | 2.960 | 1.00 | 34.36 | O |
| ATOM | 3758 | OW0 | HOH | Z | 115 | 34.566 | 0.240 | 61.652 | 1.00 | 34.36 | O |
| ATOM | 3759 | OW0 | HOH | Z | 116 | 43.766 | 32.331 | 40.763 | 1.00 | 30.61 | O |
| ATOM | 3760 | OW0 | HOH | Z | 117 | 13.521 | 46.083 | 19.695 | 1.00 | 29.81 | O |
| ATOM | 3761 | OW0 | HOH | Z | 118 | 10.891 | 24.595 | 20.675 | 1.00 | 26.07 | O |
| ATOM | 3762 | OW0 | HOH | Z | 119 | 24.216 | −3.460 | 62.415 | 1.00 | 33.30 | O |
| ATOM | 3763 | OW0 | HOH | Z | 120 | 14.526 | 7.764 | 53.236 | 1.00 | 27.09 | O |
| ATOM | 3764 | OW0 | HOH | Z | 121 | 32.467 | 33.531 | 31.210 | 1.00 | 31.63 | O |
| ATOM | 3765 | OW0 | HOH | Z | 122 | 43.690 | 32.022 | 37.913 | 1.00 | 33.60 | O |
| ATOM | 3766 | OW0 | HOH | Z | 123 | 26.856 | 14.766 | 11.731 | 1.00 | 34.14 | O |
| ATOM | 3767 | OW0 | HOH | Z | 124 | 22.483 | 15.624 | 15.244 | 1.00 | 36.61 | O |
| ATOM | 3768 | OW0 | HOH | Z | 125 | 24.197 | 27.054 | 36.096 | 1.00 | 39.81 | O |
| ATOM | 3769 | OW0 | HOH | Z | 126 | 35.806 | 27.449 | 16.681 | 1.00 | 29.95 | O |
| ATOM | 3770 | OW0 | HOH | Z | 127 | 29.895 | 33.364 | 30.795 | 1.00 | 28.11 | O |
| ATOM | 3771 | OW0 | HOH | Z | 128 | 35.259 | 8.012 | 30.913 | 1.00 | 27.34 | O |
| ATOM | 3772 | OW0 | HOH | Z | 129 | 19.977 | 22.278 | 52.011 | 1.00 | 27.26 | O |
| ATOM | 3773 | OW0 | HOH | Z | 130 | 21.679 | −3.862 | 61.103 | 1.00 | 29.77 | O |
| ATOM | 3774 | OW0 | HOH | Z | 131 | 38.336 | 35.245 | 38.625 | 1.00 | 31.39 | O |
| ATOM | 3775 | OW0 | HOH | Z | 132 | 19.497 | −4.560 | 35.579 | 1.00 | 36.99 | O |
| ATOM | 3776 | OW0 | HOH | Z | 133 | 13.626 | 24.676 | 33.030 | 1.00 | 35.95 | O |
| ATOM | 3777 | OW0 | HOH | Z | 134 | 29.966 | 0.914 | 30.456 | 1.00 | 28.42 | O |
| ATOM | 3778 | OW0 | HOH | Z | 135 | 14.818 | 32.367 | 33.364 | 1.00 | 35.79 | O |
| ATOM | 3779 | OW0 | HOH | Z | 136 | 43.100 | 32.469 | 34.116 | 1.00 | 30.84 | O |
| ATOM | 3780 | OW0 | HOH | Z | 137 | 31.293 | −11.499 | 43.457 | 1.00 | 32.64 | O |
| ATOM | 3781 | OW0 | HOH | Z | 138 | 23.652 | 44.624 | 29.787 | 1.00 | 31.22 | O |
| ATOM | 3782 | OW0 | HOH | Z | 139 | 34.426 | 23.668 | 57.286 | 1.00 | 36.73 | O |
| ATOM | 3783 | OW0 | HOH | Z | 140 | 22.057 | 3.494 | 27.457 | 1.00 | 32.84 | O |
| ATOM | 3784 | OW0 | HOH | Z | 141 | 13.333 | 10.323 | 5.028 | 1.00 | 39.48 | O |

TABLE 6-continued

Coordinates of the crystal structure of *E. coli* ExoI bound to compound 9

| ATOM | 3785 | OW0 | HOH | Z | 142 | 35.870 | 10.386 | 28.045 | 1.00 | 28.67 | O |
|---|---|---|---|---|---|---|---|---|---|---|---|
| ATOM | 3786 | OW0 | HOH | Z | 143 | 25.342 | 28.817 | 9.171 | 1.00 | 31.20 | O |
| ATOM | 3787 | OW0 | HOH | Z | 144 | 28.163 | 9.422 | 63.183 | 1.00 | 30.37 | O |
| ATOM | 3788 | OW0 | HOH | Z | 145 | 15.391 | 17.073 | 26.164 | 1.00 | 32.48 | O |
| ATOM | 3789 | OW0 | HOH | Z | 147 | 18.322 | 25.173 | 34.502 | 1.00 | 38.80 | O |
| ATOM | 3790 | OW0 | HOH | Z | 148 | 35.921 | 14.923 | 15.423 | 1.00 | 33.55 | O |
| ATOM | 3791 | OW0 | HOH | Z | 149 | 41.145 | 31.668 | 50.991 | 1.00 | 26.14 | O |
| ATOM | 3792 | OW0 | HOH | Z | 150 | 34.974 | 38.563 | 43.958 | 1.00 | 35.93 | O |
| ATOM | 3793 | OW0 | HOH | Z | 151 | 29.262 | 33.045 | 28.286 | 1.00 | 34.41 | O |
| ATOM | 3794 | OW0 | HOH | Z | 152 | 32.969 | 0.998 | 63.374 | 1.00 | 29.95 | O |
| ATOM | 3795 | OW0 | HOH | Z | 153 | 36.645 | 36.340 | 36.728 | 1.00 | 26.01 | O |
| ATOM | 3796 | OW0 | HOH | Z | 154 | 14.570 | 19.845 | 2.779 | 1.00 | 37.35 | O |
| ATOM | 3797 | OW0 | HOH | Z | 155 | 23.229 | 38.261 | 13.135 | 1.00 | 24.50 | O |
| ATOM | 3798 | OW0 | HOH | Z | 156 | 11.740 | 26.762 | 21.998 | 1.00 | 26.79 | O |
| ATOM | 3799 | OW0 | HOH | Z | 157 | 29.478 | 13.821 | 4.139 | 1.00 | 28.31 | O |
| ATOM | 3800 | OW0 | HOH | Z | 158 | 40.787 | 26.421 | 56.755 | 1.00 | 32.84 | O |
| ATOM | 3801 | OW0 | HOH | Z | 159 | 9.665 | 20.652 | 12.212 | 1.00 | 35.84 | O |
| ATOM | 3802 | OW0 | HOH | Z | 160 | 39.205 | 9.838 | 31.145 | 1.00 | 36.76 | O |
| ATOM | 3803 | OW0 | HOH | Z | 161 | 23.436 | 21.166 | 39.393 | 1.00 | 29.44 | O |
| ATOM | 3804 | OW0 | HOH | Z | 162 | 21.335 | 23.224 | 37.167 | 1.00 | 34.57 | O |
| ATOM | 3805 | OW0 | HOH | Z | 163 | 38.718 | 20.988 | 15.655 | 1.00 | 35.04 | O |
| ATOM | 3806 | OW0 | HOH | Z | 164 | 41.044 | 1.755 | 39.757 | 1.00 | 33.08 | O |
| ATOM | 3807 | OW0 | HOH | Z | 165 | 45.031 | 29.451 | 43.965 | 1.00 | 29.49 | O |
| ATOM | 3808 | OW0 | HOH | Z | 166 | 38.081 | 25.941 | 56.123 | 1.00 | 32.80 | O |
| ATOM | 3809 | OW0 | HOH | Z | 167 | 20.161 | 9.376 | 58.804 | 1.00 | 31.21 | O |
| ATOM | 3810 | OW0 | HOH | Z | 168 | 47.018 | 18.000 | 42.384 | 1.00 | 37.13 | O |
| ATOM | 3811 | OW0 | HOH | Z | 169 | 36.528 | 1.745 | 52.664 | 1.00 | 35.32 | O |
| ATOM | 3812 | OW0 | HOH | Z | 170 | 18.928 | 8.125 | 24.229 | 1.00 | 26.06 | O |
| ATOM | 3813 | OW0 | HOH | Z | 171 | 31.941 | 14.845 | 16.941 | 1.00 | 31.39 | O |
| ATOM | 3814 | OW0 | HOH | Z | 172 | 22.944 | 15.985 | 32.916 | 1.00 | 29.55 | O |
| ATOM | 3815 | OW0 | HOH | Z | 173 | 19.920 | 33.213 | 10.097 | 1.00 | 31.72 | O |
| ATOM | 3816 | OW0 | HOH | Z | 174 | 18.293 | 10.153 | 53.111 | 1.00 | 36.29 | O |
| ATOM | 3817 | OW0 | HOH | Z | 175 | 18.059 | 7.335 | 33.021 | 1.00 | 42.94 | O |
| ATOM | 3818 | OW0 | HOH | Z | 176 | 28.432 | −2.019 | 62.836 | 1.00 | 34.04 | O |
| ATOM | 3819 | OW0 | HOH | Z | 177 | 30.260 | 16.127 | 38.651 | 1.00 | 29.47 | O |
| ATOM | 3820 | OW0 | HOH | Z | 178 | 6.446 | 40.555 | 41.540 | 1.00 | 38.70 | O |
| ATOM | 3821 | OW0 | HOH | Z | 179 | 26.333 | 18.199 | 39.290 | 1.00 | 32.47 | O |
| ATOM | 3822 | OW0 | HOH | Z | 180 | 24.457 | 28.242 | 59.726 | 1.00 | 29.67 | O |
| ATOM | 3823 | OW0 | HOH | Z | 181 | 27.364 | 28.017 | 37.544 | 1.00 | 31.95 | O |
| ATOM | 3824 | OW0 | HOH | Z | 182 | 39.997 | 3.402 | 45.714 | 1.00 | 33.02 | O |
| ATOM | 3825 | OW0 | HOH | Z | 183 | 49.996 | 23.378 | 42.174 | 1.00 | 39.39 | O |
| ATOM | 3826 | OW0 | HOH | Z | 184 | 7.923 | 19.213 | 16.269 | 1.00 | 34.13 | O |
| ATOM | 3827 | OW0 | HOH | Z | 185 | 27.164 | −5.486 | 56.530 | 1.00 | 28.25 | O |
| ATOM | 3828 | OW0 | HOH | Z | 186 | 16.652 | −9.654 | 43.964 | 1.00 | 36.59 | O |
| ATOM | 3829 | OW0 | HOH | Z | 187 | 43.634 | 17.615 | 30.496 | 1.00 | 33.30 | O |
| ATOM | 3830 | OW0 | HOH | Z | 188 | 25.430 | 15.961 | 30.820 | 1.00 | 37.37 | O |
| ATOM | 3831 | OW0 | HOH | Z | 189 | 26.820 | 13.382 | 38.133 | 1.00 | 33.66 | O |
| ATOM | 3832 | OW0 | HOH | Z | 190 | 9.129 | 47.050 | 18.564 | 1.00 | 31.53 | O |
| ATOM | 3833 | OW0 | HOH | Z | 191 | 25.669 | −8.432 | 49.431 | 1.00 | 30.30 | O |
| ATOM | 3834 | OW0 | HOH | Z | 192 | 45.776 | 16.987 | 31.896 | 1.00 | 35.42 | O |
| ATOM | 3835 | OW0 | HOH | Z | 193 | 41.187 | 25.342 | 19.701 | 1.00 | 34.59 | O |
| ATOM | 3836 | OW0 | HOH | Z | 194 | 27.200 | 7.055 | 64.435 | 1.00 | 29.95 | O |
| ATOM | 3837 | OW0 | HOH | Z | 195 | 27.803 | 6.433 | 10.863 | 1.00 | 34.56 | O |
| ATOM | 3838 | OW0 | HOH | Z | 196 | 49.509 | 18.917 | 42.454 | 1.00 | 43.82 | O |
| ATOM | 3839 | OW0 | HOH | Z | 197 | 32.762 | 8.610 | 30.741 | 1.00 | 32.81 | O |
| ATOM | 3840 | OW0 | HOH | Z | 198 | 31.505 | 21.855 | 11.049 | 1.00 | 36.84 | O |
| ATOM | 3841 | OW0 | HOH | Z | 199 | 10.954 | 29.568 | 27.581 | 1.00 | 30.20 | O |
| ATOM | 3842 | OW0 | HOH | Z | 200 | 39.303 | 8.355 | 22.166 | 1.00 | 44.80 | O |
| ATOM | 3843 | OW0 | HOH | Z | 201 | 13.225 | 46.918 | 15.937 | 1.00 | 34.83 | O |
| ATOM | 3844 | OW0 | HOH | Z | 202 | 22.374 | −5.489 | 38.115 | 1.00 | 32.10 | O |
| ATOM | 3845 | OW0 | HOH | Z | 203 | 42.406 | 39.234 | 47.357 | 1.00 | 31.98 | O |
| ATOM | 3846 | OW0 | HOH | Z | 204 | 9.828 | 34.122 | 9.454 | 1.00 | 39.61 | O |
| ATOM | 3847 | OW0 | HOH | Z | 205 | 21.143 | 18.937 | 42.697 | 1.00 | 39.50 | O |
| ATOM | 3848 | OW0 | HOH | Z | 206 | 24.528 | 32.238 | 33.082 | 1.00 | 33.22 | O |
| ATOM | 3849 | OW0 | HOH | Z | 207 | 7.747 | 21.062 | 4.366 | 1.00 | 41.57 | O |
| ATOM | 3850 | OW0 | HOH | Z | 208 | 47.230 | 29.645 | 42.256 | 1.00 | 37.55 | O |
| ATOM | 3851 | OW0 | HOH | Z | 209 | 22.547 | 1.506 | 10.647 | 1.00 | 45.42 | O |
| ATOM | 3852 | OW0 | HOH | Z | 210 | 15.826 | 9.609 | 51.620 | 1.00 | 39.31 | O |
| ATOM | 3853 | OW0 | HOH | Z | 211 | 2.253 | 24.652 | 3.430 | 1.00 | 35.99 | O |
| ATOM | 3854 | OW0 | HOH | Z | 212 | 31.238 | 12.119 | 29.422 | 1.00 | 34.88 | O |
| ATOM | 3855 | OW0 | HOH | Z | 213 | 23.361 | 28.226 | 0.607 | 1.00 | 45.18 | O |
| ATOM | 3856 | OW0 | HOH | Z | 214 | 13.038 | 14.802 | 5.292 | 1.00 | 46.68 | O |
| ATOM | 3857 | OW0 | HOH | Z | 215 | 49.714 | 15.276 | 45.776 | 1.00 | 43.87 | O |
| ATOM | 3858 | OW0 | HOH | Z | 216 | 6.199 | 22.545 | 11.228 | 1.00 | 38.50 | O |
| ATOM | 3859 | OW0 | HOH | Z | 217 | 19.024 | 19.372 | 46.664 | 1.00 | 40.03 | O |
| ATOM | 3860 | OW0 | HOH | Z | 218 | 43.557 | 35.347 | 29.027 | 1.00 | 38.48 | O |
| ATOM | 3861 | OW0 | HOH | Z | 219 | 20.983 | 42.950 | 35.348 | 1.00 | 43.44 | O |
| ATOM | 3862 | OW0 | HOH | Z | 220 | 31.114 | 31.281 | 11.314 | 1.00 | 40.20 | O |

TABLE 6-continued

Coordinates of the crystal structure of *E. coli* ExoI bound to compound 9

| ATOM | 3863 | OW0 | HOH | Z | 221 | 36.177 | 0.796 | 48.006 | 1.00 | 42.56 | O |
|------|------|-----|-----|---|-----|--------|-------|--------|------|-------|---|
| ATOM | 3864 | OW0 | HOH | Z | 222 | 19.728 | 21.293 | 33.065 | 1.00 | 34.12 | O |
| ATOM | 3865 | OW0 | HOH | Z | 223 | 16.075 | 49.403 | 26.726 | 1.00 | 29.77 | O |
| ATOM | 3866 | OW0 | HOH | Z | 224 | 8.053 | 9.057 | 45.041 | 1.00 | 37.18 | O |
| ATOM | 3867 | OW0 | HOH | Z | 225 | 7.350 | 33.889 | 9.389 | 1.00 | 43.38 | O |
| ATOM | 3868 | OW0 | HOH | Z | 226 | 12.388 | 47.859 | 18.361 | 1.00 | 34.40 | O |
| ATOM | 3869 | OW0 | HOH | Z | 227 | 28.994 | 39.741 | 14.691 | 1.00 | 39.78 | O |
| ATOM | 3870 | OW0 | HOH | Z | 228 | 15.239 | 3.980 | 59.473 | 1.00 | 33.29 | O |
| ATOM | 3871 | OW0 | HOH | Z | 229 | 35.649 | 33.806 | 53.865 | 1.00 | 35.34 | O |
| ATOM | 3872 | OW0 | HOH | Z | 230 | 51.682 | 26.659 | 45.241 | 1.00 | 38.98 | O |
| ATOM | 3873 | OW0 | HOH | Z | 231 | 38.537 | 9.458 | 25.717 | 1.00 | 32.29 | O |
| ATOM | 3874 | OW0 | HOH | Z | 232 | 40.301 | 38.262 | 28.461 | 1.00 | 33.56 | O |
| ATOM | 3875 | OW0 | HOH | Z | 233 | 24.403 | 19.220 | 40.931 | 1.00 | 31.65 | O |
| ATOM | 3876 | OW0 | HOH | Z | 234 | 19.417 | 52.008 | 39.342 | 1.00 | 37.12 | O |
| ATOM | 3877 | OW0 | HOH | Z | 235 | 23.456 | −9.883 | 49.823 | 1.00 | 35.38 | O |
| ATOM | 3878 | OW0 | HOH | Z | 236 | 44.033 | 34.971 | 33.166 | 1.00 | 47.26 | O |
| ATOM | 3879 | OW0 | HOH | Z | 237 | 23.704 | 22.138 | 5.378 | 1.00 | 38.11 | O |
| ATOM | 3880 | OW0 | HOH | Z | 238 | 21.182 | 46.392 | 26.444 | 1.00 | 32.01 | O |
| ATOM | 3881 | OW0 | HOH | Z | 239 | 40.359 | 6.956 | 48.046 | 1.00 | 48.77 | O |
| ATOM | 3882 | OW0 | HOH | Z | 240 | 11.410 | 26.740 | 29.056 | 1.00 | 40.03 | O |
| ATOM | 3883 | OW0 | HOH | Z | 241 | 6.084 | 7.346 | 44.819 | 1.00 | 29.00 | O |
| ATOM | 3884 | OW0 | HOH | Z | 242 | 38.607 | 15.896 | 56.596 | 1.00 | 37.31 | O |
| ATOM | 3885 | OW0 | HOH | Z | 243 | 19.414 | 11.728 | 55.919 | 1.00 | 42.00 | O |
| ATOM | 3886 | OW0 | HOH | Z | 244 | 26.826 | −3.735 | 61.090 | 1.00 | 38.93 | O |
| ATOM | 3887 | OW0 | HOH | Z | 245 | 10.003 | 37.534 | 40.258 | 1.00 | 43.01 | O |
| ATOM | 3888 | OW0 | HOH | Z | 246 | 34.149 | 16.488 | 63.767 | 1.00 | 41.95 | O |
| ATOM | 3889 | OW0 | HOH | Z | 247 | 9.400 | 12.826 | 16.332 | 1.00 | 37.21 | O |
| ATOM | 3890 | OW0 | HOH | Z | 248 | 21.903 | −6.746 | 41.205 | 1.00 | 38.57 | O |
| ATOM | 3891 | OW0 | HOH | Z | 249 | 45.763 | 21.253 | 21.897 | 1.00 | 37.31 | O |
| ATOM | 3892 | OW0 | HOH | Z | 250 | 33.096 | 22.047 | 13.280 | 1.00 | 47.97 | O |
| ATOM | 3893 | OW0 | HOH | Z | 251 | 37.270 | 23.956 | 57.675 | 1.00 | 34.54 | O |
| ATOM | 3894 | OW0 | HOH | Z | 252 | 18.185 | 14.737 | 49.781 | 1.00 | 32.85 | O |
| ATOM | 3895 | OW0 | HOH | Z | 253 | 23.858 | 32.550 | 41.057 | 1.00 | 50.41 | O |
| ATOM | 3896 | OW0 | HOH | Z | 254 | 18.544 | 10.488 | 49.874 | 1.00 | 44.44 | O |
| ATOM | 3897 | OW0 | HOH | Z | 255 | 14.771 | 33.063 | 12.091 | 1.00 | 35.84 | O |
| ATOM | 3898 | OW0 | HOH | Z | 256 | 20.711 | 11.123 | 40.135 | 1.00 | 43.08 | O |
| ATOM | 3899 | OW0 | HOH | Z | 257 | 47.445 | 25.183 | 40.716 | 1.00 | 42.52 | O |
| ATOM | 3900 | OW0 | HOH | Z | 258 | 49.714 | 23.073 | 26.775 | 1.00 | 46.07 | O |
| ATOM | 3901 | OW0 | HOH | Z | 259 | 6.976 | 9.228 | 53.709 | 1.00 | 28.77 | O |
| ATOM | 3902 | OW0 | HOH | Z | 260 | 16.396 | 5.631 | 15.703 | 1.00 | 45.74 | O |
| ATOM | 3903 | OW0 | HOH | Z | 261 | 14.775 | 38.220 | 13.666 | 1.00 | 36.31 | O |
| ATOM | 3904 | OW0 | HOH | Z | 262 | 7.503 | 22.471 | 23.700 | 1.00 | 43.06 | O |
| ATOM | 3905 | OW0 | HOH | Z | 263 | 35.558 | 27.151 | 13.923 | 1.00 | 40.92 | O |
| ATOM | 3906 | OW0 | HOH | Z | 264 | 40.908 | 35.213 | 37.942 | 1.00 | 38.55 | O |
| ATOM | 3907 | OW0 | HOH | Z | 265 | 20.360 | 47.804 | 30.836 | 1.00 | 30.24 | O |
| ATOM | 3908 | OW0 | HOH | Z | 266 | 5.399 | 33.984 | 2.079 | 1.00 | 45.30 | O |
| ATOM | 3909 | OW0 | HOH | Z | 267 | 18.977 | 9.447 | 61.503 | 1.00 | 44.38 | O |
| ATOM | 3910 | OW0 | HOH | Z | 268 | 34.863 | 16.985 | 56.795 | 1.00 | 37.59 | O |
| ATOM | 3911 | OW0 | HOH | Z | 269 | 4.085 | 24.049 | 10.769 | 1.00 | 40.05 | O |
| ATOM | 3912 | OW0 | HOH | Z | 270 | 12.703 | −6.661 | 38.471 | 1.00 | 38.94 | O |
| ATOM | 3913 | OW0 | HOH | Z | 271 | 22.387 | 46.165 | 31.578 | 1.00 | 38.09 | O |
| ATOM | 3914 | OW0 | HOH | Z | 272 | 25.192 | 47.578 | 21.273 | 1.00 | 37.17 | O |
| ATOM | 3915 | OW0 | HOH | Z | 273 | 30.912 | 35.165 | 49.928 | 1.00 | 49.31 | O |
| ATOM | 3916 | OW0 | HOH | Z | 274 | 18.470 | 0.631 | 60.620 | 1.00 | 38.78 | O |
| ATOM | 3917 | OW0 | HOH | Z | 275 | 21.139 | 32.446 | 6.639 | 1.00 | 37.32 | O |
| ATOM | 3918 | OW0 | HOH | Z | 276 | 27.846 | −9.129 | 51.274 | 1.00 | 37.62 | O |
| ATOM | 3919 | OW0 | HOH | Z | 277 | 9.353 | 25.822 | 18.774 | 1.00 | 35.56 | O |
| ATOM | 3920 | OW0 | HOH | Z | 278 | 26.313 | 21.017 | −1.780 | 1.00 | 46.51 | O |
| ATOM | 3921 | OW0 | HOH | Z | 279 | 18.304 | 17.977 | 27.500 | 1.00 | 39.04 | O |
| ATOM | 3922 | OW0 | HOH | Z | 280 | 32.990 | −5.269 | 40.752 | 1.00 | 34.10 | O |
| ATOM | 3923 | OW0 | HOH | Z | 281 | 48.291 | 27.712 | 40.579 | 1.00 | 36.27 | O |
| ATOM | 3924 | OW0 | HOH | Z | 282 | 22.238 | 31.903 | 47.422 | 1.00 | 48.17 | O |
| ATOM | 3925 | OW0 | HOH | Z | 283 | 9.850 | 28.109 | 19.916 | 1.00 | 35.54 | O |
| ATOM | 3926 | OW0 | HOH | Z | 284 | 18.199 | 24.982 | 51.065 | 1.00 | 36.70 | O |
| ATOM | 3927 | OW0 | HOH | Z | 285 | 34.052 | 14.650 | 66.009 | 1.00 | 47.39 | O |
| ATOM | 3928 | OW0 | HOH | Z | 286 | 3.668 | 28.719 | 23.076 | 1.00 | 41.76 | O |
| ATOM | 3929 | OW0 | HOH | Z | 287 | 15.481 | 6.178 | 34.686 | 1.00 | 40.76 | O |
| ATOM | 3930 | OW0 | HOH | Z | 288 | 30.307 | 43.454 | 21.426 | 1.00 | 41.96 | O |
| ATOM | 3931 | OW0 | HOH | Z | 289 | 45.777 | 34.388 | 36.955 | 1.00 | 53.44 | O |
| ATOM | 3932 | OW0 | HOH | Z | 290 | 38.322 | 26.570 | 16.277 | 1.00 | 40.13 | O |
| ATOM | 3933 | OW0 | HOH | Z | 291 | 25.957 | 13.266 | 41.332 | 1.00 | 36.59 | O |
| ATOM | 3934 | OW0 | HOH | Z | 292 | 9.867 | 31.765 | 26.398 | 1.00 | 38.30 | O |
| ATOM | 3935 | OW0 | HOH | Z | 293 | 21.671 | 27.187 | 35.535 | 1.00 | 51.99 | O |
| ATOM | 3936 | OW0 | HOH | Z | 294 | 33.306 | 26.920 | 12.585 | 1.00 | 48.74 | O |
| ATOM | 3937 | OW0 | HOH | Z | 295 | 27.448 | 26.445 | 9.688 | 1.00 | 40.69 | O |
| ATOM | 3938 | OW0 | HOH | Z | 296 | 4.820 | 25.564 | 17.188 | 1.00 | 41.40 | O |
| ATOM | 3939 | OW0 | HOH | Z | 297 | 28.157 | 10.149 | 5.633 | 1.00 | 35.28 | O |
| ATOM | 3940 | OW0 | HOH | Z | 298 | 27.680 | 14.319 | 25.632 | 1.00 | 39.39 | O |

TABLE 6-continued

Coordinates of the crystal structure of *E. coli* ExoI bound to compound 9

| ATOM | 3941 | OW0 | HOH | Z | 299 | 21.473 | 13.639 | 30.362 | 1.00 | 36.85 | O |
|---|---|---|---|---|---|---|---|---|---|---|---|
| ATOM | 3942 | OW0 | HOH | Z | 300 | 24.994 | 25.325 | 57.875 | 1.00 | 33.41 | O |
| ATOM | 3943 | OW0 | HOH | Z | 301 | 23.556 | 38.711 | 37.340 | 1.00 | 39.57 | O |
| ATOM | 3944 | OW0 | HOH | Z | 302 | 44.768 | 34.965 | 26.428 | 1.00 | 42.42 | O |
| ATOM | 3945 | OW0 | HOH | Z | 303 | 29.731 | 21.038 | 61.890 | 1.00 | 39.74 | O |
| ATOM | 3946 | OW0 | HOH | Z | 304 | 2.707 | 35.429 | 33.045 | 1.00 | 42.38 | O |
| ATOM | 3947 | OW0 | HOH | Z | 305 | 40.241 | 9.548 | 54.479 | 1.00 | 41.51 | O |
| ATOM | 3948 | OW0 | HOH | Z | 306 | 48.716 | 29.622 | 46.334 | 1.00 | 37.26 | O |
| ATOM | 3949 | OW0 | HOH | Z | 307 | 22.146 | 37.661 | 10.735 | 1.00 | 37.70 | O |
| ATOM | 3950 | OW0 | HOH | Z | 308 | 29.721 | 33.796 | 53.597 | 1.00 | 34.03 | O |
| ATOM | 3951 | OW0 | HOH | Z | 309 | 21.832 | 9.539 | 26.316 | 1.00 | 44.04 | O |
| ATOM | 3952 | OW0 | HOH | Z | 310 | 18.625 | 11.738 | 44.175 | 1.00 | 49.66 | O |
| ATOM | 3953 | OW0 | HOH | Z | 311 | 9.568 | 8.547 | 43.046 | 1.00 | 54.12 | O |
| ATOM | 3954 | OW0 | HOH | Z | 312 | 9.559 | 17.734 | 6.257 | 1.00 | 40.96 | O |
| ATOM | 3955 | OW0 | HOH | Z | 313 | 3.194 | 18.590 | 23.129 | 1.00 | 55.89 | O |
| ATOM | 3956 | OW0 | HOH | Z | 314 | 4.647 | 38.489 | 41.572 | 1.00 | 38.75 | O |
| ATOM | 3957 | OW0 | HOH | Z | 315 | 25.720 | 11.439 | 30.384 | 1.00 | 35.40 | O |
| ATOM | 3958 | OW0 | HOH | Z | 316 | 20.644 | −6.350 | 61.065 | 1.00 | 42.44 | O |
| ATOM | 3959 | OW0 | HOH | Z | 317 | 19.281 | 29.040 | 49.588 | 1.00 | 42.23 | O |
| ATOM | 3960 | OW0 | HOH | Z | 318 | 41.042 | 29.348 | 55.582 | 1.00 | 43.07 | O |
| ATOM | 3961 | OW0 | HOH | Z | 319 | 39.711 | 24.510 | 17.303 | 1.00 | 40.26 | O |
| ATOM | 3962 | OW0 | HOH | Z | 320 | 23.173 | 6.210 | 5.587 | 1.00 | 40.02 | O |
| ATOM | 3963 | OW0 | HOH | Z | 321 | 36.405 | 35.222 | 20.283 | 1.00 | 42.88 | O |
| ATOM | 3964 | OW0 | HOH | Z | 322 | 18.439 | 9.528 | 47.448 | 1.00 | 51.07 | O |
| ATOM | 3965 | OW0 | HOH | Z | 323 | 10.573 | 7.258 | 58.154 | 1.00 | 45.42 | O |
| ATOM | 3966 | OW0 | HOH | Z | 324 | 7.309 | 32.350 | 6.803 | 1.00 | 46.10 | O |
| ATOM | 3967 | OW0 | HOH | Z | 325 | 8.176 | 23.236 | 12.922 | 1.00 | 43.35 | O |
| ATOM | 3968 | OW0 | HOH | Z | 326 | 23.542 | 8.301 | 31.788 | 1.00 | 46.64 | O |
| ATOM | 3969 | OW0 | HOH | Z | 327 | 11.408 | 26.036 | 31.693 | 1.00 | 46.43 | O |
| ATOM | 3970 | OW0 | HOH | Z | 328 | 3.612 | 41.960 | 15.708 | 1.00 | 63.20 | O |
| ATOM | 3971 | OW0 | HOH | Z | 329 | 22.848 | 17.153 | 41.528 | 1.00 | 36.33 | O |
| ATOM | 3972 | OW0 | HOH | Z | 330 | 29.811 | 8.979 | 7.489 | 1.00 | 38.38 | O |
| ATOM | 3973 | OW0 | HOH | Z | 331 | 26.967 | 6.984 | 14.844 | 1.00 | 44.87 | O |
| ATOM | 3974 | OW0 | HOH | Z | 332 | 24.860 | 23.876 | 7.037 | 1.00 | 36.03 | O |
| ATOM | 3975 | OW0 | HOH | Z | 333 | 39.537 | 16.594 | 15.749 | 1.00 | 42.23 | O |
| ATOM | 3976 | OW0 | HOH | Z | 334 | 31.132 | 27.406 | 56.220 | 1.00 | 34.41 | O |
| ATOM | 3977 | OW0 | HOH | Z | 335 | 13.304 | 7.877 | 17.789 | 1.00 | 42.52 | O |
| ATOM | 3978 | OW0 | HOH | Z | 336 | 7.728 | 49.577 | 42.457 | 1.00 | 43.66 | O |
| ATOM | 3979 | OW0 | HOH | Z | 337 | 51.361 | 20.241 | 45.329 | 1.00 | 40.12 | O |
| ATOM | 3980 | OW0 | HOH | Z | 338 | 32.407 | −4.809 | 50.652 | 1.00 | 39.95 | O |
| ATOM | 3981 | OW0 | HOH | Z | 339 | 29.986 | 40.111 | 17.160 | 1.00 | 46.22 | O |
| ATOM | 3982 | OW0 | HOH | Z | 340 | 29.950 | 10.535 | 14.992 | 1.00 | 52.45 | O |
| ATOM | 3983 | OW0 | HOH | Z | 341 | 29.042 | 9.155 | 10.271 | 1.00 | 40.54 | O |
| ATOM | 3984 | OW0 | HOH | Z | 342 | 9.599 | 33.188 | 31.757 | 1.00 | 46.01 | O |
| ATOM | 3985 | OW0 | HOH | Z | 343 | 20.572 | 18.004 | 33.607 | 1.00 | 43.84 | O |
| ATOM | 3986 | OW0 | HOH | Z | 344 | 16.649 | 17.660 | 2.196 | 1.00 | 47.16 | O |
| ATOM | 3987 | OW0 | HOH | Z | 345 | 42.868 | 15.346 | 56.539 | 1.00 | 47.25 | O |
| ATOM | 3988 | OW0 | HOH | Z | 346 | 20.132 | 31.342 | 50.528 | 1.00 | 42.58 | O |
| ATOM | 3989 | OW0 | HOH | Z | 347 | 17.112 | 34.208 | 52.883 | 1.00 | 45.69 | O |
| ATOM | 3990 | OW0 | HOH | Z | 348 | 9.715 | 22.663 | 17.042 | 1.00 | 36.52 | O |
| ATOM | 3991 | OW0 | HOH | Z | 349 | 50.385 | 16.695 | 27.607 | 1.00 | 43.85 | O |
| ATOM | 3992 | OW0 | HOH | Z | 350 | 12.167 | −5.586 | 36.085 | 1.00 | 42.62 | O |
| ATOM | 3993 | OW0 | HOH | Z | 351 | 25.445 | 35.375 | 34.031 | 1.00 | 50.62 | O |
| ATOM | 3994 | OW0 | HOH | Z | 352 | 21.784 | 12.501 | 60.870 | 1.00 | 40.16 | O |
| ATOM | 3995 | OW0 | HOH | Z | 353 | 31.839 | 19.501 | 29.680 | 1.00 | 41.28 | O |
| ATOM | 3996 | OW0 | HOH | Z | 354 | 13.013 | 17.955 | 27.174 | 1.00 | 45.80 | O |
| ATOM | 3997 | OW0 | HOH | Z | 355 | 48.602 | 5.061 | 19.549 | 1.00 | 45.60 | O |
| ATOM | 3998 | OW0 | HOH | Z | 356 | 8.859 | 16.875 | 8.707 | 1.00 | 47.36 | O |
| ATOM | 3999 | OW0 | HOH | Z | 357 | 46.442 | 32.338 | 41.142 | 1.00 | 38.09 | O |
| ATOM | 4000 | OW0 | HOH | Z | 358 | 23.723 | 6.564 | 29.066 | 1.00 | 41.80 | O |
| ATOM | 4001 | OW0 | HOH | Z | 359 | 33.801 | 10.610 | 66.323 | 1.00 | 47.53 | O |
| ATOM | 4002 | OW0 | HOH | Z | 360 | 33.595 | 14.465 | 4.553 | 1.00 | 45.19 | O |
| ATOM | 4003 | OW0 | HOH | Z | 361 | 33.437 | 11.589 | 28.090 | 1.00 | 45.12 | O |
| ATOM | 4004 | OW0 | HOH | Z | 362 | 39.566 | 29.312 | 17.089 | 1.00 | 47.78 | O |
| ATOM | 4005 | OW0 | HOH | Z | 363 | 26.913 | −7.952 | 56.987 | 1.00 | 43.09 | O |
| ATOM | 4006 | OW0 | HOH | Z | 364 | 22.795 | 14.326 | 58.303 | 1.00 | 38.53 | O |
| ATOM | 4007 | OW0 | HOH | Z | 365 | 23.110 | −10.449 | 47.395 | 1.00 | 40.34 | O |
| ATOM | 4008 | OW0 | HOH | Z | 366 | 7.713 | 14.717 | 9.625 | 1.00 | 44.66 | O |
| ATOM | 4009 | OW0 | HOH | Z | 367 | 50.975 | 28.269 | 28.930 | 1.00 | 55.08 | O |
| ATOM | 4010 | OW0 | HOH | Z | 368 | 14.482 | 0.254 | 58.552 | 1.00 | 39.56 | O |
| ATOM | 4011 | OW0 | HOH | Z | 369 | 18.764 | 10.405 | 37.621 | 1.00 | 40.03 | O |
| ATOM | 4012 | OW0 | HOH | Z | 370 | 45.669 | 16.682 | 38.548 | 1.00 | 51.04 | O |
| ATOM | 4013 | OW0 | HOH | Z | 371 | 36.035 | 30.009 | 17.161 | 1.00 | 45.79 | O |
| ATOM | 4014 | OW0 | HOH | Z | 372 | 13.495 | 30.362 | −2.110 | 1.00 | 52.87 | O |
| ATOM | 4015 | OW0 | HOH | Z | 373 | 15.990 | −7.871 | 57.592 | 1.00 | 41.45 | O |
| ATOM | 4016 | OW0 | HOH | Z | 374 | 20.806 | 10.947 | 19.868 | 1.00 | 42.56 | O |
| ATOM | 4017 | OW0 | HOH | Z | 375 | 11.600 | 6.596 | 14.566 | 1.00 | 47.69 | O |
| ATOM | 4018 | OW0 | HOH | Z | 376 | 25.679 | 15.811 | 38.248 | 1.00 | 42.62 | O |

TABLE 6-continued

Coordinates of the crystal structure of *E. coli* ExoI bound to compound 9

| ATOM | 4019 | OW0 | HOH | Z | 377 | 41.484 | 8.318 | 52.350 | 1.00 | 49.22 | O |
|---|---|---|---|---|---|---|---|---|---|---|---|
| ATOM | 4020 | OW0 | HOH | Z | 378 | 48.910 | 27.729 | 36.355 | 1.00 | 45.54 | O |
| ATOM | 4021 | OW0 | HOH | Z | 379 | 18.457 | 22.556 | −4.029 | 1.00 | 45.40 | O |
| ATOM | 4022 | OW0 | HOH | Z | 380 | 15.923 | 13.477 | 48.926 | 1.00 | 53.94 | O |
| ATOM | 4023 | OW0 | HOH | Z | 381 | 31.836 | −4.021 | 53.522 | 1.00 | 45.73 | O |
| ATOM | 4024 | OW0 | HOH | Z | 382 | 8.430 | 33.175 | 29.047 | 1.00 | 51.48 | O |
| ATOM | 4025 | OW0 | HOH | Z | 383 | 26.954 | 23.450 | 61.270 | 1.00 | 40.29 | O |
| ATOM | 4026 | OW0 | HOH | Z | 384 | 29.988 | 35.329 | 32.668 | 1.00 | 48.79 | O |
| ATOM | 4027 | OW0 | HOH | Z | 385 | 5.483 | 42.993 | 40.757 | 1.00 | 32.49 | O |
| ATOM | 4028 | OW0 | HOH | Z | 386 | 41.387 | 36.594 | 50.915 | 1.00 | 38.52 | O |
| ATOM | 4029 | OW0 | HOH | Z | 387 | 36.465 | 6.256 | 29.053 | 1.00 | 39.44 | O |
| ATOM | 4030 | OW0 | HOH | Z | 388 | 45.897 | 19.035 | 36.412 | 1.00 | 27.98 | O |
| ATOM | 4031 | OW0 | HOH | Z | 389 | 48.052 | 31.929 | 38.993 | 1.00 | 49.72 | O |
| ATOM | 4032 | OW0 | HOH | Z | 390 | 27.127 | 12.579 | 63.489 | 1.00 | 47.30 | O |
| ATOM | 4033 | OW0 | HOH | Z | 391 | 26.324 | 9.487 | 19.115 | 1.00 | 46.32 | O |
| ATOM | 4034 | OW0 | HOH | Z | 392 | 27.536 | 25.467 | 58.264 | 1.00 | 43.07 | O |
| ATOM | 4035 | OW0 | HOH | Z | 393 | 29.603 | 3.246 | 65.779 | 1.00 | 43.20 | O |
| ATOM | 4036 | OW0 | HOH | Z | 394 | 22.673 | 12.785 | 40.986 | 1.00 | 53.87 | O |
| ATOM | 4037 | OW0 | HOH | Z | 395 | 40.519 | 3.822 | 43.160 | 1.00 | 45.29 | O |
| ATOM | 4038 | OW0 | HOH | Z | 396 | 7.851 | 29.060 | −3.909 | 1.00 | 34.56 | O |
| ATOM | 4039 | OW0 | HOH | Z | 397 | 31.574 | −2.074 | 55.542 | 1.00 | 39.25 | O |
| ATOM | 4040 | OW0 | HOH | Z | 398 | 11.308 | 52.633 | 37.000 | 1.00 | 43.46 | O |
| ATOM | 4041 | OW0 | HOH | Z | 399 | 14.385 | 44.274 | 17.999 | 1.00 | 43.00 | O |
| ATOM | 4042 | OW0 | HOH | Z | 400 | 6.853 | 30.672 | 29.388 | 1.00 | 52.85 | O |
| ATOM | 4043 | OW0 | HOH | Z | 401 | 44.730 | 9.323 | 46.401 | 1.00 | 43.46 | O |
| ATOM | 4044 | OW0 | HOH | Z | 402 | 23.600 | 10.928 | 65.247 | 1.00 | 53.86 | O |
| ATOM | 4045 | OW0 | HOH | Z | 403 | 27.612 | 36.694 | 33.323 | 1.00 | 47.16 | O |
| ATOM | 4046 | OW0 | HOH | Z | 404 | 19.378 | 2.674 | 10.089 | 1.00 | 50.33 | O |
| ATOM | 4047 | OW0 | HOH | Z | 405 | 36.151 | −0.410 | 54.091 | 1.00 | 48.14 | O |
| ATOM | 4048 | OW0 | HOH | Z | 406 | 17.502 | −6.046 | 34.397 | 1.00 | 55.19 | O |
| ATOM | 4049 | OW0 | HOH | Z | 407 | 14.682 | 36.620 | 15.814 | 1.00 | 36.83 | O |
| ATOM | 4050 | OW0 | HOH | Z | 408 | 18.918 | 16.611 | 42.382 | 1.00 | 51.40 | O |
| ATOM | 4051 | OW0 | HOH | Z | 409 | 21.073 | 50.082 | 37.594 | 1.00 | 47.32 | O |
| ATOM | 4052 | OW0 | HOH | Z | 411 | 9.448 | 5.394 | 32.875 | 1.00 | 53.50 | O |
| ATOM | 4053 | OW0 | HOH | Z | 413 | 2.663 | −1.727 | 48.937 | 1.00 | 52.71 | O |
| ATOM | 4054 | OW0 | HOH | Z | 414 | 21.233 | 25.587 | 45.932 | 1.00 | 44.02 | O |
| ATOM | 4055 | OW0 | HOH | Z | 415 | 30.485 | 36.215 | 15.358 | 1.00 | 51.99 | O |
| ATOM | 4056 | OW0 | HOH | Z | 416 | 51.843 | 21.922 | 40.072 | 1.00 | 56.29 | O |
| ATOM | 4057 | OW0 | HOH | Z | 417 | 32.042 | 18.100 | 64.753 | 1.00 | 53.41 | O |
| ATOM | 4058 | OW0 | HOH | Z | 418 | 30.544 | 21.851 | 3.348 | 1.00 | 49.80 | O |
| ATOM | 4059 | OW0 | HOH | Z | 419 | 22.444 | −4.502 | 33.538 | 1.00 | 43.58 | O |
| ATOM | 4060 | OW0 | HOH | Z | 420 | 15.047 | 22.041 | 32.706 | 1.00 | 45.92 | O |
| ATOM | 4061 | OW0 | HOH | Z | 421 | 29.257 | 25.725 | 56.322 | 1.00 | 40.75 | O |
| ATOM | 4062 | OW0 | HOH | Z | 422 | 32.575 | 37.652 | 43.475 | 1.00 | 41.33 | O |
| ATOM | 4063 | OW0 | HOH | Z | 423 | 37.131 | 38.600 | 50.665 | 1.00 | 44.87 | O |
| ATOM | 4064 | OW0 | HOH | Z | 424 | 41.096 | 26.637 | 21.655 | 1.00 | 51.67 | O |
| ATOM | 4065 | OW0 | HOH | Z | 425 | 26.571 | 38.214 | 31.343 | 1.00 | 46.55 | O |
| ATOM | 4066 | OW0 | HOH | Z | 426 | 24.459 | 36.787 | 46.668 | 1.00 | 44.50 | O |
| ATOM | 4067 | OW0 | HOH | Z | 427 | 25.441 | −11.303 | 46.007 | 1.00 | 51.15 | O |
| ATOM | 4068 | OW0 | HOH | Z | 428 | 46.170 | 14.110 | 31.720 | 1.00 | 39.70 | O |
| ATOM | 4069 | OW0 | HOH | Z | 429 | 29.902 | 5.490 | 64.278 | 1.00 | 45.26 | O |
| ATOM | 4070 | OW0 | HOH | Z | 430 | 12.331 | 32.728 | 34.937 | 1.00 | 52.97 | O |
| ATOM | 4071 | OW0 | HOH | Z | 431 | 18.463 | −9.869 | 42.087 | 1.00 | 44.05 | O |
| ATOM | 4072 | OW0 | HOH | Z | 432 | 19.346 | 7.038 | 6.907 | 1.00 | 44.58 | O |
| ATOM | 4073 | OW0 | HOH | Z | 433 | 9.947 | 32.080 | 6.486 | 1.00 | 48.15 | O |
| ATOM | 4074 | OW0 | HOH | Z | 434 | 13.593 | 37.717 | 37.501 | 1.00 | 42.19 | O |
| ATOM | 4075 | OW0 | HOH | Z | 435 | −4.151 | 36.587 | 19.692 | 1.00 | 54.46 | O |
| ATOM | 4076 | OW0 | HOH | Z | 436 | 46.660 | 11.419 | 22.542 | 1.00 | 54.74 | O |
| ATOM | 4077 | OW0 | HOH | Z | 437 | 3.810 | 47.805 | 35.375 | 1.00 | 61.33 | O |
| ATOM | 4078 | OW0 | HOH | Z | 438 | 37.872 | −1.810 | 57.262 | 1.00 | 45.82 | O |
| ATOM | 4079 | OW0 | HOH | Z | 439 | 36.643 | 16.851 | 59.689 | 1.00 | 52.24 | O |
| ATOM | 4080 | OW0 | HOH | Z | 440 | 31.215 | 13.085 | 15.089 | 1.00 | 44.44 | O |
| ATOM | 4081 | OW0 | HOH | Z | 441 | 31.115 | 16.489 | 12.583 | 1.00 | 46.55 | O |
| ATOM | 4082 | OW0 | HOH | Z | 442 | 13.018 | 1.170 | 31.488 | 1.00 | 71.20 | O |
| ATOM | 4083 | OW0 | HOH | Z | 443 | 28.936 | 33.840 | 39.024 | 1.00 | 57.61 | O |
| ATOM | 4084 | OW0 | HOH | Z | 444 | 23.247 | 1.244 | 14.328 | 1.00 | 46.85 | O |
| ATOM | 4085 | OW0 | HOH | Z | 445 | 13.213 | 32.167 | 10.184 | 1.00 | 42.76 | O |
| ATOM | 4086 | OW0 | HOH | Z | 446 | 27.929 | −6.168 | 61.609 | 1.00 | 45.29 | O |
| ATOM | 4087 | OW0 | HOH | Z | 448 | 0.111 | 29.318 | 7.267 | 1.00 | 47.69 | O |
| ATOM | 4088 | OW0 | HOH | Z | 449 | 33.521 | 26.325 | 56.999 | 1.00 | 44.66 | O |
| ATOM | 4089 | OW0 | HOH | Z | 450 | 25.936 | 41.619 | 29.790 | 1.00 | 39.06 | O |
| ATOM | 4090 | OW0 | HOH | Z | 451 | 43.840 | 1.243 | 37.210 | 1.00 | 49.42 | O |
| ATOM | 4091 | OW0 | HOH | Z | 452 | 11.143 | −7.541 | 50.997 | 1.00 | 43.90 | O |
| ATOM | 4092 | OW0 | HOH | Z | 453 | 0.504 | 49.006 | 40.880 | 1.00 | 49.38 | O |
| ATOM | 4093 | OW0 | HOH | Z | 454 | 49.382 | 22.778 | 22.490 | 1.00 | 50.62 | O |
| ATOM | 4094 | OW0 | HOH | Z | 455 | 4.386 | 13.382 | 24.656 | 1.00 | 62.20 | O |
| ATOM | 4095 | OW0 | HOH | Z | 456 | 22.642 | 16.253 | 62.524 | 1.00 | 40.21 | O |
| ATOM | 4096 | OW0 | HOH | Z | 457 | 19.595 | −2.565 | 63.161 | 1.00 | 54.59 | O |

TABLE 6-continued

Coordinates of the crystal structure of *E. coli* ExoI bound to compound 9

| ATOM | 4097 | OW0 | HOH | Z | 458 | 31.135 | 14.729 | 10.815 | 1.00 | 53.37 | O |
|---|---|---|---|---|---|---|---|---|---|---|---|
| ATOM | 4098 | OW0 | HOH | Z | 459 | 15.020 | −11.363 | 55.236 | 1.00 | 55.59 | O |
| ATOM | 4099 | OW0 | HOH | Z | 460 | 11.933 | 28.886 | 34.221 | 1.00 | 49.32 | O |
| ATOM | 4100 | OW0 | HOH | Z | 461 | 20.172 | 30.465 | 32.399 | 1.00 | 56.57 | O |
| ATOM | 4101 | OW0 | HOH | Z | 462 | 11.248 | 32.686 | 4.270 | 1.00 | 45.49 | O |
| ATOM | 4102 | OW0 | HOH | Z | 463 | 52.521 | 18.959 | 21.295 | 1.00 | 59.07 | O |
| ATOM | 4103 | OW0 | HOH | Z | 464 | 5.334 | 34.592 | 30.241 | 1.00 | 63.41 | O |
| ATOM | 4104 | OW0 | HOH | Z | 465 | 44.144 | 9.608 | 51.623 | 1.00 | 57.70 | O |
| ATOM | 4105 | OW0 | HOH | Z | 466 | 37.097 | 21.260 | 13.439 | 1.00 | 52.51 | O |
| ATOM | 4106 | OW0 | HOH | Z | 467 | 44.030 | 11.832 | 31.605 | 1.00 | 41.94 | O |
| ATOM | 4107 | OW0 | HOH | Z | 468 | 34.117 | 35.918 | 18.044 | 1.00 | 44.68 | O |
| ATOM | 4108 | OW0 | HOH | Z | 469 | 18.491 | 3.996 | 21.336 | 1.00 | 55.84 | O |
| ATOM | 4109 | OW0 | HOH | Z | 471 | 29.303 | 8.886 | 20.237 | 1.00 | 53.15 | O |
| ATOM | 4110 | OW0 | HOH | Z | 472 | 14.394 | 43.313 | 12.008 | 1.00 | 50.15 | O |
| ATOM | 4111 | OW0 | HOH | Z | 473 | 23.952 | 51.031 | 33.322 | 1.00 | 54.98 | O |
| ATOM | 4112 | OW0 | HOH | Z | 474 | 1.523 | 44.166 | 37.782 | 1.00 | 54.74 | O |
| ATOM | 4113 | OW0 | HOH | Z | 475 | 24.759 | 18.478 | −3.006 | 1.00 | 48.22 | O |
| ATOM | 4114 | OW0 | HOH | Z | 476 | 12.952 | 37.928 | 39.944 | 1.00 | 39.92 | O |
| ATOM | 4115 | OW0 | HOH | Z | 477 | 28.217 | −2.061 | 20.941 | 1.00 | 50.36 | O |
| ATOM | 4116 | OW0 | HOH | Z | 478 | 30.081 | −3.165 | 57.599 | 1.00 | 44.63 | O |
| ATOM | 4117 | OW0 | HOH | Z | 479 | 19.290 | 8.314 | −1.363 | 1.00 | 55.01 | O |
| ATOM | 4118 | OW0 | HOH | Z | 481 | 41.329 | 1.293 | 56.774 | 1.00 | 73.63 | O |
| ATOM | 4119 | OW0 | HOH | Z | 482 | 44.221 | 6.919 | 35.599 | 1.00 | 52.10 | O |
| ATOM | 4120 | OW0 | HOH | Z | 484 | 20.360 | 8.140 | 60.631 | 1.00 | 61.22 | O |
| ATOM | 4121 | OW0 | HOH | Z | 485 | 11.293 | 41.055 | 12.455 | 1.00 | 51.10 | O |
| ATOM | 4122 | OW0 | HOH | Z | 486 | 38.046 | 19.111 | 59.071 | 1.00 | 54.85 | O |
| ATOM | 4123 | OW0 | HOH | Z | 487 | 31.249 | 33.416 | 15.195 | 1.00 | 53.18 | O |
| ATOM | 4124 | OW0 | HOH | Z | 488 | 31.204 | 4.552 | 23.244 | 1.00 | 54.26 | O |
| ATOM | 4125 | OW0 | HOH | Z | 489 | 30.921 | −2.726 | 61.246 | 1.00 | 47.72 | O |
| ATOM | 4126 | OW0 | HOH | Z | 490 | 14.235 | −11.022 | 44.266 | 1.00 | 50.89 | O |
| ATOM | 4127 | OW0 | HOH | Z | 491 | 4.881 | 23.737 | 15.186 | 1.00 | 53.86 | O |
| ATOM | 4128 | OW0 | HOH | Z | 492 | 42.987 | 20.340 | 15.970 | 1.00 | 41.25 | O |
| ATOM | 4129 | OW0 | HOH | Z | 493 | 6.931 | 24.571 | 18.740 | 1.00 | 46.69 | O |
| ATOM | 4130 | OW0 | HOH | Z | 494 | 27.059 | 15.692 | 64.576 | 1.00 | 55.21 | O |
| ATOM | 4131 | OW0 | HOH | Z | 496 | −2.137 | 31.883 | 17.305 | 1.00 | 52.06 | O |
| ATOM | 4132 | OW0 | HOH | Z | 497 | 16.583 | 10.141 | −2.703 | 1.00 | 55.39 | O |
| ATOM | 4133 | OW0 | HOH | Z | 498 | 29.765 | 11.212 | 3.701 | 1.00 | 45.51 | O |
| ATOM | 4134 | OW0 | HOH | Z | 500 | 36.845 | 37.334 | 21.868 | 1.00 | 56.16 | O |
| ATOM | 4135 | OW0 | HOH | Z | 501 | 32.478 | 9.326 | 7.561 | 1.00 | 51.65 | O |
| ATOM | 4136 | OW0 | HOH | Z | 502 | 41.440 | 33.814 | 54.271 | 1.00 | 51.56 | O |
| ATOM | 4137 | OW0 | HOH | Z | 503 | 15.629 | 19.817 | 31.255 | 1.00 | 46.43 | O |
| ATOM | 4138 | OW0 | HOH | Z | 504 | 36.213 | −4.072 | 40.780 | 1.00 | 52.48 | O |
| ATOM | 4139 | OW0 | HOH | Z | 505 | 21.586 | 46.192 | 37.560 | 1.00 | 49.63 | O |
| ATOM | 4140 | OW0 | HOH | Z | 506 | 20.992 | 20.522 | 38.327 | 1.00 | 49.64 | O |
| ATOM | 4141 | OW0 | HOH | Z | 507 | 46.289 | 13.609 | 39.161 | 1.00 | 44.11 | O |
| ATOM | 4142 | OW0 | HOH | Z | 508 | 46.618 | 15.202 | 18.151 | 1.00 | 55.74 | O |
| ATOM | 4143 | OW0 | HOH | Z | 509 | 18.646 | 21.311 | 49.596 | 1.00 | 42.74 | O |
| ATOM | 4144 | OW0 | HOH | Z | 510 | 33.117 | 5.574 | 24.893 | 1.00 | 58.41 | O |
| ATOM | 4145 | OW0 | HOH | Z | 511 | 18.077 | 19.235 | 32.079 | 1.00 | 50.28 | O |
| ATOM | 4146 | OW0 | HOH | Z | 512 | 13.592 | 51.634 | 46.901 | 1.00 | 53.90 | O |
| ATOM | 4147 | OW0 | HOH | Z | 514 | 40.628 | 19.164 | 15.666 | 1.00 | 47.21 | O |
| ATOM | 4148 | OW0 | HOH | Z | 515 | 26.567 | 32.671 | 35.413 | 1.00 | 53.85 | O |
| ATOM | 4149 | OW0 | HOH | Z | 517 | 0.860 | 34.594 | 0.990 | 1.00 | 51.15 | O |
| ATOM | 4150 | OW0 | HOH | Z | 518 | 21.869 | 18.466 | −3.352 | 1.00 | 48.30 | O |
| ATOM | 4151 | OW0 | HOH | Z | 519 | 14.655 | 4.120 | 14.381 | 1.00 | 59.21 | O |
| ATOM | 4152 | OW0 | HOH | Z | 520 | 27.493 | 19.252 | 62.536 | 1.00 | 51.54 | O |
| ATOM | 4153 | OW0 | HOH | Z | 521 | 26.107 | 29.405 | −5.912 | 1.00 | 57.77 | O |
| ATOM | 4154 | OW0 | HOH | Z | 523 | 24.095 | 33.282 | 7.056 | 1.00 | 56.77 | O |
| ATOM | 4155 | OW0 | HOH | Z | 525 | 25.011 | 5.492 | 15.571 | 1.00 | 57.61 | O |
| ATOM | 4156 | OW0 | HOH | Z | 526 | 46.978 | 36.267 | 24.404 | 1.00 | 62.44 | O |
| ATOM | 4157 | OW0 | HOH | Z | 527 | 26.387 | 29.281 | 4.767 | 1.00 | 50.59 | O |
| ATOM | 4158 | OW0 | HOH | Z | 528 | 29.687 | 38.296 | 31.604 | 1.00 | 60.44 | O |
| ATOM | 4159 | OW0 | HOH | Z | 530 | 21.125 | 42.041 | 40.040 | 1.00 | 51.65 | O |
| ATOM | 4160 | OW0 | HOH | Z | 531 | 26.717 | 20.913 | 56.908 | 1.00 | 18.75 | O |
| ATOM | 4161 | OW0 | HOH | Z | 532 | 44.198 | 9.134 | 42.056 | 1.00 | 25.95 | O |
| ATOM | 4162 | OW0 | HOH | Z | 534 | 40.793 | 7.373 | 60.743 | 1.00 | 50.90 | O |
| ATOM | 4163 | OW0 | HOH | Z | 535 | 17.501 | 31.827 | 33.851 | 1.00 | 56.01 | O |
| ATOM | 4164 | OW0 | HOH | Z | 536 | 6.030 | 22.869 | 3.287 | 1.00 | 54.63 | O |
| ATOM | 4165 | OW0 | HOH | Z | 537 | 10.556 | 9.347 | 47.787 | 1.00 | 50.05 | O |
| ATOM | 4166 | OW0 | HOH | Z | 538 | 15.353 | 16.546 | −5.968 | 1.00 | 62.00 | O |
| ATOM | 4167 | OW0 | HOH | Z | 539 | 19.481 | 22.979 | 35.392 | 1.00 | 46.36 | O |
| ATOM | 4168 | OW0 | HOH | Z | 540 | 10.692 | 29.584 | −4.152 | 1.00 | 51.33 | O |
| ATOM | 4169 | OW0 | HOH | Z | 541 | 44.599 | 21.886 | 17.314 | 1.00 | 51.67 | O |
| ATOM | 4170 | OW0 | HOH | Z | 542 | 22.147 | 25.599 | −6.207 | 1.00 | 59.47 | O |
| ATOM | 4171 | OW0 | HOH | Z | 543 | 3.884 | 2.935 | 39.688 | 1.00 | 59.44 | O |
| ATOM | 4172 | OW0 | HOH | Z | 544 | 27.564 | 26.874 | 34.040 | 1.00 | 17.88 | O |
| ATOM | 4173 | OW0 | HOH | Z | 545 | 4.793 | 5.591 | 43.427 | 1.00 | 66.19 | O |
| ATOM | 4174 | OW0 | HOH | Z | 546 | 3.152 | 24.054 | 13.205 | 1.00 | 52.00 | O |

TABLE 6-continued

Coordinates of the crystal structure of *E. coli* ExoI bound to compound 9

| ATOM | 4175 | OW0 | HOH | Z | 547 | 15.692 | 46.446 | 42.589 | 1.00 | 51.31 | O |
|---|---|---|---|---|---|---|---|---|---|---|---|
| ATOM | 4176 | OW0 | HOH | Z | 548 | 8.000 | 7.028 | 51.624 | 1.00 | 52.37 | O |
| ATOM | 4177 | OW0 | HOH | Z | 549 | 35.215 | −5.176 | 44.476 | 1.00 | 45.88 | O |
| ATOM | 4178 | OW0 | HOH | Z | 550 | 16.928 | 4.221 | 30.356 | 1.00 | 66.82 | O |
| ATOM | 4179 | OW0 | HOH | Z | 551 | 17.797 | 45.298 | 41.629 | 1.00 | 53.33 | O |
| ATOM | 4180 | OW0 | HOH | Z | 552 | 25.483 | 41.413 | 33.816 | 1.00 | 53.83 | O |
| ATOM | 4181 | OW0 | HOH | Z | 553 | 15.556 | 33.865 | 37.776 | 1.00 | 52.86 | O |
| ATOM | 4182 | OW0 | HOH | Z | 554 | 27.337 | −10.411 | 53.575 | 1.00 | 52.88 | O |
| ATOM | 4183 | OW0 | HOH | Z | 555 | 45.968 | 11.887 | 34.801 | 1.00 | 49.96 | O |
| ATOM | 4184 | OW0 | HOH | Z | 556 | 33.579 | −0.659 | 59.497 | 1.00 | 61.78 | O |
| ATOM | 4185 | OW0 | HOH | Z | 557 | 39.215 | 14.929 | 59.684 | 1.00 | 64.64 | O |
| ATOM | 4186 | OW0 | HOH | Z | 559 | 4.022 | 23.837 | 29.725 | 1.00 | 58.44 | O |
| ATOM | 4187 | OW0 | HOH | Z | 560 | 43.751 | 7.120 | 44.081 | 1.00 | 53.66 | O |
| ATOM | 4188 | OW0 | HOH | Z | 561 | 26.890 | 30.995 | 33.381 | 1.00 | 19.60 | O |
| ATOM | 4189 | OW0 | HOH | Z | 562 | 9.207 | 10.699 | 8.511 | 1.00 | 46.88 | O |
| ATOM | 4190 | OW0 | HOH | Z | 563 | 20.032 | 15.557 | 15.518 | 1.00 | 51.24 | O |
| ATOM | 4191 | OW0 | HOH | Z | 564 | 7.878 | 7.012 | 54.356 | 1.00 | 51.39 | O |
| ATOM | 4192 | OW0 | HOH | Z | 566 | 10.276 | 20.805 | 3.467 | 1.00 | 51.83 | O |
| ATOM | 4193 | OW0 | HOH | Z | 567 | 2.844 | 47.773 | 30.163 | 1.00 | 54.85 | O |
| ATOM | 4194 | OW0 | HOH | Z | 568 | 24.328 | −1.038 | 65.505 | 1.00 | 56.23 | O |
| ATOM | 4195 | OW0 | HOH | Z | 569 | 5.510 | 14.287 | 26.944 | 1.00 | 64.54 | O |
| ATOM | 4196 | OW0 | HOH | Z | 570 | 28.826 | 29.559 | 35.291 | 1.00 | 18.91 | O |
| ATOM | 4197 | OW0 | HOH | Z | 571 | 30.590 | 7.060 | 30.452 | 1.00 | 37.05 | O |
| ATOM | 4198 | OW0 | HOH | Z | 572 | 25.895 | 26.436 | 40.448 | 1.00 | 44.93 | O |
| ATOM | 4199 | OW0 | HOH | Z | 573 | 7.981 | 47.102 | 29.714 | 1.00 | 42.60 | O |
| ATOM | 4200 | OW0 | HOH | Z | 574 | 3.738 | 45.539 | 41.948 | 1.00 | 43.51 | O |
| ATOM | 4201 | OW0 | HOH | Z | 575 | 15.872 | 52.569 | 32.650 | 1.00 | 43.50 | O |
| ATOM | 4202 | OW0 | HOH | Z | 576 | 40.977 | 10.306 | 48.238 | 1.00 | 47.42 | O |
| ATOM | 4203 | OW0 | HOH | Z | 577 | 31.615 | 12.687 | 4.974 | 1.00 | 54.35 | O |
| ATOM | 4204 | OW0 | HOH | Z | 578 | 36.763 | 5.264 | 31.403 | 1.00 | 55.54 | O |
| ATOM | 4205 | OW0 | HOH | Z | 579 | 20.058 | 27.099 | 25.492 | 1.00 | 52.07 | O |
| ATOM | 4206 | OW0 | HOH | Z | 580 | 46.513 | 11.378 | 40.749 | 1.00 | 57.50 | O |
| ATOM | 4207 | OW0 | HOH | Z | 581 | 24.468 | −8.595 | 56.576 | 1.00 | 53.31 | O |
| ATOM | 4208 | OW0 | HOH | Z | 582 | 42.920 | 13.084 | 49.055 | 1.00 | 69.61 | O |
| ATOM | 4209 | OW0 | HOH | Z | 583 | 16.869 | 18.282 | −7.940 | 1.00 | 61.38 | O |
| ATOM | 4210 | OW0 | HOH | Z | 584 | 29.255 | 14.253 | 27.767 | 1.00 | 60.96 | O |
| ATOM | 4211 | OW0 | HOH | Z | 586 | 42.338 | 2.629 | 60.950 | 1.00 | 55.14 | O |
| ATOM | 4212 | OW0 | HOH | Z | 587 | 5.060 | 41.965 | 25.271 | 1.00 | 51.23 | O |
| ATOM | 4213 | OW0 | HOH | Z | 588 | 22.095 | 10.890 | 12.872 | 1.00 | 62.83 | O |
| ATOM | 4214 | OW0 | HOH | Z | 589 | 35.187 | 3.481 | 26.566 | 1.00 | 60.98 | O |
| ATOM | 4215 | OW0 | HOH | Z | 590 | 21.325 | 45.254 | 34.133 | 1.00 | 58.44 | O |
| ATOM | 4216 | OW0 | HOH | Z | 592 | 25.851 | 28.907 | 35.091 | 1.00 | 33.06 | O |
| ATOM | 4217 | OW0 | HOH | Z | 593 | 30.294 | 32.534 | 55.904 | 1.00 | 52.54 | O |
| ATOM | 4218 | OW0 | HOH | Z | 594 | 22.960 | 22.461 | 41.608 | 1.00 | 57.35 | O |
| ATOM | 4219 | OW0 | HOH | Z | 595 | 35.665 | 31.696 | 55.608 | 1.00 | 62.87 | O |
| ATOM | 4220 | OW0 | HOH | Z | 596 | 13.449 | −11.478 | 53.120 | 1.00 | 61.95 | O |

Table 7 shows the coordinates of the crystal structure of *E. coli* ExoI bound to compound 10 that was identified in a screen according to the present invention. Compounds that bind prokaryotic exonucleases and that have crystal structures whose models substantially represent the atomic coordinates specified in Table 7, can be used for practicing the present invention.

TABLE 7

Coordinates of the crystal structure of *E. coli* ExoI bound to compound 10

| REMARK | Written by O version 11.0.0 | | | | | | | | | | |
|---|---|---|---|---|---|---|---|---|---|---|---|
| REMARK | Wed Apr | 2 12:04:12 2008 | | | | | | | | | |
| CRYST1 | 52.671 | 91.939 | 103.081 | 90.00 | 90.00 | 90.00 | | | | | |
| ORIGX1 | 1.000000 | 0.000000 | 0.000000 | 0.00000 | | | | | | | |
| ORIGX2 | 0.000000 | 1.000000 | 0.000000 | 0.00000 | | | | | | | |
| ORIGX3 | 0.000000 | 0.000000 | 1.000000 | 0.00000 | | | | | | | |
| SCALE1 | 0.018986 | 0.000000 | 0.000000 | 0.00000 | | | | | | | |
| SCALE2 | 0.000000 | 0.010877 | 0.000000 | 0.00000 | | | | | | | |
| SCALE3 | 0.000000 | 0.000000 | 0.009701 | 0.00000 | | | | | | | |
| ATOM | 1 | N | GLN | A | 7 | 49.018 | 15.739 | 17.237 | 1.00 | 24.46 | 7 |
| ATOM | 2 | CA | GLN | A | 7 | 47.830 | 16.318 | 17.933 | 1.00 | 24.31 | 6 |
| ATOM | 3 | CB | GLN | A | 7 | 46.544 | 15.607 | 17.482 | 1.00 | 24.69 | 6 |
| ATOM | 4 | CG | GLN | A | 7 | 45.239 | 16.298 | 17.902 | 1.00 | 25.93 | 6 |
| ATOM | 5 | CD | GLN | A | 7 | 44.941 | 17.567 | 17.108 | 1.00 | 27.82 | 6 |
| ATOM | 6 | OE1 | GLN | A | 7 | 45.555 | 17.830 | 16.069 | 1.00 | 28.38 | 8 |
| ATOM | 7 | NE2 | GLN | A | 7 | 43.988 | 18.356 | 17.596 | 1.00 | 27.72 | 7 |
| ATOM | 8 | C | GLN | A | 7 | 47.998 | 16.229 | 19.449 | 1.00 | 23.82 | 6 |
| ATOM | 9 | O | GLN | A | 7 | 48.179 | 15.142 | 20.005 | 1.00 | 23.86 | 8 |
| ATOM | 10 | N | GLN | A | 8 | 47.955 | 17.383 | 20.109 | 1.00 | 23.00 | 7 |

TABLE 7-continued

Coordinates of the crystal structure of *E. coli* ExoI bound to compound 10

| ATOM | 11 | CA | GLN | A | 8 | 48.120 | 17.451 | 21.554 | 1.00 | 22.42 | 6 |
|---|---|---|---|---|---|---|---|---|---|---|---|
| ATOM | 12 | CB | GLN | A | 8 | 48.937 | 18.696 | 21.947 | 1.00 | 22.71 | 6 |
| ATOM | 13 | CG | GLN | A | 8 | 48.107 | 19.966 | 22.161 | 1.00 | 23.51 | 6 |
| ATOM | 14 | CD | GLN | A | 8 | 48.940 | 21.241 | 22.139 | 1.00 | 23.89 | 6 |
| ATOM | 15 | OE1 | GLN | A | 8 | 49.712 | 21.477 | 21.205 | 1.00 | 25.61 | 8 |
| ATOM | 16 | NE2 | GLN | A | 8 | 48.767 | 22.082 | 23.158 | 1.00 | 23.84 | 7 |
| ATOM | 17 | C | GLN | A | 8 | 46.759 | 17.465 | 22.243 | 1.00 | 21.15 | 6 |
| ATOM | 18 | O | GLN | A | 8 | 45.751 | 17.855 | 21.642 | 1.00 | 21.30 | 8 |
| ATOM | 19 | N | SER | A | 9 | 46.736 | 17.043 | 23.504 | 1.00 | 19.81 | 7 |
| ATOM | 20 | CA | SER | A | 9 | 45.531 | 17.127 | 24.307 | 1.00 | 18.37 | 6 |
| ATOM | 21 | CB | SER | A | 9 | 45.670 | 16.289 | 25.574 | 1.00 | 18.76 | 6 |
| ATOM | 22 | OG | SER | A | 9 | 45.774 | 14.908 | 25.254 | 1.00 | 18.85 | 8 |
| ATOM | 23 | C | SER | A | 9 | 45.253 | 18.585 | 24.654 | 1.00 | 17.20 | 6 |
| ATOM | 24 | O | SER | A | 9 | 46.175 | 19.342 | 24.984 | 1.00 | 16.49 | 8 |
| ATOM | 25 | N | THR | A | 10 | 43.987 | 18.985 | 24.541 | 1.00 | 15.77 | 7 |
| ATOM | 26 | CA | THR | A | 10 | 43.577 | 20.347 | 24.902 | 1.00 | 14.81 | 6 |
| ATOM | 27 | CB | THR | A | 10 | 43.376 | 21.275 | 23.650 | 1.00 | 14.71 | 6 |
| ATOM | 28 | OG1 | THR | A | 10 | 42.350 | 20.753 | 22.791 | 1.00 | 16.16 | 8 |
| ATOM | 29 | CG2 | THR | A | 10 | 44.672 | 21.429 | 22.874 | 1.00 | 15.06 | 6 |
| ATOM | 30 | C | THR | A | 10 | 42.316 | 20.355 | 25.762 | 1.00 | 13.86 | 6 |
| ATOM | 31 | O | THR | A | 10 | 41.611 | 19.354 | 25.855 | 1.00 | 12.93 | 8 |
| ATOM | 32 | N | PHE | A | 11 | 42.072 | 21.491 | 26.412 | 1.00 | 12.98 | 7 |
| ATOM | 33 | CA | PHE | A | 11 | 40.811 | 21.757 | 27.082 | 1.00 | 12.52 | 6 |
| ATOM | 34 | CB | PHE | A | 11 | 41.059 | 22.241 | 28.513 | 1.00 | 12.52 | 6 |
| ATOM | 35 | CG | PHE | A | 11 | 41.543 | 21.175 | 29.438 | 1.00 | 12.02 | 6 |
| ATOM | 36 | CD1 | PHE | A | 11 | 40.636 | 20.341 | 30.092 | 1.00 | 11.55 | 6 |
| ATOM | 37 | CE1 | PHE | A | 11 | 41.078 | 19.360 | 30.962 | 1.00 | 14.18 | 6 |
| ATOM | 38 | CZ | PHE | A | 11 | 42.438 | 19.203 | 31.196 | 1.00 | 13.48 | 6 |
| ATOM | 39 | CE2 | PHE | A | 11 | 43.355 | 20.032 | 30.557 | 1.00 | 13.73 | 6 |
| ATOM | 40 | CD2 | PHE | A | 11 | 42.903 | 21.018 | 29.688 | 1.00 | 12.71 | 6 |
| ATOM | 41 | C | PHE | A | 11 | 40.093 | 22.847 | 26.321 | 1.00 | 12.33 | 6 |
| ATOM | 42 | O | PHE | A | 11 | 40.713 | 23.831 | 25.921 | 1.00 | 12.71 | 8 |
| ATOM | 43 | N | LEU | A | 12 | 38.795 | 22.665 | 26.096 | 1.00 | 11.52 | 7 |
| ATOM | 44 | CA | LEU | A | 12 | 37.965 | 23.748 | 25.588 | 1.00 | 11.19 | 6 |
| ATOM | 45 | CB | LEU | A | 12 | 37.265 | 23.363 | 24.276 | 1.00 | 11.40 | 6 |
| ATOM | 46 | CG | LEU | A | 12 | 36.596 | 24.520 | 23.514 | 1.00 | 12.89 | 6 |
| ATOM | 47 | CD1 | LEU | A | 12 | 37.629 | 25.449 | 22.874 | 1.00 | 12.88 | 6 |
| ATOM | 48 | CD2 | LEU | A | 12 | 35.657 | 23.989 | 22.468 | 1.00 | 14.11 | 6 |
| ATOM | 49 | C | LEU | A | 12 | 36.959 | 24.160 | 26.653 | 1.00 | 10.57 | 6 |
| ATOM | 50 | O | LEU | A | 12 | 35.951 | 23.485 | 26.876 | 1.00 | 10.17 | 8 |
| ATOM | 51 | N | PHE | A | 13 | 37.278 | 25.253 | 27.340 | 1.00 | 10.48 | 7 |
| ATOM | 52 | CA | PHE | A | 13 | 36.382 | 25.847 | 28.311 | 1.00 | 10.55 | 6 |
| ATOM | 53 | CB | PHE | A | 13 | 37.162 | 26.805 | 29.223 | 1.00 | 10.60 | 6 |
| ATOM | 54 | CG | PHE | A | 13 | 38.104 | 26.108 | 30.174 | 1.00 | 9.17 | 6 |
| ATOM | 55 | CD1 | PHE | A | 13 | 37.705 | 25.808 | 31.480 | 1.00 | 9.71 | 6 |
| ATOM | 56 | CE1 | PHE | A | 13 | 38.578 | 25.147 | 32.358 | 1.00 | 9.31 | 6 |
| ATOM | 57 | CZ | PHE | A | 13 | 39.852 | 24.775 | 31.937 | 1.00 | 9.96 | 6 |
| ATOM | 58 | CE2 | PHE | A | 13 | 40.264 | 25.071 | 30.656 | 1.00 | 8.24 | 6 |
| ATOM | 59 | CD2 | PHE | A | 13 | 39.380 | 25.733 | 29.768 | 1.00 | 8.18 | 6 |
| ATOM | 60 | C | PHE | A | 13 | 35.300 | 26.596 | 27.553 | 1.00 | 10.42 | 6 |
| ATOM | 61 | O | PHE | A | 13 | 35.594 | 27.305 | 26.584 | 1.00 | 11.02 | 8 |
| ATOM | 62 | N | HIS | A | 14 | 34.048 | 26.422 | 27.965 | 1.00 | 10.45 | 7 |
| ATOM | 63 | CA | HIS | A | 14 | 32.944 | 27.090 | 27.282 | 1.00 | 10.63 | 6 |
| ATOM | 64 | CB | HIS | A | 14 | 32.417 | 26.218 | 26.148 | 1.00 | 10.60 | 6 |
| ATOM | 65 | CG | HIS | A | 14 | 31.633 | 25.037 | 26.626 | 1.00 | 9.92 | 6 |
| ATOM | 66 | ND1 | HIS | A | 14 | 30.254 | 24.986 | 26.578 | 1.00 | 12.95 | 7 |
| ATOM | 67 | CE1 | HIS | A | 14 | 29.844 | 23.836 | 27.089 | 1.00 | 10.19 | 6 |
| ATOM | 68 | NE2 | HIS | A | 14 | 30.903 | 23.145 | 27.467 | 1.00 | 10.83 | 7 |
| ATOM | 69 | CD2 | HIS | A | 14 | 32.032 | 23.881 | 27.206 | 1.00 | 10.15 | 6 |
| ATOM | 70 | C | HIS | A | 14 | 31.797 | 27.434 | 28.210 | 1.00 | 10.83 | 6 |
| ATOM | 71 | O | HIS | A | 14 | 31.660 | 26.867 | 29.306 | 1.00 | 11.10 | 8 |
| ATOM | 72 | N | ASP | A | 15 | 30.955 | 28.351 | 27.745 | 1.00 | 11.37 | 7 |
| ATOM | 73 | CA | ASP | A | 15 | 29.776 | 28.773 | 28.486 | 1.00 | 11.71 | 6 |
| ATOM | 74 | CB | ASP | A | 15 | 30.161 | 29.825 | 29.524 | 1.00 | 12.27 | 6 |
| ATOM | 75 | CG | ASP | A | 15 | 29.045 | 30.118 | 30.500 | 1.00 | 13.18 | 6 |
| ATOM | 76 | OD1 | ASP | A | 15 | 28.489 | 29.159 | 31.076 | 1.00 | 14.77 | 8 |
| ATOM | 77 | OD2 | ASP | A | 15 | 28.728 | 31.316 | 30.698 | 1.00 | 15.12 | 8 |
| ATOM | 78 | C | ASP | A | 15 | 28.722 | 29.343 | 27.528 | 1.00 | 11.86 | 6 |
| ATOM | 79 | O | ASP | A | 15 | 29.061 | 30.065 | 26.575 | 1.00 | 11.63 | 8 |
| ATOM | 80 | N | TYR | A | 16 | 27.454 | 29.009 | 27.780 | 1.00 | 11.81 | 7 |
| ATOM | 81 | CA | TYR | A | 16 | 26.327 | 29.640 | 27.069 | 1.00 | 11.91 | 6 |
| ATOM | 82 | CB | TYR | A | 16 | 25.243 | 28.613 | 26.732 | 1.00 | 12.10 | 6 |
| ATOM | 83 | CG | TYR | A | 16 | 25.583 | 27.600 | 25.659 | 1.00 | 11.13 | 6 |
| ATOM | 84 | CD1 | TYR | A | 16 | 25.346 | 27.873 | 24.308 | 1.00 | 11.76 | 6 |
| ATOM | 85 | CE1 | TYR | A | 16 | 25.625 | 26.924 | 23.317 | 1.00 | 11.01 | 6 |
| ATOM | 86 | CZ | TYR | A | 16 | 26.139 | 25.682 | 23.688 | 1.00 | 11.35 | 6 |
| ATOM | 87 | OH | TYR | A | 16 | 26.427 | 24.734 | 22.728 | 1.00 | 11.33 | 8 |
| ATOM | 88 | CE2 | TYR | A | 16 | 26.367 | 25.391 | 25.020 | 1.00 | 10.23 | 6 |

TABLE 7-continued

Coordinates of the crystal structure of *E. coli* ExoI bound to compound 10

| ATOM | 89 | CD2 | TYR | A | 16 | 26.085 | 26.344 | 25.998 | 1.00 | 11.77 | 6 |
|---|---|---|---|---|---|---|---|---|---|---|---|
| ATOM | 90 | C | TYR | A | 16 | 25.678 | 30.710 | 27.935 | 1.00 | 12.47 | 6 |
| ATOM | 91 | O | TYR | A | 16 | 25.557 | 30.544 | 29.146 | 1.00 | 12.24 | 8 |
| ATOM | 92 | N | GLU | A | 17 | 25.233 | 31.794 | 27.310 | 1.00 | 12.41 | 7 |
| ATOM | 93 | CA | GLU | A | 17 | 24.137 | 32.578 | 27.880 | 1.00 | 12.84 | 6 |
| ATOM | 94 | CB | GLU | A | 17 | 24.423 | 34.082 | 27.837 | 1.00 | 13.01 | 6 |
| ATOM | 95 | CG | GLU | A | 17 | 25.759 | 34.505 | 28.463 | 1.00 | 14.96 | 6 |
| ATOM | 96 | CD | GLU | A | 17 | 25.787 | 34.380 | 29.986 | 1.00 | 18.85 | 6 |
| ATOM | 97 | OE1 | GLU | A | 17 | 24.713 | 34.341 | 30.620 | 1.00 | 19.07 | 8 |
| ATOM | 98 | OE2 | GLU | A | 17 | 26.897 | 34.311 | 30.546 | 1.00 | 21.68 | 8 |
| ATOM | 99 | C | GLU | A | 17 | 22.911 | 32.243 | 27.049 | 1.00 | 12.28 | 6 |
| ATOM | 100 | O | GLU | A | 17 | 22.998 | 32.159 | 25.825 | 1.00 | 11.95 | 8 |
| ATOM | 101 | N | THR | A | 18 | 21.782 | 32.004 | 27.711 | 1.00 | 12.09 | 7 |
| ATOM | 102 | CA | THR | A | 18 | 20.561 | 31.608 | 27.010 | 1.00 | 11.78 | 6 |
| ATOM | 103 | CB | THR | A | 18 | 20.127 | 30.154 | 27.338 | 1.00 | 12.03 | 6 |
| ATOM | 104 | OG1 | THR | A | 18 | 19.576 | 30.108 | 28.654 | 1.00 | 11.44 | 8 |
| ATOM | 105 | CG2 | THR | A | 18 | 21.305 | 29.175 | 27.232 | 1.00 | 11.23 | 6 |
| ATOM | 106 | C | THR | A | 18 | 19.406 | 32.549 | 27.328 | 1.00 | 11.91 | 6 |
| ATOM | 107 | O | THR | A | 18 | 19.509 | 33.419 | 28.200 | 1.00 | 12.02 | 8 |
| ATOM | 108 | N | PHE | A | 19 | 18.300 | 32.361 | 26.620 | 1.00 | 11.86 | 7 |
| ATOM | 109 | CA | PHE | A | 19 | 17.111 | 33.173 | 26.828 | 1.00 | 12.22 | 6 |
| ATOM | 110 | CB | PHE | A | 19 | 16.438 | 33.464 | 25.485 | 1.00 | 12.24 | 6 |
| ATOM | 111 | CG | PHE | A | 19 | 17.136 | 34.516 | 24.692 | 1.00 | 12.23 | 6 |
| ATOM | 112 | CD1 | PHE | A | 19 | 17.305 | 35.803 | 25.215 | 1.00 | 11.27 | 6 |
| ATOM | 113 | CE1 | PHE | A | 19 | 17.969 | 36.799 | 24.481 | 1.00 | 12.54 | 6 |
| ATOM | 114 | CZ | PHE | A | 19 | 18.464 | 36.506 | 23.222 | 1.00 | 12.84 | 6 |
| ATOM | 115 | CE2 | PHE | A | 19 | 18.300 | 35.230 | 22.687 | 1.00 | 13.20 | 6 |
| ATOM | 116 | CD2 | PHE | A | 19 | 17.639 | 34.235 | 23.429 | 1.00 | 13.06 | 6 |
| ATOM | 117 | C | PHE | A | 19 | 16.136 | 32.557 | 27.836 | 1.00 | 12.67 | 6 |
| ATOM | 118 | O | PHE | A | 19 | 15.051 | 33.091 | 28.074 | 1.00 | 13.29 | 8 |
| ATOM | 119 | N | GLY | A | 20 | 16.544 | 31.457 | 28.461 | 1.00 | 13.25 | 7 |
| ATOM | 120 | CA | GLY | A | 20 | 15.726 | 30.830 | 29.500 | 1.00 | 14.08 | 6 |
| ATOM | 121 | C | GLY | A | 20 | 16.365 | 29.605 | 30.119 | 1.00 | 14.32 | 6 |
| ATOM | 122 | O | GLY | A | 20 | 17.464 | 29.197 | 29.727 | 1.00 | 14.46 | 8 |
| ATOM | 123 | N | THR | A | 21 | 15.654 | 28.993 | 31.062 | 1.00 | 14.83 | 7 |
| ATOM | 124 | CA | THR | A | 21 | 16.214 | 27.901 | 31.872 | 1.00 | 15.80 | 6 |
| ATOM | 125 | CB | THR | A | 21 | 15.575 | 27.827 | 33.293 | 1.00 | 15.79 | 6 |
| ATOM | 126 | OG1 | THR | A | 21 | 14.147 | 27.766 | 33.190 | 1.00 | 17.19 | 8 |
| ATOM | 127 | CG2 | THR | A | 21 | 15.992 | 29.022 | 34.165 | 1.00 | 17.19 | 6 |
| ATOM | 128 | C | THR | A | 21 | 16.084 | 26.523 | 31.227 | 1.00 | 15.42 | 6 |
| ATOM | 129 | O | THR | A | 21 | 16.817 | 25.606 | 31.584 | 1.00 | 15.27 | 8 |
| ATOM | 130 | N | HIS | A | 22 | 15.135 | 26.370 | 30.306 | 1.00 | 15.74 | 7 |
| ATOM | 131 | CA | HIS | A | 22 | 14.893 | 25.066 | 29.684 | 1.00 | 16.15 | 6 |
| ATOM | 132 | CB | HIS | A | 22 | 13.440 | 24.945 | 29.225 | 1.00 | 16.16 | 6 |
| ATOM | 133 | CG | HIS | A | 22 | 12.998 | 23.534 | 28.986 | 1.00 | 16.41 | 6 |
| ATOM | 134 | ND1 | HIS | A | 22 | 11.971 | 22.945 | 29.694 | 1.00 | 17.55 | 7 |
| ATOM | 135 | CE1 | HIS | A | 22 | 11.805 | 21.702 | 29.273 | 1.00 | 18.23 | 6 |
| ATOM | 136 | NE2 | HIS | A | 22 | 12.695 | 21.460 | 28.326 | 1.00 | 17.96 | 7 |
| ATOM | 137 | CD2 | HIS | A | 22 | 13.457 | 22.588 | 28.132 | 1.00 | 16.94 | 6 |
| ATOM | 138 | C | HIS | A | 22 | 15.859 | 24.827 | 28.519 | 1.00 | 16.60 | 6 |
| ATOM | 139 | O | HIS | A | 22 | 15.827 | 25.556 | 27.522 | 1.00 | 16.53 | 8 |
| ATOM | 140 | N | PRO | A | 23 | 16.727 | 23.796 | 28.644 | 1.00 | 17.14 | 7 |
| ATOM | 141 | CA | PRO | A | 23 | 17.791 | 23.552 | 27.661 | 1.00 | 17.15 | 6 |
| ATOM | 142 | CB | PRO | A | 23 | 18.491 | 22.297 | 28.199 | 1.00 | 17.23 | 6 |
| ATOM | 143 | CG | PRO | A | 23 | 18.096 | 22.196 | 29.625 | 1.00 | 17.52 | 6 |
| ATOM | 144 | CD | PRO | A | 23 | 16.733 | 22.794 | 29.722 | 1.00 | 17.32 | 6 |
| ATOM | 145 | C | PRO | A | 23 | 17.254 | 23.279 | 26.257 | 1.00 | 17.00 | 6 |
| ATOM | 146 | O | PRO | A | 23 | 17.957 | 23.518 | 25.271 | 1.00 | 17.62 | 8 |
| ATOM | 147 | N | ALA | A | 24 | 16.013 | 22.799 | 26.175 | 1.00 | 16.75 | 7 |
| ATOM | 148 | CA | ALA | A | 24 | 15.382 | 22.442 | 24.902 | 1.00 | 16.60 | 6 |
| ATOM | 149 | CB | ALA | A | 24 | 14.682 | 21.096 | 25.022 | 1.00 | 16.72 | 6 |
| ATOM | 150 | C | ALA | A | 24 | 14.405 | 23.497 | 24.374 | 1.00 | 16.34 | 6 |
| ATOM | 151 | O | ALA | A | 24 | 14.411 | 23.807 | 23.177 | 1.00 | 17.23 | 8 |
| ATOM | 152 | N | LEU | A | 25 | 13.571 | 24.039 | 25.264 | 1.00 | 15.74 | 7 |
| ATOM | 153 | CA | LEU | A | 25 | 12.443 | 24.894 | 24.863 | 1.00 | 14.72 | 6 |
| ATOM | 154 | CB | LEU | A | 25 | 11.207 | 24.588 | 25.715 | 1.00 | 15.02 | 6 |
| ATOM | 155 | CG | LEU | A | 25 | 10.619 | 23.178 | 25.556 | 1.00 | 16.37 | 6 |
| ATOM | 156 | CD1 | LEU | A | 25 | 9.476 | 22.944 | 26.541 | 1.00 | 17.06 | 6 |
| ATOM | 157 | CD2 | LEU | A | 25 | 10.164 | 22.927 | 24.121 | 1.00 | 17.74 | 6 |
| ATOM | 158 | C | LEU | A | 25 | 12.758 | 26.391 | 24.896 | 1.00 | 14.10 | 6 |
| ATOM | 159 | O | LEU | A | 25 | 11.990 | 27.211 | 24.380 | 1.00 | 13.80 | 8 |
| ATOM | 160 | N | ASP | A | 26 | 13.880 | 26.738 | 25.507 | 1.00 | 12.91 | 7 |
| ATOM | 161 | CA | ASP | A | 26 | 14.400 | 28.093 | 25.426 | 1.00 | 12.72 | 6 |
| ATOM | 162 | CB | ASP | A | 26 | 14.805 | 28.583 | 26.811 | 1.00 | 12.47 | 6 |
| ATOM | 163 | CG | ASP | A | 26 | 13.604 | 28.886 | 27.683 | 1.00 | 12.52 | 6 |
| ATOM | 164 | OD1 | ASP | A | 26 | 12.746 | 29.681 | 27.242 | 1.00 | 13.57 | 8 |
| ATOM | 165 | OD2 | ASP | A | 26 | 13.519 | 28.339 | 28.814 | 1.00 | 14.49 | 8 |
| ATOM | 166 | C | ASP | A | 26 | 15.583 | 28.102 | 24.479 | 1.00 | 12.67 | 6 |

TABLE 7-continued

Coordinates of the crystal structure of *E. coli* ExoI bound to compound 10

| ATOM | 167 | O | ASP | A | 26 | 16.211 | 27.070 | 24.271 | 1.00 | 13.61 | 8 |
|---|---|---|---|---|---|---|---|---|---|---|---|
| ATOM | 168 | N | ARG | A | 27 | 15.864 | 29.260 | 23.886 | 1.00 | 12.50 | 7 |
| ATOM | 169 | CA | ARG | A | 27 | 16.893 | 29.364 | 22.854 | 1.00 | 12.20 | 6 |
| ATOM | 170 | CB | ARG | A | 27 | 16.396 | 30.204 | 21.662 | 1.00 | 12.54 | 6 |
| ATOM | 171 | CG | ARG | A | 27 | 14.996 | 29.860 | 21.135 | 1.00 | 12.35 | 6 |
| ATOM | 172 | CD | ARG | A | 27 | 14.897 | 28.450 | 20.545 | 1.00 | 12.86 | 6 |
| ATOM | 173 | NE | ARG | A | 27 | 13.506 | 28.000 | 20.484 | 1.00 | 13.60 | 7 |
| ATOM | 174 | CZ | ARG | A | 27 | 12.628 | 28.370 | 19.548 | 1.00 | 12.96 | 6 |
| ATOM | 175 | NH1 | ARG | A | 27 | 12.988 | 29.206 | 18.581 | 1.00 | 12.94 | 7 |
| ATOM | 176 | NH2 | ARG | A | 27 | 11.380 | 27.915 | 19.593 | 1.00 | 13.40 | 7 |
| ATOM | 177 | C | ARG | A | 27 | 18.176 | 29.972 | 23.423 | 1.00 | 12.27 | 6 |
| ATOM | 178 | O | ARG | A | 27 | 18.123 | 30.804 | 24.331 | 1.00 | 12.51 | 8 |
| ATOM | 179 | N | PRO | A | 28 | 19.337 | 29.573 | 22.874 | 1.00 | 11.85 | 7 |
| ATOM | 180 | CA | PRO | A | 28 | 20.615 | 30.147 | 23.299 | 1.00 | 11.63 | 6 |
| ATOM | 181 | CB | PRO | A | 28 | 21.641 | 29.264 | 22.582 | 1.00 | 11.77 | 6 |
| ATOM | 182 | CG | PRO | A | 28 | 20.919 | 28.789 | 21.356 | 1.00 | 11.13 | 6 |
| ATOM | 183 | CD | PRO | A | 28 | 19.511 | 28.573 | 21.803 | 1.00 | 11.90 | 6 |
| ATOM | 184 | C | PRO | A | 28 | 20.742 | 31.599 | 22.834 | 1.00 | 11.77 | 6 |
| ATOM | 185 | O | PRO | A | 28 | 20.088 | 31.989 | 21.864 | 1.00 | 12.13 | 8 |
| ATOM | 186 | N | ALA | A | 29 | 21.562 | 32.388 | 23.528 | 1.00 | 11.15 | 7 |
| ATOM | 187 | CA | ALA | A | 29 | 21.807 | 33.774 | 23.142 | 1.00 | 12.03 | 6 |
| ATOM | 188 | CB | ALA | A | 29 | 21.475 | 34.719 | 24.283 | 1.00 | 11.55 | 6 |
| ATOM | 189 | C | ALA | A | 29 | 23.246 | 33.980 | 22.694 | 1.00 | 11.81 | 6 |
| ATOM | 190 | O | ALA | A | 29 | 23.504 | 34.637 | 21.693 | 1.00 | 12.43 | 8 |
| ATOM | 191 | N | GLN | A | 30 | 24.183 | 33.421 | 23.455 | 1.00 | 12.09 | 7 |
| ATOM | 192 | CA | GLN | A | 30 | 25.595 | 33.668 | 23.240 | 1.00 | 12.07 | 6 |
| ATOM | 193 | CB | GLN | A | 30 | 26.028 | 34.870 | 24.083 | 1.00 | 12.59 | 6 |
| ATOM | 194 | CG | GLN | A | 30 | 27.437 | 35.367 | 23.838 | 1.00 | 13.47 | 6 |
| ATOM | 195 | CD | GLN | A | 30 | 27.927 | 36.215 | 24.984 | 1.00 | 14.83 | 6 |
| ATOM | 196 | OE1 | GLN | A | 30 | 28.061 | 35.733 | 26.106 | 1.00 | 16.56 | 8 |
| ATOM | 197 | NE2 | GLN | A | 30 | 28.184 | 37.484 | 24.716 | 1.00 | 15.99 | 7 |
| ATOM | 198 | C | GLN | A | 30 | 26.385 | 32.426 | 23.640 | 1.00 | 12.09 | 6 |
| ATOM | 199 | O | GLN | A | 30 | 26.045 | 31.753 | 24.613 | 1.00 | 11.17 | 8 |
| ATOM | 200 | N | PHE | A | 31 | 27.438 | 32.139 | 22.882 | 1.00 | 11.30 | 7 |
| ATOM | 201 | CA | PHE | A | 31 | 28.379 | 31.072 | 23.200 | 1.00 | 11.89 | 6 |
| ATOM | 202 | CB | PHE | A | 31 | 28.444 | 30.078 | 22.034 | 1.00 | 12.06 | 6 |
| ATOM | 203 | CG | PHE | A | 31 | 29.481 | 28.995 | 22.198 | 1.00 | 11.91 | 6 |
| ATOM | 204 | CD1 | PHE | A | 31 | 29.169 | 27.804 | 22.851 | 1.00 | 12.42 | 6 |
| ATOM | 205 | CE1 | PHE | A | 31 | 30.120 | 26.791 | 22.992 | 1.00 | 11.85 | 6 |
| ATOM | 206 | CZ | PHE | A | 31 | 31.397 | 26.951 | 22.450 | 1.00 | 12.35 | 6 |
| ATOM | 207 | CE2 | PHE | A | 31 | 31.716 | 28.124 | 21.771 | 1.00 | 11.72 | 6 |
| ATOM | 208 | CD2 | PHE | A | 31 | 30.758 | 29.142 | 21.648 | 1.00 | 11.50 | 6 |
| ATOM | 209 | C | PHE | A | 31 | 29.743 | 31.709 | 23.395 | 1.00 | 12.10 | 6 |
| ATOM | 210 | O | PHE | A | 31 | 30.140 | 32.560 | 22.605 | 1.00 | 11.84 | 8 |
| ATOM | 211 | N | ALA | A | 32 | 30.452 | 31.309 | 24.452 | 1.00 | 12.21 | 7 |
| ATOM | 212 | CA | ALA | A | 32 | 31.811 | 31.801 | 24.688 | 1.00 | 12.39 | 6 |
| ATOM | 213 | CB | ALA | A | 32 | 31.831 | 32.816 | 25.826 | 1.00 | 12.54 | 6 |
| ATOM | 214 | C | ALA | A | 32 | 32.728 | 30.634 | 24.996 | 1.00 | 12.38 | 6 |
| ATOM | 215 | O | ALA | A | 32 | 32.351 | 29.720 | 25.724 | 1.00 | 12.73 | 8 |
| ATOM | 216 | N | ALA | A | 33 | 33.928 | 30.654 | 24.422 | 1.00 | 12.31 | 7 |
| ATOM | 217 | CA | ALA | A | 33 | 34.885 | 29.565 | 24.637 | 1.00 | 11.94 | 6 |
| ATOM | 218 | CB | ALA | A | 33 | 34.574 | 28.405 | 23.715 | 1.00 | 12.28 | 6 |
| ATOM | 219 | C | ALA | A | 33 | 36.328 | 30.003 | 24.449 | 1.00 | 11.89 | 6 |
| ATOM | 220 | O | ALA | A | 33 | 36.606 | 31.015 | 23.807 | 1.00 | 12.03 | 8 |
| ATOM | 221 | N | ILE | A | 34 | 37.245 | 29.229 | 25.016 | 1.00 | 11.36 | 7 |
| ATOM | 222 | CA | ILE | A | 34 | 38.667 | 29.395 | 24.730 | 1.00 | 11.33 | 6 |
| ATOM | 223 | CB | ILE | A | 34 | 39.299 | 30.571 | 25.532 | 1.00 | 11.33 | 6 |
| ATOM | 224 | CG1 | ILE | A | 34 | 40.464 | 31.201 | 24.749 | 1.00 | 10.79 | 6 |
| ATOM | 225 | CD1 | ILE | A | 34 | 40.945 | 32.519 | 25.330 | 1.00 | 12.13 | 6 |
| ATOM | 226 | CG2 | ILE | A | 34 | 39.748 | 30.123 | 26.903 | 1.00 | 12.48 | 6 |
| ATOM | 227 | C | ILE | A | 34 | 39.404 | 28.088 | 24.976 | 1.00 | 10.94 | 6 |
| ATOM | 228 | O | ILE | A | 34 | 39.032 | 27.316 | 25.854 | 1.00 | 10.90 | 8 |
| ATOM | 229 | N | ARG | A | 35 | 40.446 | 27.847 | 24.181 | 1.00 | 10.73 | 7 |
| ATOM | 230 | CA | ARG | A | 35 | 41.194 | 26.603 | 24.237 | 1.00 | 10.86 | 6 |
| ATOM | 231 | CB | ARG | A | 35 | 41.493 | 26.100 | 22.822 | 1.00 | 10.71 | 6 |
| ATOM | 232 | CG | ARG | A | 35 | 41.842 | 24.629 | 22.751 | 1.00 | 10.78 | 6 |
| ATOM | 233 | CD | ARG | A | 35 | 42.094 | 24.195 | 21.314 | 1.00 | 10.27 | 6 |
| ATOM | 234 | NE | ARG | A | 35 | 40.858 | 24.172 | 20.530 | 1.00 | 11.64 | 7 |
| ATOM | 235 | CZ | ARG | A | 35 | 39.989 | 23.166 | 20.525 | 1.00 | 11.78 | 6 |
| ATOM | 236 | NH1 | ARG | A | 35 | 40.200 | 22.092 | 21.278 | 1.00 | 13.11 | 7 |
| ATOM | 237 | NH2 | ARG | A | 35 | 38.899 | 23.238 | 19.773 | 1.00 | 13.03 | 7 |
| ATOM | 238 | C | ARG | A | 35 | 42.499 | 26.794 | 24.990 | 1.00 | 11.01 | 6 |
| ATOM | 239 | O | ARG | A | 35 | 43.199 | 27.785 | 24.792 | 1.00 | 10.81 | 8 |
| ATOM | 240 | N | THR | A | 36 | 42.821 | 25.835 | 25.851 | 1.00 | 11.74 | 7 |
| ATOM | 241 | CA | THR | A | 36 | 44.089 | 25.843 | 26.579 | 1.00 | 11.91 | 6 |
| ATOM | 242 | CB | THR | A | 36 | 43.896 | 25.976 | 28.114 | 1.00 | 12.23 | 6 |
| ATOM | 243 | OG1 | THR | A | 36 | 43.503 | 24.715 | 28.658 | 1.00 | 11.98 | 8 |
| ATOM | 244 | CG2 | THR | A | 36 | 42.868 | 27.059 | 28.480 | 1.00 | 10.73 | 6 |

TABLE 7-continued

Coordinates of the crystal structure of *E. coli* ExoI bound to compound 10

| ATOM | 245 | C | THR | A | 36 | 44.825 | 24.536 | 26.330 | 1.00 | 12.22 | 6 |
|---|---|---|---|---|---|---|---|---|---|---|---|
| ATOM | 246 | O | THR | A | 36 | 44.229 | 23.551 | 25.899 | 1.00 | 12.29 | 8 |
| ATOM | 247 | N | ASP | A | 37 | 46.118 | 24.524 | 26.629 | 1.00 | 12.85 | 7 |
| ATOM | 248 | CA | ASP | A | 37 | 46.894 | 23.290 | 26.608 | 1.00 | 13.49 | 6 |
| ATOM | 249 | CB | ASP | A | 37 | 48.398 | 23.585 | 26.428 | 1.00 | 13.79 | 6 |
| ATOM | 250 | CG | ASP | A | 37 | 49.045 | 24.213 | 27.668 | 1.00 | 13.71 | 6 |
| ATOM | 251 | OD1 | ASP | A | 37 | 48.405 | 24.279 | 28.736 | 1.00 | 15.96 | 8 |
| ATOM | 252 | OD2 | ASP | A | 37 | 50.219 | 24.636 | 27.563 | 1.00 | 15.49 | 8 |
| ATOM | 253 | C | ASP | A | 37 | 46.618 | 22.449 | 27.864 | 1.00 | 14.23 | 6 |
| ATOM | 254 | O | ASP | A | 37 | 45.781 | 22.817 | 28.701 | 1.00 | 13.85 | 8 |
| ATOM | 255 | N | SER | A | 38 | 47.325 | 21.330 | 27.991 | 1.00 | 14.98 | 7 |
| ATOM | 256 | CA | SER | A | 38 | 47.087 | 20.382 | 29.083 | 1.00 | 15.89 | 6 |
| ATOM | 257 | CB | SER | A | 38 | 47.934 | 19.125 | 28.881 | 1.00 | 15.96 | 6 |
| ATOM | 258 | OG | SER | A | 38 | 49.310 | 19.460 | 28.885 | 1.00 | 17.21 | 8 |
| ATOM | 259 | C | SER | A | 38 | 47.362 | 20.988 | 30.464 | 1.00 | 16.06 | 6 |
| ATOM | 260 | O | SER | A | 38 | 46.896 | 20.465 | 31.480 | 1.00 | 16.84 | 8 |
| ATOM | 261 | N | GLU | A | 39 | 48.099 | 22.102 | 30.485 | 1.00 | 16.50 | 7 |
| ATOM | 262 | CA | GLU | A | 39 | 48.467 | 22.799 | 31.727 | 1.00 | 16.83 | 6 |
| ATOM | 263 | CB | GLU | A | 39 | 49.970 | 23.104 | 31.729 | 1.00 | 17.33 | 6 |
| ATOM | 264 | CG | GLU | A | 39 | 50.853 | 21.861 | 31.841 | 1.00 | 20.17 | 6 |
| ATOM | 265 | CD | GLU | A | 39 | 50.625 | 21.092 | 33.140 | 1.00 | 23.25 | 6 |
| ATOM | 266 | OE1 | GLU | A | 39 | 50.540 | 21.734 | 34.213 | 1.00 | 25.80 | 8 |
| ATOM | 267 | OE2 | GLU | A | 39 | 50.525 | 19.847 | 33.087 | 1.00 | 25.70 | 8 |
| ATOM | 268 | C | GLU | A | 39 | 47.658 | 24.091 | 31.951 | 1.00 | 16.45 | 6 |
| ATOM | 269 | O | GLU | A | 39 | 47.977 | 24.895 | 32.844 | 1.00 | 16.80 | 8 |
| ATOM | 270 | N | PHE | A | 40 | 46.605 | 24.267 | 31.152 | 1.00 | 15.76 | 7 |
| ATOM | 271 | CA | PHE | A | 40 | 45.692 | 25.426 | 31.253 | 1.00 | 15.42 | 6 |
| ATOM | 272 | CB | PHE | A | 40 | 45.114 | 25.575 | 32.668 | 1.00 | 15.00 | 6 |
| ATOM | 273 | CG | PHE | A | 40 | 44.362 | 24.362 | 33.153 | 1.00 | 15.57 | 6 |
| ATOM | 274 | CD1 | PHE | A | 40 | 43.392 | 23.758 | 32.356 | 1.00 | 15.31 | 6 |
| ATOM | 275 | CE1 | PHE | A | 40 | 42.692 | 22.639 | 32.805 | 1.00 | 15.59 | 6 |
| ATOM | 276 | CZ | PHE | A | 40 | 42.953 | 22.119 | 34.059 | 1.00 | 16.22 | 6 |
| ATOM | 277 | CE2 | PHE | A | 40 | 43.921 | 22.714 | 34.869 | 1.00 | 16.87 | 6 |
| ATOM | 278 | CD2 | PHE | A | 40 | 44.613 | 23.837 | 34.413 | 1.00 | 16.55 | 6 |
| ATOM | 279 | C | PHE | A | 40 | 46.282 | 26.756 | 30.764 | 1.00 | 15.13 | 6 |
| ATOM | 280 | O | PHE | A | 40 | 45.752 | 27.834 | 31.071 | 1.00 | 15.01 | 8 |
| ATOM | 281 | N | ASN | A | 41 | 47.356 | 26.674 | 29.983 | 1.00 | 14.93 | 7 |
| ATOM | 282 | CA | ASN | A | 41 | 47.868 | 27.839 | 29.260 | 1.00 | 14.96 | 6 |
| ATOM | 283 | CB | ASN | A | 41 | 49.299 | 27.592 | 28.772 | 1.00 | 14.97 | 6 |
| ATOM | 284 | CG | ASN | A | 41 | 50.260 | 27.284 | 29.900 | 1.00 | 15.95 | 6 |
| ATOM | 285 | OD1 | ASN | A | 41 | 50.959 | 26.271 | 29.866 | 1.00 | 17.21 | 8 |
| ATOM | 286 | ND2 | ASN | A | 41 | 50.298 | 28.152 | 30.909 | 1.00 | 15.72 | 7 |
| ATOM | 287 | C | ASN | A | 41 | 46.993 | 28.142 | 28.060 | 1.00 | 14.99 | 6 |
| ATOM | 288 | O | ASN | A | 41 | 46.815 | 27.290 | 27.191 | 1.00 | 14.78 | 8 |
| ATOM | 289 | N | VAL | A | 42 | 46.468 | 29.363 | 28.000 | 1.00 | 15.05 | 7 |
| ATOM | 290 | CA | VAL | A | 42 | 45.619 | 29.765 | 26.888 | 1.00 | 15.32 | 6 |
| ATOM | 291 | CB | VAL | A | 42 | 45.033 | 31.178 | 27.096 | 1.00 | 15.10 | 6 |
| ATOM | 292 | CG1 | VAL | A | 42 | 44.346 | 31.669 | 25.825 | 1.00 | 15.35 | 6 |
| ATOM | 293 | CG2 | VAL | A | 42 | 44.068 | 31.187 | 28.275 | 1.00 | 15.41 | 6 |
| ATOM | 294 | C | VAL | A | 42 | 46.408 | 29.697 | 25.581 | 1.00 | 15.38 | 6 |
| ATOM | 295 | O | VAL | A | 42 | 47.478 | 30.297 | 25.459 | 1.00 | 15.29 | 8 |
| ATOM | 296 | N | ILE | A | 43 | 45.896 | 28.926 | 24.625 | 1.00 | 15.85 | 7 |
| ATOM | 297 | CA | ILE | A | 43 | 46.567 | 28.776 | 23.325 | 1.00 | 16.32 | 6 |
| ATOM | 298 | CB | ILE | A | 43 | 47.081 | 27.321 | 23.091 | 1.00 | 16.48 | 6 |
| ATOM | 299 | CG1 | ILE | A | 43 | 45.913 | 26.331 | 23.076 | 1.00 | 16.39 | 6 |
| ATOM | 300 | CD1 | ILE | A | 43 | 46.284 | 24.925 | 22.619 | 1.00 | 16.03 | 6 |
| ATOM | 301 | CG2 | ILE | A | 43 | 48.123 | 26.938 | 24.154 | 1.00 | 17.05 | 6 |
| ATOM | 302 | C | ILE | A | 43 | 45.705 | 29.225 | 22.140 | 1.00 | 16.88 | 6 |
| ATOM | 303 | O | ILE | A | 43 | 46.197 | 29.338 | 21.021 | 1.00 | 16.85 | 8 |
| ATOM | 304 | N | GLY | A | 44 | 44.421 | 29.475 | 22.391 | 1.00 | 17.13 | 7 |
| ATOM | 305 | CA | GLY | A | 44 | 43.516 | 29.927 | 21.337 | 1.00 | 17.42 | 6 |
| ATOM | 306 | C | GLY | A | 44 | 43.099 | 31.375 | 21.489 | 1.00 | 17.66 | 6 |
| ATOM | 307 | O | GLY | A | 44 | 43.445 | 32.033 | 22.475 | 1.00 | 18.18 | 8 |
| ATOM | 308 | N | GLU | A | 45 | 42.361 | 31.873 | 20.501 | 1.00 | 17.81 | 7 |
| ATOM | 309 | CA | GLU | A | 45 | 41.732 | 33.190 | 20.587 | 1.00 | 18.17 | 6 |
| ATOM | 310 | CB | GLU | A | 45 | 41.596 | 33.817 | 19.191 | 1.00 | 18.33 | 6 |
| ATOM | 311 | CG | GLU | A | 45 | 42.914 | 34.053 | 18.453 | 1.00 | 21.00 | 6 |
| ATOM | 312 | CD | GLU | A | 45 | 43.857 | 34.975 | 19.204 | 1.00 | 23.60 | 6 |
| ATOM | 313 | OE1 | GLU | A | 45 | 43.477 | 36.137 | 19.471 | 1.00 | 25.01 | 8 |
| ATOM | 314 | OE2 | GLU | A | 45 | 44.985 | 34.537 | 19.524 | 1.00 | 26.07 | 8 |
| ATOM | 315 | C | GLU | A | 45 | 40.351 | 33.025 | 21.202 | 1.00 | 17.41 | 6 |
| ATOM | 316 | O | GLU | A | 45 | 39.724 | 31.978 | 21.030 | 1.00 | 17.70 | 8 |
| ATOM | 317 | N | PRO | A | 46 | 39.867 | 34.051 | 21.930 | 1.00 | 17.19 | 7 |
| ATOM | 318 | CA | PRO | A | 46 | 38.490 | 33.992 | 22.437 | 1.00 | 16.54 | 6 |
| ATOM | 319 | CB | PRO | A | 46 | 38.288 | 35.385 | 23.042 | 1.00 | 17.03 | 6 |
| ATOM | 320 | CG | PRO | A | 46 | 39.663 | 35.797 | 23.461 | 1.00 | 17.48 | 6 |
| ATOM | 321 | CD | PRO | A | 46 | 40.552 | 35.286 | 22.356 | 1.00 | 16.95 | 6 |
| ATOM | 322 | C | PRO | A | 46 | 37.494 | 33.760 | 21.303 | 1.00 | 16.32 | 6 |

TABLE 7-continued

Coordinates of the crystal structure of *E. coli* ExoI bound to compound 10

| ATOM | 323 | O   | PRO | A | 46 | 37.587 | 34.413 | 20.257 | 1.00 | 15.63 | 8  |
|------|-----|-----|-----|---|----|--------|--------|--------|------|-------|----|
| ATOM | 324 | N   | GLU | A | 47 | 36.583 | 32.807 | 21.501 | 1.00 | 15.53 | 7  |
| ATOM | 325 | CA  | GLU | A | 47 | 35.528 | 32.511 | 20.532 | 1.00 | 15.92 | 6  |
| ATOM | 326 | CB  | GLU | A | 47 | 35.518 | 31.020 | 20.185 | 1.00 | 16.37 | 6  |
| ATOM | 327 | CG  | GLU | A | 47 | 36.816 | 30.510 | 19.546 | 1.00 | 17.60 | 6  |
| ATOM | 328 | CD  | GLU | A | 47 | 36.831 | 30.639 | 18.030 | 1.00 | 21.42 | 6  |
| ATOM | 329 | OE1 | GLU | A | 47 | 35.890 | 31.228 | 17.459 | 1.00 | 21.52 | 8  |
| ATOM | 330 | OE2 | GLU | A | 47 | 37.795 | 30.146 | 17.407 | 1.00 | 23.79 | 8  |
| ATOM | 331 | C   | GLU | A | 47 | 34.182 | 32.916 | 21.111 | 1.00 | 15.64 | 6  |
| ATOM | 332 | O   | GLU | A | 47 | 33.623 | 32.211 | 21.953 | 1.00 | 15.54 | 8  |
| ATOM | 333 | N   | VAL | A | 48 | 33.668 | 34.056 | 20.662 | 1.00 | 15.23 | 7  |
| ATOM | 334 | CA  | VAL | A | 48 | 32.434 | 34.625 | 21.217 | 1.00 | 15.21 | 6  |
| ATOM | 335 | CB  | VAL | A | 48 | 32.702 | 35.928 | 22.024 | 1.00 | 15.39 | 6  |
| ATOM | 336 | CG1 | VAL | A | 48 | 31.393 | 36.557 | 22.498 | 1.00 | 15.74 | 6  |
| ATOM | 337 | CG2 | VAL | A | 48 | 33.632 | 35.660 | 23.213 | 1.00 | 15.26 | 6  |
| ATOM | 338 | C   | VAL | A | 48 | 31.486 | 34.951 | 20.085 | 1.00 | 14.78 | 6  |
| ATOM | 339 | O   | VAL | A | 48 | 31.820 | 35.729 | 19.202 | 1.00 | 14.93 | 8  |
| ATOM | 340 | N   | PHE | A | 49 | 30.304 | 34.349 | 20.105 | 1.00 | 14.42 | 7  |
| ATOM | 341 | CA  | PHE | A | 49 | 29.315 | 34.650 | 19.086 | 1.00 | 14.02 | 6  |
| ATOM | 342 | CB  | PHE | A | 49 | 29.599 | 33.889 | 17.779 | 1.00 | 14.23 | 6  |
| ATOM | 343 | CG  | PHE | A | 49 | 29.882 | 32.431 | 17.970 | 1.00 | 14.42 | 6  |
| ATOM | 344 | CD1 | PHE | A | 49 | 28.873 | 31.496 | 17.838 | 1.00 | 14.89 | 6  |
| ATOM | 345 | CE1 | PHE | A | 49 | 29.130 | 30.142 | 18.014 | 1.00 | 15.80 | 6  |
| ATOM | 346 | CZ  | PHE | A | 49 | 30.420 | 29.715 | 18.311 | 1.00 | 14.95 | 6  |
| ATOM | 347 | CE2 | PHE | A | 49 | 31.438 | 30.642 | 18.440 | 1.00 | 14.78 | 6  |
| ATOM | 348 | CD2 | PHE | A | 49 | 31.171 | 31.990 | 18.268 | 1.00 | 14.37 | 6  |
| ATOM | 349 | C   | PHE | A | 49 | 27.889 | 34.449 | 19.557 | 1.00 | 13.54 | 6  |
| ATOM | 350 | O   | PHE | A | 49 | 27.637 | 33.841 | 20.611 | 1.00 | 12.57 | 8  |
| ATOM | 351 | N   | TYR | A | 50 | 26.962 | 34.990 | 18.772 | 1.00 | 13.19 | 7  |
| ATOM | 352 | CA  | TYR | A | 50 | 25.558 | 35.064 | 19.149 | 1.00 | 13.13 | 6  |
| ATOM | 353 | CB  | TYR | A | 50 | 25.058 | 36.504 | 19.045 | 1.00 | 13.64 | 6  |
| ATOM | 354 | CG  | TYR | A | 50 | 25.693 | 37.443 | 20.029 | 1.00 | 14.49 | 6  |
| ATOM | 355 | CD1 | TYR | A | 50 | 25.050 | 37.765 | 21.219 | 1.00 | 15.09 | 6  |
| ATOM | 356 | CE1 | TYR | A | 50 | 25.621 | 38.640 | 22.129 | 1.00 | 16.62 | 6  |
| ATOM | 357 | CZ  | TYR | A | 50 | 26.851 | 39.198 | 21.857 | 1.00 | 16.15 | 6  |
| ATOM | 358 | OH  | TYR | A | 50 | 27.417 | 40.065 | 22.761 | 1.00 | 17.68 | 8  |
| ATOM | 359 | CE2 | TYR | A | 50 | 27.515 | 38.900 | 20.678 | 1.00 | 16.01 | 6  |
| ATOM | 360 | CD2 | TYR | A | 50 | 26.932 | 38.024 | 19.769 | 1.00 | 15.85 | 6  |
| ATOM | 361 | C   | TYR | A | 50 | 24.712 | 34.191 | 18.259 | 1.00 | 12.63 | 6  |
| ATOM | 362 | O   | TYR | A | 50 | 25.107 | 33.857 | 17.126 | 1.00 | 12.64 | 8  |
| ATOM | 363 | N   | CYS | A | 51 | 23.537 | 33.839 | 18.768 | 1.00 | 12.47 | 7  |
| ATOM | 364 | CA  | CYS | A | 51 | 22.558 | 33.087 | 18.008 | 1.00 | 12.46 | 6  |
| ATOM | 365 | CB  | CYS | A | 51 | 22.187 | 31.802 | 18.743 | 1.00 | 12.80 | 6  |
| ATOM | 366 | SG  | CYS | A | 51 | 21.278 | 30.670 | 17.717 | 1.00 | 12.66 | 16 |
| ATOM | 367 | C   | CYS | A | 51 | 21.308 | 33.922 | 17.794 | 1.00 | 12.59 | 6  |
| ATOM | 368 | O   | CYS | A | 51 | 20.689 | 34.384 | 18.761 | 1.00 | 12.01 | 8  |
| ATOM | 369 | N   | LYS | A | 52 | 20.948 | 34.121 | 16.527 | 1.00 | 12.54 | 7  |
| ATOM | 370 | CA  | LYS | A | 52 | 19.672 | 34.742 | 16.164 | 1.00 | 12.82 | 6  |
| ATOM | 371 | CB  | LYS | A | 52 | 19.562 | 34.883 | 14.650 | 1.00 | 12.80 | 6  |
| ATOM | 372 | CG  | LYS | A | 52 | 20.423 | 35.954 | 14.034 | 1.00 | 14.17 | 6  |
| ATOM | 373 | CD  | LYS | A | 52 | 20.272 | 35.944 | 12.518 | 1.00 | 17.60 | 6  |
| ATOM | 374 | CE  | LYS | A | 52 | 18.818 | 35.924 | 12.105 | 1.00 | 18.27 | 6  |
| ATOM | 375 | NZ  | LYS | A | 52 | 18.058 | 37.111 | 12.605 | 1.00 | 22.27 | 7  |
| ATOM | 376 | C   | LYS | A | 52 | 18.502 | 33.883 | 16.629 | 1.00 | 12.59 | 6  |
| ATOM | 377 | O   | LYS | A | 52 | 18.412 | 32.714 | 16.249 | 1.00 | 12.46 | 8  |
| ATOM | 378 | N   | PRO | A | 53 | 17.586 | 34.462 | 17.433 | 1.00 | 12.78 | 7  |
| ATOM | 379 | CA  | PRO | A | 53 | 16.369 | 33.712 | 17.761 | 1.00 | 12.96 | 6  |
| ATOM | 380 | CB  | PRO | A | 53 | 15.841 | 34.413 | 19.019 | 1.00 | 12.61 | 6  |
| ATOM | 381 | CG  | PRO | A | 53 | 16.375 | 35.826 | 18.940 | 1.00 | 13.03 | 6  |
| ATOM | 382 | CD  | PRO | A | 53 | 17.623 | 35.796 | 18.062 | 1.00 | 12.66 | 6  |
| ATOM | 383 | C   | PRO | A | 53 | 15.356 | 33.791 | 16.620 | 1.00 | 13.24 | 6  |
| ATOM | 384 | O   | PRO | A | 53 | 15.181 | 34.860 | 16.022 | 1.00 | 13.74 | 8  |
| ATOM | 385 | N   | ALA | A | 54 | 14.721 | 32.662 | 16.299 | 1.00 | 13.78 | 7  |
| ATOM | 386 | CA  | ALA | A | 54 | 13.668 | 32.636 | 15.274 | 1.00 | 13.43 | 6  |
| ATOM | 387 | CB  | ALA | A | 54 | 13.350 | 31.213 | 14.871 | 1.00 | 13.87 | 6  |
| ATOM | 388 | C   | ALA | A | 54 | 12.413 | 33.343 | 15.780 | 1.00 | 13.62 | 6  |
| ATOM | 389 | O   | ALA | A | 54 | 12.250 | 33.543 | 16.982 | 1.00 | 13.41 | 8  |
| ATOM | 390 | N   | ASP | A | 55 | 11.526 | 33.720 | 14.862 | 1.00 | 13.35 | 7  |
| ATOM | 391 | CA  | ASP | A | 55 | 10.387 | 34.570 | 15.221 | 1.00 | 13.69 | 6  |
| ATOM | 392 | CB  | ASP | A | 55 | 9.940  | 35.426 | 14.027 | 1.00 | 14.38 | 6  |
| ATOM | 393 | CG  | ASP | A | 55 | 9.390  | 34.595 | 12.872 | 1.00 | 15.75 | 6  |
| ATOM | 394 | OD1 | ASP | A | 55 | 9.209  | 33.365 | 13.021 | 1.00 | 17.62 | 8  |
| ATOM | 395 | OD2 | ASP | A | 55 | 9.142  | 35.186 | 11.801 | 1.00 | 19.79 | 8  |
| ATOM | 396 | C   | ASP | A | 55 | 9.197  | 33.817 | 15.834 | 1.00 | 13.17 | 6  |
| ATOM | 397 | O   | ASP | A | 55 | 8.082  | 34.349 | 15.896 | 1.00 | 12.92 | 8  |
| ATOM | 398 | N   | ASP | A | 56 | 9.433  | 32.586 | 16.282 | 1.00 | 12.57 | 7  |
| ATOM | 399 | CA  | ASP | A | 56 | 8.391  | 31.813 | 16.959 | 1.00 | 12.30 | 6  |
| ATOM | 400 | CB  | ASP | A | 56 | 8.281  | 30.395 | 16.360 | 1.00 | 12.51 | 6  |

TABLE 7-continued

Coordinates of the crystal structure of *E. coli* ExoI bound to compound 10

| ATOM | 401 | CG | ASP | A | 56 | 9.547 | 29.562 | 16.561 | 1.00 | 12.79 | 6 |
|------|-----|-----|-----|---|----|-------|--------|--------|------|-------|---|
| ATOM | 402 | OD1 | ASP | A | 56 | 10.628 | 30.142 | 16.802 | 1.00 | 15.49 | 8 |
| ATOM | 403 | OD2 | ASP | A | 56 | 9.454 | 28.319 | 16.491 | 1.00 | 15.56 | 8 |
| ATOM | 404 | C | ASP | A | 56 | 8.639 | 31.749 | 18.469 | 1.00 | 12.36 | 6 |
| ATOM | 405 | O | ASP | A | 56 | 8.087 | 30.906 | 19.159 | 1.00 | 12.42 | 8 |
| ATOM | 406 | N | TYR | A | 57 | 9.456 | 32.666 | 18.977 | 1.00 | 12.11 | 7 |
| ATOM | 407 | CA | TYR | A | 57 | 9.928 | 32.561 | 20.350 | 1.00 | 12.08 | 6 |
| ATOM | 408 | CB | TYR | A | 57 | 11.270 | 31.823 | 20.370 | 1.00 | 11.87 | 6 |
| ATOM | 409 | CG | TYR | A | 57 | 11.913 | 31.708 | 21.732 | 1.00 | 11.72 | 6 |
| ATOM | 410 | CD1 | TYR | A | 57 | 11.494 | 30.740 | 22.643 | 1.00 | 10.75 | 6 |
| ATOM | 411 | CE1 | TYR | A | 57 | 12.091 | 30.633 | 23.892 | 1.00 | 9.98 | 6 |
| ATOM | 412 | CZ | TYR | A | 57 | 13.129 | 31.494 | 24.229 | 1.00 | 11.16 | 6 |
| ATOM | 413 | OH | TYR | A | 57 | 13.727 | 31.405 | 25.456 | 1.00 | 12.73 | 8 |
| ATOM | 414 | CE2 | TYR | A | 57 | 13.566 | 32.457 | 23.335 | 1.00 | 11.39 | 6 |
| ATOM | 415 | CD2 | TYR | A | 57 | 12.966 | 32.557 | 22.102 | 1.00 | 10.42 | 6 |
| ATOM | 416 | C | TYR | A | 57 | 10.053 | 33.915 | 21.034 | 1.00 | 12.15 | 6 |
| ATOM | 417 | O | TYR | A | 57 | 10.518 | 34.879 | 20.435 | 1.00 | 12.56 | 8 |
| ATOM | 418 | N | LEU | A | 58 | 9.626 | 33.978 | 22.296 | 1.00 | 12.41 | 7 |
| ATOM | 419 | CA | LEU | A | 58 | 9.932 | 35.124 | 23.157 | 1.00 | 12.34 | 6 |
| ATOM | 420 | CB | LEU | A | 58 | 8.657 | 35.801 | 23.663 | 1.00 | 12.56 | 6 |
| ATOM | 421 | CG | LEU | A | 58 | 7.849 | 36.615 | 22.648 | 1.00 | 13.12 | 6 |
| ATOM | 422 | CD1 | LEU | A | 58 | 6.564 | 37.099 | 23.282 | 1.00 | 14.03 | 6 |
| ATOM | 423 | CD2 | LEU | A | 58 | 8.656 | 37.789 | 22.112 | 1.00 | 13.18 | 6 |
| ATOM | 424 | C | LEU | A | 58 | 10.793 | 34.685 | 24.335 | 1.00 | 12.26 | 6 |
| ATOM | 425 | O | LEU | A | 58 | 10.521 | 33.660 | 24.952 | 1.00 | 11.94 | 8 |
| ATOM | 426 | N | PRO | A | 59 | 11.844 | 35.459 | 24.644 | 1.00 | 12.22 | 7 |
| ATOM | 427 | CA | PRO | A | 59 | 12.736 | 35.072 | 25.734 | 1.00 | 12.23 | 6 |
| ATOM | 428 | CB | PRO | A | 59 | 13.884 | 36.082 | 25.623 | 1.00 | 12.06 | 6 |
| ATOM | 429 | CG | PRO | A | 59 | 13.311 | 37.245 | 24.891 | 1.00 | 12.45 | 6 |
| ATOM | 430 | CD | PRO | A | 59 | 12.250 | 36.725 | 24.001 | 1.00 | 12.21 | 6 |
| ATOM | 431 | C | PRO | A | 59 | 12.057 | 35.174 | 27.099 | 1.00 | 12.77 | 6 |
| ATOM | 432 | O | PRO | A | 59 | 11.108 | 35.944 | 27.262 | 1.00 | 12.39 | 8 |
| ATOM | 433 | N | GLN | A | 60 | 12.523 | 34.379 | 28.061 | 1.00 | 12.95 | 7 |
| ATOM | 434 | CA | GLN | A | 60 | 12.093 | 34.545 | 29.445 | 1.00 | 14.10 | 6 |
| ATOM | 435 | CB | GLN | A | 60 | 12.576 | 33.378 | 30.318 | 1.00 | 14.10 | 6 |
| ATOM | 436 | CG | GLN | A | 60 | 11.984 | 32.027 | 29.929 | 1.00 | 15.57 | 6 |
| ATOM | 437 | CD | GLN | A | 60 | 12.275 | 30.909 | 30.930 | 1.00 | 17.12 | 6 |
| ATOM | 438 | OE1 | GLN | A | 60 | 13.120 | 31.046 | 31.829 | 1.00 | 20.38 | 8 |
| ATOM | 439 | NE2 | GLN | A | 60 | 11.582 | 29.783 | 30.765 | 1.00 | 20.41 | 7 |
| ATOM | 440 | C | GLN | A | 60 | 12.662 | 35.868 | 29.958 | 1.00 | 14.35 | 6 |
| ATOM | 441 | O | GLN | A | 60 | 13.874 | 36.065 | 29.920 | 1.00 | 13.24 | 8 |
| ATOM | 442 | N | PRO | A | 61 | 11.780 | 36.798 | 30.400 | 1.00 | 14.55 | 7 |
| ATOM | 443 | CA | PRO | A | 61 | 12.245 | 38.095 | 30.899 | 1.00 | 14.97 | 6 |
| ATOM | 444 | CB | PRO | A | 61 | 10.960 | 38.738 | 31.447 | 1.00 | 14.94 | 6 |
| ATOM | 445 | CG | PRO | A | 61 | 9.871 | 38.134 | 30.632 | 1.00 | 14.83 | 6 |
| ATOM | 446 | CD | PRO | A | 61 | 10.306 | 36.700 | 30.420 | 1.00 | 14.84 | 6 |
| ATOM | 447 | C | PRO | A | 61 | 13.303 | 37.976 | 32.007 | 1.00 | 15.13 | 6 |
| ATOM | 448 | O | PRO | A | 61 | 14.235 | 38.783 | 32.062 | 1.00 | 15.62 | 8 |
| ATOM | 449 | N | GLY | A | 62 | 13.162 | 36.971 | 32.868 | 1.00 | 15.59 | 7 |
| ATOM | 450 | CA | GLY | A | 62 | 14.108 | 36.748 | 33.949 | 1.00 | 16.07 | 6 |
| ATOM | 451 | C | GLY | A | 62 | 15.521 | 36.466 | 33.476 | 1.00 | 16.38 | 6 |
| ATOM | 452 | O | GLY | A | 62 | 16.493 | 36.860 | 34.132 | 1.00 | 17.16 | 8 |
| ATOM | 453 | N | ALA | A | 63 | 15.635 | 35.788 | 32.332 | 1.00 | 16.40 | 7 |
| ATOM | 454 | CA | ALA | A | 63 | 16.937 | 35.432 | 31.758 | 1.00 | 16.03 | 6 |
| ATOM | 455 | CB | ALA | A | 63 | 16.772 | 34.361 | 30.697 | 1.00 | 16.37 | 6 |
| ATOM | 456 | C | ALA | A | 63 | 17.659 | 36.647 | 31.183 | 1.00 | 16.03 | 6 |
| ATOM | 457 | O | ALA | A | 63 | 18.865 | 36.810 | 31.376 | 1.00 | 15.96 | 8 |
| ATOM | 458 | N | VAL | A | 64 | 16.915 | 37.495 | 30.474 | 1.00 | 15.90 | 7 |
| ATOM | 459 | CA | VAL | A | 64 | 17.464 | 38.731 | 29.925 | 1.00 | 15.95 | 6 |
| ATOM | 460 | CB | VAL | A | 64 | 16.443 | 39.451 | 29.007 | 1.00 | 15.64 | 6 |
| ATOM | 461 | GG1 | VAL | A | 64 | 16.914 | 40.872 | 28.655 | 1.00 | 15.38 | 6 |
| ATOM | 462 | CG2 | VAL | A | 64 | 16.214 | 38.633 | 27.749 | 1.00 | 15.05 | 6 |
| ATOM | 463 | C | VAL | A | 64 | 17.953 | 39.659 | 31.037 | 1.00 | 16.67 | 6 |
| ATOM | 464 | O | VAL | A | 64 | 18.984 | 40.303 | 30.893 | 1.00 | 17.04 | 8 |
| ATOM | 465 | N | LEU | A | 65 | 17.219 | 39.701 | 32.152 | 1.00 | 16.95 | 7 |
| ATOM | 466 | CA | LEU | A | 65 | 17.624 | 40.506 | 33.313 | 1.00 | 17.54 | 6 |
| ATOM | 467 | CB | LEU | A | 65 | 16.517 | 40.554 | 34.369 | 1.00 | 17.84 | 6 |
| ATOM | 468 | CG | LEU | A | 65 | 15.219 | 41.303 | 34.034 | 1.00 | 18.34 | 6 |
| ATOM | 469 | CD1 | LEU | A | 65 | 14.344 | 41.430 | 35.272 | 1.00 | 19.45 | 6 |
| ATOM | 470 | CD2 | LEU | A | 65 | 15.473 | 42.678 | 33.403 | 1.00 | 20.43 | 6 |
| ATOM | 471 | C | LEU | A | 65 | 18.938 | 40.032 | 33.948 | 1.00 | 17.82 | 6 |
| ATOM | 472 | O | LEU | A | 65 | 19.670 | 40.832 | 34.523 | 1.00 | 17.99 | 8 |
| ATOM | 473 | N | ILE | A | 66 | 19.224 | 38.734 | 33.843 | 1.00 | 17.97 | 7 |
| ATOM | 474 | CA | ILE | A | 66 | 20.485 | 38.170 | 34.350 | 1.00 | 18.30 | 6 |
| ATOM | 475 | CB | ILE | A | 66 | 20.354 | 36.654 | 34.643 | 1.00 | 18.40 | 6 |
| ATOM | 476 | CG1 | ILE | A | 66 | 19.383 | 36.417 | 35.807 | 1.00 | 19.02 | 6 |
| ATOM | 477 | CD1 | ILE | A | 66 | 18.964 | 34.950 | 35.984 | 1.00 | 19.25 | 6 |
| ATOM | 478 | CG2 | ILE | A | 66 | 21.727 | 36.034 | 34.937 | 1.00 | 19.04 | 6 |

TABLE 7-continued

Coordinates of the crystal structure of *E. coli* ExoI bound to compound 10

| ATOM | 479 | C | ILE | A | 66 | 21.649 | 38.399 | 33.376 | 1.00 | 18.39 | 6 |
|------|-----|-----|-----|---|----|--------|--------|--------|------|-------|---|
| ATOM | 480 | O | ILE | A | 66 | 22.742 | 38.820 | 33.778 | 1.00 | 18.24 | 8 |
| ATOM | 481 | N | THR | A | 67 | 21.404 | 38.116 | 32.099 | 1.00 | 17.69 | 7 |
| ATOM | 482 | CA | THR | A | 67 | 22.457 | 38.151 | 31.074 | 1.00 | 17.85 | 6 |
| ATOM | 483 | CB | THR | A | 67 | 22.112 | 37.234 | 29.878 | 1.00 | 17.75 | 6 |
| ATOM | 484 | OG1 | THR | A | 67 | 21.003 | 37.785 | 29.155 | 1.00 | 18.28 | 8 |
| ATOM | 485 | CG2 | THR | A | 67 | 21.766 | 35.818 | 30.352 | 1.00 | 18.54 | 6 |
| ATOM | 486 | C | THR | A | 67 | 22.719 | 39.555 | 30.542 | 1.00 | 17.40 | 6 |
| ATOM | 487 | O | THR | A | 67 | 23.844 | 39.876 | 30.133 | 1.00 | 18.00 | 8 |
| ATOM | 488 | N | GLY | A | 68 | 21.682 | 40.385 | 30.526 | 1.00 | 16.56 | 7 |
| ATOM | 489 | CA | GLY | A | 68 | 21.777 | 41.710 | 29.939 | 1.00 | 16.28 | 6 |
| ATOM | 490 | C | GLY | A | 68 | 21.785 | 41.683 | 28.417 | 1.00 | 15.46 | 6 |
| ATOM | 491 | O | GLY | A | 68 | 22.046 | 42.711 | 27.772 | 1.00 | 15.84 | 8 |
| ATOM | 492 | N | ILE | A | 69 | 21.493 | 40.512 | 27.839 | 1.00 | 15.26 | 7 |
| ATOM | 493 | CA | ILE | A | 69 | 21.437 | 40.360 | 26.380 | 1.00 | 14.64 | 6 |
| ATOM | 494 | CB | ILE | A | 69 | 22.159 | 39.063 | 25.881 | 1.00 | 14.55 | 6 |
| ATOM | 495 | CG1 | ILE | A | 69 | 23.608 | 39.011 | 26.376 | 1.00 | 14.87 | 6 |
| ATOM | 496 | CD1 | ILE | A | 69 | 24.328 | 37.712 | 26.007 | 1.00 | 15.26 | 6 |
| ATOM | 497 | CG2 | ILE | A | 69 | 22.120 | 38.974 | 24.348 | 1.00 | 15.35 | 6 |
| ATOM | 498 | C | ILE | A | 69 | 19.993 | 40.349 | 25.885 | 1.00 | 14.58 | 6 |
| ATOM | 499 | O | ILE | A | 69 | 19.233 | 39.424 | 26.189 | 1.00 | 14.60 | 8 |
| ATOM | 500 | N | THR | A | 70 | 19.630 | 41.377 | 25.117 | 1.00 | 14.27 | 7 |
| ATOM | 501 | CA | THR | A | 70 | 18.290 | 41.489 | 24.539 | 1.00 | 14.14 | 6 |
| ATOM | 502 | CB | THR | A | 70 | 17.955 | 42.959 | 24.127 | 1.00 | 13.96 | 6 |
| ATOM | 503 | OG1 | THR | A | 70 | 18.867 | 43.401 | 23.111 | 1.00 | 14.89 | 8 |
| ATOM | 504 | CG2 | THR | A | 70 | 18.036 | 43.885 | 25.318 | 1.00 | 15.10 | 6 |
| ATOM | 505 | C | THR | A | 70 | 18.168 | 40.595 | 23.311 | 1.00 | 13.62 | 6 |
| ATOM | 506 | O | THR | A | 70 | 19.179 | 40.280 | 22.668 | 1.00 | 13.66 | 8 |
| ATOM | 507 | N | PRO | A | 71 | 16.930 | 40.164 | 22.981 | 1.00 | 13.60 | 7 |
| ATOM | 508 | CA | PRO | A | 71 | 16.694 | 39.469 | 21.710 | 1.00 | 13.45 | 6 |
| ATOM | 509 | CB | PRO | A | 71 | 15.186 | 39.182 | 21.743 | 1.00 | 13.32 | 6 |
| ATOM | 510 | CG | PRO | A | 71 | 14.637 | 40.150 | 22.762 | 1.00 | 13.53 | 6 |
| ATOM | 511 | CD | PRO | A | 71 | 15.698 | 40.274 | 23.782 | 1.00 | 13.34 | 6 |
| ATOM | 512 | C | PRO | A | 71 | 17.062 | 40.325 | 20.486 | 1.00 | 13.67 | 6 |
| ATOM | 513 | O | PRO | A | 71 | 17.485 | 39.782 | 19.461 | 1.00 | 13.64 | 8 |
| ATOM | 514 | N | GLN | A | 72 | 16.908 | 41.647 | 20.598 | 1.00 | 13.97 | 7 |
| ATOM | 515 | CA | GLN | A | 72 | 17.346 | 42.565 | 19.534 | 1.00 | 14.07 | 6 |
| ATOM | 516 | CB | GLN | A | 72 | 17.014 | 44.024 | 19.886 | 1.00 | 14.43 | 6 |
| ATOM | 517 | CG | GLN | A | 72 | 15.531 | 44.374 | 19.828 | 1.00 | 14.67 | 6 |
| ATOM | 518 | CD | GLN | A | 72 | 14.863 | 44.331 | 21.185 | 1.00 | 14.98 | 6 |
| ATOM | 519 | OE1 | GLN | A | 72 | 15.208 | 43.513 | 22.041 | 1.00 | 16.14 | 8 |
| ATOM | 520 | NE2 | GLN | A | 72 | 13.894 | 45.212 | 21.389 | 1.00 | 15.04 | 7 |
| ATOM | 521 | C | GLN | A | 72 | 18.846 | 42.439 | 19.267 | 1.00 | 13.91 | 6 |
| ATOM | 522 | O | GLN | A | 72 | 19.282 | 42.416 | 18.108 | 1.00 | 14.07 | 8 |
| ATOM | 523 | N | GLU | A | 73 | 19.629 | 42.370 | 20.342 | 1.00 | 14.10 | 7 |
| ATOM | 524 | CA | GLU | A | 73 | 21.081 | 42.276 | 20.221 | 1.00 | 14.08 | 6 |
| ATOM | 525 | CB | GLU | A | 73 | 21.778 | 42.533 | 21.561 | 1.00 | 14.17 | 6 |
| ATOM | 526 | CG | GLU | A | 73 | 23.299 | 42.495 | 21.464 | 1.00 | 14.67 | 6 |
| ATOM | 527 | CD | GLU | A | 73 | 23.996 | 42.833 | 22.764 | 1.00 | 15.23 | 6 |
| ATOM | 528 | OE1 | GLU | A | 73 | 23.460 | 42.499 | 23.841 | 1.00 | 18.79 | 8 |
| ATOM | 529 | OE2 | GLU | A | 73 | 25.097 | 43.424 | 22.708 | 1.00 | 17.09 | 8 |
| ATOM | 530 | C | GLU | A | 73 | 21.524 | 40.943 | 19.625 | 1.00 | 13.82 | 6 |
| ATOM | 531 | O | GLU | A | 73 | 22.344 | 40.921 | 18.704 | 1.00 | 13.80 | 8 |
| ATOM | 532 | N | ALA | A | 74 | 20.986 | 39.836 | 20.142 | 1.00 | 13.17 | 7 |
| ATOM | 533 | CA | ALA | A | 74 | 21.284 | 38.503 | 19.575 | 1.00 | 12.70 | 6 |
| ATOM | 534 | CB | ALA | A | 74 | 20.645 | 37.399 | 20.411 | 1.00 | 12.95 | 6 |
| ATOM | 535 | C | ALA | A | 74 | 20.853 | 38.391 | 18.104 | 1.00 | 12.78 | 6 |
| ATOM | 536 | O | ALA | A | 74 | 21.575 | 37.816 | 17.275 | 1.00 | 12.37 | 8 |
| ATOM | 537 | N | ARG | A | 75 | 19.680 | 38.930 | 17.788 | 1.00 | 12.70 | 7 |
| ATOM | 538 | CA | ARG | A | 75 | 19.216 | 38.984 | 16.407 | 1.00 | 13.09 | 6 |
| ATOM | 539 | CB | ARG | A | 75 | 17.801 | 39.549 | 16.328 | 1.00 | 13.12 | 6 |
| ATOM | 540 | CG | ARG | A | 75 | 17.188 | 39.461 | 14.938 | 1.00 | 14.17 | 6 |
| ATOM | 541 | CD | ARG | A | 75 | 15.707 | 39.777 | 14.976 | 1.00 | 15.99 | 6 |
| ATOM | 542 | NE | ARG | A | 75 | 15.444 | 41.167 | 15.339 | 1.00 | 17.81 | 7 |
| ATOM | 543 | CZ | ARG | A | 75 | 14.242 | 41.732 | 15.316 | 1.00 | 18.68 | 6 |
| ATOM | 544 | NH1 | ARG | A | 75 | 13.177 | 41.026 | 14.945 | 1.00 | 18.04 | 7 |
| ATOM | 545 | NH2 | ARG | A | 75 | 14.101 | 43.006 | 15.662 | 1.00 | 18.75 | 7 |
| ATOM | 546 | C | ARG | A | 75 | 20.158 | 39.799 | 15.517 | 1.00 | 13.07 | 6 |
| ATOM | 547 | O | ARG | A | 75 | 20.479 | 39.383 | 14.413 | 1.00 | 13.04 | 8 |
| ATOM | 548 | N | ALA | A | 76 | 20.602 | 40.959 | 15.999 | 1.00 | 13.02 | 7 |
| ATOM | 549 | CA | ALA | A | 76 | 21.404 | 41.858 | 15.152 | 1.00 | 12.99 | 6 |
| ATOM | 550 | CB | ALA | A | 76 | 21.298 | 43.307 | 15.633 | 1.00 | 13.28 | 6 |
| ATOM | 551 | C | ALA | A | 76 | 22.869 | 41.426 | 15.038 | 1.00 | 13.53 | 6 |
| ATOM | 552 | O | ALA | A | 76 | 23.528 | 41.705 | 14.032 | 1.00 | 13.83 | 8 |
| ATOM | 553 | N | LYS | A | 77 | 23.381 | 40.749 | 16.070 | 1.00 | 13.38 | 7 |
| ATOM | 554 | CA | LYS | A | 77 | 24.792 | 40.333 | 16.086 | 1.00 | 13.73 | 6 |
| ATOM | 555 | CB | LYS | A | 77 | 25.426 | 40.628 | 17.451 | 1.00 | 13.72 | 6 |
| ATOM | 556 | CG | LYS | A | 77 | 25.422 | 42.107 | 17.818 | 1.00 | 15.21 | 6 |

TABLE 7-continued

Coordinates of the crystal structure of *E. coli* ExoI bound to compound 10

| ATOM | 557 | CD | LYS | A | 77 | 26.171 | 42.370 | 19.095 | 1.00 | 15.59 | 6 |
|------|-----|-----|-----|---|----|--------|--------|--------|------|-------|---|
| ATOM | 558 | CE | LYS | A | 77 | 26.307 | 43.858 | 19.339 | 1.00 | 16.23 | 6 |
| ATOM | 559 | NZ | LYS | A | 77 | 26.891 | 44.159 | 20.685 | 1.00 | 17.82 | 7 |
| ATOM | 560 | C | LYS | A | 77 | 24.966 | 38.858 | 15.746 | 1.00 | 13.84 | 6 |
| ATOM | 561 | O | LYS | A | 77 | 26.083 | 38.396 | 15.497 | 1.00 | 14.45 | 8 |
| ATOM | 562 | N | GLY | A | 78 | 23.862 | 38.123 | 15.718 | 1.00 | 13.79 | 7 |
| ATOM | 563 | CA | GLY | A | 78 | 23.924 | 36.666 | 15.634 | 1.00 | 14.22 | 6 |
| ATOM | 564 | C | GLY | A | 78 | 23.891 | 36.109 | 14.224 | 1.00 | 14.25 | 6 |
| ATOM | 565 | O | GLY | A | 78 | 23.579 | 36.817 | 13.265 | 1.00 | 14.82 | 8 |
| ATOM | 566 | N | GLU | A | 79 | 24.236 | 34.832 | 14.105 | 1.00 | 14.13 | 7 |
| ATOM | 567 | CA | GLU | A | 79 | 23.940 | 34.056 | 12.912 | 1.00 | 14.68 | 6 |
| ATOM | 568 | CB | GLU | A | 79 | 25.143 | 33.204 | 12.524 | 1.00 | 14.91 | 6 |
| ATOM | 569 | CG | GLU | A | 79 | 26.414 | 34.008 | 12.289 | 1.00 | 17.74 | 6 |
| ATOM | 570 | CD | GLU | A | 79 | 27.632 | 33.130 | 12.146 | 1.00 | 21.61 | 6 |
| ATOM | 571 | OE1 | GLU | A | 79 | 27.869 | 32.288 | 13.040 | 1.00 | 22.92 | 8 |
| ATOM | 572 | OE2 | GLU | A | 79 | 28.361 | 33.286 | 11.144 | 1.00 | 23.45 | 8 |
| ATOM | 573 | C | GLU | A | 79 | 22.765 | 33.156 | 13.245 | 1.00 | 14.11 | 6 |
| ATOM | 574 | O | GLU | A | 79 | 22.420 | 33.005 | 14.417 | 1.00 | 13.88 | 8 |
| ATOM | 575 | N | ASN | A | 80 | 22.141 | 32.555 | 12.231 | 1.00 | 13.72 | 7 |
| ATOM | 576 | CA | ASN | A | 80 | 21.043 | 31.632 | 12.513 | 1.00 | 13.40 | 6 |
| ATOM | 577 | CB | ASN | A | 80 | 20.285 | 31.221 | 11.246 | 1.00 | 13.79 | 6 |
| ATOM | 578 | CG | ASN | A | 80 | 21.159 | 30.486 | 10.223 | 1.00 | 14.18 | 6 |
| ATOM | 579 | OD1 | ASN | A | 80 | 22.142 | 29.824 | 10.563 | 1.00 | 13.68 | 8 |
| ATOM | 580 | ND2 | ASN | A | 80 | 20.768 | 30.578 | 8.963 | 1.00 | 15.88 | 7 |
| ATOM | 581 | C | ASN | A | 80 | 21.532 | 30.422 | 13.298 | 1.00 | 12.88 | 6 |
| ATOM | 582 | O | ASN | A | 80 | 22.733 | 30.177 | 13.382 | 1.00 | 12.27 | 8 |
| ATOM | 583 | N | GLU | A | 81 | 20.604 | 29.683 | 13.899 | 1.00 | 12.58 | 7 |
| ATOM | 584 | CA | GLU | A | 81 | 20.986 | 28.561 | 14.744 | 1.00 | 12.26 | 6 |
| ATOM | 585 | CB | GLU | A | 81 | 19.773 | 27.953 | 15.437 | 1.00 | 11.90 | 6 |
| ATOM | 586 | CG | GLU | A | 81 | 20.109 | 27.408 | 16.828 | 1.00 | 12.73 | 6 |
| ATOM | 587 | CD | GLU | A | 81 | 18.928 | 26.786 | 17.515 | 1.00 | 12.53 | 6 |
| ATOM | 588 | OE1 | GLU | A | 81 | 18.349 | 25.840 | 16.946 | 1.00 | 12.98 | 8 |
| ATOM | 589 | OE2 | GLU | A | 81 | 18.582 | 27.224 | 18.643 | 1.00 | 14.87 | 8 |
| ATOM | 590 | C | GLU | A | 81 | 21.782 | 27.492 | 13.988 | 1.00 | 12.21 | 6 |
| ATOM | 591 | O | GLU | A | 81 | 22.688 | 26.878 | 14.552 | 1.00 | 12.03 | 8 |
| ATOM | 592 | N | ALA | A | 82 | 21.472 | 27.298 | 12.705 | 1.00 | 12.78 | 7 |
| ATOM | 593 | CA | ALA | A | 82 | 22.242 | 26.363 | 11.877 | 1.00 | 12.90 | 6 |
| ATOM | 594 | CB | ALA | A | 82 | 21.707 | 26.334 | 10.438 | 1.00 | 13.31 | 6 |
| ATOM | 595 | C | ALA | A | 82 | 23.742 | 26.689 | 11.885 | 1.00 | 13.22 | 6 |
| ATOM | 596 | O | ALA | A | 82 | 24.574 | 25.807 | 12.101 | 1.00 | 13.38 | 8 |
| ATOM | 597 | N | ALA | A | 83 | 24.072 | 27.960 | 11.661 | 1.00 | 12.96 | 7 |
| ATOM | 598 | CA | ALA | A | 83 | 25.460 | 28.406 | 11.589 | 1.00 | 13.11 | 6 |
| ATOM | 599 | CB | ALA | A | 83 | 25.546 | 29.763 | 10.899 | 1.00 | 13.08 | 6 |
| ATOM | 600 | C | ALA | A | 83 | 26.094 | 28.464 | 12.981 | 1.00 | 13.06 | 6 |
| ATOM | 601 | O | ALA | A | 83 | 27.277 | 28.193 | 13.142 | 1.00 | 13.43 | 8 |
| ATOM | 602 | N | PHE | A | 84 | 25.282 | 28.816 | 13.977 | 1.00 | 12.44 | 7 |
| ATOM | 603 | CA | PHE | A | 84 | 25.683 | 28.820 | 15.388 | 1.00 | 12.44 | 6 |
| ATOM | 604 | CB | PHE | A | 84 | 24.476 | 29.257 | 16.231 | 1.00 | 12.30 | 6 |
| ATOM | 605 | CG | PHE | A | 84 | 24.784 | 29.527 | 17.683 | 1.00 | 12.81 | 6 |
| ATOM | 606 | CD1 | PHE | A | 84 | 25.584 | 30.607 | 18.061 | 1.00 | 11.94 | 6 |
| ATOM | 607 | CE1 | PHE | A | 84 | 25.836 | 30.871 | 19.405 | 1.00 | 12.19 | 6 |
| ATOM | 608 | CZ | PHE | A | 84 | 25.267 | 30.080 | 20.383 | 1.00 | 11.98 | 6 |
| ATOM | 609 | CE2 | PHE | A | 84 | 24.448 | 29.011 | 20.021 | 1.00 | 12.37 | 6 |
| ATOM | 610 | CD2 | PHE | A | 84 | 24.207 | 28.747 | 18.677 | 1.00 | 11.92 | 6 |
| ATOM | 611 | C | PHE | A | 84 | 26.150 | 27.418 | 15.799 | 1.00 | 12.49 | 6 |
| ATOM | 612 | O | PHE | A | 84 | 27.205 | 27.256 | 16.430 | 1.00 | 12.19 | 8 |
| ATOM | 613 | N | ALA | A | 85 | 25.359 | 26.418 | 15.409 | 1.00 | 12.22 | 7 |
| ATOM | 614 | CA | ALA | A | 85 | 25.661 | 25.009 | 15.644 | 1.00 | 12.13 | 6 |
| ATOM | 615 | CB | ALA | A | 85 | 24.494 | 24.146 | 15.176 | 1.00 | 11.23 | 6 |
| ATOM | 616 | C | ALA | A | 85 | 26.957 | 24.574 | 14.952 | 1.00 | 12.26 | 6 |
| ATOM | 617 | O | ALA | A | 85 | 27.790 | 23.880 | 15.555 | 1.00 | 12.18 | 8 |
| ATOM | 618 | N | ALA | A | 86 | 27.118 | 24.975 | 13.686 | 1.00 | 11.99 | 7 |
| ATOM | 619 | CA | ALA | A | 86 | 28.304 | 24.625 | 12.897 | 1.00 | 12.33 | 6 |
| ATOM | 620 | CB | ALA | A | 86 | 28.182 | 25.167 | 11.447 | 1.00 | 11.70 | 6 |
| ATOM | 621 | C | ALA | A | 86 | 29.593 | 25.104 | 13.540 | 1.00 | 12.55 | 6 |
| ATOM | 622 | O | ALA | A | 86 | 30.586 | 24.375 | 13.570 | 1.00 | 13.03 | 8 |
| ATOM | 623 | N | ARG | A | 87 | 29.567 | 26.327 | 14.069 | 1.00 | 13.24 | 7 |
| ATOM | 624 | CA | ARG | A | 87 | 30.720 | 26.904 | 14.754 | 1.00 | 13.60 | 6 |
| ATOM | 625 | CB | ARG | A | 87 | 30.455 | 28.374 | 15.096 | 1.00 | 13.81 | 6 |
| ATOM | 626 | CG | ARG | A | 87 | 30.556 | 29.336 | 13.925 | 1.00 | 15.20 | 6 |
| ATOM | 627 | CD | ARG | A | 87 | 30.584 | 30.781 | 14.414 | 1.00 | 17.78 | 6 |
| ATOM | 628 | NE | ARG | A | 87 | 30.344 | 31.745 | 13.338 | 1.00 | 21.20 | 7 |
| ATOM | 629 | CZ | ARG | A | 87 | 31.289 | 32.259 | 12.548 | 1.00 | 22.71 | 6 |
| ATOM | 630 | NH1 | ARG | A | 87 | 32.561 | 31.908 | 12.696 | 1.00 | 23.42 | 7 |
| ATOM | 631 | NH2 | ARG | A | 87 | 30.958 | 33.130 | 11.604 | 1.00 | 23.43 | 7 |
| ATOM | 632 | C | ARG | A | 87 | 31.071 | 26.121 | 16.031 | 1.00 | 13.48 | 6 |
| ATOM | 633 | O | ARG | A | 87 | 32.222 | 25.738 | 16.240 | 1.00 | 13.61 | 8 |
| ATOM | 634 | N | ILE | A | 88 | 30.068 | 25.886 | 16.873 | 1.00 | 13.61 | 7 |

TABLE 7-continued

Coordinates of the crystal structure of *E. coli* ExoI bound to compound 10

| ATOM | 635 | CA | ILE | A | 88 | 30.251 | 25.109 | 18.093 | 1.00 | 13.81 | 6 |
|---|---|---|---|---|---|---|---|---|---|---|---|
| ATOM | 636 | CB | ILE | A | 88 | 28.946 | 25.071 | 18.930 | 1.00 | 13.72 | 6 |
| ATOM | 637 | CG1 | ILE | A | 88 | 28.569 | 26.489 | 19.380 | 1.00 | 13.09 | 6 |
| ATOM | 638 | CD1 | ILE | A | 88 | 27.163 | 26.616 | 19.913 | 1.00 | 13.63 | 6 |
| ATOM | 639 | CG2 | ILE | A | 88 | 29.082 | 24.108 | 20.105 | 1.00 | 13.89 | 6 |
| ATOM | 640 | C | ILE | A | 88 | 30.739 | 23.683 | 17.793 | 1.00 | 14.15 | 6 |
| ATOM | 641 | O | ILE | A | 88 | 31.679 | 23.200 | 18.418 | 1.00 | 13.95 | 8 |
| ATOM | 642 | N | HIS | A | 89 | 30.104 | 23.033 | 16.818 | 1.00 | 14.67 | 7 |
| ATOM | 643 | CA | HIS | A | 89 | 30.462 | 21.669 | 16.422 | 1.00 | 14.87 | 6 |
| ATOM | 644 | CB | HIS | A | 89 | 29.488 | 21.141 | 15.368 | 1.00 | 15.06 | 6 |
| ATOM | 645 | CG | HIS | A | 89 | 29.723 | 19.710 | 14.990 | 1.00 | 15.19 | 6 |
| ATOM | 646 | ND1 | HIS | A | 89 | 30.465 | 19.345 | 13.888 | 1.00 | 15.49 | 7 |
| ATOM | 647 | CE1 | HIS | A | 89 | 30.497 | 18.027 | 13.798 | 1.00 | 14.66 | 6 |
| ATOM | 648 | NE2 | HIS | A | 89 | 29.809 | 17.524 | 14.807 | 1.00 | 15.16 | 7 |
| ATOM | 649 | CD2 | HIS | A | 89 | 29.316 | 18.555 | 15.569 | 1.00 | 15.52 | 6 |
| ATOM | 650 | C | HIS | A | 89 | 31.902 | 21.571 | 15.902 | 1.00 | 15.22 | 6 |
| ATOM | 651 | O | HIS | A | 89 | 32.596 | 20.595 | 16.166 | 1.00 | 15.06 | 8 |
| ATOM | 652 | N | SER | A | 90 | 32.342 | 22.596 | 15.176 | 1.00 | 15.51 | 7 |
| ATOM | 653 | CA | SER | A | 90 | 33.710 | 22.646 | 14.669 | 1.00 | 16.24 | 6 |
| ATOM | 654 | CB | SER | A | 90 | 33.891 | 23.827 | 13.709 | 1.00 | 16.26 | 6 |
| ATOM | 655 | OG | SER | A | 90 | 33.852 | 25.063 | 14.412 | 1.00 | 18.36 | 8 |
| ATOM | 656 | C | SER | A | 90 | 34.734 | 22.717 | 15.809 | 1.00 | 15.89 | 6 |
| ATOM | 657 | O | SER | A | 90 | 35.788 | 22.078 | 15.744 | 1.00 | 16.86 | 8 |
| ATOM | 658 | N | LEU | A | 91 | 34.410 | 23.481 | 16.853 | 1.00 | 15.75 | 7 |
| ATOM | 659 | CA | LEU | A | 91 | 35.275 | 23.607 | 18.030 | 1.00 | 14.94 | 6 |
| ATOM | 660 | CB | LEU | A | 91 | 34.820 | 24.779 | 18.907 | 1.00 | 14.86 | 6 |
| ATOM | 661 | CG | LEU | A | 91 | 35.010 | 26.197 | 18.359 | 1.00 | 15.05 | 6 |
| ATOM | 662 | CD1 | LEU | A | 91 | 34.327 | 27.205 | 19.271 | 1.00 | 16.20 | 6 |
| ATOM | 663 | CD2 | LEU | A | 91 | 36.490 | 26.525 | 18.209 | 1.00 | 16.84 | 6 |
| ATOM | 664 | C | LEU | A | 91 | 35.302 | 22.327 | 18.861 | 1.00 | 14.49 | 6 |
| ATOM | 665 | O | LEU | A | 91 | 36.363 | 21.909 | 19.342 | 1.00 | 14.78 | 8 |
| ATOM | 666 | N | PHE | A | 92 | 34.129 | 21.717 | 19.027 | 1.00 | 13.44 | 7 |
| ATOM | 667 | CA | PHE | A | 92 | 33.958 | 20.570 | 19.907 | 1.00 | 13.12 | 6 |
| ATOM | 668 | CB | PHE | A | 92 | 32.465 | 20.367 | 20.255 | 1.00 | 12.46 | 6 |
| ATOM | 669 | CG | PHE | A | 92 | 31.934 | 21.290 | 21.344 | 1.00 | 12.19 | 6 |
| ATOM | 670 | CD1 | PHE | A | 92 | 32.612 | 22.448 | 21.714 | 1.00 | 11.10 | 6 |
| ATOM | 671 | CE1 | PHE | A | 92 | 32.102 | 23.290 | 22.707 | 1.00 | 10.74 | 6 |
| ATOM | 672 | CZ | PHE | A | 92 | 30.905 | 22.980 | 23.338 | 1.00 | 11.11 | 6 |
| ATOM | 673 | CE2 | PHE | A | 92 | 30.214 | 21.830 | 22.987 | 1.00 | 12.08 | 6 |
| ATOM | 674 | CD2 | PHE | A | 92 | 30.729 | 20.987 | 21.985 | 1.00 | 11.63 | 6 |
| ATOM | 675 | C | PHE | A | 92 | 34.520 | 19.278 | 19.301 | 1.00 | 12.89 | 6 |
| ATOM | 676 | O | PHE | A | 92 | 34.759 | 18.319 | 20.021 | 1.00 | 13.28 | 8 |
| ATOM | 677 | N | THR | A | 93 | 34.709 | 19.240 | 17.980 | 1.00 | 12.89 | 7 |
| ATOM | 678 | CA | THR | A | 93 | 35.126 | 17.991 | 17.334 | 1.00 | 13.04 | 6 |
| ATOM | 679 | CB | THR | A | 93 | 34.237 | 17.618 | 16.135 | 1.00 | 13.01 | 6 |
| ATOM | 680 | OG1 | THR | A | 93 | 34.195 | 18.714 | 15.216 | 1.00 | 12.12 | 8 |
| ATOM | 681 | CG2 | THR | A | 93 | 32.821 | 17.271 | 16.609 | 1.00 | 14.51 | 6 |
| ATOM | 682 | C | THR | A | 93 | 36.599 | 17.948 | 16.931 | 1.00 | 13.18 | 6 |
| ATOM | 683 | O | THR | A | 93 | 37.034 | 17.014 | 16.259 | 1.00 | 13.01 | 8 |
| ATOM | 684 | N | VAL | A | 94 | 37.362 | 18.954 | 17.350 | 1.00 | 12.97 | 7 |
| ATOM | 685 | CA | VAL | A | 94 | 38.819 | 18.880 | 17.285 | 1.00 | 12.81 | 6 |
| ATOM | 686 | CB | VAL | A | 94 | 39.466 | 20.211 | 17.753 | 1.00 | 12.92 | 6 |
| ATOM | 687 | CG1 | VAL | A | 94 | 40.983 | 20.077 | 17.873 | 1.00 | 12.48 | 6 |
| ATOM | 688 | CG2 | VAL | A | 94 | 39.097 | 21.346 | 16.794 | 1.00 | 13.06 | 6 |
| ATOM | 689 | C | VAL | A | 94 | 39.271 | 17.705 | 18.172 | 1.00 | 12.77 | 6 |
| ATOM | 690 | O | VAL | A | 94 | 38.851 | 17.610 | 19.333 | 1.00 | 12.20 | 8 |
| ATOM | 691 | N | PRO | A | 95 | 40.079 | 16.777 | 17.609 | 1.00 | 13.06 | 7 |
| ATOM | 692 | CA | PRO | A | 95 | 40.550 | 15.592 | 18.345 | 1.00 | 13.26 | 6 |
| ATOM | 693 | CB | PRO | A | 95 | 41.524 | 14.938 | 17.361 | 1.00 | 13.42 | 6 |
| ATOM | 694 | CG | PRO | A | 95 | 41.037 | 15.356 | 16.025 | 1.00 | 13.24 | 6 |
| ATOM | 695 | CD | PRO | A | 95 | 40.561 | 16.771 | 16.213 | 1.00 | 13.23 | 6 |
| ATOM | 696 | C | PRO | A | 95 | 41.279 | 15.907 | 19.649 | 1.00 | 13.38 | 6 |
| ATOM | 697 | O | PRO | A | 95 | 41.921 | 16.951 | 19.765 | 1.00 | 14.01 | 8 |
| ATOM | 698 | N | LYS | A | 96 | 41.184 | 14.988 | 20.610 | 1.00 | 13.06 | 7 |
| ATOM | 699 | CA | LYS | A | 96 | 41.880 | 15.098 | 21.897 | 1.00 | 13.39 | 6 |
| ATOM | 700 | CB | LYS | A | 96 | 43.410 | 15.036 | 21.713 | 1.00 | 13.10 | 6 |
| ATOM | 701 | CG | LYS | A | 96 | 43.919 | 13.754 | 21.051 | 1.00 | 14.33 | 6 |
| ATOM | 702 | CD | LYS | A | 96 | 45.439 | 13.678 | 21.098 | 1.00 | 14.88 | 6 |
| ATOM | 703 | CE | LYS | A | 96 | 45.931 | 12.886 | 22.307 | 1.00 | 18.63 | 6 |
| ATOM | 704 | NZ | LYS | A | 96 | 45.840 | 11.412 | 22.079 | 1.00 | 19.29 | 7 |
| ATOM | 705 | C | LYS | A | 96 | 41.470 | 16.345 | 22.694 | 1.00 | 13.00 | 6 |
| ATOM | 706 | O | LYS | A | 96 | 42.276 | 16.912 | 23.443 | 1.00 | 13.26 | 8 |
| ATOM | 707 | N | THR | A | 97 | 40.216 | 16.761 | 22.525 | 1.00 | 12.75 | 7 |
| ATOM | 708 | CA | THR | A | 97 | 39.651 | 17.879 | 23.298 | 1.00 | 12.67 | 6 |
| ATOM | 709 | CB | THR | A | 97 | 38.711 | 18.754 | 22.430 | 1.00 | 12.99 | 6 |
| ATOM | 710 | OG1 | THR | A | 97 | 39.433 | 19.270 | 21.313 | 1.00 | 13.19 | 8 |
| ATOM | 711 | CG2 | THR | A | 97 | 38.154 | 19.924 | 23.244 | 1.00 | 13.21 | 6 |
| ATOM | 712 | C | THR | A | 97 | 38.855 | 17.387 | 24.493 | 1.00 | 12.55 | 6 |

TABLE 7-continued

Coordinates of the crystal structure of *E. coli* ExoI bound to compound 10

| ATOM | 713 | O | THR | A | 97 | 37.980 | 16.526 | 24.350 | 1.00 | 12.80 | 8 |
|---|---|---|---|---|---|---|---|---|---|---|---|
| ATOM | 714 | N | CYS | A | 98 | 39.149 | 17.953 | 25.666 | 1.00 | 11.73 | 7 |
| ATOM | 715 | CA | CYS | A | 98 | 38.279 | 17.818 | 26.822 | 1.00 | 11.31 | 6 |
| ATOM | 716 | CB | CYS | A | 98 | 39.085 | 17.647 | 28.106 | 1.00 | 11.35 | 6 |
| ATOM | 717 | SG | CYS | A | 98 | 38.052 | 17.609 | 29.610 | 1.00 | 12.81 | 16 |
| ATOM | 718 | C | CYS | A | 98 | 37.395 | 19.056 | 26.911 | 1.00 | 10.55 | 6 |
| ATOM | 719 | O | CYS | A | 98 | 37.877 | 20.157 | 27.188 | 1.00 | 9.88 | 8 |
| ATOM | 720 | N | ILE | A | 99 | 36.109 | 18.869 | 26.636 | 1.00 | 10.46 | 7 |
| ATOM | 721 | CA | ILE | A | 99 | 35.147 | 19.967 | 26.622 | 1.00 | 10.53 | 6 |
| ATOM | 722 | CB | ILE | A | 99 | 33.979 | 19.686 | 25.626 | 1.00 | 10.72 | 6 |
| ATOM | 723 | CG1 | ILE | A | 99 | 34.514 | 19.469 | 24.199 | 1.00 | 11.33 | 6 |
| ATOM | 724 | CD1 | ILE | A | 99 | 34.577 | 18.015 | 23.786 | 1.00 | 13.60 | 6 |
| ATOM | 725 | CG2 | ILE | A | 99 | 32.945 | 20.806 | 25.678 | 1.00 | 11.06 | 6 |
| ATOM | 726 | C | ILE | A | 99 | 34.579 | 20.117 | 28.009 | 1.00 | 10.69 | 6 |
| ATOM | 727 | O | ILE | A | 99 | 33.984 | 19.180 | 28.542 | 1.00 | 10.93 | 8 |
| ATOM | 728 | N | LEU | A | 100 | 34.770 | 21.288 | 28.615 | 1.00 | 10.45 | 7 |
| ATOM | 729 | CA | LEU | A | 100 | 34.360 | 21.464 | 30.009 | 1.00 | 10.47 | 6 |
| ATOM | 730 | CB | LEU | A | 100 | 35.500 | 21.089 | 30.980 | 1.00 | 10.45 | 6 |
| ATOM | 731 | CG | LEU | A | 100 | 36.689 | 22.043 | 31.181 | 1.00 | 11.09 | 6 |
| ATOM | 732 | CD1 | LEU | A | 100 | 37.637 | 21.503 | 32.249 | 1.00 | 11.45 | 6 |
| ATOM | 733 | CD2 | LEU | A | 100 | 37.447 | 22.275 | 29.889 | 1.00 | 11.97 | 6 |
| ATOM | 734 | C | LEU | A | 100 | 33.835 | 22.853 | 30.299 | 1.00 | 10.83 | 6 |
| ATOM | 735 | O | LEU | A | 100 | 34.066 | 23.790 | 29.543 | 1.00 | 11.82 | 8 |
| ATOM | 736 | N | GLY | A | 101 | 33.111 | 22.976 | 31.400 | 1.00 | 11.08 | 7 |
| ATOM | 737 | CA | GLY | A | 101 | 32.553 | 24.253 | 31.784 | 1.00 | 10.95 | 6 |
| ATOM | 738 | C | GLY | A | 101 | 32.315 | 24.278 | 33.270 | 1.00 | 10.91 | 6 |
| ATOM | 739 | O | GLY | A | 101 | 33.000 | 23.580 | 34.041 | 1.00 | 11.15 | 8 |
| ATOM | 740 | N | TYR | A | 102 | 31.340 | 25.079 | 33.673 | 1.00 | 11.01 | 7 |
| ATOM | 741 | CA | TYR | A | 102 | 30.942 | 25.144 | 35.064 | 1.00 | 11.18 | 6 |
| ATOM | 742 | CB | TYR | A | 102 | 31.344 | 26.479 | 35.692 | 1.00 | 11.65 | 6 |
| ATOM | 743 | CG | TYR | A | 102 | 31.350 | 26.407 | 37.190 | 1.00 | 11.24 | 6 |
| ATOM | 744 | CD1 | TYR | A | 102 | 32.476 | 25.954 | 37.875 | 1.00 | 11.51 | 6 |
| ATOM | 745 | CE1 | TYR | A | 102 | 32.475 | 25.853 | 39.262 | 1.00 | 12.12 | 6 |
| ATOM | 746 | CZ | TYR | A | 102 | 31.339 | 26.200 | 39.970 | 1.00 | 12.65 | 6 |
| ATOM | 747 | OH | TYR | A | 102 | 31.349 | 26.100 | 41.345 | 1.00 | 12.00 | 8 |
| ATOM | 748 | CE2 | TYR | A | 102 | 30.200 | 26.640 | 39.303 | 1.00 | 12.68 | 6 |
| ATOM | 749 | CD2 | TYR | A | 102 | 30.211 | 26.734 | 37.926 | 1.00 | 11.67 | 6 |
| ATOM | 750 | C | TYR | A | 102 | 29.436 | 24.945 | 35.139 | 1.00 | 11.33 | 6 |
| ATOM | 751 | O | TYR | A | 102 | 28.659 | 25.843 | 34.784 | 1.00 | 11.24 | 8 |
| ATOM | 752 | N | ASN | A | 103 | 29.041 | 23.760 | 35.602 | 1.00 | 12.10 | 7 |
| ATOM | 753 | CA | ASN | A | 103 | 27.656 | 23.275 | 35.527 | 1.00 | 12.63 | 6 |
| ATOM | 754 | CB | ASN | A | 103 | 26.650 | 24.281 | 36.121 | 1.00 | 12.54 | 6 |
| ATOM | 755 | CG | ASN | A | 103 | 25.297 | 23.641 | 36.434 | 1.00 | 13.23 | 6 |
| ATOM | 756 | OD1 | ASN | A | 103 | 25.225 | 22.470 | 36.800 | 1.00 | 14.60 | 8 |
| ATOM | 757 | ND2 | ASN | A | 103 | 24.221 | 24.410 | 36.272 | 1.00 | 16.03 | 7 |
| ATOM | 758 | C | ASN | A | 103 | 27.232 | 22.834 | 34.115 | 1.00 | 13.09 | 6 |
| ATOM | 759 | O | ASN | A | 103 | 26.034 | 22.764 | 33.802 | 1.00 | 13.38 | 8 |
| ATOM | 760 | N | ASN | A | 104 | 28.210 | 22.502 | 33.276 | 1.00 | 13.06 | 7 |
| ATOM | 761 | CA | ASN | A | 104 | 27.905 | 22.089 | 31.901 | 1.00 | 13.07 | 6 |
| ATOM | 762 | CB | ASN | A | 104 | 29.148 | 22.131 | 31.008 | 1.00 | 12.99 | 6 |
| ATOM | 763 | CG | ASN | A | 104 | 30.298 | 21.337 | 31.571 | 1.00 | 12.31 | 6 |
| ATOM | 764 | OD1 | ASN | A | 104 | 30.783 | 21.629 | 32.662 | 1.00 | 12.01 | 8 |
| ATOM | 765 | ND2 | ASN | A | 104 | 30.755 | 20.326 | 30.824 | 1.00 | 12.75 | 7 |
| ATOM | 766 | C | ASN | A | 104 | 27.208 | 20.736 | 31.793 | 1.00 | 13.48 | 6 |
| ATOM | 767 | O | ASN | A | 104 | 26.386 | 20.534 | 30.914 | 1.00 | 13.40 | 8 |
| ATOM | 768 | N | VAL | A | 105 | 27.522 | 19.814 | 32.697 | 1.00 | 14.08 | 7 |
| ATOM | 769 | CA | VAL | A | 105 | 26.940 | 18.473 | 32.619 | 1.00 | 14.71 | 6 |
| ATOM | 770 | CB | VAL | A | 105 | 27.525 | 17.526 | 33.685 | 1.00 | 14.68 | 6 |
| ATOM | 771 | CG1 | VAL | A | 105 | 26.727 | 16.229 | 33.759 | 1.00 | 14.95 | 6 |
| ATOM | 772 | CG2 | VAL | A | 105 | 28.970 | 17.220 | 33.364 | 1.00 | 14.65 | 6 |
| ATOM | 773 | C | VAL | A | 105 | 25.409 | 18.512 | 32.679 | 1.00 | 15.13 | 6 |
| ATOM | 774 | O | VAL | A | 105 | 24.733 | 17.824 | 31.898 | 1.00 | 16.46 | 8 |
| ATOM | 775 | N | ARG | A | 106 | 24.870 | 19.356 | 33.556 | 1.00 | 15.56 | 7 |
| ATOM | 776 | CA | ARG | A | 106 | 23.417 | 19.450 | 33.749 | 1.00 | 15.86 | 6 |
| ATOM | 777 | CB | ARG | A | 106 | 23.080 | 19.643 | 35.229 | 1.00 | 16.46 | 6 |
| ATOM | 778 | CG | ARG | A | 106 | 23.635 | 18.548 | 36.120 | 1.00 | 18.79 | 6 |
| ATOM | 779 | CD | ARG | A | 106 | 23.313 | 18.804 | 37.586 | 1.00 | 23.08 | 6 |
| ATOM | 780 | NE | ARG | A | 106 | 24.490 | 18.823 | 38.476 | 1.00 | 27.18 | 7 |
| ATOM | 781 | CZ | ARG | A | 106 | 25.685 | 18.278 | 38.218 | 1.00 | 27.90 | 6 |
| ATOM | 782 | NH1 | ARG | A | 106 | 25.923 | 17.626 | 37.083 | 1.00 | 27.99 | 7 |
| ATOM | 783 | NH2 | ARG | A | 106 | 26.654 | 18.391 | 39.111 | 1.00 | 28.51 | 7 |
| ATOM | 784 | C | ARG | A | 106 | 22.743 | 20.541 | 32.906 | 1.00 | 15.30 | 6 |
| ATOM | 785 | O | ARG | A | 106 | 21.532 | 20.480 | 32.665 | 1.00 | 15.59 | 8 |
| ATOM | 786 | N | PHE | A | 107 | 23.515 | 21.529 | 32.452 | 1.00 | 14.34 | 7 |
| ATOM | 787 | CA | PHE | A | 107 | 22.941 | 22.616 | 31.662 | 1.00 | 13.07 | 6 |
| ATOM | 788 | CB | PHE | A | 107 | 23.016 | 23.951 | 32.407 | 1.00 | 13.02 | 6 |
| ATOM | 789 | CG | PHE | A | 107 | 22.298 | 25.065 | 31.706 | 1.00 | 12.39 | 6 |
| ATOM | 790 | CD1 | PHE | A | 107 | 20.911 | 25.019 | 31.536 | 1.00 | 13.22 | 6 |

TABLE 7-continued

Coordinates of the crystal structure of *E. coli* ExoI bound to compound 10

| ATOM | 791 | CE1 | PHE | A | 107 | 20.236 | 26.047 | 30.863 | 1.00 | 13.50 | 6 |
|---|---|---|---|---|---|---|---|---|---|---|---|
| ATOM | 792 | CZ | PHE | A | 107 | 20.946 | 27.129 | 30.373 | 1.00 | 12.88 | 6 |
| ATOM | 793 | CE2 | PHE | A | 107 | 22.333 | 27.183 | 30.531 | 1.00 | 12.85 | 6 |
| ATOM | 794 | CD2 | PHE | A | 107 | 23.000 | 26.151 | 31.188 | 1.00 | 12.71 | 6 |
| ATOM | 795 | C | PHE | A | 107 | 23.517 | 22.752 | 30.253 | 1.00 | 12.78 | 6 |
| ATOM | 796 | O | PHE | A | 107 | 22.840 | 22.441 | 29.276 | 1.00 | 12.53 | 8 |
| ATOM | 797 | N | ASP | A | 108 | 24.756 | 23.229 | 30.154 | 1.00 | 12.65 | 7 |
| ATOM | 798 | CA | ASP | A | 108 | 25.334 | 23.603 | 28.853 | 1.00 | 12.55 | 6 |
| ATOM | 799 | CB | ASP | A | 108 | 26.725 | 24.228 | 29.027 | 1.00 | 12.85 | 6 |
| ATOM | 800 | CG | ASP | A | 108 | 26.713 | 25.417 | 29.956 | 1.00 | 12.52 | 6 |
| ATOM | 801 | OD1 | ASP | A | 108 | 26.824 | 26.561 | 29.454 | 1.00 | 12.38 | 8 |
| ATOM | 802 | OD2 | ASP | A | 108 | 26.588 | 25.210 | 31.188 | 1.00 | 14.32 | 8 |
| ATOM | 803 | C | ASP | A | 108 | 25.390 | 22.441 | 27.862 | 1.00 | 12.78 | 6 |
| ATOM | 804 | O | ASP | A | 108 | 25.125 | 22.627 | 26.662 | 1.00 | 12.59 | 8 |
| ATOM | 805 | N | ASP | A | 109 | 25.728 | 21.248 | 28.355 | 1.00 | 12.76 | 7 |
| ATOM | 806 | CA | ASP | A | 109 | 25.757 | 20.050 | 27.510 | 1.00 | 13.49 | 6 |
| ATOM | 807 | CB | ASP | A | 109 | 26.316 | 18.855 | 28.283 | 1.00 | 13.76 | 6 |
| ATOM | 808 | CG | ASP | A | 109 | 27.803 | 18.985 | 28.571 | 1.00 | 15.55 | 6 |
| ATOM | 809 | OD1 | ASP | A | 109 | 28.448 | 19.933 | 28.060 | 1.00 | 15.92 | 8 |
| ATOM | 810 | OD2 | ASP | A | 109 | 28.335 | 18.124 | 29.311 | 1.00 | 17.53 | 8 |
| ATOM | 811 | C | ASP | A | 109 | 24.375 | 19.713 | 26.964 | 1.00 | 13.33 | 6 |
| ATOM | 812 | O | ASP | A | 109 | 24.236 | 19.255 | 25.824 | 1.00 | 13.67 | 8 |
| ATOM | 813 | N | GLU | A | 110 | 23.352 | 19.969 | 27.771 | 1.00 | 13.06 | 7 |
| ATOM | 814 | CA | GLU | A | 110 | 21.972 | 19.752 | 27.352 | 1.00 | 13.09 | 6 |
| ATOM | 815 | CB | GLU | A | 110 | 21.043 | 19.737 | 28.561 | 1.00 | 13.28 | 6 |
| ATOM | 816 | CG | GLU | A | 110 | 21.229 | 18.525 | 29.437 | 1.00 | 15.94 | 6 |
| ATOM | 817 | CD | GLU | A | 110 | 20.969 | 17.222 | 28.689 | 1.00 | 18.22 | 6 |
| ATOM | 818 | OE1 | GLU | A | 110 | 19.877 | 17.086 | 28.094 | 1.00 | 20.07 | 8 |
| ATOM | 819 | OE2 | GLU | A | 110 | 21.863 | 16.344 | 28.685 | 1.00 | 20.95 | 8 |
| ATOM | 820 | C | GLU | A | 110 | 21.515 | 20.780 | 26.318 | 1.00 | 12.47 | 6 |
| ATOM | 821 | O | GLU | A | 110 | 20.766 | 20.449 | 25.391 | 1.00 | 12.47 | 8 |
| ATOM | 822 | N | VAL | A | 111 | 21.973 | 22.023 | 26.464 | 1.00 | 11.80 | 7 |
| ATOM | 823 | CA | VAL | A | 111 | 21.793 | 23.022 | 25.399 | 1.00 | 11.50 | 6 |
| ATOM | 824 | CB | VAL | A | 111 | 22.323 | 24.421 | 25.809 | 1.00 | 11.38 | 6 |
| ATOM | 825 | CG1 | VAL | A | 111 | 22.190 | 25.408 | 24.669 | 1.00 | 11.22 | 6 |
| ATOM | 826 | CG2 | VAL | A | 111 | 21.582 | 24.937 | 27.037 | 1.00 | 11.05 | 6 |
| ATOM | 827 | C | VAL | A | 111 | 22.472 | 22.548 | 24.112 | 1.00 | 11.66 | 6 |
| ATOM | 828 | O | VAL | A | 111 | 21.860 | 22.546 | 23.045 | 1.00 | 12.10 | 8 |
| ATOM | 829 | N | THR | A | 112 | 23.732 | 22.131 | 24.227 | 1.00 | 11.70 | 7 |
| ATOM | 830 | CA | THR | A | 112 | 24.482 | 21.604 | 23.092 | 1.00 | 11.96 | 6 |
| ATOM | 831 | CB | THR | A | 112 | 25.878 | 21.132 | 23.525 | 1.00 | 11.97 | 6 |
| ATOM | 832 | OG1 | THR | A | 112 | 26.601 | 22.243 | 24.073 | 1.00 | 12.20 | 8 |
| ATOM | 833 | CG2 | THR | A | 112 | 26.650 | 20.558 | 22.339 | 1.00 | 11.65 | 6 |
| ATOM | 834 | C | THR | A | 112 | 23.731 | 20.465 | 22.400 | 1.00 | 12.19 | 6 |
| ATOM | 835 | O | THR | A | 112 | 23.548 | 20.483 | 21.180 | 1.00 | 11.83 | 8 |
| ATOM | 836 | N | ARG | A | 113 | 23.281 | 19.484 | 23.180 | 1.00 | 12.38 | 7 |
| ATOM | 837 | CA | ARG | A | 113 | 22.587 | 18.324 | 22.610 | 1.00 | 12.75 | 6 |
| ATOM | 838 | CB | ARG | A | 113 | 22.217 | 17.312 | 23.692 | 1.00 | 13.58 | 6 |
| ATOM | 839 | CG | ARG | A | 113 | 23.417 | 16.602 | 24.287 | 1.00 | 15.46 | 6 |
| ATOM | 840 | CD | ARG | A | 113 | 23.003 | 15.467 | 25.216 | 1.00 | 20.60 | 6 |
| ATOM | 841 | NE | ARG | A | 113 | 24.116 | 15.008 | 26.059 | 1.00 | 24.49 | 7 |
| ATOM | 842 | CZ | ARG | A | 113 | 25.241 | 14.450 | 25.600 | 1.00 | 27.34 | 6 |
| ATOM | 843 | NH1 | ARG | A | 113 | 25.440 | 14.294 | 24.293 | 1.00 | 28.57 | 7 |
| ATOM | 844 | NH2 | ARG | A | 113 | 26.182 | 14.056 | 26.449 | 1.00 | 28.87 | 7 |
| ATOM | 845 | C | ARG | A | 113 | 21.357 | 18.736 | 21.817 | 1.00 | 12.65 | 6 |
| ATOM | 846 | O | ARG | A | 113 | 21.089 | 18.188 | 20.747 | 1.00 | 12.92 | 8 |
| ATOM | 847 | N | ASN | A | 114 | 20.633 | 19.727 | 22.331 | 1.00 | 11.97 | 7 |
| ATOM | 848 | CA | ASN | A | 114 | 19.404 | 20.196 | 21.702 | 1.00 | 11.72 | 6 |
| ATOM | 849 | CB | ASN | A | 114 | 18.543 | 20.938 | 22.725 | 1.00 | 12.26 | 6 |
| ATOM | 850 | CG | ASN | A | 114 | 17.783 | 19.985 | 23.633 | 1.00 | 12.54 | 6 |
| ATOM | 851 | OD1 | ASN | A | 114 | 18.139 | 19.791 | 24.806 | 1.00 | 15.86 | 8 |
| ATOM | 852 | ND2 | ASN | A | 114 | 16.751 | 19.364 | 23.090 | 1.00 | 11.70 | 7 |
| ATOM | 853 | C | ASN | A | 114 | 19.631 | 21.031 | 20.440 | 1.00 | 11.53 | 6 |
| ATOM | 854 | O | ASN | A | 114 | 18.922 | 20.864 | 19.445 | 1.00 | 11.14 | 8 |
| ATOM | 855 | N | ILE | A | 115 | 20.631 | 21.909 | 20.472 | 1.00 | 11.38 | 7 |
| ATOM | 856 | CA | ILE | A | 115 | 21.030 | 22.669 | 19.281 | 1.00 | 12.11 | 6 |
| ATOM | 857 | CB | ILE | A | 115 | 22.187 | 23.643 | 19.596 | 1.00 | 12.40 | 6 |
| ATOM | 858 | CG1 | ILE | A | 115 | 21.733 | 24.729 | 20.577 | 1.00 | 12.59 | 6 |
| ATOM | 859 | CD1 | ILE | A | 115 | 22.890 | 25.485 | 21.210 | 1.00 | 12.12 | 6 |
| ATOM | 860 | CG2 | ILE | A | 115 | 22.716 | 24.285 | 18.333 | 1.00 | 12.89 | 6 |
| ATOM | 861 | C | ILE | A | 115 | 21.463 | 21.729 | 18.144 | 1.00 | 12.20 | 6 |
| ATOM | 862 | O | ILE | A | 115 | 21.117 | 21.940 | 16.981 | 1.00 | 12.10 | 8 |
| ATOM | 863 | N | PHE | A | 116 | 22.225 | 20.693 | 18.501 | 1.00 | 12.63 | 7 |
| ATOM | 864 | CA | PHE | A | 116 | 22.696 | 19.697 | 17.541 | 1.00 | 12.35 | 6 |
| ATOM | 865 | CB | PHE | A | 116 | 23.721 | 18.770 | 18.210 | 1.00 | 12.67 | 6 |
| ATOM | 866 | CG | PHE | A | 116 | 25.100 | 19.391 | 18.389 | 1.00 | 11.93 | 6 |
| ATOM | 867 | CD1 | PHE | A | 116 | 25.364 | 20.712 | 18.006 | 1.00 | 11.56 | 6 |
| ATOM | 868 | CE1 | PHE | A | 116 | 26.639 | 21.264 | 18.180 | 1.00 | 11.52 | 6 |

TABLE 7-continued

Coordinates of the crystal structure of *E. coli* ExoI bound to compound 10

| ATOM | 869 | CZ | PHE | A | 116 | 27.655 | 20.505 | 18.748 | 1.00 | 12.24 | 6 |
|---|---|---|---|---|---|---|---|---|---|---|---|
| ATOM | 870 | CE2 | PHE | A | 116 | 27.411 | 19.194 | 19.121 | 1.00 | 11.81 | 6 |
| ATOM | 871 | CD2 | PHE | A | 116 | 26.138 | 18.643 | 18.947 | 1.00 | 12.39 | 6 |
| ATOM | 872 | C | PHE | A | 116 | 21.515 | 18.892 | 16.994 | 1.00 | 12.80 | 6 |
| ATOM | 873 | O | PHE | A | 116 | 21.382 | 18.718 | 15.780 | 1.00 | 12.64 | 8 |
| ATOM | 874 | N | TYR | A | 117 | 20.653 | 18.438 | 17.906 | 1.00 | 13.04 | 7 |
| ATOM | 875 | CA | TYR | A | 117 | 19.387 | 17.763 | 17.571 | 1.00 | 13.50 | 6 |
| ATOM | 876 | CB | TYR | A | 117 | 18.622 | 17.426 | 18.869 | 1.00 | 13.97 | 6 |
| ATOM | 877 | CG | TYR | A | 117 | 17.168 | 17.010 | 18.714 | 1.00 | 14.55 | 6 |
| ATOM | 878 | CD1 | TYR | A | 117 | 16.825 | 15.738 | 18.241 | 1.00 | 16.18 | 6 |
| ATOM | 879 | CE1 | TYR | A | 117 | 15.487 | 15.344 | 18.124 | 1.00 | 15.17 | 6 |
| ATOM | 880 | CZ | TYR | A | 117 | 14.478 | 16.229 | 18.490 | 1.00 | 15.35 | 6 |
| ATOM | 881 | OH | TYR | A | 117 | 13.151 | 15.848 | 18.376 | 1.00 | 15.17 | 8 |
| ATOM | 882 | CE2 | TYR | A | 117 | 14.797 | 17.493 | 18.978 | 1.00 | 14.92 | 6 |
| ATOM | 883 | CD2 | TYR | A | 117 | 16.136 | 17.872 | 19.095 | 1.00 | 15.36 | 6 |
| ATOM | 884 | C | TYR | A | 117 | 18.514 | 18.569 | 16.599 | 1.00 | 13.52 | 6 |
| ATOM | 885 | O | TYR | A | 117 | 18.053 | 18.037 | 15.592 | 1.00 | 13.17 | 8 |
| ATOM | 886 | N | ARG | A | 118 | 18.305 | 19.854 | 16.889 | 1.00 | 13.25 | 7 |
| ATOM | 887 | CA | ARG | A | 118 | 17.463 | 20.692 | 16.028 | 1.00 | 13.20 | 6 |
| ATOM | 888 | CB | ARG | A | 118 | 17.145 | 22.027 | 16.701 | 1.00 | 13.03 | 6 |
| ATOM | 889 | CG | ARG | A | 118 | 16.295 | 21.903 | 17.954 | 1.00 | 12.95 | 6 |
| ATOM | 890 | CD | ARG | A | 118 | 15.677 | 23.240 | 18.331 | 1.00 | 13.09 | 6 |
| ATOM | 891 | NE | ARG | A | 118 | 16.644 | 24.190 | 18.887 | 1.00 | 12.69 | 7 |
| ATOM | 892 | CZ | ARG | A | 118 | 16.891 | 24.327 | 20.187 | 1.00 | 13.30 | 6 |
| ATOM | 893 | NH1 | ARG | A | 118 | 16.265 | 23.553 | 21.071 | 1.00 | 13.22 | 7 |
| ATOM | 894 | NH2 | ARG | A | 118 | 17.762 | 25.237 | 20.608 | 1.00 | 13.43 | 7 |
| ATOM | 895 | C | ARG | A | 118 | 18.071 | 20.939 | 14.645 | 1.00 | 13.42 | 6 |
| ATOM | 896 | O | ARG | A | 118 | 17.346 | 21.178 | 13.670 | 1.00 | 14.04 | 8 |
| ATOM | 897 | N | ASN | A | 119 | 19.398 | 20.880 | 14.564 | 1.00 | 13.34 | 7 |
| ATOM | 898 | CA | ASN | A | 119 | 20.111 | 21.326 | 13.377 | 1.00 | 13.62 | 6 |
| ATOM | 899 | CB | ASN | A | 119 | 20.995 | 22.520 | 13.730 | 1.00 | 13.54 | 6 |
| ATOM | 900 | CG | ASN | A | 119 | 20.172 | 23.723 | 14.176 | 1.00 | 12.59 | 6 |
| ATOM | 901 | OD1 | ASN | A | 119 | 19.609 | 24.445 | 13.345 | 1.00 | 11.81 | 8 |
| ATOM | 902 | ND2 | ASN | A | 119 | 20.055 | 23.915 | 15.491 | 1.00 | 13.00 | 7 |
| ATOM | 903 | C | ASN | A | 119 | 20.869 | 20.212 | 12.651 | 1.00 | 14.14 | 6 |
| ATOM | 904 | O | ASN | A | 119 | 21.810 | 20.468 | 11.876 | 1.00 | 14.12 | 8 |
| ATOM | 905 | N | PHE | A | 120 | 20.428 | 18.976 | 12.895 | 1.00 | 14.24 | 7 |
| ATOM | 906 | CA | PHE | A | 120 | 20.834 | 17.803 | 12.112 | 1.00 | 14.75 | 6 |
| ATOM | 907 | CB | PHE | A | 120 | 20.464 | 17.974 | 10.635 | 1.00 | 15.23 | 6 |
| ATOM | 908 | CG | PHE | A | 120 | 18.989 | 17.925 | 10.386 | 1.00 | 15.86 | 6 |
| ATOM | 909 | CD1 | PHE | A | 120 | 18.381 | 16.740 | 9.990 | 1.00 | 16.57 | 6 |
| ATOM | 910 | CE1 | PHE | A | 120 | 17.014 | 16.678 | 9.783 | 1.00 | 16.66 | 6 |
| ATOM | 911 | CZ | PHE | A | 120 | 16.234 | 17.808 | 9.977 | 1.00 | 16.99 | 6 |
| ATOM | 912 | CE2 | PHE | A | 120 | 16.824 | 18.997 | 10.373 | 1.00 | 17.14 | 6 |
| ATOM | 913 | CD2 | PHE | A | 120 | 18.199 | 19.050 | 10.586 | 1.00 | 16.48 | 6 |
| ATOM | 914 | C | PHE | A | 120 | 22.287 | 17.394 | 12.295 | 1.00 | 15.09 | 6 |
| ATOM | 915 | O | PHE | A | 120 | 22.906 | 16.828 | 11.386 | 1.00 | 14.87 | 8 |
| ATOM | 916 | N | TYR | A | 121 | 22.816 | 17.692 | 13.480 | 1.00 | 14.93 | 7 |
| ATOM | 917 | CA | TYR | A | 121 | 24.066 | 17.107 | 13.970 | 1.00 | 15.72 | 6 |
| ATOM | 918 | CB | TYR | A | 121 | 24.906 | 18.160 | 14.704 | 1.00 | 15.59 | 6 |
| ATOM | 919 | CG | TYR | A | 121 | 25.483 | 19.223 | 13.810 | 1.00 | 15.53 | 6 |
| ATOM | 920 | CD1 | TYR | A | 121 | 26.726 | 19.048 | 13.201 | 1.00 | 15.17 | 6 |
| ATOM | 921 | CE1 | TYR | A | 121 | 27.260 | 20.024 | 12.375 | 1.00 | 15.11 | 6 |
| ATOM | 922 | CZ | TYR | A | 121 | 26.549 | 21.188 | 12.150 | 1.00 | 15.67 | 6 |
| ATOM | 923 | OH | TYR | A | 121 | 27.073 | 22.147 | 11.322 | 1.00 | 17.50 | 8 |
| ATOM | 924 | CE2 | TYR | A | 121 | 25.309 | 21.388 | 12.743 | 1.00 | 15.64 | 6 |
| ATOM | 925 | CD2 | TYR | A | 121 | 24.784 | 20.409 | 13.564 | 1.00 | 14.74 | 6 |
| ATOM | 926 | C | TYR | A | 121 | 23.772 | 15.955 | 14.924 | 1.00 | 15.93 | 6 |
| ATOM | 927 | O | TYR | A | 121 | 22.711 | 15.915 | 15.556 | 1.00 | 16.24 | 8 |
| ATOM | 928 | N | ASP | A | 122 | 24.718 | 15.025 | 15.039 | 1.00 | 16.38 | 7 |
| ATOM | 929 | CA | ASP | A | 122 | 24.672 | 14.013 | 16.098 | 1.00 | 16.43 | 6 |
| ATOM | 930 | CB | ASP | A | 122 | 25.795 | 12.990 | 15.912 | 1.00 | 16.51 | 6 |
| ATOM | 931 | CG | ASP | A | 122 | 25.590 | 11.732 | 16.752 | 1.00 | 17.23 | 6 |
| ATOM | 932 | OD1 | ASP | A | 122 | 25.727 | 11.794 | 17.993 | 1.00 | 18.13 | 8 |
| ATOM | 933 | OD2 | ASP | A | 122 | 25.305 | 10.676 | 16.163 | 1.00 | 19.91 | 8 |
| ATOM | 934 | C | ASP | A | 122 | 24.795 | 14.695 | 17.466 | 1.00 | 16.67 | 6 |
| ATOM | 935 | O | ASP | A | 122 | 25.774 | 15.387 | 17.724 | 1.00 | 16.39 | 8 |
| ATOM | 936 | N | PRO | A | 123 | 23.790 | 14.501 | 18.343 | 1.00 | 16.80 | 7 |
| ATOM | 937 | CA | PRO | A | 123 | 23.777 | 15.146 | 19.658 | 1.00 | 17.07 | 6 |
| ATOM | 938 | CB | PRO | A | 123 | 22.364 | 14.840 | 20.188 | 1.00 | 17.05 | 6 |
| ATOM | 939 | CG | PRO | A | 123 | 21.578 | 14.389 | 18.985 | 1.00 | 16.74 | 6 |
| ATOM | 940 | CD | PRO | A | 123 | 22.579 | 13.694 | 18.127 | 1.00 | 16.70 | 6 |
| ATOM | 941 | C | PRO | A | 123 | 24.813 | 14.605 | 20.637 | 1.00 | 17.59 | 6 |
| ATOM | 942 | O | PRO | A | 123 | 25.054 | 15.231 | 21.671 | 1.00 | 17.72 | 8 |
| ATOM | 943 | N | TYR | A | 124 | 25.425 | 13.465 | 20.313 | 1.00 | 17.96 | 7 |
| ATOM | 944 | CA | TYR | A | 124 | 26.207 | 12.712 | 21.299 | 1.00 | 18.77 | 6 |
| ATOM | 945 | CB | TYR | A | 124 | 25.549 | 11.360 | 21.585 | 1.00 | 19.53 | 6 |
| ATOM | 946 | CG | TYR | A | 124 | 24.102 | 11.460 | 21.996 | 1.00 | 20.40 | 6 |

TABLE 7-continued

Coordinates of the crystal structure of *E. coli* ExoI bound to compound 10

| ATOM | 947 | CD1 | TYR | A | 124 | 23.753 | 11.839 | 23.291 | 1.00 | 21.05 | 6 |
|---|---|---|---|---|---|---|---|---|---|---|---|
| ATOM | 948 | CE1 | TYR | A | 124 | 22.427 | 11.942 | 23.675 | 1.00 | 21.48 | 6 |
| ATOM | 949 | CZ | TYR | A | 124 | 21.428 | 11.660 | 22.762 | 1.00 | 21.42 | 6 |
| ATOM | 950 | OH | TYR | A | 124 | 20.116 | 11.762 | 23.149 | 1.00 | 22.21 | 8 |
| ATOM | 951 | CE2 | TYR | A | 124 | 21.744 | 11.280 | 21.466 | 1.00 | 21.11 | 6 |
| ATOM | 952 | CD2 | TYR | A | 124 | 23.079 | 11.182 | 21.090 | 1.00 | 20.18 | 6 |
| ATOM | 953 | C | TYR | A | 124 | 27.671 | 12.494 | 20.927 | 1.00 | 18.59 | 6 |
| ATOM | 954 | O | TYR | A | 124 | 28.542 | 12.529 | 21.800 | 1.00 | 18.82 | 8 |
| ATOM | 955 | N | ALA | A | 125 | 27.934 | 12.262 | 19.639 | 1.00 | 18.17 | 7 |
| ATOM | 956 | CA | ALA | A | 125 | 29.252 | 11.791 | 19.179 | 1.00 | 18.03 | 6 |
| ATOM | 957 | CB | ALA | A | 125 | 29.213 | 11.461 | 17.684 | 1.00 | 17.91 | 6 |
| ATOM | 958 | C | ALA | A | 125 | 30.405 | 12.751 | 19.485 | 1.00 | 17.64 | 6 |
| ATOM | 959 | O | ALA | A | 125 | 31.550 | 12.325 | 19.629 | 1.00 | 18.03 | 8 |
| ATOM | 960 | N | TRP | A | 126 | 30.094 | 14.043 | 19.579 | 1.00 | 17.14 | 7 |
| ATOM | 961 | CA | TRP | A | 126 | 31.102 | 15.086 | 19.774 | 1.00 | 16.85 | 6 |
| ATOM | 962 | CB | TRP | A | 126 | 30.440 | 16.468 | 19.824 | 1.00 | 16.86 | 6 |
| ATOM | 963 | CG | TRP | A | 126 | 29.392 | 16.596 | 20.903 | 1.00 | 16.99 | 6 |
| ATOM | 964 | CD1 | TRP | A | 126 | 28.079 | 16.234 | 20.814 | 1.00 | 16.78 | 6 |
| ATOM | 965 | NE1 | TRP | A | 126 | 27.432 | 16.499 | 21.995 | 1.00 | 17.08 | 7 |
| ATOM | 966 | CE2 | TRP | A | 126 | 28.325 | 17.047 | 22.880 | 1.00 | 16.96 | 6 |
| ATOM | 967 | CD2 | TRP | A | 126 | 29.575 | 17.121 | 22.226 | 1.00 | 16.61 | 6 |
| ATOM | 968 | CE3 | TRP | A | 126 | 30.675 | 17.646 | 22.925 | 1.00 | 17.18 | 6 |
| ATOM | 969 | CZ3 | TRP | A | 126 | 30.491 | 18.072 | 24.235 | 1.00 | 16.50 | 6 |
| ATOM | 970 | CH2 | TRP | A | 126 | 29.230 | 17.989 | 24.858 | 1.00 | 16.04 | 6 |
| ATOM | 971 | CZ2 | TRP | A | 126 | 28.141 | 17.475 | 24.201 | 1.00 | 16.55 | 6 |
| ATOM | 972 | C | TRP | A | 126 | 31.915 | 14.874 | 21.044 | 1.00 | 16.55 | 6 |
| ATOM | 973 | O | TRP | A | 126 | 33.080 | 15.260 | 21.109 | 1.00 | 16.76 | 8 |
| ATOM | 974 | N | SER | A | 127 | 31.293 | 14.242 | 22.039 | 1.00 | 15.96 | 7 |
| ATOM | 975 | CA | SER | A | 127 | 31.850 | 14.181 | 23.390 | 1.00 | 16.27 | 6 |
| ATOM | 976 | CB | SER | A | 127 | 30.724 | 14.164 | 24.429 | 1.00 | 15.79 | 6 |
| ATOM | 977 | OG | SER | A | 127 | 30.123 | 12.885 | 24.518 | 1.00 | 17.24 | 8 |
| ATOM | 978 | C | SER | A | 127 | 32.814 | 13.018 | 23.632 | 1.00 | 16.11 | 6 |
| ATOM | 979 | O | SER | A | 127 | 33.485 | 12.974 | 24.669 | 1.00 | 15.88 | 8 |
| ATOM | 980 | N | TRP | A | 128 | 32.881 | 12.077 | 22.691 | 1.00 | 16.51 | 7 |
| ATOM | 981 | CA | TRP | A | 128 | 33.727 | 10.894 | 22.874 | 1.00 | 16.47 | 6 |
| ATOM | 982 | CB | TRP | A | 128 | 32.901 | 9.680 | 23.323 | 1.00 | 16.28 | 6 |
| ATOM | 983 | CG | TRP | A | 128 | 31.877 | 9.210 | 22.328 | 1.00 | 16.51 | 6 |
| ATOM | 984 | CD1 | TRP | A | 128 | 30.561 | 9.580 | 22.265 | 1.00 | 16.56 | 6 |
| ATOM | 985 | NE1 | TRP | A | 128 | 29.933 | 8.922 | 21.232 | 1.00 | 16.33 | 7 |
| ATOM | 986 | CE2 | TRP | A | 128 | 30.842 | 8.113 | 20.602 | 1.00 | 16.34 | 6 |
| ATOM | 987 | CD2 | TRP | A | 128 | 32.078 | 8.261 | 21.273 | 1.00 | 16.30 | 6 |
| ATOM | 988 | CE3 | TRP | A | 128 | 33.186 | 7.529 | 20.821 | 1.00 | 16.23 | 6 |
| ATOM | 989 | CZ3 | TRP | A | 128 | 33.024 | 6.678 | 19.729 | 1.00 | 16.51 | 6 |
| ATOM | 990 | CH2 | TRP | A | 128 | 31.776 | 6.552 | 19.084 | 1.00 | 16.57 | 6 |
| ATOM | 991 | CZ2 | TRP | A | 128 | 30.680 | 7.260 | 19.503 | 1.00 | 15.83 | 6 |
| ATOM | 992 | C | TRP | A | 128 | 34.618 | 10.536 | 21.684 | 1.00 | 16.92 | 6 |
| ATOM | 993 | O | TRP | A | 128 | 35.686 | 9.957 | 21.875 | 1.00 | 16.97 | 8 |
| ATOM | 994 | N | GLN | A | 129 | 34.180 | 10.876 | 20.469 | 1.00 | 17.59 | 7 |
| ATOM | 995 | CA | GLN | A | 129 | 34.947 | 10.560 | 19.246 | 1.00 | 18.35 | 6 |
| ATOM | 996 | CB | GLN | A | 129 | 34.151 | 10.940 | 17.993 | 1.00 | 18.24 | 6 |
| ATOM | 997 | CG | GLN | A | 129 | 32.995 | 9.992 | 17.663 | 1.00 | 19.55 | 6 |
| ATOM | 998 | CD | GLN | A | 129 | 32.395 | 10.239 | 16.279 | 1.00 | 20.30 | 6 |
| ATOM | 999 | OE1 | GLN | A | 129 | 32.560 | 11.315 | 15.698 | 1.00 | 22.16 | 8 |
| ATOM | 1000 | NE2 | GLN | A | 129 | 31.704 | 9.231 | 15.741 | 1.00 | 21.07 | 7 |
| ATOM | 1001 | C | GLN | A | 129 | 36.302 | 11.273 | 19.228 | 1.00 | 18.43 | 6 |
| ATOM | 1002 | O | GLN | A | 129 | 36.453 | 12.326 | 19.834 | 1.00 | 18.58 | 8 |
| ATOM | 1003 | N | HIS | A | 130 | 37.276 | 10.689 | 18.526 | 1.00 | 19.05 | 7 |
| ATOM | 1004 | CA | HIS | A | 130 | 38.622 | 11.283 | 18.385 | 1.00 | 19.20 | 6 |
| ATOM | 1005 | CB | HIS | A | 130 | 38.577 | 12.608 | 17.599 | 1.00 | 19.81 | 6 |
| ATOM | 1006 | CG | HIS | A | 130 | 37.703 | 12.578 | 16.381 | 1.00 | 20.84 | 6 |
| ATOM | 1007 | ND1 | HIS | A | 130 | 37.977 | 11.791 | 15.283 | 1.00 | 22.57 | 7 |
| ATOM | 1008 | CE1 | HIS | A | 130 | 37.049 | 11.986 | 14.363 | 1.00 | 22.36 | 6 |
| ATOM | 1009 | NE2 | HIS | A | 130 | 36.190 | 12.879 | 14.818 | 1.00 | 22.91 | 7 |
| ATOM | 1010 | CD2 | HIS | A | 130 | 36.580 | 13.272 | 16.076 | 1.00 | 21.95 | 6 |
| ATOM | 1011 | C | HIS | A | 130 | 39.324 | 11.522 | 19.736 | 1.00 | 18.98 | 6 |
| ATOM | 1012 | O | HIS | A | 130 | 40.096 | 12.480 | 19.881 | 1.00 | 19.06 | 8 |
| ATOM | 1013 | N | ASP | A | 131 | 39.053 | 10.653 | 20.712 | 1.00 | 18.67 | 7 |
| ATOM | 1014 | CA | ASP | A | 131 | 39.667 | 10.729 | 22.048 | 1.00 | 18.57 | 6 |
| ATOM | 1015 | CB | ASP | A | 131 | 41.205 | 10.794 | 21.961 | 1.00 | 19.43 | 6 |
| ATOM | 1016 | CG | ASP | A | 131 | 41.827 | 9.483 | 21.524 | 1.00 | 21.89 | 6 |
| ATOM | 1017 | OD1 | ASP | A | 131 | 41.223 | 8.409 | 21.765 | 1.00 | 24.99 | 8 |
| ATOM | 1018 | OD2 | ASP | A | 131 | 42.940 | 9.526 | 20.948 | 1.00 | 24.98 | 8 |
| ATOM | 1019 | C | ASP | A | 131 | 39.151 | 11.896 | 22.893 | 1.00 | 17.54 | 6 |
| ATOM | 1020 | O | ASP | A | 131 | 39.745 | 12.229 | 23.924 | 1.00 | 17.28 | 8 |
| ATOM | 1021 | N | ASN | A | 132 | 38.045 | 12.505 | 22.469 | 1.00 | 16.25 | 7 |
| ATOM | 1022 | CA | ASN | A | 132 | 37.463 | 13.610 | 23.220 | 1.00 | 15.55 | 6 |
| ATOM | 1023 | CB | ASN | A | 132 | 36.412 | 14.353 | 22.389 | 1.00 | 15.22 | 6 |
| ATOM | 1024 | CG | ASN | A | 132 | 37.032 | 15.280 | 21.355 | 1.00 | 15.64 | 6 |

TABLE 7-continued

Coordinates of the crystal structure of *E. coli* ExoI bound to compound 10

| ATOM | 1025 | OD1 | ASN | A | 132 | 38.237 | 15.257 | 21.128 | 1.00 | 15.95 | 8 |
|------|------|-----|-----|---|-----|--------|--------|--------|------|-------|---|
| ATOM | 1026 | ND2 | ASN | A | 132 | 36.197 | 16.106 | 20.721 | 1.00 | 15.87 | 7 |
| ATOM | 1027 | C | ASN | A | 132 | 36.869 | 13.164 | 24.551 | 1.00 | 15.12 | 6 |
| ATOM | 1028 | O | ASN | A | 132 | 36.631 | 11.979 | 24.772 | 1.00 | 15.02 | 8 |
| ATOM | 1029 | N | SER | A | 133 | 36.645 | 14.125 | 25.439 | 1.00 | 14.92 | 7 |
| ATOM | 1030 | CA | SER | A | 133 | 36.028 | 13.847 | 26.725 | 1.00 | 14.40 | 6 |
| ATOM | 1031 | CB | SER | A | 133 | 37.088 | 13.418 | 27.745 | 1.00 | 14.47 | 6 |
| ATOM | 1032 | OG | SER | A | 133 | 37.968 | 14.493 | 28.064 | 1.00 | 13.85 | 8 |
| ATOM | 1033 | C | SER | A | 133 | 35.291 | 15.074 | 27.216 | 1.00 | 14.57 | 6 |
| ATOM | 1034 | O | SER | A | 133 | 35.308 | 16.122 | 26.563 | 1.00 | 14.41 | 8 |
| ATOM | 1035 | N | ARG | A | 134 | 34.629 | 14.937 | 28.356 | 1.00 | 14.55 | 7 |
| ATOM | 1036 | CA | ARG | A | 134 | 34.045 | 16.082 | 29.016 | 1.00 | 14.90 | 6 |
| ATOM | 1037 | CB | ARG | A | 134 | 32.540 | 16.203 | 28.744 | 1.00 | 15.97 | 6 |
| ATOM | 1038 | CG | ARG | A | 134 | 31.667 | 15.070 | 29.258 | 1.00 | 17.72 | 6 |
| ATOM | 1039 | CD | ARG | A | 134 | 30.207 | 15.397 | 28.947 | 1.00 | 22.47 | 6 |
| ATOM | 1040 | NE | ARG | A | 134 | 29.281 | 14.322 | 29.286 | 1.00 | 24.59 | 7 |
| ATOM | 1041 | CZ | ARG | A | 134 | 27.960 | 14.474 | 29.361 | 1.00 | 25.83 | 6 |
| ATOM | 1042 | NH1 | ARG | A | 134 | 27.406 | 15.662 | 29.130 | 1.00 | 27.15 | 7 |
| ATOM | 1043 | NH2 | ARG | A | 134 | 27.190 | 13.444 | 29.673 | 1.00 | 26.83 | 7 |
| ATOM | 1044 | C | ARG | A | 134 | 34.357 | 16.072 | 30.495 | 1.00 | 14.31 | 6 |
| ATOM | 1045 | O | ARG | A | 134 | 34.701 | 15.038 | 31.062 | 1.00 | 14.01 | 8 |
| ATOM | 1046 | N | TRP | A | 135 | 34.255 | 17.244 | 31.099 | 1.00 | 13.27 | 7 |
| ATOM | 1047 | CA | TRP | A | 135 | 34.474 | 17.420 | 32.516 | 1.00 | 12.49 | 6 |
| ATOM | 1048 | CB | TRP | A | 135 | 35.961 | 17.659 | 32.796 | 1.00 | 12.56 | 6 |
| ATOM | 1049 | CG | TRP | A | 135 | 36.408 | 17.280 | 34.188 | 1.00 | 11.49 | 6 |
| ATOM | 1050 | CD1 | TRP | A | 135 | 35.770 | 16.432 | 35.062 | 1.00 | 11.76 | 6 |
| ATOM | 1051 | NE1 | TRP | A | 135 | 36.497 | 16.317 | 36.225 | 1.00 | 10.56 | 7 |
| ATOM | 1052 | CE2 | TRP | A | 135 | 37.628 | 17.085 | 36.123 | 1.00 | 11.76 | 6 |
| ATOM | 1053 | CD2 | TRP | A | 135 | 37.613 | 17.697 | 34.847 | 1.00 | 12.04 | 6 |
| ATOM | 1054 | CE3 | TRP | A | 135 | 38.679 | 18.541 | 34.488 | 1.00 | 12.85 | 6 |
| ATOM | 1055 | CZ3 | TRP | A | 135 | 39.709 | 18.742 | 35.401 | 1.00 | 12.12 | 6 |
| ATOM | 1056 | CH2 | TRP | A | 135 | 39.696 | 18.115 | 36.662 | 1.00 | 12.51 | 6 |
| ATOM | 1057 | CZ2 | TRP | A | 135 | 38.670 | 17.292 | 37.042 | 1.00 | 11.64 | 6 |
| ATOM | 1058 | C | TRP | A | 135 | 33.636 | 18.618 | 32.930 | 1.00 | 12.61 | 6 |
| ATOM | 1059 | O | TRP | A | 135 | 33.064 | 19.309 | 32.081 | 1.00 | 12.34 | 8 |
| ATOM | 1060 | N | ASP | A | 136 | 33.529 | 18.847 | 34.230 | 1.00 | 12.04 | 7 |
| ATOM | 1061 | CA | ASP | A | 136 | 32.679 | 19.909 | 34.755 | 1.00 | 12.12 | 6 |
| ATOM | 1062 | CB | ASP | A | 136 | 31.253 | 19.383 | 34.960 | 1.00 | 12.12 | 6 |
| ATOM | 1063 | CG | ASP | A | 136 | 30.251 | 20.482 | 35.336 | 1.00 | 13.38 | 6 |
| ATOM | 1064 | OD1 | ASP | A | 136 | 30.663 | 21.538 | 35.856 | 1.00 | 14.75 | 8 |
| ATOM | 1065 | OD2 | ASP | A | 136 | 29.034 | 20.266 | 35.122 | 1.00 | 14.58 | 8 |
| ATOM | 1066 | C | ASP | A | 136 | 33.272 | 20.317 | 36.083 | 1.00 | 12.00 | 6 |
| ATOM | 1067 | O | ASP | A | 136 | 33.411 | 19.484 | 36.968 | 1.00 | 12.06 | 8 |
| ATOM | 1068 | N | LEU | A | 137 | 33.646 | 21.593 | 36.210 | 1.00 | 12.04 | 7 |
| ATOM | 1069 | CA | LEU | A | 137 | 34.324 | 22.074 | 37.420 | 1.00 | 12.35 | 6 |
| ATOM | 1070 | CB | LEU | A | 137 | 35.080 | 23.390 | 37.160 | 1.00 | 12.51 | 6 |
| ATOM | 1071 | CG | LEU | A | 137 | 36.546 | 23.321 | 36.699 | 1.00 | 14.36 | 6 |
| ATOM | 1072 | CD1 | LEU | A | 137 | 37.426 | 22.512 | 37.646 | 1.00 | 16.05 | 6 |
| ATOM | 1073 | CD2 | LEU | A | 137 | 36.661 | 22.802 | 35.268 | 1.00 | 13.72 | 6 |
| ATOM | 1074 | C | LEU | A | 137 | 33.405 | 22.220 | 38.625 | 1.00 | 12.12 | 6 |
| ATOM | 1075 | O | LEU | A | 137 | 33.879 | 22.289 | 39.763 | 1.00 | 12.23 | 8 |
| ATOM | 1076 | N | LEU | A | 138 | 32.095 | 22.257 | 38.390 | 1.00 | 11.86 | 7 |
| ATOM | 1077 | CA | LEU | A | 138 | 31.146 | 22.370 | 39.495 | 1.00 | 12.24 | 6 |
| ATOM | 1078 | CB | LEU | A | 138 | 29.699 | 22.480 | 38.989 | 1.00 | 12.09 | 6 |
| ATOM | 1079 | CG | LEU | A | 138 | 28.598 | 22.428 | 40.069 | 1.00 | 11.81 | 6 |
| ATOM | 1080 | CD1 | LEU | A | 138 | 28.788 | 23.517 | 41.123 | 1.00 | 12.67 | 6 |
| ATOM | 1081 | CD2 | LEU | A | 138 | 27.215 | 22.524 | 39.444 | 1.00 | 12.98 | 6 |
| ATOM | 1082 | C | LEU | A | 138 | 31.284 | 21.209 | 40.483 | 1.00 | 12.62 | 6 |
| ATOM | 1083 | O | LEU | A | 138 | 31.443 | 21.430 | 41.685 | 1.00 | 12.80 | 8 |
| ATOM | 1084 | N | ASP | A | 139 | 31.213 | 19.972 | 39.988 | 1.00 | 13.12 | 7 |
| ATOM | 1085 | CA | ASP | A | 139 | 31.338 | 18.826 | 40.884 | 1.00 | 13.51 | 6 |
| ATOM | 1086 | CB | ASP | A | 139 | 30.817 | 17.531 | 40.245 | 1.00 | 14.42 | 6 |
| ATOM | 1087 | CG | ASP | A | 139 | 29.290 | 17.425 | 40.285 | 1.00 | 16.19 | 6 |
| ATOM | 1088 | OD1 | ASP | A | 139 | 28.627 | 18.220 | 41.000 | 1.00 | 18.88 | 8 |
| ATOM | 1089 | OD2 | ASP | A | 139 | 28.748 | 16.530 | 39.603 | 1.00 | 20.15 | 8 |
| ATOM | 1090 | C | ASP | A | 139 | 32.760 | 18.660 | 41.420 | 1.00 | 12.95 | 6 |
| ATOM | 1091 | O | ASP | A | 139 | 32.950 | 18.092 | 42.483 | 1.00 | 13.00 | 8 |
| ATOM | 1092 | N | VAL | A | 140 | 33.746 | 19.205 | 40.708 | 1.00 | 12.48 | 7 |
| ATOM | 1093 | CA | VAL | A | 140 | 35.117 | 19.273 | 41.230 | 1.00 | 11.93 | 6 |
| ATOM | 1094 | CB | VAL | A | 140 | 36.128 | 19.770 | 40.153 | 1.00 | 11.93 | 6 |
| ATOM | 1095 | CG1 | VAL | A | 140 | 37.510 | 20.050 | 40.779 | 1.00 | 11.40 | 6 |
| ATOM | 1096 | CG2 | VAL | A | 140 | 36.247 | 18.750 | 39.015 | 1.00 | 11.91 | 6 |
| ATOM | 1097 | C | VAL | A | 140 | 35.183 | 20.156 | 42.489 | 1.00 | 11.81 | 6 |
| ATOM | 1098 | O | VAL | A | 140 | 35.746 | 19.749 | 43.512 | 1.00 | 11.72 | 8 |
| ATOM | 1099 | N | MET | A | 141 | 34.585 | 21.348 | 42.424 | 1.00 | 11.06 | 7 |
| ATOM | 1100 | CA | MET | A | 141 | 34.556 | 22.246 | 43.589 | 1.00 | 10.98 | 6 |
| ATOM | 1101 | CB | MET | A | 141 | 33.934 | 23.610 | 43.238 | 1.00 | 11.16 | 6 |
| ATOM | 1102 | CG | MET | A | 141 | 34.693 | 24.428 | 42.186 | 1.00 | 11.87 | 6 |

TABLE 7-continued

Coordinates of the crystal structure of *E. coli* ExoI bound to compound 10

| ATOM | 1103 | SD | MET | A | 141 | 36.491 | 24.451 | 42.337 | 1.00 | 14.74 | 16 |
|---|---|---|---|---|---|---|---|---|---|---|---|
| ATOM | 1104 | CE | MET | A | 141 | 36.734 | 25.126 | 43.973 | 1.00 | 15.71 | 6 |
| ATOM | 1105 | C | MET | A | 141 | 33.802 | 21.601 | 44.750 | 1.00 | 10.49 | 6 |
| ATOM | 1106 | O | MET | A | 141 | 34.245 | 21.670 | 45.897 | 1.00 | 10.83 | 8 |
| ATOM | 1107 | N | ARG | A | 142 | 32.668 | 20.960 | 44.447 | 1.00 | 10.16 | 7 |
| ATOM | 1108 | CA | ARG | A | 142 | 31.880 | 20.264 | 45.469 | 1.00 | 10.59 | 6 |
| ATOM | 1109 | CB | ARG | A | 142 | 30.614 | 19.665 | 44.859 | 1.00 | 10.26 | 6 |
| ATOM | 1110 | CG | ARG | A | 142 | 29.550 | 20.695 | 44.532 | 1.00 | 10.62 | 6 |
| ATOM | 1111 | CD | ARG | A | 142 | 28.331 | 20.039 | 43.915 | 1.00 | 12.16 | 6 |
| ATOM | 1112 | NE | ARG | A | 142 | 27.202 | 20.963 | 43.822 | 1.00 | 14.23 | 7 |
| ATOM | 1113 | CZ | ARG | A | 142 | 26.296 | 20.940 | 42.845 | 1.00 | 14.32 | 6 |
| ATOM | 1114 | NH1 | ARG | A | 142 | 26.387 | 20.039 | 41.863 | 1.00 | 15.14 | 7 |
| ATOM | 1115 | NH2 | ARG | A | 142 | 25.302 | 21.817 | 42.847 | 1.00 | 15.34 | 7 |
| ATOM | 1116 | C | ARG | A | 142 | 32.691 | 19.166 | 46.146 | 1.00 | 10.62 | 6 |
| ATOM | 1117 | O | ARG | A | 142 | 32.651 | 19.016 | 47.365 | 1.00 | 11.76 | 8 |
| ATOM | 1118 | N | ALA | A | 143 | 33.415 | 18.398 | 45.335 | 1.00 | 11.35 | 7 |
| ATOM | 1119 | CA | ALA | A | 143 | 34.258 | 17.320 | 45.819 | 1.00 | 11.68 | 6 |
| ATOM | 1120 | CB | ALA | A | 143 | 34.841 | 16.521 | 44.638 | 1.00 | 11.74 | 6 |
| ATOM | 1121 | C | ALA | A | 143 | 35.372 | 17.847 | 46.727 | 1.00 | 12.02 | 6 |
| ATOM | 1122 | O | ALA | A | 143 | 35.670 | 17.240 | 47.747 | 1.00 | 12.10 | 8 |
| ATOM | 1123 | N | CYS | A | 144 | 35.975 | 18.979 | 46.359 | 1.00 | 12.27 | 7 |
| ATOM | 1124 | CA | CYS | A | 144 | 37.004 | 19.602 | 47.203 | 1.00 | 13.89 | 6 |
| ATOM | 1125 | CB | CYS | A | 144 | 37.589 | 20.847 | 46.543 | 1.00 | 13.89 | 6 |
| ATOM | 1126 | SG | CYS | A | 144 | 38.736 | 20.503 | 45.219 | 1.00 | 19.77 | 16 |
| ATOM | 1127 | C | CYS | A | 144 | 36.450 | 19.976 | 48.559 | 1.00 | 13.44 | 6 |
| ATOM | 1128 | O | CYS | A | 144 | 37.067 | 19.694 | 49.578 | 1.00 | 13.92 | 8 |
| ATOM | 1129 | N | TYR | A | 145 | 35.284 | 20.620 | 48.567 | 1.00 | 13.37 | 7 |
| ATOM | 1130 | CA | TYR | A | 145 | 34.666 | 21.061 | 49.810 | 1.00 | 13.40 | 6 |
| ATOM | 1131 | CB | TYR | A | 145 | 33.370 | 21.828 | 49.526 | 1.00 | 13.97 | 6 |
| ATOM | 1132 | CG | TYR | A | 145 | 32.588 | 22.149 | 50.779 | 1.00 | 13.99 | 6 |
| ATOM | 1133 | CD1 | TYR | A | 145 | 32.935 | 23.246 | 51.581 | 1.00 | 17.07 | 6 |
| ATOM | 1134 | CE1 | TYR | A | 145 | 32.232 | 23.534 | 52.741 | 1.00 | 15.19 | 6 |
| ATOM | 1135 | CZ | TYR | A | 145 | 31.172 | 22.723 | 53.121 | 1.00 | 14.57 | 6 |
| ATOM | 1136 | OH | TYR | A | 145 | 30.480 | 23.014 | 54.275 | 1.00 | 15.08 | 8 |
| ATOM | 1137 | CE2 | TYR | A | 145 | 30.810 | 21.621 | 52.349 | 1.00 | 13.56 | 6 |
| ATOM | 1138 | CD2 | TYR | A | 145 | 31.525 | 21.335 | 51.192 | 1.00 | 12.90 | 6 |
| ATOM | 1139 | C | TYR | A | 145 | 34.379 | 19.889 | 50.739 | 1.00 | 13.12 | 6 |
| ATOM | 1140 | O | TYR | A | 145 | 34.623 | 19.969 | 51.945 | 1.00 | 12.83 | 8 |
| ATOM | 1141 | N | ALA | A | 146 | 33.845 | 18.810 | 50.175 | 1.00 | 12.30 | 7 |
| ATOM | 1142 | CA | ALA | A | 146 | 33.457 | 17.654 | 50.966 | 1.00 | 12.79 | 6 |
| ATOM | 1143 | CB | ALA | A | 146 | 32.519 | 16.769 | 50.173 | 1.00 | 12.80 | 6 |
| ATOM | 1144 | C | ALA | A | 146 | 34.673 | 16.860 | 51.413 | 1.00 | 12.62 | 6 |
| ATOM | 1145 | O | ALA | A | 146 | 34.772 | 16.460 | 52.572 | 1.00 | 12.86 | 8 |
| ATOM | 1146 | N | LEU | A | 147 | 35.607 | 16.654 | 50.488 | 1.00 | 12.83 | 7 |
| ATOM | 1147 | CA | LEU | A | 147 | 36.637 | 15.641 | 50.669 | 1.00 | 12.59 | 6 |
| ATOM | 1148 | CB | LEU | A | 147 | 36.780 | 14.785 | 49.403 | 1.00 | 12.65 | 6 |
| ATOM | 1149 | CG | LEU | A | 147 | 35.555 | 14.040 | 48.868 | 1.00 | 12.45 | 6 |
| ATOM | 1150 | CD1 | LEU | A | 147 | 35.883 | 13.423 | 47.531 | 1.00 | 11.07 | 6 |
| ATOM | 1151 | CD2 | LEU | A | 147 | 35.053 | 12.971 | 49.835 | 1.00 | 11.34 | 6 |
| ATOM | 1152 | C | LEU | A | 147 | 37.998 | 16.183 | 51.072 | 1.00 | 12.61 | 6 |
| ATOM | 1153 | O | LEU | A | 147 | 38.724 | 15.534 | 51.821 | 1.00 | 13.21 | 8 |
| ATOM | 1154 | N | ARG | A | 148 | 38.349 | 17.360 | 50.556 | 1.00 | 12.50 | 7 |
| ATOM | 1155 | CA | ARG | A | 148 | 39.688 | 17.928 | 50.741 | 1.00 | 12.23 | 6 |
| ATOM | 1156 | CB | ARG | A | 148 | 40.611 | 17.529 | 49.574 | 1.00 | 12.30 | 6 |
| ATOM | 1157 | CG | ARG | A | 148 | 40.894 | 16.025 | 49.431 | 1.00 | 12.32 | 6 |
| ATOM | 1158 | CD | ARG | A | 148 | 41.714 | 15.480 | 50.600 | 1.00 | 13.52 | 6 |
| ATOM | 1159 | NE | ARG | A | 148 | 42.100 | 14.080 | 50.409 | 1.00 | 15.56 | 7 |
| ATOM | 1160 | CZ | ARG | A | 148 | 41.340 | 13.038 | 50.745 | 1.00 | 15.44 | 6 |
| ATOM | 1161 | NH1 | ARG | A | 148 | 40.146 | 13.232 | 51.289 | 1.00 | 14.42 | 7 |
| ATOM | 1162 | NH2 | ARG | A | 148 | 41.773 | 11.799 | 50.530 | 1.00 | 16.11 | 7 |
| ATOM | 1163 | C | ARG | A | 148 | 39.604 | 19.456 | 50.832 | 1.00 | 11.99 | 6 |
| ATOM | 1164 | O | ARG | A | 148 | 40.122 | 20.155 | 49.961 | 1.00 | 11.82 | 8 |
| ATOM | 1165 | N | PRO | A | 149 | 38.924 | 19.979 | 51.878 | 1.00 | 12.09 | 7 |
| ATOM | 1166 | CA | PRO | A | 149 | 38.625 | 21.426 | 51.933 | 1.00 | 12.04 | 6 |
| ATOM | 1167 | CB | PRO | A | 149 | 37.615 | 21.524 | 53.079 | 1.00 | 12.21 | 6 |
| ATOM | 1168 | CG | PRO | A | 149 | 37.973 | 20.382 | 53.978 | 1.00 | 11.98 | 6 |
| ATOM | 1169 | CD | PRO | A | 149 | 38.353 | 19.263 | 53.032 | 1.00 | 11.95 | 6 |
| ATOM | 1170 | C | PRO | A | 149 | 39.824 | 22.344 | 52.217 | 1.00 | 11.96 | 6 |
| ATOM | 1171 | O | PRO | A | 149 | 39.710 | 23.570 | 52.057 | 1.00 | 11.64 | 8 |
| ATOM | 1172 | N | GLU | A | 150 | 40.960 | 21.769 | 52.598 | 1.00 | 12.34 | 7 |
| ATOM | 1173 | CA | GLU | A | 150 | 42.139 | 22.575 | 52.983 | 1.00 | 13.08 | 6 |
| ATOM | 1174 | CB | GLU | A | 150 | 43.264 | 21.668 | 53.490 | 1.00 | 12.78 | 6 |
| ATOM | 1175 | CG | GLU | A | 150 | 44.601 | 22.384 | 53.677 | 1.00 | 13.74 | 6 |
| ATOM | 1176 | CD | GLU | A | 150 | 45.738 | 21.444 | 54.056 | 1.00 | 14.91 | 6 |
| ATOM | 1177 | OE1 | GLU | A | 150 | 45.483 | 20.243 | 54.303 | 1.00 | 18.13 | 8 |
| ATOM | 1178 | OE2 | GLU | A | 150 | 46.893 | 21.915 | 54.113 | 1.00 | 18.64 | 8 |
| ATOM | 1179 | C | GLU | A | 150 | 42.659 | 23.496 | 51.860 | 1.00 | 13.48 | 6 |
| ATOM | 1180 | O | GLU | A | 150 | 42.866 | 23.054 | 50.718 | 1.00 | 13.90 | 8 |

TABLE 7-continued

Coordinates of the crystal structure of *E. coli* ExoI bound to compound 10

| ATOM | 1181 | N | GLY | A | 151 | 42.863 | 24.770 | 52.192 | 1.00 | 13.52 | 7 |
|---|---|---|---|---|---|---|---|---|---|---|---|
| ATOM | 1182 | CA | GLY | A | 151 | 43.538 | 25.705 | 51.285 | 1.00 | 13.84 | 6 |
| ATOM | 1183 | C | GLY | A | 151 | 42.630 | 26.597 | 50.456 | 1.00 | 14.13 | 6 |
| ATOM | 1184 | O | GLY | A | 151 | 43.085 | 27.570 | 49.851 | 1.00 | 14.44 | 8 |
| ATOM | 1185 | N | ILE | A | 152 | 41.344 | 26.276 | 50.433 | 1.00 | 14.41 | 7 |
| ATOM | 1186 | CA | ILE | A | 152 | 40.372 | 27.077 | 49.704 | 1.00 | 14.85 | 6 |
| ATOM | 1187 | CB | ILE | A | 152 | 39.660 | 26.223 | 48.617 | 1.00 | 14.98 | 6 |
| ATOM | 1188 | CG1 | ILE | A | 152 | 40.684 | 25.742 | 47.587 | 1.00 | 15.34 | 6 |
| ATOM | 1189 | CD1 | ILE | A | 152 | 40.199 | 24.605 | 46.716 | 1.00 | 16.38 | 6 |
| ATOM | 1190 | CG2 | ILE | A | 152 | 38.543 | 27.006 | 47.936 | 1.00 | 16.02 | 6 |
| ATOM | 1191 | C | ILE | A | 152 | 39.358 | 27.713 | 50.651 | 1.00 | 14.69 | 6 |
| ATOM | 1192 | O | ILE | A | 152 | 38.902 | 27.078 | 51.588 | 1.00 | 14.63 | 8 |
| ATOM | 1193 | N | ASN | A | 153 | 39.023 | 28.977 | 50.403 | 1.00 | 14.67 | 7 |
| ATOM | 1194 | CA | ASN | A | 153 | 37.954 | 29.642 | 51.135 | 1.00 | 15.20 | 6 |
| ATOM | 1195 | CB | ASN | A | 153 | 38.106 | 31.167 | 51.063 | 1.00 | 15.27 | 6 |
| ATOM | 1196 | CG | ASN | A | 153 | 39.343 | 31.674 | 51.804 | 1.00 | 17.87 | 6 |
| ATOM | 1197 | OD1 | ASN | A | 153 | 40.004 | 32.618 | 51.356 | 1.00 | 21.55 | 8 |
| ATOM | 1198 | ND2 | ASN | A | 153 | 39.657 | 31.053 | 52.945 | 1.00 | 19.96 | 7 |
| ATOM | 1199 | C | ASN | A | 153 | 36.596 | 29.219 | 50.597 | 1.00 | 14.76 | 6 |
| ATOM | 1200 | O | ASN | A | 153 | 36.330 | 29.330 | 49.393 | 1.00 | 15.14 | 8 |
| ATOM | 1201 | N | TRP | A | 154 | 35.747 | 28.724 | 51.493 | 1.00 | 14.52 | 7 |
| ATOM | 1202 | CA | TRP | A | 154 | 34.435 | 28.212 | 51.118 | 1.00 | 14.46 | 6 |
| ATOM | 1203 | CB | TRP | A | 154 | 34.233 | 26.802 | 51.671 | 1.00 | 13.79 | 6 |
| ATOM | 1204 | CG | TRP | A | 154 | 35.263 | 25.856 | 51.161 | 1.00 | 12.68 | 6 |
| ATOM | 1205 | CD1 | TRP | A | 154 | 36.330 | 25.352 | 51.850 | 1.00 | 12.25 | 6 |
| ATOM | 1206 | NE1 | TRP | A | 154 | 37.071 | 24.524 | 51.037 | 1.00 | 12.34 | 7 |
| ATOM | 1207 | CE2 | TRP | A | 154 | 36.500 | 24.499 | 49.791 | 1.00 | 11.74 | 6 |
| ATOM | 1208 | CD2 | TRP | A | 154 | 35.355 | 25.330 | 49.833 | 1.00 | 11.94 | 6 |
| ATOM | 1209 | CE3 | TRP | A | 154 | 34.577 | 25.473 | 48.676 | 1.00 | 11.13 | 6 |
| ATOM | 1210 | CZ3 | TRP | A | 154 | 34.960 | 24.797 | 47.530 | 1.00 | 11.51 | 6 |
| ATOM | 1211 | CH2 | TRP | A | 154 | 36.104 | 23.973 | 47.515 | 1.00 | 12.83 | 6 |
| ATOM | 1212 | CZ2 | TRP | A | 154 | 36.885 | 23.811 | 48.635 | 1.00 | 11.80 | 6 |
| ATOM | 1213 | C | TRP | A | 154 | 33.327 | 29.154 | 51.580 | 1.00 | 15.21 | 6 |
| ATOM | 1214 | O | TRP | A | 154 | 32.987 | 29.190 | 52.764 | 1.00 | 15.69 | 8 |
| ATOM | 1215 | N | PRO | A | 155 | 32.757 | 29.918 | 50.637 | 1.00 | 15.87 | 7 |
| ATOM | 1216 | CA | PRO | A | 155 | 31.777 | 30.943 | 50.981 | 1.00 | 15.97 | 6 |
| ATOM | 1217 | CB | PRO | A | 155 | 31.670 | 31.761 | 49.691 | 1.00 | 15.86 | 6 |
| ATOM | 1218 | CG | PRO | A | 155 | 31.977 | 30.806 | 48.617 | 1.00 | 16.20 | 6 |
| ATOM | 1219 | CD | PRO | A | 155 | 33.003 | 29.857 | 49.180 | 1.00 | 15.99 | 6 |
| ATOM | 1220 | C | PRO | A | 155 | 30.417 | 30.347 | 51.343 | 1.00 | 16.18 | 6 |
| ATOM | 1221 | O | PRO | A | 155 | 30.048 | 29.291 | 50.835 | 1.00 | 15.97 | 8 |
| ATOM | 1222 | N | GLU | A | 156 | 29.700 | 31.025 | 52.236 | 1.00 | 16.45 | 7 |
| ATOM | 1223 | CA | GLU | A | 156 | 28.339 | 30.650 | 52.606 | 1.00 | 16.71 | 6 |
| ATOM | 1224 | CB | GLU | A | 156 | 28.135 | 30.795 | 54.101 | 1.00 | 17.19 | 6 |
| ATOM | 1225 | CG | GLU | A | 156 | 28.584 | 29.622 | 54.927 | 1.00 | 19.16 | 6 |
| ATOM | 1226 | CD | GLU | A | 156 | 28.212 | 29.791 | 56.388 | 1.00 | 22.32 | 6 |
| ATOM | 1227 | OE1 | GLU | A | 156 | 27.408 | 30.699 | 56.699 | 1.00 | 24.65 | 8 |
| ATOM | 1228 | OE2 | GLU | A | 156 | 28.727 | 29.024 | 57.223 | 1.00 | 23.32 | 8 |
| ATOM | 1229 | C | GLU | A | 156 | 27.367 | 31.578 | 51.923 | 1.00 | 16.31 | 6 |
| ATOM | 1230 | O | GLU | A | 156 | 27.601 | 32.791 | 51.868 | 1.00 | 16.58 | 8 |
| ATOM | 1231 | N | ASN | A | 157 | 26.255 | 31.029 | 51.439 | 1.00 | 15.73 | 7 |
| ATOM | 1232 | CA | ASN | A | 157 | 25.196 | 31.870 | 50.874 | 1.00 | 15.61 | 6 |
| ATOM | 1233 | CB | ASN | A | 157 | 24.352 | 31.096 | 49.852 | 1.00 | 15.40 | 6 |
| ATOM | 1234 | CG | ASN | A | 157 | 23.648 | 29.890 | 50.450 | 1.00 | 15.22 | 6 |
| ATOM | 1235 | OD1 | ASN | A | 157 | 23.247 | 29.898 | 51.614 | 1.00 | 14.29 | 8 |
| ATOM | 1236 | ND2 | ASN | A | 157 | 23.476 | 28.845 | 49.639 | 1.00 | 13.74 | 7 |
| ATOM | 1237 | C | ASN | A | 157 | 24.331 | 32.505 | 51.976 | 1.00 | 15.47 | 6 |
| ATOM | 1238 | O | ASN | A | 157 | 24.559 | 32.257 | 53.157 | 1.00 | 15.71 | 8 |
| ATOM | 1239 | N | ASP | A | 158 | 23.343 | 33.313 | 51.580 | 1.00 | 15.83 | 7 |
| ATOM | 1240 | CA | ASP | A | 158 | 22.492 | 34.047 | 52.541 | 1.00 | 15.56 | 6 |
| ATOM | 1241 | CB | ASP | A | 158 | 21.543 | 35.004 | 51.810 | 1.00 | 16.35 | 6 |
| ATOM | 1242 | CG | ASP | A | 158 | 22.263 | 36.185 | 51.175 | 1.00 | 18.10 | 6 |
| ATOM | 1243 | OD1 | ASP | A | 158 | 23.376 | 36.535 | 51.626 | 1.00 | 19.35 | 8 |
| ATOM | 1244 | OD2 | ASP | A | 158 | 21.703 | 36.770 | 50.220 | 1.00 | 20.70 | 8 |
| ATOM | 1245 | C | ASP | A | 158 | 21.671 | 33.131 | 53.449 | 1.00 | 14.72 | 6 |
| ATOM | 1246 | O | ASP | A | 158 | 21.087 | 33.585 | 54.441 | 1.00 | 14.75 | 8 |
| ATOM | 1247 | N | ASP | A | 159 | 21.633 | 31.845 | 53.110 | 1.00 | 13.87 | 7 |
| ATOM | 1248 | CA | ASP | A | 159 | 20.880 | 30.867 | 53.879 | 1.00 | 13.04 | 6 |
| ATOM | 1249 | CB | ASP | A | 159 | 20.162 | 29.885 | 52.942 | 1.00 | 13.41 | 6 |
| ATOM | 1250 | CG | ASP | A | 159 | 19.082 | 30.567 | 52.095 | 1.00 | 13.56 | 6 |
| ATOM | 1251 | OD1 | ASP | A | 159 | 18.644 | 31.680 | 52.470 | 1.00 | 15.49 | 8 |
| ATOM | 1252 | OD2 | ASP | A | 159 | 18.663 | 29.991 | 51.071 | 1.00 | 14.66 | 8 |
| ATOM | 1253 | C | ASP | A | 159 | 21.759 | 30.129 | 54.891 | 1.00 | 12.70 | 6 |
| ATOM | 1254 | O | ASP | A | 159 | 21.250 | 29.400 | 55.732 | 1.00 | 12.09 | 8 |
| ATOM | 1255 | N | GLY | A | 160 | 23.074 | 30.351 | 54.815 | 1.00 | 12.05 | 7 |
| ATOM | 1256 | CA | GLY | A | 160 | 24.028 | 29.751 | 55.758 | 1.00 | 12.10 | 6 |
| ATOM | 1257 | C | GLY | A | 160 | 24.553 | 28.401 | 55.312 | 1.00 | 11.86 | 6 |
| ATOM | 1258 | O | GLY | A | 160 | 25.075 | 27.625 | 56.122 | 1.00 | 11.81 | 8 |

TABLE 7-continued

Coordinates of the crystal structure of *E. coli* ExoI bound to compound 10

| ATOM | 1259 | N   | LEU | A | 161 | 24.432 | 28.134 | 54.015 | 1.00 | 11.86 | 7 |
|------|------|-----|-----|---|-----|--------|--------|--------|------|-------|---|
| ATOM | 1260 | CA  | LEU | A | 161 | 24.862 | 26.870 | 53.420 | 1.00 | 11.83 | 6 |
| ATOM | 1261 | CB  | LEU | A | 161 | 23.715 | 26.245 | 52.611 | 1.00 | 12.11 | 6 |
| ATOM | 1262 | CG  | LEU | A | 161 | 22.433 | 25.881 | 53.366 | 1.00 | 12.70 | 6 |
| ATOM | 1263 | CD1 | LEU | A | 161 | 21.265 | 25.734 | 52.416 | 1.00 | 12.37 | 6 |
| ATOM | 1264 | CD2 | LEU | A | 161 | 22.622 | 24.615 | 54.208 | 1.00 | 12.62 | 6 |
| ATOM | 1265 | C   | LEU | A | 161 | 26.050 | 27.115 | 52.502 | 1.00 | 11.84 | 6 |
| ATOM | 1266 | O   | LEU | A | 161 | 26.169 | 28.200 | 51.925 | 1.00 | 11.42 | 8 |
| ATOM | 1267 | N   | PRO | A | 162 | 26.931 | 26.104 | 52.348 | 1.00 | 12.16 | 7 |
| ATOM | 1268 | CA  | PRO | A | 162 | 28.066 | 26.304 | 51.451 | 1.00 | 12.38 | 6 |
| ATOM | 1269 | CB  | PRO | A | 162 | 28.793 | 24.955 | 51.469 | 1.00 | 12.71 | 6 |
| ATOM | 1270 | CG  | PRO | A | 162 | 27.841 | 23.982 | 52.074 | 1.00 | 12.59 | 6 |
| ATOM | 1271 | CD  | PRO | A | 162 | 26.924 | 24.762 | 52.958 | 1.00 | 12.59 | 6 |
| ATOM | 1272 | C   | PRO | A | 162 | 27.563 | 26.613 | 50.055 | 1.00 | 12.51 | 6 |
| ATOM | 1273 | O   | PRO | A | 162 | 26.634 | 25.959 | 49.575 | 1.00 | 12.79 | 8 |
| ATOM | 1274 | N   | SER | A | 163 | 28.161 | 27.619 | 49.428 | 1.00 | 13.08 | 7 |
| ATOM | 1275 | CA  | SER | A | 163 | 27.755 | 28.063 | 48.099 | 1.00 | 13.05 | 6 |
| ATOM | 1276 | CB  | SER | A | 163 | 27.612 | 29.582 | 48.065 | 1.00 | 13.35 | 6 |
| ATOM | 1277 | OG  | SER | A | 163 | 27.218 | 30.022 | 46.775 | 1.00 | 14.58 | 8 |
| ATOM | 1278 | C   | SER | A | 163 | 28.760 | 27.622 | 47.038 | 1.00 | 13.31 | 6 |
| ATOM | 1279 | O   | SER | A | 163 | 29.970 | 27.653 | 47.266 | 1.00 | 13.16 | 8 |
| ATOM | 1280 | N   | PHE | A | 164 | 28.250 | 27.231 | 45.877 | 1.00 | 13.51 | 7 |
| ATOM | 1281 | CA  | PHE | A | 164 | 29.109 | 26.833 | 44.771 | 1.00 | 13.47 | 6 |
| ATOM | 1282 | CB  | PHE | A | 164 | 29.028 | 25.323 | 44.549 | 1.00 | 13.49 | 6 |
| ATOM | 1283 | CG  | PHE | A | 164 | 29.461 | 24.538 | 45.742 | 1.00 | 12.97 | 6 |
| ATOM | 1284 | CD1 | PHE | A | 164 | 30.812 | 24.293 | 45.974 | 1.00 | 14.02 | 6 |
| ATOM | 1285 | CE1 | PHE | A | 164 | 31.222 | 23.597 | 47.108 | 1.00 | 11.87 | 6 |
| ATOM | 1286 | CZ  | PHE | A | 164 | 30.286 | 23.156 | 48.027 | 1.00 | 12.69 | 6 |
| ATOM | 1287 | CE2 | PHE | A | 164 | 28.939 | 23.411 | 47.825 | 1.00 | 13.71 | 6 |
| ATOM | 1288 | CD2 | PHE | A | 164 | 28.530 | 24.112 | 46.687 | 1.00 | 12.87 | 6 |
| ATOM | 1289 | C   | PHE | A | 164 | 28.825 | 27.620 | 43.498 | 1.00 | 14.18 | 6 |
| ATOM | 1290 | O   | PHE | A | 164 | 29.220 | 27.219 | 42.404 | 1.00 | 14.01 | 8 |
| ATOM | 1291 | N   | ARG | A | 165 | 28.172 | 28.766 | 43.655 | 1.00 | 14.63 | 7 |
| ATOM | 1292 | CA  | ARG | A | 165 | 28.023 | 29.702 | 42.557 | 1.00 | 15.46 | 6 |
| ATOM | 1293 | CB  | ARG | A | 165 | 27.098 | 30.853 | 42.954 | 1.00 | 15.36 | 6 |
| ATOM | 1294 | CG  | ARG | A | 165 | 25.681 | 30.390 | 43.284 | 1.00 | 17.75 | 6 |
| ATOM | 1295 | CD  | ARG | A | 165 | 24.836 | 31.512 | 43.852 | 1.00 | 19.73 | 6 |
| ATOM | 1296 | NE  | ARG | A | 165 | 24.649 | 32.605 | 42.900 | 1.00 | 22.69 | 7 |
| ATOM | 1297 | CZ  | ARG | A | 165 | 23.933 | 33.701 | 43.146 | 1.00 | 24.60 | 6 |
| ATOM | 1298 | NH1 | ARG | A | 165 | 23.326 | 33.862 | 44.321 | 1.00 | 25.88 | 7 |
| ATOM | 1299 | NH2 | ARG | A | 165 | 23.824 | 34.642 | 42.217 | 1.00 | 26.54 | 7 |
| ATOM | 1300 | C   | ARG | A | 165 | 29.404 | 30.217 | 42.169 | 1.00 | 15.30 | 6 |
| ATOM | 1301 | O   | ARG | A | 165 | 30.214 | 30.568 | 43.029 | 1.00 | 14.95 | 8 |
| ATOM | 1302 | N   | LEU | A | 166 | 29.680 | 30.222 | 40.870 | 1.00 | 15.78 | 7 |
| ATOM | 1303 | CA  | LEU | A | 166 | 31.001 | 30.585 | 40.377 | 1.00 | 16.42 | 6 |
| ATOM | 1304 | CB  | LEU | A | 166 | 31.007 | 30.595 | 38.841 | 1.00 | 16.03 | 6 |
| ATOM | 1305 | CG  | LEU | A | 166 | 32.331 | 30.772 | 38.095 | 1.00 | 17.33 | 6 |
| ATOM | 1306 | CD1 | LEU | A | 166 | 33.346 | 29.702 | 38.482 | 1.00 | 17.51 | 6 |
| ATOM | 1307 | CD2 | LEU | A | 166 | 32.061 | 30.734 | 36.606 | 1.00 | 16.48 | 6 |
| ATOM | 1308 | C   | LEU | A | 166 | 31.452 | 31.933 | 40.935 | 1.00 | 16.73 | 6 |
| ATOM | 1309 | O   | LEU | A | 166 | 32.602 | 32.086 | 41.354 | 1.00 | 17.53 | 8 |
| ATOM | 1310 | N   | GLU | A | 167 | 30.531 | 32.894 | 40.963 | 1.00 | 17.35 | 7 |
| ATOM | 1311 | CA  | GLU | A | 167 | 30.828 | 34.251 | 41.414 | 1.00 | 17.88 | 6 |
| ATOM | 1312 | CB  | GLU | A | 167 | 29.680 | 35.220 | 41.062 | 1.00 | 18.44 | 6 |
| ATOM | 1313 | CG  | GLU | A | 167 | 28.287 | 34.794 | 41.560 | 1.00 | 20.26 | 6 |
| ATOM | 1314 | CD  | GLU | A | 167 | 27.475 | 34.050 | 40.509 | 1.00 | 23.46 | 6 |
| ATOM | 1315 | OE1 | GLU | A | 167 | 28.039 | 33.172 | 39.813 | 1.00 | 23.39 | 8 |
| ATOM | 1316 | OE2 | GLU | A | 167 | 26.258 | 34.346 | 40.378 | 1.00 | 25.10 | 8 |
| ATOM | 1317 | C   | GLU | A | 167 | 31.199 | 34.364 | 42.902 | 1.00 | 17.77 | 6 |
| ATOM | 1318 | O   | GLU | A | 167 | 31.981 | 35.233 | 43.275 | 1.00 | 18.10 | 8 |
| ATOM | 1319 | N   | HIS | A | 168 | 30.643 | 33.481 | 43.736 | 1.00 | 17.07 | 7 |
| ATOM | 1320 | CA  | HIS | A | 168 | 30.955 | 33.464 | 45.170 | 1.00 | 16.85 | 6 |
| ATOM | 1321 | CB  | HIS | A | 168 | 29.894 | 32.690 | 45.959 | 1.00 | 16.71 | 6 |
| ATOM | 1322 | CG  | HIS | A | 168 | 28.561 | 33.366 | 46.007 | 1.00 | 16.61 | 6 |
| ATOM | 1323 | ND1 | HIS | A | 168 | 27.399 | 32.694 | 46.318 | 1.00 | 17.09 | 7 |
| ATOM | 1324 | CE1 | HIS | A | 168 | 26.384 | 33.540 | 46.296 | 1.00 | 17.64 | 6 |
| ATOM | 1325 | NE2 | HIS | A | 168 | 26.844 | 34.733 | 45.963 | 1.00 | 17.96 | 7 |
| ATOM | 1326 | CD2 | HIS | A | 168 | 28.202 | 34.652 | 45.780 | 1.00 | 16.80 | 6 |
| ATOM | 1327 | C   | HIS | A | 168 | 32.322 | 32.860 | 45.425 | 1.00 | 16.62 | 6 |
| ATOM | 1328 | O   | HIS | A | 168 | 33.074 | 33.339 | 46.282 | 1.00 | 16.69 | 8 |
| ATOM | 1329 | N   | LEU | A | 169 | 32.636 | 31.803 | 44.680 | 1.00 | 16.15 | 7 |
| ATOM | 1330 | CA  | LEU | A | 169 | 33.910 | 31.102 | 44.810 | 1.00 | 16.47 | 6 |
| ATOM | 1331 | CB  | LEU | A | 169 | 33.852 | 29.744 | 44.101 | 1.00 | 16.52 | 6 |
| ATOM | 1332 | CG  | LEU | A | 169 | 33.013 | 28.638 | 44.747 | 1.00 | 16.98 | 6 |
| ATOM | 1333 | CD1 | LEU | A | 169 | 32.795 | 27.495 | 43.772 | 1.00 | 17.70 | 6 |
| ATOM | 1334 | CD2 | LEU | A | 169 | 33.651 | 28.130 | 46.041 | 1.00 | 16.82 | 6 |
| ATOM | 1335 | C   | LEU | A | 169 | 35.095 | 31.929 | 44.304 | 1.00 | 16.48 | 6 |
| ATOM | 1336 | O   | LEU | A | 169 | 36.181 | 31.862 | 44.870 | 1.00 | 16.35 | 8 |

TABLE 7-continued

Coordinates of the crystal structure of *E. coli* ExoI bound to compound 10

| ATOM | 1337 | N | THR | A | 170 | 34.888 | 32.713 | 43.243 | 1.00 | 16.89 | 7 |
|---|---|---|---|---|---|---|---|---|---|---|---|
| ATOM | 1338 | CA | THR | A | 170 | 35.937 | 33.633 | 42.776 | 1.00 | 17.53 | 6 |
| ATOM | 1339 | CB | THR | A | 170 | 35.633 | 34.242 | 41.390 | 1.00 | 17.67 | 6 |
| ATOM | 1340 | OG1 | THR | A | 170 | 34.336 | 34.850 | 41.402 | 1.00 | 17.23 | 8 |
| ATOM | 1341 | CG2 | THR | A | 170 | 35.682 | 33.173 | 40.312 | 1.00 | 17.43 | 6 |
| ATOM | 1342 | C | THR | A | 170 | 36.189 | 34.751 | 43.790 | 1.00 | 17.94 | 6 |
| ATOM | 1343 | O | THR | A | 170 | 37.324 | 34.955 | 44.217 | 1.00 | 18.14 | 8 |
| ATOM | 1344 | N | LYS | A | 171 | 35.122 | 35.449 | 44.189 | 1.00 | 18.32 | 7 |
| ATOM | 1345 | CA | LYS | A | 171 | 35.209 | 36.521 | 45.189 | 1.00 | 18.97 | 6 |
| ATOM | 1346 | CB | LYS | A | 171 | 33.816 | 37.109 | 45.467 | 1.00 | 18.97 | 6 |
| ATOM | 1347 | CG | LYS | A | 171 | 33.816 | 38.417 | 46.259 | 1.00 | 21.23 | 6 |
| ATOM | 1348 | CD | LYS | A | 171 | 34.155 | 39.612 | 45.371 | 1.00 | 24.05 | 6 |
| ATOM | 1349 | CE | LYS | A | 171 | 33.873 | 40.924 | 46.088 | 1.00 | 25.72 | 6 |
| ATOM | 1350 | NZ | LYS | A | 171 | 33.961 | 42.096 | 45.167 | 1.00 | 27.61 | 7 |
| ATOM | 1351 | C | LYS | A | 171 | 35.845 | 36.050 | 46.500 | 1.00 | 19.09 | 6 |
| ATOM | 1352 | O | LYS | A | 171 | 36.670 | 36.757 | 47.090 | 1.00 | 18.84 | 8 |
| ATOM | 1353 | N | ALA | A | 172 | 35.461 | 34.857 | 46.949 | 1.00 | 19.24 | 7 |
| ATOM | 1354 | CA | ALA | A | 172 | 35.952 | 34.309 | 48.215 | 1.00 | 19.56 | 6 |
| ATOM | 1355 | CB | ALA | A | 172 | 35.125 | 33.100 | 48.622 | 1.00 | 19.46 | 6 |
| ATOM | 1356 | C | ALA | A | 172 | 37.442 | 33.952 | 48.188 | 1.00 | 19.94 | 6 |
| ATOM | 1357 | O | ALA | A | 172 | 38.077 | 33.852 | 49.235 | 1.00 | 19.66 | 8 |
| ATOM | 1358 | N | ASN | A | 173 | 37.989 | 33.756 | 46.991 | 1.00 | 20.95 | 7 |
| ATOM | 1359 | CA | ASN | A | 173 | 39.381 | 33.325 | 46.853 | 1.00 | 21.67 | 6 |
| ATOM | 1360 | CB | ASN | A | 173 | 39.447 | 31.940 | 46.200 | 1.00 | 21.38 | 6 |
| ATOM | 1361 | CG | ASN | A | 173 | 38.875 | 30.855 | 47.090 | 1.00 | 20.21 | 6 |
| ATOM | 1362 | OD1 | ASN | A | 173 | 37.723 | 30.445 | 46.933 | 1.00 | 19.52 | 8 |
| ATOM | 1363 | ND2 | ASN | A | 173 | 39.669 | 30.403 | 48.051 | 1.00 | 17.17 | 7 |
| ATOM | 1364 | C | ASN | A | 173 | 40.269 | 34.337 | 46.124 | 1.00 | 22.78 | 6 |
| ATOM | 1365 | O | ASN | A | 173 | 41.377 | 34.005 | 45.688 | 1.00 | 22.90 | 8 |
| ATOM | 1366 | N | GLY | A | 174 | 39.778 | 35.571 | 46.011 | 1.00 | 23.91 | 7 |
| ATOM | 1367 | CA | GLY | A | 174 | 40.559 | 36.684 | 45.461 | 1.00 | 25.64 | 6 |
| ATOM | 1368 | C | GLY | A | 174 | 40.823 | 36.599 | 43.970 | 1.00 | 26.95 | 6 |
| ATOM | 1369 | O | GLY | A | 174 | 41.813 | 37.143 | 43.475 | 1.00 | 27.21 | 8 |
| ATOM | 1370 | N | ILE | A | 175 | 39.932 | 35.923 | 43.251 | 1.00 | 28.25 | 7 |
| ATOM | 1371 | CA | ILE | A | 175 | 40.046 | 35.781 | 41.803 | 1.00 | 29.65 | 6 |
| ATOM | 1372 | CB | ILE | A | 175 | 39.584 | 34.375 | 41.333 | 1.00 | 29.60 | 6 |
| ATOM | 1373 | CG1 | ILE | A | 175 | 40.532 | 33.295 | 41.871 | 1.00 | 29.47 | 6 |
| ATOM | 1374 | CD1 | ILE | A | 175 | 39.986 | 31.867 | 41.768 | 1.00 | 29.87 | 6 |
| ATOM | 1375 | CG2 | ILE | A | 175 | 39.491 | 34.317 | 39.806 | 1.00 | 29.44 | 6 |
| ATOM | 1376 | C | ILE | A | 175 | 39.237 | 36.865 | 41.088 | 1.00 | 30.74 | 6 |
| ATOM | 1377 | O | ILE | A | 175 | 38.020 | 36.970 | 41.276 | 1.00 | 30.58 | 8 |
| ATOM | 1378 | N | GLU | A | 176 | 39.922 | 37.670 | 40.273 | 1.00 | 32.23 | 7 |
| ATOM | 1379 | CA | GLU | A | 176 | 39.269 | 38.732 | 39.498 | 1.00 | 33.84 | 6 |
| ATOM | 1380 | CB | GLU | A | 176 | 40.300 | 39.590 | 38.744 | 1.00 | 33.85 | 6 |
| ATOM | 1381 | CG | GLU | A | 176 | 41.406 | 38.801 | 38.025 | 1.00 | 34.65 | 6 |
| ATOM | 1382 | CD | GLU | A | 176 | 42.385 | 39.702 | 37.268 | 1.00 | 35.04 | 6 |
| ATOM | 1383 | OE1 | GLU | A | 176 | 41.927 | 40.606 | 36.532 | 1.00 | 36.26 | 8 |
| ATOM | 1384 | OE2 | GLU | A | 176 | 43.615 | 39.496 | 37.403 | 1.00 | 36.02 | 8 |
| ATOM | 1385 | C | GLU | A | 176 | 38.212 | 38.170 | 38.542 | 1.00 | 34.48 | 6 |
| ATOM | 1386 | O | GLU | A | 176 | 38.492 | 37.271 | 37.747 | 1.00 | 34.80 | 8 |
| ATOM | 1387 | N | HIS | A | 177 | 36.999 | 38.706 | 38.647 | 1.00 | 35.35 | 7 |
| ATOM | 1388 | CA | HIS | A | 177 | 35.841 | 38.199 | 37.920 | 1.00 | 36.08 | 6 |
| ATOM | 1389 | CB | HIS | A | 177 | 35.124 | 37.136 | 38.765 | 1.00 | 35.96 | 6 |
| ATOM | 1390 | CG | HIS | A | 177 | 34.106 | 36.334 | 38.013 | 1.00 | 35.77 | 6 |
| ATOM | 1391 | ND1 | HIS | A | 177 | 33.159 | 35.557 | 38.647 | 1.00 | 35.39 | 7 |
| ATOM | 1392 | CE1 | HIS | A | 177 | 32.402 | 34.962 | 37.743 | 1.00 | 35.38 | 6 |
| ATOM | 1393 | NE2 | HIS | A | 177 | 32.820 | 35.328 | 36.544 | 1.00 | 35.21 | 7 |
| ATOM | 1394 | CD2 | HIS | A | 177 | 33.885 | 36.186 | 36.685 | 1.00 | 35.24 | 6 |
| ATOM | 1395 | C | HIS | A | 177 | 34.900 | 39.360 | 37.597 | 1.00 | 36.63 | 6 |
| ATOM | 1396 | O | HIS | A | 177 | 34.486 | 40.102 | 38.496 | 1.00 | 36.97 | 8 |
| ATOM | 1397 | N | SER | A | 178 | 34.573 | 39.520 | 36.316 | 1.00 | 37.21 | 7 |
| ATOM | 1398 | CA | SER | A | 178 | 33.792 | 40.671 | 35.857 | 1.00 | 37.57 | 6 |
| ATOM | 1399 | CB | SER | A | 178 | 34.705 | 41.689 | 35.165 | 1.00 | 37.65 | 6 |
| ATOM | 1400 | OG | SER | A | 178 | 33.989 | 42.856 | 34.803 | 1.00 | 37.97 | 8 |
| ATOM | 1401 | C | SER | A | 178 | 32.646 | 40.259 | 34.929 | 1.00 | 37.78 | 6 |
| ATOM | 1402 | O | SER | A | 178 | 31.956 | 41.108 | 34.349 | 1.00 | 37.96 | 8 |
| ATOM | 1403 | N | ASP | A | 182 | 34.571 | 40.474 | 29.995 | 0.50 | 15.23 | 7 |
| ATOM | 1404 | CA | ASP | A | 182 | 33.167 | 40.814 | 29.783 | 0.50 | 15.04 | 6 |
| ATOM | 1405 | CB | ASP | A | 182 | 33.038 | 41.896 | 28.710 | 0.50 | 15.49 | 6 |
| ATOM | 1406 | CG | ASP | A | 182 | 31.872 | 42.839 | 28.965 | 0.50 | 16.16 | 6 |
| ATOM | 1407 | OD1 | ASP | A | 182 | 30.738 | 42.354 | 29.165 | 0.50 | 18.07 | 8 |
| ATOM | 1408 | OD2 | ASP | A | 182 | 32.094 | 44.073 | 28.957 | 0.50 | 18.37 | 8 |
| ATOM | 1409 | C | ASP | A | 182 | 32.376 | 39.570 | 29.384 | 0.50 | 14.62 | 6 |
| ATOM | 1410 | O | ASP | A | 182 | 31.899 | 38.827 | 30.239 | 0.50 | 14.80 | 8 |
| ATOM | 1411 | N | ALA | A | 183 | 32.247 | 39.337 | 28.082 | 0.50 | 13.88 | 7 |
| ATOM | 1412 | CA | ALA | A | 183 | 31.562 | 38.139 | 27.603 | 0.50 | 12.83 | 6 |
| ATOM | 1413 | CB | ALA | A | 183 | 31.299 | 38.233 | 26.114 | 0.50 | 13.22 | 6 |
| ATOM | 1414 | C | ALA | A | 183 | 32.373 | 36.880 | 27.930 | 0.50 | 12.32 | 6 |

TABLE 7-continued

Coordinates of the crystal structure of E. coli ExoI bound to compound 10

| ATOM | 1415 | O | ALA | A | 183 | 31.833 | 35.781 | 27.991 | 0.50 | 11.94 | 8 |
|---|---|---|---|---|---|---|---|---|---|---|---|
| ATOM | 1416 | N | MET | A | 184 | 33.671 | 37.058 | 28.145 | 0.50 | 11.69 | 7 |
| ATOM | 1417 | CA | MET | A | 184 | 34.564 | 35.945 | 28.445 | 0.50 | 11.31 | 6 |
| ATOM | 1418 | CB | MET | A | 184 | 35.934 | 36.183 | 27.802 | 0.50 | 11.25 | 6 |
| ATOM | 1419 | CG | MET | A | 184 | 35.968 | 35.988 | 26.294 | 0.50 | 10.01 | 6 |
| ATOM | 1420 | SD | MET | A | 184 | 35.675 | 34.287 | 25.788 | 0.50 | 9.86 | 16 |
| ATOM | 1421 | CE | MET | A | 184 | 37.109 | 33.467 | 26.459 | 0.50 | 8.77 | 6 |
| ATOM | 1422 | C | MET | A | 184 | 34.725 | 35.737 | 29.953 | 0.50 | 11.29 | 6 |
| ATOM | 1423 | O | MET | A | 184 | 35.394 | 34.803 | 30.396 | 0.50 | 11.11 | 8 |
| ATOM | 1424 | N | ALA | A | 185 | 34.087 | 36.600 | 30.735 | 0.50 | 11.41 | 7 |
| ATOM | 1425 | CA | ALA | A | 185 | 34.241 | 36.587 | 32.189 | 0.50 | 11.95 | 6 |
| ATOM | 1426 | CB | ALA | A | 185 | 33.255 | 37.549 | 32.829 | 0.50 | 11.84 | 6 |
| ATOM | 1427 | C | ALA | A | 185 | 34.105 | 35.193 | 32.808 | 0.50 | 12.38 | 6 |
| ATOM | 1428 | O | ALA | A | 185 | 34.966 | 34.765 | 33.582 | 0.50 | 11.91 | 8 |
| ATOM | 1429 | N | ASP | A | 186 | 33.025 | 34.494 | 32.620 | 1.00 | 13.56 | 7 |
| ATOM | 1430 | CA | ASP | A | 186 | 32.702 | 33.191 | 33.053 | 1.00 | 14.47 | 6 |
| ATOM | 1431 | CB | ASP | A | 186 | 31.260 | 32.790 | 32.719 | 1.00 | 15.00 | 6 |
| ATOM | 1432 | CG | ASP | A | 186 | 30.229 | 33.666 | 33.423 | 1.00 | 17.39 | 6 |
| ATOM | 1433 | OD1 | ASP | A | 186 | 29.039 | 33.592 | 33.055 | 1.00 | 21.39 | 8 |
| ATOM | 1434 | OD2 | ASP | A | 186 | 30.607 | 34.414 | 34.348 | 1.00 | 19.82 | 8 |
| ATOM | 1435 | C | ASP | A | 186 | 33.671 | 32.089 | 32.622 | 1.00 | 14.62 | 6 |
| ATOM | 1436 | O | ASP | A | 186 | 34.022 | 31.208 | 33.417 | 1.00 | 15.17 | 8 |
| ATOM | 1437 | N | VAL | A | 187 | 34.104 | 32.146 | 31.364 | 1.00 | 14.28 | 7 |
| ATOM | 1438 | CA | VAL | A | 187 | 35.093 | 31.193 | 30.855 | 1.00 | 14.37 | 6 |
| ATOM | 1439 | CB | VAL | A | 187 | 35.263 | 31.294 | 29.312 | 1.00 | 14.35 | 6 |
| ATOM | 1440 | CG1 | VAL | A | 187 | 36.449 | 30.461 | 28.833 | 1.00 | 13.97 | 6 |
| ATOM | 1441 | CG2 | VAL | A | 187 | 33.974 | 30.865 | 28.593 | 1.00 | 15.55 | 6 |
| ATOM | 1442 | C | VAL | A | 187 | 36.443 | 31.348 | 31.566 | 1.00 | 14.34 | 6 |
| ATOM | 1443 | O | VAL | A | 187 | 37.038 | 30.360 | 31.995 | 1.00 | 14.59 | 8 |
| ATOM | 1444 | N | TYR | A | 188 | 36.915 | 32.592 | 31.709 | 1.00 | 14.01 | 7 |
| ATOM | 1445 | CA | TYR | A | 188 | 38.162 | 32.847 | 32.432 | 1.00 | 14.23 | 6 |
| ATOM | 1446 | CB | TYR | A | 188 | 38.592 | 34.308 | 32.287 | 1.00 | 14.43 | 6 |
| ATOM | 1447 | CG | TYR | A | 188 | 39.108 | 34.674 | 30.906 | 1.00 | 14.96 | 6 |
| ATOM | 1448 | CD1 | TYR | A | 188 | 40.082 | 33.902 | 30.275 | 1.00 | 15.78 | 6 |
| ATOM | 1449 | CE1 | TYR | A | 188 | 40.563 | 34.240 | 29.009 | 1.00 | 17.16 | 6 |
| ATOM | 1450 | CZ | TYR | A | 188 | 40.081 | 35.374 | 28.372 | 1.00 | 16.40 | 6 |
| ATOM | 1451 | OH | TYR | A | 188 | 40.561 | 35.721 | 27.126 | 1.00 | 17.69 | 8 |
| ATOM | 1452 | CE2 | TYR | A | 188 | 39.130 | 36.166 | 28.984 | 1.00 | 16.08 | 6 |
| ATOM | 1453 | CD2 | TYR | A | 188 | 38.650 | 35.820 | 30.246 | 1.00 | 15.95 | 6 |
| ATOM | 1454 | C | TYR | A | 188 | 38.055 | 32.460 | 33.914 | 1.00 | 14.23 | 6 |
| ATOM | 1455 | O | TYR | A | 188 | 38.994 | 31.894 | 34.479 | 1.00 | 13.98 | 8 |
| ATOM | 1456 | N | ALA | A | 189 | 36.909 | 32.754 | 34.530 | 1.00 | 14.31 | 7 |
| ATOM | 1457 | CA | ALA | A | 189 | 36.648 | 32.347 | 35.920 | 1.00 | 14.37 | 6 |
| ATOM | 1458 | CB | ALA | A | 189 | 35.278 | 32.854 | 36.384 | 1.00 | 14.64 | 6 |
| ATOM | 1459 | C | ALA | A | 189 | 36.753 | 30.826 | 36.100 | 1.00 | 14.54 | 6 |
| ATOM | 1460 | O | ALA | A | 189 | 37.296 | 30.339 | 37.108 | 1.00 | 14.81 | 8 |
| ATOM | 1461 | N | THR | A | 190 | 36.233 | 30.083 | 35.126 | 1.00 | 14.35 | 7 |
| ATOM | 1462 | CA | THR | A | 190 | 36.251 | 28.618 | 35.166 | 1.00 | 14.19 | 6 |
| ATOM | 1463 | CB | THR | A | 190 | 35.400 | 27.996 | 34.027 | 1.00 | 14.31 | 6 |
| ATOM | 1464 | OG1 | THR | A | 190 | 34.077 | 28.549 | 34.044 | 1.00 | 14.06 | 8 |
| ATOM | 1465 | CG2 | THR | A | 190 | 35.307 | 26.476 | 34.189 | 1.00 | 14.09 | 6 |
| ATOM | 1466 | C | THR | A | 190 | 37.684 | 28.087 | 35.092 | 1.00 | 14.10 | 6 |
| ATOM | 1467 | O | THR | A | 190 | 38.067 | 27.188 | 35.858 | 1.00 | 14.09 | 8 |
| ATOM | 1468 | N | ILE | A | 191 | 38.474 | 28.644 | 34.173 | 1.00 | 13.92 | 7 |
| ATOM | 1469 | CA | ILE | A | 191 | 39.903 | 28.311 | 34.075 | 1.00 | 13.91 | 6 |
| ATOM | 1470 | CB | ILE | A | 191 | 40.589 | 29.100 | 32.931 | 1.00 | 13.75 | 6 |
| ATOM | 1471 | CG1 | ILE | A | 191 | 39.906 | 28.795 | 31.599 | 1.00 | 13.60 | 6 |
| ATOM | 1472 | CD1 | ILE | A | 191 | 40.350 | 29.690 | 30.464 | 1.00 | 14.24 | 6 |
| ATOM | 1473 | CG2 | ILE | A | 191 | 42.079 | 28.757 | 32.837 | 1.00 | 13.69 | 6 |
| ATOM | 1474 | C | ILE | A | 191 | 40.592 | 28.587 | 35.418 | 1.00 | 14.43 | 6 |
| ATOM | 1475 | O | ILE | A | 191 | 41.369 | 27.767 | 35.913 | 1.00 | 14.45 | 8 |
| ATOM | 1476 | N | ALA | A | 192 | 40.265 | 29.725 | 36.026 | 1.00 | 14.74 | 7 |
| ATOM | 1477 | CA | ALA | A | 192 | 40.862 | 30.101 | 37.309 | 1.00 | 15.21 | 6 |
| ATOM | 1478 | CB | ALA | A | 192 | 40.414 | 31.492 | 37.718 | 1.00 | 15.29 | 6 |
| ATOM | 1479 | C | ALA | A | 192 | 40.539 | 29.084 | 38.404 | 1.00 | 15.60 | 6 |
| ATOM | 1480 | O | ALA | A | 192 | 41.394 | 28.774 | 39.234 | 1.00 | 15.50 | 8 |
| ATOM | 1481 | N | MET | A | 193 | 39.318 | 28.549 | 38.390 | 1.00 | 16.15 | 7 |
| ATOM | 1482 | CA | MET | A | 193 | 38.909 | 27.535 | 39.373 | 1.00 | 17.25 | 6 |
| ATOM | 1483 | CB | MET | A | 193 | 37.407 | 27.247 | 39.268 | 1.00 | 18.07 | 6 |
| ATOM | 1484 | CG | MET | A | 193 | 36.511 | 28.441 | 39.570 | 1.00 | 21.14 | 6 |
| ATOM | 1485 | SD | MET | A | 193 | 36.789 | 29.173 | 41.204 | 1.00 | 28.40 | 16 |
| ATOM | 1486 | CE | MET | A | 193 | 36.177 | 27.877 | 42.237 | 1.00 | 28.37 | 6 |
| ATOM | 1487 | C | MET | A | 193 | 39.694 | 26.245 | 39.176 | 1.00 | 16.97 | 6 |
| ATOM | 1488 | O | MET | A | 193 | 40.109 | 25.605 | 40.146 | 1.00 | 16.53 | 8 |
| ATOM | 1489 | N | ALA | A | 194 | 39.899 | 25.878 | 37.910 | 1.00 | 16.44 | 7 |
| ATOM | 1490 | CA | ALA | A | 194 | 40.702 | 24.710 | 37.554 | 1.00 | 15.93 | 6 |
| ATOM | 1491 | CB | ALA | A | 194 | 40.710 | 24.510 | 36.049 | 1.00 | 16.22 | 6 |
| ATOM | 1492 | C | ALA | A | 194 | 42.127 | 24.838 | 38.091 | 1.00 | 15.72 | 6 |

TABLE 7-continued

Coordinates of the crystal structure of *E. coli* ExoI bound to compound 10

| ATOM | 1493 | O | ALA | A | 194 | 42.649 | 23.908 | 38.710 | 1.00 | 15.37 | 8 |
|---|---|---|---|---|---|---|---|---|---|---|---|
| ATOM | 1494 | N | LYS | A | 195 | 42.744 | 25.997 | 37.870 | 1.00 | 15.57 | 7 |
| ATOM | 1495 | CA | LYS | A | 195 | 44.097 | 26.247 | 38.367 | 1.00 | 15.53 | 6 |
| ATOM | 1496 | CB | LYS | A | 195 | 44.615 | 27.600 | 37.876 | 1.00 | 15.59 | 6 |
| ATOM | 1497 | CG | LYS | A | 195 | 44.917 | 27.655 | 36.403 | 1.00 | 16.39 | 6 |
| ATOM | 1498 | CD | LYS | A | 195 | 45.420 | 29.035 | 36.008 | 1.00 | 18.30 | 6 |
| ATOM | 1499 | CE | LYS | A | 195 | 45.494 | 29.183 | 34.514 | 1.00 | 19.05 | 6 |
| ATOM | 1500 | NZ | LYS | A | 195 | 46.039 | 30.515 | 34.088 | 1.00 | 21.67 | 7 |
| ATOM | 1501 | C | LYS | A | 195 | 44.135 | 26.199 | 39.892 | 1.00 | 15.81 | 6 |
| ATOM | 1502 | O | LYS | A | 195 | 45.084 | 25.678 | 40.478 | 1.00 | 15.53 | 8 |
| ATOM | 1503 | N | LEU | A | 196 | 43.093 | 26.744 | 40.520 | 1.00 | 15.88 | 7 |
| ATOM | 1504 | CA | LEU | A | 196 | 42.978 | 26.784 | 41.979 | 1.00 | 16.34 | 6 |
| ATOM | 1505 | CB | LEU | A | 196 | 41.653 | 27.444 | 42.372 | 1.00 | 16.85 | 6 |
| ATOM | 1506 | CG | LEU | A | 196 | 41.417 | 27.747 | 43.850 | 1.00 | 17.42 | 6 |
| ATOM | 1507 | CD1 | LEU | A | 196 | 42.162 | 28.986 | 44.241 | 1.00 | 19.30 | 6 |
| ATOM | 1508 | CD2 | LEU | A | 196 | 39.928 | 27.926 | 44.116 | 1.00 | 19.06 | 6 |
| ATOM | 1509 | C | LEU | A | 196 | 43.059 | 25.383 | 42.584 | 1.00 | 16.42 | 6 |
| ATOM | 1510 | O | LEU | A | 196 | 43.872 | 25.123 | 43.475 | 1.00 | 16.57 | 8 |
| ATOM | 1511 | N | VAL | A | 197 | 42.222 | 24.482 | 42.084 | 1.00 | 16.10 | 7 |
| ATOM | 1512 | CA | VAL | A | 197 | 42.157 | 23.118 | 42.606 | 1.00 | 16.07 | 6 |
| ATOM | 1513 | CB | VAL | A | 197 | 40.907 | 22.383 | 42.075 | 1.00 | 16.21 | 6 |
| ATOM | 1514 | CG1 | VAL | A | 197 | 40.839 | 20.962 | 42.628 | 1.00 | 16.46 | 6 |
| ATOM | 1515 | CG2 | VAL | A | 197 | 39.659 | 23.152 | 42.442 | 1.00 | 15.68 | 6 |
| ATOM | 1516 | C | VAL | A | 197 | 43.433 | 22.330 | 42.279 | 1.00 | 15.93 | 6 |
| ATOM | 1517 | O | VAL | A | 197 | 43.972 | 21.621 | 43.131 | 1.00 | 16.31 | 8 |
| ATOM | 1518 | N | LYS | A | 198 | 43.912 | 22.466 | 41.044 | 1.00 | 15.56 | 7 |
| ATOM | 1519 | CA | LYS | A | 198 | 45.152 | 21.822 | 40.614 | 1.00 | 15.39 | 6 |
| ATOM | 1520 | CB | LYS | A | 198 | 45.470 | 22.189 | 39.162 | 1.00 | 15.41 | 6 |
| ATOM | 1521 | CG | LYS | A | 198 | 46.709 | 21.497 | 38.598 | 1.00 | 15.70 | 6 |
| ATOM | 1522 | CD | LYS | A | 198 | 46.937 | 21.867 | 37.133 | 1.00 | 16.82 | 6 |
| ATOM | 1523 | CE | LYS | A | 198 | 48.200 | 21.220 | 36.581 | 1.00 | 17.97 | 6 |
| ATOM | 1524 | NZ | LYS | A | 198 | 48.014 | 19.765 | 36.301 | 1.00 | 20.73 | 7 |
| ATOM | 1525 | C | LYS | A | 198 | 46.327 | 22.195 | 41.511 | 1.00 | 14.85 | 6 |
| ATOM | 1526 | O | LYS | A | 198 | 47.167 | 21.348 | 41.822 | 1.00 | 14.91 | 8 |
| ATOM | 1527 | N | THR | A | 199 | 46.384 | 23.463 | 41.919 | 1.00 | 14.63 | 7 |
| ATOM | 1528 | CA | THR | A | 199 | 47.488 | 23.954 | 42.754 | 1.00 | 14.66 | 6 |
| ATOM | 1529 | CB | THR | A | 199 | 47.669 | 25.497 | 42.619 | 1.00 | 14.98 | 6 |
| ATOM | 1530 | OG1 | THR | A | 199 | 47.981 | 25.821 | 41.259 | 1.00 | 15.83 | 8 |
| ATOM | 1531 | CG2 | THR | A | 199 | 48.799 | 25.997 | 43.514 | 1.00 | 15.86 | 6 |
| ATOM | 1532 | C | THR | A | 199 | 47.309 | 23.579 | 44.221 | 1.00 | 14.17 | 6 |
| ATOM | 1533 | O | THR | A | 199 | 48.271 | 23.201 | 44.893 | 1.00 | 13.93 | 8 |
| ATOM | 1534 | N | ARG | A | 200 | 46.078 | 23.668 | 44.714 | 1.00 | 13.57 | 7 |
| ATOM | 1535 | CA | ARG | A | 200 | 45.836 | 23.530 | 46.151 | 1.00 | 13.08 | 6 |
| ATOM | 1536 | CB | ARG | A | 200 | 44.846 | 24.596 | 46.652 | 1.00 | 13.41 | 6 |
| ATOM | 1537 | CG | ARG | A | 200 | 45.253 | 26.024 | 46.252 | 1.00 | 13.52 | 6 |
| ATOM | 1538 | CD | ARG | A | 200 | 44.457 | 27.091 | 46.961 | 1.00 | 13.50 | 6 |
| ATOM | 1539 | NE | ARG | A | 200 | 44.756 | 28.425 | 46.430 | 1.00 | 13.22 | 7 |
| ATOM | 1540 | CZ | ARG | A | 200 | 44.169 | 29.546 | 46.843 | 1.00 | 13.91 | 6 |
| ATOM | 1541 | NH1 | ARG | A | 200 | 43.246 | 29.509 | 47.798 | 1.00 | 14.65 | 7 |
| ATOM | 1542 | NH2 | ARG | A | 200 | 44.497 | 30.709 | 46.290 | 1.00 | 15.99 | 7 |
| ATOM | 1543 | C | ARG | A | 200 | 45.439 | 22.118 | 46.578 | 1.00 | 12.61 | 6 |
| ATOM | 1544 | O | ARG | A | 200 | 45.646 | 21.741 | 47.730 | 1.00 | 11.64 | 8 |
| ATOM | 1545 | N | GLN | A | 201 | 44.908 | 21.329 | 45.640 | 1.00 | 11.66 | 7 |
| ATOM | 1546 | CA | GLN | A | 201 | 44.626 | 19.908 | 45.894 | 1.00 | 11.35 | 6 |
| ATOM | 1547 | CB | GLN | A | 201 | 43.140 | 19.696 | 46.224 | 1.00 | 11.05 | 6 |
| ATOM | 1548 | CG | GLN | A | 201 | 42.729 | 20.218 | 47.590 | 1.00 | 9.96 | 6 |
| ATOM | 1549 | CD | GLN | A | 201 | 43.431 | 19.495 | 48.744 | 1.00 | 9.52 | 6 |
| ATOM | 1550 | OE1 | GLN | A | 201 | 43.895 | 18.349 | 48.600 | 1.00 | 9.28 | 8 |
| ATOM | 1551 | NE2 | GLN | A | 201 | 43.505 | 20.159 | 49.896 | 1.00 | 11.21 | 7 |
| ATOM | 1552 | C | GLN | A | 201 | 45.059 | 19.018 | 44.715 | 1.00 | 11.22 | 6 |
| ATOM | 1553 | O | GLN | A | 201 | 44.220 | 18.449 | 44.019 | 1.00 | 11.30 | 8 |
| ATOM | 1554 | N | PRO | A | 202 | 46.380 | 18.889 | 44.510 | 1.00 | 11.61 | 7 |
| ATOM | 1555 | CA | PRO | A | 202 | 46.983 | 18.277 | 43.317 | 1.00 | 12.06 | 6 |
| ATOM | 1556 | CB | PRO | A | 202 | 48.486 | 18.348 | 43.617 | 1.00 | 11.93 | 6 |
| ATOM | 1557 | CG | PRO | A | 202 | 48.621 | 19.431 | 44.610 | 1.00 | 11.58 | 6 |
| ATOM | 1558 | CD | PRO | A | 202 | 47.415 | 19.346 | 45.457 | 1.00 | 11.92 | 6 |
| ATOM | 1559 | C | PRO | A | 202 | 46.571 | 16.822 | 43.062 | 1.00 | 12.45 | 6 |
| ATOM | 1560 | O | PRO | A | 202 | 46.242 | 16.463 | 41.917 | 1.00 | 12.38 | 8 |
| ATOM | 1561 | N | ARG | A | 203 | 46.617 | 15.991 | 44.105 | 1.00 | 12.80 | 7 |
| ATOM | 1562 | CA | ARG | A | 203 | 46.281 | 14.572 | 43.969 | 1.00 | 13.00 | 6 |
| ATOM | 1563 | CB | ARG | A | 203 | 46.701 | 13.780 | 45.214 | 1.00 | 13.35 | 6 |
| ATOM | 1564 | CG | ARG | A | 203 | 48.176 | 13.895 | 45.543 | 1.00 | 14.48 | 6 |
| ATOM | 1565 | CD | ARG | A | 203 | 49.012 | 12.746 | 45.003 | 1.00 | 18.79 | 6 |
| ATOM | 1566 | NE | ARG | A | 203 | 50.383 | 12.819 | 45.517 | 1.00 | 21.14 | 7 |
| ATOM | 1567 | CZ | ARG | A | 203 | 50.828 | 12.173 | 46.597 | 1.00 | 21.94 | 6 |
| ATOM | 1568 | NH1 | ARG | A | 203 | 50.018 | 11.383 | 47.295 | 1.00 | 24.20 | 7 |
| ATOM | 1569 | NH2 | ARG | A | 203 | 52.089 | 12.319 | 46.981 | 1.00 | 22.21 | 7 |
| ATOM | 1570 | C | ARG | A | 203 | 44.795 | 14.366 | 43.682 | 1.00 | 13.11 | 6 |

TABLE 7-continued

Coordinates of the crystal structure of E. coli ExoI bound to compound 10

| ATOM | 1571 | O | ARG | A | 203 | 44.432 | 13.538 | 42.845 | 1.00 | 13.70 | 8 |
|------|------|------|-----|---|-----|--------|--------|--------|------|-------|---|
| ATOM | 1572 | N | LEU | A | 204 | 43.942 | 15.119 | 44.379 | 1.00 | 13.22 | 7 |
| ATOM | 1573 | CA | LEU | A | 204 | 42.499 | 15.048 | 44.138 | 1.00 | 13.24 | 6 |
| ATOM | 1574 | CB | LEU | A | 204 | 41.704 | 15.853 | 45.178 | 1.00 | 13.22 | 6 |
| ATOM | 1575 | CG | LEU | A | 204 | 40.171 | 15.725 | 45.111 | 1.00 | 13.20 | 6 |
| ATOM | 1576 | CD1 | LEU | A | 204 | 39.714 | 14.294 | 45.397 | 1.00 | 13.81 | 6 |
| ATOM | 1577 | CD2 | LEU | A | 204 | 39.501 | 16.693 | 46.059 | 1.00 | 13.54 | 6 |
| ATOM | 1578 | C | LEU | A | 204 | 42.162 | 15.507 | 42.727 | 1.00 | 13.65 | 6 |
| ATOM | 1579 | O | LEU | A | 204 | 41.359 | 14.875 | 42.041 | 1.00 | 13.87 | 8 |
| ATOM | 1580 | N | PHE | A | 205 | 42.794 | 16.594 | 42.287 | 1.00 | 13.49 | 7 |
| ATOM | 1581 | CA | PHE | A | 205 | 42.587 | 17.102 | 40.929 | 1.00 | 13.52 | 6 |
| ATOM | 1582 | CB | PHE | A | 205 | 43.441 | 18.345 | 40.679 | 1.00 | 13.70 | 6 |
| ATOM | 1583 | CG | PHE | A | 205 | 43.052 | 19.097 | 39.439 | 1.00 | 14.74 | 6 |
| ATOM | 1584 | CD1 | PHE | A | 205 | 41.975 | 19.975 | 39.454 | 1.00 | 15.30 | 6 |
| ATOM | 1585 | CE1 | PHE | A | 205 | 41.607 | 20.670 | 38.305 | 1.00 | 16.10 | 6 |
| ATOM | 1586 | CZ | PHE | A | 205 | 42.324 | 20.489 | 37.131 | 1.00 | 15.73 | 6 |
| ATOM | 1587 | CE2 | PHE | A | 205 | 43.394 | 19.615 | 37.102 | 1.00 | 15.12 | 6 |
| ATOM | 1588 | CD2 | PHE | A | 205 | 43.758 | 18.923 | 38.253 | 1.00 | 16.09 | 6 |
| ATOM | 1589 | C | PHE | A | 205 | 42.901 | 16.029 | 39.878 | 1.00 | 13.54 | 6 |
| ATOM | 1590 | O | PHE | A | 205 | 42.082 | 15.743 | 39.014 | 1.00 | 13.05 | 8 |
| ATOM | 1591 | N | ASP | A | 206 | 44.090 | 15.438 | 39.989 | 1.00 | 13.80 | 7 |
| ATOM | 1592 | CA | ASP | A | 206 | 44.535 | 14.361 | 39.108 | 1.00 | 14.29 | 6 |
| ATOM | 1593 | CB | ASP | A | 206 | 45.939 | 13.903 | 39.523 | 1.00 | 14.93 | 6 |
| ATOM | 1594 | CG | ASP | A | 206 | 46.608 | 13.010 | 38.486 | 1.00 | 18.25 | 6 |
| ATOM | 1595 | OD1 | ASP | A | 206 | 46.012 | 11.983 | 38.086 | 1.00 | 23.29 | 8 |
| ATOM | 1596 | OD2 | ASP | A | 206 | 47.752 | 13.320 | 38.088 | 1.00 | 23.48 | 8 |
| ATOM | 1597 | C | ASP | A | 206 | 43.563 | 13.185 | 39.152 | 1.00 | 13.70 | 6 |
| ATOM | 1598 | O | ASP | A | 206 | 43.215 | 12.616 | 38.109 | 1.00 | 13.46 | 8 |
| ATOM | 1599 | N | TYR | A | 207 | 43.118 | 12.829 | 40.358 | 1.00 | 13.43 | 7 |
| ATOM | 1600 | CA | TYR | A | 207 | 42.202 | 11.703 | 40.525 | 1.00 | 12.98 | 6 |
| ATOM | 1601 | CB | TYR | A | 207 | 41.912 | 11.431 | 42.010 | 1.00 | 13.61 | 6 |
| ATOM | 1602 | CG | TYR | A | 207 | 40.850 | 10.374 | 42.191 | 1.00 | 13.23 | 6 |
| ATOM | 1603 | CD1 | TYR | A | 207 | 41.189 | 9.029 | 42.237 | 1.00 | 13.68 | 6 |
| ATOM | 1604 | CE1 | TYR | A | 207 | 40.209 | 8.043 | 42.366 | 1.00 | 15.29 | 6 |
| ATOM | 1605 | CZ | TYR | A | 207 | 38.874 | 8.408 | 42.446 | 1.00 | 13.86 | 6 |
| ATOM | 1606 | OH | TYR | A | 207 | 37.915 | 7.437 | 42.567 | 1.00 | 14.70 | 8 |
| ATOM | 1607 | CE2 | TYR | A | 207 | 38.502 | 9.742 | 42.397 | 1.00 | 13.03 | 6 |
| ATOM | 1608 | CD2 | TYR | A | 207 | 39.489 | 10.720 | 42.259 | 1.00 | 14.11 | 6 |
| ATOM | 1609 | C | TYR | A | 207 | 40.886 | 11.956 | 39.797 | 1.00 | 13.25 | 6 |
| ATOM | 1610 | O | TYR | A | 207 | 40.377 | 11.089 | 39.084 | 1.00 | 13.56 | 8 |
| ATOM | 1611 | N | LEU | A | 208 | 40.328 | 13.142 | 40.014 | 1.00 | 13.12 | 7 |
| ATOM | 1612 | CA | LEU | A | 208 | 39.043 | 13.499 | 39.437 | 1.00 | 12.88 | 6 |
| ATOM | 1613 | CB | LEU | A | 208 | 38.513 | 14.799 | 40.042 | 1.00 | 12.52 | 6 |
| ATOM | 1614 | CG | LEU | A | 208 | 38.132 | 14.703 | 41.528 | 1.00 | 13.07 | 6 |
| ATOM | 1615 | CD1 | LEU | A | 208 | 37.920 | 16.080 | 42.126 | 1.00 | 12.35 | 6 |
| ATOM | 1616 | CD2 | LEU | A | 208 | 36.894 | 13.836 | 41.725 | 1.00 | 11.77 | 6 |
| ATOM | 1617 | C | LEU | A | 208 | 39.107 | 13.590 | 37.916 | 1.00 | 12.66 | 6 |
| ATOM | 1618 | O | LEU | A | 208 | 38.183 | 13.157 | 37.244 | 1.00 | 13.36 | 8 |
| ATOM | 1619 | N | PHE | A | 209 | 40.202 | 14.156 | 37.389 | 1.00 | 12.62 | 7 |
| ATOM | 1620 | CA | PHE | A | 209 | 40.420 | 14.250 | 35.944 | 1.00 | 12.65 | 6 |
| ATOM | 1621 | CB | PHE | A | 209 | 41.685 | 15.066 | 35.631 | 1.00 | 12.13 | 6 |
| ATOM | 1622 | CG | PHE | A | 209 | 42.012 | 15.161 | 34.153 | 1.00 | 13.29 | 6 |
| ATOM | 1623 | CD1 | PHE | A | 209 | 41.216 | 15.921 | 33.290 | 1.00 | 11.93 | 6 |
| ATOM | 1624 | CE1 | PHE | A | 209 | 41.521 | 16.012 | 31.923 | 1.00 | 12.87 | 6 |
| ATOM | 1625 | CZ | PHE | A | 209 | 42.638 | 15.350 | 31.412 | 1.00 | 12.61 | 6 |
| ATOM | 1626 | CE2 | PHE | A | 209 | 43.443 | 14.594 | 32.265 | 1.00 | 14.03 | 6 |
| ATOM | 1627 | CD2 | PHE | A | 209 | 43.130 | 14.507 | 33.629 | 1.00 | 13.02 | 6 |
| ATOM | 1628 | C | PHE | A | 209 | 40.512 | 12.868 | 35.304 | 1.00 | 13.00 | 6 |
| ATOM | 1629 | O | PHE | A | 209 | 39.867 | 12.599 | 34.289 | 1.00 | 13.00 | 8 |
| ATOM | 1630 | N | THR | A | 210 | 41.314 | 11.994 | 35.904 | 1.00 | 13.10 | 7 |
| ATOM | 1631 | CA | THR | A | 210 | 41.469 | 10.629 | 35.404 | 1.00 | 13.88 | 6 |
| ATOM | 1632 | CB | THR | A | 210 | 42.510 | 9.853 | 36.228 | 1.00 | 13.82 | 6 |
| ATOM | 1633 | OG1 | THR | A | 210 | 43.775 | 10.517 | 36.141 | 1.00 | 15.00 | 8 |
| ATOM | 1634 | CG2 | THR | A | 210 | 42.663 | 8.431 | 35.719 | 1.00 | 14.67 | 6 |
| ATOM | 1635 | C | THR | A | 210 | 40.124 | 9.883 | 35.412 | 1.00 | 13.91 | 6 |
| ATOM | 1636 | O | THR | A | 210 | 39.784 | 9.174 | 34.455 | 1.00 | 14.05 | 8 |
| ATOM | 1637 | N | HIS | A | 211 | 39.349 | 10.078 | 36.472 | 1.00 | 14.13 | 7 |
| ATOM | 1638 | CA | HIS | A | 211 | 38.096 | 9.353 | 36.637 | 1.00 | 14.28 | 6 |
| ATOM | 1639 | CB | HIS | A | 211 | 37.856 | 9.028 | 38.109 | 1.00 | 14.55 | 6 |
| ATOM | 1640 | CG | HIS | A | 211 | 38.848 | 8.053 | 38.656 | 1.00 | 15.29 | 6 |
| ATOM | 1641 | ND1 | HIS | A | 211 | 38.523 | 6.746 | 38.952 | 1.00 | 17.69 | 7 |
| ATOM | 1642 | CE1 | HIS | A | 211 | 39.604 | 6.113 | 39.372 | 1.00 | 15.87 | 6 |
| ATOM | 1643 | NE2 | HIS | A | 211 | 40.624 | 6.948 | 39.320 | 1.00 | 17.19 | 7 |
| ATOM | 1644 | CD2 | HIS | A | 211 | 40.181 | 8.164 | 38.859 | 1.00 | 14.71 | 6 |
| ATOM | 1645 | C | HIS | A | 211 | 36.893 | 10.025 | 35.982 | 1.00 | 14.06 | 6 |
| ATOM | 1646 | O | HIS | A | 211 | 35.754 | 9.672 | 36.264 | 1.00 | 14.58 | 8 |
| ATOM | 1647 | N | ARG | A | 212 | 37.155 | 10.958 | 35.067 | 1.00 | 14.17 | 7 |
| ATOM | 1648 | CA | ARG | A | 212 | 36.103 | 11.484 | 34.205 | 1.00 | 14.39 | 6 |

TABLE 7-continued

Coordinates of the crystal structure of *E. coli* ExoI bound to compound 10

| ATOM | 1649 | CB  | ARG | A | 212 | 36.552 | 12.787 | 33.538 | 1.00 | 14.33 | 6  |
|------|------|-----|-----|---|-----|--------|--------|--------|------|-------|----|
| ATOM | 1650 | CG  | ARG | A | 212 | 37.300 | 12.576 | 32.216 | 1.00 | 13.41 | 6  |
| ATOM | 1651 | CD  | ARG | A | 212 | 38.074 | 13.823 | 31.806 | 1.00 | 13.05 | 6  |
| ATOM | 1652 | NE  | ARG | A | 212 | 38.890 | 13.621 | 30.605 | 1.00 | 13.41 | 7  |
| ATOM | 1653 | CZ  | ARG | A | 212 | 40.056 | 12.972 | 30.575 | 1.00 | 13.67 | 6  |
| ATOM | 1654 | NH1 | ARG | A | 212 | 40.559 | 12.414 | 31.677 | 1.00 | 12.39 | 7  |
| ATOM | 1655 | NH2 | ARG | A | 212 | 40.713 | 12.859 | 29.432 | 1.00 | 12.54 | 7  |
| ATOM | 1656 | C   | ARG | A | 212 | 35.746 | 10.438 | 33.133 | 1.00 | 15.04 | 6  |
| ATOM | 1657 | O   | ARG | A | 212 | 34.706 | 10.532 | 32.485 | 1.00 | 15.58 | 8  |
| ATOM | 1658 | N   | ASN | A | 213 | 36.634 | 9.459  | 32.954 | 1.00 | 15.64 | 7  |
| ATOM | 1659 | CA  | ASN | A | 213 | 36.465 | 8.383  | 31.973 | 1.00 | 16.37 | 6  |
| ATOM | 1660 | CB  | ASN | A | 213 | 37.850 | 7.850  | 31.558 | 1.00 | 16.74 | 6  |
| ATOM | 1661 | CG  | ASN | A | 213 | 37.779 | 6.589  | 30.721 | 1.00 | 17.30 | 6  |
| ATOM | 1662 | OD1 | ASN | A | 213 | 37.680 | 5.481  | 31.252 | 1.00 | 19.16 | 8  |
| ATOM | 1663 | ND2 | ASN | A | 213 | 37.880 | 6.746  | 29.403 | 1.00 | 19.82 | 7  |
| ATOM | 1664 | C   | ASN | A | 213 | 35.582 | 7.265  | 32.534 | 1.00 | 16.38 | 6  |
| ATOM | 1665 | O   | ASN | A | 213 | 35.796 | 6.805  | 33.653 | 1.00 | 16.27 | 8  |
| ATOM | 1666 | N   | LYS | A | 214 | 34.581 | 6.842  | 31.760 | 1.00 | 16.55 | 7  |
| ATOM | 1667 | CA  | LYS | A | 214 | 33.581 | 5.892  | 32.268 | 1.00 | 16.84 | 6  |
| ATOM | 1668 | CB  | LYS | A | 214 | 32.412 | 5.723  | 31.290 | 1.00 | 17.04 | 6  |
| ATOM | 1669 | CG  | LYS | A | 214 | 32.765 | 5.049  | 29.982 | 1.00 | 17.62 | 6  |
| ATOM | 1670 | CD  | LYS | A | 214 | 31.534 | 4.876  | 29.101 | 1.00 | 17.60 | 6  |
| ATOM | 1671 | CE  | LYS | A | 214 | 31.911 | 4.269  | 27.761 | 1.00 | 19.76 | 6  |
| ATOM | 1672 | NZ  | LYS | A | 214 | 30.726 | 4.105  | 26.865 | 1.00 | 20.59 | 7  |
| ATOM | 1673 | C   | LYS | A | 214 | 34.179 | 4.539  | 32.648 | 1.00 | 16.84 | 6  |
| ATOM | 1674 | O   | LYS | A | 214 | 33.710 | 3.895  | 33.588 | 1.00 | 16.84 | 8  |
| ATOM | 1675 | N   | HIS | A | 215 | 35.225 | 4.125  | 31.936 | 1.00 | 16.78 | 7  |
| ATOM | 1676 | CA  | HIS | A | 215 | 35.832 | 2.813  | 32.165 | 1.00 | 17.28 | 6  |
| ATOM | 1677 | CB  | HIS | A | 215 | 36.702 | 2.389  | 30.974 | 1.00 | 17.65 | 6  |
| ATOM | 1678 | CG  | HIS | A | 215 | 35.937 | 2.236  | 29.694 | 1.00 | 18.04 | 6  |
| ATOM | 1679 | ND1 | HIS | A | 215 | 34.976 | 1.265  | 29.515 | 1.00 | 19.00 | 7  |
| ATOM | 1680 | CE1 | HIS | A | 215 | 34.463 | 1.372  | 28.301 | 1.00 | 18.51 | 6  |
| ATOM | 1681 | NE2 | HIS | A | 215 | 35.056 | 2.379  | 27.688 | 1.00 | 19.90 | 7  |
| ATOM | 1682 | CD2 | HIS | A | 215 | 35.982 | 2.937  | 28.536 | 1.00 | 19.66 | 6  |
| ATOM | 1683 | C   | HIS | A | 215 | 36.610 | 2.758  | 33.485 | 1.00 | 17.13 | 6  |
| ATOM | 1684 | O   | HIS | A | 215 | 36.643 | 1.717  | 34.147 | 1.00 | 17.51 | 8  |
| ATOM | 1685 | N   | LYS | A | 216 | 37.209 | 3.885  | 33.870 | 1.00 | 17.20 | 7  |
| ATOM | 1686 | CA  | LYS | A | 216 | 37.843 | 4.028  | 35.190 | 1.00 | 17.24 | 6  |
| ATOM | 1687 | CB  | LYS | A | 216 | 38.688 | 5.306  | 35.261 | 1.00 | 17.58 | 6  |
| ATOM | 1688 | CG  | LYS | A | 216 | 39.921 | 5.305  | 34.356 | 1.00 | 18.27 | 6  |
| ATOM | 1689 | CD  | LYS | A | 216 | 40.997 | 4.329  | 34.847 | 1.00 | 20.51 | 6  |
| ATOM | 1690 | CE  | LYS | A | 216 | 41.804 | 4.912  | 35.995 | 1.00 | 21.67 | 6  |
| ATOM | 1691 | NZ  | LYS | A | 216 | 43.031 | 4.117  | 36.284 | 1.00 | 23.96 | 7  |
| ATOM | 1692 | C   | LYS | A | 216 | 36.811 | 4.044  | 36.313 | 1.00 | 17.13 | 6  |
| ATOM | 1693 | O   | LYS | A | 216 | 37.056 | 3.514  | 37.395 | 1.00 | 17.48 | 8  |
| ATOM | 1694 | N   | LEU | A | 217 | 35.669 | 4.685  | 36.062 | 1.00 | 17.16 | 7  |
| ATOM | 1695 | CA  | LEU | A | 217 | 34.566 | 4.676  | 37.014 | 1.00 | 16.82 | 6  |
| ATOM | 1696 | CB  | LEU | A | 217 | 33.449 | 5.632  | 36.574 | 1.00 | 16.58 | 6  |
| ATOM | 1697 | CG  | LEU | A | 217 | 33.743 | 7.131  | 36.686 | 1.00 | 15.75 | 6  |
| ATOM | 1698 | CD1 | LEU | A | 217 | 32.686 | 7.925  | 35.959 | 1.00 | 16.55 | 6  |
| ATOM | 1699 | CD2 | LEU | A | 217 | 33.846 | 7.574  | 38.160 | 1.00 | 15.59 | 6  |
| ATOM | 1700 | C   | LEU | A | 217 | 34.028 | 3.259  | 37.205 | 1.00 | 16.77 | 6  |
| ATOM | 1701 | O   | LEU | A | 217 | 33.735 | 2.845  | 38.332 | 1.00 | 16.81 | 8  |
| ATOM | 1702 | N   | MET | A | 218 | 33.929 | 2.516  | 36.103 | 1.00 | 16.90 | 7  |
| ATOM | 1703 | CA  | MET | A | 218 | 33.451 | 1.129  | 36.131 | 1.00 | 17.24 | 6  |
| ATOM | 1704 | CB  | MET | A | 218 | 33.481 | 0.515  | 34.722 | 1.00 | 16.98 | 6  |
| ATOM | 1705 | CG  | MET | A | 218 | 32.299 | 0.887  | 33.819 | 1.00 | 17.78 | 6  |
| ATOM | 1706 | SD  | MET | A | 218 | 32.371 | -0.006 | 32.241 | 1.00 | 20.08 | 16 |
| ATOM | 1707 | CE  | MET | A | 218 | 30.702 | 0.179  | 31.616 | 1.00 | 18.58 | 6  |
| ATOM | 1708 | C   | MET | A | 218 | 34.260 | 0.258  | 37.101 | 1.00 | 16.57 | 6  |
| ATOM | 1709 | O   | MET | A | 218 | 33.705 | -0.631 | 37.748 | 1.00 | 16.75 | 8  |
| ATOM | 1710 | N   | ALA | A | 219 | 35.564 | 0.532  | 37.203 | 1.00 | 16.30 | 7  |
| ATOM | 1711 | CA  | ALA | A | 219 | 36.478 | -0.245 | 38.062 | 1.00 | 16.23 | 6  |
| ATOM | 1712 | CB  | ALA | A | 219 | 37.924 | 0.142  | 37.789 | 1.00 | 15.99 | 6  |
| ATOM | 1713 | C   | ALA | A | 219 | 36.170 | -0.121 | 39.557 | 1.00 | 16.23 | 6  |
| ATOM | 1714 | O   | ALA | A | 219 | 36.572 | -0.979 | 40.359 | 1.00 | 15.84 | 8  |
| ATOM | 1715 | N   | LEU | A | 220 | 35.474 | 0.950  | 39.927 | 1.00 | 16.33 | 7  |
| ATOM | 1716 | CA  | LEU | A | 220 | 35.114 | 1.195  | 41.327 | 1.00 | 16.78 | 6  |
| ATOM | 1717 | CB  | LEU | A | 220 | 34.886 | 2.691  | 41.567 | 1.00 | 16.95 | 6  |
| ATOM | 1718 | CG  | LEU | A | 220 | 36.003 | 3.684  | 41.221 | 1.00 | 17.43 | 6  |
| ATOM | 1719 | CD1 | LEU | A | 220 | 35.459 | 5.106  | 41.202 | 1.00 | 18.75 | 6  |
| ATOM | 1720 | CD2 | LEU | A | 220 | 37.181 | 3.573  | 42.180 | 1.00 | 17.78 | 6  |
| ATOM | 1721 | C   | LEU | A | 220 | 33.862 | 0.427  | 41.725 | 1.00 | 16.95 | 6  |
| ATOM | 1722 | O   | LEU | A | 220 | 33.561 | 0.285  | 42.917 | 1.00 | 16.90 | 8  |
| ATOM | 1723 | N   | ILE | A | 221 | 33.137 | -0.070 | 40.727 | 1.00 | 17.36 | 7  |
| ATOM | 1724 | CA  | ILE | A | 221 | 31.809 | -0.639 | 40.939 | 1.00 | 17.60 | 6  |
| ATOM | 1725 | CB  | ILE | A | 221 | 30.835 | -0.239 | 39.785 | 1.00 | 17.59 | 6  |
| ATOM | 1726 | CG1 | ILE | A | 221 | 30.583 | 1.279  | 39.814 | 1.00 | 17.89 | 6  |

TABLE 7-continued

Coordinates of the crystal structure of *E. coli* ExoI bound to compound 10

| ATOM | 1727 | CD1 | ILE | A | 221 | 30.253 | 1.886 | 38.462 | 1.00 | 20.35 | 6 |
|------|------|-----|-----|---|-----|--------|-------|--------|------|-------|---|
| ATOM | 1728 | CG2 | ILE | A | 221 | 29.520 | −1.018 | 39.877 | 1.00 | 17.41 | 6 |
| ATOM | 1729 | C   | ILE | A | 221 | 31.842 | −2.158 | 41.134 | 1.00 | 18.01 | 6 |
| ATOM | 1730 | O   | ILE | A | 221 | 32.277 | −2.900 | 40.251 | 1.00 | 17.44 | 8 |
| ATOM | 1731 | N   | ASP | A | 222 | 31.397 | −2.602 | 42.311 | 1.00 | 18.37 | 7 |
| ATOM | 1732 | CA  | ASP | A | 222 | 31.273 | −4.028 | 42.622 | 1.00 | 19.05 | 6 |
| ATOM | 1733 | CB  | ASP | A | 222 | 32.328 | −4.437 | 43.665 | 1.00 | 19.17 | 6 |
| ATOM | 1734 | CG  | ASP | A | 222 | 32.518 | −5.947 | 43.765 | 1.00 | 20.60 | 6 |
| ATOM | 1735 | OD1 | ASP | A | 222 | 31.595 | −6.709 | 43.414 | 1.00 | 20.94 | 8 |
| ATOM | 1736 | OD2 | ASP | A | 222 | 33.602 | −6.369 | 44.224 | 1.00 | 22.12 | 8 |
| ATOM | 1737 | C   | ASP | A | 222 | 29.853 | −4.312 | 43.126 | 1.00 | 19.09 | 6 |
| ATOM | 1738 | O   | ASP | A | 222 | 29.551 | −4.138 | 44.313 | 1.00 | 19.36 | 8 |
| ATOM | 1739 | N   | VAL | A | 223 | 28.986 | −4.744 | 42.210 | 1.00 | 19.41 | 7 |
| ATOM | 1740 | CA  | VAL | A | 223 | 27.581 | −5.014 | 42.525 | 1.00 | 19.75 | 6 |
| ATOM | 1741 | CB  | VAL | A | 223 | 26.710 | −5.150 | 41.235 | 1.00 | 19.86 | 6 |
| ATOM | 1742 | CG1 | VAL | A | 223 | 25.277 | −5.552 | 41.578 | 1.00 | 20.05 | 6 |
| ATOM | 1743 | CG2 | VAL | A | 223 | 26.723 | −3.857 | 40.450 | 1.00 | 20.09 | 6 |
| ATOM | 1744 | C   | VAL | A | 223 | 27.387 | −6.230 | 43.461 | 1.00 | 19.78 | 6 |
| ATOM | 1745 | O   | VAL | A | 223 | 26.704 | −6.109 | 44.477 | 1.00 | 19.65 | 8 |
| ATOM | 1746 | N   | PRO | A | 224 | 27.987 | −7.400 | 43.124 | 1.00 | 19.92 | 7 |
| ATOM | 1747 | CA  | PRO | A | 224 | 27.799 | −8.572 | 43.992 | 1.00 | 20.19 | 6 |
| ATOM | 1748 | CB  | PRO | A | 224 | 28.699 | −9.631 | 43.349 | 1.00 | 20.26 | 6 |
| ATOM | 1749 | CG  | PRO | A | 224 | 28.788 | −9.224 | 41.922 | 1.00 | 20.12 | 6 |
| ATOM | 1750 | CD  | PRO | A | 224 | 28.831 | −7.729 | 41.957 | 1.00 | 20.08 | 6 |
| ATOM | 1751 | C   | PRO | A | 224 | 28.220 | −8.340 | 45.443 | 1.00 | 20.36 | 6 |
| ATOM | 1752 | O   | PRO | A | 224 | 27.578 | −8.859 | 46.356 | 1.00 | 20.24 | 8 |
| ATOM | 1753 | N   | GLN | A | 225 | 29.289 | −7.573 | 45.643 | 1.00 | 20.74 | 7 |
| ATOM | 1754 | CA  | GLN | A | 225 | 29.795 | −7.284 | 46.988 | 1.00 | 21.15 | 6 |
| ATOM | 1755 | CB  | GLN | A | 225 | 31.304 | −7.020 | 46.954 | 1.00 | 21.14 | 6 |
| ATOM | 1756 | CG  | GLN | A | 225 | 32.167 | −8.272 | 47.020 | 1.00 | 22.23 | 6 |
| ATOM | 1757 | CD  | GLN | A | 225 | 33.641 | −7.966 | 47.287 | 1.00 | 22.85 | 6 |
| ATOM | 1758 | OE1 | GLN | A | 225 | 34.097 | −6.818 | 47.153 | 1.00 | 24.66 | 8 |
| ATOM | 1759 | NE2 | GLN | A | 225 | 34.398 | −8.999 | 47.658 | 1.00 | 24.30 | 7 |
| ATOM | 1760 | C   | GLN | A | 225 | 29.079 | −6.100 | 47.638 | 1.00 | 20.88 | 6 |
| ATOM | 1761 | O   | GLN | A | 225 | 29.185 | −5.898 | 48.851 | 1.00 | 20.82 | 8 |
| ATOM | 1762 | N   | MET | A | 226 | 28.340 | −5.337 | 46.829 | 1.00 | 20.77 | 7 |
| ATOM | 1763 | CA  | MET | A | 226 | 27.776 | −4.040 | 47.237 | 1.00 | 20.93 | 6 |
| ATOM | 1764 | CB  | MET | A | 226 | 26.588 | −4.213 | 48.202 | 1.00 | 21.17 | 6 |
| ATOM | 1765 | CG  | MET | A | 226 | 25.362 | −4.889 | 47.595 | 1.00 | 21.57 | 6 |
| ATOM | 1766 | SD  | MET | A | 226 | 23.964 | −4.878 | 48.740 | 1.00 | 22.39 | 16 |
| ATOM | 1767 | CE  | MET | A | 226 | 22.884 | −6.114 | 48.014 | 1.00 | 23.45 | 6 |
| ATOM | 1768 | C   | MET | A | 226 | 28.846 | −3.140 | 47.857 | 1.00 | 20.67 | 6 |
| ATOM | 1769 | O   | MET | A | 226 | 28.631 | −2.538 | 48.909 | 1.00 | 20.39 | 8 |
| ATOM | 1770 | N   | LYS | A | 227 | 29.996 | −3.049 | 47.189 | 1.00 | 20.10 | 7 |
| ATOM | 1771 | CA  | LYS | A | 227 | 31.130 | −2.291 | 47.705 | 1.00 | 19.62 | 6 |
| ATOM | 1772 | CB  | LYS | A | 227 | 32.331 | −2.426 | 46.763 | 1.00 | 19.99 | 6 |
| ATOM | 1773 | CG  | LYS | A | 227 | 33.577 | −1.693 | 47.230 | 1.00 | 22.00 | 6 |
| ATOM | 1774 | CD  | LYS | A | 227 | 34.838 | −2.383 | 46.738 | 1.00 | 24.37 | 6 |
| ATOM | 1775 | CE  | LYS | A | 227 | 36.083 | −1.744 | 47.332 | 1.00 | 26.67 | 6 |
| ATOM | 1776 | NZ  | LYS | A | 227 | 37.278 | −2.634 | 47.179 | 1.00 | 28.20 | 7 |
| ATOM | 1777 | C   | LYS | A | 227 | 30.757 | −0.814 | 47.899 | 1.00 | 18.73 | 6 |
| ATOM | 1778 | O   | LYS | A | 227 | 30.327 | −0.161 | 46.955 | 1.00 | 18.60 | 8 |
| ATOM | 1779 | N   | PRO | A | 228 | 30.908 | −0.297 | 49.132 | 1.00 | 18.10 | 7 |
| ATOM | 1780 | CA  | PRO | A | 228 | 30.583 | 1.109 | 49.398 | 1.00 | 17.36 | 6 |
| ATOM | 1781 | CB  | PRO | A | 228 | 30.681 | 1.213 | 50.925 | 1.00 | 17.56 | 6 |
| ATOM | 1782 | CG  | PRO | A | 228 | 31.580 | 0.128 | 51.327 | 1.00 | 18.03 | 6 |
| ATOM | 1783 | CD  | PRO | A | 228 | 31.375 | −0.994 | 50.345 | 1.00 | 17.90 | 6 |
| ATOM | 1784 | C   | PRO | A | 228 | 31.542 | 2.098 | 48.727 | 1.00 | 16.76 | 6 |
| ATOM | 1785 | O   | PRO | A | 228 | 32.745 | 1.846 | 48.651 | 1.00 | 16.20 | 8 |
| ATOM | 1786 | N   | LEU | A | 229 | 30.987 | 3.205 | 48.228 | 1.00 | 15.78 | 7 |
| ATOM | 1787 | CA  | LEU | A | 229 | 31.768 | 4.299 | 47.651 | 1.00 | 15.53 | 6 |
| ATOM | 1788 | CB  | LEU | A | 229 | 31.582 | 4.351 | 46.122 | 1.00 | 15.75 | 6 |
| ATOM | 1789 | CG  | LEU | A | 229 | 31.890 | 3.099 | 45.300 | 1.00 | 15.95 | 6 |
| ATOM | 1790 | CD1 | LEU | A | 229 | 31.273 | 3.216 | 43.905 | 1.00 | 17.34 | 6 |
| ATOM | 1791 | CD2 | LEU | A | 229 | 33.393 | 2.842 | 45.223 | 1.00 | 16.41 | 6 |
| ATOM | 1792 | C   | LEU | A | 229 | 31.302 | 5.620 | 48.243 | 1.00 | 15.35 | 6 |
| ATOM | 1793 | O   | LEU | A | 229 | 30.161 | 5.735 | 48.695 | 1.00 | 15.10 | 8 |
| ATOM | 1794 | N   | VAL | A | 230 | 32.177 | 6.622 | 48.246 | 1.00 | 14.74 | 7 |
| ATOM | 1795 | CA  | VAL | A | 230 | 31.712 | 7.979 | 48.485 | 1.00 | 15.19 | 6 |
| ATOM | 1796 | CB  | VAL | A | 230 | 32.782 | 8.871 | 49.197 | 1.00 | 15.47 | 6 |
| ATOM | 1797 | CG1 | VAL | A | 230 | 34.080 | 8.920 | 48.413 | 1.00 | 16.18 | 6 |
| ATOM | 1798 | CG2 | VAL | A | 230 | 32.238 | 10.276 | 49.461 | 1.00 | 17.25 | 6 |
| ATOM | 1799 | C   | VAL | A | 230 | 31.247 | 8.562 | 47.151 | 1.00 | 14.57 | 6 |
| ATOM | 1800 | O   | VAL | A | 230 | 31.851 | 8.317 | 46.110 | 1.00 | 14.85 | 8 |
| ATOM | 1801 | N   | HIS | A | 231 | 30.141 | 9.287 | 47.187 | 1.00 | 14.53 | 7 |
| ATOM | 1802 | CA  | HIS | A | 231 | 29.582 | 9.880 | 45.991 | 1.00 | 13.71 | 6 |
| ATOM | 1803 | CB  | HIS | A | 231 | 28.322 | 9.114 | 45.576 | 1.00 | 13.94 | 6 |
| ATOM | 1804 | CG  | HIS | A | 231 | 27.632 | 9.663 | 44.363 | 1.00 | 12.94 | 6 |

TABLE 7-continued

Coordinates of the crystal structure of *E. coli* ExoI bound to compound 10

| ATOM | 1805 | ND1 | HIS | A | 231 | 28.308 | 10.033 | 43.219 | 1.00 | 13.82 | 7 |
|---|---|---|---|---|---|---|---|---|---|---|---|
| ATOM | 1806 | CE1 | HIS | A | 231 | 27.439 | 10.449 | 42.312 | 1.00 | 12.18 | 6 |
| ATOM | 1807 | NE2 | HIS | A | 231 | 26.225 | 10.346 | 42.821 | 1.00 | 13.09 | 7 |
| ATOM | 1808 | CD2 | HIS | A | 231 | 26.317 | 9.853 | 44.100 | 1.00 | 13.14 | 6 |
| ATOM | 1809 | C | HIS | A | 231 | 29.268 | 11.333 | 46.308 | 1.00 | 14.30 | 6 |
| ATOM | 1810 | O | HIS | A | 231 | 28.628 | 11.623 | 47.317 | 1.00 | 14.18 | 8 |
| ATOM | 1811 | N | VAL | A | 232 | 29.772 | 12.235 | 45.472 | 1.00 | 14.51 | 7 |
| ATOM | 1812 | CA | VAL | A | 232 | 29.472 | 13.659 | 45.598 | 1.00 | 14.51 | 6 |
| ATOM | 1813 | CB | VAL | A | 232 | 30.762 | 14.532 | 45.594 | 1.00 | 14.88 | 6 |
| ATOM | 1814 | CG1 | VAL | A | 232 | 30.414 | 16.020 | 45.791 | 1.00 | 14.32 | 6 |
| ATOM | 1815 | CG2 | VAL | A | 232 | 31.740 | 14.052 | 46.682 | 1.00 | 14.13 | 6 |
| ATOM | 1816 | C | VAL | A | 232 | 28.524 | 14.081 | 44.487 | 1.00 | 15.20 | 6 |
| ATOM | 1817 | O | VAL | A | 232 | 28.839 | 13.947 | 43.295 | 1.00 | 15.23 | 8 |
| ATOM | 1818 | N | SER | A | 233 | 27.354 | 14.575 | 44.883 | 1.00 | 15.31 | 7 |
| ATOM | 1819 | CA | SER | A | 233 | 26.292 | 14.900 | 43.953 | 1.00 | 15.75 | 6 |
| ATOM | 1820 | CB | SER | A | 233 | 25.382 | 13.692 | 43.742 | 1.00 | 15.55 | 6 |
| ATOM | 1821 | OG | SER | A | 233 | 24.330 | 14.015 | 42.850 | 1.00 | 17.12 | 8 |
| ATOM | 1822 | C | SER | A | 233 | 25.464 | 16.058 | 44.493 | 1.00 | 15.65 | 6 |
| ATOM | 1823 | O | SER | A | 233 | 25.147 | 16.100 | 45.684 | 1.00 | 15.67 | 8 |
| ATOM | 1824 | N | GLY | A | 234 | 25.107 | 16.987 | 43.613 | 1.00 | 15.99 | 7 |
| ATOM | 1825 | CA | GLY | A | 234 | 24.217 | 18.096 | 43.984 | 1.00 | 16.27 | 6 |
| ATOM | 1826 | C | GLY | A | 234 | 22.866 | 17.624 | 44.513 | 1.00 | 16.69 | 6 |
| ATOM | 1827 | O | GLY | A | 234 | 22.194 | 18.347 | 45.260 | 1.00 | 17.48 | 8 |
| ATOM | 1828 | N | MET | A | 235 | 22.473 | 16.408 | 44.131 | 1.00 | 16.74 | 7 |
| ATOM | 1829 | CA | MET | A | 235 | 21.201 | 15.821 | 44.564 | 1.00 | 17.05 | 6 |
| ATOM | 1830 | CB | MET | A | 235 | 20.904 | 14.531 | 43.784 | 1.00 | 17.78 | 6 |
| ATOM | 1831 | CG | MET | A | 235 | 20.673 | 14.732 | 42.283 | 1.00 | 21.45 | 6 |
| ATOM | 1832 | SD | MET | A | 235 | 19.162 | 15.639 | 41.872 | 1.00 | 29.38 | 16 |
| ATOM | 1833 | CE | MET | A | 235 | 19.794 | 17.287 | 41.562 | 1.00 | 28.47 | 6 |
| ATOM | 1834 | C | MET | A | 235 | 21.181 | 15.538 | 46.065 | 1.00 | 16.24 | 6 |
| ATOM | 1835 | O | MET | A | 235 | 20.112 | 15.483 | 46.682 | 1.00 | 16.70 | 8 |
| ATOM | 1836 | N | PHE | A | 236 | 22.363 | 15.364 | 46.654 | 1.00 | 15.55 | 7 |
| ATOM | 1837 | CA | PHE | A | 236 | 22.464 | 15.115 | 48.093 | 1.00 | 14.98 | 6 |
| ATOM | 1838 | CB | PHE | A | 236 | 23.822 | 14.501 | 48.439 | 1.00 | 14.62 | 6 |
| ATOM | 1839 | CG | PHE | A | 236 | 23.971 | 13.056 | 48.009 | 1.00 | 14.77 | 6 |
| ATOM | 1840 | CD1 | PHE | A | 236 | 22.881 | 12.182 | 48.041 | 1.00 | 14.91 | 6 |
| ATOM | 1841 | CE1 | PHE | A | 236 | 23.022 | 10.836 | 47.658 | 1.00 | 15.23 | 6 |
| ATOM | 1842 | CZ | PHE | A | 236 | 24.261 | 10.362 | 47.251 | 1.00 | 13.93 | 6 |
| ATOM | 1843 | CE2 | PHE | A | 236 | 25.359 | 11.225 | 47.227 | 1.00 | 14.40 | 6 |
| ATOM | 1844 | CD2 | PHE | A | 236 | 25.207 | 12.564 | 47.607 | 1.00 | 14.85 | 6 |
| ATOM | 1845 | C | PHE | A | 236 | 22.215 | 16.380 | 48.929 | 1.00 | 14.67 | 6 |
| ATOM | 1846 | O | PHE | A | 236 | 21.808 | 16.297 | 50.095 | 1.00 | 14.95 | 8 |
| ATOM | 1847 | N | GLY | A | 237 | 22.474 | 17.547 | 48.348 | 1.00 | 14.01 | 7 |
| ATOM | 1848 | CA | GLY | A | 237 | 22.184 | 18.813 | 49.038 | 1.00 | 13.81 | 6 |
| ATOM | 1849 | C | GLY | A | 237 | 23.361 | 19.369 | 49.824 | 1.00 | 13.87 | 6 |
| ATOM | 1850 | O | GLY | A | 237 | 24.117 | 18.616 | 50.464 | 1.00 | 13.27 | 8 |
| ATOM | 1851 | N | ALA | A | 238 | 23.510 | 20.692 | 49.774 | 1.00 | 13.61 | 7 |
| ATOM | 1852 | CA | ALA | A | 238 | 24.639 | 21.389 | 50.399 | 1.00 | 13.96 | 6 |
| ATOM | 1853 | CB | ALA | A | 238 | 24.641 | 22.845 | 49.987 | 1.00 | 14.18 | 6 |
| ATOM | 1854 | C | ALA | A | 238 | 24.658 | 21.271 | 51.924 | 1.00 | 13.87 | 6 |
| ATOM | 1855 | O | ALA | A | 238 | 25.709 | 21.469 | 52.558 | 1.00 | 13.19 | 8 |
| ATOM | 1856 | N | TRP | A | 239 | 23.502 | 20.955 | 52.513 | 1.00 | 14.04 | 7 |
| ATOM | 1857 | CA | TRP | A | 239 | 23.391 | 20.823 | 53.970 | 1.00 | 14.13 | 6 |
| ATOM | 1858 | CB | TRP | A | 239 | 21.929 | 20.617 | 54.403 | 1.00 | 14.31 | 6 |
| ATOM | 1859 | CG | TRP | A | 239 | 21.299 | 19.359 | 53.865 | 1.00 | 14.66 | 6 |
| ATOM | 1860 | CD1 | TRP | A | 239 | 20.614 | 19.221 | 52.694 | 1.00 | 15.69 | 6 |
| ATOM | 1861 | NE1 | TRP | A | 239 | 20.184 | 17.925 | 52.543 | 1.00 | 15.17 | 7 |
| ATOM | 1862 | CE2 | TRP | A | 239 | 20.590 | 17.196 | 53.630 | 1.00 | 15.91 | 6 |
| ATOM | 1863 | CD2 | TRP | A | 239 | 21.291 | 18.070 | 54.488 | 1.00 | 14.80 | 6 |
| ATOM | 1864 | CE3 | TRP | A | 239 | 21.808 | 17.570 | 55.693 | 1.00 | 16.09 | 6 |
| ATOM | 1865 | CZ3 | TRP | A | 239 | 21.621 | 16.223 | 55.989 | 1.00 | 15.31 | 6 |
| ATOM | 1866 | CH2 | TRP | A | 239 | 20.920 | 15.380 | 55.111 | 1.00 | 15.67 | 6 |
| ATOM | 1867 | CZ2 | TRP | A | 239 | 20.397 | 15.845 | 53.932 | 1.00 | 15.63 | 6 |
| ATOM | 1868 | C | TRP | A | 239 | 24.268 | 19.684 | 54.492 | 1.00 | 14.03 | 6 |
| ATOM | 1869 | O | TRP | A | 239 | 24.673 | 19.688 | 55.651 | 1.00 | 13.54 | 8 |
| ATOM | 1870 | N | ARG | A | 240 | 24.540 | 18.705 | 53.635 | 1.00 | 13.47 | 7 |
| ATOM | 1871 | CA | ARG | A | 240 | 25.468 | 17.628 | 53.979 | 1.00 | 13.54 | 6 |
| ATOM | 1872 | CB | ARG | A | 240 | 24.762 | 16.271 | 53.974 | 1.00 | 13.59 | 6 |
| ATOM | 1873 | CG | ARG | A | 240 | 23.952 | 15.979 | 52.719 | 1.00 | 13.69 | 6 |
| ATOM | 1874 | CD | ARG | A | 240 | 23.549 | 14.520 | 52.693 | 1.00 | 13.99 | 6 |
| ATOM | 1875 | NE | ARG | A | 240 | 22.384 | 14.272 | 51.858 | 1.00 | 14.86 | 7 |
| ATOM | 1876 | CZ | ARG | A | 240 | 21.912 | 13.056 | 51.577 | 1.00 | 13.53 | 6 |
| ATOM | 1877 | NH1 | ARG | A | 240 | 22.517 | 11.977 | 52.058 | 1.00 | 15.69 | 7 |
| ATOM | 1878 | NH2 | ARG | A | 240 | 20.835 | 12.919 | 50.814 | 1.00 | 15.33 | 7 |
| ATOM | 1879 | C | ARG | A | 240 | 26.668 | 17.622 | 53.034 | 1.00 | 13.66 | 6 |
| ATOM | 1880 | O | ARG | A | 240 | 27.235 | 16.571 | 52.746 | 1.00 | 14.06 | 8 |
| ATOM | 1881 | N | GLY | A | 241 | 27.039 | 18.810 | 52.549 | 1.00 | 13.86 | 7 |
| ATOM | 1882 | CA | GLY | A | 241 | 28.174 | 18.951 | 51.638 | 1.00 | 13.42 | 6 |

TABLE 7-continued

Coordinates of the crystal structure of E. coli ExoI bound to compound 10

| ATOM | 1883 | C | GLY | A | 241 | 28.058 | 18.112 | 50.379 | 1.00 | 13.72 | 6 |
|------|------|------|------|---|-----|--------|--------|--------|------|-------|---|
| ATOM | 1884 | O | GLY | A | 241 | 29.071 | 17.675 | 49.829 | 1.00 | 13.79 | 8 |
| ATOM | 1885 | N | ASN | A | 242 | 26.821 | 17.894 | 49.917 | 1.00 | 13.27 | 7 |
| ATOM | 1886 | CA | ASN | A | 242 | 26.551 | 17.150 | 48.667 | 1.00 | 13.18 | 6 |
| ATOM | 1887 | CB | ASN | A | 242 | 27.039 | 17.942 | 47.453 | 1.00 | 13.15 | 6 |
| ATOM | 1888 | CG | ASN | A | 242 | 26.381 | 19.280 | 47.341 | 1.00 | 13.61 | 6 |
| ATOM | 1889 | OD1 | ASN | A | 242 | 25.162 | 19.372 | 47.189 | 1.00 | 14.76 | 8 |
| ATOM | 1890 | ND2 | ASN | A | 242 | 27.178 | 20.339 | 47.406 | 1.00 | 15.97 | 7 |
| ATOM | 1891 | C | ASN | A | 242 | 27.134 | 15.736 | 48.614 | 1.00 | 13.01 | 6 |
| ATOM | 1892 | O | ASN | A | 242 | 27.378 | 15.200 | 47.524 | 1.00 | 12.74 | 8 |
| ATOM | 1893 | N | THR | A | 243 | 27.293 | 15.120 | 49.778 | 1.00 | 12.81 | 7 |
| ATOM | 1894 | CA | THR | A | 243 | 28.096 | 13.910 | 49.901 | 1.00 | 13.09 | 6 |
| ATOM | 1895 | CB | THR | A | 243 | 29.461 | 14.251 | 50.545 | 1.00 | 13.52 | 6 |
| ATOM | 1896 | OG1 | THR | A | 243 | 30.143 | 15.188 | 49.706 | 1.00 | 13.64 | 8 |
| ATOM | 1897 | CG2 | THR | A | 243 | 30.329 | 13.017 | 50.717 | 1.00 | 13.34 | 6 |
| ATOM | 1898 | C | THR | A | 243 | 27.377 | 12.835 | 50.706 | 1.00 | 13.15 | 6 |
| ATOM | 1899 | O | THR | A | 243 | 26.699 | 13.130 | 51.691 | 1.00 | 13.24 | 8 |
| ATOM | 1900 | N | SER | A | 244 | 27.510 | 11.588 | 50.261 | 1.00 | 13.25 | 7 |
| ATOM | 1901 | CA | SER | A | 244 | 27.110 | 10.448 | 51.073 | 1.00 | 13.21 | 6 |
| ATOM | 1902 | CB | SER | A | 244 | 25.629 | 10.127 | 50.891 | 1.00 | 13.30 | 6 |
| ATOM | 1903 | OG | SER | A | 244 | 25.160 | 9.331 | 51.974 | 1.00 | 13.88 | 8 |
| ATOM | 1904 | C | SER | A | 244 | 27.949 | 9.230 | 50.737 | 1.00 | 13.09 | 6 |
| ATOM | 1905 | O | SER | A | 244 | 28.767 | 9.265 | 49.816 | 1.00 | 13.10 | 8 |
| ATOM | 1906 | N | TRP | A | 245 | 27.763 | 8.169 | 51.517 | 1.00 | 13.47 | 7 |
| ATOM | 1907 | CA | TRP | A | 245 | 28.262 | 6.845 | 51.165 | 1.00 | 13.66 | 6 |
| ATOM | 1908 | CB | TRP | A | 245 | 28.744 | 6.093 | 52.410 | 1.00 | 14.15 | 6 |
| ATOM | 1909 | CG | TRP | A | 245 | 30.148 | 6.463 | 52.832 | 1.00 | 13.65 | 6 |
| ATOM | 1910 | CD1 | TRP | A | 245 | 31.282 | 6.388 | 52.069 | 1.00 | 14.03 | 6 |
| ATOM | 1911 | NE1 | TRP | A | 245 | 32.372 | 6.802 | 52.796 | 1.00 | 14.33 | 7 |
| ATOM | 1912 | CE2 | TRP | A | 245 | 31.955 | 7.154 | 54.054 | 1.00 | 14.70 | 6 |
| ATOM | 1913 | CD2 | TRP | A | 245 | 30.557 | 6.950 | 54.111 | 1.00 | 14.81 | 6 |
| ATOM | 1914 | CE3 | TRP | A | 245 | 29.877 | 7.240 | 55.304 | 1.00 | 13.42 | 6 |
| ATOM | 1915 | CZ3 | TRP | A | 245 | 30.603 | 7.716 | 56.386 | 1.00 | 13.91 | 6 |
| ATOM | 1916 | CH2 | TRP | A | 245 | 31.992 | 7.910 | 56.298 | 1.00 | 14.30 | 6 |
| ATOM | 1917 | CZ2 | TRP | A | 245 | 32.683 | 7.642 | 55.137 | 1.00 | 13.87 | 6 |
| ATOM | 1918 | C | TRP | A | 245 | 27.154 | 6.069 | 50.472 | 1.00 | 14.09 | 6 |
| ATOM | 1919 | O | TRP | A | 245 | 26.019 | 6.032 | 50.953 | 1.00 | 14.21 | 8 |
| ATOM | 1920 | N | VAL | A | 246 | 27.487 | 5.463 | 49.337 | 1.00 | 14.32 | 7 |
| ATOM | 1921 | CA | VAL | A | 246 | 26.506 | 4.743 | 48.521 | 1.00 | 14.39 | 6 |
| ATOM | 1922 | CB | VAL | A | 246 | 26.226 | 5.472 | 47.183 | 1.00 | 14.57 | 6 |
| ATOM | 1923 | CG1 | VAL | A | 246 | 25.711 | 6.880 | 47.443 | 1.00 | 13.84 | 6 |
| ATOM | 1924 | CG2 | VAL | A | 246 | 27.485 | 5.512 | 46.304 | 1.00 | 14.53 | 6 |
| ATOM | 1925 | C | VAL | A | 246 | 26.958 | 3.320 | 48.245 | 1.00 | 15.10 | 6 |
| ATOM | 1926 | O | VAL | A | 246 | 28.137 | 2.996 | 48.390 | 1.00 | 15.41 | 8 |
| ATOM | 1927 | N | ALA | A | 247 | 26.010 | 2.473 | 47.852 | 1.00 | 15.43 | 7 |
| ATOM | 1928 | CA | ALA | A | 247 | 26.316 | 1.105 | 47.444 | 1.00 | 16.07 | 6 |
| ATOM | 1929 | CB | ALA | A | 247 | 25.913 | 0.131 | 48.523 | 1.00 | 16.42 | 6 |
| ATOM | 1930 | C | ALA | A | 247 | 25.578 | 0.795 | 46.151 | 1.00 | 16.26 | 6 |
| ATOM | 1931 | O | ALA | A | 247 | 24.402 | 1.131 | 46.022 | 1.00 | 16.24 | 8 |
| ATOM | 1932 | N | PRO | A | 248 | 26.264 | 0.156 | 45.183 | 1.00 | 16.78 | 7 |
| ATOM | 1933 | CA | PRO | A | 248 | 25.573 | −0.252 | 43.964 | 1.00 | 17.28 | 6 |
| ATOM | 1934 | CB | PRO | A | 248 | 26.717 | −0.513 | 42.977 | 1.00 | 17.46 | 6 |
| ATOM | 1935 | CG | PRO | A | 248 | 27.887 | −0.844 | 43.810 | 1.00 | 17.27 | 6 |
| ATOM | 1936 | CD | PRO | A | 248 | 27.698 | −0.196 | 45.161 | 1.00 | 16.54 | 6 |
| ATOM | 1937 | C | PRO | A | 248 | 24.740 | −1.518 | 44.170 | 1.00 | 17.69 | 6 |
| ATOM | 1938 | O | PRO | A | 248 | 25.243 | −2.516 | 44.694 | 1.00 | 17.84 | 8 |
| ATOM | 1939 | N | LEU | A | 249 | 23.476 | −1.471 | 43.754 | 1.00 | 18.15 | 7 |
| ATOM | 1940 | CA | LEU | A | 249 | 22.572 | −2.615 | 43.920 | 1.00 | 18.51 | 6 |
| ATOM | 1941 | CB | LEU | A | 249 | 21.204 | −2.152 | 44.420 | 1.00 | 19.03 | 6 |
| ATOM | 1942 | CG | LEU | A | 249 | 21.062 | −1.575 | 45.829 | 1.00 | 20.20 | 6 |
| ATOM | 1943 | CD1 | LEU | A | 249 | 19.592 | −1.352 | 46.121 | 1.00 | 21.74 | 6 |
| ATOM | 1944 | CD2 | LEU | A | 249 | 21.685 | −2.476 | 46.892 | 1.00 | 22.27 | 6 |
| ATOM | 1945 | C | LEU | A | 249 | 22.396 | −3.409 | 42.632 | 1.00 | 18.48 | 6 |
| ATOM | 1946 | O | LEU | A | 249 | 22.305 | −4.643 | 42.649 | 1.00 | 18.65 | 8 |
| ATOM | 1947 | N | ALA | A | 250 | 22.299 | −2.688 | 41.523 | 1.00 | 18.26 | 7 |
| ATOM | 1948 | CA | ALA | A | 250 | 22.127 | −3.293 | 40.212 | 1.00 | 18.04 | 6 |
| ATOM | 1949 | CB | ALA | A | 250 | 20.732 | −3.874 | 40.077 | 1.00 | 17.83 | 6 |
| ATOM | 1950 | C | ALA | A | 250 | 22.362 | −2.246 | 39.147 | 1.00 | 17.93 | 6 |
| ATOM | 1951 | O | ALA | A | 250 | 22.480 | −1.049 | 39.448 | 1.00 | 18.06 | 8 |
| ATOM | 1952 | N | TRP | A | 251 | 22.437 | −2.697 | 37.903 | 1.00 | 17.94 | 7 |
| ATOM | 1953 | CA | TRP | A | 251 | 22.515 | −1.806 | 36.772 | 1.00 | 18.27 | 6 |
| ATOM | 1954 | CB | TRP | A | 251 | 23.480 | −2.355 | 35.726 | 1.00 | 18.21 | 6 |
| ATOM | 1955 | CG | TRP | A | 251 | 24.904 | −2.207 | 36.134 | 1.00 | 17.39 | 6 |
| ATOM | 1956 | CD1 | TRP | A | 251 | 25.621 | −3.053 | 36.931 | 1.00 | 16.61 | 6 |
| ATOM | 1957 | NE1 | TRP | A | 251 | 26.900 | −2.576 | 37.097 | 1.00 | 16.75 | 7 |
| ATOM | 1958 | CE2 | TRP | A | 251 | 27.027 | −1.395 | 36.412 | 1.00 | 16.95 | 6 |
| ATOM | 1959 | CD2 | TRP | A | 251 | 25.784 | −1.130 | 35.794 | 1.00 | 16.91 | 6 |
| ATOM | 1960 | CE3 | TRP | A | 251 | 25.644 | 0.036 | 35.025 | 1.00 | 17.57 | 6 |

TABLE 7-continued

Coordinates of the crystal structure of *E. coli* ExoI bound to compound 10

| ATOM | 1961 | CZ3 | TRP | A | 251 | 26.742 | 0.892 | 34.900 | 1.00 | 17.56 | 6 |
|---|---|---|---|---|---|---|---|---|---|---|---|
| ATOM | 1962 | CH2 | TRP | A | 251 | 27.965 | 0.596 | 35.522 | 1.00 | 17.80 | 6 |
| ATOM | 1963 | CZ2 | TRP | A | 251 | 28.129 | −0.542 | 36.279 | 1.00 | 17.98 | 6 |
| ATOM | 1964 | C | TRP | A | 251 | 21.131 | −1.597 | 36.179 | 1.00 | 19.04 | 6 |
| ATOM | 1965 | O | TRP | A | 251 | 20.283 | −2.499 | 36.216 | 1.00 | 18.74 | 8 |
| ATOM | 1966 | N | HIS | A | 252 | 20.900 | −0.397 | 35.658 | 1.00 | 19.75 | 7 |
| ATOM | 1967 | CA | HIS | A | 252 | 19.625 | −0.055 | 35.050 | 1.00 | 20.70 | 6 |
| ATOM | 1968 | CB | HIS | A | 252 | 19.674 | 1.369 | 34.505 | 1.00 | 20.60 | 6 |
| ATOM | 1969 | CG | HIS | A | 252 | 18.329 | 1.957 | 34.224 | 1.00 | 20.81 | 6 |
| ATOM | 1970 | ND1 | HIS | A | 252 | 17.600 | 1.642 | 33.097 | 1.00 | 20.57 | 7 |
| ATOM | 1971 | CE1 | HIS | A | 252 | 16.463 | 2.314 | 33.110 | 1.00 | 20.70 | 6 |
| ATOM | 1972 | NE2 | HIS | A | 252 | 16.432 | 3.060 | 34.200 | 1.00 | 21.32 | 7 |
| ATOM | 1973 | CD2 | HIS | A | 252 | 17.587 | 2.854 | 34.914 | 1.00 | 20.42 | 6 |
| ATOM | 1974 | C | HIS | A | 252 | 19.302 | −1.063 | 33.936 | 1.00 | 21.37 | 6 |
| ATOM | 1975 | O | HIS | A | 252 | 20.156 | −1.360 | 33.096 | 1.00 | 21.57 | 8 |
| ATOM | 1976 | N | PRO | A | 253 | 18.077 | −1.621 | 33.951 | 1.00 | 22.27 | 7 |
| ATOM | 1977 | CA | PRO | A | 253 | 17.707 | −2.669 | 32.993 | 1.00 | 22.77 | 6 |
| ATOM | 1978 | CB | PRO | A | 253 | 16.342 | −3.140 | 33.503 | 1.00 | 22.79 | 6 |
| ATOM | 1979 | CG | PRO | A | 253 | 15.801 | −1.984 | 34.252 | 1.00 | 22.68 | 6 |
| ATOM | 1980 | CD | PRO | A | 253 | 16.978 | −1.319 | 34.887 | 1.00 | 22.15 | 6 |
| ATOM | 1981 | C | PRO | A | 253 | 17.597 | −2.188 | 31.540 | 1.00 | 23.44 | 6 |
| ATOM | 1982 | O | PRO | A | 253 | 17.578 | −3.012 | 30.626 | 1.00 | 23.61 | 8 |
| ATOM | 1983 | N | GLU | A | 254 | 17.535 | −0.873 | 31.335 | 1.00 | 23.97 | 7 |
| ATOM | 1984 | CA | GLU | A | 254 | 17.409 | −0.303 | 29.989 | 1.00 | 24.25 | 6 |
| ATOM | 1985 | CB | GLU | A | 254 | 16.075 | 0.444 | 29.835 | 1.00 | 24.50 | 6 |
| ATOM | 1986 | CG | GLU | A | 254 | 14.827 | −0.395 | 30.139 | 1.00 | 25.98 | 6 |
| ATOM | 1987 | CD | GLU | A | 254 | 14.722 | −1.657 | 29.282 | 1.00 | 27.85 | 6 |
| ATOM | 1988 | OE1 | GLU | A | 254 | 15.258 | −1.668 | 28.150 | 1.00 | 28.69 | 8 |
| ATOM | 1989 | OE2 | GLU | A | 254 | 14.091 | −2.638 | 29.743 | 1.00 | 28.74 | 8 |
| ATOM | 1990 | C | GLU | A | 254 | 18.574 | 0.619 | 29.619 | 1.00 | 24.10 | 6 |
| ATOM | 1991 | O | GLU | A | 254 | 19.053 | 0.602 | 28.482 | 1.00 | 24.16 | 8 |
| ATOM | 1992 | N | ASN | A | 255 | 19.019 | 1.425 | 30.580 | 1.00 | 23.78 | 7 |
| ATOM | 1993 | CA | ASN | A | 255 | 20.098 | 2.381 | 30.354 | 1.00 | 23.59 | 6 |
| ATOM | 1994 | CB | ASN | A | 255 | 19.918 | 3.607 | 31.258 | 1.00 | 23.74 | 6 |
| ATOM | 1995 | CG | ASN | A | 255 | 20.753 | 4.809 | 30.809 | 1.00 | 24.62 | 6 |
| ATOM | 1996 | OD1 | ASN | A | 255 | 21.780 | 4.666 | 30.140 | 1.00 | 25.73 | 8 |
| ATOM | 1997 | ND2 | ASN | A | 255 | 20.313 | 6.002 | 31.194 | 1.00 | 25.16 | 7 |
| ATOM | 1998 | C | ASN | A | 255 | 21.464 | 1.742 | 30.586 | 1.00 | 23.14 | 6 |
| ATOM | 1999 | O | ASN | A | 255 | 21.818 | 1.412 | 31.717 | 1.00 | 22.76 | 8 |
| ATOM | 2000 | N | ARG | A | 256 | 22.225 | 1.582 | 29.504 | 1.00 | 22.74 | 7 |
| ATOM | 2001 | CA | ARG | A | 256 | 23.532 | 0.915 | 29.543 | 1.00 | 22.32 | 6 |
| ATOM | 2002 | CB | ARG | A | 256 | 24.107 | 0.812 | 28.124 | 1.00 | 22.70 | 6 |
| ATOM | 2003 | CG | ARG | A | 256 | 25.121 | −0.303 | 27.929 | 1.00 | 23.54 | 6 |
| ATOM | 2004 | CD | ARG | A | 256 | 25.415 | −0.527 | 26.456 | 1.00 | 24.61 | 6 |
| ATOM | 2005 | NE | ARG | A | 256 | 26.269 | −1.697 | 26.244 | 1.00 | 25.65 | 7 |
| ATOM | 2006 | CZ | ARG | A | 256 | 26.583 | −2.196 | 25.051 | 1.00 | 25.61 | 6 |
| ATOM | 2007 | NH1 | ARG | A | 256 | 26.113 | −1.635 | 23.941 | 1.00 | 25.69 | 7 |
| ATOM | 2008 | NH2 | ARG | A | 256 | 27.368 | −3.264 | 24.967 | 1.00 | 26.14 | 7 |
| ATOM | 2009 | C | ARG | A | 256 | 24.537 | 1.613 | 30.475 | 1.00 | 21.82 | 6 |
| ATOM | 2010 | O | ARG | A | 256 | 25.368 | 0.954 | 31.101 | 1.00 | 21.80 | 8 |
| ATOM | 2011 | N | ASN | A | 257 | 24.441 | 2.940 | 30.566 | 1.00 | 21.11 | 7 |
| ATOM | 2012 | CA | ASN | A | 257 | 25.393 | 3.750 | 31.338 | 1.00 | 20.82 | 6 |
| ATOM | 2013 | CB | ASN | A | 257 | 25.724 | 5.041 | 30.590 | 1.00 | 21.21 | 6 |
| ATOM | 2014 | CG | ASN | A | 257 | 26.349 | 4.788 | 29.241 | 1.00 | 22.48 | 6 |
| ATOM | 2015 | OD1 | ASN | A | 257 | 25.856 | 5.268 | 28.219 | 1.00 | 24.94 | 8 |
| ATOM | 2016 | ND2 | ASN | A | 257 | 27.439 | 4.028 | 29.223 | 1.00 | 23.25 | 7 |
| ATOM | 2017 | C | ASN | A | 257 | 24.936 | 4.099 | 32.752 | 1.00 | 19.99 | 6 |
| ATOM | 2018 | O | ASN | A | 257 | 25.632 | 4.815 | 33.468 | 1.00 | 19.95 | 8 |
| ATOM | 2019 | N | ALA | A | 258 | 23.767 | 3.609 | 33.149 | 1.00 | 19.28 | 7 |
| ATOM | 2020 | CA | ALA | A | 258 | 23.229 | 3.942 | 34.465 | 1.00 | 18.46 | 6 |
| ATOM | 2021 | CB | ALA | A | 258 | 21.802 | 4.463 | 34.348 | 1.00 | 18.55 | 6 |
| ATOM | 2022 | C | ALA | A | 258 | 23.301 | 2.777 | 35.438 | 1.00 | 18.25 | 6 |
| ATOM | 2023 | O | ALA | A | 258 | 22.886 | 1.653 | 35.116 | 1.00 | 17.66 | 8 |
| ATOM | 2024 | N | VAL | A | 259 | 23.844 | 3.055 | 36.627 | 1.00 | 17.53 | 7 |
| ATOM | 2025 | CA | VAL | A | 259 | 23.877 | 2.099 | 37.728 | 1.00 | 17.46 | 6 |
| ATOM | 2026 | CB | VAL | A | 259 | 25.333 | 1.885 | 38.268 | 1.00 | 17.84 | 6 |
| ATOM | 2027 | CG1 | VAL | A | 259 | 25.928 | 3.190 | 38.802 | 1.00 | 17.61 | 6 |
| ATOM | 2028 | CG2 | VAL | A | 259 | 25.373 | 0.786 | 39.324 | 1.00 | 17.59 | 6 |
| ATOM | 2029 | C | VAL | A | 259 | 22.952 | 2.593 | 38.838 | 1.00 | 17.01 | 6 |
| ATOM | 2030 | O | VAL | A | 259 | 22.828 | 3.803 | 39.066 | 1.00 | 16.30 | 8 |
| ATOM | 2031 | N | ILE | A | 260 | 22.291 | 1.653 | 39.509 | 1.00 | 17.04 | 7 |
| ATOM | 2032 | CA | ILE | A | 260 | 21.334 | 1.978 | 40.562 | 1.00 | 17.28 | 6 |
| ATOM | 2033 | CB | ILE | A | 260 | 20.098 | 1.027 | 40.537 | 1.00 | 17.31 | 6 |
| ATOM | 2034 | CG1 | ILE | A | 260 | 19.441 | 1.023 | 39.150 | 1.00 | 17.29 | 6 |
| ATOM | 2035 | CD1 | ILE | A | 260 | 18.563 | −0.202 | 38.868 | 1.00 | 17.13 | 6 |
| ATOM | 2036 | CG2 | ILE | A | 260 | 19.092 | 1.442 | 41.598 | 1.00 | 16.90 | 6 |
| ATOM | 2037 | C | ILE | A | 260 | 22.016 | 1.911 | 41.925 | 1.00 | 17.69 | 6 |
| ATOM | 2038 | O | ILE | A | 260 | 22.482 | 0.850 | 42.347 | 1.00 | 17.67 | 8 |

TABLE 7-continued

Coordinates of the crystal structure of *E. coli* ExoI bound to compound 10

| ATOM | 2039 | N | MET | A | 261 | 22.078 | 3.058 | 42.598 | 1.00 | 17.90 | 7 |
|---|---|---|---|---|---|---|---|---|---|---|---|
| ATOM | 2040 | CA | MET | A | 261 | 22.766 | 3.185 | 43.882 | 1.00 | 18.30 | 6 |
| ATOM | 2041 | CB | MET | A | 261 | 23.692 | 4.402 | 43.859 | 1.00 | 18.67 | 6 |
| ATOM | 2042 | CG | MET | A | 261 | 24.843 | 4.294 | 42.885 | 1.00 | 19.51 | 6 |
| ATOM | 2043 | SD | MET | A | 261 | 26.176 | 3.276 | 43.530 | 1.00 | 22.87 | 16 |
| ATOM | 2044 | CE | MET | A | 261 | 27.533 | 3.810 | 42.490 | 1.00 | 19.74 | 6 |
| ATOM | 2045 | C | MET | A | 261 | 21.768 | 3.362 | 45.007 | 1.00 | 18.17 | 6 |
| ATOM | 2046 | O | MET | A | 261 | 20.721 | 3.983 | 44.813 | 1.00 | 17.92 | 8 |
| ATOM | 2047 | N | VAL | A | 262 | 22.094 | 2.826 | 46.187 | 1.00 | 17.88 | 7 |
| ATOM | 2048 | CA | VAL | A | 262 | 21.383 | 3.195 | 47.410 | 1.00 | 17.88 | 6 |
| ATOM | 2049 | CB | VAL | A | 262 | 20.984 | 1.964 | 48.276 | 1.00 | 18.06 | 6 |
| ATOM | 2050 | CG1 | VAL | A | 262 | 20.640 | 2.382 | 49.723 | 1.00 | 19.13 | 6 |
| ATOM | 2051 | CG2 | VAL | A | 262 | 19.806 | 1.277 | 47.672 | 1.00 | 19.52 | 6 |
| ATOM | 2052 | C | VAL | A | 262 | 22.235 | 4.150 | 48.227 | 1.00 | 17.60 | 6 |
| ATOM | 2053 | O | VAL | A | 262 | 23.436 | 3.951 | 48.374 | 1.00 | 17.13 | 8 |
| ATOM | 2054 | N | ASP | A | 263 | 21.603 | 5.203 | 48.724 | 1.00 | 16.99 | 7 |
| ATOM | 2055 | CA | ASP | A | 263 | 22.233 | 6.115 | 49.658 | 1.00 | 17.03 | 6 |
| ATOM | 2056 | CB | ASP | A | 263 | 21.476 | 7.445 | 49.658 | 1.00 | 16.56 | 6 |
| ATOM | 2057 | CG | ASP | A | 263 | 22.015 | 8.438 | 50.673 | 1.00 | 16.33 | 6 |
| ATOM | 2058 | OD1 | ASP | A | 263 | 22.997 | 8.128 | 51.381 | 1.00 | 16.88 | 8 |
| ATOM | 2059 | OD2 | ASP | A | 263 | 21.442 | 9.540 | 50.756 | 1.00 | 17.38 | 8 |
| ATOM | 2060 | C | ASP | A | 263 | 22.189 | 5.453 | 51.031 | 1.00 | 17.03 | 6 |
| ATOM | 2061 | O | ASP | A | 263 | 21.107 | 5.247 | 51.593 | 1.00 | 17.19 | 8 |
| ATOM | 2062 | N | LEU | A | 264 | 23.362 | 5.103 | 51.561 | 1.00 | 17.34 | 7 |
| ATOM | 2063 | CA | LEU | A | 264 | 23.440 | 4.357 | 52.826 | 1.00 | 17.57 | 6 |
| ATOM | 2064 | CB | LEU | A | 264 | 24.825 | 3.720 | 53.005 | 1.00 | 17.59 | 6 |
| ATOM | 2065 | CG | LEU | A | 264 | 25.254 | 2.605 | 52.045 | 1.00 | 17.00 | 6 |
| ATOM | 2066 | CD1 | LEU | A | 264 | 26.732 | 2.302 | 52.210 | 1.00 | 16.09 | 6 |
| ATOM | 2067 | CD2 | LEU | A | 264 | 24.421 | 1.330 | 52.226 | 1.00 | 16.43 | 6 |
| ATOM | 2068 | C | LEU | A | 264 | 23.073 | 5.199 | 54.056 | 1.00 | 18.25 | 6 |
| ATOM | 2069 | O | LEU | A | 264 | 22.771 | 4.658 | 55.123 | 1.00 | 18.17 | 8 |
| ATOM | 2070 | N | ALA | A | 265 | 23.088 | 6.520 | 53.898 | 1.00 | 18.46 | 7 |
| ATOM | 2071 | CA | ALA | A | 265 | 22.668 | 7.426 | 54.964 | 1.00 | 18.74 | 6 |
| ATOM | 2072 | CB | ALA | A | 265 | 23.297 | 8.790 | 54.773 | 1.00 | 18.88 | 6 |
| ATOM | 2073 | C | ALA | A | 265 | 21.148 | 7.546 | 55.040 | 1.00 | 19.01 | 6 |
| ATOM | 2074 | O | ALA | A | 265 | 20.605 | 8.049 | 56.027 | 1.00 | 19.41 | 8 |
| ATOM | 2075 | N | GLY | A | 266 | 20.464 | 7.087 | 53.995 | 1.00 | 18.99 | 7 |
| ATOM | 2076 | CA | GLY | A | 266 | 19.006 | 7.181 | 53.929 | 1.00 | 19.57 | 6 |
| ATOM | 2077 | C | GLY | A | 266 | 18.303 | 6.171 | 54.818 | 1.00 | 19.83 | 6 |
| ATOM | 2078 | O | GLY | A | 266 | 18.943 | 5.444 | 55.580 | 1.00 | 19.94 | 8 |
| ATOM | 2079 | N | ASP | A | 267 | 16.976 | 6.141 | 54.719 | 1.00 | 20.35 | 7 |
| ATOM | 2080 | CA | ASP | A | 267 | 16.150 | 5.153 | 55.402 | 1.00 | 21.00 | 6 |
| ATOM | 2081 | CB | ASP | A | 267 | 14.879 | 5.823 | 55.951 | 1.00 | 21.02 | 6 |
| ATOM | 2082 | CG | ASP | A | 267 | 13.842 | 4.820 | 56.462 | 1.00 | 22.22 | 6 |
| ATOM | 2083 | OD1 | ASP | A | 267 | 14.226 | 3.720 | 56.928 | 1.00 | 23.40 | 8 |
| ATOM | 2084 | OD2 | ASP | A | 267 | 12.634 | 5.149 | 56.406 | 1.00 | 22.86 | 8 |
| ATOM | 2085 | C | ASP | A | 267 | 15.792 | 4.053 | 54.413 | 1.00 | 21.20 | 6 |
| ATOM | 2086 | O | ASP | A | 267 | 15.074 | 4.296 | 53.438 | 1.00 | 21.21 | 8 |
| ATOM | 2087 | N | ILE | A | 268 | 16.295 | 2.845 | 54.659 | 1.00 | 21.65 | 7 |
| ATOM | 2088 | CA | ILE | A | 268 | 16.088 | 1.735 | 53.724 | 1.00 | 22.09 | 6 |
| ATOM | 2089 | CB | ILE | A | 268 | 17.322 | 0.781 | 53.636 | 1.00 | 22.05 | 6 |
| ATOM | 2090 | CG1 | ILE | A | 268 | 17.655 | 0.187 | 55.007 | 1.00 | 21.91 | 6 |
| ATOM | 2091 | CD1 | ILE | A | 268 | 18.443 | −1.110 | 54.936 | 1.00 | 22.50 | 6 |
| ATOM | 2092 | CG2 | ILE | A | 268 | 18.525 | 1.507 | 53.012 | 1.00 | 21.71 | 6 |
| ATOM | 2093 | C | ILE | A | 268 | 14.810 | 0.931 | 53.992 | 1.00 | 22.52 | 6 |
| ATOM | 2094 | O | ILE | A | 268 | 14.504 | −0.007 | 53.253 | 1.00 | 22.71 | 8 |
| ATOM | 2095 | N | SER | A | 269 | 14.061 | 1.316 | 55.029 | 1.00 | 23.11 | 7 |
| ATOM | 2096 | CA | SER | A | 269 | 12.784 | 0.654 | 55.373 | 1.00 | 23.57 | 6 |
| ATOM | 2097 | CB | SER | A | 269 | 12.032 | 1.423 | 56.469 | 1.00 | 23.63 | 6 |
| ATOM | 2098 | OG | SER | A | 269 | 12.653 | 1.259 | 57.733 | 1.00 | 23.20 | 8 |
| ATOM | 2099 | C | SER | A | 269 | 11.860 | 0.407 | 54.166 | 1.00 | 24.17 | 6 |
| ATOM | 2100 | O | SER | A | 269 | 11.387 | −0.714 | 53.987 | 1.00 | 23.84 | 8 |
| ATOM | 2101 | N | PRO | A | 270 | 11.607 | 1.452 | 53.334 | 1.00 | 24.71 | 7 |
| ATOM | 2102 | CA | PRO | A | 270 | 10.720 | 1.275 | 52.172 | 1.00 | 25.34 | 6 |
| ATOM | 2103 | CB | PRO | A | 270 | 10.725 | 2.657 | 51.508 | 1.00 | 25.44 | 6 |
| ATOM | 2104 | CG | PRO | A | 270 | 11.151 | 3.598 | 52.574 | 1.00 | 25.14 | 6 |
| ATOM | 2105 | CD | PRO | A | 270 | 12.104 | 2.839 | 53.425 | 1.00 | 24.80 | 6 |
| ATOM | 2106 | C | PRO | A | 270 | 11.226 | 0.225 | 51.184 | 1.00 | 25.96 | 6 |
| ATOM | 2107 | O | PRO | A | 270 | 10.425 | −0.459 | 50.552 | 1.00 | 25.83 | 8 |
| ATOM | 2108 | N | LEU | A | 271 | 12.546 | 0.108 | 51.054 | 1.00 | 26.77 | 7 |
| ATOM | 2109 | CA | LEU | A | 271 | 13.150 | −0.908 | 50.190 | 1.00 | 27.62 | 6 |
| ATOM | 2110 | CB | LEU | A | 271 | 14.648 | −0.659 | 50.030 | 1.00 | 27.56 | 6 |
| ATOM | 2111 | CG | LEU | A | 271 | 15.100 | 0.596 | 49.292 | 1.00 | 27.99 | 6 |
| ATOM | 2112 | CD1 | LEU | A | 271 | 16.612 | 0.675 | 49.335 | 1.00 | 27.52 | 6 |
| ATOM | 2113 | CD2 | LEU | A | 271 | 14.599 | 0.593 | 47.851 | 1.00 | 27.69 | 6 |
| ATOM | 2114 | C | LEU | A | 271 | 12.935 | −2.316 | 50.729 | 1.00 | 28.33 | 6 |
| ATOM | 2115 | O | LEU | A | 271 | 12.900 | −3.279 | 49.966 | 1.00 | 28.38 | 8 |
| ATOM | 2116 | N | LEU | A | 272 | 12.806 | −2.426 | 52.047 | 1.00 | 29.24 | 7 |

TABLE 7-continued

Coordinates of the crystal structure of *E. coli* ExoI bound to compound 10

| ATOM | 2117 | CA  | LEU | A | 272 | 12.671 | −3.721 | 52.703 | 1.00 | 30.15 | 6 |
|------|------|-----|-----|---|-----|--------|--------|--------|------|-------|---|
| ATOM | 2118 | CB  | LEU | A | 272 | 13.278 | −3.681 | 54.112 | 1.00 | 30.10 | 6 |
| ATOM | 2119 | CG  | LEU | A | 272 | 14.717 | −3.177 | 54.294 | 1.00 | 30.15 | 6 |
| ATOM | 2120 | CD1 | LEU | A | 272 | 15.129 | −3.294 | 55.750 | 1.00 | 30.47 | 6 |
| ATOM | 2121 | CD2 | LEU | A | 272 | 15.712 | −3.907 | 53.388 | 1.00 | 30.28 | 6 |
| ATOM | 2122 | C   | LEU | A | 272 | 11.220 | −4.194 | 52.773 | 1.00 | 30.81 | 6 |
| ATOM | 2123 | O   | LEU | A | 272 | 10.924 | −5.345 | 52.454 | 1.00 | 30.93 | 8 |
| ATOM | 2124 | N   | GLU | A | 273 | 10.321 | −3.301 | 53.183 | 1.00 | 31.65 | 7 |
| ATOM | 2125 | CA  | GLU | A | 273 | 8.949  | −3.694 | 53.527 | 1.00 | 32.45 | 6 |
| ATOM | 2126 | CB  | GLU | A | 273 | 8.588  | −3.206 | 54.941 | 1.00 | 32.44 | 6 |
| ATOM | 2127 | CG  | GLU | A | 273 | 8.545  | −1.691 | 55.107 | 1.00 | 32.58 | 6 |
| ATOM | 2128 | CD  | GLU | A | 273 | 8.584  | −1.255 | 56.565 | 1.00 | 32.88 | 6 |
| ATOM | 2129 | OE1 | GLU | A | 273 | 7.635  | −0.568 | 57.006 | 1.00 | 33.17 | 8 |
| ATOM | 2130 | OE2 | GLU | A | 273 | 9.561  | −1.596 | 57.270 | 1.00 | 32.64 | 8 |
| ATOM | 2131 | C   | GLU | A | 273 | 7.883  | −3.258 | 52.508 | 1.00 | 32.95 | 6 |
| ATOM | 2132 | O   | GLU | A | 273 | 6.682  | −3.434 | 52.745 | 1.00 | 33.07 | 8 |
| ATOM | 2133 | N   | LEU | A | 274 | 8.323  | −2.720 | 51.374 | 1.00 | 33.45 | 7 |
| ATOM | 2134 | CA  | LEU | A | 274 | 7.402  | −2.208 | 50.360 | 1.00 | 34.04 | 6 |
| ATOM | 2135 | CB  | LEU | A | 274 | 7.506  | −0.683 | 50.283 | 1.00 | 33.97 | 6 |
| ATOM | 2136 | CG  | LEU | A | 274 | 6.236  | 0.150  | 50.124 | 1.00 | 34.16 | 6 |
| ATOM | 2137 | CD1 | LEU | A | 274 | 5.282  | −0.062 | 51.301 | 1.00 | 34.18 | 6 |
| ATOM | 2138 | CD2 | LEU | A | 274 | 6.603  | 1.620  | 49.992 | 1.00 | 34.16 | 6 |
| ATOM | 2139 | C   | LEU | A | 274 | 7.687  | −2.829 | 48.994 | 1.00 | 34.44 | 6 |
| ATOM | 2140 | O   | LEU | A | 274 | 8.845  | −3.032 | 48.630 | 1.00 | 34.54 | 8 |
| ATOM | 2141 | N   | ASP | A | 275 | 6.626  | −3.125 | 48.242 | 1.00 | 35.01 | 7 |
| ATOM | 2142 | CA  | ASP | A | 275 | 6.755  | −3.782 | 46.933 | 1.00 | 35.42 | 6 |
| ATOM | 2143 | CB  | ASP | A | 275 | 5.427  | −4.430 | 46.514 | 1.00 | 35.48 | 6 |
| ATOM | 2144 | CG  | ASP | A | 275 | 4.312  | −3.418 | 46.337 | 1.00 | 35.85 | 6 |
| ATOM | 2145 | OD1 | ASP | A | 275 | 3.510  | −3.246 | 47.280 | 1.00 | 36.48 | 8 |
| ATOM | 2146 | OD2 | ASP | A | 275 | 4.240  | −2.790 | 45.259 | 1.00 | 36.29 | 8 |
| ATOM | 2147 | C   | ASP | A | 275 | 7.269  | −2.832 | 45.844 | 1.00 | 35.72 | 6 |
| ATOM | 2148 | O   | ASP | A | 275 | 7.333  | −1.616 | 46.047 | 1.00 | 35.80 | 8 |
| ATOM | 2149 | N   | SER | A | 276 | 7.624  | −3.397 | 44.691 | 1.00 | 35.93 | 7 |
| ATOM | 2150 | CA  | SER | A | 276 | 8.289  | −2.647 | 43.619 | 1.00 | 36.22 | 6 |
| ATOM | 2151 | CB  | SER | A | 276 | 8.898  | −3.605 | 42.592 | 1.00 | 36.27 | 6 |
| ATOM | 2152 | OG  | SER | A | 276 | 7.902  | −4.407 | 41.984 | 1.00 | 36.57 | 8 |
| ATOM | 2153 | C   | SER | A | 276 | 7.387  | −1.620 | 42.921 | 1.00 | 36.32 | 6 |
| ATOM | 2154 | O   | SER | A | 276 | 7.873  | −0.618 | 42.391 | 1.00 | 36.34 | 8 |
| ATOM | 2155 | N   | ASP | A | 277 | 6.081  | −1.876 | 42.919 | 1.00 | 36.42 | 7 |
| ATOM | 2156 | CA  | ASP | A | 277 | 5.116  | −0.956 | 42.315 | 1.00 | 36.57 | 6 |
| ATOM | 2157 | CB  | ASP | A | 277 | 3.773  | −1.656 | 42.080 | 1.00 | 36.60 | 6 |
| ATOM | 2158 | CG  | ASP | A | 277 | 3.790  | −2.565 | 40.862 | 1.00 | 36.84 | 6 |
| ATOM | 2159 | OD1 | ASP | A | 277 | 4.314  | −2.145 | 39.806 | 1.00 | 37.07 | 8 |
| ATOM | 2160 | OD2 | ASP | A | 277 | 3.264  | −3.695 | 40.958 | 1.00 | 36.61 | 8 |
| ATOM | 2161 | C   | ASP | A | 277 | 4.919  | 0.301  | 43.162 | 1.00 | 36.56 | 6 |
| ATOM | 2162 | O   | ASP | A | 277 | 4.825  | 1.411  | 42.629 | 1.00 | 36.46 | 8 |
| ATOM | 2163 | N   | THR | A | 278 | 4.861  | 0.116  | 44.481 | 1.00 | 36.62 | 7 |
| ATOM | 2164 | CA  | THR | A | 278 | 4.682  | 1.223  | 45.419 | 1.00 | 36.66 | 6 |
| ATOM | 2165 | CB  | THR | A | 278 | 4.329  | 0.712  | 46.833 | 1.00 | 36.65 | 6 |
| ATOM | 2166 | OG1 | THR | A | 278 | 3.410  | −0.382 | 46.733 | 1.00 | 36.38 | 8 |
| ATOM | 2167 | CG2 | THR | A | 278 | 3.697  | 1.822  | 47.667 | 1.00 | 36.69 | 6 |
| ATOM | 2168 | C   | THR | A | 278 | 5.938  | 2.096  | 45.482 | 1.00 | 36.82 | 6 |
| ATOM | 2169 | O   | THR | A | 278 | 5.849  | 3.315  | 45.656 | 1.00 | 36.84 | 8 |
| ATOM | 2170 | N   | LEU | A | 279 | 7.100  | 1.463  | 45.332 | 1.00 | 36.94 | 7 |
| ATOM | 2171 | CA  | LEU | A | 279 | 8.377  | 2.173  | 45.279 | 1.00 | 37.06 | 6 |
| ATOM | 2172 | CB  | LEU | A | 279 | 9.548  | 1.193  | 45.414 | 1.00 | 37.03 | 6 |
| ATOM | 2173 | CG  | LEU | A | 279 | 9.747  | 0.495  | 46.767 | 1.00 | 36.91 | 6 |
| ATOM | 2174 | CD1 | LEU | A | 279 | 10.610 | −0.749 | 46.612 | 1.00 | 36.89 | 6 |
| ATOM | 2175 | CD2 | LEU | A | 279 | 10.338 | 1.440  | 47.807 | 1.00 | 36.58 | 6 |
| ATOM | 2176 | C   | LEU | A | 279 | 8.510  | 2.990  | 43.995 | 1.00 | 37.17 | 6 |
| ATOM | 2177 | O   | LEU | A | 279 | 9.136  | 4.052  | 43.989 | 1.00 | 37.26 | 8 |
| ATOM | 2178 | N   | ARG | A | 280 | 7.913  | 2.493  | 42.912 | 1.00 | 37.40 | 7 |
| ATOM | 2179 | CA  | ARG | A | 280 | 7.874  | 3.225  | 41.647 | 1.00 | 37.69 | 6 |
| ATOM | 2180 | CB  | ARG | A | 280 | 7.628  | 2.272  | 40.474 | 1.00 | 37.74 | 6 |
| ATOM | 2181 | CG  | ARG | A | 280 | 8.019  | 2.854  | 39.114 | 1.00 | 38.23 | 6 |
| ATOM | 2182 | CD  | ARG | A | 280 | 7.385  | 2.101  | 37.947 | 1.00 | 38.72 | 6 |
| ATOM | 2183 | NE  | ARG | A | 280 | 7.840  | 0.714  | 37.859 | 1.00 | 39.36 | 7 |
| ATOM | 2184 | CZ  | ARG | A | 280 | 7.064  | −0.347 | 38.066 | 1.00 | 39.83 | 6 |
| ATOM | 2185 | NH1 | ARG | A | 280 | 5.778  | −0.192 | 38.365 | 1.00 | 40.20 | 7 |
| ATOM | 2186 | NH2 | ARG | A | 280 | 7.570  | −1.568 | 37.965 | 1.00 | 39.89 | 7 |
| ATOM | 2187 | C   | ARG | A | 280 | 6.795  | 4.308  | 41.675 | 1.00 | 37.76 | 6 |
| ATOM | 2188 | O   | ARG | A | 280 | 6.858  | 5.246  | 42.472 | 1.00 | 37.89 | 8 |
| ATOM | 2189 | N   | ALA | A | 295 | 10.621 | 8.192  | 52.084 | 1.00 | 25.34 | 7 |
| ATOM | 2190 | CA  | ALA | A | 295 | 11.604 | 8.462  | 51.036 | 1.00 | 25.42 | 6 |
| ATOM | 2191 | CB  | ALA | A | 295 | 12.610 | 9.502  | 51.506 | 1.00 | 25.37 | 6 |
| ATOM | 2192 | C   | ALA | A | 295 | 12.318 | 7.186  | 50.604 | 1.00 | 25.41 | 6 |
| ATOM | 2193 | O   | ALA | A | 295 | 12.677 | 6.354  | 51.437 | 1.00 | 26.03 | 8 |
| ATOM | 2194 | N   | VAL | A | 296 | 12.514 | 7.037  | 49.298 | 1.00 | 25.14 | 7 |

TABLE 7-continued

Coordinates of the crystal structure of *E. coli* ExoI bound to compound 10

| ATOM | 2195 | CA | VAL | A | 296 | 13.261 | 5.906 | 48.751 | 1.00 | 24.60 | 6 |
|---|---|---|---|---|---|---|---|---|---|---|---|
| ATOM | 2196 | CB | VAL | A | 296 | 12.630 | 5.376 | 47.439 | 1.00 | 24.64 | 6 |
| ATOM | 2197 | CG1 | VAL | A | 296 | 13.259 | 4.053 | 47.038 | 1.00 | 24.60 | 6 |
| ATOM | 2198 | CG2 | VAL | A | 296 | 11.119 | 5.217 | 47.596 | 1.00 | 24.23 | 6 |
| ATOM | 2199 | C | VAL | A | 296 | 14.706 | 6.344 | 48.501 | 1.00 | 24.40 | 6 |
| ATOM | 2200 | O | VAL | A | 296 | 14.959 | 7.187 | 47.638 | 1.00 | 24.50 | 8 |
| ATOM | 2201 | N | PRO | A | 297 | 15.660 | 5.781 | 49.269 | 1.00 | 24.02 | 7 |
| ATOM | 2202 | CA | PRO | A | 297 | 17.061 | 6.208 | 49.187 | 1.00 | 23.76 | 6 |
| ATOM | 2203 | CB | PRO | A | 297 | 17.651 | 5.700 | 50.505 | 1.00 | 23.78 | 6 |
| ATOM | 2204 | CG | PRO | A | 297 | 16.855 | 4.480 | 50.819 | 1.00 | 23.88 | 6 |
| ATOM | 2205 | CD | PRO | A | 297 | 15.466 | 4.705 | 50.261 | 1.00 | 24.07 | 6 |
| ATOM | 2206 | C | PRO | A | 297 | 17.790 | 5.595 | 47.985 | 1.00 | 23.58 | 6 |
| ATOM | 2207 | O | PRO | A | 297 | 18.804 | 4.913 | 48.148 | 1.00 | 23.52 | 8 |
| ATOM | 2208 | N | VAL | A | 298 | 17.275 | 5.860 | 46.790 | 1.00 | 23.17 | 7 |
| ATOM | 2209 | CA | VAL | A | 298 | 17.780 | 5.255 | 45.564 | 1.00 | 23.25 | 6 |
| ATOM | 2210 | CB | VAL | A | 298 | 16.784 | 4.185 | 45.029 | 1.00 | 23.01 | 6 |
| ATOM | 2211 | CG1 | VAL | A | 298 | 17.071 | 3.829 | 43.573 | 1.00 | 23.88 | 6 |
| ATOM | 2212 | CG2 | VAL | A | 298 | 16.800 | 2.940 | 45.915 | 1.00 | 23.31 | 6 |
| ATOM | 2213 | C | VAL | A | 298 | 18.001 | 6.334 | 44.504 | 1.00 | 23.14 | 6 |
| ATOM | 2214 | O | VAL | A | 298 | 17.177 | 7.236 | 44.350 | 1.00 | 23.07 | 8 |
| ATOM | 2215 | N | LYS | A | 299 | 19.116 | 6.244 | 43.785 | 1.00 | 23.13 | 7 |
| ATOM | 2216 | CA | LYS | A | 299 | 19.380 | 7.168 | 42.681 | 1.00 | 23.24 | 6 |
| ATOM | 2217 | CB | LYS | A | 299 | 20.072 | 8.447 | 43.178 | 1.00 | 23.39 | 6 |
| ATOM | 2218 | CG | LYS | A | 299 | 21.537 | 8.285 | 43.573 | 1.00 | 23.24 | 6 |
| ATOM | 2219 | CD | LYS | A | 299 | 22.274 | 9.626 | 43.577 | 1.00 | 23.83 | 6 |
| ATOM | 2220 | CE | LYS | A | 299 | 22.384 | 10.200 | 42.173 | 1.00 | 24.10 | 6 |
| ATOM | 2221 | NZ | LYS | A | 299 | 23.620 | 10.991 | 41.958 | 1.00 | 23.51 | 7 |
| ATOM | 2222 | C | LYS | A | 299 | 20.182 | 6.519 | 41.560 | 1.00 | 22.98 | 6 |
| ATOM | 2223 | O | LYS | A | 299 | 20.913 | 5.550 | 41.786 | 1.00 | 23.45 | 8 |
| ATOM | 2224 | N | LEU | A | 300 | 20.023 | 7.048 | 40.350 | 1.00 | 22.51 | 7 |
| ATOM | 2225 | CA | LEU | A | 300 | 20.823 | 6.613 | 39.207 | 1.00 | 22.13 | 6 |
| ATOM | 2226 | CB | LEU | A | 300 | 20.053 | 6.799 | 37.895 | 1.00 | 22.32 | 6 |
| ATOM | 2227 | CG | LEU | A | 300 | 18.733 | 6.053 | 37.692 | 1.00 | 22.01 | 6 |
| ATOM | 2228 | CD1 | LEU | A | 300 | 18.184 | 6.340 | 36.301 | 1.00 | 22.82 | 6 |
| ATOM | 2229 | CD2 | LEU | A | 300 | 18.897 | 4.546 | 37.912 | 1.00 | 22.32 | 6 |
| ATOM | 2230 | C | LEU | A | 300 | 22.118 | 7.399 | 39.145 | 1.00 | 21.88 | 6 |
| ATOM | 2231 | O | LEU | A | 300 | 22.117 | 8.625 | 39.275 | 1.00 | 22.04 | 8 |
| ATOM | 2232 | N | VAL | A | 301 | 23.222 | 6.687 | 38.944 | 1.00 | 21.12 | 7 |
| ATOM | 2233 | CA | VAL | A | 301 | 24.500 | 7.316 | 38.641 | 1.00 | 20.46 | 6 |
| ATOM | 2234 | CB | VAL | A | 301 | 25.616 | 6.802 | 39.580 | 1.00 | 20.35 | 6 |
| ATOM | 2235 | CG1 | VAL | A | 301 | 26.979 | 7.334 | 39.150 | 1.00 | 20.43 | 6 |
| ATOM | 2236 | CG2 | VAL | A | 301 | 25.310 | 7.181 | 41.033 | 1.00 | 19.99 | 6 |
| ATOM | 2237 | C | VAL | A | 301 | 24.852 | 7.031 | 37.179 | 1.00 | 20.21 | 6 |
| ATOM | 2238 | O | VAL | A | 301 | 24.966 | 5.870 | 36.779 | 1.00 | 20.01 | 8 |
| ATOM | 2239 | N | HIS | A | 302 | 24.991 | 8.091 | 36.386 | 1.00 | 19.71 | 7 |
| ATOM | 2240 | CA | HIS | A | 302 | 25.262 | 7.962 | 34.949 | 1.00 | 19.59 | 6 |
| ATOM | 2241 | CB | HIS | A | 302 | 24.476 | 9.006 | 34.151 | 1.00 | 20.12 | 6 |
| ATOM | 2242 | CG | HIS | A | 302 | 22.992 | 8.896 | 34.315 | 1.00 | 21.05 | 6 |
| ATOM | 2243 | ND1 | HIS | A | 302 | 22.315 | 9.478 | 35.365 | 1.00 | 22.18 | 7 |
| ATOM | 2244 | CE1 | HIS | A | 302 | 21.026 | 9.206 | 35.259 | 1.00 | 22.11 | 6 |
| ATOM | 2245 | NE2 | HIS | A | 302 | 20.846 | 8.455 | 34.189 | 1.00 | 21.70 | 7 |
| ATOM | 2246 | CD2 | HIS | A | 302 | 22.060 | 8.244 | 33.581 | 1.00 | 21.43 | 6 |
| ATOM | 2247 | C | HIS | A | 302 | 26.753 | 8.098 | 34.688 | 1.00 | 19.07 | 6 |
| ATOM | 2248 | O | HIS | A | 302 | 27.319 | 9.179 | 34.830 | 1.00 | 18.57 | 8 |
| ATOM | 2249 | N | ILE | A | 303 | 27.385 | 6.992 | 34.301 | 1.00 | 18.30 | 7 |
| ATOM | 2250 | CA | ILE | A | 303 | 28.846 | 6.925 | 34.258 | 1.00 | 18.00 | 6 |
| ATOM | 2251 | CB | ILE | A | 303 | 29.364 | 5.465 | 34.226 | 1.00 | 18.13 | 6 |
| ATOM | 2252 | CG1 | ILE | A | 303 | 28.809 | 4.724 | 32.998 | 1.00 | 18.15 | 6 |
| ATOM | 2253 | CD1 | ILE | A | 303 | 29.434 | 3.372 | 32.751 | 1.00 | 18.23 | 6 |
| ATOM | 2254 | CG2 | ILE | A | 303 | 29.027 | 4.756 | 35.543 | 1.00 | 19.14 | 6 |
| ATOM | 2255 | C | ILE | A | 303 | 29.476 | 7.733 | 33.123 | 1.00 | 17.56 | 6 |
| ATOM | 2256 | O | ILE | A | 303 | 30.679 | 7.985 | 33.144 | 1.00 | 17.17 | 8 |
| ATOM | 2257 | N | ASN | A | 304 | 28.659 | 8.136 | 32.147 | 1.00 | 17.49 | 7 |
| ATOM | 2258 | CA | ASN | A | 304 | 29.105 | 9.024 | 31.068 | 1.00 | 17.68 | 6 |
| ATOM | 2259 | CB | ASN | A | 304 | 28.415 | 8.648 | 29.750 | 1.00 | 17.81 | 6 |
| ATOM | 2260 | CG | ASN | A | 304 | 26.929 | 8.968 | 29.757 | 1.00 | 18.29 | 6 |
| ATOM | 2261 | OD1 | ASN | A | 304 | 26.189 | 8.545 | 30.649 | 1.00 | 17.64 | 8 |
| ATOM | 2262 | ND2 | ASN | A | 304 | 26.481 | 9.711 | 28.746 | 1.00 | 20.26 | 7 |
| ATOM | 2263 | C | ASN | A | 304 | 28.863 | 10.509 | 31.373 | 1.00 | 17.93 | 6 |
| ATOM | 2264 | O | ASN | A | 304 | 29.026 | 11.368 | 30.495 | 1.00 | 18.09 | 8 |
| ATOM | 2265 | N | LYS | A | 305 | 28.482 | 10.805 | 32.616 | 1.00 | 17.72 | 7 |
| ATOM | 2266 | CA | LYS | A | 305 | 28.155 | 12.174 | 33.016 | 1.00 | 17.83 | 6 |
| ATOM | 2267 | CB | LYS | A | 305 | 26.675 | 12.276 | 33.401 | 1.00 | 18.11 | 6 |
| ATOM | 2268 | CG | LYS | A | 305 | 25.737 | 12.191 | 32.202 | 1.00 | 19.13 | 6 |
| ATOM | 2269 | CD | LYS | A | 305 | 24.292 | 12.462 | 32.578 | 1.00 | 21.75 | 6 |
| ATOM | 2270 | CE | LYS | A | 305 | 23.470 | 12.752 | 31.330 | 1.00 | 22.85 | 6 |
| ATOM | 2271 | NZ | LYS | A | 305 | 22.020 | 12.892 | 31.633 | 1.00 | 24.04 | 7 |
| ATOM | 2272 | C | LYS | A | 305 | 29.069 | 12.695 | 34.142 | 1.00 | 17.68 | 6 |

TABLE 7-continued

Coordinates of the crystal structure of *E. coli* ExoI bound to compound 10

| ATOM | 2273 | O   | LYS | A | 305 | 28.645 | 13.490 | 34.992 | 1.00 | 17.81 | 8  |
|------|------|-----|-----|---|-----|--------|--------|--------|------|-------|----|
| ATOM | 2274 | N   | CYS | A | 306 | 30.323 | 12.239 | 34.124 | 1.00 | 17.47 | 7  |
| ATOM | 2275 | CA  | CYS | A | 306 | 31.351 | 12.656 | 35.096 | 1.00 | 17.66 | 6  |
| ATOM | 2276 | CB  | CYS | A | 306 | 31.885 | 14.050 | 34.765 | 1.00 | 18.21 | 6  |
| ATOM | 2277 | SG  | CYS | A | 306 | 32.338 | 14.276 | 33.080 | 1.00 | 22.01 | 16 |
| ATOM | 2278 | C   | CYS | A | 306 | 30.885 | 12.653 | 36.549 | 1.00 | 16.80 | 6  |
| ATOM | 2279 | O   | CYS | A | 306 | 31.097 | 13.640 | 37.258 | 1.00 | 17.11 | 8  |
| ATOM | 2280 | N   | PRO | A | 307 | 30.273 | 11.550 | 37.014 | 1.00 | 16.12 | 7  |
| ATOM | 2281 | CA  | PRO | A | 307 | 29.924 | 11.554 | 38.438 | 1.00 | 15.54 | 6  |
| ATOM | 2282 | CB  | PRO | A | 307 | 29.065 | 10.305 | 38.589 | 1.00 | 15.62 | 6  |
| ATOM | 2283 | CG  | PRO | A | 307 | 29.548 | 9.385  | 37.502 | 1.00 | 15.98 | 6  |
| ATOM | 2284 | CD  | PRO | A | 307 | 29.892 | 10.290 | 36.351 | 1.00 | 16.06 | 6  |
| ATOM | 2285 | C   | PRO | A | 307 | 31.163 | 11.436 | 39.306 | 1.00 | 15.17 | 6  |
| ATOM | 2286 | O   | PRO | A | 307 | 32.145 | 10.807 | 38.903 | 1.00 | 14.80 | 8  |
| ATOM | 2287 | N   | VAL | A | 308 | 31.119 | 12.048 | 40.487 | 1.00 | 14.15 | 7  |
| ATOM | 2288 | CA  | VAL | A | 308 | 32.218 | 11.941 | 41.424 | 1.00 | 13.90 | 6  |
| ATOM | 2289 | CB  | VAL | A | 308 | 32.378 | 13.217 | 42.271 | 1.00 | 13.72 | 6  |
| ATOM | 2290 | CG1 | VAL | A | 308 | 33.415 | 13.010 | 43.364 | 1.00 | 13.75 | 6  |
| ATOM | 2291 | CG2 | VAL | A | 308 | 32.769 | 14.389 | 41.369 | 1.00 | 13.17 | 6  |
| ATOM | 2292 | C   | VAL | A | 308 | 32.036 | 10.700 | 42.290 | 1.00 | 14.08 | 6  |
| ATOM | 2293 | O   | VAL | A | 308 | 31.091 | 10.612 | 43.077 | 1.00 | 13.79 | 8  |
| ATOM | 2294 | N   | LEU | A | 309 | 32.919 | 9.724  | 42.078 | 1.00 | 14.49 | 7  |
| ATOM | 2295 | CA  | LEU | A | 309 | 32.931 | 8.472  | 42.838 | 1.00 | 14.34 | 6  |
| ATOM | 2296 | CB  | LEU | A | 309 | 32.390 | 7.311  | 41.993 | 1.00 | 14.97 | 6  |
| ATOM | 2297 | CG  | LEU | A | 309 | 30.912 | 7.300  | 41.603 | 1.00 | 15.28 | 6  |
| ATOM | 2298 | CD1 | LEU | A | 309 | 30.660 | 6.290  | 40.474 | 1.00 | 14.92 | 6  |
| ATOM | 2299 | CD2 | LEU | A | 309 | 30.028 | 6.990  | 42.811 | 1.00 | 15.39 | 6  |
| ATOM | 2300 | C   | LEU | A | 309 | 34.351 | 8.149  | 43.264 | 1.00 | 14.48 | 6  |
| ATOM | 2301 | O   | LEU | A | 309 | 35.300 | 8.378  | 42.512 | 1.00 | 13.62 | 8  |
| ATOM | 2302 | N   | ALA | A | 310 | 34.489 | 7.597  | 44.469 | 1.00 | 14.21 | 7  |
| ATOM | 2303 | CA  | ALA | A | 310 | 35.784 | 7.154  | 44.977 | 1.00 | 14.57 | 6  |
| ATOM | 2304 | CB  | ALA | A | 310 | 36.562 | 8.335  | 45.566 | 1.00 | 14.47 | 6  |
| ATOM | 2305 | C   | ALA | A | 310 | 35.592 | 6.078  | 46.023 | 1.00 | 14.97 | 6  |
| ATOM | 2306 | O   | ALA | A | 310 | 34.503 | 5.937  | 46.580 | 1.00 | 14.05 | 8  |
| ATOM | 2307 | N   | GLN | A | 311 | 36.650 | 5.317  | 46.299 | 1.00 | 15.60 | 7  |
| ATOM | 2308 | CA  | GLN | A | 311 | 36.594 | 4.316  | 47.358 | 1.00 | 17.03 | 6  |
| ATOM | 2309 | CB  | GLN | A | 311 | 37.934 | 3.578  | 47.517 | 1.00 | 16.88 | 6  |
| ATOM | 2310 | CG  | GLN | A | 311 | 39.117 | 4.464  | 47.874 | 1.00 | 18.50 | 6  |
| ATOM | 2311 | CD  | GLN | A | 311 | 40.389 | 3.670  | 48.141 | 1.00 | 19.48 | 6  |
| ATOM | 2312 | OE1 | GLN | A | 311 | 40.435 | 2.818  | 49.035 | 1.00 | 22.53 | 8  |
| ATOM | 2313 | NE2 | GLN | A | 311 | 41.429 | 3.950  | 47.369 | 1.00 | 21.87 | 7  |
| ATOM | 2314 | C   | GLN | A | 311 | 36.161 | 4.965  | 48.670 | 1.00 | 16.84 | 6  |
| ATOM | 2315 | O   | GLN | A | 311 | 36.436 | 6.148  | 48.919 | 1.00 | 17.36 | 8  |
| ATOM | 2316 | N   | ALA | A | 312 | 35.471 | 4.188  | 49.493 | 1.00 | 16.84 | 7  |
| ATOM | 2317 | CA  | ALA | A | 312 | 34.773 | 4.715  | 50.658 | 1.00 | 16.78 | 6  |
| ATOM | 2318 | CB  | ALA | A | 312 | 34.020 | 3.599  | 51.362 | 1.00 | 16.66 | 6  |
| ATOM | 2319 | C   | ALA | A | 312 | 35.658 | 5.499  | 51.649 | 1.00 | 16.67 | 6  |
| ATOM | 2320 | O   | ALA | A | 312 | 35.201 | 6.468  | 52.236 | 1.00 | 16.21 | 8  |
| ATOM | 2321 | N   | ASN | A | 313 | 36.919 | 5.089  | 51.808 | 1.00 | 16.92 | 7  |
| ATOM | 2322 | CA  | ASN | A | 313 | 37.821 | 5.737  | 52.780 | 1.00 | 17.32 | 6  |
| ATOM | 2323 | CB  | ASN | A | 313 | 38.939 | 4.775  | 53.237 | 1.00 | 17.92 | 6  |
| ATOM | 2324 | CG  | ASN | A | 313 | 40.068 | 4.638  | 52.221 | 1.00 | 19.28 | 6  |
| ATOM | 2325 | OD1 | ASN | A | 313 | 39.994 | 5.154  | 51.106 | 1.00 | 20.50 | 8  |
| ATOM | 2326 | ND2 | ASN | A | 313 | 41.126 | 3.931  | 52.615 | 1.00 | 21.31 | 7  |
| ATOM | 2327 | C   | ASN | A | 313 | 38.382 | 7.093  | 52.321 | 1.00 | 17.34 | 6  |
| ATOM | 2328 | O   | ASN | A | 313 | 39.155 | 7.729  | 53.037 | 1.00 | 17.22 | 8  |
| ATOM | 2329 | N   | THR | A | 314 | 37.983 | 7.520  | 51.124 | 1.00 | 17.12 | 7  |
| ATOM | 2330 | CA  | THR | A | 314 | 38.349 | 8.839  | 50.605 | 1.00 | 17.09 | 6  |
| ATOM | 2331 | CB  | THR | A | 314 | 37.974 | 8.976  | 49.118 | 1.00 | 17.16 | 6  |
| ATOM | 2332 | OG1 | THR | A | 314 | 38.580 | 7.907  | 48.386 | 1.00 | 17.59 | 8  |
| ATOM | 2333 | CG2 | THR | A | 314 | 38.455 | 10.314 | 48.544 | 1.00 | 16.81 | 6  |
| ATOM | 2334 | C   | THR | A | 314 | 37.687 | 9.948  | 51.417 | 1.00 | 16.74 | 6  |
| ATOM | 2335 | O   | THR | A | 314 | 38.215 | 11.063 | 51.505 | 1.00 | 17.26 | 8  |
| ATOM | 2336 | N   | LEU | A | 315 | 36.529 | 9.644  | 52.006 | 1.00 | 16.36 | 7  |
| ATOM | 2337 | CA  | LEU | A | 315 | 35.912 | 10.543 | 52.977 | 1.00 | 16.48 | 6  |
| ATOM | 2338 | CB  | LEU | A | 315 | 34.379 | 10.427 | 52.954 | 1.00 | 16.42 | 6  |
| ATOM | 2339 | CG  | LEU | A | 315 | 33.582 | 11.274 | 53.963 | 1.00 | 16.43 | 6  |
| ATOM | 2340 | CD1 | LEU | A | 315 | 33.759 | 12.776 | 53.706 | 1.00 | 16.50 | 6  |
| ATOM | 2341 | CD2 | LEU | A | 315 | 32.089 | 10.886 | 53.972 | 1.00 | 16.53 | 6  |
| ATOM | 2342 | C   | LEU | A | 315 | 36.468 | 10.246 | 54.366 | 1.00 | 16.28 | 6  |
| ATOM | 2343 | O   | LEU | A | 315 | 36.164 | 9.206  | 54.952 | 1.00 | 15.88 | 8  |
| ATOM | 2344 | N   | ARG | A | 316 | 37.296 | 11.163 | 54.873 | 1.00 | 16.21 | 7  |
| ATOM | 2345 | CA  | ARG | A | 316 | 37.976 | 10.993 | 56.153 | 1.00 | 16.48 | 6  |
| ATOM | 2346 | CB  | ARG | A | 316 | 39.172 | 11.957 | 56.258 | 1.00 | 16.38 | 6  |
| ATOM | 2347 | CG  | ARG | A | 316 | 40.324 | 11.589 | 55.340 | 1.00 | 15.89 | 6  |
| ATOM | 2348 | CD  | ARG | A | 316 | 41.289 | 12.745 | 55.119 | 1.00 | 16.12 | 6  |
| ATOM | 2349 | NE  | ARG | A | 316 | 42.392 | 12.340 | 54.246 | 1.00 | 16.37 | 7  |
| ATOM | 2350 | CZ  | ARG | A | 316 | 43.106 | 13.169 | 53.484 | 1.00 | 17.30 | 6  |

TABLE 7-continued

Coordinates of the crystal structure of *E. coli* ExoI bound to compound 10

| ATOM | 2351 | NH1 | ARG | A | 316 | 42.838 | 14.474 | 53.467 | 1.00 | 16.55 | 7 |
|---|---|---|---|---|---|---|---|---|---|---|---|
| ATOM | 2352 | NH2 | ARG | A | 316 | 44.088 | 12.690 | 52.728 | 1.00 | 17.52 | 7 |
| ATOM | 2353 | C | ARG | A | 316 | 37.010 | 11.201 | 57.325 | 1.00 | 16.65 | 6 |
| ATOM | 2354 | O | ARG | A | 316 | 36.056 | 11.971 | 57.211 | 1.00 | 16.26 | 8 |
| ATOM | 2355 | N | PRO | A | 317 | 37.237 | 10.485 | 58.450 | 1.00 | 17.32 | 7 |
| ATOM | 2356 | CA | PRO | A | 317 | 36.368 | 10.624 | 59.618 | 1.00 | 17.54 | 6 |
| ATOM | 2357 | CB | PRO | A | 317 | 37.172 | 9.939 | 60.731 | 1.00 | 17.52 | 6 |
| ATOM | 2358 | CG | PRO | A | 317 | 37.951 | 8.895 | 60.021 | 1.00 | 17.53 | 6 |
| ATOM | 2359 | CD | PRO | A | 317 | 38.290 | 9.472 | 58.669 | 1.00 | 17.36 | 6 |
| ATOM | 2360 | C | PRO | A | 317 | 36.080 | 12.078 | 59.989 | 1.00 | 17.91 | 6 |
| ATOM | 2361 | O | PRO | A | 317 | 34.917 | 12.440 | 60.180 | 1.00 | 17.77 | 8 |
| ATOM | 2362 | N | GLU | A | 318 | 37.129 | 12.897 | 60.086 | 1.00 | 18.53 | 7 |
| ATOM | 2363 | CA | GLU | A | 318 | 36.983 | 14.303 | 60.471 | 1.00 | 19.05 | 6 |
| ATOM | 2364 | CB | GLU | A | 318 | 38.351 | 14.998 | 60.588 | 1.00 | 19.27 | 6 |
| ATOM | 2365 | CG | GLU | A | 318 | 39.206 | 14.992 | 59.311 | 1.00 | 20.97 | 6 |
| ATOM | 2366 | CD | GLU | A | 318 | 40.249 | 13.874 | 59.283 | 1.00 | 24.08 | 6 |
| ATOM | 2367 | OE1 | GLU | A | 318 | 41.394 | 14.155 | 58.864 | 1.00 | 25.28 | 8 |
| ATOM | 2368 | OE2 | GLU | A | 318 | 39.933 | 12.721 | 59.668 | 1.00 | 24.58 | 8 |
| ATOM | 2369 | C | GLU | A | 318 | 36.054 | 15.074 | 59.520 | 1.00 | 18.89 | 6 |
| ATOM | 2370 | O | GLU | A | 318 | 35.327 | 15.971 | 59.941 | 1.00 | 19.64 | 8 |
| ATOM | 2371 | N | ASP | A | 319 | 36.076 | 14.709 | 58.244 | 1.00 | 18.93 | 7 |
| ATOM | 2372 | CA | ASP | A | 319 | 35.214 | 15.347 | 57.258 | 1.00 | 18.62 | 6 |
| ATOM | 2373 | CB | ASP | A | 319 | 35.816 | 15.235 | 55.860 | 1.00 | 18.66 | 6 |
| ATOM | 2374 | CG | ASP | A | 319 | 37.060 | 16.088 | 55.705 | 1.00 | 18.52 | 6 |
| ATOM | 2375 | OD1 | ASP | A | 319 | 36.959 | 17.327 | 55.882 | 1.00 | 18.49 | 8 |
| ATOM | 2376 | OD2 | ASP | A | 319 | 38.137 | 15.520 | 55.432 | 1.00 | 18.14 | 8 |
| ATOM | 2377 | C | ASP | A | 319 | 33.796 | 14.804 | 57.295 | 1.00 | 18.72 | 6 |
| ATOM | 2378 | O | ASP | A | 319 | 32.840 | 15.565 | 57.165 | 1.00 | 18.32 | 8 |
| ATOM | 2379 | N | ALA | A | 320 | 33.661 | 13.490 | 57.485 | 1.00 | 18.88 | 7 |
| ATOM | 2380 | CA | ALA | A | 320 | 32.348 | 12.877 | 57.692 | 1.00 | 19.13 | 6 |
| ATOM | 2381 | CB | ALA | A | 320 | 32.489 | 11.370 | 57.911 | 1.00 | 19.62 | 6 |
| ATOM | 2382 | C | ALA | A | 320 | 31.671 | 13.538 | 58.892 | 1.00 | 19.42 | 6 |
| ATOM | 2383 | O | ALA | A | 320 | 30.489 | 13.884 | 58.843 | 1.00 | 19.04 | 8 |
| ATOM | 2384 | N | ASP | A | 321 | 32.448 | 13.745 | 59.953 | 1.00 | 19.43 | 7 |
| ATOM | 2385 | CA | ASP | A | 321 | 31.993 | 14.476 | 61.133 | 1.00 | 20.01 | 6 |
| ATOM | 2386 | CB | ASP | A | 321 | 33.114 | 14.527 | 62.175 | 1.00 | 20.71 | 6 |
| ATOM | 2387 | CG | ASP | A | 321 | 32.687 | 15.195 | 63.468 | 1.00 | 22.52 | 6 |
| ATOM | 2388 | OD1 | ASP | A | 321 | 31.819 | 14.637 | 64.177 | 1.00 | 26.24 | 8 |
| ATOM | 2389 | OD2 | ASP | A | 321 | 33.238 | 16.273 | 63.786 | 1.00 | 25.69 | 8 |
| ATOM | 2390 | C | ASP | A | 321 | 31.543 | 15.894 | 60.769 | 1.00 | 19.66 | 6 |
| ATOM | 2391 | O | ASP | A | 321 | 30.442 | 16.320 | 61.134 | 1.00 | 19.86 | 8 |
| ATOM | 2392 | N | ARG | A | 322 | 32.396 | 16.608 | 60.036 | 1.00 | 19.12 | 7 |
| ATOM | 2393 | CA | ARG | A | 322 | 32.110 | 17.974 | 59.599 | 1.00 | 18.88 | 6 |
| ATOM | 2394 | CB | ARG | A | 322 | 33.274 | 18.502 | 58.740 | 1.00 | 18.93 | 6 |
| ATOM | 2395 | CG | ARG | A | 322 | 33.138 | 19.955 | 58.276 | 1.00 | 18.80 | 6 |
| ATOM | 2396 | CD | ARG | A | 322 | 34.418 | 20.446 | 57.581 | 1.00 | 18.83 | 6 |
| ATOM | 2397 | NE | ARG | A | 322 | 34.861 | 19.514 | 56.543 | 1.00 | 19.15 | 7 |
| ATOM | 2398 | CZ | ARG | A | 322 | 34.529 | 19.605 | 55.257 | 1.00 | 18.83 | 6 |
| ATOM | 2399 | NH1 | ARG | A | 322 | 33.769 | 20.603 | 54.830 | 1.00 | 19.04 | 7 |
| ATOM | 2400 | NH2 | ARG | A | 322 | 34.967 | 18.702 | 54.398 | 1.00 | 18.79 | 7 |
| ATOM | 2401 | C | ARG | A | 322 | 30.782 | 18.058 | 58.827 | 1.00 | 18.51 | 6 |
| ATOM | 2402 | O | ARG | A | 322 | 30.002 | 18.988 | 59.026 | 1.00 | 18.47 | 8 |
| ATOM | 2403 | N | LEU | A | 323 | 30.532 | 17.070 | 57.967 | 1.00 | 18.43 | 7 |
| ATOM | 2404 | CA | LEU | A | 323 | 29.343 | 17.065 | 57.103 | 1.00 | 18.00 | 6 |
| ATOM | 2405 | CB | LEU | A | 323 | 29.642 | 16.348 | 55.777 | 1.00 | 18.10 | 6 |
| ATOM | 2406 | CG | LEU | A | 323 | 30.782 | 16.916 | 54.918 | 1.00 | 17.20 | 6 |
| ATOM | 2407 | CD1 | LEU | A | 323 | 31.002 | 16.091 | 53.661 | 1.00 | 17.72 | 6 |
| ATOM | 2408 | CD2 | LEU | A | 323 | 30.552 | 18.390 | 54.562 | 1.00 | 16.29 | 6 |
| ATOM | 2409 | C | LEU | A | 323 | 28.109 | 16.455 | 57.780 | 1.00 | 18.26 | 6 |
| ATOM | 2410 | O | LEU | A | 323 | 27.017 | 16.471 | 57.218 | 1.00 | 18.25 | 8 |
| ATOM | 2411 | N | GLY | A | 324 | 28.297 | 15.905 | 58.979 | 1.00 | 18.16 | 7 |
| ATOM | 2412 | CA | GLY | A | 324 | 27.198 | 15.332 | 59.759 | 1.00 | 18.68 | 6 |
| ATOM | 2413 | C | GLY | A | 324 | 26.771 | 13.942 | 59.317 | 1.00 | 18.99 | 6 |
| ATOM | 2414 | O | GLY | A | 324 | 25.688 | 13.481 | 59.669 | 1.00 | 19.21 | 8 |
| ATOM | 2415 | N | ILE | A | 325 | 27.630 | 13.267 | 58.557 | 1.00 | 19.24 | 7 |
| ATOM | 2416 | CA | ILE | A | 325 | 27.320 | 11.937 | 58.028 | 1.00 | 19.72 | 6 |
| ATOM | 2417 | CB | ILE | A | 325 | 28.128 | 11.640 | 56.733 | 1.00 | 19.37 | 6 |
| ATOM | 2418 | CG1 | ILE | A | 325 | 27.786 | 12.671 | 55.654 | 1.00 | 19.77 | 6 |
| ATOM | 2419 | CD1 | ILE | A | 325 | 28.832 | 12.806 | 54.570 | 1.00 | 20.67 | 6 |
| ATOM | 2420 | CG2 | ILE | A | 325 | 27.865 | 10.201 | 56.240 | 1.00 | 19.89 | 6 |
| ATOM | 2421 | C | ILE | A | 325 | 27.577 | 10.856 | 59.079 | 1.00 | 20.15 | 6 |
| ATOM | 2422 | O | ILE | A | 325 | 28.688 | 10.727 | 59.589 | 1.00 | 20.85 | 8 |
| ATOM | 2423 | N | ASN | A | 326 | 26.537 | 10.087 | 59.398 | 1.00 | 20.42 | 7 |
| ATOM | 2424 | CA | ASN | A | 326 | 26.619 | 9.057 | 60.433 | 1.00 | 20.40 | 6 |
| ATOM | 2425 | CB | ASN | A | 326 | 25.254 | 8.881 | 61.116 | 1.00 | 20.48 | 6 |
| ATOM | 2426 | CG | ASN | A | 326 | 25.278 | 7.836 | 62.222 | 1.00 | 20.98 | 6 |
| ATOM | 2427 | OD1 | ASN | A | 326 | 26.157 | 6.973 | 62.268 | 1.00 | 21.02 | 8 |
| ATOM | 2428 | ND2 | ASN | A | 326 | 24.294 | 7.900 | 63.111 | 1.00 | 22.87 | 7 |

TABLE 7-continued

Coordinates of the crystal structure of *E. coli* ExoI bound to compound 10

| ATOM | 2429 | C | ASN | A | 326 | 27.149 | 7.717 | 59.898 | 1.00 | 20.44 | 6 |
|---|---|---|---|---|---|---|---|---|---|---|---|
| ATOM | 2430 | O | ASN | A | 326 | 26.425 | 6.967 | 59.243 | 1.00 | 20.31 | 8 |
| ATOM | 2431 | N | ARG | A | 327 | 28.408 | 7.424 | 60.215 | 1.00 | 20.35 | 7 |
| ATOM | 2432 | CA | ARG | A | 327 | 29.114 | 6.251 | 59.685 | 1.00 | 20.35 | 6 |
| ATOM | 2433 | CB | ARG | A | 327 | 30.563 | 6.257 | 60.171 | 1.00 | 20.35 | 6 |
| ATOM | 2434 | CG | ARG | A | 327 | 31.451 | 5.230 | 59.509 | 1.00 | 21.65 | 6 |
| ATOM | 2435 | CD | ARG | A | 327 | 32.799 | 5.165 | 60.190 | 1.00 | 22.69 | 6 |
| ATOM | 2436 | NE | ARG | A | 327 | 33.723 | 4.300 | 59.465 | 1.00 | 25.02 | 7 |
| ATOM | 2437 | CZ | ARG | A | 327 | 34.576 | 4.715 | 58.530 | 1.00 | 25.86 | 6 |
| ATOM | 2438 | NH1 | ARG | A | 327 | 34.639 | 6.000 | 58.192 | 1.00 | 26.09 | 7 |
| ATOM | 2439 | NH2 | ARG | A | 327 | 35.374 | 3.838 | 57.935 | 1.00 | 26.78 | 7 |
| ATOM | 2440 | C | ARG | A | 327 | 28.442 | 4.938 | 60.080 | 1.00 | 20.50 | 6 |
| ATOM | 2441 | O | ARG | A | 327 | 28.260 | 4.042 | 59.242 | 1.00 | 20.53 | 8 |
| ATOM | 2442 | N | GLN | A | 328 | 28.068 | 4.835 | 61.353 | 1.00 | 20.30 | 7 |
| ATOM | 2443 | CA | GLN | A | 328 | 27.468 | 3.610 | 61.886 | 1.00 | 20.64 | 6 |
| ATOM | 2444 | CB | GLN | A | 328 | 27.358 | 3.672 | 63.411 | 1.00 | 20.92 | 6 |
| ATOM | 2445 | CG | GLN | A | 328 | 27.081 | 2.311 | 64.081 | 1.00 | 21.67 | 6 |
| ATOM | 2446 | CD | GLN | A | 328 | 28.031 | 1.209 | 63.613 | 1.00 | 23.09 | 6 |
| ATOM | 2447 | OE1 | GLN | A | 328 | 29.255 | 1.372 | 63.620 | 1.00 | 23.75 | 8 |
| ATOM | 2448 | NE2 | GLN | A | 328 | 27.466 | 0.083 | 63.205 | 1.00 | 23.92 | 7 |
| ATOM | 2449 | C | GLN | A | 328 | 26.111 | 3.302 | 61.249 | 1.00 | 20.45 | 6 |
| ATOM | 2450 | O | GLN | A | 328 | 25.795 | 2.145 | 60.990 | 1.00 | 20.50 | 8 |
| ATOM | 2451 | N | HIS | A | 329 | 25.324 | 4.345 | 60.990 | 1.00 | 20.24 | 7 |
| ATOM | 2452 | CA | HIS | A | 329 | 24.057 | 4.203 | 60.270 | 1.00 | 20.11 | 6 |
| ATOM | 2453 | CB | HIS | A | 329 | 23.359 | 5.565 | 60.138 | 1.00 | 20.60 | 6 |
| ATOM | 2454 | CG | HIS | A | 329 | 22.046 | 5.506 | 59.419 | 1.00 | 21.78 | 6 |
| ATOM | 2455 | ND1 | HIS | A | 329 | 20.857 | 5.235 | 60.061 | 1.00 | 23.34 | 7 |
| ATOM | 2456 | CE1 | HIS | A | 329 | 19.872 | 5.245 | 59.181 | 1.00 | 24.18 | 6 |
| ATOM | 2457 | NE2 | HIS | A | 329 | 20.379 | 5.511 | 57.991 | 1.00 | 23.80 | 7 |
| ATOM | 2458 | CD2 | HIS | A | 329 | 21.737 | 5.678 | 58.111 | 1.00 | 23.01 | 6 |
| ATOM | 2459 | C | HIS | A | 329 | 24.284 | 3.597 | 58.886 | 1.00 | 19.67 | 6 |
| ATOM | 2460 | O | HIS | A | 329 | 23.585 | 2.661 | 58.479 | 1.00 | 18.85 | 8 |
| ATOM | 2461 | N | CYS | A | 330 | 25.264 | 4.142 | 58.168 | 1.00 | 19.17 | 7 |
| ATOM | 2462 | CA | CYS | A | 330 | 25.615 | 3.647 | 56.845 | 1.00 | 19.01 | 6 |
| ATOM | 2463 | CB | CYS | A | 330 | 26.662 | 4.547 | 56.200 | 1.00 | 18.89 | 6 |
| ATOM | 2464 | SG | CYS | A | 330 | 26.065 | 6.222 | 55.830 | 1.00 | 18.67 | 16 |
| ATOM | 2465 | C | CYS | A | 330 | 26.096 | 2.199 | 56.900 | 1.00 | 19.15 | 6 |
| ATOM | 2466 | O | CYS | A | 330 | 25.693 | 1.389 | 56.077 | 1.00 | 19.29 | 8 |
| ATOM | 2467 | N | LEU | A | 331 | 26.947 | 1.883 | 57.880 | 1.00 | 19.22 | 7 |
| ATOM | 2468 | CA | LEU | A | 331 | 27.420 | 0.503 | 58.097 | 1.00 | 19.91 | 6 |
| ATOM | 2469 | CB | LEU | A | 331 | 28.437 | 0.437 | 59.243 | 1.00 | 19.96 | 6 |
| ATOM | 2470 | CG | LEU | A | 331 | 29.908 | 0.307 | 58.845 | 1.00 | 21.65 | 6 |
| ATOM | 2471 | CD1 | LEU | A | 331 | 30.670 | 1.547 | 59.234 | 1.00 | 22.54 | 6 |
| ATOM | 2472 | CD2 | LEU | A | 331 | 30.524 | −0.914 | 59.524 | 1.00 | 22.49 | 6 |
| ATOM | 2473 | C | LEU | A | 331 | 26.281 | −0.467 | 58.376 | 1.00 | 19.81 | 6 |
| ATOM | 2474 | O | LEU | A | 331 | 26.235 | −1.564 | 57.805 | 1.00 | 19.80 | 8 |
| ATOM | 2475 | N | ASP | A | 332 | 25.366 | −0.062 | 59.257 | 1.00 | 19.78 | 7 |
| ATOM | 2476 | CA | ASP | A | 332 | 24.220 | −0.897 | 59.619 | 1.00 | 20.10 | 6 |
| ATOM | 2477 | CB | ASP | A | 332 | 23.408 | −0.256 | 60.753 | 1.00 | 20.33 | 6 |
| ATOM | 2478 | CG | ASP | A | 332 | 24.145 | −0.261 | 62.087 | 1.00 | 21.59 | 6 |
| ATOM | 2479 | OD1 | ASP | A | 332 | 25.191 | −0.942 | 62.210 | 1.00 | 22.98 | 8 |
| ATOM | 2480 | OD2 | ASP | A | 332 | 23.670 | 0.422 | 63.022 | 1.00 | 23.86 | 8 |
| ATOM | 2481 | C | ASP | A | 332 | 23.323 | −1.165 | 58.413 | 1.00 | 19.89 | 6 |
| ATOM | 2482 | O | ASP | A | 332 | 22.888 | −2.297 | 58.198 | 1.00 | 19.92 | 8 |
| ATOM | 2483 | N | ASN | A | 333 | 23.061 | −0.119 | 57.627 | 1.00 | 19.48 | 7 |
| ATOM | 2484 | CA | ASN | A | 333 | 22.299 | −0.250 | 56.391 | 1.00 | 19.35 | 6 |
| ATOM | 2485 | CB | ASN | A | 333 | 22.053 | 1.127 | 55.752 | 1.00 | 19.04 | 6 |
| ATOM | 2486 | CG | ASN | A | 333 | 20.868 | 1.864 | 56.366 | 1.00 | 19.49 | 6 |
| ATOM | 2487 | OD1 | ASN | A | 333 | 20.703 | 3.076 | 56.165 | 1.00 | 18.93 | 8 |
| ATOM | 2488 | ND2 | ASN | A | 333 | 20.033 | 1.143 | 57.099 | 1.00 | 18.69 | 7 |
| ATOM | 2489 | C | ASN | A | 333 | 22.995 | −1.174 | 55.392 | 1.00 | 19.44 | 6 |
| ATOM | 2490 | O | ASN | A | 333 | 22.347 | −2.005 | 54.754 | 1.00 | 19.71 | 8 |
| ATOM | 2491 | N | LEU | A | 334 | 24.316 | −1.028 | 55.268 | 1.00 | 19.53 | 7 |
| ATOM | 2492 | CA | LEU | A | 334 | 25.092 | −1.849 | 54.336 | 1.00 | 19.61 | 6 |
| ATOM | 2493 | CB | LEU | A | 334 | 26.560 | −1.416 | 54.302 | 1.00 | 19.82 | 6 |
| ATOM | 2494 | CG | LEU | A | 334 | 27.477 | −2.115 | 53.286 | 1.00 | 19.61 | 6 |
| ATOM | 2495 | CD1 | LEU | A | 334 | 26.985 | −1.939 | 51.843 | 1.00 | 20.01 | 6 |
| ATOM | 2496 | CD2 | LEU | A | 334 | 28.905 | −1.620 | 53.440 | 1.00 | 19.55 | 6 |
| ATOM | 2497 | C | LEU | A | 334 | 24.981 | −3.336 | 54.670 | 1.00 | 19.79 | 6 |
| ATOM | 2498 | O | LEU | A | 334 | 24.756 | −4.154 | 53.777 | 1.00 | 19.48 | 8 |
| ATOM | 2499 | N | LYS | A | 335 | 25.138 | −3.672 | 55.952 | 1.00 | 20.08 | 7 |
| ATOM | 2500 | CA | LYS | A | 335 | 25.012 | −5.060 | 56.416 | 1.00 | 21.16 | 6 |
| ATOM | 2501 | CB | LYS | A | 335 | 25.289 | −5.159 | 57.921 | 1.00 | 21.01 | 6 |
| ATOM | 2502 | CG | LYS | A | 335 | 25.374 | −6.589 | 58.443 | 1.00 | 22.32 | 6 |
| ATOM | 2503 | CD | LYS | A | 335 | 25.769 | −6.626 | 59.910 | 1.00 | 22.83 | 6 |
| ATOM | 2504 | CE | LYS | A | 335 | 25.499 | −7.998 | 60.521 | 1.00 | 24.73 | 6 |
| ATOM | 2505 | NZ | LYS | A | 335 | 24.038 | −8.271 | 60.634 | 1.00 | 25.63 | 7 |
| ATOM | 2506 | C | LYS | A | 335 | 23.637 | −5.637 | 56.091 | 1.00 | 21.23 | 6 |

TABLE 7-continued

Coordinates of the crystal structure of *E. coli* ExoI bound to compound 10

| ATOM | 2507 | O | LYS | A | 335 | 23.533 | −6.759 | 55.590 | 1.00 | 21.44 | 8 |
|---|---|---|---|---|---|---|---|---|---|---|---|
| ATOM | 2508 | N | ILE | A | 336 | 22.589 | −4.860 | 56.363 | 1.00 | 21.44 | 7 |
| ATOM | 2509 | CA | ILE | A | 336 | 21.210 | −5.288 | 56.096 | 1.00 | 21.69 | 6 |
| ATOM | 2510 | CB | ILE | A | 336 | 20.172 | −4.259 | 56.624 | 1.00 | 21.75 | 6 |
| ATOM | 2511 | CG1 | ILE | A | 336 | 20.167 | −4.249 | 58.158 | 1.00 | 22.07 | 6 |
| ATOM | 2512 | CD1 | ILE | A | 336 | 19.544 | −2.998 | 58.778 | 1.00 | 22.69 | 6 |
| ATOM | 2513 | CG2 | ILE | A | 336 | 18.770 | −4.576 | 56.091 | 1.00 | 21.66 | 6 |
| ATOM | 2514 | C | ILE | A | 336 | 20.988 | −5.560 | 54.605 | 1.00 | 21.92 | 6 |
| ATOM | 2515 | O | ILE | A | 336 | 20.445 | −6.603 | 54.236 | 1.00 | 21.84 | 8 |
| ATOM | 2516 | N | LEU | A | 337 | 21.432 | −4.633 | 53.754 | 1.00 | 21.98 | 7 |
| ATOM | 2517 | CA | LEU | A | 337 | 21.277 | −4.785 | 52.305 | 1.00 | 22.50 | 6 |
| ATOM | 2518 | CB | LEU | A | 337 | 21.762 | −3.537 | 51.566 | 1.00 | 22.09 | 6 |
| ATOM | 2519 | CG | LEU | A | 337 | 20.932 | −2.256 | 51.713 | 1.00 | 22.02 | 6 |
| ATOM | 2520 | CD1 | LEU | A | 337 | 21.780 | −1.042 | 51.385 | 1.00 | 21.70 | 6 |
| ATOM | 2521 | CD2 | LEU | A | 337 | 19.669 | −2.292 | 50.846 | 1.00 | 22.24 | 6 |
| ATOM | 2522 | C | LEU | A | 337 | 22.000 | −6.026 | 51.781 | 1.00 | 22.99 | 6 |
| ATOM | 2523 | O | LEU | A | 337 | 21.483 | −6.731 | 50.910 | 1.00 | 23.37 | 8 |
| ATOM | 2524 | N | ARG | A | 338 | 23.188 | −6.289 | 52.322 | 1.00 | 23.58 | 7 |
| ATOM | 2525 | CA | ARG | A | 338 | 23.975 | −7.467 | 51.937 | 1.00 | 24.38 | 6 |
| ATOM | 2526 | CB | ARG | A | 338 | 25.383 | −7.391 | 52.531 | 1.00 | 24.30 | 6 |
| ATOM | 2527 | CG | ARG | A | 338 | 26.323 | −6.492 | 51.754 | 1.00 | 23.96 | 6 |
| ATOM | 2528 | CD | ARG | A | 338 | 27.632 | −6.265 | 52.495 | 1.00 | 23.56 | 6 |
| ATOM | 2529 | NE | ARG | A | 338 | 28.613 | −5.594 | 51.646 | 1.00 | 22.34 | 7 |
| ATOM | 2530 | CZ | ARG | A | 338 | 29.794 | −5.140 | 52.060 | 1.00 | 22.32 | 6 |
| ATOM | 2531 | NH1 | ARG | A | 338 | 30.160 | −5.270 | 53.331 | 1.00 | 22.83 | 7 |
| ATOM | 2532 | NH2 | ARG | A | 338 | 30.609 | −4.548 | 51.200 | 1.00 | 22.28 | 7 |
| ATOM | 2533 | C | ARG | A | 338 | 23.303 | −8.780 | 52.338 | 1.00 | 25.05 | 6 |
| ATOM | 2534 | O | ARG | A | 338 | 23.446 | −9.792 | 51.646 | 1.00 | 24.77 | 8 |
| ATOM | 2535 | N | GLU | A | 339 | 22.567 | −8.753 | 53.449 | 1.00 | 25.86 | 7 |
| ATOM | 2536 | CA | GLU | A | 339 | 21.854 | −9.937 | 53.948 | 1.00 | 27.24 | 6 |
| ATOM | 2537 | CB | GLU | A | 339 | 21.703 | −9.872 | 55.470 | 1.00 | 27.32 | 6 |
| ATOM | 2538 | CG | GLU | A | 339 | 23.019 | −9.983 | 56.233 | 1.00 | 28.40 | 6 |
| ATOM | 2539 | CD | GLU | A | 339 | 22.908 | −9.502 | 57.670 | 1.00 | 29.57 | 6 |
| ATOM | 2540 | OE1 | GLU | A | 339 | 22.146 | −8.540 | 57.925 | 1.00 | 30.40 | 8 |
| ATOM | 2541 | OE2 | GLU | A | 339 | 23.590 | −10.079 | 58.544 | 1.00 | 30.29 | 8 |
| ATOM | 2542 | C | GLU | A | 339 | 20.481 | −10.103 | 53.288 | 1.00 | 27.73 | 6 |
| ATOM | 2543 | O | GLU | A | 339 | 19.803 | −11.116 | 53.489 | 1.00 | 27.75 | 8 |
| ATOM | 2544 | N | ASN | A | 340 | 20.083 | −9.106 | 52.500 | 1.00 | 28.43 | 7 |
| ATOM | 2545 | CA | ASN | A | 340 | 18.814 | −9.143 | 51.777 | 1.00 | 29.16 | 6 |
| ATOM | 2546 | CB | ASN | A | 340 | 17.826 | −8.148 | 52.392 | 1.00 | 29.16 | 6 |
| ATOM | 2547 | CG | ASN | A | 340 | 17.479 | −8.487 | 53.825 | 1.00 | 29.55 | 6 |
| ATOM | 2548 | OD1 | ASN | A | 340 | 16.859 | −9.516 | 54.099 | 1.00 | 29.43 | 8 |
| ATOM | 2549 | ND2 | ASN | A | 340 | 17.871 | −7.621 | 54.749 | 1.00 | 29.85 | 7 |
| ATOM | 2550 | C | ASN | A | 340 | 18.985 | −8.871 | 50.275 | 1.00 | 29.59 | 6 |
| ATOM | 2551 | O | ASN | A | 340 | 18.555 | −7.827 | 49.779 | 1.00 | 29.62 | 8 |
| ATOM | 2552 | N | PRO | A | 341 | 19.588 | −9.829 | 49.539 | 1.00 | 30.24 | 7 |
| ATOM | 2553 | CA | PRO | A | 341 | 19.910 | −9.628 | 48.121 | 1.00 | 30.66 | 6 |
| ATOM | 2554 | CB | PRO | A | 341 | 20.760 | −10.862 | 47.768 | 1.00 | 30.66 | 6 |
| ATOM | 2555 | CG | PRO | A | 341 | 21.111 | −11.502 | 49.088 | 1.00 | 30.55 | 6 |
| ATOM | 2556 | CD | PRO | A | 341 | 19.988 | −11.170 | 49.998 | 1.00 | 30.37 | 6 |
| ATOM | 2557 | C | PRO | A | 341 | 18.676 | −9.553 | 47.210 | 1.00 | 31.08 | 6 |
| ATOM | 2558 | O | PRO | A | 341 | 18.807 | −9.236 | 46.026 | 1.00 | 31.16 | 8 |
| ATOM | 2559 | N | GLN | A | 342 | 17.496 | −9.839 | 47.758 | 1.00 | 31.68 | 7 |
| ATOM | 2560 | CA | GLN | A | 342 | 16.242 | −9.722 | 47.004 | 1.00 | 32.33 | 6 |
| ATOM | 2561 | CB | GLN | A | 342 | 15.077 | −10.381 | 47.756 | 1.00 | 32.34 | 6 |
| ATOM | 2562 | CG | GLN | A | 342 | 14.705 | −9.715 | 49.085 | 1.00 | 32.97 | 6 |
| ATOM | 2563 | CD | GLN | A | 342 | 15.417 | −10.331 | 50.284 | 1.00 | 33.61 | 6 |
| ATOM | 2564 | OE1 | GLN | A | 342 | 16.330 | −11.146 | 50.135 | 1.00 | 33.60 | 8 |
| ATOM | 2565 | NE2 | GLN | A | 342 | 14.994 | −9.943 | 51.484 | 1.00 | 34.10 | 7 |
| ATOM | 2566 | C | GLN | A | 342 | 15.907 | −8.265 | 46.675 | 1.00 | 32.67 | 6 |
| ATOM | 2567 | O | GLN | A | 342 | 15.036 | −7.990 | 45.844 | 1.00 | 32.86 | 8 |
| ATOM | 2568 | N | VAL | A | 343 | 16.603 | −7.339 | 47.333 | 1.00 | 33.09 | 7 |
| ATOM | 2569 | CA | VAL | A | 343 | 16.420 | −5.911 | 47.090 | 1.00 | 33.29 | 6 |
| ATOM | 2570 | CB | VAL | A | 343 | 17.059 | −5.050 | 48.225 | 1.00 | 33.39 | 6 |
| ATOM | 2571 | CG1 | VAL | A | 343 | 18.577 | −4.920 | 48.041 | 1.00 | 33.38 | 6 |
| ATOM | 2572 | CG2 | VAL | A | 343 | 16.400 | −3.684 | 48.298 | 1.00 | 33.43 | 6 |
| ATOM | 2573 | C | VAL | A | 343 | 16.948 | −5.495 | 45.707 | 1.00 | 33.47 | 6 |
| ATOM | 2574 | O | VAL | A | 343 | 16.491 | −4.500 | 45.137 | 1.00 | 33.44 | 8 |
| ATOM | 2575 | N | ARG | A | 344 | 17.900 | −6.267 | 45.177 | 1.00 | 33.65 | 7 |
| ATOM | 2576 | CA | ARG | A | 344 | 18.460 | −6.028 | 43.844 | 1.00 | 34.02 | 6 |
| ATOM | 2577 | CB | ARG | A | 344 | 19.572 | −7.031 | 43.530 | 1.00 | 34.01 | 6 |
| ATOM | 2578 | CG | ARG | A | 344 | 20.754 | −7.037 | 44.475 | 1.00 | 33.95 | 6 |
| ATOM | 2579 | CD | ARG | A | 344 | 21.813 | −7.993 | 43.936 | 1.00 | 34.05 | 6 |
| ATOM | 2580 | NE | ARG | A | 344 | 22.876 | −8.292 | 44.893 | 1.00 | 33.29 | 7 |
| ATOM | 2581 | CZ | ARG | A | 344 | 23.918 | −7.500 | 45.129 | 1.00 | 33.06 | 6 |
| ATOM | 2582 | NH1 | ARG | A | 344 | 24.031 | −6.334 | 44.504 | 1.00 | 32.76 | 7 |
| ATOM | 2583 | NH2 | ARG | A | 344 | 24.842 | −7.867 | 46.008 | 1.00 | 32.74 | 7 |
| ATOM | 2584 | C | ARG | A | 344 | 17.384 | −6.156 | 42.775 | 1.00 | 34.29 | 6 |

TABLE 7-continued

Coordinates of the crystal structure of *E. coli* ExoI bound to compound 10

| ATOM | 2585 | O   | ARG | A | 344 | 17.299 | −5.333  | 41.865 | 1.00 | 34.31 | 8 |
|------|------|-----|-----|---|-----|--------|---------|--------|------|-------|---|
| ATOM | 2586 | N   | GLU | A | 345 | 16.575 | −7.208  | 42.889 | 1.00 | 34.65 | 7 |
| ATOM | 2587 | CA  | GLU | A | 345 | 15.495 | −7.473  | 41.946 | 1.00 | 35.00 | 6 |
| ATOM | 2588 | CB  | GLU | A | 345 | 14.923 | −8.866  | 42.192 | 1.00 | 34.98 | 6 |
| ATOM | 2589 | CG  | GLU | A | 345 | 14.387 | −9.552  | 40.954 | 1.00 | 35.52 | 6 |
| ATOM | 2590 | CD  | GLU | A | 345 | 13.661 | −10.839 | 41.285 | 1.00 | 35.71 | 6 |
| ATOM | 2591 | OE1 | GLU | A | 345 | 12.439 | −10.782 | 41.546 | 1.00 | 35.80 | 8 |
| ATOM | 2592 | OE2 | GLU | A | 345 | 14.314 | −11.904 | 41.288 | 1.00 | 35.68 | 8 |
| ATOM | 2593 | C   | GLU | A | 345 | 14.394 | −6.423  | 42.079 | 1.00 | 35.09 | 6 |
| ATOM | 2594 | O   | GLU | A | 345 | 13.767 | −6.038  | 41.092 | 1.00 | 35.27 | 8 |
| ATOM | 2595 | N   | LYS | A | 346 | 14.182 | −5.962  | 43.309 | 1.00 | 35.32 | 7 |
| ATOM | 2596 | CA  | LYS | A | 346 | 13.179 | −4.952  | 43.619 | 1.00 | 35.52 | 6 |
| ATOM | 2597 | CB  | LYS | A | 346 | 13.117 | −4.729  | 45.128 | 1.00 | 35.51 | 6 |
| ATOM | 2598 | CG  | LYS | A | 346 | 11.720 | −4.700  | 45.701 | 1.00 | 35.58 | 6 |
| ATOM | 2599 | CD  | LYS | A | 346 | 11.774 | −4.667  | 47.215 | 1.00 | 35.76 | 6 |
| ATOM | 2600 | CE  | LYS | A | 346 | 10.646 | −5.469  | 47.830 | 1.00 | 36.00 | 6 |
| ATOM | 2601 | NZ  | LYS | A | 346 | 10.636 | −5.347  | 49.314 | 1.00 | 35.94 | 7 |
| ATOM | 2602 | C   | LYS | A | 346 | 13.460 | −3.625  | 42.909 | 1.00 | 35.67 | 6 |
| ATOM | 2603 | O   | LYS | A | 346 | 12.565 | −3.049  | 42.292 | 1.00 | 35.78 | 8 |
| ATOM | 2604 | N   | VAL | A | 347 | 14.704 | −3.150  | 42.996 | 1.00 | 35.88 | 7 |
| ATOM | 2605 | CA  | VAL | A | 347 | 15.076 | −1.857  | 42.401 | 1.00 | 36.07 | 6 |
| ATOM | 2606 | CB  | VAL | A | 347 | 16.398 | −1.269  | 42.992 | 1.00 | 36.04 | 6 |
| ATOM | 2607 | CG1 | VAL | A | 347 | 16.185 | −0.808  | 44.429 | 1.00 | 36.01 | 6 |
| ATOM | 2608 | CG2 | VAL | A | 347 | 17.550 | −2.272  | 42.898 | 1.00 | 35.88 | 6 |
| ATOM | 2609 | C   | VAL | A | 347 | 15.140 | −1.890  | 40.870 | 1.00 | 36.33 | 6 |
| ATOM | 2610 | O   | VAL | A | 347 | 14.891 | −0.874  | 40.215 | 1.00 | 36.41 | 8 |
| ATOM | 2611 | N   | VAL | A | 348 | 15.472 | −3.052  | 40.307 | 1.00 | 36.52 | 7 |
| ATOM | 2612 | CA  | VAL | A | 348 | 15.461 | −3.233  | 38.854 | 1.00 | 36.81 | 6 |
| ATOM | 2613 | CB  | VAL | A | 348 | 16.093 | −4.590  | 38.428 | 1.00 | 36.85 | 6 |
| ATOM | 2614 | CG1 | VAL | A | 348 | 15.800 | −4.894  | 36.958 | 1.00 | 36.84 | 6 |
| ATOM | 2615 | CG2 | VAL | A | 348 | 17.587 | −4.578  | 38.667 | 1.00 | 36.61 | 6 |
| ATOM | 2616 | C   | VAL | A | 348 | 14.027 | −3.129  | 38.331 | 1.00 | 37.13 | 6 |
| ATOM | 2617 | O   | VAL | A | 348 | 13.776 | −2.488  | 37.305 | 1.00 | 37.13 | 8 |
| ATOM | 2618 | N   | ALA | A | 349 | 13.094 | −3.740  | 39.063 | 1.00 | 37.45 | 7 |
| ATOM | 2619 | CA  | ALA | A | 349 | 11.675 | −3.731  | 38.701 | 1.00 | 37.83 | 6 |
| ATOM | 2620 | CB  | ALA | A | 349 | 10.880 | −4.597  | 39.660 | 1.00 | 37.72 | 6 |
| ATOM | 2621 | C   | ALA | A | 349 | 11.096 | −2.316  | 38.648 | 1.00 | 38.08 | 6 |
| ATOM | 2622 | O   | ALA | A | 349 | 10.208 | −2.035  | 37.843 | 1.00 | 38.12 | 8 |
| ATOM | 2623 | N   | ILE | A | 350 | 11.609 | −1.435  | 39.507 | 1.00 | 38.41 | 7 |
| ATOM | 2624 | CA  | ILE | A | 350 | 11.217 | −0.023  | 39.509 | 1.00 | 38.79 | 6 |
| ATOM | 2625 | CB  | ILE | A | 350 | 11.884 | 0.754   | 40.677 | 1.00 | 38.76 | 6 |
| ATOM | 2626 | CG1 | ILE | A | 350 | 11.542 | 0.109   | 42.024 | 1.00 | 38.80 | 6 |
| ATOM | 2627 | CD1 | ILE | A | 350 | 12.390 | 0.607   | 43.182 | 1.00 | 38.67 | 6 |
| ATOM | 2628 | CG2 | ILE | A | 350 | 11.469 | 2.233   | 40.658 | 1.00 | 38.85 | 6 |
| ATOM | 2629 | C   | ILE | A | 350 | 11.577 | 0.652   | 38.184 | 1.00 | 39.08 | 6 |
| ATOM | 2630 | O   | ILE | A | 350 | 10.773 | 1.394   | 37.616 | 1.00 | 39.19 | 8 |
| ATOM | 2631 | N   | PHE | A | 351 | 12.785 | 0.378   | 37.695 | 1.00 | 39.46 | 7 |
| ATOM | 2632 | CA  | PHE | A | 351 | 13.306 | 1.025   | 36.490 | 1.00 | 39.78 | 6 |
| ATOM | 2633 | CB  | PHE | A | 351 | 14.798 | 1.340   | 36.658 | 1.00 | 39.67 | 6 |
| ATOM | 2634 | CG  | PHE | A | 351 | 15.094 | 2.312   | 37.767 | 1.00 | 39.46 | 6 |
| ATOM | 2635 | CD1 | PHE | A | 351 | 15.440 | 1.857   | 39.038 | 1.00 | 39.40 | 6 |
| ATOM | 2636 | CE1 | PHE | A | 351 | 15.715 | 2.752   | 40.069 | 1.00 | 39.18 | 6 |
| ATOM | 2637 | CZ  | PHE | A | 351 | 15.647 | 4.120   | 39.834 | 1.00 | 39.41 | 6 |
| ATOM | 2638 | CE2 | PHE | A | 351 | 15.304 | 4.590   | 38.569 | 1.00 | 39.12 | 6 |
| ATOM | 2639 | CD2 | PHE | A | 351 | 15.030 | 3.685   | 37.543 | 1.00 | 39.35 | 6 |
| ATOM | 2640 | C   | PHE | A | 351 | 13.072 | 0.199   | 35.220 | 1.00 | 40.14 | 6 |
| ATOM | 2641 | O   | PHE | A | 351 | 13.471 | 0.608   | 34.123 | 1.00 | 40.10 | 8 |
| ATOM | 2642 | N   | ALA | A | 352 | 12.420 | −0.955  | 35.375 | 1.00 | 40.59 | 7 |
| ATOM | 2643 | CA  | ALA | A | 352 | 12.122 | −1.847  | 34.248 | 1.00 | 41.09 | 6 |
| ATOM | 2644 | CB  | ALA | A | 352 | 11.628 | −3.201  | 34.751 | 1.00 | 41.04 | 6 |
| ATOM | 2645 | C   | ALA | A | 352 | 11.113 | −1.235  | 33.271 | 1.00 | 41.44 | 6 |
| ATOM | 2646 | O   | ALA | A | 352 | 11.161 | −1.508  | 32.067 | 1.00 | 41.51 | 8 |
| ATOM | 2647 | N   | GLU | A | 353 | 10.202 | −0.418  | 33.798 | 1.00 | 41.79 | 7 |
| ATOM | 2648 | CA  | GLU | A | 353 | 9.239  | 0.306   | 32.970 | 1.00 | 42.19 | 6 |
| ATOM | 2649 | CB  | GLU | A | 353 | 7.818  | 0.137   | 33.515 | 1.00 | 42.19 | 6 |
| ATOM | 2650 | CG  | GLU | A | 353 | 6.732  | 0.761   | 32.632 | 1.00 | 42.62 | 6 |
| ATOM | 2651 | CD  | GLU | A | 353 | 5.417  | 0.987   | 33.368 | 1.00 | 42.93 | 6 |
| ATOM | 2652 | OE1 | GLU | A | 353 | 5.393  | 0.879   | 34.616 | 1.00 | 43.76 | 8 |
| ATOM | 2653 | OE2 | GLU | A | 353 | 4.405  | 1.282   | 32.695 | 1.00 | 43.62 | 8 |
| ATOM | 2654 | C   | GLU | A | 353 | 9.602  | 1.788   | 32.889 | 1.00 | 42.15 | 6 |
| ATOM | 2655 | O   | GLU | A | 353 | 9.853  | 2.432   | 33.908 | 1.00 | 42.24 | 8 |
| ATOM | 2656 | N   | SER | A | 360 | 5.006  | 15.462  | 24.991 | 1.00 | 33.60 | 7 |
| ATOM | 2657 | CA  | SER | A | 360 | 4.227  | 16.498  | 24.316 | 1.00 | 33.33 | 6 |
| ATOM | 2658 | CB  | SER | A | 360 | 4.624  | 17.890  | 24.826 | 1.00 | 33.56 | 6 |
| ATOM | 2659 | OG  | SER | A | 360 | 5.972  | 18.190  | 24.507 | 1.00 | 34.29 | 8 |
| ATOM | 2660 | C   | SER | A | 360 | 4.386  | 16.417  | 22.798 | 1.00 | 32.91 | 6 |
| ATOM | 2661 | O   | SEP | A | 360 | 5.261  | 15.706  | 22.292 | 1.00 | 32.93 | 8 |
| ATOM | 2662 | N   | ASP | A | 361 | 3.536  | 17.149  | 22.078 | 1.00 | 32.32 | 7 |

TABLE 7-continued

Coordinates of the crystal structure of *E. coli* ExoI bound to compound 10

| ATOM | 2663 | CA | ASP | A | 361 | 3.544 | 17.133 | 20.613 | 1.00 | 31.78 | 6 |
|---|---|---|---|---|---|---|---|---|---|---|---|
| ATOM | 2664 | CB | ASP | A | 361 | 2.160 | 17.514 | 20.061 | 1.00 | 32.17 | 6 |
| ATOM | 2665 | CG | ASP | A | 361 | 1.741 | 18.933 | 20.441 | 1.00 | 33.38 | 6 |
| ATOM | 2666 | OD1 | ASP | A | 361 | 2.355 | 19.524 | 21.362 | 1.00 | 34.59 | 8 |
| ATOM | 2667 | OD2 | ASP | A | 361 | 0.788 | 19.455 | 19.818 | 1.00 | 34.63 | 8 |
| ATOM | 2668 | C | ASP | A | 361 | 4.624 | 18.041 | 20.018 | 1.00 | 30.91 | 6 |
| ATOM | 2669 | O | ASP | A | 361 | 4.754 | 18.144 | 18.793 | 1.00 | 31.02 | 8 |
| ATOM | 2670 | N | ASN | A | 362 | 5.388 | 18.698 | 20.892 | 1.00 | 29.69 | 7 |
| ATOM | 2671 | CA | ASN | A | 362 | 6.452 | 19.606 | 20.475 | 1.00 | 28.43 | 6 |
| ATOM | 2672 | CB | ASN | A | 362 | 6.709 | 20.655 | 21.566 | 1.00 | 28.33 | 6 |
| ATOM | 2673 | CG | ASN | A | 362 | 7.528 | 21.849 | 21.072 | 1.00 | 28.33 | 6 |
| ATOM | 2674 | OD1 | ASN | A | 362 | 7.667 | 22.847 | 21.779 | 1.00 | 28.67 | 8 |
| ATOM | 2675 | ND2 | ASN | A | 362 | 8.072 | 21.749 | 19.867 | 1.00 | 28.47 | 7 |
| ATOM | 2676 | C | ASN | A | 362 | 7.729 | 18.837 | 20.158 | 1.00 | 27.58 | 6 |
| ATOM | 2677 | O | ASN | A | 362 | 8.379 | 18.295 | 21.059 | 1.00 | 27.24 | 8 |
| ATOM | 2678 | N | VAL | A | 363 | 8.078 | 18.792 | 18.871 | 1.00 | 26.42 | 7 |
| ATOM | 2679 | CA | VAL | A | 363 | 9.273 | 18.081 | 18.399 | 1.00 | 25.51 | 6 |
| ATOM | 2680 | CB | VAL | A | 363 | 9.370 | 18.085 | 16.837 | 1.00 | 25.64 | 6 |
| ATOM | 2681 | CG1 | VAL | A | 363 | 9.858 | 19.438 | 16.309 | 1.00 | 25.68 | 6 |
| ATOM | 2682 | CG2 | VAL | A | 363 | 10.260 | 16.947 | 16.337 | 1.00 | 25.67 | 6 |
| ATOM | 2683 | C | VAL | A | 363 | 10.575 | 18.605 | 19.043 | 1.00 | 24.70 | 6 |
| ATOM | 2684 | O | VAL | A | 363 | 11.533 | 17.853 | 19.200 | 1.00 | 24.39 | 8 |
| ATOM | 2685 | N | ASP | A | 364 | 10.585 | 19.885 | 19.427 | 1.00 | 23.77 | 7 |
| ATOM | 2686 | CA | ASP | A | 364 | 11.713 | 20.488 | 20.159 | 1.00 | 22.98 | 6 |
| ATOM | 2687 | CB | ASP | A | 364 | 11.452 | 21.975 | 20.424 | 1.00 | 22.81 | 6 |
| ATOM | 2688 | CG | ASP | A | 364 | 11.733 | 22.855 | 19.213 | 1.00 | 22.40 | 6 |
| ATOM | 2689 | OD1 | ASP | A | 364 | 12.408 | 22.402 | 18.269 | 1.00 | 22.47 | 8 |
| ATOM | 2690 | OD2 | ASP | A | 364 | 11.278 | 24.017 | 19.213 | 1.00 | 22.46 | 8 |
| ATOM | 2691 | C | ASP | A | 364 | 11.987 | 19.792 | 21.496 | 1.00 | 22.98 | 6 |
| ATOM | 2692 | O | ASP | A | 364 | 13.103 | 19.848 | 22.017 | 1.00 | 22.61 | 8 |
| ATOM | 2693 | N | ALA | A | 365 | 10.960 | 19.147 | 22.045 | 1.00 | 22.74 | 7 |
| ATOM | 2694 | CA | ALA | A | 365 | 11.042 | 18.546 | 23.371 | 1.00 | 22.77 | 6 |
| ATOM | 2695 | CB | ALA | A | 365 | 9.782 | 18.881 | 24.175 | 1.00 | 22.69 | 6 |
| ATOM | 2696 | C | ALA | A | 365 | 11.256 | 17.032 | 23.315 | 1.00 | 22.89 | 6 |
| ATOM | 2697 | O | ALA | A | 365 | 11.188 | 16.354 | 24.344 | 1.00 | 22.67 | 8 |
| ATOM | 2698 | N | GLN | A | 366 | 11.551 | 16.515 | 22.123 | 1.00 | 22.86 | 7 |
| ATOM | 2699 | CA | GLN | A | 366 | 11.510 | 15.069 | 21.875 | 1.00 | 23.42 | 6 |
| ATOM | 2700 | CB | GLN | A | 366 | 10.559 | 14.761 | 20.713 | 1.00 | 23.34 | 6 |
| ATOM | 2701 | CG | GLN | A | 366 | 9.085 | 14.743 | 21.110 | 1.00 | 23.19 | 6 |
| ATOM | 2702 | CD | GLN | A | 366 | 8.141 | 14.648 | 19.915 | 1.00 | 23.54 | 6 |
| ATOM | 2703 | OE1 | GLN | A | 366 | 8.548 | 14.312 | 18.805 | 1.00 | 24.15 | 8 |
| ATOM | 2704 | NE2 | GLN | A | 366 | 6.872 | 14.952 | 20.145 | 1.00 | 23.82 | 7 |
| ATOM | 2705 | C | GLN | A | 366 | 12.869 | 14.390 | 21.638 | 1.00 | 23.76 | 6 |
| ATOM | 2706 | O | GLN | A | 366 | 12.915 | 13.258 | 21.150 | 1.00 | 23.61 | 8 |
| ATOM | 2707 | N | LEU | A | 367 | 13.961 | 15.060 | 22.010 | 1.00 | 24.33 | 7 |
| ATOM | 2708 | CA | LEU | A | 367 | 15.310 | 14.488 | 21.860 | 1.00 | 24.97 | 6 |
| ATOM | 2709 | CB | LEU | A | 367 | 16.363 | 15.382 | 22.541 | 1.00 | 24.97 | 6 |
| ATOM | 2710 | CG | LEU | A | 367 | 17.811 | 14.873 | 22.685 | 1.00 | 24.94 | 6 |
| ATOM | 2711 | CD1 | LEU | A | 367 | 18.431 | 14.477 | 21.343 | 1.00 | 24.94 | 6 |
| ATOM | 2712 | CD2 | LEU | A | 367 | 18.672 | 15.907 | 23.386 | 1.00 | 24.99 | 6 |
| ATOM | 2713 | C | LEU | A | 367 | 15.416 | 13.047 | 22.381 | 1.00 | 25.45 | 6 |
| ATOM | 2714 | O | LEU | A | 367 | 15.978 | 12.173 | 21.707 | 1.00 | 25.48 | 8 |
| ATOM | 2715 | N | TYR | A | 368 | 14.861 | 12.803 | 23.567 | 1.00 | 26.04 | 7 |
| ATOM | 2716 | CA | TYR | A | 368 | 15.042 | 11.518 | 24.250 | 1.00 | 26.75 | 6 |
| ATOM | 2717 | CB | TYR | A | 368 | 15.254 | 11.731 | 25.751 | 1.00 | 26.76 | 6 |
| ATOM | 2718 | CG | TYR | A | 368 | 16.489 | 12.544 | 26.073 | 1.00 | 27.28 | 6 |
| ATOM | 2719 | CD1 | TYR | A | 368 | 17.758 | 12.082 | 25.726 | 1.00 | 27.42 | 6 |
| ATOM | 2720 | CE1 | TYR | A | 368 | 18.896 | 12.825 | 26.008 | 1.00 | 27.53 | 6 |
| ATOM | 2721 | CZ | TYR | A | 368 | 18.775 | 14.044 | 26.648 | 1.00 | 27.37 | 6 |
| ATOM | 2722 | OH | TYR | A | 368 | 19.908 | 14.772 | 26.926 | 1.00 | 27.63 | 8 |
| ATOM | 2723 | CE2 | TYR | A | 368 | 17.528 | 14.530 | 27.007 | 1.00 | 27.01 | 6 |
| ATOM | 2724 | CD2 | TYR | A | 368 | 16.390 | 13.779 | 26.715 | 1.00 | 27.03 | 6 |
| ATOM | 2725 | C | TYR | A | 368 | 13.912 | 10.521 | 23.997 | 1.00 | 27.12 | 6 |
| ATOM | 2726 | O | TYR | A | 368 | 13.786 | 9.525 | 24.708 | 1.00 | 27.07 | 8 |
| ATOM | 2727 | N | ASN | A | 369 | 13.105 | 10.784 | 22.970 | 1.00 | 27.74 | 7 |
| ATOM | 2728 | CA | ASN | A | 369 | 12.064 | 9.842 | 22.549 | 1.00 | 28.40 | 6 |
| ATOM | 2729 | CB | ASN | A | 369 | 11.006 | 10.545 | 21.698 | 1.00 | 28.44 | 6 |
| ATOM | 2730 | CG | ASN | A | 369 | 9.994 | 11.311 | 22.532 | 1.00 | 29.10 | 6 |
| ATOM | 2731 | OD1 | ASN | A | 369 | 10.304 | 11.803 | 23.621 | 1.00 | 29.89 | 8 |
| ATOM | 2732 | ND2 | ASN | A | 369 | 8.773 | 11.423 | 22.019 | 1.00 | 29.54 | 7 |
| ATOM | 2733 | C | ASN | A | 369 | 12.628 | 8.622 | 21.811 | 1.00 | 28.68 | 6 |
| ATOM | 2734 | O | ASN | A | 369 | 11.880 | 7.834 | 21.233 | 1.00 | 29.02 | 8 |
| ATOM | 2735 | N | GLY | A | 370 | 13.950 | 8.471 | 21.847 | 1.00 | 29.10 | 7 |
| ATOM | 2736 | CA | GLY | A | 370 | 14.612 | 7.307 | 21.268 | 1.00 | 29.41 | 6 |
| ATOM | 2737 | C | GLY | A | 370 | 15.756 | 7.670 | 20.345 | 1.00 | 29.60 | 6 |
| ATOM | 2738 | O | GLY | A | 370 | 15.851 | 8.808 | 19.867 | 1.00 | 29.84 | 8 |
| ATOM | 2739 | N | PHE | A | 371 | 16.636 | 6.701 | 20.103 | 1.00 | 29.62 | 7 |
| ATOM | 2740 | CA | PHE | A | 371 | 17.723 | 6.874 | 19.151 | 1.00 | 29.63 | 6 |

TABLE 7-continued

Coordinates of the crystal structure of *E. coli* ExoI bound to compound 10

| ATOM | 2741 | CB | PHE | A | 371 | 18.865 | 5.896 | 19.442 | 1.00 | 29.99 | 6 |
|------|------|-----|-----|---|-----|--------|--------|--------|------|-------|---|
| ATOM | 2742 | CG | PHE | A | 371 | 19.574 | 6.155 | 20.745 | 1.00 | 30.35 | 6 |
| ATOM | 2743 | CD1 | PHE | A | 371 | 20.516 | 7.177 | 20.851 | 1.00 | 30.97 | 6 |
| ATOM | 2744 | CE1 | PHE | A | 371 | 21.179 | 7.416 | 22.057 | 1.00 | 30.97 | 6 |
| ATOM | 2745 | CZ | PHE | A | 371 | 20.904 | 6.620 | 23.170 | 1.00 | 31.41 | 6 |
| ATOM | 2746 | CE2 | PHE | A | 371 | 19.969 | 5.595 | 23.074 | 1.00 | 30.97 | 6 |
| ATOM | 2747 | CD2 | PHE | A | 371 | 19.312 | 5.364 | 21.864 | 1.00 | 30.71 | 6 |
| ATOM | 2748 | C | PHE | A | 371 | 17.205 | 6.668 | 17.733 | 1.00 | 29.29 | 6 |
| ATOM | 2749 | O | PHE | A | 371 | 16.379 | 5.788 | 17.487 | 1.00 | 29.33 | 8 |
| ATOM | 2750 | N | PHE | A | 372 | 17.681 | 7.496 | 16.808 | 1.00 | 29.08 | 7 |
| ATOM | 2751 | CA | PHE | A | 372 | 17.369 | 7.324 | 15.393 | 1.00 | 28.88 | 6 |
| ATOM | 2752 | CB | PHE | A | 372 | 17.803 | 8.556 | 14.594 | 1.00 | 28.77 | 6 |
| ATOM | 2753 | CG | PHE | A | 372 | 17.118 | 9.831 | 15.013 | 1.00 | 28.94 | 6 |
| ATOM | 2754 | CD1 | PHE | A | 372 | 15.859 | 10.160 | 14.514 | 1.00 | 29.09 | 6 |
| ATOM | 2755 | CE1 | PHE | A | 372 | 15.225 | 11.344 | 14.894 | 1.00 | 29.05 | 6 |
| ATOM | 2756 | CZ | PHE | A | 372 | 15.855 | 12.213 | 15.776 | 1.00 | 29.07 | 6 |
| ATOM | 2757 | CE2 | PHE | A | 372 | 17.112 | 11.898 | 16.277 | 1.00 | 29.09 | 6 |
| ATOM | 2758 | CD2 | PHE | A | 372 | 17.739 | 10.713 | 15.892 | 1.00 | 28.80 | 6 |
| ATOM | 2759 | C | PHE | A | 372 | 18.090 | 6.089 | 14.868 | 1.00 | 28.71 | 6 |
| ATOM | 2760 | O | PHE | A | 372 | 19.146 | 5.720 | 15.381 | 1.00 | 28.76 | 8 |
| ATOM | 2761 | N | SER | A | 373 | 17.517 | 5.451 | 13.850 | 1.00 | 28.68 | 7 |
| ATOM | 2762 | CA | SER | A | 373 | 18.163 | 4.308 | 13.206 | 1.00 | 28.51 | 6 |
| ATOM | 2763 | CB | SER | A | 373 | 17.193 | 3.605 | 12.251 | 1.00 | 28.57 | 6 |
| ATOM | 2764 | OG | SER | A | 373 | 16.772 | 4.476 | 11.216 | 1.00 | 28.59 | 8 |
| ATOM | 2765 | C | SER | A | 373 | 19.420 | 4.755 | 12.460 | 1.00 | 28.51 | 6 |
| ATOM | 2766 | O | SER | A | 373 | 19.623 | 5.953 | 12.227 | 1.00 | 28.35 | 8 |
| ATOM | 2767 | N | ASP | A | 374 | 20.265 | 3.794 | 12.101 | 1.00 | 28.35 | 7 |
| ATOM | 2768 | CA | ASP | A | 374 | 21.471 | 4.077 | 11.325 | 1.00 | 28.40 | 6 |
| ATOM | 2769 | CB | ASP | A | 374 | 22.252 | 2.788 | 11.048 | 1.00 | 28.57 | 6 |
| ATOM | 2770 | CG | ASP | A | 374 | 23.128 | 2.362 | 12.219 | 1.00 | 28.94 | 6 |
| ATOM | 2771 | OD1 | ASP | A | 374 | 23.078 | 3.008 | 13.291 | 1.00 | 29.85 | 8 |
| ATOM | 2772 | OD2 | ASP | A | 374 | 23.874 | 1.373 | 12.062 | 1.00 | 29.40 | 8 |
| ATOM | 2773 | C | ASP | A | 374 | 21.132 | 4.779 | 10.009 | 1.00 | 28.18 | 6 |
| ATOM | 2774 | O | ASP | A | 374 | 21.797 | 5.741 | 9.624 | 1.00 | 28.04 | 8 |
| ATOM | 2775 | N | ALA | A | 375 | 20.088 | 4.293 | 9.334 | 1.00 | 28.00 | 7 |
| ATOM | 2776 | CA | ALA | A | 375 | 19.644 | 4.859 | 8.058 | 1.00 | 27.81 | 6 |
| ATOM | 2777 | CB | ALA | A | 375 | 18.574 | 3.976 | 7.427 | 1.00 | 27.84 | 6 |
| ATOM | 2778 | C | ALA | A | 375 | 19.133 | 6.293 | 8.217 | 1.00 | 27.59 | 6 |
| ATOM | 2779 | O | ALA | A | 375 | 19.440 | 7.161 | 7.399 | 1.00 | 27.70 | 8 |
| ATOM | 2780 | N | ASP | A | 376 | 18.362 | 6.535 | 9.277 | 1.00 | 27.48 | 7 |
| ATOM | 2781 | CA | ASP | A | 376 | 17.840 | 7.875 | 9.567 | 1.00 | 27.20 | 6 |
| ATOM | 2782 | CB | ASP | A | 376 | 16.904 | 7.848 | 10.780 | 1.00 | 27.40 | 6 |
| ATOM | 2783 | CG | ASP | A | 376 | 15.481 | 7.445 | 10.415 | 1.00 | 27.81 | 6 |
| ATOM | 2784 | OD1 | ASP | A | 376 | 15.093 | 7.582 | 9.235 | 1.00 | 27.89 | 8 |
| ATOM | 2785 | OD2 | ASP | A | 376 | 14.746 | 6.996 | 11.317 | 1.00 | 29.32 | 8 |
| ATOM | 2786 | C | ASP | A | 376 | 18.952 | 8.909 | 9.766 | 1.00 | 26.85 | 6 |
| ATOM | 2787 | O | ASP | A | 376 | 18.857 | 10.027 | 9.261 | 1.00 | 26.80 | 8 |
| ATOM | 2788 | N | ARG | A | 377 | 20.004 | 8.521 | 10.487 | 1.00 | 26.44 | 7 |
| ATOM | 2789 | CA | ARG | A | 377 | 21.169 | 9.388 | 10.708 | 1.00 | 26.42 | 6 |
| ATOM | 2790 | CB | ARG | A | 377 | 22.107 | 8.781 | 11.766 | 1.00 | 26.71 | 6 |
| ATOM | 2791 | CG | ARG | A | 377 | 23.458 | 9.518 | 11.965 | 1.00 | 28.22 | 6 |
| ATOM | 2792 | CD | ARG | A | 377 | 23.281 | 10.986 | 12.387 | 1.00 | 30.39 | 6 |
| ATOM | 2793 | NE | ARG | A | 377 | 22.424 | 11.120 | 13.564 | 1.00 | 31.49 | 7 |
| ATOM | 2794 | CZ | ARG | A | 377 | 21.860 | 12.257 | 13.961 | 1.00 | 31.86 | 6 |
| ATOM | 2795 | NH1 | ARG | A | 377 | 22.055 | 13.378 | 13.277 | 1.00 | 32.25 | 7 |
| ATOM | 2796 | NH2 | ARG | A | 377 | 21.093 | 12.271 | 15.043 | 1.00 | 31.79 | 7 |
| ATOM | 2797 | C | ARG | A | 377 | 21.924 | 9.671 | 9.407 | 1.00 | 25.85 | 6 |
| ATOM | 2798 | O | ARG | A | 377 | 22.355 | 10.802 | 9.166 | 1.00 | 25.70 | 8 |
| ATOM | 2799 | N | ALA | A | 378 | 22.076 | 8.641 | 8.574 | 1.00 | 25.25 | 7 |
| ATOM | 2800 | CA | ALA | A | 378 | 22.675 | 8.801 | 7.250 | 1.00 | 24.71 | 6 |
| ATOM | 2801 | CB | ALA | A | 378 | 22.779 | 7.450 | 6.541 | 1.00 | 24.87 | 6 |
| ATOM | 2802 | C | ALA | A | 378 | 21.869 | 9.795 | 6.410 | 1.00 | 24.39 | 6 |
| ATOM | 2803 | O | ALA | A | 378 | 22.442 | 10.626 | 5.699 | 1.00 | 24.49 | 8 |
| ATOM | 2804 | N | ALA | A | 379 | 20.542 | 9.706 | 6.512 | 1.00 | 23.71 | 7 |
| ATOM | 2805 | CA | ALA | A | 379 | 19.635 | 10.619 | 5.816 | 1.00 | 23.08 | 6 |
| ATOM | 2806 | CB | ALA | A | 379 | 18.191 | 10.109 | 5.912 | 1.00 | 23.21 | 6 |
| ATOM | 2807 | C | ALA | A | 379 | 19.739 | 12.045 | 6.363 | 1.00 | 22.67 | 6 |
| ATOM | 2808 | O | ALA | A | 379 | 19.781 | 13.009 | 5.599 | 1.00 | 21.90 | 8 |
| ATOM | 2809 | N | MET | A | 380 | 19.794 | 12.168 | 7.690 | 1.00 | 22.16 | 7 |
| ATOM | 2810 | CA | MET | A | 380 | 19.915 | 13.475 | 8.343 | 1.00 | 22.18 | 6 |
| ATOM | 2811 | CB | MET | A | 380 | 19.674 | 13.346 | 9.852 | 1.00 | 22.10 | 6 |
| ATOM | 2812 | CG | MET | A | 380 | 18.234 | 12.968 | 10.214 | 1.00 | 22.50 | 6 |
| ATOM | 2813 | SD | MET | A | 380 | 17.978 | 12.667 | 11.988 | 1.00 | 24.18 | 16 |
| ATOM | 2814 | CE | MET | A | 380 | 17.743 | 14.328 | 12.597 | 1.00 | 24.12 | 6 |
| ATOM | 2815 | C | MET | A | 380 | 21.275 | 14.129 | 8.062 | 1.00 | 21.74 | 6 |
| ATOM | 2816 | O | MET | A | 380 | 21.386 | 15.355 | 8.022 | 1.00 | 21.39 | 8 |
| ATOM | 2817 | N | LYS | A | 381 | 22.297 | 13.297 | 7.857 | 1.00 | 21.31 | 7 |
| ATOM | 2818 | CA | LYS | A | 381 | 23.625 | 13.768 | 7.458 | 1.00 | 21.13 | 6 |

TABLE 7-continued

Coordinates of the crystal structure of *E. coli* ExoI bound to compound 10

| ATOM | 2819 | CB | LYS | A | 381 | 24.644 | 12.623 | 7.534 | 1.00 | 20.93 | 6 |
|---|---|---|---|---|---|---|---|---|---|---|---|
| ATOM | 2820 | CG | LYS | A | 381 | 26.078 | 13.025 | 7.195 | 1.00 | 21.65 | 6 |
| ATOM | 2821 | CD | LYS | A | 381 | 27.047 | 11.864 | 7.401 | 1.00 | 21.67 | 6 |
| ATOM | 2822 | CE | LYS | A | 381 | 28.488 | 12.305 | 7.191 | 1.00 | 22.46 | 6 |
| ATOM | 2823 | NZ | LYS | A | 381 | 29.396 | 11.150 | 6.934 | 1.00 | 22.12 | 7 |
| ATOM | 2824 | C | LYS | A | 381 | 23.606 | 14.379 | 6.049 | 1.00 | 20.78 | 6 |
| ATOM | 2825 | O | LYS | A | 381 | 24.323 | 15.345 | 5.773 | 1.00 | 20.57 | 8 |
| ATOM | 2826 | N | ILE | A | 382 | 22.790 | 13.810 | 5.164 | 1.00 | 20.48 | 7 |
| ATOM | 2827 | CA | ILE | A | 382 | 22.581 | 14.394 | 3.836 | 1.00 | 20.43 | 6 |
| ATOM | 2828 | CB | ILE | A | 382 | 21.766 | 13.455 | 2.901 | 1.00 | 20.56 | 6 |
| ATOM | 2829 | CG1 | ILE | A | 382 | 22.596 | 12.212 | 2.545 | 1.00 | 20.26 | 6 |
| ATOM | 2830 | CD1 | ILE | A | 382 | 21.828 | 11.133 | 1.794 | 1.00 | 20.99 | 6 |
| ATOM | 2831 | CG2 | ILE | A | 382 | 21.327 | 14.196 | 1.635 | 1.00 | 19.44 | 6 |
| ATOM | 2832 | C | ILE | A | 382 | 21.924 | 15.780 | 3.947 | 1.00 | 20.55 | 6 |
| ATOM | 2833 | O | ILE | A | 382 | 22.313 | 16.716 | 3.244 | 1.00 | 20.65 | 8 |
| ATOM | 2834 | N | VAL | A | 383 | 20.952 | 15.914 | 4.849 | 1.00 | 20.73 | 7 |
| ATOM | 2835 | CA | VAL | A | 383 | 20.307 | 17.211 | 5.083 | 1.00 | 20.72 | 6 |
| ATOM | 2836 | CB | VAL | A | 383 | 19.166 | 17.118 | 6.137 | 1.00 | 20.92 | 6 |
| ATOM | 2837 | CG1 | VAL | A | 383 | 18.723 | 18.510 | 6.571 | 1.00 | 20.94 | 6 |
| ATOM | 2838 | CG2 | VAL | A | 383 | 17.988 | 16.330 | 5.582 | 1.00 | 20.80 | 6 |
| ATOM | 2839 | C | VAL | A | 383 | 21.336 | 18.246 | 5.525 | 1.00 | 20.80 | 6 |
| ATOM | 2840 | O | VAL | A | 383 | 21.402 | 19.347 | 4.979 | 1.00 | 20.54 | 8 |
| ATOM | 2841 | N | LEU | A | 384 | 22.147 | 17.871 | 6.509 | 1.00 | 21.06 | 7 |
| ATOM | 2842 | CA | LEU | A | 384 | 23.175 | 18.742 | 7.050 | 1.00 | 21.36 | 6 |
| ATOM | 2843 | CB | LEU | A | 384 | 23.929 | 18.009 | 8.166 | 1.00 | 21.22 | 6 |
| ATOM | 2844 | CG | LEU | A | 384 | 25.140 | 18.682 | 8.804 | 1.00 | 21.34 | 6 |
| ATOM | 2845 | CD1 | LEU | A | 384 | 24.724 | 19.968 | 9.490 | 1.00 | 20.96 | 6 |
| ATOM | 2846 | CD2 | LEU | A | 384 | 25.800 | 17.728 | 9.785 | 1.00 | 20.69 | 6 |
| ATOM | 2847 | C | LEU | A | 384 | 24.154 | 19.222 | 5.972 | 1.00 | 21.96 | 6 |
| ATOM | 2848 | O | LEU | A | 384 | 24.540 | 20.394 | 5.945 | 1.00 | 21.43 | 8 |
| ATOM | 2849 | N | GLU | A | 385 | 24.533 | 18.318 | 5.075 | 1.00 | 22.80 | 7 |
| ATOM | 2850 | CA | GLU | A | 385 | 25.612 | 18.590 | 4.139 | 1.00 | 24.07 | 6 |
| ATOM | 2851 | CB | GLU | A | 385 | 26.560 | 17.385 | 4.052 | 1.00 | 23.85 | 6 |
| ATOM | 2852 | CG | GLU | A | 385 | 27.179 | 17.028 | 5.418 | 1.00 | 24.42 | 6 |
| ATOM | 2853 | CD | GLU | A | 385 | 28.210 | 15.910 | 5.358 | 1.00 | 25.16 | 6 |
| ATOM | 2854 | OE1 | GLU | A | 385 | 28.292 | 15.205 | 4.328 | 1.00 | 26.14 | 8 |
| ATOM | 2855 | OE2 | GLU | A | 385 | 28.935 | 15.732 | 6.361 | 1.00 | 26.19 | 8 |
| ATOM | 2856 | C | GLU | A | 385 | 25.116 | 19.044 | 2.764 | 1.00 | 24.64 | 6 |
| ATOM | 2857 | O | GLU | A | 385 | 25.911 | 19.297 | 1.865 | 1.00 | 24.84 | 8 |
| ATOM | 2858 | N | THR | A | 386 | 23.798 | 19.160 | 2.620 | 1.00 | 25.75 | 7 |
| ATOM | 2859 | CA | THR | A | 386 | 23.194 | 19.748 | 1.424 | 1.00 | 26.53 | 6 |
| ATOM | 2860 | CB | THR | A | 386 | 21.802 | 19.114 | 1.111 | 1.00 | 26.26 | 6 |
| ATOM | 2861 | OG1 | THR | A | 386 | 21.964 | 17.718 | 0.831 | 1.00 | 25.28 | 8 |
| ATOM | 2862 | CG2 | THR | A | 386 | 21.144 | 19.786 | −0.090 | 1.00 | 26.38 | 6 |
| ATOM | 2863 | C | THR | A | 386 | 23.064 | 21.265 | 1.585 | 1.00 | 27.66 | 6 |
| ATOM | 2864 | O | THR | A | 386 | 22.743 | 21.764 | 2.668 | 1.00 | 27.98 | 8 |
| ATOM | 2865 | N | GLU | A | 387 | 23.334 | 21.991 | 0.503 | 1.00 | 29.12 | 7 |
| ATOM | 2866 | CA | GLU | A | 387 | 23.162 | 23.445 | 0.473 | 1.00 | 30.48 | 6 |
| ATOM | 2867 | CB | GLU | A | 387 | 23.592 | 24.009 | −0.887 | 1.00 | 30.60 | 6 |
| ATOM | 2868 | CG | GLU | A | 387 | 24.936 | 23.485 | −1.374 | 1.00 | 31.46 | 6 |
| ATOM | 2869 | CD | GLU | A | 387 | 25.792 | 24.560 | −2.009 | 1.00 | 33.21 | 6 |
| ATOM | 2870 | OE1 | GLU | A | 387 | 25.768 | 25.713 | −1.519 | 1.00 | 34.12 | 8 |
| ATOM | 2871 | OE2 | GLU | A | 387 | 26.507 | 24.247 | −2.985 | 1.00 | 33.67 | 8 |
| ATOM | 2872 | C | GLU | A | 387 | 21.712 | 23.831 | 0.767 | 1.00 | 31.33 | 6 |
| ATOM | 2873 | O | GLU | A | 387 | 20.785 | 23.220 | 0.228 | 1.00 | 31.57 | 8 |
| ATOM | 2874 | N | PRO | A | 388 | 21.512 | 24.849 | 1.628 | 1.00 | 32.04 | 7 |
| ATOM | 2875 | CA | PRO | A | 388 | 20.176 | 25.261 | 2.074 | 1.00 | 32.56 | 6 |
| ATOM | 2876 | CB | PRO | A | 388 | 20.451 | 26.558 | 2.834 | 1.00 | 32.54 | 6 |
| ATOM | 2877 | CG | PRO | A | 388 | 21.848 | 26.410 | 3.319 | 1.00 | 32.35 | 6 |
| ATOM | 2878 | CD | PRO | A | 388 | 22.571 | 25.678 | 2.237 | 1.00 | 32.36 | 6 |
| ATOM | 2879 | C | PRO | A | 388 | 19.217 | 25.517 | 0.910 | 1.00 | 32.99 | 6 |
| ATOM | 2880 | O | PRO | A | 388 | 18.030 | 25.181 | 0.996 | 1.00 | 33.09 | 8 |
| ATOM | 2881 | N | ARG | A | 389 | 19.741 | 26.090 | −0.172 | 1.00 | 33.52 | 7 |
| ATOM | 2882 | CA | ARG | A | 389 | 18.949 | 26.379 | −1.369 | 1.00 | 34.09 | 6 |
| ATOM | 2883 | CB | ARG | A | 389 | 19.723 | 27.302 | −2.322 | 1.00 | 34.15 | 6 |
| ATOM | 2884 | CG | ARG | A | 389 | 21.085 | 26.770 | −2.763 | 1.00 | 34.53 | 6 |
| ATOM | 2885 | CD | ARG | A | 389 | 21.702 | 27.661 | −3.831 | 1.00 | 34.96 | 6 |
| ATOM | 2886 | NE | ARG | A | 389 | 23.133 | 27.407 | −4.015 | 1.00 | 36.37 | 7 |
| ATOM | 2887 | CZ | ARG | A | 389 | 23.642 | 26.430 | −4.766 | 1.00 | 36.73 | 6 |
| ATOM | 2888 | NH1 | ARG | A | 389 | 22.844 | 25.585 | −5.410 | 1.00 | 36.62 | 7 |
| ATOM | 2889 | NH2 | ARG | A | 389 | 24.958 | 26.295 | −4.869 | 1.00 | 37.32 | 7 |
| ATOM | 2890 | C | ARG | A | 389 | 18.499 | 25.112 | −2.107 | 1.00 | 34.18 | 6 |
| ATOM | 2891 | O | ARG | A | 389 | 17.590 | 25.162 | −2.938 | 1.00 | 34.13 | 8 |
| ATOM | 2892 | N | ASN | A | 390 | 19.133 | 23.982 | −1.789 | 1.00 | 34.27 | 7 |
| ATOM | 2893 | CA | ASN | A | 390 | 18.845 | 22.708 | −2.452 | 1.00 | 34.26 | 6 |
| ATOM | 2894 | CB | ASN | A | 390 | 20.147 | 22.026 | −2.878 | 1.00 | 34.43 | 6 |
| ATOM | 2895 | CG | ASN | A | 390 | 20.818 | 22.720 | −4.048 | 1.00 | 34.48 | 6 |
| ATOM | 2896 | OD1 | ASN | A | 390 | 20.181 | 23.453 | −4.805 | 1.00 | 35.38 | 8 |

TABLE 7-continued

Coordinates of the crystal structure of E. coli ExoI bound to compound 10

| ATOM | 2897 | ND2 | ASN | A | 390 | 22.114 | 22.482 | −4.206 | 1.00 | 34.81 | 7 |
|---|---|---|---|---|---|---|---|---|---|---|---|
| ATOM | 2898 | C | ASN | A | 390 | 18.005 | 21.740 | −1.617 | 1.00 | 34.15 | 6 |
| ATOM | 2899 | O | ASN | A | 390 | 17.795 | 20.593 | −2.017 | 1.00 | 34.10 | 8 |
| ATOM | 2900 | N | LEU | A | 391 | 17.526 | 22.204 | −0.463 | 1.00 | 34.05 | 7 |
| ATOM | 2901 | CA | LEU | A | 391 | 16.720 | 21.365 | 0.436 | 1.00 | 33.90 | 6 |
| ATOM | 2902 | CB | LEU | A | 391 | 16.736 | 21.908 | 1.874 | 1.00 | 33.73 | 6 |
| ATOM | 2903 | CG | LEU | A | 391 | 17.985 | 21.612 | 2.712 | 1.00 | 32.85 | 6 |
| ATOM | 2904 | CD1 | LEU | A | 391 | 17.889 | 22.297 | 4.073 | 1.00 | 32.38 | 6 |
| ATOM | 2905 | CD2 | LEU | A | 391 | 18.201 | 20.109 | 2.880 | 1.00 | 31.92 | 6 |
| ATOM | 2906 | C | LEU | A | 391 | 15.275 | 21.116 | −0.035 | 1.00 | 34.07 | 6 |
| ATOM | 2907 | O | LEU | A | 391 | 14.740 | 20.031 | 0.197 | 1.00 | 34.10 | 8 |
| ATOM | 2908 | N | PRO | A | 392 | 14.634 | 22.122 | −0.679 | 1.00 | 34.29 | 7 |
| ATOM | 2909 | CA | PRO | A | 392 | 13.293 | 21.895 | −1.235 | 1.00 | 34.54 | 6 |
| ATOM | 2910 | CB | PRO | A | 392 | 12.980 | 23.219 | −1.942 | 1.00 | 34.58 | 6 |
| ATOM | 2911 | CG | PRO | A | 392 | 13.819 | 24.222 | −1.250 | 1.00 | 34.49 | 6 |
| ATOM | 2912 | CD | PRO | A | 392 | 15.082 | 23.511 | −0.899 | 1.00 | 34.40 | 6 |
| ATOM | 2913 | C | PRO | A | 392 | 13.248 | 20.739 | −2.240 | 1.00 | 34.86 | 6 |
| ATOM | 2914 | O | PRO | A | 392 | 12.278 | 19.979 | −2.262 | 1.00 | 34.92 | 8 |
| ATOM | 2915 | N | ALA | A | 393 | 14.299 | 20.607 | −3.049 | 1.00 | 35.12 | 7 |
| ATOM | 2916 | CA | ALA | A | 393 | 14.345 | 19.599 | −4.111 | 1.00 | 35.33 | 6 |
| ATOM | 2917 | CB | ALA | A | 393 | 15.112 | 20.136 | −5.318 | 1.00 | 35.30 | 6 |
| ATOM | 2918 | C | ALA | A | 393 | 14.927 | 18.255 | −3.659 | 1.00 | 35.50 | 6 |
| ATOM | 2919 | O | ALA | A | 393 | 14.965 | 17.300 | −4.438 | 1.00 | 35.59 | 8 |
| ATOM | 2920 | N | LEU | A | 394 | 15.370 | 18.181 | −2.404 | 1.00 | 35.73 | 7 |
| ATOM | 2921 | CA | LEU | A | 394 | 15.972 | 16.953 | −1.867 | 1.00 | 35.99 | 6 |
| ATOM | 2922 | CB | LEU | A | 394 | 16.553 | 17.197 | −0.467 | 1.00 | 35.98 | 6 |
| ATOM | 2923 | CG | LEU | A | 394 | 17.430 | 16.108 | 0.171 | 1.00 | 35.86 | 6 |
| ATOM | 2924 | CD1 | LEU | A | 394 | 18.642 | 15.763 | −0.696 | 1.00 | 35.75 | 6 |
| ATOM | 2925 | CD2 | LEU | A | 394 | 17.873 | 16.533 | 1.563 | 1.00 | 35.96 | 6 |
| ATOM | 2926 | C | LEU | A | 394 | 14.970 | 15.795 | −1.852 | 1.00 | 36.28 | 6 |
| ATOM | 2927 | O | LEU | A | 394 | 13.812 | 15.967 | −1.466 | 1.00 | 36.29 | 8 |
| ATOM | 2928 | N | ASP | A | 395 | 15.433 | 14.619 | −2.274 | 1.00 | 36.61 | 7 |
| ATOM | 2929 | CA | ASP | A | 395 | 14.552 | 13.483 | −2.555 | 1.00 | 36.96 | 6 |
| ATOM | 2930 | CB | ASP | A | 395 | 14.614 | 13.124 | −4.052 | 1.00 | 37.19 | 6 |
| ATOM | 2931 | CG | ASP | A | 395 | 16.049 | 12.907 | −4.553 | 1.00 | 37.77 | 6 |
| ATOM | 2932 | OD1 | ASP | A | 395 | 17.012 | 13.263 | −3.829 | 1.00 | 38.34 | 8 |
| ATOM | 2933 | OD2 | ASP | A | 395 | 16.210 | 12.383 | −5.679 | 1.00 | 38.22 | 8 |
| ATOM | 2934 | C | ASP | A | 395 | 14.858 | 12.247 | −1.698 | 1.00 | 36.85 | 6 |
| ATOM | 2935 | O | ASP | A | 395 | 14.892 | 11.120 | −2.207 | 1.00 | 36.99 | 8 |
| ATOM | 2936 | N | ILE | A | 396 | 15.053 | 12.458 | −0.398 | 1.00 | 36.67 | 7 |
| ATOM | 2937 | CA | ILE | A | 396 | 15.412 | 11.362 | 0.513 | 1.00 | 36.40 | 6 |
| ATOM | 2938 | CB | ILE | A | 396 | 16.673 | 11.688 | 1.359 | 1.00 | 36.50 | 6 |
| ATOM | 2939 | CG1 | ILE | A | 396 | 16.477 | 12.981 | 2.158 | 1.00 | 36.43 | 6 |
| ATOM | 2940 | CD1 | ILE | A | 396 | 17.479 | 13.165 | 3.279 | 1.00 | 36.78 | 6 |
| ATOM | 2941 | CG2 | ILE | A | 396 | 17.917 | 11.758 | 0.460 | 1.00 | 36.55 | 6 |
| ATOM | 2942 | C | ILE | A | 396 | 14.257 | 10.913 | 1.419 | 1.00 | 36.12 | 6 |
| ATOM | 2943 | O | ILE | A | 396 | 13.197 | 11.545 | 1.454 | 1.00 | 36.03 | 8 |
| ATOM | 2944 | N | THR | A | 397 | 14.482 | 9.824 | 2.154 | 1.00 | 35.81 | 7 |
| ATOM | 2945 | CA | THR | A | 397 | 13.424 | 9.159 | 2.913 | 1.00 | 35.49 | 6 |
| ATOM | 2946 | CB | THR | A | 397 | 13.129 | 7.752 | 2.333 | 1.00 | 35.54 | 6 |
| ATOM | 2947 | OG1 | THR | A | 397 | 12.949 | 7.841 | 0.913 | 1.00 | 36.23 | 8 |
| ATOM | 2948 | CG2 | THR | A | 397 | 11.879 | 7.159 | 2.957 | 1.00 | 35.57 | 6 |
| ATOM | 2949 | C | THR | A | 397 | 13.769 | 9.030 | 4.399 | 1.00 | 35.06 | 6 |
| ATOM | 2950 | O | THR | A | 397 | 14.891 | 8.660 | 4.756 | 1.00 | 35.10 | 8 |
| ATOM | 2951 | N | PHE | A | 398 | 12.796 | 9.340 | 5.255 | 1.00 | 34.49 | 7 |
| ATOM | 2952 | CA | PHE | A | 398 | 12.927 | 9.145 | 6.702 | 1.00 | 33.98 | 6 |
| ATOM | 2953 | CB | PHE | A | 398 | 12.780 | 10.475 | 7.455 | 1.00 | 34.19 | 6 |
| ATOM | 2954 | CG | PHE | A | 398 | 13.592 | 11.599 | 6.881 | 1.00 | 34.43 | 6 |
| ATOM | 2955 | CD1 | PHE | A | 398 | 14.972 | 11.660 | 7.086 | 1.00 | 34.71 | 6 |
| ATOM | 2956 | CE1 | PHE | A | 398 | 15.725 | 12.708 | 6.557 | 1.00 | 34.76 | 6 |
| ATOM | 2957 | CZ | PHE | A | 398 | 15.097 | 13.710 | 5.820 | 1.00 | 34.92 | 6 |
| ATOM | 2958 | CE2 | PHE | A | 398 | 13.720 | 13.660 | 5.613 | 1.00 | 34.74 | 6 |
| ATOM | 2959 | CD2 | PHE | A | 398 | 12.976 | 12.610 | 6.146 | 1.00 | 34.51 | 6 |
| ATOM | 2960 | C | PHE | A | 398 | 11.863 | 8.176 | 7.204 | 1.00 | 33.50 | 6 |
| ATOM | 2961 | O | PHE | A | 398 | 10.778 | 8.079 | 6.622 | 1.00 | 33.42 | 8 |
| ATOM | 2962 | N | VAL | A | 399 | 12.169 | 7.473 | 8.292 | 1.00 | 32.78 | 7 |
| ATOM | 2963 | CA | VAL | A | 399 | 11.183 | 6.622 | 8.952 | 1.00 | 32.26 | 6 |
| ATOM | 2964 | CB | VAL | A | 399 | 11.723 | 5.187 | 9.219 | 1.00 | 32.22 | 6 |
| ATOM | 2965 | CG1 | VAL | A | 399 | 10.639 | 4.312 | 9.848 | 1.00 | 32.33 | 6 |
| ATOM | 2966 | CG2 | VAL | A | 399 | 12.227 | 4.553 | 7.923 | 1.00 | 32.59 | 6 |
| ATOM | 2967 | C | VAL | A | 399 | 10.707 | 7.268 | 10.253 | 1.00 | 31.72 | 6 |
| ATOM | 2968 | O | VAL | A | 399 | 9.505 | 7.380 | 10.490 | 1.00 | 31.85 | 8 |
| ATOM | 2969 | N | ASP | A | 400 | 11.659 | 7.707 | 11.078 | 1.00 | 31.03 | 7 |
| ATOM | 2970 | CA | ASP | A | 400 | 11.350 | 8.326 | 12.367 | 1.00 | 30.39 | 6 |
| ATOM | 2971 | CB | ASP | A | 400 | 12.633 | 8.762 | 13.080 | 1.00 | 30.47 | 6 |
| ATOM | 2972 | CG | ASP | A | 400 | 12.404 | 9.105 | 14.539 | 1.00 | 30.50 | 6 |
| ATOM | 2973 | OD1 | ASP | A | 400 | 11.746 | 10.131 | 14.819 | 1.00 | 29.80 | 8 |
| ATOM | 2974 | OD2 | ASP | A | 400 | 12.889 | 8.352 | 15.408 | 1.00 | 31.06 | 8 |

TABLE 7-continued

Coordinates of the crystal structure of E. coli ExoI bound to compound 10

| ATOM | 2975 | C | ASP | A | 400 | 10.406 | 9.511 | 12.195 | 1.00 | 29.85 | 6 |
|---|---|---|---|---|---|---|---|---|---|---|---|
| ATOM | 2976 | O | ASP | A | 400 | 10.649 | 10.397 | 11.375 | 1.00 | 29.84 | 8 |
| ATOM | 2977 | N | LYS | A | 401 | 9.332 | 9.513 | 12.981 | 1.00 | 29.15 | 7 |
| ATOM | 2978 | CA | LYS | A | 401 | 8.240 | 10.477 | 12.829 | 1.00 | 28.50 | 6 |
| ATOM | 2979 | CB | LYS | A | 401 | 7.026 | 10.042 | 13.662 | 1.00 | 28.69 | 6 |
| ATOM | 2980 | CG | LYS | A | 401 | 6.427 | 8.690 | 13.246 | 1.00 | 29.56 | 6 |
| ATOM | 2981 | CD | LYS | A | 401 | 5.299 | 8.849 | 12.222 | 1.00 | 31.12 | 6 |
| ATOM | 2982 | CE | LYS | A | 401 | 3.947 | 9.071 | 12.908 | 1.00 | 31.76 | 6 |
| ATOM | 2983 | NZ | LYS | A | 401 | 2.831 | 9.216 | 11.932 | 1.00 | 32.57 | 7 |
| ATOM | 2984 | C | LYS | A | 401 | 8.646 | 11.908 | 13.187 | 1.00 | 27.77 | 6 |
| ATOM | 2985 | O | LYS | A | 401 | 8.044 | 12.867 | 12.701 | 1.00 | 27.88 | 8 |
| ATOM | 2986 | N | ARG | A | 402 | 9.673 | 12.045 | 14.027 | 1.00 | 26.67 | 7 |
| ATOM | 2987 | CA | ARG | A | 402 | 10.144 | 13.360 | 14.470 | 1.00 | 25.83 | 6 |
| ATOM | 2988 | CB | ARG | A | 402 | 11.170 | 13.215 | 15.595 | 1.00 | 25.44 | 6 |
| ATOM | 2989 | CG | ARG | A | 402 | 10.636 | 12.604 | 16.876 | 1.00 | 24.77 | 6 |
| ATOM | 2990 | CD | ARG | A | 402 | 11.769 | 12.361 | 17.865 | 1.00 | 22.45 | 6 |
| ATOM | 2991 | NE | ARG | A | 402 | 12.590 | 11.208 | 17.496 | 1.00 | 20.66 | 7 |
| ATOM | 2992 | CZ | ARG | A | 402 | 13.667 | 10.809 | 18.167 | 1.00 | 19.71 | 6 |
| ATOM | 2993 | NH1 | ARG | A | 402 | 14.073 | 11.475 | 19.242 | 1.00 | 18.90 | 7 |
| ATOM | 2994 | NH2 | ARG | A | 402 | 14.340 | 9.742 | 17.763 | 1.00 | 19.13 | 7 |
| ATOM | 2995 | C | ARG | A | 402 | 10.769 | 14.169 | 13.333 | 1.00 | 25.37 | 6 |
| ATOM | 2996 | O | ARG | A | 402 | 10.671 | 15.399 | 13.315 | 1.00 | 25.39 | 8 |
| ATOM | 2997 | N | ILE | A | 403 | 11.411 | 13.476 | 12.395 | 1.00 | 24.74 | 7 |
| ATOM | 2998 | CA | ILE | A | 403 | 12.288 | 14.129 | 11.411 | 1.00 | 24.21 | 6 |
| ATOM | 2999 | CB | ILE | A | 403 | 13.160 | 13.113 | 10.620 | 1.00 | 24.36 | 6 |
| ATOM | 3000 | CG1 | ILE | A | 403 | 13.896 | 12.177 | 11.586 | 1.00 | 24.46 | 6 |
| ATOM | 3001 | CD1 | ILE | A | 403 | 14.659 | 11.041 | 10.908 | 1.00 | 23.96 | 6 |
| ATOM | 3002 | CG2 | ILE | A | 403 | 14.170 | 13.854 | 9.730 | 1.00 | 24.51 | 6 |
| ATOM | 3003 | C | ILE | A | 403 | 11.565 | 15.102 | 10.458 | 1.00 | 23.96 | 6 |
| ATOM | 3004 | O | ILE | A | 403 | 12.099 | 16.171 | 10.148 | 1.00 | 23.88 | 8 |
| ATOM | 3005 | N | GLU | A | 404 | 10.360 | 14.737 | 10.013 | 1.00 | 23.47 | 7 |
| ATOM | 3006 | CA | GLU | A | 404 | 9.563 | 15.613 | 9.138 | 1.00 | 22.96 | 6 |
| ATOM | 3007 | CB | GLU | A | 404 | 8.213 | 14.966 | 8.788 | 1.00 | 23.13 | 6 |
| ATOM | 3008 | CG | GLU | A | 404 | 7.498 | 15.584 | 7.560 | 1.00 | 24.03 | 6 |
| ATOM | 3009 | CD | GLU | A | 404 | 6.828 | 16.938 | 7.853 | 1.00 | 25.31 | 6 |
| ATOM | 3010 | OE1 | GLU | A | 404 | 6.226 | 17.101 | 8.942 | 1.00 | 26.78 | 8 |
| ATOM | 3011 | OE2 | GLU | A | 404 | 6.912 | 17.842 | 6.991 | 1.00 | 24.96 | 8 |
| ATOM | 3012 | C | GLU | A | 404 | 9.342 | 16.980 | 9.784 | 1.00 | 22.57 | 6 |
| ATOM | 3013 | O | GLU | A | 404 | 9.489 | 18.018 | 9.131 | 1.00 | 21.94 | 8 |
| ATOM | 3014 | N | LYS | A | 405 | 8.991 | 16.966 | 11.069 | 1.00 | 22.05 | 7 |
| ATOM | 3015 | CA | LYS | A | 405 | 8.772 | 18.189 | 11.833 | 1.00 | 21.97 | 6 |
| ATOM | 3016 | CB | LYS | A | 405 | 8.099 | 17.866 | 13.175 | 1.00 | 22.00 | 6 |
| ATOM | 3017 | CG | LYS | A | 405 | 6.824 | 17.030 | 13.051 | 1.00 | 22.65 | 6 |
| ATOM | 3018 | CD | LYS | A | 405 | 6.321 | 16.543 | 14.417 | 1.00 | 23.92 | 6 |
| ATOM | 3019 | CE | LYS | A | 405 | 5.144 | 15.581 | 14.255 | 1.00 | 26.28 | 6 |
| ATOM | 3020 | NZ | LYS | A | 405 | 4.636 | 15.069 | 15.564 | 1.00 | 26.95 | 7 |
| ATOM | 3021 | C | LYS | A | 405 | 10.092 | 18.923 | 12.069 | 1.00 | 21.21 | 6 |
| ATOM | 3022 | O | LYS | A | 405 | 10.158 | 20.153 | 11.963 | 1.00 | 21.26 | 8 |
| ATOM | 3023 | N | LEU | A | 406 | 11.144 | 18.166 | 12.373 | 1.00 | 20.28 | 7 |
| ATOM | 3024 | CA | LEU | A | 406 | 12.463 | 18.758 | 12.575 | 1.00 | 19.71 | 6 |
| ATOM | 3025 | CB | LEU | A | 406 | 13.491 | 17.703 | 13.001 | 1.00 | 20.01 | 6 |
| ATOM | 3026 | CG | LEU | A | 406 | 13.441 | 17.215 | 14.454 | 1.00 | 19.85 | 6 |
| ATOM | 3027 | CD1 | LEU | A | 406 | 14.268 | 15.952 | 14.615 | 1.00 | 19.87 | 6 |
| ATOM | 3028 | CD2 | LEU | A | 406 | 13.897 | 18.293 | 15.446 | 1.00 | 20.53 | 6 |
| ATOM | 3029 | C | LEU | A | 406 | 12.925 | 19.462 | 11.313 | 1.00 | 19.32 | 6 |
| ATOM | 3030 | O | LEU | A | 406 | 13.421 | 20.589 | 11.370 | 1.00 | 19.21 | 8 |
| ATOM | 3031 | N | LEU | A | 407 | 12.742 | 18.805 | 10.172 | 1.00 | 18.83 | 7 |
| ATOM | 3032 | CA | LEU | A | 407 | 13.170 | 19.370 | 8.902 | 1.00 | 18.57 | 6 |
| ATOM | 3033 | CB | LEU | A | 407 | 13.028 | 18.348 | 7.768 | 1.00 | 18.53 | 6 |
| ATOM | 3034 | CG | LEU | A | 407 | 13.509 | 18.842 | 6.397 | 1.00 | 18.48 | 6 |
| ATOM | 3035 | CD1 | LEU | A | 407 | 14.974 | 19.258 | 6.440 | 1.00 | 19.88 | 6 |
| ATOM | 3036 | CD2 | LEU | A | 407 | 13.270 | 17.799 | 5.307 | 1.00 | 18.90 | 6 |
| ATOM | 3037 | C | LEU | A | 407 | 12.405 | 20.648 | 8.571 | 1.00 | 18.84 | 6 |
| ATOM | 3038 | O | LEU | A | 407 | 12.995 | 21.618 | 8.089 | 1.00 | 18.90 | 8 |
| ATOM | 3039 | N | PHE | A | 408 | 11.095 | 20.647 | 8.819 | 1.00 | 18.64 | 7 |
| ATOM | 3040 | CA | PHE | A | 408 | 10.287 | 21.827 | 8.534 | 1.00 | 19.04 | 6 |
| ATOM | 3041 | CB | PHE | A | 408 | 8.797 | 21.578 | 8.735 | 1.00 | 19.21 | 6 |
| ATOM | 3042 | CG | PHE | A | 408 | 7.962 | 22.812 | 8.531 | 1.00 | 19.93 | 6 |
| ATOM | 3043 | CD1 | PHE | A | 408 | 7.833 | 23.374 | 7.257 | 1.00 | 20.23 | 6 |
| ATOM | 3044 | CE1 | PHE | A | 408 | 7.092 | 24.536 | 7.059 | 1.00 | 20.75 | 6 |
| ATOM | 3045 | CZ | PHE | A | 408 | 6.477 | 25.158 | 8.138 | 1.00 | 19.52 | 6 |
| ATOM | 3046 | CE2 | PHE | A | 408 | 6.609 | 24.617 | 9.422 | 1.00 | 19.66 | 6 |
| ATOM | 3047 | CD2 | PHE | A | 408 | 7.358 | 23.451 | 9.611 | 1.00 | 19.92 | 6 |
| ATOM | 3048 | C | PHE | A | 408 | 10.712 | 23.013 | 9.385 | 1.00 | 18.98 | 6 |
| ATOM | 3049 | O | PHE | A | 408 | 10.918 | 24.108 | 8.861 | 1.00 | 18.89 | 8 |
| ATOM | 3050 | N | ASN | A | 409 | 10.812 | 22.785 | 10.700 | 1.00 | 18.64 | 7 |
| ATOM | 3051 | CA | ASN | A | 409 | 11.253 | 23.812 | 11.654 | 1.00 | 18.84 | 6 |
| ATOM | 3052 | CB | ASN | A | 409 | 11.259 | 23.252 | 13.075 | 1.00 | 19.12 | 6 |

TABLE 7-continued

Coordinates of the crystal structure of *E. coli* ExoI bound to compound 10

| ATOM | 3053 | CG | ASN | A | 409 | 9.876 | 23.187 | 13.688 | 1.00 | 19.32 | 6 |
|---|---|---|---|---|---|---|---|---|---|---|---|
| ATOM | 3054 | OD1 | ASN | A | 409 | 8.886 | 23.611 | 13.089 | 1.00 | 20.07 | 8 |
| ATOM | 3055 | ND2 | ASN | A | 409 | 9.805 | 22.668 | 14.908 | 1.00 | 19.67 | 7 |
| ATOM | 3056 | C | ASN | A | 409 | 12.634 | 24.348 | 11.318 | 1.00 | 18.74 | 6 |
| ATOM | 3057 | O | ASN | A | 409 | 12.894 | 25.548 | 11.433 | 1.00 | 18.69 | 8 |
| ATOM | 3058 | N | TYR | A | 410 | 13.508 | 23.444 | 10.885 | 1.00 | 18.82 | 7 |
| ATOM | 3059 | CA | TYR | A | 410 | 14.873 | 23.781 | 10.511 | 1.00 | 18.34 | 6 |
| ATOM | 3060 | CB | TYR | A | 410 | 15.638 | 22.487 | 10.222 | 1.00 | 18.67 | 6 |
| ATOM | 3061 | CG | TYR | A | 410 | 17.043 | 22.648 | 9.702 | 1.00 | 18.88 | 6 |
| ATOM | 3062 | CD1 | TYR | A | 410 | 18.090 | 23.044 | 10.545 | 1.00 | 19.44 | 6 |
| ATOM | 3063 | CE1 | TYR | A | 410 | 19.389 | 23.173 | 10.063 | 1.00 | 18.92 | 6 |
| ATOM | 3064 | CZ | TYR | A | 410 | 19.652 | 22.882 | 8.727 | 1.00 | 18.31 | 6 |
| ATOM | 3065 | OH | TYR | A | 410 | 20.931 | 22.991 | 8.232 | 1.00 | 19.44 | 8 |
| ATOM | 3066 | CE2 | TYR | A | 410 | 18.632 | 22.473 | 7.883 | 1.00 | 19.61 | 6 |
| ATOM | 3067 | CD2 | TYR | A | 410 | 17.340 | 22.352 | 8.374 | 1.00 | 18.93 | 6 |
| ATOM | 3068 | C | TYR | A | 410 | 14.898 | 24.744 | 9.315 | 1.00 | 18.15 | 6 |
| ATOM | 3069 | O | TYR | A | 410 | 15.539 | 25.796 | 9.365 | 1.00 | 18.32 | 8 |
| ATOM | 3070 | N | ARG | A | 411 | 14.160 | 24.405 | 8.263 | 1.00 | 17.91 | 7 |
| ATOM | 3071 | CA | ARG | A | 411 | 14.062 | 25.278 | 7.093 | 1.00 | 17.70 | 6 |
| ATOM | 3072 | CB | ARG | A | 411 | 13.369 | 24.553 | 5.928 | 1.00 | 17.55 | 6 |
| ATOM | 3073 | CG | ARG | A | 411 | 14.069 | 23.272 | 5.485 | 1.00 | 17.37 | 6 |
| ATOM | 3074 | CD | ARG | A | 411 | 13.507 | 22.730 | 4.162 | 1.00 | 18.08 | 6 |
| ATOM | 3075 | NE | ARG | A | 411 | 13.321 | 23.806 | 3.195 | 1.00 | 19.85 | 7 |
| ATOM | 3076 | CZ | ARG | A | 411 | 12.218 | 24.013 | 2.478 | 1.00 | 20.73 | 6 |
| ATOM | 3077 | NH1 | ARG | A | 411 | 11.185 | 23.184 | 2.559 | 1.00 | 20.45 | 7 |
| ATOM | 3078 | NH2 | ARG | A | 411 | 12.166 | 25.046 | 1.653 | 1.00 | 20.58 | 7 |
| ATOM | 3079 | C | ARG | A | 411 | 13.343 | 26.595 | 7.424 | 1.00 | 17.61 | 6 |
| ATOM | 3080 | O | ARG | A | 411 | 13.824 | 27.670 | 7.082 | 1.00 | 18.08 | 8 |
| ATOM | 3081 | N | ALA | A | 412 | 12.188 | 26.501 | 8.079 | 1.00 | 17.49 | 7 |
| ATOM | 3082 | CA | ALA | A | 412 | 11.402 | 27.685 | 8.447 | 1.00 | 17.63 | 6 |
| ATOM | 3083 | CB | ALA | A | 412 | 10.116 | 27.268 | 9.124 | 1.00 | 17.68 | 6 |
| ATOM | 3084 | C | ALA | A | 412 | 12.171 | 28.665 | 9.334 | 1.00 | 17.94 | 6 |
| ATOM | 3085 | O | ALA | A | 412 | 12.152 | 29.873 | 9.095 | 1.00 | 18.32 | 8 |
| ATOM | 3086 | N | ARG | A | 413 | 12.856 | 28.140 | 10.347 | 1.00 | 18.19 | 7 |
| ATOM | 3087 | CA | ARG | A | 413 | 13.562 | 28.993 | 11.309 | 1.00 | 17.94 | 6 |
| ATOM | 3088 | CB | ARG | A | 413 | 13.883 | 28.226 | 12.585 | 1.00 | 18.37 | 6 |
| ATOM | 3089 | CG | ARG | A | 413 | 12.677 | 27.928 | 13.429 | 1.00 | 17.52 | 6 |
| ATOM | 3090 | CD | ARG | A | 413 | 13.075 | 27.092 | 14.622 | 1.00 | 18.65 | 6 |
| ATOM | 3091 | NE | ARG | A | 413 | 11.943 | 26.813 | 15.494 | 1.00 | 19.98 | 7 |
| ATOM | 3092 | CZ | ARG | A | 413 | 11.836 | 25.720 | 16.235 | 1.00 | 20.14 | 6 |
| ATOM | 3093 | NH1 | ARG | A | 413 | 12.784 | 24.787 | 16.185 | 1.00 | 20.05 | 7 |
| ATOM | 3094 | NH2 | ARG | A | 413 | 10.776 | 25.552 | 17.016 | 1.00 | 20.78 | 7 |
| ATOM | 3095 | C | ARG | A | 413 | 14.832 | 29.598 | 10.745 | 1.00 | 18.29 | 6 |
| ATOM | 3096 | O | ARG | A | 413 | 15.133 | 30.762 | 11.006 | 1.00 | 18.74 | 8 |
| ATOM | 3097 | N | ASN | A | 414 | 15.576 | 28.811 | 9.968 | 1.00 | 18.54 | 7 |
| ATOM | 3098 | CA | ASN | A | 414 | 16.899 | 29.227 | 9.522 | 1.00 | 19.31 | 6 |
| ATOM | 3099 | CB | ASN | A | 414 | 17.873 | 28.050 | 9.558 | 1.00 | 19.40 | 6 |
| ATOM | 3100 | CG | ASN | A | 414 | 18.164 | 27.577 | 10.965 | 1.00 | 21.04 | 6 |
| ATOM | 3101 | OD1 | ASN | A | 414 | 17.837 | 26.450 | 11.329 | 1.00 | 23.62 | 8 |
| ATOM | 3102 | ND2 | ASN | A | 414 | 18.768 | 28.442 | 11.773 | 1.00 | 21.00 | 7 |
| ATOM | 3103 | C | ASN | A | 414 | 16.897 | 29.864 | 8.142 | 1.00 | 19.66 | 6 |
| ATOM | 3104 | O | ASN | A | 414 | 17.654 | 30.807 | 7.885 | 1.00 | 19.89 | 8 |
| ATOM | 3105 | N | PHE | A | 415 | 16.037 | 29.348 | 7.262 | 1.00 | 19.68 | 7 |
| ATOM | 3106 | CA | PHE | A | 415 | 16.052 | 29.712 | 5.842 | 1.00 | 20.51 | 6 |
| ATOM | 3107 | CB | PHE | A | 415 | 16.673 | 28.567 | 5.027 | 1.00 | 20.04 | 6 |
| ATOM | 3108 | CG | PHE | A | 415 | 17.913 | 27.971 | 5.654 | 1.00 | 20.86 | 6 |
| ATOM | 3109 | CD1 | PHE | A | 415 | 19.077 | 28.729 | 5.795 | 1.00 | 20.73 | 6 |
| ATOM | 3110 | CE1 | PHE | A | 415 | 20.223 | 28.181 | 6.379 | 1.00 | 20.29 | 6 |
| ATOM | 3111 | CZ | PHE | A | 415 | 20.213 | 26.861 | 6.826 | 1.00 | 19.99 | 6 |
| ATOM | 3112 | CE2 | PHE | A | 415 | 19.069 | 26.096 | 6.688 | 1.00 | 21.34 | 6 |
| ATOM | 3113 | CD2 | PHE | A | 415 | 17.922 | 26.649 | 6.100 | 1.00 | 20.91 | 6 |
| ATOM | 3114 | C | PHE | A | 415 | 14.641 | 30.052 | 5.313 | 1.00 | 21.15 | 6 |
| ATOM | 3115 | O | PHE | A | 415 | 14.144 | 29.397 | 4.388 | 1.00 | 21.43 | 8 |
| ATOM | 3116 | N | PRO | A | 416 | 13.996 | 31.086 | 5.896 | 1.00 | 22.16 | 7 |
| ATOM | 3117 | CA | PRO | A | 416 | 12.593 | 31.376 | 5.550 | 1.00 | 22.37 | 6 |
| ATOM | 3118 | CB | PRO | A | 416 | 12.203 | 32.507 | 6.514 | 1.00 | 22.54 | 6 |
| ATOM | 3119 | CG | PRO | A | 416 | 13.488 | 33.086 | 7.002 | 1.00 | 22.48 | 6 |
| ATOM | 3120 | CD | PRO | A | 416 | 14.540 | 32.029 | 6.895 | 1.00 | 21.91 | 6 |
| ATOM | 3121 | C | PRO | A | 416 | 12.376 | 31.793 | 4.084 | 1.00 | 22.77 | 6 |
| ATOM | 3122 | O | PRO | A | 416 | 11.300 | 31.563 | 3.547 | 1.00 | 22.99 | 8 |
| ATOM | 3123 | N | GLY | A | 417 | 13.402 | 32.367 | 3.451 | 1.00 | 23.02 | 7 |
| ATOM | 3124 | CA | GLY | A | 417 | 13.334 | 32.769 | 2.037 | 1.00 | 23.31 | 6 |
| ATOM | 3125 | C | GLY | A | 417 | 13.267 | 31.608 | 1.052 | 1.00 | 23.43 | 6 |
| ATOM | 3126 | O | GLY | A | 417 | 13.128 | 31.816 | −0.161 | 1.00 | 23.99 | 8 |
| ATOM | 3127 | N | THR | A | 418 | 13.367 | 30.386 | 1.576 | 1.00 | 23.63 | 7 |
| ATOM | 3128 | CA | THR | A | 418 | 13.331 | 29.168 | 0.759 | 1.00 | 23.57 | 6 |
| ATOM | 3129 | CB | THR | A | 418 | 14.425 | 28.154 | 1.190 | 1.00 | 23.50 | 6 |
| ATOM | 3130 | OG1 | THR | A | 418 | 14.070 | 27.560 | 2.443 | 1.00 | 23.59 | 8 |

TABLE 7-continued

Coordinates of the crystal structure of *E. coli* ExoI bound to compound 10

| ATOM | 3131 | CG2 | THR | A | 418 | 15.786 | 28.831 | 1.310 | 1.00 | 23.19 | 6 |
|---|---|---|---|---|---|---|---|---|---|---|---|
| ATOM | 3132 | C | THR | A | 418 | 11.966 | 28.475 | 0.824 | 1.00 | 23.55 | 6 |
| ATOM | 3133 | O | THR | A | 418 | 11.746 | 27.461 | 0.160 | 1.00 | 23.89 | 8 |
| ATOM | 3134 | N | LEU | A | 419 | 11.061 | 29.019 | 1.638 | 1.00 | 23.34 | 7 |
| ATOM | 3135 | CA | LEU | A | 419 | 9.722 | 28.450 | 1.799 | 1.00 | 22.71 | 6 |
| ATOM | 3136 | CB | LEU | A | 419 | 9.135 | 28.813 | 3.166 | 1.00 | 22.30 | 6 |
| ATOM | 3137 | CG | LEU | A | 419 | 9.888 | 28.432 | 4.447 | 1.00 | 21.68 | 6 |
| ATOM | 3138 | CD1 | LEU | A | 419 | 9.022 | 28.766 | 5.653 | 1.00 | 21.75 | 6 |
| ATOM | 3139 | CD2 | LEU | A | 419 | 10.271 | 26.955 | 4.450 | 1.00 | 19.91 | 6 |
| ATOM | 3140 | C | LEU | A | 419 | 8.773 | 28.922 | 0.708 | 1.00 | 22.56 | 6 |
| ATOM | 3141 | O | LEU | A | 419 | 8.732 | 30.112 | 0.382 | 1.00 | 22.76 | 8 |
| ATOM | 3142 | N | ASP | A | 420 | 8.001 | 27.991 | 0.154 | 1.00 | 22.56 | 7 |
| ATOM | 3143 | CA | ASP | A | 420 | 6.935 | 28.350 | −0.783 | 1.00 | 22.05 | 6 |
| ATOM | 3144 | CB | ASP | A | 420 | 6.623 | 27.199 | −1.758 | 1.00 | 22.46 | 6 |
| ATOM | 3145 | CG | ASP | A | 420 | 6.020 | 25.979 | −1.072 | 1.00 | 22.60 | 6 |
| ATOM | 3146 | OD1 | ASP | A | 420 | 5.596 | 26.075 | 0.103 | 1.00 | 23.08 | 8 |
| ATOM | 3147 | OD2 | ASP | A | 420 | 5.965 | 24.918 | −1.721 | 1.00 | 23.60 | 8 |
| ATOM | 3148 | C | ASP | A | 420 | 5.688 | 28.811 | −0.019 | 1.00 | 21.92 | 6 |
| ATOM | 3149 | O | ASP | A | 420 | 5.678 | 28.805 | 1.215 | 1.00 | 21.76 | 8 |
| ATOM | 3150 | N | TYR | A | 421 | 4.648 | 29.214 | −0.749 | 1.00 | 21.37 | 7 |
| ATOM | 3151 | CA | TYR | A | 421 | 3.454 | 29.789 | −0.127 | 1.00 | 21.07 | 6 |
| ATOM | 3152 | CB | TYR | A | 421 | 2.402 | 30.151 | −1.179 | 1.00 | 20.95 | 6 |
| ATOM | 3153 | CG | TYR | A | 421 | 1.164 | 30.799 | −0.597 | 1.00 | 21.02 | 6 |
| ATOM | 3154 | CD1 | TYR | A | 421 | 1.121 | 32.172 | −0.362 | 1.00 | 21.22 | 6 |
| ATOM | 3155 | CE1 | TYR | A | 421 | −0.013 | 32.774 | 0.172 | 1.00 | 21.77 | 6 |
| ATOM | 3156 | CZ | TYR | A | 421 | −1.120 | 32.001 | 0.484 | 1.00 | 21.08 | 6 |
| ATOM | 3157 | OH | TYR | A | 421 | −2.238 | 32.601 | 1.016 | 1.00 | 21.11 | 8 |
| ATOM | 3158 | CE2 | TYR | A | 421 | −1.104 | 30.633 | 0.262 | 1.00 | 20.96 | 6 |
| ATOM | 3159 | CD2 | TYR | A | 421 | 0.034 | 30.039 | −0.281 | 1.00 | 20.97 | 6 |
| ATOM | 3160 | C | TYR | A | 421 | 2.842 | 28.882 | 0.942 | 1.00 | 21.18 | 6 |
| ATOM | 3161 | O | TYR | A | 421 | 2.588 | 29.324 | 2.066 | 1.00 | 20.82 | 8 |
| ATOM | 3162 | N | ALA | A | 422 | 2.608 | 27.620 | 0.583 | 1.00 | 21.26 | 7 |
| ATOM | 3163 | CA | ALA | A | 422 | 2.016 | 26.649 | 1.499 | 1.00 | 21.65 | 6 |
| ATOM | 3164 | CB | ALA | A | 422 | 1.841 | 25.303 | 0.814 | 1.00 | 21.74 | 6 |
| ATOM | 3165 | C | ALA | A | 422 | 2.853 | 26.502 | 2.767 | 1.00 | 22.07 | 6 |
| ATOM | 3166 | O | ALA | A | 422 | 2.311 | 26.408 | 3.865 | 1.00 | 22.27 | 8 |
| ATOM | 3167 | N | GLU | A | 423 | 4.176 | 26.497 | 2.606 | 1.00 | 22.51 | 7 |
| ATOM | 3168 | CA | GLU | A | 423 | 5.094 | 26.386 | 3.741 | 1.00 | 23.04 | 6 |
| ATOM | 3169 | CB | GLU | A | 423 | 6.519 | 26.106 | 3.258 | 1.00 | 23.15 | 6 |
| ATOM | 3170 | CG | GLU | A | 423 | 6.761 | 24.658 | 2.867 | 1.00 | 23.80 | 6 |
| ATOM | 3171 | CD | GLU | A | 423 | 8.049 | 24.455 | 2.086 | 1.00 | 24.72 | 6 |
| ATOM | 3172 | OE1 | GLU | A | 423 | 8.510 | 25.404 | 1.418 | 1.00 | 26.01 | 8 |
| ATOM | 3173 | OE2 | GLU | A | 423 | 8.598 | 23.334 | 2.133 | 1.00 | 25.39 | 8 |
| ATOM | 3174 | C | GLU | A | 423 | 5.056 | 27.626 | 4.638 | 1.00 | 23.24 | 6 |
| ATOM | 3175 | O | GLU | A | 423 | 5.173 | 27.517 | 5.859 | 1.00 | 23.72 | 8 |
| ATOM | 3176 | N | GLN | A | 424 | 4.882 | 28.796 | 4.026 | 1.00 | 23.33 | 7 |
| ATOM | 3177 | CA | GLN | A | 424 | 4.737 | 30.051 | 4.773 | 1.00 | 23.64 | 6 |
| ATOM | 3178 | CB | GLN | A | 424 | 4.725 | 31.247 | 3.819 | 1.00 | 23.81 | 6 |
| ATOM | 3179 | CG | GLN | A | 424 | 6.064 | 31.540 | 3.152 | 1.00 | 24.01 | 6 |
| ATOM | 3180 | CD | GLN | A | 424 | 5.937 | 32.505 | 1.979 | 1.00 | 24.45 | 6 |
| ATOM | 3181 | OE1 | GLN | A | 424 | 4.842 | 32.949 | 1.636 | 1.00 | 25.87 | 8 |
| ATOM | 3182 | NE2 | GLN | A | 424 | 7.065 | 32.834 | 1.363 | 1.00 | 25.39 | 7 |
| ATOM | 3183 | C | GLN | A | 424 | 3.466 | 30.052 | 5.625 | 1.00 | 23.40 | 6 |
| ATOM | 3184 | O | GLN | A | 424 | 3.464 | 30.548 | 6.748 | 1.00 | 23.59 | 8 |
| ATOM | 3185 | N | GLN | A | 425 | 2.388 | 29.501 | 5.071 | 1.00 | 23.22 | 7 |
| ATOM | 3186 | CA | GLN | A | 425 | 1.113 | 29.407 | 5.779 | 1.00 | 23.02 | 6 |
| ATOM | 3187 | CB | GLN | A | 425 | −0.008 | 29.014 | 4.811 | 1.00 | 23.05 | 6 |
| ATOM | 3188 | CG | GLN | A | 425 | −0.342 | 30.106 | 3.805 | 1.00 | 23.06 | 6 |
| ATOM | 3189 | CD | GLN | A | 425 | −0.763 | 31.408 | 4.476 | 1.00 | 23.69 | 6 |
| ATOM | 3190 | OE1 | GLN | A | 425 | −0.058 | 32.417 | 4.399 | 1.00 | 24.45 | 8 |
| ATOM | 3191 | NE2 | GLN | A | 425 | −1.903 | 31.382 | 5.156 | 1.00 | 24.12 | 7 |
| ATOM | 3192 | C | GLN | A | 425 | 1.185 | 28.434 | 6.955 | 1.00 | 22.88 | 6 |
| ATOM | 3193 | O | GLN | A | 425 | 0.577 | 28.671 | 8.005 | 1.00 | 23.24 | 8 |
| ATOM | 3194 | N | ARG | A | 426 | 1.949 | 27.358 | 6.779 | 1.00 | 22.56 | 7 |
| ATOM | 3195 | CA | ARG | A | 426 | 2.153 | 26.371 | 7.830 | 1.00 | 22.54 | 6 |
| ATOM | 3196 | CB | ARG | A | 426 | 2.895 | 25.142 | 7.290 | 1.00 | 22.35 | 6 |
| ATOM | 3197 | CG | ARG | A | 426 | 3.003 | 24.000 | 8.294 | 1.00 | 22.51 | 6 |
| ATOM | 3198 | CD | ARG | A | 426 | 3.884 | 22.869 | 7.796 | 1.00 | 22.62 | 6 |
| ATOM | 3199 | NE | ARG | A | 426 | 4.286 | 21.983 | 8.891 | 1.00 | 21.79 | 7 |
| ATOM | 3200 | CZ | ARG | A | 426 | 4.929 | 20.829 | 8.730 | 1.00 | 22.00 | 6 |
| ATOM | 3201 | NH1 | ARG | A | 426 | 5.258 | 20.407 | 7.511 | 1.00 | 20.70 | 7 |
| ATOM | 3202 | NH2 | ARG | A | 426 | 5.245 | 20.095 | 9.791 | 1.00 | 20.99 | 7 |
| ATOM | 3203 | C | ARG | A | 426 | 2.923 | 26.999 | 8.993 | 1.00 | 22.53 | 6 |
| ATOM | 3204 | O | ARG | A | 426 | 2.602 | 26.758 | 10.160 | 1.00 | 22.93 | 8 |
| ATOM | 3205 | N | TRP | A | 427 | 3.918 | 27.821 | 8.663 | 1.00 | 22.67 | 7 |
| ATOM | 3206 | CA | TRP | A | 427 | 4.717 | 28.532 | 9.671 | 1.00 | 22.89 | 6 |
| ATOM | 3207 | CB | TRP | A | 427 | 5.958 | 29.159 | 9.026 | 1.00 | 23.11 | 6 |
| ATOM | 3208 | CG | TRP | A | 427 | 6.907 | 29.791 | 10.005 | 1.00 | 23.53 | 6 |

TABLE 7-continued

Coordinates of the crystal structure of E. coli ExoI bound to compound 10

| ATOM | 3209 | CD1 | TRP | A | 427 | 7.222 | 31.114 | 10.102 | 1.00 | 23.91 | 6 |
|---|---|---|---|---|---|---|---|---|---|---|---|
| ATOM | 3210 | NE1 | TRP | A | 427 | 8.119 | 31.316 | 11.118 | 1.00 | 23.46 | 7 |
| ATOM | 3211 | CE2 | TRP | A | 427 | 8.403 | 30.111 | 11.707 | 1.00 | 24.42 | 6 |
| ATOM | 3212 | CD2 | TRP | A | 427 | 7.654 | 29.125 | 11.031 | 1.00 | 24.10 | 6 |
| ATOM | 3213 | CE3 | TRP | A | 427 | 7.761 | 27.789 | 11.445 | 1.00 | 24.38 | 6 |
| ATOM | 3214 | CZ3 | TRP | A | 427 | 8.613 | 27.486 | 12.503 | 1.00 | 23.53 | 6 |
| ATOM | 3215 | CH2 | TRP | A | 427 | 9.341 | 28.495 | 13.160 | 1.00 | 23.89 | 6 |
| ATOM | 3216 | CZ2 | TRP | A | 427 | 9.255 | 29.808 | 12.770 | 1.00 | 24.49 | 6 |
| ATOM | 3217 | C | TRP | A | 427 | 3.900 | 29.596 | 10.406 | 1.00 | 23.13 | 6 |
| ATOM | 3218 | O | TRP | A | 427 | 4.038 | 29.765 | 11.625 | 1.00 | 23.22 | 8 |
| ATOM | 3219 | N | LEU | A | 428 | 3.052 | 30.312 | 9.668 | 1.00 | 23.41 | 7 |
| ATOM | 3220 | CA | LEU | A | 428 | 2.164 | 31.304 | 10.278 | 1.00 | 23.78 | 6 |
| ATOM | 3221 | CB | LEU | A | 428 | 1.357 | 32.068 | 9.217 | 1.00 | 23.93 | 6 |
| ATOM | 3222 | CG | LEU | A | 428 | 2.116 | 33.127 | 8.403 | 1.00 | 25.03 | 6 |
| ATOM | 3223 | CD1 | LEU | A | 428 | 1.188 | 33.838 | 7.424 | 1.00 | 25.26 | 6 |
| ATOM | 3224 | CD2 | LEU | A | 428 | 2.819 | 34.138 | 9.306 | 1.00 | 25.54 | 6 |
| ATOM | 3225 | C | LEU | A | 428 | 1.242 | 30.663 | 11.312 | 1.00 | 23.87 | 6 |
| ATOM | 3226 | O | LEU | A | 428 | 1.048 | 31.215 | 12.395 | 1.00 | 23.81 | 8 |
| ATOM | 3227 | N | GLU | A | 429 | 0.704 | 29.486 | 10.981 | 1.00 | 23.88 | 7 |
| ATOM | 3228 | CA | GLU | A | 429 | −0.114 | 28.714 | 11.919 | 1.00 | 23.99 | 6 |
| ATOM | 3229 | CB | GLU | A | 429 | −0.745 | 27.504 | 11.231 | 1.00 | 24.08 | 6 |
| ATOM | 3230 | CG | GLU | A | 429 | −1.851 | 26.828 | 12.052 | 1.00 | 25.69 | 6 |
| ATOM | 3231 | CD | GLU | A | 429 | −2.977 | 27.792 | 12.447 | 1.00 | 28.08 | 6 |
| ATOM | 3232 | OE1 | GLU | A | 429 | −3.300 | 28.707 | 11.653 | 1.00 | 29.53 | 8 |
| ATOM | 3233 | OE2 | GLU | A | 429 | −3.539 | 27.630 | 13.553 | 1.00 | 29.02 | 8 |
| ATOM | 3234 | C | GLU | A | 429 | 0.693 | 28.267 | 13.141 | 1.00 | 23.68 | 6 |
| ATOM | 3235 | O | GLU | A | 429 | 0.221 | 28.367 | 14.276 | 1.00 | 23.61 | 8 |
| ATOM | 3236 | N | HIS | A | 430 | 1.905 | 27.777 | 12.894 | 1.00 | 23.62 | 7 |
| ATOM | 3237 | CA | HIS | A | 430 | 2.829 | 27.400 | 13.958 | 1.00 | 23.67 | 6 |
| ATOM | 3238 | CB | HIS | A | 430 | 4.187 | 27.003 | 13.366 | 1.00 | 23.58 | 6 |
| ATOM | 3239 | CG | HIS | A | 430 | 5.289 | 26.917 | 14.377 | 1.00 | 23.49 | 6 |
| ATOM | 3240 | ND1 | HIS | A | 430 | 5.461 | 25.824 | 15.199 | 1.00 | 23.55 | 7 |
| ATOM | 3241 | CE1 | HIS | A | 430 | 6.508 | 26.025 | 15.980 | 1.00 | 23.00 | 6 |
| ATOM | 3242 | NE2 | HIS | A | 430 | 7.019 | 27.208 | 15.696 | 1.00 | 22.62 | 7 |
| ATOM | 3243 | CD2 | HIS | A | 430 | 6.277 | 27.786 | 14.696 | 1.00 | 23.79 | 6 |
| ATOM | 3244 | C | HIS | A | 430 | 2.999 | 28.529 | 14.975 | 1.00 | 23.90 | 6 |
| ATOM | 3245 | O | HIS | A | 430 | 2.923 | 28.299 | 16.188 | 1.00 | 24.00 | 8 |
| ATOM | 3246 | N | ARG | A | 431 | 3.228 | 29.744 | 14.479 | 1.00 | 24.05 | 7 |
| ATOM | 3247 | CA | ARG | A | 431 | 3.474 | 30.896 | 15.351 | 1.00 | 24.65 | 6 |
| ATOM | 3248 | CB | ARG | A | 431 | 4.016 | 32.080 | 14.552 | 1.00 | 24.67 | 6 |
| ATOM | 3249 | CG | ARG | A | 431 | 5.363 | 31.811 | 13.895 | 1.00 | 25.11 | 6 |
| ATOM | 3250 | CD | ARG | A | 431 | 5.835 | 32.995 | 13.068 | 1.00 | 25.85 | 6 |
| ATOM | 3251 | NE | ARG | A | 431 | 6.238 | 34.130 | 13.895 | 1.00 | 25.71 | 7 |
| ATOM | 3252 | CZ | ARG | A | 431 | 5.668 | 35.332 | 13.850 | 1.00 | 27.06 | 6 |
| ATOM | 3253 | NH1 | ARG | A | 431 | 4.674 | 35.568 | 13.001 | 1.00 | 27.51 | 7 |
| ATOM | 3254 | NH2 | ARG | A | 431 | 6.103 | 36.305 | 14.640 | 1.00 | 26.77 | 7 |
| ATOM | 3255 | C | ARG | A | 431 | 2.230 | 31.309 | 16.136 | 1.00 | 24.89 | 6 |
| ATOM | 3256 | O | ARG | A | 431 | 2.334 | 31.778 | 17.275 | 1.00 | 24.94 | 8 |
| ATOM | 3257 | N | ARG | A | 432 | 1.060 | 31.131 | 15.525 | 1.00 | 25.45 | 7 |
| ATOM | 3258 | CA | ARG | A | 432 | −0.215 | 31.423 | 16.191 | 1.00 | 25.97 | 6 |
| ATOM | 3259 | CB | ARG | A | 432 | −1.370 | 31.410 | 15.187 | 1.00 | 26.24 | 6 |
| ATOM | 3260 | CG | ARG | A | 432 | −1.419 | 32.632 | 14.289 | 1.00 | 27.84 | 6 |
| ATOM | 3261 | CD | ARG | A | 432 | −2.578 | 32.558 | 13.308 | 1.00 | 30.85 | 6 |
| ATOM | 3262 | NE | ARG | A | 432 | −2.375 | 33.459 | 12.175 | 1.00 | 32.77 | 7 |
| ATOM | 3263 | CZ | ARG | A | 432 | −3.129 | 33.478 | 11.077 | 1.00 | 33.96 | 6 |
| ATOM | 3264 | NH1 | ARG | A | 432 | −4.158 | 32.648 | 10.949 | 1.00 | 34.46 | 7 |
| ATOM | 3265 | NH2 | ARG | A | 432 | −2.854 | 34.335 | 10.103 | 1.00 | 34.72 | 7 |
| ATOM | 3266 | C | ARG | A | 432 | −0.507 | 30.456 | 17.336 | 1.00 | 25.97 | 6 |
| ATOM | 3267 | O | ARG | A | 432 | −1.142 | 30.830 | 18.324 | 1.00 | 25.98 | 8 |
| ATOM | 3268 | N | GLN | A | 433 | −0.044 | 29.216 | 17.200 | 1.00 | 25.92 | 7 |
| ATOM | 3269 | CA | GLN | A | 433 | −0.272 | 28.195 | 18.222 | 1.00 | 26.14 | 6 |
| ATOM | 3270 | CB | GLN | A | 433 | −0.145 | 26.793 | 17.627 | 1.00 | 26.15 | 6 |
| ATOM | 3271 | CG | GLN | A | 433 | −1.275 | 26.422 | 16.676 | 1.00 | 27.27 | 6 |
| ATOM | 3272 | CD | GLN | A | 433 | −1.112 | 25.035 | 16.081 | 1.00 | 28.02 | 6 |
| ATOM | 3273 | OE1 | GLN | A | 433 | −0.274 | 24.244 | 16.528 | 1.00 | 30.66 | 8 |
| ATOM | 3274 | NE2 | GLN | A | 433 | −1.914 | 24.730 | 15.066 | 1.00 | 29.12 | 7 |
| ATOM | 3275 | C | GLN | A | 433 | 0.673 | 28.359 | 19.408 | 1.00 | 25.65 | 6 |
| ATOM | 3276 | O | GLN | A | 433 | 0.375 | 27.903 | 20.513 | 1.00 | 25.91 | 8 |
| ATOM | 3277 | N | VAL | A | 434 | 1.816 | 29.002 | 19.169 | 1.00 | 25.30 | 7 |
| ATOM | 3278 | CA | VAL | A | 434 | 2.733 | 29.370 | 20.249 | 1.00 | 24.78 | 6 |
| ATOM | 3279 | CB | VAL | A | 434 | 4.155 | 29.668 | 19.719 | 1.00 | 24.94 | 6 |
| ATOM | 3280 | CG1 | VAL | A | 434 | 5.073 | 30.116 | 20.858 | 1.00 | 24.75 | 6 |
| ATOM | 3281 | CG2 | VAL | A | 434 | 4.730 | 28.448 | 19.007 | 1.00 | 25.19 | 6 |
| ATOM | 3282 | C | VAL | A | 434 | 2.209 | 30.605 | 20.971 | 1.00 | 24.51 | 6 |
| ATOM | 3283 | O | VAL | A | 434 | 2.075 | 30.614 | 22.200 | 1.00 | 24.62 | 8 |
| ATOM | 3284 | N | PHE | A | 435 | 1.911 | 31.644 | 20.200 | 1.00 | 24.08 | 7 |
| ATOM | 3285 | CA | PHE | A | 435 | 1.487 | 32.918 | 20.751 | 1.00 | 24.09 | 6 |
| ATOM | 3286 | CB | PHE | A | 435 | 1.928 | 34.070 | 19.834 | 1.00 | 23.80 | 6 |

TABLE 7-continued

Coordinates of the crystal structure of E. coli ExoI bound to compound 10

| ATOM | 3287 | CG  | PHE | A | 435 | 3.424  | 34.098 | 19.564 | 1.00 | 24.00 | 6 |
|------|------|-----|-----|---|-----|--------|--------|--------|------|-------|---|
| ATOM | 3288 | CD1 | PHE | A | 435 | 4.343  | 33.950 | 20.610 | 1.00 | 23.54 | 6 |
| ATOM | 3289 | CE1 | PHE | A | 435 | 5.721  | 33.978 | 20.363 | 1.00 | 22.80 | 6 |
| ATOM | 3290 | CZ  | PHE | A | 435 | 6.189  | 34.160 | 19.061 | 1.00 | 23.69 | 6 |
| ATOM | 3291 | CE2 | PHE | A | 435 | 5.284  | 34.315 | 18.017 | 1.00 | 23.32 | 6 |
| ATOM | 3292 | CD2 | PHE | A | 435 | 3.909  | 34.286 | 18.273 | 1.00 | 23.76 | 6 |
| ATOM | 3293 | C   | PHE | A | 435 | −0.026 | 32.933 | 21.023 | 1.00 | 24.14 | 6 |
| ATOM | 3294 | O   | PHE | A | 435 | −0.774 | 33.721 | 20.441 | 1.00 | 24.23 | 8 |
| ATOM | 3295 | N   | THR | A | 436 | −0.452 | 32.042 | 21.917 | 1.00 | 24.33 | 7 |
| ATOM | 3296 | CA  | THR | A | 436 | −1.854 | 31.937 | 22.342 | 1.00 | 24.39 | 6 |
| ATOM | 3297 | CB  | THR | A | 436 | −2.076 | 30.703 | 23.258 | 1.00 | 24.49 | 6 |
| ATOM | 3298 | OG1 | THR | A | 436 | −1.265 | 30.820 | 24.437 | 1.00 | 25.08 | 8 |
| ATOM | 3299 | CG2 | THR | A | 436 | −1.736 | 29.417 | 22.531 | 1.00 | 24.96 | 6 |
| ATOM | 3300 | C   | THR | A | 436 | −2.295 | 33.184 | 23.109 | 1.00 | 24.29 | 6 |
| ATOM | 3301 | O   | THR | A | 436 | −1.452 | 33.977 | 23.537 | 1.00 | 24.55 | 8 |
| ATOM | 3302 | N   | PRO | A | 437 | −3.624 | 33.362 | 23.287 | 1.00 | 24.19 | 7 |
| ATOM | 3303 | CA  | PRO | A | 437 | −4.166 | 34.436 | 24.131 | 1.00 | 24.01 | 6 |
| ATOM | 3304 | CB  | PRO | A | 437 | −5.668 | 34.135 | 24.150 | 1.00 | 24.02 | 6 |
| ATOM | 3305 | CG  | PRO | A | 437 | −5.915 | 33.385 | 22.890 | 1.00 | 23.90 | 6 |
| ATOM | 3306 | CD  | PRO | A | 437 | −4.698 | 32.557 | 22.671 | 1.00 | 24.00 | 6 |
| ATOM | 3307 | C   | PRO | A | 437 | −3.607 | 34.413 | 25.558 | 1.00 | 23.91 | 6 |
| ATOM | 3308 | O   | PRO | A | 437 | −3.292 | 35.469 | 26.112 | 1.00 | 23.67 | 8 |
| ATOM | 3309 | N   | GLU | A | 438 | −3.483 | 33.215 | 26.138 | 1.00 | 23.83 | 7 |
| ATOM | 3310 | CA  | GLU | A | 438 | −2.983 | 33.055 | 27.507 | 1.00 | 23.91 | 6 |
| ATOM | 3311 | CB  | GLU | A | 438 | −3.169 | 31.610 | 27.989 | 1.00 | 24.06 | 6 |
| ATOM | 3312 | CG  | GLU | A | 438 | −3.118 | 31.433 | 29.509 | 1.00 | 23.80 | 6 |
| ATOM | 3313 | CD  | GLU | A | 438 | −4.375 | 31.932 | 30.208 | 1.00 | 23.67 | 6 |
| ATOM | 3314 | OE1 | GLU | A | 438 | −5.493 | 31.658 | 29.715 | 1.00 | 22.83 | 8 |
| ATOM | 3315 | OE2 | GLU | A | 438 | −4.243 | 32.595 | 31.261 | 1.00 | 24.20 | 8 |
| ATOM | 3316 | C   | GLU | A | 438 | −1.516 | 33.459 | 27.605 | 1.00 | 23.96 | 6 |
| ATOM | 3317 | O   | GLU | A | 438 | −1.119 | 34.168 | 28.535 | 1.00 | 23.84 | 8 |
| ATOM | 3318 | N   | PHE | A | 439 | −0.725 | 33.019 | 26.626 | 1.00 | 23.86 | 7 |
| ATOM | 3319 | CA  | PHE | A | 439 | 0.700  | 33.338 | 26.562 | 1.00 | 23.64 | 6 |
| ATOM | 3320 | CB  | PHE | A | 439 | 1.351  | 32.632 | 25.369 | 1.00 | 23.93 | 6 |
| ATOM | 3321 | CG  | PHE | A | 439 | 2.821  | 32.891 | 25.248 | 1.00 | 24.27 | 6 |
| ATOM | 3322 | CD1 | PHE | A | 439 | 3.729  | 32.162 | 26.005 | 1.00 | 25.20 | 6 |
| ATOM | 3323 | CE1 | PHE | A | 439 | 5.094  | 32.405 | 25.909 | 1.00 | 26.17 | 6 |
| ATOM | 3324 | CZ  | PHE | A | 439 | 5.560  | 33.390 | 25.050 | 1.00 | 25.59 | 6 |
| ATOM | 3325 | CE2 | PHE | A | 439 | 4.663  | 34.133 | 24.295 | 1.00 | 25.83 | 6 |
| ATOM | 3326 | CD2 | PHE | A | 439 | 3.298  | 33.884 | 24.396 | 1.00 | 25.12 | 6 |
| ATOM | 3327 | C   | PHE | A | 439 | 0.966  | 34.843 | 26.483 | 1.00 | 23.38 | 6 |
| ATOM | 3328 | O   | PHE | A | 439 | 1.742  | 35.382 | 27.273 | 1.00 | 23.11 | 8 |
| ATOM | 3329 | N   | LEU | A | 440 | 0.332  | 35.507 | 25.521 | 1.00 | 23.00 | 7 |
| ATOM | 3330 | CA  | LEU | A | 440 | 0.542  | 36.937 | 25.291 | 1.00 | 23.12 | 6 |
| ATOM | 3331 | CB  | LEU | A | 440 | −0.229 | 37.408 | 24.051 | 1.00 | 23.50 | 6 |
| ATOM | 3332 | CG  | LEU | A | 440 | 0.087  | 36.722 | 22.716 | 1.00 | 24.05 | 6 |
| ATOM | 3333 | CD1 | LEU | A | 440 | −0.761 | 37.307 | 21.594 | 1.00 | 25.69 | 6 |
| ATOM | 3334 | CD2 | LEU | A | 440 | 1.564  | 36.829 | 22.388 | 1.00 | 25.16 | 6 |
| ATOM | 3335 | C   | LEU | A | 440 | 0.151  | 37.778 | 26.504 | 1.00 | 22.94 | 6 |
| ATOM | 3336 | O   | LEU | A | 440 | 0.883  | 38.687 | 26.905 | 1.00 | 22.98 | 8 |
| ATOM | 3337 | N   | GLN | A | 441 | −1.000 | 37.467 | 27.092 | 1.00 | 22.46 | 7 |
| ATOM | 3338 | CA  | GLN | A | 441 | −1.467 | 38.202 | 28.256 | 1.00 | 22.12 | 6 |
| ATOM | 3339 | CB  | GLN | A | 441 | −2.877 | 37.763 | 28.659 | 1.00 | 22.48 | 6 |
| ATOM | 3340 | CG  | GLN | A | 441 | −3.569 | 38.745 | 29.592 | 1.00 | 22.58 | 6 |
| ATOM | 3341 | CD  | GLN | A | 441 | −3.574 | 40.165 | 29.040 | 1.00 | 23.12 | 6 |
| ATOM | 3342 | OE1 | GLN | A | 441 | −4.206 | 40.444 | 28.020 | 1.00 | 24.29 | 8 |
| ATOM | 3343 | NE2 | GLN | A | 441 | −2.863 | 41.065 | 29.710 | 1.00 | 23.68 | 7 |
| ATOM | 3344 | C   | GLN | A | 441 | −0.497 | 38.019 | 29.414 | 1.00 | 21.78 | 6 |
| ATOM | 3345 | O   | GLN | A | 441 | −0.095 | 38.991 | 30.054 | 1.00 | 22.11 | 8 |
| ATOM | 3346 | N   | GLY | A | 442 | −0.103 | 36.772 | 29.655 | 1.00 | 21.20 | 7 |
| ATOM | 3347 | CA  | GLY | A | 442 | 0.842  | 36.448 | 30.719 | 1.00 | 20.66 | 6 |
| ATOM | 3348 | C   | GLY | A | 442 | 2.172  | 37.161 | 30.546 | 1.00 | 20.25 | 6 |
| ATOM | 3349 | O   | GLY | A | 442 | 2.773  | 37.619 | 31.520 | 1.00 | 20.34 | 8 |
| ATOM | 3350 | N   | TYR | A | 443 | 2.628  | 37.262 | 29.301 | 1.00 | 19.78 | 7 |
| ATOM | 3351 | CA  | TYR | A | 443 | 3.902  | 37.914 | 29.004 | 1.00 | 19.42 | 6 |
| ATOM | 3352 | CB  | TYR | A | 443 | 4.300  | 37.673 | 27.550 | 1.00 | 19.04 | 6 |
| ATOM | 3353 | CG  | TYR | A | 443 | 5.784  | 37.827 | 27.293 | 1.00 | 18.78 | 6 |
| ATOM | 3354 | CD1 | TYR | A | 443 | 6.646  | 36.746 | 27.437 | 1.00 | 18.27 | 6 |
| ATOM | 3355 | CE1 | TYR | A | 443 | 8.011  | 36.879 | 27.205 | 1.00 | 18.70 | 6 |
| ATOM | 3356 | CZ  | TYR | A | 443 | 8.521  | 38.103 | 26.817 | 1.00 | 18.74 | 6 |
| ATOM | 3357 | OH  | TYR | A | 443 | 9.870  | 38.232 | 26.585 | 1.00 | 18.29 | 8 |
| ATOM | 3358 | CE2 | TYR | A | 443 | 7.681  | 39.201 | 26.669 | 1.00 | 18.28 | 6 |
| ATOM | 3359 | CD2 | TYR | A | 443 | 6.323  | 39.057 | 26.909 | 1.00 | 18.09 | 6 |
| ATOM | 3360 | C   | TYR | A | 443 | 3.825  | 39.414 | 29.283 | 1.00 | 19.44 | 6 |
| ATOM | 3361 | O   | TYR | A | 443 | 4.714  | 39.983 | 29.918 | 1.00 | 19.42 | 8 |
| ATOM | 3362 | N   | ALA | A | 444 | 2.758  | 40.047 | 28.795 | 1.00 | 19.73 | 7 |
| ATOM | 3363 | CA  | ALA | A | 444 | 2.507  | 41.459 | 29.064 | 1.00 | 20.07 | 6 |
| ATOM | 3364 | CB  | ALA | A | 444 | 1.228  | 41.906 | 28.374 | 1.00 | 20.31 | 6 |

TABLE 7-continued

Coordinates of the crystal structure of *E. coli* ExoI bound to compound 10

| ATOM | 3365 | C | ALA | A | 444 | 2.431 | 41.722 | 30.571 | 1.00 | 20.42 | 6 |
|---|---|---|---|---|---|---|---|---|---|---|---|
| ATOM | 3366 | O | ALA | A | 444 | 3.015 | 42.687 | 31.072 | 1.00 | 20.26 | 8 |
| ATOM | 3367 | N | ASP | A | 445 | 1.731 | 40.841 | 31.288 | 1.00 | 20.66 | 7 |
| ATOM | 3368 | CA | ASP | A | 445 | 1.575 | 40.962 | 32.744 | 1.00 | 21.16 | 6 |
| ATOM | 3369 | CB | ASP | A | 445 | 0.588 | 39.920 | 33.274 | 1.00 | 21.25 | 6 |
| ATOM | 3370 | CG | ASP | A | 445 | −0.843 | 40.198 | 32.854 | 1.00 | 22.08 | 6 |
| ATOM | 3371 | OD1 | ASP | A | 445 | −1.124 | 41.306 | 32.333 | 1.00 | 23.14 | 8 |
| ATOM | 3372 | OD2 | ASP | A | 445 | −1.695 | 39.304 | 33.053 | 1.00 | 23.52 | 8 |
| ATOM | 3373 | C | ASP | A | 445 | 2.901 | 40.846 | 33.494 | 1.00 | 21.07 | 6 |
| ATOM | 3374 | O | ASP | A | 445 | 3.149 | 41.603 | 34.436 | 1.00 | 21.11 | 8 |
| ATOM | 3375 | N | GLU | A | 446 | 3.746 | 39.898 | 33.077 | 1.00 | 21.09 | 7 |
| ATOM | 3376 | CA | GLU | A | 446 | 5.042 | 39.683 | 33.731 | 1.00 | 21.14 | 6 |
| ATOM | 3377 | CB | GLU | A | 446 | 5.730 | 38.406 | 33.219 | 1.00 | 20.98 | 6 |
| ATOM | 3378 | CG | GLU | A | 446 | 6.973 | 38.013 | 34.044 | 1.00 | 21.95 | 6 |
| ATOM | 3379 | CD | GLU | A | 446 | 7.739 | 36.816 | 33.490 | 1.00 | 22.88 | 6 |
| ATOM | 3380 | OE1 | GLU | A | 446 | 7.189 | 36.067 | 32.648 | 1.00 | 25.21 | 8 |
| ATOM | 3381 | OE2 | GLU | A | 446 | 8.905 | 36.626 | 33.909 | 1.00 | 24.54 | 8 |
| ATOM | 3382 | C | GLU | A | 446 | 5.962 | 40.889 | 33.549 | 1.00 | 20.73 | 6 |
| ATOM | 3383 | O | GLU | A | 446 | 6.628 | 41.317 | 34.492 | 1.00 | 20.06 | 8 |
| ATOM | 3384 | N | LEU | A | 447 | 5.993 | 41.430 | 32.334 | 1.00 | 20.30 | 7 |
| ATOM | 3385 | CA | LEU | A | 447 | 6.818 | 42.599 | 32.036 | 1.00 | 20.56 | 6 |
| ATOM | 3386 | CB | LEU | A | 447 | 6.743 | 42.943 | 30.551 | 1.00 | 20.01 | 6 |
| ATOM | 3387 | CG | LEU | A | 447 | 7.458 | 42.024 | 29.560 | 1.00 | 19.89 | 6 |
| ATOM | 3388 | CD1 | LEU | A | 447 | 7.258 | 42.554 | 28.158 | 1.00 | 19.01 | 6 |
| ATOM | 3389 | CD2 | LEU | A | 447 | 8.948 | 41.907 | 29.879 | 1.00 | 19.15 | 6 |
| ATOM | 3390 | C | LEU | A | 447 | 6.394 | 43.807 | 32.866 | 1.00 | 20.96 | 6 |
| ATOM | 3391 | O | LEU | A | 447 | 7.237 | 44.503 | 33.446 | 1.00 | 21.08 | 8 |
| ATOM | 3392 | N | GLN | A | 448 | 5.082 | 44.041 | 32.929 | 1.00 | 21.54 | 7 |
| ATOM | 3393 | CA | GLN | A | 448 | 4.522 | 45.144 | 33.715 | 1.00 | 22.06 | 6 |
| ATOM | 3394 | CB | GLN | A | 448 | 3.022 | 45.308 | 33.429 | 1.00 | 22.25 | 6 |
| ATOM | 3395 | CG | GLN | A | 448 | 2.700 | 45.943 | 32.066 | 1.00 | 22.77 | 6 |
| ATOM | 3396 | CD | GLN | A | 448 | 1.223 | 45.818 | 31.684 | 1.00 | 23.39 | 6 |
| ATOM | 3397 | OE1 | GLN | A | 448 | 0.771 | 44.764 | 31.221 | 1.00 | 24.95 | 8 |
| ATOM | 3398 | NE2 | GLN | A | 448 | 0.471 | 46.901 | 31.865 | 1.00 | 23.35 | 7 |
| ATOM | 3399 | C | GLN | A | 448 | 4.770 | 44.944 | 35.212 | 1.00 | 22.26 | 6 |
| ATOM | 3400 | O | GLN | A | 448 | 5.030 | 45.901 | 35.941 | 1.00 | 21.92 | 8 |
| ATOM | 3401 | N | MET | A | 449 | 4.702 | 43.694 | 35.658 | 1.00 | 22.38 | 7 |
| ATOM | 3402 | CA | MET | A | 449 | 5.014 | 43.362 | 37.042 | 1.00 | 23.27 | 6 |
| ATOM | 3403 | CB | MET | A | 449 | 4.647 | 41.915 | 37.339 | 1.00 | 23.26 | 6 |
| ATOM | 3404 | CG | MET | A | 449 | 4.629 | 41.583 | 38.812 | 1.00 | 24.06 | 6 |
| ATOM | 3405 | SD | MET | A | 449 | 5.150 | 39.896 | 39.132 | 1.00 | 27.08 | 16 |
| ATOM | 3406 | CE | MET | A | 449 | 6.874 | 40.005 | 38.673 | 1.00 | 27.87 | 6 |
| ATOM | 3407 | C | MET | A | 449 | 6.492 | 43.604 | 37.354 | 1.00 | 22.38 | 6 |
| ATOM | 3408 | O | MET | A | 449 | 6.825 | 44.222 | 38.367 | 1.00 | 22.47 | 8 |
| ATOM | 3409 | N | LEU | A | 450 | 7.368 | 43.135 | 36.465 | 1.00 | 21.90 | 7 |
| ATOM | 3410 | CA | LEU | A | 450 | 8.810 | 43.242 | 36.677 | 1.00 | 21.35 | 6 |
| ATOM | 3411 | CB | LEU | A | 450 | 9.590 | 42.378 | 35.672 | 1.00 | 20.75 | 6 |
| ATOM | 3412 | CG | LEU | A | 450 | 9.503 | 40.847 | 35.842 | 1.00 | 19.52 | 6 |
| ATOM | 3413 | CD1 | LEU | A | 450 | 10.124 | 40.136 | 34.662 | 1.00 | 17.72 | 6 |
| ATOM | 3414 | CD2 | LEU | A | 450 | 10.146 | 40.363 | 37.157 | 1.00 | 16.51 | 6 |
| ATOM | 3415 | C | LEU | A | 450 | 9.299 | 44.689 | 36.644 | 1.00 | 21.44 | 6 |
| ATOM | 3416 | O | LEU | A | 450 | 10.203 | 45.055 | 37.395 | 1.00 | 21.74 | 8 |
| ATOM | 3417 | N | VAL | A | 451 | 8.685 | 45.516 | 35.797 | 1.00 | 21.64 | 7 |
| ATOM | 3418 | CA | VAL | A | 451 | 9.071 | 46.930 | 35.704 | 1.00 | 21.97 | 6 |
| ATOM | 3419 | CB | VAL | A | 451 | 8.458 | 47.626 | 34.445 | 1.00 | 22.18 | 6 |
| ATOM | 3420 | CG1 | VAL | A | 451 | 7.007 | 48.035 | 34.687 | 1.00 | 22.69 | 6 |
| ATOM | 3421 | CG2 | VAL | A | 451 | 9.299 | 48.823 | 34.030 | 1.00 | 22.54 | 6 |
| ATOM | 3422 | C | VAL | A | 451 | 8.750 | 47.702 | 36.999 | 1.00 | 22.09 | 6 |
| ATOM | 3423 | O | VAL | A | 451 | 9.425 | 48.677 | 37.337 | 1.00 | 22.08 | 8 |
| ATOM | 3424 | N | GLN | A | 452 | 7.725 | 47.246 | 37.716 | 1.00 | 22.24 | 7 |
| ATOM | 3425 | CA | GLN | A | 452 | 7.392 | 47.772 | 39.039 | 1.00 | 22.88 | 6 |
| ATOM | 3426 | CB | GLN | A | 452 | 5.929 | 47.478 | 39.382 | 1.00 | 22.95 | 6 |
| ATOM | 3427 | CG | GLN | A | 452 | 4.921 | 48.254 | 38.554 | 1.00 | 23.68 | 6 |
| ATOM | 3428 | CD | GLN | A | 452 | 3.485 | 47.946 | 38.935 | 1.00 | 23.99 | 6 |
| ATOM | 3429 | OE1 | GLN | A | 452 | 3.173 | 47.727 | 40.105 | 1.00 | 25.35 | 8 |
| ATOM | 3430 | NE2 | GLN | A | 452 | 2.598 | 47.943 | 37.944 | 1.00 | 25.72 | 7 |
| ATOM | 3431 | C | GLN | A | 452 | 8.299 | 47.162 | 40.105 | 1.00 | 22.83 | 6 |
| ATOM | 3432 | O | GLN | A | 452 | 8.748 | 47.856 | 41.021 | 1.00 | 22.95 | 8 |
| ATOM | 3433 | N | GLN | A | 453 | 8.561 | 45.860 | 39.981 | 1.00 | 22.86 | 7 |
| ATOM | 3434 | CA | GLN | A | 453 | 9.429 | 45.147 | 40.919 | 1.00 | 23.22 | 6 |
| ATOM | 3435 | CB | GLN | A | 453 | 9.505 | 43.660 | 40.559 | 1.00 | 23.09 | 6 |
| ATOM | 3436 | CG | GLN | A | 453 | 10.409 | 42.841 | 41.473 | 1.00 | 23.75 | 6 |
| ATOM | 3437 | CD | GLN | A | 453 | 10.227 | 41.346 | 41.299 | 1.00 | 24.12 | 6 |
| ATOM | 3438 | OE1 | GLN | A | 453 | 9.308 | 40.891 | 40.613 | 1.00 | 26.13 | 8 |
| ATOM | 3439 | NE2 | GLN | A | 453 | 11.108 | 40.570 | 41.920 | 1.00 | 25.32 | 7 |
| ATOM | 3440 | C | GLN | A | 453 | 10.830 | 45.753 | 40.954 | 1.00 | 23.23 | 6 |
| ATOM | 3441 | O | GLN | A | 453 | 11.395 | 45.975 | 42.036 | 1.00 | 22.72 | 8 |
| ATOM | 3442 | N | TYR | A | 454 | 11.374 | 46.027 | 39.769 | 1.00 | 23.30 | 7 |

TABLE 7-continued

Coordinates of the crystal structure of *E. coli* ExoI bound to compound 10

| ATOM | 3443 | CA  | TYR | A | 454 | 12.735 | 46.545 | 39.631 | 1.00 | 23.90 | 6 |
|------|------|-----|-----|---|-----|--------|--------|--------|------|-------|---|
| ATOM | 3444 | CB  | TYR | A | 454 | 13.531 | 45.686 | 38.648 | 1.00 | 24.07 | 6 |
| ATOM | 3445 | CG  | TYR | A | 454 | 13.745 | 44.278 | 39.142 | 1.00 | 24.27 | 6 |
| ATOM | 3446 | CD1 | TYR | A | 454 | 14.619 | 44.017 | 40.198 | 1.00 | 24.54 | 6 |
| ATOM | 3447 | CE1 | TYR | A | 454 | 14.814 | 42.730 | 40.664 | 1.00 | 24.49 | 6 |
| ATOM | 3448 | CZ  | TYR | A | 454 | 14.129 | 41.684 | 40.078 | 1.00 | 24.69 | 6 |
| ATOM | 3449 | OH  | TYR | A | 454 | 14.323 | 40.406 | 40.540 | 1.00 | 25.29 | 8 |
| ATOM | 3450 | CE2 | TYR | A | 454 | 13.251 | 41.915 | 39.031 | 1.00 | 24.39 | 6 |
| ATOM | 3451 | CD2 | TYR | A | 454 | 13.061 | 43.208 | 38.574 | 1.00 | 24.13 | 6 |
| ATOM | 3452 | C   | TYR | A | 454 | 12.757 | 48.012 | 39.217 | 1.00 | 24.19 | 6 |
| ATOM | 3453 | O   | TYR | A | 454 | 13.678 | 48.463 | 38.520 | 1.00 | 24.02 | 8 |
| ATOM | 3454 | N   | ALA | A | 455 | 11.749 | 48.754 | 39.676 | 1.00 | 24.70 | 7 |
| ATOM | 3455 | CA  | ALA | A | 455 | 11.597 | 50.178 | 39.366 | 1.00 | 25.24 | 6 |
| ATOM | 3456 | CB  | ALA | A | 455 | 10.389 | 50.753 | 40.107 | 1.00 | 24.90 | 6 |
| ATOM | 3457 | C   | ALA | A | 455 | 12.850 | 50.992 | 39.687 | 1.00 | 25.55 | 6 |
| ATOM | 3458 | O   | ALA | A | 455 | 13.196 | 51.922 | 38.957 | 1.00 | 26.17 | 8 |
| ATOM | 3459 | N   | ASP | A | 456 | 13.525 | 50.636 | 40.777 | 1.00 | 26.19 | 7 |
| ATOM | 3460 | CA  | ASP | A | 456 | 14.702 | 51.376 | 41.227 | 1.00 | 26.41 | 6 |
| ATOM | 3461 | CB  | ASP | A | 456 | 14.826 | 51.315 | 42.754 | 1.00 | 26.75 | 6 |
| ATOM | 3462 | CG  | ASP | A | 456 | 13.680 | 52.025 | 43.458 | 1.00 | 27.82 | 6 |
| ATOM | 3463 | OD1 | ASP | A | 456 | 13.581 | 53.269 | 43.341 | 1.00 | 28.98 | 8 |
| ATOM | 3464 | OD2 | ASP | A | 456 | 12.876 | 51.339 | 44.130 | 1.00 | 29.60 | 8 |
| ATOM | 3465 | C   | ASP | A | 456 | 16.001 | 50.929 | 40.544 | 1.00 | 26.25 | 6 |
| ATOM | 3466 | O   | ASP | A | 456 | 17.055 | 51.545 | 40.733 | 1.00 | 26.14 | 8 |
| ATOM | 3467 | N   | ASP | A | 457 | 15.917 | 49.871 | 39.740 | 1.00 | 25.98 | 7 |
| ATOM | 3468 | CA  | ASP | A | 457 | 17.060 | 49.404 | 38.965 | 1.00 | 25.84 | 6 |
| ATOM | 3469 | CB  | ASP | A | 457 | 17.166 | 47.876 | 39.027 | 1.00 | 26.05 | 6 |
| ATOM | 3470 | CG  | ASP | A | 457 | 18.527 | 47.357 | 38.573 | 1.00 | 27.14 | 6 |
| ATOM | 3471 | OD1 | ASP | A | 457 | 19.009 | 47.759 | 37.485 | 1.00 | 26.99 | 8 |
| ATOM | 3472 | OD2 | ASP | A | 457 | 19.109 | 46.521 | 39.300 | 1.00 | 28.05 | 8 |
| ATOM | 3473 | C   | ASP | A | 457 | 16.926 | 49.881 | 37.518 | 1.00 | 25.36 | 6 |
| ATOM | 3474 | O   | ASP | A | 457 | 16.162 | 49.319 | 36.735 | 1.00 | 25.31 | 8 |
| ATOM | 3475 | N   | LYS | A | 458 | 17.674 | 50.927 | 37.177 | 1.00 | 24.98 | 7 |
| ATOM | 3476 | CA  | LYS | A | 458 | 17.531 | 51.600 | 35.881 | 1.00 | 24.54 | 6 |
| ATOM | 3477 | CB  | LYS | A | 458 | 18.289 | 52.932 | 35.881 | 1.00 | 24.70 | 6 |
| ATOM | 3478 | CG  | LYS | A | 458 | 17.809 | 53.912 | 36.944 | 1.00 | 25.23 | 6 |
| ATOM | 3479 | CD  | LYS | A | 458 | 16.310 | 54.183 | 36.810 | 1.00 | 26.62 | 6 |
| ATOM | 3480 | CE  | LYS | A | 458 | 15.741 | 54.837 | 38.067 | 1.00 | 27.52 | 6 |
| ATOM | 3481 | NZ  | LYS | A | 458 | 15.771 | 53.929 | 39.240 | 1.00 | 29.10 | 7 |
| ATOM | 3482 | C   | LYS | A | 458 | 17.953 | 50.740 | 34.689 | 1.00 | 24.45 | 6 |
| ATOM | 3483 | O   | LYS | A | 458 | 17.380 | 50.857 | 33.603 | 1.00 | 23.97 | 8 |
| ATOM | 3484 | N   | GLU | A | 459 | 18.944 | 49.875 | 34.899 | 1.00 | 24.33 | 7 |
| ATOM | 3485 | CA  | GLU | A | 459 | 19.410 | 48.960 | 33.851 | 1.00 | 24.57 | 6 |
| ATOM | 3486 | CB  | GLU | A | 459 | 20.708 | 48.271 | 34.273 | 1.00 | 24.62 | 6 |
| ATOM | 3487 | CG  | GLU | A | 459 | 21.930 | 49.172 | 34.239 | 1.00 | 26.21 | 6 |
| ATOM | 3488 | CD  | GLU | A | 459 | 23.172 | 48.502 | 34.802 | 1.00 | 27.01 | 6 |
| ATOM | 3489 | OE1 | GLU | A | 459 | 23.326 | 47.269 | 34.629 | 1.00 | 29.74 | 8 |
| ATOM | 3490 | OE2 | GLU | A | 459 | 23.998 | 49.214 | 35.416 | 1.00 | 29.82 | 8 |
| ATOM | 3491 | C   | GLU | A | 459 | 18.358 | 47.913 | 33.492 | 1.00 | 23.75 | 6 |
| ATOM | 3492 | O   | GLU | A | 459 | 18.090 | 47.672 | 32.315 | 1.00 | 23.90 | 8 |
| ATOM | 3493 | N   | LYS | A | 460 | 17.775 | 47.289 | 34.515 | 1.00 | 23.14 | 7 |
| ATOM | 3494 | CA  | LYS | A | 460 | 16.705 | 46.308 | 34.320 | 1.00 | 22.28 | 6 |
| ATOM | 3495 | CB  | LYS | A | 460 | 16.317 | 45.652 | 35.656 | 1.00 | 22.25 | 6 |
| ATOM | 3496 | CG  | LYS | A | 460 | 17.458 | 44.923 | 36.364 | 1.00 | 22.79 | 6 |
| ATOM | 3497 | CD  | LYS | A | 460 | 16.929 | 44.006 | 37.465 | 1.00 | 23.87 | 6 |
| ATOM | 3498 | CE  | LYS | A | 460 | 18.037 | 43.542 | 38.403 | 1.00 | 25.80 | 6 |
| ATOM | 3499 | NZ  | LYS | A | 460 | 18.924 | 42.520 | 37.785 | 1.00 | 26.75 | 7 |
| ATOM | 3500 | C   | LYS | A | 460 | 15.474 | 46.948 | 33.660 | 1.00 | 21.70 | 6 |
| ATOM | 3501 | O   | LYS | A | 460 | 14.875 | 46.364 | 32.750 | 1.00 | 20.70 | 8 |
| ATOM | 3502 | N   | VAL | A | 461 | 15.108 | 48.149 | 34.113 | 1.00 | 20.71 | 7 |
| ATOM | 3503 | CA  | VAL | A | 461 | 13.976 | 48.879 | 33.518 | 1.00 | 20.36 | 6 |
| ATOM | 3504 | CB  | VAL | A | 461 | 13.731 | 50.253 | 34.207 | 1.00 | 20.51 | 6 |
| ATOM | 3505 | CG1 | VAL | A | 461 | 12.753 | 51.103 | 33.399 | 1.00 | 20.47 | 6 |
| ATOM | 3506 | CG2 | VAL | A | 461 | 13.200 | 50.045 | 35.621 | 1.00 | 20.69 | 6 |
| ATOM | 3507 | C   | VAL | A | 461 | 14.170 | 49.050 | 32.005 | 1.00 | 20.06 | 6 |
| ATOM | 3508 | O   | VAL | A | 461 | 13.252 | 48.788 | 31.224 | 1.00 | 19.80 | 8 |
| ATOM | 3509 | N   | ALA | A | 462 | 15.373 | 49.455 | 31.601 | 1.00 | 19.89 | 7 |
| ATOM | 3510 | CA  | ALA | A | 462 | 15.692 | 49.622 | 30.175 | 1.00 | 19.77 | 6 |
| ATOM | 3511 | CB  | ALA | A | 462 | 17.050 | 50.298 | 30.000 | 1.00 | 19.84 | 6 |
| ATOM | 3512 | C   | ALA | A | 462 | 15.646 | 48.299 | 29.413 | 1.00 | 20.08 | 6 |
| ATOM | 3513 | O   | ALA | A | 462 | 15.192 | 48.254 | 28.266 | 1.00 | 20.07 | 8 |
| ATOM | 3514 | N   | LEU | A | 463 | 16.104 | 47.224 | 30.057 | 1.00 | 19.97 | 7 |
| ATOM | 3515 | CA  | LEU | A | 463 | 16.035 | 45.887 | 29.469 | 1.00 | 20.08 | 6 |
| ATOM | 3516 | CB  | LEU | A | 463 | 16.808 | 44.870 | 30.315 | 1.00 | 20.26 | 6 |
| ATOM | 3517 | CG  | LEU | A | 463 | 18.344 | 44.897 | 30.255 | 1.00 | 20.34 | 6 |
| ATOM | 3518 | CD1 | LEU | A | 463 | 18.921 | 43.995 | 31.322 | 1.00 | 19.89 | 6 |
| ATOM | 3519 | CD2 | LEU | A | 463 | 18.871 | 44.505 | 28.875 | 1.00 | 20.59 | 6 |
| ATOM | 3520 | C   | LEU | A | 463 | 14.584 | 45.432 | 29.293 | 1.00 | 19.87 | 6 |

TABLE 7-continued

Coordinates of the crystal structure of *E. coli* ExoI bound to compound 10

| ATOM | 3521 | O | LEU | A | 463 | 14.236 | 44.839 | 28.281 | 1.00 | 20.39 | 8 |
|------|------|------|-----|---|-----|--------|--------|--------|------|-------|---|
| ATOM | 3522 | N | LEU | A | 464 | 13.742 | 45.748 | 30.271 | 1.00 | 19.79 | 7 |
| ATOM | 3523 | CA | LEU | A | 464 | 12.333 | 45.364 | 30.231 | 1.00 | 19.47 | 6 |
| ATOM | 3524 | CB | LEU | A | 464 | 11.681 | 45.549 | 31.605 | 1.00 | 19.53 | 6 |
| ATOM | 3525 | CG | LEU | A | 464 | 12.159 | 44.519 | 32.643 | 1.00 | 18.88 | 6 |
| ATOM | 3526 | CD1 | LEU | A | 464 | 11.937 | 45.000 | 34.074 | 1.00 | 19.80 | 6 |
| ATOM | 3527 | CD2 | LEU | A | 464 | 11.510 | 43.149 | 32.413 | 1.00 | 17.25 | 6 |
| ATOM | 3528 | C | LEU | A | 464 | 11.547 | 46.097 | 29.139 | 1.00 | 19.49 | 6 |
| ATOM | 3529 | O | LEU | A | 464 | 10.701 | 45.497 | 28.468 | 1.00 | 19.63 | 8 |
| ATOM | 3530 | N | LYS | A | 465 | 11.836 | 47.384 | 28.952 | 1.00 | 19.77 | 7 |
| ATOM | 3531 | CA | LYS | A | 465 | 11.227 | 48.150 | 27.857 | 1.00 | 20.15 | 6 |
| ATOM | 3532 | CB | LYS | A | 465 | 11.588 | 49.641 | 27.952 | 1.00 | 20.63 | 6 |
| ATOM | 3533 | CG | LYS | A | 465 | 11.212 | 50.318 | 29.285 | 1.00 | 22.22 | 6 |
| ATOM | 3534 | CD | LYS | A | 465 | 9.700 | 50.442 | 29.473 | 1.00 | 23.96 | 6 |
| ATOM | 3535 | CE | LYS | A | 465 | 9.346 | 51.051 | 30.830 | 1.00 | 23.54 | 6 |
| ATOM | 3536 | NZ | LYS | A | 465 | 9.485 | 52.540 | 30.838 | 1.00 | 25.59 | 7 |
| ATOM | 3537 | C | LYS | A | 465 | 11.649 | 47.573 | 26.500 | 1.00 | 20.03 | 6 |
| ATOM | 3538 | O | LYS | A | 465 | 10.858 | 47.550 | 25.548 | 1.00 | 19.79 | 8 |
| ATOM | 3539 | N | ALA | A | 466 | 12.892 | 47.092 | 26.433 | 1.00 | 20.19 | 7 |
| ATOM | 3540 | CA | ALA | A | 466 | 13.414 | 46.404 | 25.246 | 1.00 | 20.37 | 6 |
| ATOM | 3541 | CB | ALA | A | 466 | 14.896 | 46.098 | 25.425 | 1.00 | 20.51 | 6 |
| ATOM | 3542 | C | ALA | A | 466 | 12.634 | 45.114 | 24.952 | 1.00 | 20.34 | 6 |
| ATOM | 3543 | O | ALA | A | 466 | 12.311 | 44.816 | 23.792 | 1.00 | 20.41 | 8 |
| ATOM | 3544 | N | LEU | A | 467 | 12.331 | 44.361 | 26.007 | 1.00 | 20.46 | 7 |
| ATOM | 3545 | CA | LEU | A | 467 | 11.548 | 43.133 | 25.882 | 1.00 | 20.44 | 6 |
| ATOM | 3546 | CB | LEU | A | 467 | 11.554 | 42.345 | 27.189 | 1.00 | 20.75 | 6 |
| ATOM | 3547 | CG | LEU | A | 467 | 12.911 | 41.784 | 27.607 | 1.00 | 20.77 | 6 |
| ATOM | 3548 | CD1 | LEU | A | 467 | 12.872 | 41.353 | 29.061 | 1.00 | 20.29 | 6 |
| ATOM | 3549 | CD2 | LEU | A | 467 | 13.311 | 40.630 | 26.702 | 1.00 | 22.45 | 6 |
| ATOM | 3550 | C | LEU | A | 467 | 10.121 | 43.416 | 25.435 | 1.00 | 20.78 | 6 |
| ATOM | 3551 | O | LEU | A | 467 | 9.573 | 42.685 | 24.610 | 1.00 | 20.48 | 8 |
| ATOM | 3552 | N | TRP | A | 468 | 9.526 | 44.484 | 25.968 | 1.00 | 20.99 | 7 |
| ATOM | 3553 | CA | TRP | A | 468 | 8.208 | 44.918 | 25.508 | 1.00 | 21.63 | 6 |
| ATOM | 3554 | CB | TRP | A | 468 | 7.714 | 46.127 | 26.302 | 1.00 | 22.17 | 6 |
| ATOM | 3555 | CG | TRP | A | 468 | 6.287 | 46.499 | 25.973 | 1.00 | 22.71 | 6 |
| ATOM | 3556 | CD1 | TRP | A | 468 | 5.849 | 47.222 | 24.890 | 1.00 | 23.71 | 6 |
| ATOM | 3557 | NE1 | TRP | A | 468 | 4.481 | 47.343 | 24.923 | 1.00 | 23.94 | 7 |
| ATOM | 3558 | CE2 | TRP | A | 468 | 4.003 | 46.701 | 26.038 | 1.00 | 23.95 | 6 |
| ATOM | 3559 | CD2 | TRP | A | 468 | 5.114 | 46.151 | 26.722 | 1.00 | 23.90 | 6 |
| ATOM | 3560 | CE3 | TRP | A | 468 | 4.892 | 45.431 | 27.907 | 1.00 | 23.41 | 6 |
| ATOM | 3561 | CZ3 | TRP | A | 468 | 3.582 | 45.283 | 28.367 | 1.00 | 23.80 | 6 |
| ATOM | 3562 | CH2 | TRP | A | 468 | 2.495 | 45.842 | 27.662 | 1.00 | 23.71 | 6 |
| ATOM | 3563 | CZ2 | TRP | A | 468 | 2.685 | 46.552 | 26.501 | 1.00 | 23.80 | 6 |
| ATOM | 3564 | C | TRP | A | 468 | 8.217 | 45.246 | 24.013 | 1.00 | 21.67 | 6 |
| ATOM | 3565 | O | TRP | A | 468 | 7.337 | 44.807 | 23.270 | 1.00 | 21.85 | 8 |
| ATOM | 3566 | N | GLN | A | 469 | 9.210 | 46.023 | 23.585 | 1.00 | 21.78 | 7 |
| ATOM | 3567 | CA | GLN | A | 469 | 9.334 | 46.424 | 22.183 | 1.00 | 22.07 | 6 |
| ATOM | 3568 | CB | GLN | A | 469 | 10.508 | 47.388 | 22.001 | 1.00 | 22.69 | 6 |
| ATOM | 3569 | CG | GLN | A | 469 | 10.198 | 48.841 | 22.349 | 1.00 | 24.91 | 6 |
| ATOM | 3570 | CD | GLN | A | 469 | 11.391 | 49.564 | 22.970 | 1.00 | 27.79 | 6 |
| ATOM | 3571 | OE1 | GLN | A | 469 | 12.547 | 49.188 | 22.755 | 1.00 | 28.89 | 8 |
| ATOM | 3572 | NE2 | GLN | A | 469 | 11.110 | 50.603 | 23.755 | 1.00 | 28.75 | 7 |
| ATOM | 3573 | C | GLN | A | 469 | 9.499 | 45.223 | 21.253 | 1.00 | 21.80 | 6 |
| ATOM | 3574 | O | GLN | A | 469 | 8.918 | 45.188 | 20.172 | 1.00 | 21.45 | 8 |
| ATOM | 3575 | N | TYR | A | 470 | 10.286 | 44.235 | 21.685 | 1.00 | 21.34 | 7 |
| ATOM | 3576 | CA | TYR | A | 470 | 10.520 | 43.040 | 20.871 | 1.00 | 21.34 | 6 |
| ATOM | 3577 | CB | TYR | A | 470 | 11.647 | 42.194 | 21.454 | 1.00 | 20.73 | 6 |
| ATOM | 3578 | CG | TYR | A | 470 | 12.023 | 41.005 | 20.592 | 1.00 | 20.38 | 6 |
| ATOM | 3579 | CD1 | TYR | A | 470 | 12.753 | 41.179 | 19.417 | 1.00 | 20.34 | 6 |
| ATOM | 3580 | CE1 | TYR | A | 470 | 13.114 | 40.092 | 18.623 | 1.00 | 19.64 | 6 |
| ATOM | 3581 | CZ | TYR | A | 470 | 12.743 | 38.814 | 18.998 | 1.00 | 19.36 | 6 |
| ATOM | 3582 | OH | TYR | A | 470 | 13.108 | 37.746 | 18.207 | 1.00 | 19.18 | 8 |
| ATOM | 3583 | CE2 | TYR | A | 470 | 12.017 | 38.606 | 20.169 | 1.00 | 20.34 | 6 |
| ATOM | 3584 | CD2 | TYR | A | 470 | 11.664 | 39.705 | 20.961 | 1.00 | 19.79 | 6 |
| ATOM | 3585 | C | TYR | A | 470 | 9.255 | 42.202 | 20.719 | 1.00 | 21.88 | 6 |
| ATOM | 3586 | O | TYR | A | 470 | 8.938 | 41.733 | 19.621 | 1.00 | 21.16 | 8 |
| ATOM | 3587 | N | ALA | A | 471 | 8.537 | 42.023 | 21.825 | 1.00 | 22.90 | 7 |
| ATOM | 3588 | CA | ALA | A | 471 | 7.269 | 41.307 | 21.811 | 1.00 | 24.35 | 6 |
| ATOM | 3589 | CB | ALA | A | 471 | 6.738 | 41.119 | 23.232 | 1.00 | 24.27 | 6 |
| ATOM | 3590 | C | ALA | A | 471 | 6.245 | 42.034 | 20.944 | 1.00 | 25.46 | 6 |
| ATOM | 3591 | O | ALA | A | 471 | 5.509 | 41.400 | 20.194 | 1.00 | 25.50 | 8 |
| ATOM | 3592 | N | ASP | A | 472 | 6.215 | 43.365 | 21.036 | 1.00 | 26.95 | 7 |
| ATOM | 3593 | CA | ASP | A | 472 | 5.311 | 44.173 | 20.212 | 1.00 | 28.53 | 6 |
| ATOM | 3594 | CB | ASP | A | 472 | 5.456 | 45.668 | 20.527 | 1.00 | 28.64 | 6 |
| ATOM | 3595 | CG | ASP | A | 472 | 4.520 | 46.131 | 21.640 | 1.00 | 30.11 | 6 |
| ATOM | 3596 | OD1 | ASP | A | 472 | 4.284 | 45.356 | 22.596 | 1.00 | 32.36 | 8 |
| ATOM | 3597 | OD2 | ASP | A | 472 | 4.023 | 47.282 | 21.562 | 1.00 | 32.11 | 8 |
| ATOM | 3598 | C | ASP | A | 472 | 5.537 | 43.910 | 18.721 | 1.00 | 29.26 | 6 |

TABLE 7-continued

Coordinates of the crystal structure of *E. coli* ExoI bound to compound 10

| ATOM | 3599 | O | ASP | A | 472 | 4.578 | 43.751 | 17.965 | 1.00 | 29.51 | 8 |
|---|---|---|---|---|---|---|---|---|---|---|---|
| ATOM | 3600 | N | GLU | A | 473 | 6.806 | 43.839 | 18.314 | 1.00 | 30.31 | 7 |
| ATOM | 3601 | CA | GLU | A | 473 | 7.164 | 43.542 | 16.923 | 1.00 | 31.47 | 6 |
| ATOM | 3602 | CB | GLU | A | 473 | 8.662 | 43.793 | 16.681 | 1.00 | 31.31 | 6 |
| ATOM | 3603 | CG | GLU | A | 473 | 9.119 | 43.550 | 15.228 | 1.00 | 31.98 | 6 |
| ATOM | 3604 | CD | GLU | A | 473 | 10.629 | 43.342 | 15.084 | 1.00 | 32.05 | 6 |
| ATOM | 3605 | OE1 | GLU | A | 473 | 11.400 | 43.875 | 15.912 | 1.00 | 32.71 | 8 |
| ATOM | 3606 | OE2 | GLU | A | 473 | 11.044 | 42.648 | 14.127 | 1.00 | 32.42 | 8 |
| ATOM | 3607 | C | GLU | A | 473 | 6.805 | 42.101 | 16.540 | 1.00 | 32.31 | 6 |
| ATOM | 3608 | O | GLU | A | 473 | 6.126 | 41.867 | 15.537 | 1.00 | 32.39 | 8 |
| ATOM | 3609 | N | ILE | A | 474 | 7.264 | 41.149 | 17.351 | 1.00 | 33.34 | 7 |
| ATOM | 3610 | CA | ILE | A | 474 | 7.190 | 39.725 | 17.016 | 1.00 | 34.42 | 6 |
| ATOM | 3611 | CB | ILE | A | 474 | 8.296 | 38.902 | 17.780 | 1.00 | 34.32 | 6 |
| ATOM | 3612 | CG1 | ILE | A | 474 | 9.700 | 39.344 | 17.342 | 1.00 | 34.34 | 6 |
| ATOM | 3613 | CD1 | ILE | A | 474 | 10.074 | 38.977 | 15.901 | 1.00 | 34.40 | 6 |
| ATOM | 3614 | CG2 | ILE | A | 474 | 8.119 | 37.383 | 17.592 | 1.00 | 34.61 | 6 |
| ATOM | 3615 | C | ILE | A | 474 | 5.799 | 39.132 | 17.253 | 1.00 | 35.23 | 6 |
| ATOM | 3616 | O | ILE | A | 474 | 5.382 | 38.222 | 16.533 | 1.00 | 35.39 | 8 |
| ATOM | 3617 | N | VAL | A | 475 | 5.080 | 39.659 | 18.245 | 1.00 | 36.28 | 7 |
| ATOM | 3618 | CA | VAL | A | 475 | 3.804 | 39.061 | 18.675 | 1.00 | 37.41 | 6 |
| ATOM | 3619 | CB | VAL | A | 475 | 3.989 | 38.175 | 19.949 | 1.00 | 37.31 | 6 |
| ATOM | 3620 | CG1 | VAL | A | 475 | 5.244 | 37.354 | 19.846 | 1.00 | 37.72 | 6 |
| ATOM | 3621 | CG2 | VAL | A | 475 | 4.037 | 39.025 | 21.222 | 1.00 | 37.83 | 6 |
| ATOM | 3622 | C | VAL | A | 475 | 2.663 | 40.069 | 18.917 | 1.00 | 37.93 | 6 |
| ATOM | 3623 | O | VAL | A | 475 | 1.500 | 39.772 | 18.628 | 1.00 | 38.21 | 8 |
| ATOM | 3624 | N | GLU | A | 476 | 3.017 | 41.257 | 19.420 | 1.00 | 38.57 | 7 |
| ATOM | 3625 | CA | GLU | A | 476 | 2.078 | 42.200 | 20.072 | 1.00 | 39.02 | 6 |
| ATOM | 3626 | CB | GLU | A | 476 | 0.719 | 42.274 | 19.363 | 1.00 | 39.13 | 6 |
| ATOM | 3627 | CG | GLU | A | 476 | −0.230 | 43.320 | 19.974 | 1.00 | 40.06 | 6 |
| ATOM | 3628 | CD | GLU | A | 476 | −1.711 | 42.991 | 19.790 | 1.00 | 41.26 | 6 |
| ATOM | 3629 | OE1 | GLU | A | 476 | −2.038 | 41.853 | 19.381 | 1.00 | 41.94 | 8 |
| ATOM | 3630 | OE2 | GLU | A | 476 | −2.551 | 43.875 | 20.071 | 1.00 | 41.62 | 8 |
| ATOM | 3631 | C | GLU | A | 476 | 1.884 | 41.853 | 21.549 | 1.00 | 38.98 | 6 |
| ATOM | 3632 | O | GLU | A | 476 | 2.722 | 42.182 | 22.392 | 1.00 | 39.17 | 8 |
| ATOM | 3633 | O3 | XXX | B | 1 | 36.620 | 0.299 | 53.346 | 1.00 | 31.59 | 8 |
| ATOM | 3634 | C16 | XXX | B | 1 | 36.394 | −0.943 | 53.264 | 1.00 | 30.79 | 6 |
| ATOM | 3635 | O2 | XXX | B | 1 | 37.256 | −1.724 | 52.792 | 1.00 | 32.22 | 8 |
| ATOM | 3636 | C6 | XXX | B | 1 | 35.034 | −1.437 | 53.555 | 1.00 | 29.59 | 6 |
| ATOM | 3637 | C5 | XXX | B | 1 | 34.807 | −2.745 | 53.216 | 1.00 | 29.56 | 6 |
| ATOM | 3638 | C4 | XXX | B | 1 | 33.540 | −3.262 | 53.396 | 1.00 | 29.83 | 6 |
| ATOM | 3639 | O1 | XXX | B | 1 | 33.336 | −4.577 | 53.106 | 1.00 | 30.11 | 8 |
| ATOM | 3640 | C2 | XXX | B | 1 | 33.810 | −5.534 | 54.078 | 1.00 | 30.31 | 6 |
| ATOM | 3641 | C3 | XXX | B | 1 | 32.508 | −2.454 | 53.901 | 1.00 | 29.73 | 6 |
| ATOM | 3642 | C8 | XXX | B | 1 | 32.754 | −1.115 | 54.228 | 1.00 | 29.61 | 6 |
| ATOM | 3643 | C7 | XXX | B | 1 | 34.038 | −0.587 | 54.034 | 1.00 | 29.31 | 6 |
| ATOM | 3644 | N1 | XXX | B | 1 | 34.363 | 0.697 | 54.335 | 1.00 | 34.18 | 7 |
| ATOM | 3645 | C9 | XXX | B | 1 | 33.570 | 1.759 | 54.668 | 1.00 | 34.35 | 6 |
| ATOM | 3646 | C10 | XXX | B | 1 | 34.206 | 2.952 | 54.992 | 1.00 | 34.37 | 6 |
| ATOM | 3647 | CL1 | XXX | B | 1 | 35.990 | 3.017 | 54.990 | 1.00 | 35.08 | 17 |
| ATOM | 3648 | C11 | XXX | B | 1 | 33.491 | 4.090 | 55.340 | 1.00 | 34.31 | 6 |
| ATOM | 3649 | C12 | XXX | B | 1 | 32.105 | 4.031 | 55.375 | 1.00 | 34.37 | 6 |
| ATOM | 3650 | C15 | XXX | B | 1 | 32.179 | 1.702 | 54.697 | 1.00 | 34.22 | 6 |
| ATOM | 3651 | C13 | XXX | B | 1 | 31.458 | 2.834 | 55.071 | 1.00 | 34.29 | 6 |
| ATOM | 3652 | C14 | XXX | B | 1 | 29.980 | 2.811 | 55.031 | 1.00 | 34.34 | 6 |
| ATOM | 3653 | F2 | XXX | B | 1 | 29.542 | 1.620 | 54.665 | 1.00 | 34.23 | 9 |
| ATOM | 3654 | F1 | XXX | B | 1 | 29.423 | 3.256 | 56.133 | 1.00 | 34.40 | 9 |
| ATOM | 3655 | F3 | XXX | B | 1 | 29.667 | 3.628 | 54.034 | 1.00 | 33.85 | 9 |
| ATOM | 3656 | OW0 | HOH | Z | 1 | 37.822 | 13.622 | 53.680 | 1.00 | 15.33 | 8 |
| ATOM | 3657 | OW0 | HOH | Z | 2 | 18.685 | 32.491 | 19.622 | 1.00 | 13.60 | 8 |
| ATOM | 3658 | OW0 | HOH | Z | 3 | 38.854 | 5.704 | 44.654 | 1.00 | 15.09 | 8 |
| ATOM | 3659 | OW0 | HOH | Z | 4 | 27.903 | 21.019 | 56.001 | 1.00 | 19.13 | 8 |
| ATOM | 3660 | OW0 | HOH | Z | 5 | 18.488 | 29.463 | 56.125 | 1.00 | 12.99 | 8 |
| ATOM | 3661 | OW0 | HOH | Z | 6 | 25.385 | 26.563 | 45.292 | 1.00 | 19.53 | 8 |
| ATOM | 3662 | OW0 | HOH | Z | 7 | 25.083 | 10.850 | 37.888 | 1.00 | 17.27 | 8 |
| ATOM | 3663 | OW0 | HOH | Z | 8 | 18.171 | 25.457 | 23.312 | 1.00 | 13.96 | 8 |
| ATOM | 3664 | OW0 | HOH | Z | 9 | 34.748 | 0.785 | 58.071 | 1.00 | 25.49 | 8 |
| ATOM | 3665 | OW0 | HOH | Z | 10 | 15.402 | 20.878 | 20.971 | 1.00 | 18.20 | 8 |
| ATOM | 3666 | OW0 | HOH | Z | 11 | 33.766 | 11.435 | 36.799 | 1.00 | 14.84 | 8 |
| ATOM | 3667 | OW0 | HOH | Z | 12 | 31.486 | 26.934 | 49.667 | 1.00 | 15.39 | 8 |
| ATOM | 3668 | OW0 | HOH | Z | 13 | 26.745 | 31.060 | 32.322 | 1.00 | 17.29 | 8 |
| ATOM | 3669 | OW0 | HOH | Z | 14 | 36.010 | −0.330 | 50.274 | 1.00 | 35.76 | 8 |
| ATOM | 3670 | OW0 | HOH | Z | 15 | 21.934 | 32.232 | 30.615 | 1.00 | 26.33 | 8 |
| ATOM | 3671 | OW0 | HOH | Z | 16 | 41.814 | 32.600 | 33.985 | 1.00 | 19.62 | 8 |
| ATOM | 3672 | OW0 | HOH | Z | 17 | 30.209 | 26.754 | 31.566 | 1.00 | 17.55 | 8 |
| ATOM | 3673 | OW0 | HOH | Z | 18 | 28.352 | 15.062 | 17.636 | 1.00 | 21.36 | 8 |
| ATOM | 3674 | OW0 | HOH | Z | 19 | 14.792 | 24.142 | 14.382 | 1.00 | 20.89 | 8 |
| ATOM | 3675 | OW0 | HOH | Z | 20 | 31.192 | −0.541 | 44.151 | 1.00 | 17.74 | 8 |
| ATOM | 3676 | OW0 | HOH | Z | 21 | 37.963 | 2.333 | 50.889 | 1.00 | 28.89 | 8 |

TABLE 7-continued

Coordinates of the crystal structure of *E. coli* ExoI bound to compound 10

| ATOM | 3677 | OW0 | HOH | Z | 22 | 28.011 | 36.495 | 16.475 | 1.00 | 18.28 | 8 |
|---|---|---|---|---|---|---|---|---|---|---|---|
| ATOM | 3678 | OW0 | HOH | Z | 23 | 13.139 | 25.476 | 21.409 | 1.00 | 22.29 | 8 |
| ATOM | 3679 | OW0 | HOH | Z | 24 | 43.167 | 10.915 | 31.847 | 1.00 | 19.40 | 8 |
| ATOM | 3680 | OW0 | HOH | Z | 25 | 12.632 | 21.429 | 15.684 | 1.00 | 23.33 | 8 |
| ATOM | 3681 | OW0 | HOH | Z | 26 | 28.232 | 21.780 | 25.905 | 1.00 | 15.83 | 8 |
| ATOM | 3682 | OW0 | HOH | Z | 27 | 41.619 | 18.732 | 53.427 | 1.00 | 18.13 | 8 |
| ATOM | 3683 | OW0 | HOH | Z | 28 | 28.934 | 28.618 | 10.813 | 1.00 | 22.82 | 8 |
| ATOM | 3684 | OW0 | HOH | Z | 29 | 25.750 | 28.578 | 31.056 | 1.00 | 16.06 | 8 |
| ATOM | 3685 | OW0 | HOH | Z | 30 | 14.431 | 17.847 | 23.211 | 1.00 | 23.94 | 8 |
| ATOM | 3686 | OW0 | HOH | Z | 31 | 28.500 | 29.572 | 34.250 | 1.00 | 16.88 | 8 |
| ATOM | 3687 | OW0 | HOH | Z | 32 | 26.444 | 20.176 | 36.005 | 1.00 | 19.45 | 8 |
| ATOM | 3688 | OW0 | HOH | Z | 33 | 45.495 | 23.199 | 49.991 | 1.00 | 17.53 | 8 |
| ATOM | 3689 | OW0 | HOH | Z | 34 | 31.253 | 29.028 | 33.200 | 1.00 | 19.70 | 8 |
| ATOM | 3690 | OW0 | HOH | Z | 35 | 25.130 | 11.609 | 53.672 | 1.00 | 15.27 | 8 |
| ATOM | 3691 | OW0 | HOH | Z | 36 | 14.722 | 21.507 | 13.868 | 1.00 | 15.75 | 8 |
| ATOM | 3692 | OW0 | HOH | Z | 37 | 22.718 | 22.669 | 10.485 | 1.00 | 21.08 | 8 |
| ATOM | 3693 | OW0 | HOH | Z | 38 | 43.259 | 18.983 | 21.022 | 1.00 | 28.09 | 8 |
| ATOM | 3694 | OW0 | HOH | Z | 39 | 17.542 | 43.226 | 16.007 | 1.00 | 21.00 | 8 |
| ATOM | 3695 | OW0 | HOH | Z | 40 | 17.230 | 25.687 | 14.371 | 1.00 | 18.65 | 8 |
| ATOM | 3696 | OW0 | HOH | Z | 41 | 47.216 | 23.783 | 52.019 | 1.00 | 18.04 | 8 |
| ATOM | 3697 | OW0 | HOH | Z | 42 | 18.267 | 27.408 | 27.308 | 1.00 | 19.35 | 8 |
| ATOM | 3698 | OW0 | HOH | Z | 43 | 18.176 | 9.114 | 40.214 | 1.00 | 28.57 | 8 |
| ATOM | 3699 | OW0 | HOH | Z | 44 | 39.197 | 3.317 | 39.068 | 1.00 | 28.47 | 8 |
| ATOM | 3700 | OW0 | HOH | Z | 45 | 17.803 | 30.035 | 18.612 | 1.00 | 16.42 | 8 |
| ATOM | 3701 | OW0 | HOH | Z | 46 | 24.483 | 29.548 | 46.805 | 1.00 | 28.93 | 8 |
| ATOM | 3702 | OW0 | HOH | Z | 47 | 18.064 | 30.991 | 14.064 | 1.00 | 18.70 | 8 |
| ATOM | 3703 | OW0 | HOH | Z | 48 | 35.800 | 12.559 | 38.381 | 1.00 | 14.71 | 8 |
| ATOM | 3704 | OW0 | HOH | Z | 49 | 16.166 | 37.300 | 36.944 | 1.00 | 22.52 | 8 |
| ATOM | 3705 | OW0 | HOH | Z | 50 | 27.074 | 15.074 | 12.960 | 1.00 | 22.10 | 8 |
| ATOM | 3706 | OW0 | HOH | Z | 51 | 35.244 | 15.402 | 38.632 | 1.00 | 20.62 | 8 |
| ATOM | 3707 | OW0 | HOH | Z | 52 | 29.144 | 19.248 | 2.533 | 1.00 | 32.02 | 8 |
| ATOM | 3708 | OW0 | HOH | Z | 53 | 30.023 | 19.663 | 48.274 | 1.00 | 20.38 | 8 |
| ATOM | 3709 | OW0 | HOH | Z | 54 | 16.485 | 32.550 | 4.015 | 1.00 | 22.22 | 8 |
| ATOM | 3710 | OW0 | HOH | Z | 55 | 34.237 | −3.231 | 38.221 | 1.00 | 22.14 | 8 |
| ATOM | 3711 | OW0 | HOH | Z | 56 | 32.859 | 13.776 | 16.407 | 1.00 | 33.97 | 8 |
| ATOM | 3712 | OW0 | HOH | Z | 57 | 16.387 | 28.781 | 14.798 | 1.00 | 20.46 | 8 |
| ATOM | 3713 | OW0 | HOH | Z | 58 | 23.463 | 21.736 | 38.714 | 1.00 | 20.50 | 8 |
| ATOM | 3714 | OW0 | HOH | Z | 59 | 28.599 | 13.684 | 40.844 | 1.00 | 22.55 | 8 |
| ATOM | 3715 | OW0 | HOH | Z | 60 | 25.509 | 22.712 | 46.019 | 1.00 | 18.42 | 8 |
| ATOM | 3716 | OW0 | HOH | Z | 61 | 15.655 | 29.984 | 17.139 | 1.00 | 15.72 | 8 |
| ATOM | 3717 | OW0 | HOH | Z | 62 | 19.467 | 31.603 | 31.434 | 1.00 | 36.87 | 8 |
| ATOM | 3718 | OW0 | HOH | Z | 63 | 40.126 | 14.067 | 26.325 | 1.00 | 18.04 | 8 |
| ATOM | 3719 | OW0 | HOH | Z | 64 | 36.413 | 28.366 | 54.314 | 1.00 | 27.75 | 8 |
| ATOM | 3720 | OW0 | HOH | Z | 65 | 30.152 | 16.353 | 37.179 | 1.00 | 25.23 | 8 |
| ATOM | 3721 | OW0 | HOH | Z | 66 | 15.155 | 50.449 | 26.574 | 1.00 | 23.49 | 8 |
| ATOM | 3722 | OW0 | HOH | Z | 67 | 24.302 | 14.378 | 11.006 | 1.00 | 35.27 | 8 |
| ATOM | 3723 | OW0 | HOH | Z | 68 | 40.627 | 16.095 | 54.612 | 1.00 | 20.22 | 8 |
| ATOM | 3724 | OW0 | HOH | Z | 69 | 24.088 | 20.337 | −2.432 | 1.00 | 26.18 | 8 |
| ATOM | 3725 | OW0 | HOH | Z | 70 | 48.658 | 20.278 | 25.536 | 1.00 | 28.46 | 8 |
| ATOM | 3726 | OW0 | HOH | Z | 71 | 32.047 | 10.197 | 32.662 | 1.00 | 20.68 | 8 |
| ATOM | 3727 | OW0 | HOH | Z | 72 | 19.918 | 36.104 | 27.470 | 1.00 | 22.48 | 8 |
| ATOM | 3728 | OW0 | HOH | Z | 73 | 22.987 | 21.121 | 45.859 | 1.00 | 19.68 | 8 |
| ATOM | 3729 | OW0 | HOH | Z | 74 | 18.380 | 34.430 | 53.619 | 1.00 | 25.04 | 8 |
| ATOM | 3730 | OW0 | HOH | Z | 75 | 28.549 | 32.967 | 26.882 | 1.00 | 22.48 | 8 |
| ATOM | 3731 | OW0 | HOH | Z | 76 | 41.296 | 9.330 | 52.172 | 1.00 | 22.60 | 8 |
| ATOM | 3732 | OW0 | HOH | Z | 77 | 10.988 | 35.127 | 33.410 | 1.00 | 18.15 | 8 |
| ATOM | 3733 | OW0 | HOH | Z | 78 | 35.295 | 10.622 | 40.452 | 1.00 | 15.95 | 8 |
| ATOM | 3734 | OW0 | HOH | Z | 79 | 17.949 | 27.440 | 50.589 | 1.00 | 19.93 | 8 |
| ATOM | 3735 | OW0 | HOH | Z | 80 | 10.767 | 39.966 | 24.397 | 1.00 | 23.87 | 8 |
| ATOM | 3736 | OW0 | HOH | Z | 81 | 45.901 | 11.280 | 42.434 | 1.00 | 19.40 | 8 |
| ATOM | 3737 | OW0 | HOH | Z | 82 | 7.978 | 31.749 | 23.537 | 1.00 | 21.58 | 8 |
| ATOM | 3738 | OW0 | HOH | Z | 83 | 24.952 | 25.325 | 47.596 | 1.00 | 20.04 | 8 |
| ATOM | 3739 | OW0 | HOH | Z | 84 | 25.229 | 23.737 | 10.203 | 1.00 | 13.90 | 8 |
| ATOM | 3740 | OW0 | HOH | Z | 85 | 10.484 | 27.190 | 22.207 | 1.00 | 23.26 | 8 |
| ATOM | 3741 | OW0 | HOH | Z | 86 | 10.102 | 29.856 | 27.603 | 1.00 | 29.94 | 8 |
| ATOM | 3742 | OW0 | HOH | Z | 87 | 8.946 | 32.409 | 26.777 | 1.00 | 36.89 | 8 |
| ATOM | 3743 | OW0 | HOH | Z | 88 | 35.821 | 10.369 | 29.087 | 1.00 | 31.98 | 8 |
| ATOM | 3744 | OW0 | HOH | Z | 89 | 8.443 | 28.533 | 19.890 | 1.00 | 28.09 | 8 |
| ATOM | 3745 | OW0 | HOH | Z | 90 | 45.395 | 30.512 | 31.462 | 1.00 | 19.93 | 8 |
| ATOM | 3746 | OW0 | HOH | Z | 91 | 7.807 | 22.983 | 17.578 | 1.00 | 33.34 | 8 |
| ATOM | 3747 | OW0 | HOH | Z | 92 | 32.197 | 33.701 | 29.608 | 1.00 | 33.95 | 8 |
| ATOM | 3748 | OW0 | HOH | Z | 93 | 33.089 | 16.643 | 36.962 | 1.00 | 29.54 | 8 |
| ATOM | 3749 | OW0 | HOH | Z | 94 | 31.422 | 22.669 | 11.824 | 1.00 | 31.11 | 8 |
| ATOM | 3750 | OW0 | HOH | Z | 95 | 9.295 | 11.972 | 9.825 | 1.00 | 31.39 | 8 |
| ATOM | 3751 | OW0 | HOH | Z | 96 | 27.520 | 29.277 | 38.934 | 1.00 | 17.79 | 8 |
| ATOM | 3752 | OW0 | HOH | Z | 97 | 22.829 | −0.768 | 32.759 | 1.00 | 30.73 | 8 |
| ATOM | 3753 | OW0 | HOH | Z | 98 | 13.120 | 14.386 | 25.369 | 1.00 | 29.64 | 8 |
| ATOM | 3754 | OW0 | HOH | Z | 99 | 12.752 | 33.382 | 12.039 | 1.00 | 46.98 | 8 |

TABLE 7-continued

Coordinates of the crystal structure of *E. coli* ExoI bound to compound 10

| ATOM | 3755 | OW0 | HOH | Z | 100 | 39.623 | 25.028 | 17.741 | 1.00 | 37.05 | 8 |
|---|---|---|---|---|---|---|---|---|---|---|---|
| ATOM | 3756 | OW0 | HOH | Z | 101 | 44.001 | 32.051 | 35.403 | 1.00 | 28.33 | 8 |
| ATOM | 3757 | OW0 | HOH | Z | 102 | 34.319 | 12.395 | 29.727 | 1.00 | 26.70 | 8 |
| ATOM | 3758 | OW0 | HOH | Z | 103 | 40.241 | 29.254 | 21.534 | 1.00 | 19.18 | 8 |
| ATOM | 3759 | OW0 | HOH | Z | 104 | 34.506 | 14.424 | 18.601 | 1.00 | 31.18 | 8 |
| ATOM | 3760 | OW0 | HOH | Z | 105 | 43.862 | 13.985 | 47.722 | 1.00 | 20.99 | 8 |
| ATOM | 3761 | OW0 | HOH | Z | 106 | 22.975 | 17.226 | 40.496 | 1.00 | 30.41 | 8 |
| ATOM | 3762 | OW0 | HOH | Z | 107 | 38.656 | 10.110 | 28.761 | 1.00 | 31.21 | 8 |
| ATOM | 3763 | OW0 | HOH | Z | 108 | 25.585 | 29.128 | 33.955 | 1.00 | 16.75 | 8 |
| ATOM | 3764 | OW0 | HOH | Z | 109 | 2.167 | 36.413 | 33.710 | 1.00 | 28.37 | 8 |
| ATOM | 3765 | OW0 | HOH | Z | 110 | 17.638 | 2.594 | 57.322 | 1.00 | 26.05 | 8 |
| ATOM | 3766 | OW0 | HOH | Z | 111 | 11.751 | 19.947 | 2.718 | 1.00 | 27.71 | 8 |
| ATOM | 3767 | OW0 | HOH | Z | 112 | 16.958 | 32.577 | 12.152 | 1.00 | 14.35 | 8 |
| ATOM | 3768 | OW0 | HOH | Z | 113 | 21.418 | 43.736 | 24.993 | 1.00 | 31.71 | 8 |
| ATOM | 3769 | OW0 | HOH | Z | 114 | 42.968 | 11.107 | 45.905 | 1.00 | 27.38 | 8 |
| ATOM | 3770 | OW0 | HOH | Z | 115 | 10.369 | 20.726 | 5.200 | 1.00 | 22.98 | 8 |
| ATOM | 3771 | OW0 | HOH | Z | 116 | 12.841 | 38.505 | 13.745 | 1.00 | 29.31 | 8 |
| ATOM | 3772 | OW0 | HOH | Z | 117 | 23.993 | 27.166 | 34.757 | 1.00 | 37.52 | 8 |
| ATOM | 3773 | OW0 | HOH | Z | 118 | 4.067 | 22.772 | 11.599 | 1.00 | 33.53 | 8 |
| ATOM | 3774 | OW0 | HOH | Z | 119 | 36.685 | 36.532 | 34.585 | 1.00 | 28.02 | 8 |
| ATOM | 3775 | OW0 | HOH | Z | 120 | 13.334 | 5.898 | 18.696 | 1.00 | 37.68 | 8 |
| ATOM | 3776 | OW0 | HOH | Z | 121 | 12.697 | 35.375 | 18.933 | 1.00 | 17.13 | 8 |
| ATOM | 3777 | OW0 | HOH | Z | 122 | 8.129 | 28.979 | 22.405 | 1.00 | 28.71 | 8 |
| ATOM | 3778 | OW0 | HOH | Z | 123 | 24.067 | 10.544 | 58.129 | 1.00 | 23.85 | 8 |
| ATOM | 3779 | OW0 | HOH | Z | 124 | 12.618 | 46.765 | 19.149 | 1.00 | 35.48 | 8 |
| ATOM | 3780 | OW0 | HOH | Z | 125 | 34.377 | 27.461 | 14.842 | 1.00 | 30.14 | 8 |
| ATOM | 3781 | OW0 | HOH | Z | 126 | 39.812 | 7.571 | 55.629 | 1.00 | 27.98 | 8 |
| ATOM | 3782 | OW0 | HOH | Z | 127 | 23.824 | 12.244 | 55.913 | 1.00 | 20.56 | 8 |
| ATOM | 3783 | OW0 | HOH | Z | 128 | 24.421 | 14.594 | 57.356 | 1.00 | 30.28 | 8 |
| ATOM | 3784 | OW0 | HOH | Z | 129 | 13.103 | 25.051 | 32.881 | 1.00 | 32.37 | 8 |
| ATOM | 3785 | OW0 | HOH | Z | 130 | 41.353 | 8.304 | 32.306 | 1.00 | 24.37 | 8 |
| ATOM | 3786 | OW0 | HOH | Z | 131 | 24.902 | 18.010 | 57.781 | 1.00 | 24.38 | 8 |
| ATOM | 3787 | OW0 | HOH | Z | 132 | 43.169 | 32.138 | 31.595 | 1.00 | 25.80 | 8 |
| ATOM | 3788 | OW0 | HOH | Z | 133 | 13.080 | 36.914 | 15.756 | 1.00 | 26.12 | 8 |
| ATOM | 3789 | OW0 | HOH | Z | 134 | 32.686 | 32.912 | 15.360 | 1.00 | 44.56 | 8 |
| ATOM | 3790 | OW0 | HOH | Z | 135 | 30.118 | −5.020 | 39.780 | 1.00 | 43.54 | 8 |
| ATOM | 3791 | OW0 | HOH | Z | 136 | 46.349 | 28.908 | 43.950 | 1.00 | 25.34 | 8 |
| ATOM | 3792 | OW0 | HOH | Z | 137 | 15.834 | 53.176 | 32.767 | 1.00 | 24.36 | 8 |
| ATOM | 3793 | OW0 | HOH | Z | 138 | 15.758 | 45.060 | 16.791 | 1.00 | 29.03 | 8 |
| ATOM | 3794 | OW0 | HOH | Z | 139 | 35.319 | 1.432 | 48.753 | 1.00 | 21.30 | 8 |
| ATOM | 3795 | OW0 | HOH | Z | 140 | 9.445 | 25.069 | 20.886 | 1.00 | 20.28 | 8 |
| ATOM | 3796 | OW0 | HOH | Z | 141 | 21.792 | 9.271 | 58.485 | 1.00 | 32.74 | 8 |
| ATOM | 3797 | OW0 | HOH | Z | 142 | 42.205 | 25.913 | 54.888 | 1.00 | 27.36 | 8 |
| ATOM | 3798 | OW0 | HOH | Z | 143 | 26.020 | 16.812 | 41.060 | 1.00 | 25.66 | 8 |
| ATOM | 3799 | OW0 | HOH | Z | 144 | 9.426 | 18.328 | 6.516 | 1.00 | 26.81 | 8 |
| ATOM | 3800 | OW0 | HOH | Z | 145 | 29.345 | 18.825 | 37.732 | 1.00 | 32.18 | 8 |
| ATOM | 3801 | OW0 | HOH | Z | 146 | 27.286 | 8.358 | 20.729 | 1.00 | 34.20 | 8 |
| ATOM | 3802 | OW0 | HOH | Z | 147 | 5.192 | 29.609 | −3.540 | 1.00 | 29.15 | 8 |
| ATOM | 3803 | OW0 | HOH | Z | 148 | 43.225 | 30.320 | 40.375 | 1.00 | 26.17 | 8 |
| ATOM | 3804 | OW0 | HOH | Z | 149 | 23.005 | 33.152 | 9.707 | 1.00 | 20.56 | 8 |
| ATOM | 3805 | OW0 | HOH | Z | 150 | 1.301 | 24.310 | 14.139 | 1.00 | 27.77 | 8 |
| ATOM | 3806 | OW0 | HOH | Z | 151 | 14.773 | 22.679 | 33.210 | 1.00 | 47.52 | 8 |
| ATOM | 3807 | OW0 | HOH | Z | 152 | 14.441 | 16.781 | 25.645 | 1.00 | 29.72 | 8 |
| ATOM | 3808 | OW0 | HOH | Z | 153 | 15.832 | 25.353 | 2.636 | 1.00 | 32.00 | 8 |
| ATOM | 3809 | OW0 | HOH | Z | 154 | 33.917 | 27.535 | 31.100 | 1.00 | 24.90 | 8 |
| ATOM | 3810 | OW0 | HOH | Z | 155 | 16.573 | 18.337 | 26.993 | 1.00 | 30.65 | 8 |
| ATOM | 3811 | OW0 | HOH | Z | 156 | 49.083 | 24.041 | 35.174 | 1.00 | 50.65 | 8 |
| ATOM | 3812 | OW0 | HOH | Z | 157 | 25.656 | 28.124 | 58.668 | 1.00 | 25.06 | 8 |
| ATOM | 3813 | OW0 | HOH | Z | 158 | 29.025 | 35.725 | 30.500 | 1.00 | 29.89 | 8 |
| ATOM | 3814 | OW0 | HOH | Z | 159 | 29.404 | 33.380 | 29.383 | 1.00 | 27.48 | 8 |
| ATOM | 3815 | OW0 | HOH | Z | 160 | 3.036 | 33.894 | 29.099 | 1.00 | 34.64 | 8 |
| ATOM | 3816 | OW0 | HOH | Z | 161 | 36.806 | 20.478 | 13.785 | 1.00 | 31.35 | 8 |
| ATOM | 3817 | OW0 | HOH | Z | 162 | 22.710 | 28.005 | −0.360 | 1.00 | 40.32 | 8 |
| ATOM | 3818 | OW0 | HOH | Z | 163 | 49.395 | 29.484 | 44.215 | 1.00 | 27.87 | 8 |
| ATOM | 3819 | OW0 | HOH | Z | 164 | 38.195 | 7.496 | 21.008 | 1.00 | 35.78 | 8 |
| ATOM | 3820 | OW0 | HOH | Z | 165 | 27.362 | 27.286 | 32.830 | 1.00 | 24.87 | 8 |
| ATOM | 3821 | OW0 | HOH | Z | 166 | 35.178 | 20.590 | 11.628 | 1.00 | 41.69 | 8 |
| ATOM | 3822 | OW0 | HOH | Z | 167 | 1.900 | 24.512 | 11.600 | 1.00 | 27.52 | 8 |
| ATOM | 3823 | OW0 | HOH | Z | 168 | 17.133 | 32.107 | 33.189 | 1.00 | 51.63 | 8 |
| ATOM | 3824 | OW0 | HOH | Z | 169 | 23.236 | 28.962 | 8.047 | 1.00 | 22.58 | 8 |
| ATOM | 3825 | OW0 | HOH | Z | 170 | 48.158 | 23.950 | 55.109 | 1.00 | 25.58 | 8 |
| ATOM | 3826 | OW0 | HOH | Z | 171 | 3.245 | 43.682 | 24.450 | 1.00 | 52.57 | 8 |
| ATOM | 3827 | OW0 | HOH | Z | 172 | 48.636 | 28.997 | 19.770 | 1.00 | 31.29 | 8 |
| ATOM | 3828 | OW0 | HOH | Z | 173 | 29.325 | 21.740 | 10.162 | 1.00 | 38.25 | 8 |
| ATOM | 3829 | OW0 | HOH | Z | 174 | 43.154 | 38.981 | 44.762 | 1.00 | 31.59 | 8 |
| ATOM | 3830 | OW0 | HOH | Z | 175 | 40.336 | 27.024 | 19.307 | 1.00 | 40.82 | 8 |
| ATOM | 3831 | OW0 | HOH | Z | 176 | 22.845 | 32.080 | 46.844 | 1.00 | 29.32 | 8 |
| ATOM | 3832 | OW0 | HOH | Z | 177 | 18.470 | 17.527 | 50.146 | 1.00 | 26.02 | 8 |

TABLE 7-continued

Coordinates of the crystal structure of *E. coli* ExoI bound to compound 10

| ATOM | 3833 | OW0 | HOH | Z | 178 | 35.329 | 23.084 | 10.710 | 1.00 | 57.72 | 8 |
|------|------|-----|-----|---|-----|--------|--------|--------|------|-------|---|
| ATOM | 3834 | OW0 | HOH | Z | 179 | 16.593 | 37.497 | 10.415 | 1.00 | 51.98 | 8 |
| ATOM | 3835 | OW0 | HOH | Z | 180 | 14.291 | 50.563 | 24.073 | 1.00 | 47.83 | 8 |
| ATOM | 3836 | OW0 | HOH | Z | 181 | 27.396 | 3.187 | 67.249 | 1.00 | 33.61 | 8 |
| ATOM | 3837 | OW0 | HOH | Z | 182 | 27.769 | 27.390 | 8.617 | 1.00 | 26.03 | 8 |
| ATOM | 3838 | OW0 | HOH | Z | 183 | 7.562 | 9.332 | 53.022 | 1.00 | 32.97 | 8 |
| ATOM | 3839 | OW0 | HOH | Z | 184 | 22.829 | 34.060 | 48.715 | 1.00 | 35.59 | 8 |
| ATOM | 3840 | OW0 | HOH | Z | 185 | 50.459 | 15.517 | 43.604 | 1.00 | 35.09 | 8 |
| ATOM | 3841 | OW0 | HOH | Z | 186 | 33.695 | 8.260 | 29.443 | 1.00 | 32.85 | 8 |
| ATOM | 3842 | OW0 | HOH | Z | 187 | 14.359 | 48.227 | 42.474 | 1.00 | 45.87 | 8 |
| ATOM | 3843 | OW0 | HOH | Z | 188 | 24.143 | 19.814 | 40.471 | 1.00 | 35.57 | 8 |
| ATOM | 3844 | OW0 | HOH | Z | 189 | 38.593 | 8.163 | 17.010 | 1.00 | 39.72 | 8 |
| ATOM | 3845 | OW0 | HOH | Z | 190 | 7.857 | 26.087 | 19.027 | 1.00 | 36.57 | 8 |
| ATOM | 3846 | OW0 | HOH | Z | 191 | 9.017 | 7.035 | 14.732 | 1.00 | 44.76 | 8 |
| ATOM | 3847 | OW0 | HOH | Z | 192 | 19.795 | 51.849 | 39.250 | 1.00 | 33.06 | 8 |
| ATOM | 3848 | OW0 | HOH | Z | 193 | 45.205 | 9.722 | 39.677 | 1.00 | 36.05 | 8 |
| ATOM | 3849 | OW0 | HOH | Z | 194 | 24.718 | 9.870 | 4.590 | 1.00 | 28.64 | 8 |
| ATOM | 3850 | OW0 | HOH | Z | 195 | 37.810 | 24.483 | 15.049 | 1.00 | 40.21 | 8 |
| ATOM | 3851 | OW0 | HOH | Z | 196 | 38.824 | 18.936 | 57.170 | 1.00 | 27.46 | 8 |
| ATOM | 3852 | OW0 | HOH | Z | 197 | 40.110 | 3.376 | 43.825 | 1.00 | 31.70 | 8 |
| ATOM | 3853 | OW0 | HOH | Z | 198 | 28.698 | 16.252 | 10.769 | 1.00 | 38.76 | 8 |
| ATOM | 3854 | OW0 | HOH | Z | 199 | 9.187 | 32.983 | 4.147 | 1.00 | 38.86 | 8 |
| ATOM | 3855 | OW0 | HOH | Z | 200 | 51.813 | 20.350 | 42.847 | 1.00 | 29.38 | 8 |
| ATOM | 3856 | OW0 | HOH | Z | 201 | 28.748 | 15.079 | 63.026 | 1.00 | 35.69 | 8 |
| ATOM | 3857 | OW0 | HOH | Z | 202 | 20.468 | 37.756 | 10.039 | 1.00 | 48.67 | 8 |
| ATOM | 3858 | OW0 | HOH | Z | 203 | 17.990 | 8.848 | 56.759 | 1.00 | 35.68 | 8 |
| ATOM | 3859 | OW0 | HOH | Z | 204 | 5.145 | 25.229 | 19.650 | 1.00 | 34.82 | 8 |
| ATOM | 3860 | OW0 | HOH | Z | 205 | 31.863 | 11.213 | 29.933 | 1.00 | 39.80 | 8 |
| ATOM | 3861 | OW0 | HOH | Z | 206 | 22.608 | −5.570 | 37.559 | 1.00 | 36.84 | 8 |
| ATOM | 3862 | OW0 | HOH | Z | 207 | 48.062 | 25.072 | 37.444 | 1.00 | 44.17 | 8 |
| ATOM | 3863 | OW0 | HOH | Z | 208 | 13.541 | 20.150 | 31.969 | 1.00 | 57.25 | 8 |
| ATOM | 3864 | OW0 | HOH | Z | 209 | 31.863 | 0.830 | 25.886 | 1.00 | 39.37 | 8 |
| ATOM | 3865 | OW0 | HOH | Z | 210 | 35.449 | 17.282 | 62.211 | 1.00 | 38.11 | 8 |
| ATOM | 3866 | OW0 | HOH | Z | 211 | 19.296 | 9.780 | 18.915 | 1.00 | 74.89 | 8 |
| ATOM | 3867 | OW0 | HOH | Z | 212 | 9.113 | 8.119 | 43.855 | 1.00 | 42.78 | 8 |
| ATOM | 3868 | OW0 | HOH | Z | 213 | 25.316 | 26.074 | 8.860 | 1.00 | 30.16 | 8 |
| ATOM | 3869 | OW0 | HOH | Z | 214 | 20.140 | 29.894 | 48.350 | 1.00 | 43.12 | 8 |
| ATOM | 3870 | OW0 | HOH | Z | 215 | 29.660 | 14.503 | 15.123 | 1.00 | 48.14 | 8 |
| ATOM | 3871 | OW0 | HOH | Z | 216 | 41.481 | 8.331 | 18.292 | 1.00 | 39.82 | 8 |
| ATOM | 3872 | OW0 | HOH | Z | 217 | −3.523 | 31.903 | 18.867 | 1.00 | 35.80 | 8 |
| ATOM | 3873 | OW0 | HOH | Z | 218 | 51.266 | 25.888 | 25.263 | 1.00 | 23.86 | 8 |
| ATOM | 3874 | OW0 | HOH | Z | 219 | 36.513 | 7.196 | 56.549 | 1.00 | 27.66 | 8 |
| ATOM | 3875 | OW0 | HOH | Z | 220 | 12.213 | 18.423 | 27.309 | 1.00 | 37.25 | 8 |
| ATOM | 3876 | OW0 | HOH | Z | 221 | 32.240 | 1.474 | 62.119 | 1.00 | 53.64 | 8 |
| ATOM | 3877 | OW0 | HOH | Z | 222 | 33.674 | 8.526 | 60.220 | 1.00 | 37.38 | 8 |
| ATOM | 3878 | OW0 | HOH | Z | 223 | 21.183 | 22.012 | 5.098 | 1.00 | 47.51 | 8 |
| ATOM | 3879 | OW0 | HOH | Z | 224 | 17.780 | 33.381 | 9.563 | 1.00 | 33.21 | 8 |
| ATOM | 3880 | OW0 | HOH | Z | 225 | 32.481 | 11.769 | 63.015 | 1.00 | 53.06 | 8 |
| ATOM | 3881 | OW0 | HOH | Z | 226 | 21.211 | 10.090 | 17.270 | 1.00 | 48.88 | 8 |
| ATOM | 3882 | OW0 | HOH | Z | 227 | 3.413 | 13.486 | 25.700 | 1.00 | 57.93 | 8 |
| ATOM | 3883 | OW0 | HOH | Z | 228 | 41.372 | 7.528 | 49.259 | 1.00 | 57.18 | 8 |
| ATOM | 3884 | OW0 | HOH | Z | 229 | 44.091 | 13.172 | 15.975 | 1.00 | 48.72 | 8 |
| ATOM | 3885 | OW0 | HOH | Z | 230 | 22.649 | 45.181 | 28.556 | 1.00 | 38.14 | 8 |
| ATOM | 3886 | OW0 | HOH | Z | 231 | 32.314 | 27.093 | 54.668 | 1.00 | 34.77 | 8 |
| ATOM | 3887 | OW0 | HOH | Z | 232 | −2.290 | 26.794 | 20.664 | 1.00 | 42.85 | 8 |
| ATOM | 3888 | OW0 | HOH | Z | 233 | 37.329 | −3.664 | 39.804 | 1.00 | 35.89 | 8 |
| ATOM | 3889 | OW0 | HOH | Z | 234 | 5.340 | 32.703 | 7.314 | 1.00 | 45.25 | 8 |
| ATOM | 3890 | OW0 | HOH | Z | 235 | 2.333 | 33.544 | 2.954 | 1.00 | 35.13 | 8 |
| ATOM | 3891 | OW0 | HOH | Z | 236 | 25.900 | 13.080 | 40.172 | 1.00 | 43.16 | 8 |
| ATOM | 3892 | OW0 | HOH | Z | 237 | 19.138 | 14.576 | 49.299 | 1.00 | 42.79 | 8 |
| ATOM | 3893 | OW0 | HOH | Z | 238 | 25.567 | 26.472 | 40.031 | 1.00 | 39.97 | 8 |
| ATOM | 3894 | OW0 | HOH | Z | 239 | 17.546 | −9.985 | 43.762 | 1.00 | 58.18 | 8 |
| ATOM | 3895 | OW0 | HOH | Z | 240 | −1.672 | 29.072 | 26.286 | 1.00 | 52.04 | 8 |
| ATOM | 3896 | OW0 | HOH | Z | 241 | 6.097 | 34.431 | 9.544 | 1.00 | 38.91 | 8 |
| ATOM | 3897 | OW0 | HOH | Z | 242 | 50.812 | 22.728 | 44.664 | 1.00 | 36.96 | 8 |
| ATOM | 3898 | OW0 | HOH | Z | 243 | 45.963 | 17.701 | 32.633 | 1.00 | 34.09 | 8 |
| ATOM | 3899 | OW0 | HOH | Z | 244 | 22.571 | 15.881 | 32.301 | 1.00 | 39.52 | 8 |
| ATOM | 3900 | OW0 | HOH | Z | 245 | 29.466 | 34.586 | 49.675 | 1.00 | 30.29 | 8 |
| ATOM | 3901 | OW0 | HOH | Z | 246 | −0.096 | 25.184 | 4.188 | 1.00 | 30.65 | 8 |
| ATOM | 3902 | OW0 | HOH | Z | 247 | 18.238 | 39.484 | 37.998 | 1.00 | 39.98 | 8 |
| ATOM | 3903 | OW0 | HOH | Z | 248 | 23.712 | 15.984 | 61.484 | 1.00 | 44.49 | 8 |
| ATOM | 3904 | OW0 | HOH | Z | 249 | 42.851 | 17.446 | 27.926 | 1.00 | 29.01 | 8 |
| ATOM | 3905 | OW0 | HOH | Z | 250 | 21.804 | 38.564 | 12.235 | 1.00 | 49.41 | 8 |
| ATOM | 3906 | OW0 | HOH | Z | 251 | 36.403 | 39.596 | 28.126 | 1.00 | 44.13 | 8 |
| END | | | | | | | | | | | |

Table 8 illustrates the number and identity of known protein interactions with bacterial SSBs.

TABLE 8

Protein interactions with bacterial SSBs

| SSB-interacting protein | SSB-Ct required? | References |
|---|---|---|
| Chi (DNA polymerase III) | Yes | Butland et al., 2005, *Nature* 433: 531-537 |
| DNA polymerase II | Yes | Molineux and Gefter, 1974, *Proc. Natl. Acad. Sci. USA* 71: 3858-3862 |
| DNA polymerase V | Yes | Arad et al., 2008, *J. Biol. Chem.* 283: 8274-8282 |
| Exonuclease I | Yes | Butland et al., 2005, *Nature* 433: 531-537 |
| Exonuclease IX | Unknown | Hodskinson et al., 2007, *Nucl. Acids Res.* 35: 4094-4102 |
| PriA | Yes | Butland et al., 2005, *Nature* 433: 531-537 |
| PriB | Unknown | Low et al., 1982, *J. Biol.* 257: 6242-6250 |
| Primase | Yes | Yuzhakov et al., 1999, *Cell* 96: 153-163 |
| RecG | Unknown | Butland et al., 2005, *Nature* 433: 531-537 |
| RecJ | Unknown | Butland et al., 2005, *Nature* 433: 531-537 |
| RecO | Unknown | Umezu et al., 1993, *Proc. Natl. Acad. Sci.* 90: 3875-3879 |
| RecQ | Yes | Butland et al., 2005, *Nature* 433: 531-537 |
| Topoisomerase III | Unknown | Butland et al., 2005, *Nature* 433: 531-537 |
| Uracil DNA glycosylase | Yes | Purnapatre et al., 1999, *Nucl. Acids Res.* 27: 3487-3492 |

Table 9 illustrates the crystallographic data collection and structure refinement statistics.

TABLE 9

Crystallographic data collection and structure refinement statistics

| | | |
|---|---|---|
| Space group | $P2_12_12_1$ | $P2_12_12_1$ |
| Unit cell parameters (a, b, c (Å)) (α, β, γ (°)) | 52, 63, 92.08, 102.79 90, 90, 90 | 67.15, 92.19, 91.28 90, 90, 90 |
| Resolution range (High resolution) (Å) | 20-1.7 (1.77-1.70) | 20-2.7 (2.77-2.70) |
| $R_{sym}$ (%)* | 6.1 (47.9) | 7.9 (38.3) |
| Completeness (%) | 92.5 (91.5) | 98.0 (88.2) |
| Redundancy | 4.0 (4.0) | 3.7 (3.8) |
| <I/σ> | 37.7 (4.0) | 25.9 (4.0) |
| Refinement | | |
| Resolution (Å) | 20-1.7 | 20-2.7 |
| $R_{work}/R_{free}$ (%)** | 18.0/21.3 | 19.8/25.2 |
| Residues | 446 | 465 |
| Protein atoms*** | 3740 | 3782 |
| Solvent atoms | 436 | 42 |
| <B factor> protein | 23.9 | 52.5 |
| <B factor> peptide A | Not applicable | 50.4 |
| <B factor> peptide B | Not applicable | 80.4 |
| <B factor> solvent | 37.0 | 43.1 |
| RMSD bond lengths (Å) | 0.013 | 0.013 |
| RMSD bond angles (°) | 1.10 | 1.05 |
| Ramachandran statistics, % core | 92.7 | 90.4 |
| % allowed | 7.3 | 9.6 |
| % generously allowed | 0 | 0 |
| % disallowed | 0 | 0 |

*$R_{sym} = \Sigma\Sigma_j|I_j - <I>|/\Sigma I_j$, where $I_j$ is the intensity measurement for reflection j and <I> is the mean intensity for multiply recorded reflections.
**$R_{work, free} = \Sigma||F_{obs}| - |F_{calc}||/|F_{obs}|$, where the working and free R factors are calculated using the working and free reflection sets, respectively. The free R reflections (5% of the total) were held aside throughout refinement.
***Note that for the apo-ExoI structure, several side-chains and one loop sequence were modeled in multiple rotamers/conformations; in cases where atoms have been modeled in multiple conformations, each modeled position is counted in the number of protein atoms (i.e. if a given atom is modeled in two positions it is counted as two protein atoms rather than one in the SI Table 9).

Table 10 shows $K_{d, app}$ values for F-SSB-Ct binding by ExoI and variants.

TABLE 10

$K_{d, app}$ values for F-SSB-Ct binding by ExoI and variants

| Protein | Role of mutated residue in ExoI | $K_{d, app}$ (nM) |
|---|---|---|
| ExoI | — | 136 +/- 11 |
| Arg148Ala | peptide A binding | >>1000 |
| Tyr207Ala | peptide A binding | >1000 |
| Gln311Ala | peptide A binding | 304 +/- 14 |
| Arg316Ala | flanks peptide A | >1000 |
| Arg327Ala | peptide B binding | 270 +/- 22 |
| Leu331Ala | peptide B binding | 193 +/- 3 |
| Lys227Ala | basic ridge | ~1000 |
| Arg338Ala | basic ridge | 398 +/- 15 |
| Glu150Ala | $Mg^{2+}$ binding | 72 +/- 1 |
| Glu318Ala | $Mg^{2+}$ binding | 80 +/- 6 |
| Asp319Ala | $Mg^{2+}$ binding | 299 +/- 8 |
| Gln448Ala | helical domain | 181 +/- 25 |
| Gln452Ala | helical domain | 212 +/- 6 |

Topoisomerase III Peptide Binding

Topoisomerase III binding assays were conducted (FIG. 24) to determine if the candidate compounds can inhibit the binding of the C-terminal tail of *E. coli* SSB to other proteins that are known SSB binding partners. One such binding partner is Topoisomerase III (TopoIII), one of a number of proteins that interact with the C-terminal tail of SSB (Shereda, Bernstein, and Keck, unpublished observation). TopoIII was titrated into 10 nM fluorescent peptide, as described above for the ExoI binding assays. The buffer conditions for this binding assay were: 300 mM NaCl, 20 mM Tris pH 8.0, 10% Glycerol, 1 mM BME (Beta-Mercaptoethanol), and 1% DMSO. Concentrations of TopoIII used are given on the graph in FIG. 24. Changes in anisotropy upon binding were read using PanVera Beacon 2000 FP.

The data indicate that peptide binding is much weaker in the case of TopoIII/peptide, making it difficult to accurately determine a binding constant ($K_d$). In order to determine if the compounds had an effect on peptide binding to TopoIII, a similar set of experiments as stated above was set up, except for the omission of DMSO from the buffer solution. Either unlabeled peptide or various compounds were then added to a final concentration of 100 μM. These compounds and unlabeled peptide were dissolved in DMSO and their addition brought the final concentration of DMSO to 1%.

Figure 24:
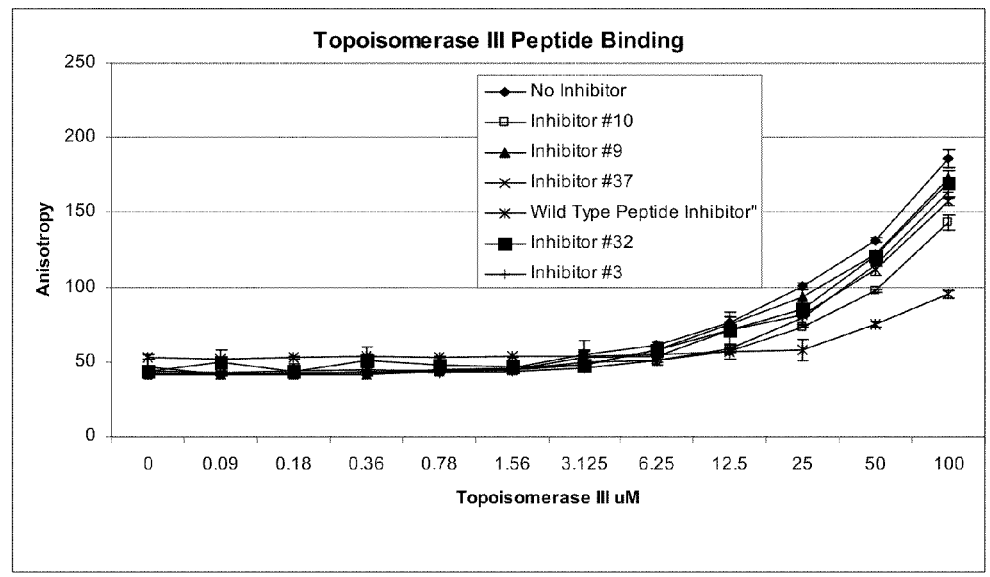
FIG. 24 is a graph showing Topoisomerase III peptide binding in the absence and in the presence of various inhibitors.

Some of the candidate compounds were able to inhibit binding of the peptide to TopoIII, lowering the observed anisotropy value. As shown in FIG. 24, even addition of 100 μM unlabeled peptide did not bring the anisotropy values down to the baseline (the values that would be expected with no binding of fluorescently labeled peptide). This is due to the very high concentrations of TopoIII that need to be used in order to observe binding. Thus, some of the compounds such as 10 can not only inhibit binding of the fluorescent peptide to ExoI but also to other known binding partners, such TopoIII. Therefore, at least some of the identified inhibitors can actually inhibit binding of the C-terminal tail of SSB to more than one of its binding partners, and not just ExoI.

Mammalian Cell Toxicity

The toxicity of the identified antimicrobial candidate compounds was tested using human colorectal adenocarcinoma cells in vitro. The tested compounds are significantly less toxic to HT-29 (human colorectal adenocarcinoma) than to Gram-positive bacterial cells or the cell wall compromised *E. coli* cells. The mammalian cells were tested using a CellTiter-Glo cell viability assay (Promega, Madison, Wis.).

According to the data obtained with this assay compound 3 had an $IC_{50}$>100 µM, compound 8 had an $IC_{50}$>100 µM, compound 9 had an $IC_{50}$=38 µM, compound 10 had an $IC_{50}$=60 µM, compounds 28, 29, 32, and 37 all had an $IC_{50}$>100 µM, compound 42 had an $IC_{50}$=51 µM, and compound 46 had an $IC_{50}$=55 µM. Comparing these data to the $IC_{50}$ from the bacterial growth curves, the conclusion is that the compounds are much more effective at killing bacteria than mammalian cells.

Hemolysis

In vitro hemolysis experiments were carried out to determine if the identified drug candidates merely inhibited bacterial growth by causing cell lysis. The identified small molecules were incubated with red blood cells to see what percentage of cells would lyse after 1 hour. The results from these experiments are shown in Table 11. Estimated hemolysis data are due to problem with reading absorbance, when the compound absorbs at the same wavelength as heme or if the compound precipitates. In such instances it is difficult to quantitate the absorbance readings; however, visual determination of how many cells have lysed can then be performed, which provides an estimate of cell lysis.

TABLE 11

Results from hemolysis experiments

| Inhibitor | % hemolysis at given concentration | % hemolysis at given concentration |
|---|---|---|
| 3 | 20% 100 µM | |
| 8 | estimated 0% 200 µM | estimated 90% 400 uM |
| 9 | 0% >800 µM | |
| 10 | 0% 400 µM | 85% at 800 µM |
| 32 | 0% >800 µM | |
| 37 | estimated 0% 800 µM | |
| 28 | 0% >800 µM | |
| 29 | 0% >800 µM | |
| 31 | 0% >800 µM | |
| 46 | 0% >800 µM | |
| 42 | 0% >800 µM | |

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of biochemistry and pharmaceutical chemistry, are within the scope of this invention. All publications, patents, and patent applications cited herein are incorporated by reference in their entirety for all purposes.

What is claimed is:

1. A method of inhibiting the growth of a bacterium, the method comprising:
contacting the bacterium with a compound of the formula

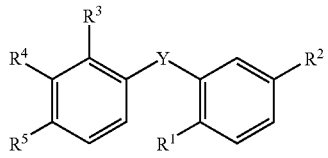

wherein Y represents NH, $R^1$ represents Cl, $R^2$ represents $CF_3$, $R^3$ represents $CO_2H$, $R^4$ represents H, and $R^3$ represents $OCH_3$.

2. A method of inhibiting the growth of a microorganism, the method comprising:
contacting the microorganism with a compound of the formula

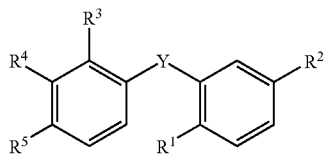

wherein Y is selected from the group consisting of $CH_2$, O, and NH,
$R^1$ is selected from the group consisting of H, F, Cl, Br, and I,
$R^2$ is selected from the group consisting of H and $CF_3$,
$R^3$ is selected from the group consisting of H and $CO_2H$,
$R^4$ is selected from the group consisting of H and OH,
$R^5$ is selected from the group consisting of H, alkoxy, and $NO_2$,
at least one of $R^1$, $R^2$, $R^3$, $R^4$, and $R^5$ is a group other than H, and
when $R^4$ is OH, at least one of $R^1$, $R^2$, $R^3$, and $R^5$ is a group other than H,
the microorganism comprising at least one of *Bacillus anthracis, Clostridium difficile, Francisella tularensis, Shigella dysenteriae, Salmonella typhimurium, Listeria monocytogenes, Campylobacter jejuni, Yersinia enterocolitica, Mycobacterium tuberculosis, Brucella abortus, Coxiella burnetii, Burkholderia mallei, Clostridium perfringens, Rickettsia prowazekii, Staphylococcus aureus, Streptococcus pneumoniae, Streptococcus pyogenes, Streptococcus sanguinis, Streptococcus thermophilus, Streptococcus agalactiae, Streptococcus mutans, Streptococcus suis*, and *Enterococcus faecalis*.

3. A method of treating a subject having a bacterial infection, the method comprising:
administering a therapeutically effective amount of an antibacterial pharmaceutical composition to a subject experiencing a bacterial infection from bacteria comprising at least one of *Bacillus anthracis, Clostridium difficile, Francisella tularensis, Shigella dysenteriae, Salmonella typhimurium, Listeria monocytogenes, Campylobacter jejuni, Yersinia enterocolitica, Mycobacterium tuberculosis, Brucella abortus, Coxiella burnetii, Burkholderia mallei, Clostridium perfringens, Rickettsia prowazekii, Staphylococcus aureus, Streptococcus pneumoniae, Streptococcus pyogenes, Streptococcus sanguinis, Streptococcus thermophilus, Streptococcus agalactiae, Streptococcus mutans, Streptococcus suis*, and *Enterococcus faecalis*,
the antibacterial pharmaceutical composition comprising, as an active agent, a compound having the formula

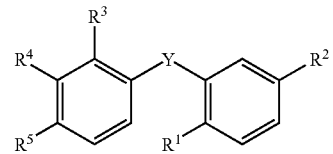

wherein Y is selected from the group consisting of $CH_2$, O, and NH,
$R^1$ is selected from the group consisting of H, F, Cl, Br, and I,
$R^2$ is selected from the group consisting of H and $CF_3$,
$R^3$ is selected from the group consisting of H and $CO_2H$,
$R^4$ is selected from the group consisting of H and OH,
$R^5$ is selected from the group consisting of H, alkoxy, and $NO_2$, and
at least one of $R^1$, $R^2$, $R^3$, $R^4$, and $R^5$ is a group other than H,
the compound being present in the composition in an amount sufficient to inhibit the growth of a bacterium.

4. The method of claim 3, wherein Y represents NH, $R^1$ represents Cl, $R^2$ represents $CF_3$, $R^3$ represents $CO_2H$, $R^4$ represents H, and $R^5$ represents $OCH_3$.

5. The method of claim 3, wherein $R^1$ is F, Cl or Br.

6. A method of inhibiting the growth of a microorganism, the method comprising: contacting the microorganism with a compound of the formula

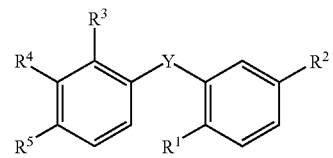

wherein Y is selected from the group consisting of $CH_2$, O, and NH,
$R^1$ is selected from the group consisting of H, F, Cl, Br, and I,
$R^2$ is selected from the group consisting of H and $CF_3$,
$R^3$ is selected from the group consisting of H and $CO_2H$,
$R^4$ is selected from the group consisting of H and OH,
$R^5$ is selected from the group consisting of H, alkoxy, and $NO_2$, and
at least one of $R^1$, $R^2$, $R^3$, $R^4$, and $R^3$ is a group other than H
the microorganism comprising at least one of *Bacillus anthracia, Clostridium difficile, Francisella tularensis, Shigella dysenteriae, Salmonella typhimurium, Listeria monocytogenes, Campylobacter jejuni, Yersinia enterocolitica, Mycobacterium tuberculosis, Brucella abortus, Coxiella burnetii, Burkholderia mallei, Clostridium perfringens, Rickettsia prowazekii, Staphylococcus aureus, Streptococcus pneumoniae, Streptococcus pyogenes, Streptococcus sanguinis, Streptococcus thermophilus, Streptococcus agalactiae, Streptococcus mutans, Streptococcus suis*, and *Enterococcus faecalis*.

7. The method of claim 6, wherein contacting the microorganism with the compound inhibits binding of a prokaryotic single-stranded DNA binding protein to a polypeptide that binds to the prokaryotic single-stranded DNA binding protein of the microorganism.

8. The method according to claim 6, wherein Y represents NH, $R^1$ represents Cl, $R^2$ represents $CF_3$, $R^3$ represents $CO_2H$, $R^4$ represents H, and $R^5$ represents $OCH_3$.

9. An antimicrobial pharmaceutical composition comprising:
as an active agent a compound of the formula

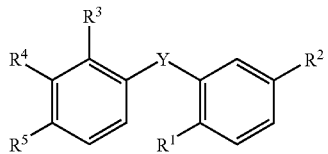

wherein Y is NH, $R^1$ is F, Cl or Br, $R^2$ is $CF_3$, $R^3$ is $CO_2H$, $R^4$ is H, and $R^5$ is $OCH_3$.

10. The antibacterial pharmaceutical composition of claim 9, wherein the compound is present in an amount sufficient to inhibit the rate of growth of a population of bacteria.

11. The antimicrobial pharmaceutical composition of claim 9, wherein $R^1$ is Cl.

12. A method of inhibiting the growth of a microorganism, the method comprising:
administering a composition to a subject, the composition comprising a compound; and
contacting a microorganism comprising at least one of *Bacillus anthracis, Clostridium difficile, Francisella tularensis, Shigella dysenteriae, Salmonella typhimurium, Listeria monocytogenes, Campylobacter jejuni, Yersinia enterocolitica, Mycobacterium tuberculosis, Brucella abortus, Coxiella burnetii, Burkholderia mallei, Clostridium perfringens, Rickettsia prowazekii, Staphylococcus aureus, Streptococcus pneumoniae, Streptococcus pyogenes, Streptococcus sanguinis, Streptococcus thermophilus, Streptococcus agalactiae, Streptococcus mutans, Streptococcus suis,* and *Enterococcus faecalis* with the compound,
the compound having the formula

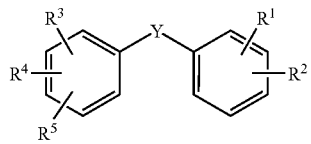

wherein Y is NH, $R^1$ is Cl, $R^2$ is $CF_3$, $R^3$ is $CO_2H$, $R^4$ is H, and $R^{15}$ is $OCH_3$.

13. An antimicrobial pharmaceutical composition comprising:
as an active agent a compound of the formula

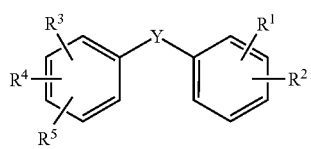

wherein Y is NH, $R^1$ is Cl, $R^2$ is $CF_3$, $R^3$ is $CO_2H$, $R^4$ is H, and $R^{15}$ is $OCH_3$; and
at least one of a pharmaceutically acceptable carrier and a pharmaceutically acceptable excipient,
the composition being in a dosage form selected from the group consisting of an orally administered dosage form and a parenterally administered dosage form, and
the compound being present in the composition in an amount sufficient to inhibit the growth of a microbe comprising at least one of *Bacillus anthracis, Clostridium difficile, Francisella tularensis, Shigella dysenteriae, Salmonella typhimurium, Listeria monocytogenes, Campylobacter jejuni, Yersinia enterocolitica, Mycobacterium tuberculosis, Brucella abortus, Coxiella burnetii, Burkholderia mallei, Clostridium perfringens, Rickettsia prowazekii, Staphylococcus aureus, Streptococcus pneumoniae, Streptococcus pyogenes, Streptococcus sanguinis, Streptococcus thermophilus, Streptococcus agalactiae, Streptococcus mutans, Streptococcus suis,* and *Enterococcus faecalis*.

14. An antimicrobial pharmaceutical composition comprising:
as an active agent a compound of the formula

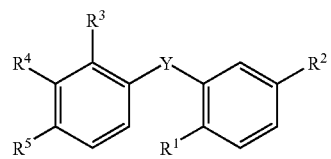

wherein Y is NH, $R^1$ is Cl, $R^2$ is $CF_3$, $R^3$ is $CO_2H$, $R^4$ is H, and $R^{15}$ is $OCH_3$; and
at least one of a pharmaceutically acceptable carrier and a pharmaceutically acceptable excipient,
the compound being present in the composition in an amount sufficient to inhibit the rate of growth of a population of bacteria, the bacteria comprising at least one of *Bacillus anthracis, Clostridium difficile, Francisella tularensis, Shigella dysenteriae, Salmonella typhimurium, Listeria monocytogenes, Campylobacter jejuni, Yersinia enterocolitica, Mycobacterium tuberculosis, Brucella abortus, Coxiella burnetii, Burkholderia mallei, Clostridium perfringens, Rickettsia prowazekii, Staphylococcus aureus, Streptococcus pneumoniae, Streptococcus pyogenes, Streptococcus sanguinis, Streptococcus thermophilus, Streptococcus agalactiae, Streptococcus mutans, Streptococcus suis,* and *Enterococcus faecalis*.

15. A method of treating a subject having a microbial infection, the method comprising:
administering a therapeutically effective amount of a pharmaceutical composition to a subject experiencing a microbial infection from bacteria comprising at least one of *Bacillus anthracis, Clostridium difficile, Francisella tularensis, Shigella dysenteriae, Salmonella typhimurium, Listeria monocytogenes, Campylobacter jejuni, Yersinia enterocolitica, Mycobacterium tuberculosis, Brucella abortus, Coxiella burnetii, Burkholderia mallei, Clostridium perfringens, Rickettsia prowazekii, Staphylococcus aureus, Streptococcus pneumoniae, Streptococcus pyogenes, Streptococcus sanguinis, Streptococcus thermophilus, Streptococcus agalactiae, Streptococcus mutans, Streptococcus suis,* and *Enterococcus faecalis*, the pharmaceutical composition comprising, as an active agent, a compound of the formula

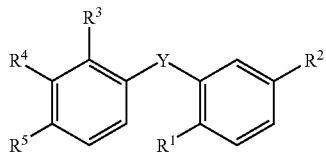

wherein Y is selected from the group consisting of $CH_2$, O, and NH,
$R^1$ is selected from the group consisting of H, F, Cl, Br, and I,
$R^2$ is selected from the group consisting of H and $CF_3$,
$R^3$ is selected from the group consisting of H and $CO_2H$,
$R^4$ is selected from the group consisting of H and OH,
$R^5$ is selected from the group consisting of H, alkoxy, and $NO_2$, and
at least one of $R^1$, $R^2$, $R^3$, $R^4$, and $R^5$ is a group other than H; and
at least one of a pharmaceutically acceptable carrier and a pharmaceutically acceptable excipient,
the compound being present in the composition in an amount sufficient to inhibit the rate of growth of a population of bacteria, the bacteria comprising at least one of *Bacillus anthracis, Clostridium difficile, Francisella tularensis, Shigella dysenteriae, Salmonella typhimurium, Listeria monocytogenes, Campylobacter jejuni, Yersinia enterocolitica, Mycobacterium tuberculosis, Brucella abortus, Coxiella burnetii, Burkholderia mallei, Clostridium perfringens, Rickettsia prowazekii, Staphylococcus aureus, Streptococcus pneumoniae, Streptococcus pyogenes, Streptococcus sanguinis, Streptococcus thermophilus, Streptococcus agalactiae, Streptococcus mutans, Streptococcus suis*, and *Enterococcus faecalis.*

* * * * *

UNITED STATES PATENT AND TRADEMARK OFFICE
CERTIFICATE OF CORRECTION

Page 1 of 2

PATENT NO. : 8,415,393 B2
APPLICATION NO. : 12/124251
DATED : April 9, 2013
INVENTOR(S) : James L. Keck and Douglas A. Bernstein It is certified that error appears in the above-identified patent and that said Letters Patent is hereby corrected as shown below:

In the Specification:

Col. 47, Line 36, replace "wee" with --were--

Col. 50, Line 5, replace "Gin" with --Gln--

Col. 7, SEQ ID No. 29, should read --Pasteurella_mult ------------------PAPQNEPPMDMGFEEDNIPF (SEQ ID NO: 29)

Col. 11, SEQ ID No. 73, should read --Pseudomonas_stutzeri -------------PAARQQPAPDYDSFDDDIPF (SEQ ID NO: 73)--

Col. 13, SEQ ID No. 85, replace "Burkhoideria" with --Burkholderia--

Col. 13, SEQ ID No. 109, replace "Bordetelia" with --Bordetella--

Col. 15, SEQ ID No. 124, should read --Caulobacter_crescentus -----------SQPSGPRESFS-ADLDDEIPF (SEQ ID NO: 124)--

Col. 15, SEQ ID No. 125, should read --Maricaulis_maris ---------------SMDGPKEDFRNADLDDEIPF (SEQ ID NO: 125)--

Col. 17, SEQ ID No. 136, should read --Rhodobacter_sphaeroides ----------RGNAPSGGGRRS-DLDDEIPF (SEQ ID NO:136)--

Col. 17, SEQ ID No. 139, should read --Magnetospirillum_magneticum ------GGGGGQSWEPPA-DLDDEIPF (SEQ ID NO:139)--

Col. 17, SEQ ID No. 154, should read --Gluconobacter_oxydans ------------GSNGGWDAPPDND-LDDEIPF (SEQ ID NO: 154)--

Col. 19, SEQ ID No. 161, replace "Desulfitobacteriurn" with --Desulfitobacterium--

Col. 19, SEQ ID No. 163, should read --Candidatus_blochmannia -------------NNHELNSESIVNFNEDDIPF (SEQ ID NO: 163)--

Signed and Sealed this
Second Day of July, 2013

Teresa Stanek Rea
*Acting Director of the United States Patent and Trademark Office*

CERTIFICATE OF CORRECTION (continued)
U.S. Pat. No. 8,415,393 B2

Col. 21, SEQ ID No. 186, replace "Anaplasma" with --Anaplasma--

Col. 21, SEQ ID No. 191, should read --Mycoplasma_penetrans ---------------DDEDPDQVVSNLDWLDEFKE (SEQ ID NO:191)--

Col. 21, SEQ ID No. 208, replace "inobilis" with --mobilis--

Col. 23, SEQ ID No. 211, replace "therinoacetica" with --thermoacetica--

Col. 25, SEQ ID No. 252, should read --Prochlorococcus_marinus ----------ASNFGGGGFGDG-PSEEEVPF (SEQ ID NO: 252)--

Col. 27, SEQ ID No. 263, should read --Mycobacterium_leprae ------------PWGSAPTSGSFGVG---DEEPPF (SEQ ID NO: 263)--

Col. 27, SEQ ID No. 276, should read --Leifsonia_xyli ------------------PSAGTDVWNTPGAYN---DETPF (SEQ ID NO: 276)--

Col. 27, SEQ ID No. 282, replace "Trichodesinium" with --Trichodesmium--

In the Claims:

Col. 373, Claim 1, Line 15, replace "and R3" with --and $R^5$--

Col. 374, Claim 6, Line 55, replace "and R3" with --and $R^5$--

Col. 374, Claim 6, Line 58, replace "anthracia" with --*anthracis*--

Col. 376, Claim 14, Line 35, replace "and R15" with --and $R^5$--

SEQUENCE LISTING

<160> NUMBER OF SEQ ID NOS: 293

<210> SEQ ID NO 1
<211> LENGTH: 537
<212> TYPE: DNA
<213> ORGANISM: Escherichia coli

<400> SEQUENCE: 1

```
atggccagca gaggcgtaaa caaggttatt ctcgttggta atctgggtca ggacccggaa      60
gtacgctaca tgccaaatgg tggcgcagtt gccaacatta cgctggctac ttccgaatcc     120
tggcgtgata aagcgaccgg cgagatgaaa gaacagactg aatggcaccg cgttgtgctg     180
ttcggcaaac tggcagaagt ggcgagcgaa tatctgcgta aaggttctca ggtttatatc     240
gaaggtcagc tgcgtacccg taaatggacc gatcaatccg gtcaggatcg ctacaccaca     300
gaagtcgtgg tgaacgttgg cggcaccatg cagatgctgg tggtcgtca  gggtggtggc     360 gctccggcag gtggcaatat cggtggtggt cagccgcagg gcggttgggg tcagcctcag     420
cagccgcagg gtggcaatca gttcagcggc ggcgcgcagt ctcgcccgca gcagtccgct     480
ccggcagcgc cgtctaacga gccgccgatg gactttgatg atgacattcc gttctga         537
```

<210> SEQ ID NO 2
<211> LENGTH: 178
<212> TYPE: PRT
<213> ORGANISM: Escherichia coli

<400> SEQUENCE: 2

Met Ala Ser Arg Gly Val Asn Lys Val Ile Leu Val Gly Asn Leu Gly

```
              1               5                  10                 15
Gln Asp Pro Glu Val Arg Tyr Met Pro Asn Gly Gly Ala Val Ala Asn
                    20                  25                  30

Ile Thr Leu Ala Thr Ser Glu Ser Trp Arg Asp Lys Ala Thr Gly Glu
            35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe

<210> SEQ ID NO 3
<211> LENGTH: 1427
<212> TYPE: DNA
<213> ORGANISM: Escherichia coli

<400> SEQUENCE: 3
atgatgaatg acggtaagca acaatctacc tttttgtttc acgattacga aacctttggc      60
acgcaccccg cgttagatcg ccctgcacag ttcgcagcca ttcgcaccga tagcgaattc     120
aatgtcatcg gcgaacccga agtcttttac tgcaagcccg ctgatgacta tttaccccag     180
ccaggagccg tattaattac cggtattacc ccgcaggaag cacgggcgaa aggagaaaac     240
gaagccgcgt tgccgccccg tattcactcg cttttttaccg taccgaagac tgtattctgg     300
gctacaacaa tgtgcgtttc gacgacgaag tcacacgcaa cattttttat cgtaatttct     360
acgatcctta cgcctggagc tggcagcatg ataactcgcg ctgggattta ctggatgtta     420
tgcgtgcctg ttatgccctg cgcccggaag gaataaactg gcctgaaaat gatgacggtc     480
taccgagctt tcgccttgag catttaacca aagcgaatgg tattgaacat agcaacgccc     540
acgatgcgat ggctgatgtg tacgccacta ttgcgatggc aaagctggta aaaacgcgtc     600
agccacgcct gtttgattat ctctttaccc atcgtaataa acacaaactg atggcgttga     660
ttgatgttcc gcagatgaaa cccctggtgc acgtttccgg aatgtttgga gcatggcgcg     720
gcaataccag ctgggtggca ccgctggcgt ggcatcctga aaatcgcaat gccgtaatta     780
tggtggattt gcaggagac atttcgccat tactggaact ggatagcgac acattgcgcg     840
agcgtttata taccgcaaaa accgatcttg gcgataacgc cgccgttccg gttaagctgg     900
tgcatatcaa taaatgtccg gtgctggccc aggcgaatac gctacgcccg gaagatgccg     960
accgactggg aattaatcgt cagcattgcc tcgataacct gaaaattctg cgtgaaaatc    1020
cgcaagtgcg cgaaaaagtg gtggcgatat tcgcggaagc cgaaccgttt acgccttcag    1080
ataacgtgga tgcacagctt tataacggct ttttcagtga cgcagatcgt gcagcaatga    1140
```

-continued

```
aaattgtgct ggaaaccgag ccgcgtaatt taccggcact ggatatcact tttgttgata    1200
aacggattga aaagctgttg ttcaattatc gggcacgcaa cttcccgggg acgctggatt    1260
atgccgagca gcaacgctgg ctggagcacc gtcgccaggt cttcacgcca gagttttgc     1320 agggttatgc tgatgaattg cagatgctgg tacaacaata tgccgatgac aaagagaaag    1380
tggcgctgtt aaaagcactt tggcagtacg cggaagagat tgtctaa                  1427
```

<210> SEQ ID NO 4
<211> LENGTH: 475
<212> TYPE: PRT
<213> ORGANISM: Escherichia coli

<400> SEQUENCE: 4

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335
```

Leu Arg Glu Asn Pro Gln Val Arg Glu Lys Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
            405                 410                 415

Gly Thr Leu Asp Tyr Ala Glu Gln Gln Arg Trp Leu Glu His Arg Arg
        420                 425                 430

Gln Val Phe Thr Pro Glu Phe Leu Gln Gly Tyr Ala Asp Glu Leu Gln
    435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val
465                 470                 475

<210> SEQ ID NO 5
<211> LENGTH: 4
<212> TYPE: PRT
<213> ORGANISM: Escherichia coli

<400> SEQUENCE: 5

Ala Ile Pro Phe
1

<210> SEQ ID NO 6
<211> LENGTH: 10
<212> TYPE: PRT
<213> ORGANISM: Escherichia coli

<400> SEQUENCE: 6

Thr Met Asp Phe Asp Asp Asp Ile Pro Phe
1               5                   10

<210> SEQ ID NO 7
<211> LENGTH: 6
<212> TYPE: PRT
<213> ORGANISM: Escherichia coli

<400> SEQUENCE: 7

Trp Asp Asp Ile Pro Phe
1               5

<210> SEQ ID NO 8
<211> LENGTH: 10
<212> TYPE: PRT
<213> ORGANISM: Escherichia coli

<400> SEQUENCE: 8

Trp Asp Phe Met Asp Asp Pro Phe Ile Asp
1               5                   10

<210> SEQ ID NO 9
<211> LENGTH: 20
<212> TYPE: PRT
<213> ORGANISM: Desulfovibrio_desulfuricans

<400> SEQUENCE: 9

Phe Asp Asp Leu Gly Pro Ala Phe Pro Ser Glu Val Ser Gly Met Asp
1               5                   10                  15

Asp Val Pro Phe
            20

<210> SEQ ID NO 10
<211> LENGTH: 20
<212> TYPE: PRT
<213> ORGANISM: Desulfovibrio_vulgaris

<400> SEQUENCE: 10

Asp Asp Asp Leu Gly Pro Ala Phe Pro Ser Glu Ala Ser Gly Met Asp
1               5                   10                  15

Asp Val Pro Phe
            20

<210> SEQ ID NO 11
<211> LENGTH: 20
<212> TYPE: PRT
<213> ORGANISM: Lawsonia_intracellularis

<400> SEQUENCE: 11

Gly Phe Glu Asp Ile Ser Pro Phe Pro Ser Glu Ala Ser Gly Met Asp
1               5                   10                  15

Asp Val Pro Phe
            20

<210> SEQ ID NO 12
<211> LENGTH: 20
<212> TYPE: PRT
<213> ORGANISM: Deinococcus_geothermalis

<400> SEQUENCE: 12

Gly Leu Asp Ile Asp Gln Gly Leu Asp Asp Phe Pro Pro Glu Glu Glu
1               5                   10                  15

Asp Leu Pro Phe
            20

<210> SEQ ID NO 13
<211> LENGTH: 20
<212> TYPE: PRT
<213> ORGANISM: Deinococcus_radiodurans

<400> SEQUENCE: 13

Gly Leu Asp Ile Asp Gln Gly Leu Asp Asp Phe Pro Pro Glu Glu Asp
1               5                   10                  15

Asp Leu Pro Phe
            20

<210> SEQ ID NO 14
<211> LENGTH: 20
<212> TYPE: PRT
<213> ORGANISM: Thermus_thermophilus

<400> SEQUENCE: 14

Gly Gly Val Asp Ile Asp Glu Gly Leu Glu Asp Phe Pro Pro Glu Glu
1               5                   10                  15

Asp Leu Pro Phe
            20

<210> SEQ ID NO 15
<211> LENGTH: 20
<212> TYPE: PRT

```
<213> ORGANISM: Streptococcus_pneumoniae

<400> SEQUENCE: 15

Glu Asn Asn Ala Gly Gln Asp Leu Ala Asp Leu Val Leu Glu Glu Glu
1               5                   10                  15

Glu Leu Pro Phe
        20

<210> SEQ ID NO 16
<211> LENGTH: 20
<212> TYPE: PRT
<213> ORGANISM: Caldicellulosiruptor_saccharol

<400> SEQUENCE: 16

Asp Ile Gly Thr Ser Ser Lys Leu Asp Leu Asp Glu Asn Pro Glu Asp
1               5                   10                  15

Asp Leu Pro Phe
        20

<210> SEQ ID NO 17
<211> LENGTH: 20
<212> TYPE: PRT
<213> ORGANISM: Streptococcus_pyogenes

<400> SEQUENCE: 17

Asn Thr Ser Ser Leu Ala Asp Ser Met Pro Asp Tyr Gly Pro Glu Pro
1               5                   10                  15

Asp Leu Pro Phe
        20

<210> SEQ ID NO 18
<211> LENGTH: 20
<212> TYPE: PRT
<213> ORGANISM: Bacteroides_thetaiotaomicron

<400> SEQUENCE: 18

Gln Ala Gln Pro Ser Gln Ala Gln Pro Ile Gln Asp Asn Pro Ala Asp
1               5                   10                  15

Asp Leu Pro Phe
        20

<210> SEQ ID NO 19
<211> LENGTH: 20
<212> TYPE: PRT
<213> ORGANISM: Bacteroides_fragilis

<400> SEQUENCE: 19

Ser Gln Gln Pro Gln Gln Pro Val Ser Ser Gln Asp Asn Ser Ala Asp
1               5                   10                  15

Asp Leu Pro Phe
        20

<210> SEQ ID NO 20
<211> LENGTH: 20
<212> TYPE: PRT
<213> ORGANISM: Gramella_forsetii

<400> SEQUENCE: 20

Asn Phe Ala Asn Lys Asn Glu Phe Tyr Ser Gln Asp Glu Glu Glu Asp
1               5                   10                  15

Asp Leu Pro Phe
        20
```

```
<210> SEQ ID NO 21
<211> LENGTH: 20
<212> TYPE: PRT
<213> ORGANISM: Escherichia_coli_K12

<400> SEQUENCE: 21

Ser Ala Pro Ala Ala Pro Ser Asn Glu Pro Pro Met Asp Phe Asp Asp
1               5                   10                  15

Asp Ile Pro Phe
        20

<210> SEQ ID NO 22
<211> LENGTH: 20
<212> TYPE: PRT
<213> ORGANISM: Shigella_dysenteriae_Sd197

<400> SEQUENCE: 22

Ser Ala Pro Ala Ala Pro Ser Asn Glu Pro Pro Met Asp Phe Asp Asp
1               5                   10                  15

Asp Ile Pro Phe
        20

<210> SEQ ID NO 23
<211> LENGTH: 20
<212> TYPE: PRT
<213> ORGANISM: Shigella_flexneri

<400> SEQUENCE: 23

Ser Ala Pro Ala Ala Pro Ser Asn Glu Pro Pro Met Asp Phe Asp Asp
1               5                   10                  15

Asp Ile Pro Phe
        20

<210> SEQ ID NO 24
<211> LENGTH: 20
<212> TYPE: PRT
<213> ORGANISM: Shigella_sonnei_Ss046

<400> SEQUENCE: 24

Ser Ala Pro Ala Ala Pro Ser Asn Glu Pro Pro Met Asp Phe Asp Asp
1               5                   10                  15

Asp Ile Pro Phe
        20

<210> SEQ ID NO 25
<211> LENGTH: 20
<212> TYPE: PRT
<213> ORGANISM: Shigella_boydii_Sb227

<400> SEQUENCE: 25

Ser Ala Pro Ala Ala Pro Ser Asn Glu Pro Pro Met Asp Phe Asp Asp
1               5                   10                  15

Asp Ile Pro Phe
        20

<210> SEQ ID NO 26
<211> LENGTH: 20
<212> TYPE: PRT
<213> ORGANISM: Haemophilus_influenzae

<400> SEQUENCE: 26

Gln Gln Ala Ala Pro Gln Ala Glu Pro Pro Met Asp Gly Phe Asp Asp
1               5                   10                  15
```

Asp Ile Pro Phe
            20

<210> SEQ ID NO 27
<211> LENGTH: 20
<212> TYPE: PRT
<213> ORGANISM: Pseudoalteromonas_atlantica

<400> SEQUENCE: 27

Gln Asn Lys Pro Ala Pro Met Ala Glu Pro Asp Phe Asp Phe Asp Asp
1               5                   10                  15

Asp Ile Pro Phe
            20

<210> SEQ ID NO 28
<211> LENGTH: 20
<212> TYPE: PRT
<213> ORGANISM: Mannheimia_succiniciproducens

<400> SEQUENCE: 28

Thr Arg Pro Ala Pro Ala Ala Glu Pro Ala Met Asp Asn Phe Asp Asp
1               5                   10                  15

Asp Ile Pro Phe
            20

<210> SEQ ID NO 29
<211> LENGTH: 20
<212> TYPE: PRT
<213> ORGANISM: Pasteurella_mult

<400> SEQUENCE: 29

Pro Ala Pro Gln Asn Glu Pro Pro Met Asp Met Gly Phe Glu Glu Asp
1               5                   10                  15

Asn Ile Pro Phe
            20

<210> SEQ ID NO 30
<211> LENGTH: 20
<212> TYPE: PRT
<213> ORGANISM: Salmonella_enterica

<400> SEQUENCE: 30

Gln Ser Ala Pro Ala Pro Ser Asn Glu Pro Pro Met Asp Phe Asp Asp
1               5                   10                  15

Asp Ile Pro Phe
            20

<210> SEQ ID NO 31
<211> LENGTH: 20
<212> TYPE: PRT
<213> ORGANISM: Salmonella_typhimurium

<400> SEQUENCE: 31

Gln Ser Ala Pro Ala Pro Ser Asn Glu Pro Pro Met Asp Phe Asp Asp
1               5                   10                  15

Asp Ile Pro Phe
            20

<210> SEQ ID NO 32
<211> LENGTH: 20
<212> TYPE: PRT
<213> ORGANISM: Sodalis_glossinidius -continued

```
<400> SEQUENCE: 32

Asn Ser Ala Pro Ala Pro Ser Asn Glu Pro Pro Met Asp Phe Asp Asp
1               5                   10                  15

Asp Ile Pro Phe
            20

<210> SEQ ID NO 33
<211> LENGTH: 20
<212> TYPE: PRT
<213> ORGANISM: Erwinia_carotovora

<400> SEQUENCE: 33

Asn Asn Ala Pro Ala Gln Ser Asn Glu Pro Pro Met Asp Phe Asp Asp
1               5                   10                  15

Asp Ile Pro Phe
            20

<210> SEQ ID NO 34
<211> LENGTH: 20
<212> TYPE: PRT
<213> ORGANISM: Aeromonas_hydrophila

<400> SEQUENCE: 34

Gln Ser Ala Pro Pro Val Tyr Asn Glu Pro Pro Met Asp Phe Asp Asp
1               5                   10                  15

Asp Ile Pro Phe
            20

<210> SEQ ID NO 35
<211> LENGTH: 20
<212> TYPE: PRT
<213> ORGANISM: Aeromonas_salmonicida

<400> SEQUENCE: 35

Gln Ser Ala Pro Pro Val Tyr Asn Glu Pro Pro Met Asp Phe Asp Asp
1               5                   10                  15

Asp Ile Pro Phe
            20

<210> SEQ ID NO 36
<211> LENGTH: 20
<212> TYPE: PRT
<213> ORGANISM: Vibrio_parahaemolyticus

<400> SEQUENCE: 36

Gln Gln Pro Gln Gln Gln Tyr Asn Glu Pro Pro Met Asp Phe Asp Asp
1               5                   10                  15

Asp Ile Pro Phe
            20

<210> SEQ ID NO 37
<211> LENGTH: 20
<212> TYPE: PRT
<213> ORGANISM: Photobacterium_profundum

<400> SEQUENCE: 37

Gln Gln Pro Gln Gln Gln Tyr Asn Glu Pro Pro Met Asp Phe Asp Asp
1               5                   10                  15

Asp Ile Pro Phe
            20

<210> SEQ ID NO 38
```

```
<211> LENGTH: 20
<212> TYPE: PRT
<213> ORGANISM: Vibrio_cholerae

<400> SEQUENCE: 38

Gln Tyr Ser Gln Pro Gln Tyr Asn Glu Pro Pro Met Asp Phe Asp Asp
1               5                   10                  15

Asp Ile Pro Phe
            20

<210> SEQ ID NO 39
<211> LENGTH: 20
<212> TYPE: PRT
<213> ORGANISM: Vibrio_vulnificus

<400> SEQUENCE: 39

Met Gln Ser Gln Pro Gln Tyr Asn Glu Pro Pro Met Asp Phe Asp Asp
1               5                   10                  15

Asp Ile Pro Phe
            20

<210> SEQ ID NO 40
<211> LENGTH: 20
<212> TYPE: PRT
<213> ORGANISM: Vibrio_fischeri

<400> SEQUENCE: 40

Gln Ala Ala Gln Pro Gln Tyr Asn Glu Pro Pro Met Asp Phe Asp Asp
1               5                   10                  15

Asp Ile Pro Phe
            20

<210> SEQ ID NO 41
<211> LENGTH: 20
<212> TYPE: PRT
<213> ORGANISM: Psychromonas_ingrahamii

<400> SEQUENCE: 41

Gln Pro Thr Gln Thr Gln Tyr Asn Glu Pro Ser Met Asp Phe Asp Asp
1               5                   10                  15

Asp Ile Pro Phe
            20

<210> SEQ ID NO 42
<211> LENGTH: 20
<212> TYPE: PRT
<213> ORGANISM: Yersinia_enterocolitica

<400> SEQUENCE: 42

Ala Ala Gln Pro Gln Gly Gly Asn Glu Pro Pro Met Asp Phe Asp Asp
1               5                   10                  15

Asp Ile Pro Phe
            20

<210> SEQ ID NO 43
<211> LENGTH: 20
<212> TYPE: PRT
<213> ORGANISM: Shewanella_oneidensis

<400> SEQUENCE: 43

Gln Pro Gln Gln Asn Phe Thr Pro Asp Leu Asp Asp Gly Trp Asp Asp
1               5                   10                  15

Asp Ile Pro Phe
```

```
            20

<210> SEQ ID NO 44
<211> LENGTH: 20
<212> TYPE: PRT
<213> ORGANISM: Shewanella_loihica

<400> SEQUENCE: 44

Gln Pro Gln Gln Asn Phe Thr Pro Asp Leu Asp Asp Gly Trp Asp Asp
1               5                   10                  15

Asp Ile Pro Phe
            20

<210> SEQ ID NO 45
<211> LENGTH: 20
<212> TYPE: PRT
<213> ORGANISM: Shewanella_putrefaciens

<400> SEQUENCE: 45

Gln Pro Gln Gln Asn Phe Thr Pro Asp Leu Asp Asp Gly Trp Asp Asp
1               5                   10                  15

Asp Ile Pro Phe
            20

<210> SEQ ID NO 46
<211> LENGTH: 20
<212> TYPE: PRT
<213> ORGANISM: Shewanella_baltica

<400> SEQUENCE: 46

Gln Pro Gln Gln Asn Phe Thr Pro Asp Leu Asp Asp Gly Trp Asp Asp
1               5                   10                  15

Asp Ile Pro Phe
            20

<210> SEQ ID NO 47
<211> LENGTH: 20
<212> TYPE: PRT
<213> ORGANISM: Shewanella_amazonensis

<400> SEQUENCE: 47

Pro Gln Gln Gln Asn Tyr Thr Pro Asp Leu Asp Asp Gly Trp Asp Asp
1               5                   10                  15

Asp Ile Pro Phe
            20

<210> SEQ ID NO 48
<211> LENGTH: 20
<212> TYPE: PRT
<213> ORGANISM: Xanthomonas_campestris

<400> SEQUENCE: 48

Pro Ala Gln Gln Gln Ser Ala Pro Pro Met Asp Asp Phe Ala Asp Asp
1               5                   10                  15

Asp Ile Pro Phe
            20

<210> SEQ ID NO 49
<211> LENGTH: 20
<212> TYPE: PRT
<213> ORGANISM: Xanthomonas_axonopodis

<400> SEQUENCE: 49
```

```
Pro Ala Gln Gln Gln Ser Ala Pro Pro Met Asp Asp Phe Ala Asp Asp
1               5                   10                  15

Asp Ile Pro Phe
            20

<210> SEQ ID NO 50
<211> LENGTH: 20
<212> TYPE: PRT
<213> ORGANISM: Xanthomonas_oryzae

<400> SEQUENCE: 50

Pro Ala Gln Gln Gln Ser Val Pro Pro Met Asp Asp Phe Ala Asp Asp
1               5                   10                  15

Asp Ile Pro Phe
            20

<210> SEQ ID NO 51
<211> LENGTH: 20
<212> TYPE: PRT
<213> ORGANISM: Xylella_fastidiosa

<400> SEQUENCE: 51

Gln Ser Pro Gln Ser Ser Pro Pro Pro Met Asp Asp Phe Ala Asp Asp
1               5                   10                  15

Asp Ile Pro Phe
            20

<210> SEQ ID NO 52
<211> LENGTH: 20
<212> TYPE: PRT
<213> ORGANISM: Hahella_chejuensis

<400> SEQUENCE: 52

Gln Gln Pro Lys Pro Pro Met Pro Glu Pro Met Asp Asp Phe Asp Asp
1               5                   10                  15

Asp Ile Pro Phe
            20

<210> SEQ ID NO 53
<211> LENGTH: 20
<212> TYPE: PRT
<213> ORGANISM: Marinobacter_aquaeolei

<400> SEQUENCE: 53

Gln Gln Gln Gly Gly Gly Met Pro Glu Pro Ile Asp Asp Phe Asp Asp
1               5                   10                  15

Asp Ile Pro Phe
            20

<210> SEQ ID NO 54
<211> LENGTH: 20
<212> TYPE: PRT
<213> ORGANISM: Alcanivorax_borkumensis

<400> SEQUENCE: 54

Thr Asn Gln Gly Gly Gly Phe Ser Gly Pro Ala Asp Phe Asp Asp Asp
1               5                   10                  15

Asp Ile Pro Phe
            20

<210> SEQ ID NO 55
<211> LENGTH: 20
<212> TYPE: PRT
```

<213> ORGANISM: Magnetococcus_MC-1

<400> SEQUENCE: 55

Phe Ser Ser Pro Ala Asp Thr Phe Asn Glu Gly Pro Asp Phe Asp Asp
1               5                   10                  15

Asp Ile Pro Phe
            20

<210> SEQ ID NO 56
<211> LENGTH: 20
<212> TYPE: PRT
<213> ORGANISM: Geobacter_metallireducens

<400> SEQUENCE: 56

Phe Gly Gly Gly Pro Ala Tyr Asp Glu Pro Ala Phe Asn Pro Asp Asp
1               5                   10                  15

Asp Ile Pro Phe
            20

<210> SEQ ID NO 57
<211> LENGTH: 20
<212> TYPE: PRT
<213> ORGANISM: Geobacter_sulfurreducens

<400> SEQUENCE: 57

Gly Phe Gly Gly Pro Ser Tyr Asp Glu Pro Ala Phe Asn Pro Asp Asp
1               5                   10                  15

Asp Ile Pro Phe
            20

<210> SEQ ID NO 58
<211> LENGTH: 20
<212> TYPE: PRT
<213> ORGANISM: Pelobacter_carbinolicus

<400> SEQUENCE: 58

Gln Pro Gln Gln Asn Gln Tyr Glu Glu Pro Pro Phe Asn Pro Asp Asp
1               5                   10                  15

Asp Ile Pro Phe
            20

<210> SEQ ID NO 59
<211> LENGTH: 20
<212> TYPE: PRT
<213> ORGANISM: Syntrophobacter_fumaroxidans

<400> SEQUENCE: 59

Ser Arg Ala Asp Glu Leu Pro Pro His Pro Gly Gly Gly Pro Asp Asp
1               5                   10                  15

Asp Ile Pro Phe
            20

<210> SEQ ID NO 60
<211> LENGTH: 20
<212> TYPE: PRT
<213> ORGANISM: Leptospira_borgpetersenii

<400> SEQUENCE: 60

Ser Ser Ser Pro Glu Ser Tyr Asn Pro Pro Ala Pro Asp Gly Asp Asp
1               5                   10                  15

Asp Ile Pro Phe
            20

```
<210> SEQ ID NO 61
<211> LENGTH: 20
<212> TYPE: PRT
<213> ORGANISM: Buchnera_aphidicola

<400> SEQUENCE: 61

Pro Lys Lys Ile Glu Lys Ile Asp Ser Ser Glu Ile Asp Phe Asp Asp
1               5                   10                  15

Glu Ile Pro Phe
            20

<210> SEQ ID NO 62
<211> LENGTH: 20
<212> TYPE: PRT
<213> ORGANISM: Coxiella_burnetii

<400> SEQUENCE: 62

Gln Thr Pro Thr Ala Gly Asp Asp Ser Ser Val Ala Asp Phe Asp Asp
1               5                   10                  15

Asp Ile Pro Phe
            20

<210> SEQ ID NO 63
<211> LENGTH: 20
<212> TYPE: PRT
<213> ORGANISM: Photorhabdus_luminescens

<400> SEQUENCE: 63

Ser Ser Val Pro Pro Arg Gly Ser Glu Pro Pro Ile Asp Phe Asp Glu
1               5                   10                  15

Leu Ile Pro Phe
            20

<210> SEQ ID NO 64
<211> LENGTH: 20
<212> TYPE: PRT
<213> ORGANISM: Nitrosococcus_oceani

<400> SEQUENCE: 64

Pro Arg Pro Ser Ala Pro Pro Ser Ser Asn Asp Asp Phe Glu Asp
1               5                   10                  15

Asp Ile Pro Phe
            20

<210> SEQ ID NO 65
<211> LENGTH: 20
<212> TYPE: PRT
<213> ORGANISM: Colwellia_psychrerythraea

<400> SEQUENCE: 65

Gln Ala Pro Lys Val Asn Pro Gln Glu Pro Ser Ile Asp Phe Asp Asp
1               5                   10                  15

Asp Ile Pro Phe
            20

<210> SEQ ID NO 66
<211> LENGTH: 20
<212> TYPE: PRT
<213> ORGANISM: Pseudoalteromonas_haloplanktis

<400> SEQUENCE: 66

Gln Gly Gly Ala Ser Asn Pro Met Glu Pro Thr Ile Asp Phe Asp Asp
1               5                   10                  15
```

Asp Ile Pro Phe
        20

<210> SEQ ID NO 67
<211> LENGTH: 20
<212> TYPE: PRT
<213> ORGANISM: Wigglesworthia_glossinidia

<400> SEQUENCE: 67

Lys Glu Ser Lys Lys Asn Lys Ile Glu Glu Ile Asn Phe Asp Asp
1               5                   10                  15

Asp Ile Pro Phe
        20

<210> SEQ ID NO 68
<211> LENGTH: 20
<212> TYPE: PRT
<213> ORGANISM: Pseudomonas_entomophila

<400> SEQUENCE: 68

Gln Gln Pro Ala Pro Gln Pro Ala Ala Asp Phe Asp Ser Phe Asp Asp
1               5                   10                  15

Asp Ile Pro Phe
        20

<210> SEQ ID NO 69
<211> LENGTH: 20
<212> TYPE: PRT
<213> ORGANISM: Pseudomonas_putida

<400> SEQUENCE: 69

Gln Gln Pro Ala Pro Gln Pro Ala Ala Asp Phe Asp Ser Phe Asp Asp
1               5                   10                  15

Asp Ile Pro Phe
        20

<210> SEQ ID NO 70
<211> LENGTH: 20
<212> TYPE: PRT
<213> ORGANISM: Pseudomonas_syringae

<400> SEQUENCE: 70

Gln Gln Gln Ala Pro Gln Pro Ala Ala Asp Phe Asp Ser Phe Asp Asp
1               5                   10                  15

Asp Ile Pro Phe
        20

<210> SEQ ID NO 71
<211> LENGTH: 20
<212> TYPE: PRT
<213> ORGANISM: Pseudomonas_fluorescens

<400> SEQUENCE: 71

Gln Gln Ala Ala Pro Gln Pro Ala Pro Asp Phe Asp Ser Phe Asp Asp
1               5                   10                  15

Asp Ile Pro Phe
        20

<210> SEQ ID NO 72
<211> LENGTH: 20
<212> TYPE: PRT
<213> ORGANISM: Pseudomonas_aeruginosa -continued

```
<400> SEQUENCE: 72

Gln Gln Pro Ala Pro Gln Pro Ala Gln Asp Tyr Asp Ser Phe Asp Asp
1               5                   10                  15

Asp Ile Pro Phe
            20

<210> SEQ ID NO 73
<211> LENGTH: 20
<212> TYPE: PRT
<213> ORGANISM: Pseudomonas_stutzeri

<400> SEQUENCE: 73

Pro Ala Ala Arg Gln Gln Pro Ala Pro Asp Tyr Asp Ser Phe Asp Asp
1               5                   10                  15

Asp Ile Pro Phe
            20

<210> SEQ ID NO 74
<211> LENGTH: 20
<212> TYPE: PRT
<213> ORGANISM: Pseudomonas_mendocina

<400> SEQUENCE: 74

Ala Pro Gln Gln Ala Gln Pro Ala Pro Asp Tyr Asp Ser Phe Asp Asp
1               5                   10                  15

Asp Ile Pro Phe
            20

<210> SEQ ID NO 75
<211> LENGTH: 20
<212> TYPE: PRT
<213> ORGANISM: Saccharophagus_degradans

<400> SEQUENCE: 75

Pro Ala Pro Ala Ala Pro Pro Ala Pro Asp Met Asp Ser Phe Asp Asp
1               5                   10                  15

Asp Ile Pro Phe
            20

<210> SEQ ID NO 76
<211> LENGTH: 20
<212> TYPE: PRT
<213> ORGANISM: Methylibium_petroleiphilum

<400> SEQUENCE: 76

Arg Gln Gln Ala Arg Gln Pro Ala Thr Ala Gly Asp Gly Phe Asp Asp
1               5                   10                  15

Glu Ile Pro Phe
            20

<210> SEQ ID NO 77
<211> LENGTH: 20
<212> TYPE: PRT
<213> ORGANISM: Thiomicrospira_crunogena

<400> SEQUENCE: 77

Pro Ala Gln Gln Val Pro Ala Tyr Thr Ala Asn Asp Phe Asp Asp Asp
1               5                   10                  15

Asp Val Pro Phe
            20

<210> SEQ ID NO 78
```

```
<211> LENGTH: 20
<212> TYPE: PRT
<213> ORGANISM: Solibacter_usitatus

<400> SEQUENCE: 78

Ala Pro Ala Gln His Asn Asp Asp Phe Asn Gln Gly Ile Thr Asp Asp
1               5                   10                  15

Asp Val Pro Phe
            20

<210> SEQ ID NO 79
<211> LENGTH: 20
<212> TYPE: PRT
<213> ORGANISM: Idiomarina_loihiensis

<400> SEQUENCE: 79

Lys Pro Ala Glu Pro Ala Pro Phe Ser Pro Asp Asn Asp Phe Asp Asp
1               5                   10                  15

Asp Ile Pro Phe
            20

<210> SEQ ID NO 80
<211> LENGTH: 20
<212> TYPE: PRT
<213> ORGANISM: Burkholderia_383

<400> SEQUENCE: 80

Ser Arg Pro Ser Ala Pro Ala Gly Gly Gly Phe Asp Glu Met Asp Asp
1               5                   10                  15

Asp Ile Pro Phe
            20

<210> SEQ ID NO 81
<211> LENGTH: 20
<212> TYPE: PRT
<213> ORGANISM: Burkholderia_cepacia

<400> SEQUENCE: 81

Ser Arg Pro Ser Ala Pro Ala Gly Gly Gly Phe Asp Glu Met Asp Asp
1               5                   10                  15

Asp Ile Pro Phe
            20

<210> SEQ ID NO 82
<211> LENGTH: 20
<212> TYPE: PRT
<213> ORGANISM: Burkholderia_pseudomallei

<400> SEQUENCE: 82

Ser Arg Pro Ser Ala Pro Ala Gly Gly Gly Phe Asp Glu Met Asp Asp
1               5                   10                  15

Asp Ile Pro Phe
            20

<210> SEQ ID NO 83
<211> LENGTH: 20
<212> TYPE: PRT
<213> ORGANISM: Burkholderia_mallei

<400> SEQUENCE: 83

Ser Arg Pro Ser Ala Pro Ala Gly Gly Gly Phe Asp Glu Met Asp Asp
1               5                   10                  15

Asp Ile Pro Phe
```

<210> SEQ ID NO 84
<211> LENGTH: 20
<212> TYPE: PRT
<213> ORGANISM: Burkholderia_cenocepacia

<400> SEQUENCE: 84

Ser Arg Pro Ser Ala Pro Ala Gly Gly Gly Phe Asp Glu Met Asp Asp
1               5                   10                  15

Asp Ile Pro Phe
            20

<210> SEQ ID NO 85
<211> LENGTH: 20
<212> TYPE: PRT
<213> ORGANISM: Burkholderia_xenovorans

<400> SEQUENCE: 85

Ser Arg Pro Ser Ala Pro Ala Gly Gly Gly Phe Asp Glu Met Asp Asp
1               5                   10                  15

Asp Ile Pro Phe
            20

<210> SEQ ID NO 86
<211> LENGTH: 20
<212> TYPE: PRT
<213> ORGANISM: Burkholderia_vietnamiensis

<400> SEQUENCE: 86

Ser Arg Pro Ser Ala Pro Ala Gly Gly Gly Phe Asp Glu Met Asp Asp
1               5                   10                  15

Asp Ile Pro Phe
            20

<210> SEQ ID NO 87
<211> LENGTH: 20
<212> TYPE: PRT
<213> ORGANISM: Acidovorax_avenae

<400> SEQUENCE: 87

Ala Ala Gln Ala Pro Arg Ala Ala Ser Gly Phe Asp Asp Met Asp Asp
1               5                   10                  15

Asp Ile Pro Phe
            20

<210> SEQ ID NO 88
<211> LENGTH: 20
<212> TYPE: PRT
<213> ORGANISM: Verminephrobacter_eiseniae

<400> SEQUENCE: 88

Ala Ala Pro Gly Pro Arg Ala Ala Ser Gly Phe Asp Asp Met Asp Asp
1               5                   10                  15

Asp Ile Pro Phe
            20

<210> SEQ ID NO 89
<211> LENGTH: 20
<212> TYPE: PRT
<213> ORGANISM: Polaromonas_JS666

<400> SEQUENCE: 89

Ala Pro Ala Pro Thr Lys Ala Ala Ser Gly Phe Asp Asp Met Asp Asp
1               5                   10                  15

Asp Ile Pro Phe
        20

<210> SEQ ID NO 90
<211> LENGTH: 20
<212> TYPE: PRT
<213> ORGANISM: Rhodoferax_ferrireducens

<400> SEQUENCE: 90

Ala Pro Ala Gln Ala Lys Pro Ser Ser Gly Phe Asp Asp Met Asp Asp
1               5                   10                  15

Asp Ile Pro Phe
        20

<210> SEQ ID NO 91
<211> LENGTH: 20
<212> TYPE: PRT
<213> ORGANISM: Thiobacillus_denitrificans

<400> SEQUENCE: 91

Ala Gly Ser Gln Arg Pro Ala Ser Ser Gly Phe Asp Asp Met Asp Asp
1               5                   10                  15

Asp Ile Pro Phe
        20

<210> SEQ ID NO 92
<211> LENGTH: 20
<212> TYPE: PRT
<213> ORGANISM: Polaromonas_naphthalenivorans

<400> SEQUENCE: 92

Pro Ala Ala Ser Arg Ala Ser Pro Ser Gly Phe Asp Asp Met Asp Asp
1               5                   10                  15

Asp Ile Pro Phe
        20

<210> SEQ ID NO 93
<211> LENGTH: 20
<212> TYPE: PRT
<213> ORGANISM: Nitrosomonas_eutropha

<400> SEQUENCE: 93

Lys Thr Gly Thr Thr Gly Ser Ser Thr Gly Phe Asp Asp Met Glu Asp
1               5                   10                  15

Asp Ile Pro Phe
        20

<210> SEQ ID NO 94
<211> LENGTH: 20
<212> TYPE: PRT
<213> ORGANISM: Nitrosomonas_europaea

<400> SEQUENCE: 94

Ser Thr Pro Pro Ala Lys Ser Asn Thr Gly Phe Asp Asp Met Glu Asp
1               5                   10                  15

Asp Ile Pro Phe
        20

<210> SEQ ID NO 95
<211> LENGTH: 20
<212> TYPE: PRT

<213> ORGANISM: Nitrosospira_multiformis

<400> SEQUENCE: 95

Gly Arg Ala Pro Ala Arg Ser Ser Thr Gly Phe Asp Asp Met Asp Asp
1               5                   10                  15

Asp Ile Pro Phe
            20

<210> SEQ ID NO 96
<211> LENGTH: 20
<212> TYPE: PRT
<213> ORGANISM: Azoarcus_EbN1

<400> SEQUENCE: 96

Lys Ala Pro Thr Lys Ser Ser Gly Ala Gly Phe Gly Asp Phe Asp Asp
1               5                   10                  15

Asp Ile Pro Phe
            20

<210> SEQ ID NO 97
<211> LENGTH: 20
<212> TYPE: PRT
<213> ORGANISM: Methylobacillus_flagellatus

<400> SEQUENCE: 97

Ala Ala Ser Lys Pro Ala Gly Gly Ser Asn Phe Asp Asp Phe Glu Asp
1               5                   10                  15

Asp Ile Pro Phe
            20

<210> SEQ ID NO 98
<211> LENGTH: 20
<212> TYPE: PRT
<213> ORGANISM: Rhodospirillum_rubrum

<400> SEQUENCE: 98

Thr Ala Pro Ala Ser Gly Pro Ala Gly Gly Pro Val Asp Met Asp Asp
1               5                   10                  15

Asp Ile Pro Phe
            20

<210> SEQ ID NO 99
<211> LENGTH: 20
<212> TYPE: PRT
<213> ORGANISM: Ralstonia_eutropha

<400> SEQUENCE: 99

Arg Arg Gln Gln Gln Ala Pro Ser Asn Gly Phe Glu Asp Met Asp Asp
1               5                   10                  15

Asp Ile Pro Phe
            20

<210> SEQ ID NO 100
<211> LENGTH: 20
<212> TYPE: PRT
<213> ORGANISM: Ralstonia_solanacearum

<400> SEQUENCE: 100

Ala Arg Arg Gln Gln Ala Pro Ser Asn Gly Phe Glu Asp Met Asp Asp
1               5                   10                  15

Asp Ile Pro Phe
            20

```
<210> SEQ ID NO 101
<211> LENGTH: 20
<212> TYPE: PRT
<213> ORGANISM: Agrobacterium_tumefaciens

<400> SEQUENCE: 101

Arg Gly Gly Gly Gln Pro Ser Gly Gly Phe Ser Asn Asp Met Asp Asp
1               5                   10                  15

Asp Ile Pro Phe
            20

<210> SEQ ID NO 102
<211> LENGTH: 20
<212> TYPE: PRT
<213> ORGANISM: Neisseria_gonorrhoeae

<400> SEQUENCE: 102

Arg Arg Gln Pro Val Pro Ala Ala Ala Pro Val Glu Asp Ile Asp Asp
1               5                   10                  15

Asp Ile Pro Phe
            20

<210> SEQ ID NO 103
<211> LENGTH: 20
<212> TYPE: PRT
<213> ORGANISM: Neisseria_meningitidis

<400> SEQUENCE: 103

Arg Arg Gln Pro Val Pro Ala Ala Ala Pro Val Glu Asp Ile Asp Asp
1               5                   10                  15

Asp Ile Pro Phe
            20

<210> SEQ ID NO 104
<211> LENGTH: 20
<212> TYPE: PRT
<213> ORGANISM: Herminiimonas_arsenicoxydans

<400> SEQUENCE: 104

Arg Pro Ala Ala Lys Pro Ala Ala Ser Asn Phe Asn Asp Met Asp Asp
1               5                   10                  15

Asp Ile Pro Phe
            20

<210> SEQ ID NO 105
<211> LENGTH: 20
<212> TYPE: PRT
<213> ORGANISM: Nitrobacter_hamburgensis

<400> SEQUENCE: 105

Pro Arg Arg Thr Val Ala Ala Gly Ala Arg Arg Ser Asp Met Asp Asp
1               5                   10                  15

Asp Ile Pro Phe
            20

<210> SEQ ID NO 106
<211> LENGTH: 20
<212> TYPE: PRT
<213> ORGANISM: Nitrobacter_winogradskyi

<400> SEQUENCE: 106

Pro Arg Arg Ala Ala Pro Ala Ser Ser His Arg Gly Asp Met Asp Asp
1               5                   10                  15
```

Asp Ile Pro Phe
        20

<210> SEQ ID NO 107
<211> LENGTH: 20
<212> TYPE: PRT
<213> ORGANISM: Bordetella_parapertussis

<400> SEQUENCE: 107

Pro Ala Pro Gln Ala Ala Pro Ala Ala Asn Leu Ala Asp Met Asp Asp
1               5                   10                  15

Asp Ile Pro Phe
        20

<210> SEQ ID NO 108
<211> LENGTH: 20
<212> TYPE: PRT
<213> ORGANISM: Bordetella_pertussis

<400> SEQUENCE: 108

Pro Ala Pro Gln Ala Ala Pro Ala Ala Asn Leu Ala Asp Met Asp Asp
1               5                   10                  15

Asp Ile Pro Phe
        20

<210> SEQ ID NO 109
<211> LENGTH: 20
<212> TYPE: PRT
<213> ORGANISM: Bordetella_bronchiseptica

<400> SEQUENCE: 109

Pro Ala Pro Gln Ala Ala Pro Ala Ala Asn Leu Ala Asp Met Asp Asp
1               5                   10                  15

Asp Ile Pro Phe
        20

<210> SEQ ID NO 110
<211> LENGTH: 20
<212> TYPE: PRT
<213> ORGANISM: Polynucleobacter_QLW-P1DMWA-1

<400> SEQUENCE: 110

Ser Ala Pro Ser Ala Ser Asn Ala Ala Ser Leu Gly Ala Met Asp Asp
1               5                   10                  15

Asp Ile Pro Phe
        20

<210> SEQ ID NO 111
<211> LENGTH: 20
<212> TYPE: PRT
<213> ORGANISM: Acidobacteria_bacterium

<400> SEQUENCE: 111

Asn Asp Phe Asp Ser Ala Pro Ala Ala Ser Thr Gly Ile Thr Asp Asp
1               5                   10                  15

Asp Ile Pro Phe
        20

<210> SEQ ID NO 112
<211> LENGTH: 20
<212> TYPE: PRT
<213> ORGANISM: Candidatus_pelagibacter

```
<400> SEQUENCE: 112

Ala Asn Asn Phe Glu Asp Ser Pro Gln Thr Ser Asn Asp Met Asp Asp
1               5                   10                  15

Glu Ile Pro Phe
            20

<210> SEQ ID NO 113
<211> LENGTH: 20
<212> TYPE: PRT
<213> ORGANISM: Psychrobacter_arcticus

<400> SEQUENCE: 113

Pro Ala Gln Ser Lys Pro Thr Ala Met Leu Asp Gly Pro Val Asp Asp
1               5                   10                  15

Asp Ile Pro Phe
            20

<210> SEQ ID NO 114
<211> LENGTH: 20
<212> TYPE: PRT
<213> ORGANISM: Psychrobacter_cryohalolentis

<400> SEQUENCE: 114

Pro Ala Gln Ser Lys Pro Thr Ala Met Pro Asp Gly Pro Val Asp Asp
1               5                   10                  15

Asp Ile Pro Phe
            20

<210> SEQ ID NO 115
<211> LENGTH: 20
<212> TYPE: PRT
<213> ORGANISM: Haemophilus_ducreyi

<400> SEQUENCE: 115

Asn Lys Ser Ser Lys Lys Ser Thr Thr Gln Gln Pro Glu Val Asp Asp
1               5                   10                  15

Asp Ile Pro Phe
            20

<210> SEQ ID NO 116
<211> LENGTH: 20
<212> TYPE: PRT
<213> ORGANISM: Dechloromonas_aromatica

<400> SEQUENCE: 116

Ala Pro Pro Lys Asn Lys Pro Lys Pro Ser Phe Asp Asp Leu Gly Asp
1               5                   10                  15

Asp Ile Pro Phe
            20

<210> SEQ ID NO 117
<211> LENGTH: 20
<212> TYPE: PRT
<213> ORGANISM: Neorickettsia_sennetsu

<400> SEQUENCE: 117

Asp Leu Gly Thr Pro Thr Asn His Val Asn Asp Thr Leu Asp Asp Asp
1               5                   10                  15

Asp Ile Pro Phe
            20

<210> SEQ ID NO 118
```

-continued

```
<211> LENGTH: 20
<212> TYPE: PRT
<213> ORGANISM: Baumannia_cicadellinicola

<400> SEQUENCE: 118

Asn Lys Ile Gln Asp Met Gly Asn Glu Gln Pro Ile Glu Phe Asp Asp
1               5                   10                  15

Glu Ile Pro Phe
            20

<210> SEQ ID NO 119
<211> LENGTH: 20
<212> TYPE: PRT
<213> ORGANISM: Bdellovibrio_bacteriovorus

<400> SEQUENCE: 119

Phe Asn Phe Gln Asp Phe Gly Pro Glu Pro Ser Phe Asn Ser Asn Asp
1               5                   10                  15

Glu Ile Pro Phe
            20

<210> SEQ ID NO 120
<211> LENGTH: 20
<212> TYPE: PRT
<213> ORGANISM: Chromohalobacter_salexigens

<400> SEQUENCE: 120

Asp Asn Tyr Gly Ala Pro Asn Pro Gly Asn Phe Asp Asp Phe Asp Asp
1               5                   10                  15

Glu Ile Pro Phe
            20

<210> SEQ ID NO 121
<211> LENGTH: 20
<212> TYPE: PRT
<213> ORGANISM: Dichelobacter_nodosus

<400> SEQUENCE: 121

Ser Ser Pro Asp Tyr Gly Pro Asp Gly Ala Phe Asp Asp Pro Asp Asp
1               5                   10                  15

Glu Ile Pro Phe
            20

<210> SEQ ID NO 122
<211> LENGTH: 20
<212> TYPE: PRT
<213> ORGANISM: Aquifex_aeolicus

<400> SEQUENCE: 122

Glu Lys Leu Gly Lys Glu Glu Lys Pro Phe Thr Asp Glu Glu Asp
1               5                   10                  15

Glu Ile Pro Phe
            20

<210> SEQ ID NO 123
<211> LENGTH: 20
<212> TYPE: PRT
<213> ORGANISM: Hyphomonas_neptunium

<400> SEQUENCE: 123

Gln Gln Met Ser Gly Pro Lys Glu Ser Phe Ser Gln Asp Leu Asp Asp
1               5                   10                  15

Glu Ile Pro Phe
```

<210> SEQ ID NO 124
<211> LENGTH: 20
<212> TYPE: PRT
<213> ORGANISM: Caulobacter_crescentus

<400> SEQUENCE: 124

Ser Gln Pro Ser Gly Pro Arg Glu Ser Phe Ser Ala Asp Leu Asp Asp
1               5                   10                  15

Glu Ile Pro Phe
            20

<210> SEQ ID NO 125
<211> LENGTH: 20
<212> TYPE: PRT
<213> ORGANISM: Maricaulis_maris

<400> SEQUENCE: 125

Ser Met Asp Gly Pro Lys Glu Asp Phe Arg Asn Ala Asp Leu Asp Asp
1               5                   10                  15

Glu Ile Pro Phe
            20

<210> SEQ ID NO 126
<211> LENGTH: 20
<212> TYPE: PRT
<213> ORGANISM: Rickettsia_felis

<400> SEQUENCE: 126

His Pro Glu Ala Lys Asn His Ser Phe Asp His Ser Asp Leu Asp Asp
1               5                   10                  15

Glu Ile Pro Phe
            20

<210> SEQ ID NO 127
<211> LENGTH: 20
<212> TYPE: PRT
<213> ORGANISM: Rickettsia_conorii

<400> SEQUENCE: 127

His Pro Glu Thr Lys Asn His Ser Phe Asp His Ser Asp Leu Asp Asp
1               5                   10                  15

Glu Ile Pro Phe
            20

<210> SEQ ID NO 128
<211> LENGTH: 20
<212> TYPE: PRT
<213> ORGANISM: Rickettsia_typhi

<400> SEQUENCE: 128

Tyr Pro Glu Ile Lys Asn His Ser Phe Asp His Ser Asp Leu Asp Asp
1               5                   10                  15

Glu Ile Pro Phe
            20

<210> SEQ ID NO 129
<211> LENGTH: 20
<212> TYPE: PRT
<213> ORGANISM: Rickettsia_prowazekii

<400> SEQUENCE: 129

```
Tyr Pro Glu Thr Lys Asn His Ser Phe Asp His Ser Asp Leu Asp Asp
1               5                   10                  15

Glu Ile Pro Phe
            20
```

<210> SEQ ID NO 130
<211> LENGTH: 20
<212> TYPE: PRT
<213> ORGANISM: Rickettsia_bellii

<400> SEQUENCE: 130

```
Glu Tyr Lys His Ser Lys Pro Ser Phe Asp His Ser Asp Leu Asp Asp
1               5                   10                  15

Glu Ile Pro Phe
            20
```

<210> SEQ ID NO 131
<211> LENGTH: 20
<212> TYPE: PRT
<213> ORGANISM: Halorhodospira_halophila

<400> SEQUENCE: 131

```
Gly Ser Gly Gly Gly Gly Met Gln Glu Ala Pro Ala Asp Phe Asp Asp
1               5                   10                  15

Asp Ile Pro Phe
            20
```

<210> SEQ ID NO 132
<211> LENGTH: 20
<212> TYPE: PRT
<213> ORGANISM: Paracoccus_denitrificans

<400> SEQUENCE: 132

```
Ser Gly Gly Gly Gly Gly Gln Ser Gln Ser Arg Pro Asp Phe Asp Asp
1               5                   10                  15

Asp Ile Pro Phe
            20
```

<210> SEQ ID NO 133
<211> LENGTH: 20
<212> TYPE: PRT
<213> ORGANISM: Rhodopseudomonas_palustris

<400> SEQUENCE: 133

```
Arg Pro Met Pro Ala Ser Ser Gly Gly Gly Arg Ser Asp Met Asp Asp
1               5                   10                  15

Asp Ile Pro Phe
            20
```

<210> SEQ ID NO 134
<211> LENGTH: 20
<212> TYPE: PRT
<213> ORGANISM: Bradyrhizobium_japonicum

<400> SEQUENCE: 134

```
Arg Ala Val Ala Ala Gly Gly Gly Gly Arg Asn Ser Asp Met Asp Asp
1               5                   10                  15

Asp Ile Pro Phe
            20
```

<210> SEQ ID NO 135
<211> LENGTH: 20
<212> TYPE: PRT

```
<213> ORGANISM: Granulibacter_bethesdensis

<400> SEQUENCE: 135

Ser Gly Gly Ser Gly Trp Glu Pro Ser His Gly Gly Asp Leu Asp Asp
1               5                   10                  15

Glu Ile Pro Phe
            20

<210> SEQ ID NO 136
<211> LENGTH: 20
<212> TYPE: PRT
<213> ORGANISM: Rhodobacter_sphaeroides

<400> SEQUENCE: 136

Arg Gly Asn Ala Pro Ser Gly Gly Arg Arg Ser Asp Leu Asp Asp
1               5                   10                  15

Glu Ile Pro Phe
            20

<210> SEQ ID NO 137
<211> LENGTH: 20
<212> TYPE: PRT
<213> ORGANISM: Silicibacter_pomeroyi

<400> SEQUENCE: 137

Gly Gly Gly Arg Gly Arg Gly Pro Ala Ser Gly Gly Ile Asp Asp Asp
1               5                   10                  15

Glu Ile Pro Phe
            20

<210> SEQ ID NO 138
<211> LENGTH: 20
<212> TYPE: PRT
<213> ORGANISM: Roseobacter_denitrificans

<400> SEQUENCE: 138

Gly Gly Gly Asn Ala Pro Ser Pro Ala Pro Ser Arg Asp Leu Asp Asp
1               5                   10                  15

Glu Ile Pro Phe
            20

<210> SEQ ID NO 139
<211> LENGTH: 20
<212> TYPE: PRT
<213> ORGANISM: Magnetospirillum_magneticum

<400> SEQUENCE: 139

Gly Gly Gly Gly Gly Gln Ser Trp Glu Pro Pro Ala Asp Leu Asp Asp
1               5                   10                  15

Glu Ile Pro Phe
            20

<210> SEQ ID NO 140
<211> LENGTH: 20
<212> TYPE: PRT
<213> ORGANISM: Mesorhizobium_BNC1

<400> SEQUENCE: 140

Pro Ala Glu Ser Gly Gly Gly Gly Gly His Ser Arg Asp Leu Asp Asp
1               5                   10                  15

Glu Ile Pro Phe
            20
```

<210> SEQ ID NO 141
<211> LENGTH: 20
<212> TYPE: PRT
<213> ORGANISM: Mesorhizobium_loti

<400> SEQUENCE: 141

Ala Pro Arg Gly Gly Gly Gly Gly Ser Ser Arg Glu Leu Asp Asp
1               5                   10                  15

Glu Ile Pro Phe
            20

<210> SEQ ID NO 142
<211> LENGTH: 20
<212> TYPE: PRT
<213> ORGANISM: Brucella_melitensis

<400> SEQUENCE: 142

Gly Pro Ser Ser Gly Ser Ser Gly Gly Phe Ser Arg Asp Leu Asp Asp
1               5                   10                  15

Glu Ile Pro Phe
            20

<210> SEQ ID NO 143
<211> LENGTH: 20
<212> TYPE: PRT
<213> ORGANISM: Brucella_suis

<400> SEQUENCE: 143

Gly Pro Ser Ser Gly Ser Ser Gly Gly Phe Ser Arg Asp Leu Asp Asp
1               5                   10                  15

Glu Ile Pro Phe
            20

<210> SEQ ID NO 144
<211> LENGTH: 20
<212> TYPE: PRT
<213> ORGANISM: Brucella_abortus

<400> SEQUENCE: 144

Gly Pro Ser Ser Gly Ser Ser Gly Gly Phe Ser Arg Asp Leu Asp Asp
1               5                   10                  15

Glu Ile Pro Phe
            20

<210> SEQ ID NO 145
<211> LENGTH: 20
<212> TYPE: PRT
<213> ORGANISM: Jannaschia_CCS1

<400> SEQUENCE: 145

Ser Gly Gly Gly Tyr Gly Gly Gly Gly Ser Ser Asp Leu Asp Asp
1               5                   10                  15

Glu Ile Pro Phe
            20

<210> SEQ ID NO 146
<211> LENGTH: 20
<212> TYPE: PRT
<213> ORGANISM: Silicibacter_TM1040

<400> SEQUENCE: 146

Asn Arg Gly Gly Gly Tyr Gly Ser Gly Ser Gln Ser Ile Asp Asp Asp
1               5                   10                  15

Glu Ile Pro Phe
          20

<210> SEQ ID NO 147
<211> LENGTH: 20
<212> TYPE: PRT
<213> ORGANISM: Novosphingobium_aromaticivoran

<400> SEQUENCE: 147

Asn Gln Gly Gly Gly Ser Gly Gly Gly Phe Gly Asp Asp Leu Asp Asp
1               5                   10                  15

Asp Ile Pro Phe
          20

<210> SEQ ID NO 148
<211> LENGTH: 20
<212> TYPE: PRT
<213> ORGANISM: Myxococcus_xanthus

<400> SEQUENCE: 148

Pro Pro Asp Asp Met Gly Gly Gly His Gly Gly Gly Asn Gly Asp Asp
1               5                   10                  15

Asp Ile Pro Phe
          20

<210> SEQ ID NO 149
<211> LENGTH: 20
<212> TYPE: PRT
<213> ORGANISM: Erythrobacter_litoralis

<400> SEQUENCE: 149

Gly Gly Ser Gly Gly Gly Gly Ser Asn Tyr Asp Asp Leu Asp Asp
1               5                   10                  15

Asp Ile Pro Phe
          20

<210> SEQ ID NO 150
<211> LENGTH: 20
<212> TYPE: PRT
<213> ORGANISM: Anaeromyxobacter_dehalogenans

<400> SEQUENCE: 150

Gly Pro Gly Phe Gly Ser Gly Gly Gly Ala Gly Gly Gly Pro Asp
1               5                   10                  15

Asp Ile Pro Phe
          20

<210> SEQ ID NO 151
<211> LENGTH: 20
<212> TYPE: PRT
<213> ORGANISM: Desulfotomaculum_reducens

<400> SEQUENCE: 151

Ser Gly Ser Gly Ser Gly Phe Gly Ser Glu Ile Ser Phe Asn Gly Asp
1               5                   10                  15

Asp Ile Pro Phe
          20

<210> SEQ ID NO 152
<211> LENGTH: 20
<212> TYPE: PRT
<213> ORGANISM: Sphingopyxis_alaskensis

```
<400> SEQUENCE: 152

Gly Ala Pro Gly Gly Arg Pro Pro Phe Asp Asp Asp Leu Asp Asp
1               5                   10                  15

Asp Val Pro Phe
            20

<210> SEQ ID NO 153
<211> LENGTH: 20
<212> TYPE: PRT
<213> ORGANISM: Pelobacter_propionicus

<400> SEQUENCE: 153

Ala Gly Thr Ser Gly Gly Gly Tyr Glu Pro Pro Phe Gln Asp Asp
1               5                   10                  15

Asp Ile Pro Phe
            20

<210> SEQ ID NO 154
<211> LENGTH: 20
<212> TYPE: PRT
<213> ORGANISM: Gluconobacter_oxydans

<400> SEQUENCE: 154

Gly Ser Asn Gly Gly Trp Asp Ala Pro Pro Asp Asn Asp Leu Asp Asp
1               5                   10                  15

Glu Ile Pro Phe
            20

<210> SEQ ID NO 155
<211> LENGTH: 20
<212> TYPE: PRT
<213> ORGANISM: Bartonella_quintana

<400> SEQUENCE: 155

Gln Asn Asn Ser Gln Ser Glu Glu Ser Phe Ser His Lys Leu Asp Asp
1               5                   10                  15

Asp Val Pro Phe
            20

<210> SEQ ID NO 156
<211> LENGTH: 20
<212> TYPE: PRT
<213> ORGANISM: Bartonella_henselae

<400> SEQUENCE: 156

Ser Asn Asn Ser Gln Leu Gly Glu Ser Phe Ser His Lys Leu Asp Asp
1               5                   10                  15

Asp Val Pro Phe
            20

<210> SEQ ID NO 157
<211> LENGTH: 20
<212> TYPE: PRT
<213> ORGANISM: Bartonella_bacilliformis

<400> SEQUENCE: 157

Gln Asn Asn Asn Gln Ser Gly Gly Ser Phe Ser His Gln Leu Asp Asp
1               5                   10                  15

Asp Val Pro Phe
            20

<210> SEQ ID NO 158
```

```
<211> LENGTH: 20
<212> TYPE: PRT
<213> ORGANISM: Rhizobium_etli

<400> SEQUENCE: 158

Ser Ser Asn Arg Gly Gly Gly Gly Asn Phe Ser Arg Asp Leu Asp Asp
1               5                   10                  15

Asp Ile Pro Phe
            20

<210> SEQ ID NO 159
<211> LENGTH: 20
<212> TYPE: PRT
<213> ORGANISM: Rhizobium_leguminosarum

<400> SEQUENCE: 159

Ser Arg Gly Gly Gly Gly Gly Gly Asn Phe Ser Arg Asp Leu Asp Asp
1               5                   10                  15

Asp Ile Pro Phe
            20

<210> SEQ ID NO 160
<211> LENGTH: 20
<212> TYPE: PRT
<213> ORGANISM: Sinorhizobium_meliloti

<400> SEQUENCE: 160

Ser Asn Gln Pro Asn Gln Gly Gly Asn Phe Ser Arg Asp Leu Asp Asp
1               5                   10                  15

Asp Ile Pro Phe
            20

<210> SEQ ID NO 161
<211> LENGTH: 20
<212> TYPE: PRT
<213> ORGANISM: Desulfitobacterium_hafniense

<400> SEQUENCE: 161

His Thr Ala Ser Gly Glu Ala Tyr Gly His Glu Met Ser Leu Asp Asp
1               5                   10                  15

Asp Ile Pro Phe
            20

<210> SEQ ID NO 162
<211> LENGTH: 20
<212> TYPE: PRT
<213> ORGANISM: Shewanella_denitrificans

<400> SEQUENCE: 162

Lys Ser His Leu Val Asp Ser Thr Ser Lys Ile Asp Phe Asp Asp Glu
1               5                   10                  15

Asp Ile Pro Phe
            20

<210> SEQ ID NO 163
<211> LENGTH: 20
<212> TYPE: PRT
<213> ORGANISM: Candidatus_blochmannia

<400> SEQUENCE: 163

Asn Asn His Glu Leu Asn Ser Glu Ser Ile Val Asn Phe Asn Glu Asp
1               5                   10                  15

Asp Ile Pro Phe
```

```
<210> SEQ ID NO 164
<211> LENGTH: 20
<212> TYPE: PRT
<213> ORGANISM: Wolbachia_endosymbiont

<400> SEQUENCE: 164

Gln Tyr Glu Asn Phe Asp Ser Glu Val Lys Glu Glu Leu Ile Asp Asp
1               5                   10                  15

Glu Ile Pro Phe
            20

<210> SEQ ID NO 165
<211> LENGTH: 20
<212> TYPE: PRT
<213> ORGANISM: Tropheryma_whipplei

<400> SEQUENCE: 165

Lys Val Leu Val Gly Asp Asn Val Ser Tyr Glu Asp Phe Asp Ser Asp
1               5                   10                  15

Glu Val Pro Phe
            20

<210> SEQ ID NO 166
<211> LENGTH: 20
<212> TYPE: PRT
<213> ORGANISM: Ehrlichia_chaffeensis

<400> SEQUENCE: 166

Lys Glu Asn Ser Leu Asn Ser Ser Cys Asp Asp Ile Ile Ile Asp Asp
1               5                   10                  15

Glu Ile Pro Phe
            20

<210> SEQ ID NO 167
<211> LENGTH: 20
<212> TYPE: PRT
<213> ORGANISM: Ehrlichia_canis

<400> SEQUENCE: 167

Lys Glu Asn Phe Gln Asp Ser Ser Cys Asp Asp Ile Ile Ile Asp Asp
1               5                   10                  15

Glu Ile Pro Phe
            20

<210> SEQ ID NO 168
<211> LENGTH: 20
<212> TYPE: PRT
<213> ORGANISM: Ehrlichia_ruminantium

<400> SEQUENCE: 168

Asn Lys Met Pro Phe Gln Asn Ser Cys Glu Asp Val Ile Ile Asp Asp
1               5                   10                  15

Glu Ile Pro Phe
            20

<210> SEQ ID NO 169
<211> LENGTH: 20
<212> TYPE: PRT
<213> ORGANISM: Helicobacter_acinonychis

<400> SEQUENCE: 169
```

Pro Ser Lys Tyr Gln Asn Ser Val Pro Glu Ile Asn Ile Asp Glu Glu
1               5                   10                  15

Glu Ile Pro Phe
            20

<210> SEQ ID NO 170
<211> LENGTH: 20
<212> TYPE: PRT
<213> ORGANISM: Helicobacter_pylori

<400> SEQUENCE: 170

Pro Ser Lys Tyr Gln Asn Ser Val Pro Glu Ile Asn Ile Asp Glu Glu
1               5                   10                  15

Glu Ile Pro Phe
            20

<210> SEQ ID NO 171
<211> LENGTH: 20
<212> TYPE: PRT
<213> ORGANISM: Thiomicrospira_denitrificans

<400> SEQUENCE: 171

Gln Met Pro Ser Asn Ser Ser Ile Pro Glu Ile Asp Ile Asp Glu Asp
1               5                   10                  15

Glu Ile Pro Phe
            20

<210> SEQ ID NO 172
<211> LENGTH: 20
<212> TYPE: PRT
<213> ORGANISM: Wolinella_succinogenes

<400> SEQUENCE: 172

Ala Pro Tyr Lys Glu Pro Gln Ile Pro Glu Ile Asn Ile Asp Asp Asp
1               5                   10                  15

Glu Ile Pro Phe
            20

<210> SEQ ID NO 173
<211> LENGTH: 20
<212> TYPE: PRT
<213> ORGANISM: Helicobacter_hepaticus

<400> SEQUENCE: 173

Thr Gly Asn Tyr Pro Gln Asn Ile Pro Glu Ile Asn Ile Asp Asp Glu
1               5                   10                  15

Asp Ile Pro Phe
            20

<210> SEQ ID NO 174
<211> LENGTH: 20
<212> TYPE: PRT
<213> ORGANISM: Campylobacter_fetus

<400> SEQUENCE: 174

Arg Gln Asn Lys Pro Lys Gln Asn Ile Asp Val Asn Ile Asp Asp Glu
1               5                   10                  15

Glu Ile Pro Phe
            20

<210> SEQ ID NO 175
<211> LENGTH: 20
<212> TYPE: PRT

```
<213> ORGANISM: Dehalococcoides_ethenogenes

<400> SEQUENCE: 175

Met Asp Ala Arg Asp Asp Asn Gly Gly Gly Glu Leu Glu Pro Glu
1               5                   10                  15

Asp Ile Pro Phe
            20

<210> SEQ ID NO 176
<211> LENGTH: 20
<212> TYPE: PRT
<213> ORGANISM: Dehalococcoides_CBDB1

<400> SEQUENCE: 176

Ile Asp Ala Arg Glu Asp Asp Asn Gly Gly Gly Glu Leu Glu Pro Glu
1               5                   10                  15

Asp Ile Pro Phe
            20

<210> SEQ ID NO 177
<211> LENGTH: 20
<212> TYPE: PRT
<213> ORGANISM: Symbiobacterium_thermophilum

<400> SEQUENCE: 177

Arg Arg Glu Asp Gly Met Gly Ser Glu Leu Thr Leu Gly Asp Asp Glu
1               5                   10                  15

Asp Val Pro Phe
            20

<210> SEQ ID NO 178
<211> LENGTH: 20
<212> TYPE: PRT
<213> ORGANISM: Clostridium_novyi

<400> SEQUENCE: 178

Ile Phe Asp Gln Gly Tyr Asp Glu Glu Ile Thr Pro Ile Asp Asp Gly
1               5                   10                  15

Asp Ile Pro Phe
            20

<210> SEQ ID NO 179
<211> LENGTH: 20
<212> TYPE: PRT
<213> ORGANISM: Clostridium_acetobutylicum

<400> SEQUENCE: 179

Asp Phe Gly Val Pro Val Gln Glu Asp Ile Thr Pro Val Asp Asn Ser
1               5                   10                  15

Asp Ile Pro Phe
            20

<210> SEQ ID NO 180
<211> LENGTH: 20
<212> TYPE: PRT
<213> ORGANISM: Clostridium_perfringens

<400> SEQUENCE: 180

Asp Ser Ser Phe Asn Ser Asn Asp Asp Met Thr Pro Ile Asp Asp Gly
1               5                   10                  15

Asp Ile Pro Phe
            20
```

-continued

<210> SEQ ID NO 181
<211> LENGTH: 20
<212> TYPE: PRT
<213> ORGANISM: Clostridium_tetani

<400> SEQUENCE: 181

```
Asn Asn Glu Asp Asn Tyr Asn Asp Asp Ile Thr Pro Val Asp Glu Gly
1               5                   10                  15

Glu Val Pro Phe
            20
```

<210> SEQ ID NO 182
<211> LENGTH: 20
<212> TYPE: PRT
<213> ORGANISM: Borrelia_afzelii

<400> SEQUENCE: 182

```
Glu Asp Val Ile Lys Asp Ile Asp Ile Val Asp Asp Lys Phe Asn Glu
1               5                   10                  15

Asp Ile Pro Phe
            20
```

<210> SEQ ID NO 183
<211> LENGTH: 20
<212> TYPE: PRT
<213> ORGANISM: Borrelia_burgdorferi

<400> SEQUENCE: 183

```
Glu Asp Val Val Lys Asp Ile Asp Ile Val Asp Asp Lys Phe Ser Glu
1               5                   10                  15

Asp Ile Pro Phe
            20
```

<210> SEQ ID NO 184
<211> LENGTH: 20
<212> TYPE: PRT
<213> ORGANISM: Borrelia_garinii

<400> SEQUENCE: 184

```
Glu Asp Ala Ile Lys Asn Ile Asp Ile Val Asp Asp Lys Phe Asn Glu
1               5                   10                  15

Asp Ile Pro Phe
            20
```

<210> SEQ ID NO 185
<211> LENGTH: 20
<212> TYPE: PRT
<213> ORGANISM: Syntrophomonas_wolfei

<400> SEQUENCE: 185

```
Glu Val Asn Met Asp Asn Ile Asp Leu Val Asp Gln His Glu Asp Glu
1               5                   10                  15

Asp Ile Pro Phe
            20
```

<210> SEQ ID NO 186
<211> LENGTH: 20
<212> TYPE: PRT
<213> ORGANISM: Anaplasma_marginale

<400> SEQUENCE: 186

```
Glu Asn Ala Ile Val Glu Glu Val Ser Phe Ala Asp Glu Asp Met Asp
1               5                   10                  15
```

Glu Ile Pro Phe
            20

<210> SEQ ID NO 187
<211> LENGTH: 20
<212> TYPE: PRT
<213> ORGANISM: Anaplasma_phagocytophilum

<400> SEQUENCE: 187

Ala Gly Ser Phe Gly Gly Gly Val Asp Phe Leu Asp Pro Asp Val Asp
1               5                   10                  15

Glu Ile Pro Phe
            20

<210> SEQ ID NO 188
<211> LENGTH: 20
<212> TYPE: PRT
<213> ORGANISM: Treponema_pallidum

<400> SEQUENCE: 188

Ala Thr Ser Ser Leu Asp Glu Ala Asp Phe Ser Ser Ser Asp Leu Asp
1               5                   10                  15

Thr Val Pro Phe
            20

<210> SEQ ID NO 189
<211> LENGTH: 20
<212> TYPE: PRT
<213> ORGANISM: Rubrobacter_xylanophilus

<400> SEQUENCE: 189

Gly Arg Gly Ala Gly Asp Glu Val Asp Ile Asn Glu Ser Asp Phe Asp
1               5                   10                  15

Asp Ile Pro Phe
            20

<210> SEQ ID NO 190
<211> LENGTH: 20
<212> TYPE: PRT
<213> ORGANISM: Treponema_denticola

<400> SEQUENCE: 190

Pro Ser Tyr Asp Asp Tyr Gln Pro Asp Met Gly Asn Ser Asp Leu Asp
1               5                   10                  15

Asn Ile Pro Phe
            20

<210> SEQ ID NO 191
<211> LENGTH: 20
<212> TYPE: PRT
<213> ORGANISM: Mycoplasma_penetrans

<400> SEQUENCE: 191

Asp Asp Glu Asp Pro Asp Gln Val Val Ser Asn Leu Asp Trp Leu Asp
1               5                   10                  15

Glu Phe Lys Glu
            20

<210> SEQ ID NO 192
<211> LENGTH: 20
<212> TYPE: PRT
<213> ORGANISM: Candidatus_ruthia

<400> SEQUENCE: 192

Pro Val Leu Asp Pro Ile Ala Pro Val Asp Asn Ser Glu Phe Asp Asp
1 5 10 15

Asp Ile Pro Phe
20

<210> SEQ ID NO 193
<211> LENGTH: 20
<212> TYPE: PRT
<213> ORGANISM: Acidovorax_JS42

<400> SEQUENCE: 193

Pro Val Leu Asp Pro Ile Ala Pro Val Asp Asn Ser Glu Phe Asp Asp
1 5 10 15

Asp Ile Pro Phe
20

<210> SEQ ID NO 194
<211> LENGTH: 20
<212> TYPE: PRT
<213> ORGANISM: Francisella_tularensis

<400> SEQUENCE: 194

Asp Asn Met Pro Asp Phe Ala Glu Ile Asn Ser Ser Asn Phe Asp Asp
1 5 10 15

Asp Ile Pro Phe
20

<210> SEQ ID NO 195
<211> LENGTH: 20
<212> TYPE: PRT
<213> ORGANISM: Porphyromonas_gingivalis

<400> SEQUENCE: 195

Ser Ser Val Arg Asp Thr Ala Lys Glu Glu Ser Ser Glu Pro Pro Ser
1 5 10 15

Asp Leu Pro Phe
20

<210> SEQ ID NO 196
<211> LENGTH: 20
<212> TYPE: PRT
<213> ORGANISM: Acinetobacter_ADP1

<400> SEQUENCE: 196

Tyr Val Pro Lys Ala Pro Gln Gln Pro Ala Pro Ala Asp Leu Asp Asp
1 5 10 15

Asp Leu Pro Phe
20

<210> SEQ ID NO 197
<211> LENGTH: 20
<212> TYPE: PRT
<213> ORGANISM: Acinetobacter_baumannii

<400> SEQUENCE: 197

Pro Lys Ala Pro Gln Gln Pro Ala Ser Ala Pro Ala Asp Leu Asp Asp
1 5 10 15

Asp Leu Pro Phe
20

<210> SEQ ID NO 198

```
<211> LENGTH: 20
<212> TYPE: PRT
<213> ORGANISM: Synechococcus_elongates

<400> SEQUENCE: 198

Gly Ser Arg Arg Asp Gln Glu Gly Gly Met Ala Pro Arg Asp Pro Asp
1               5                   10                  15

Ser Asp Leu Phe
            20

<210> SEQ ID NO 199
<211> LENGTH: 20
<212> TYPE: PRT
<213> ORGANISM: Clostridium_thermocellum

<400> SEQUENCE: 199

Glu Pro Glu Asn Thr Asp Gly Glu Gly Phe Phe Pro Ala Glu Asp Asp
1               5                   10                  15

Glu Leu Pro Phe
            20

<210> SEQ ID NO 200
<211> LENGTH: 20
<212> TYPE: PRT
<213> ORGANISM: Clostridium_difficile

<400> SEQUENCE: 200

Glu Pro Gln Gly Leu Asp Pro Gln Gly Phe Gln Ala Ile Asp Asp Asp
1               5                   10                  15

Asp Ile Pro Phe
            20

<210> SEQ ID NO 201
<211> LENGTH: 20
<212> TYPE: PRT
<213> ORGANISM: Thermoanaerobacter_tengcongens

<400> SEQUENCE: 201

Asp Ile Pro Asp Asp Phe Asp Gly Phe Thr Pro Ile Glu Ser Glu Asp
1               5                   10                  15

Asp Leu Pro Phe
            20

<210> SEQ ID NO 202
<211> LENGTH: 20
<212> TYPE: PRT
<213> ORGANISM: Streptococcus_sanguinis

<400> SEQUENCE: 202

Asp Glu Ser Pro Phe Gly Asn Ser Asn Pro Met Asp Ile Ser Asp Asp
1               5                   10                  15

Asp Leu Pro Phe
            20

<210> SEQ ID NO 203
<211> LENGTH: 20
<212> TYPE: PRT
<213> ORGANISM: Streptococcus_thermophilus

<400> SEQUENCE: 203

Asp Glu Ser Pro Phe Gly Asn Ser Asn Pro Met Asp Ile Ser Asp Asp
1               5                   10                  15

Asp Leu Pro Phe
```

<210> SEQ ID NO 204
<211> LENGTH: 20
<212> TYPE: PRT
<213> ORGANISM: Streptococcus_agalactiae

<400> SEQUENCE: 204

Asp Glu Ser Pro Phe Gly Asn Ser Asn Pro Met Asp Ile Ser Asp Asp
1               5                   10                  15

Asp Leu Pro Phe
            20

<210> SEQ ID NO 205
<211> LENGTH: 20
<212> TYPE: PRT
<213> ORGANISM: Streptococcus_mutans

<400> SEQUENCE: 205

Asp Glu Ser Pro Phe Gly Asp Ser Asn Pro Met Asp Ile Ser Asp Asp
1               5                   10                  15

Asp Leu Pro Phe
            20

<210> SEQ ID NO 206
<211> LENGTH: 20
<212> TYPE: PRT
<213> ORGANISM: Streptococcus_suis

<400> SEQUENCE: 206

Glu Glu Ser Pro Phe Gly Ala Ser Asn Pro Met Asp Ile Ser Asp Asp
1               5                   10                  15

Asp Leu Pro Phe
            20

<210> SEQ ID NO 207
<211> LENGTH: 20
<212> TYPE: PRT
<213> ORGANISM: Lactococcus_lactis

<400> SEQUENCE: 207

Gln Asn Asn Asp Ser Phe Gly Ser Asp Pro Met Glu Ile Ser Asp Asp
1               5                   10                  15

Asp Leu Pro Phe
            20

<210> SEQ ID NO 208
<211> LENGTH: 20
<212> TYPE: PRT
<213> ORGANISM: Zymomonas_mobilis

<400> SEQUENCE: 208

Ser Ser Asn Thr Asn His Asp Pro Phe Gly Met Asp Asp Leu Asp Asp
1               5                   10                  15

Asp Val Pro Phe
            20

<210> SEQ ID NO 209
<211> LENGTH: 20
<212> TYPE: PRT
<213> ORGANISM: Oenococcus_oeni

<400> SEQUENCE: 209

```
Pro Phe Asn Thr Asp Thr Gly Asn Asp Ser Leu Asp Ile Ser Asp Asp
1               5                   10                  15

Asp Leu Pro Phe
            20
```

<210> SEQ ID NO 210
<211> LENGTH: 20
<212> TYPE: PRT
<213> ORGANISM: Carboxydothermus_hydrogenoform

<400> SEQUENCE: 210

```
Asp Phe Asp Pro Ser Asp Phe Gly Thr Glu Ile Glu Ile Ser Asp Glu
1               5                   10                  15

Asp Ile Pro Phe
            20
```

<210> SEQ ID NO 211
<211> LENGTH: 20
<212> TYPE: PRT
<213> ORGANISM: Moorella_thermoacetica

<400> SEQUENCE: 211

```
Asn Gln Asp Phe Ser Asp Leu Gly Thr Glu Val Glu Ile Gly Glu Asp
1               5                   10                  15

Asp Leu Pro Phe
            20
```

<210> SEQ ID NO 212
<211> LENGTH: 20
<212> TYPE: PRT
<213> ORGANISM: Geobacillus_kaustophilus

<400> SEQUENCE: 212

```
Asp Asp Pro Phe Ala Asn Asp Gly Gln Pro Ile Asp Ile Ser Asp Asp
1               5                   10                  15

Asp Leu Pro Phe
            20
```

<210> SEQ ID NO 213
<211> LENGTH: 20
<212> TYPE: PRT
<213> ORGANISM: Geobacillus_thermodenitrifican

<400> SEQUENCE: 213

```
Glu Asp Pro Phe Ala Asn Asp Gly Gln Pro Ile Asp Ile Ser Asp Asp
1               5                   10                  15

Asp Leu Pro Phe
            20
```

<210> SEQ ID NO 214
<211> LENGTH: 20
<212> TYPE: PRT
<213> ORGANISM: Bacillus_licheniformis

<400> SEQUENCE: 214

```
Asp Asp Pro Phe Ala Asn Asp Gly Lys Pro Ile Asp Ile Ser Asp Asp
1               5                   10                  15

Asp Leu Pro Phe
            20
```

<210> SEQ ID NO 215
<211> LENGTH: 20
<212> TYPE: PRT

<213> ORGANISM: Bacillus_subtilis

<400> SEQUENCE: 215

Asp Asp Pro Phe Ala Asn Asp Gly Lys Pro Ile Asp Ile Ser Asp Asp
1               5                   10                  15

Asp Leu Pro Phe
            20

<210> SEQ ID NO 216
<211> LENGTH: 20
<212> TYPE: PRT
<213> ORGANISM: Bacillus_halodurans

<400> SEQUENCE: 216

Glu Asp Pro Phe Ala Asn Asp Gly Lys Pro Ile Asp Ile Ser Asp Asp
1               5                   10                  15

Asp Leu Pro Phe
            20

<210> SEQ ID NO 217
<211> LENGTH: 20
<212> TYPE: PRT
<213> ORGANISM: Listeria_welshimeri

<400> SEQUENCE: 217

Asn Asp Pro Phe Ala Ser Asp Gly Lys Pro Ile Asp Ile Ser Asp Asp
1               5                   10                  15

Asp Leu Pro Phe
            20

<210> SEQ ID NO 218
<211> LENGTH: 20
<212> TYPE: PRT
<213> ORGANISM: Lactobacillus_casei

<400> SEQUENCE: 218

Pro Asp Pro Phe Ala Asn Asn Gly Lys Pro Ile Asp Ile Ser Asp Asp
1               5                   10                  15

Asp Leu Pro Phe
            20

<210> SEQ ID NO 219
<211> LENGTH: 20
<212> TYPE: PRT
<213> ORGANISM: Oceanobacillus_iheyensis

<400> SEQUENCE: 219

Glu Asp Pro Phe Lys Asn Asn Gly Glu Pro Ile Asp Ile Ser Asp Asp
1               5                   10                  15

Asp Leu Pro Phe
            20

<210> SEQ ID NO 220
<211> LENGTH: 20
<212> TYPE: PRT
<213> ORGANISM: Bacillus_thuringiensis

<400> SEQUENCE: 220

Asp Asp Pro Phe Ser Asn Val Gly Gln Pro Ile Asp Ile Ser Asp Asp
1               5                   10                  15

Asp Leu Pro Phe
            20

<210> SEQ ID NO 221
<211> LENGTH: 20
<212> TYPE: PRT
<213> ORGANISM: Bacillus_anthracis

<400> SEQUENCE: 221

Asp Asp Pro Phe Ser Asn Val Gly Gln Pro Ile Asp Ile Ser Asp Asp
1 5 10 15

Asp Leu Pro Phe
20

<210> SEQ ID NO 222
<211> LENGTH: 20
<212> TYPE: PRT
<213> ORGANISM: Bacillus_cereus

<400> SEQUENCE: 222

Asp Asp Pro Phe Ser Asn Val Gly Gln Pro Ile Asp Ile Ser Asp Asp
1 5 10 15

Asp Leu Pro Phe
20

<210> SEQ ID NO 223
<211> LENGTH: 20
<212> TYPE: PRT
<213> ORGANISM: Bacillus_clausii

<400> SEQUENCE: 223

Asp Asn Asp Pro Phe Ser Asn Asp Gly Ser Ile Asp Ile Ser Asp Asp
1 5 10 15

Asp Leu Pro Phe
20

<210> SEQ ID NO 224
<211> LENGTH: 20
<212> TYPE: PRT
<213> ORGANISM: Pediococcus_pentosaceus

<400> SEQUENCE: 224

Asn Asp Pro Phe Ala Asn Ser Gly Gln Ser Ile Asp Ile Ser Asp Asp
1 5 10 15

Asp Leu Pro Phe
20

<210> SEQ ID NO 225
<211> LENGTH: 20
<212> TYPE: PRT
<213> ORGANISM: Lactobacillus_plantarum

<400> SEQUENCE: 225

Ala Asp Pro Phe Ala Asn Asn Gly Asp Gln Ile Asp Ile Ser Asp Asp
1 5 10 15

Asp Leu Pro Phe
20

<210> SEQ ID NO 226
<211> LENGTH: 20
<212> TYPE: PRT
<213> ORGANISM: Lactobacillus_brevis

<400> SEQUENCE: 226

Ala Asp Pro Phe Ala Asn Ser Gly Asp Ser Ile Asp Ile Ser Asp Asp
1 5 10 15

Asp Leu Pro Phe
        20

<210> SEQ ID NO 227
<211> LENGTH: 20
<212> TYPE: PRT
<213> ORGANISM: Lactobacillus_sakei

<400> SEQUENCE: 227

Ala Asp Pro Phe Ala Asn Asn Gly Gln Ala Ile Asp Ile Ser Asp Asp
1               5                   10                  15

Asp Leu Pro Phe
        20

<210> SEQ ID NO 228
<211> LENGTH: 20
<212> TYPE: PRT
<213> ORGANISM: Lactobacillus_salivarius

<400> SEQUENCE: 228

Ala Asp Pro Phe Ala Asp Asn Gly Gln Ser Ile Asp Ile Ser Asp Asp
1               5                   10                  15

Asp Leu Pro Phe
        20

<210> SEQ ID NO 229
<211> LENGTH: 20
<212> TYPE: PRT
<213> ORGANISM: Leuconostoc_mesenteroides

<400> SEQUENCE: 229

Asn Pro Phe Ala Ala Ser Gly Asn Thr Glu Ile Asp Ile Ser Asp Asp
1               5                   10                  15

Asp Leu Pro Phe
        20

<210> SEQ ID NO 230
<211> LENGTH: 20
<212> TYPE: PRT
<213> ORGANISM: Lactobacillus_gasseri

<400> SEQUENCE: 230

Gln Asp Pro Phe Ala Asp Ser Gly Ser Thr Ile Asp Ile Ser Asp Asp
1               5                   10                  15

Asp Leu Pro Phe
        20

<210> SEQ ID NO 231
<211> LENGTH: 20
<212> TYPE: PRT
<213> ORGANISM: Enterococcus_faecalis

<400> SEQUENCE: 231

Ser Asp Pro Phe Gly Gly Ser Gly Ser Ser Ile Asp Ile Ser Asp Asp
1               5                   10                  15

Asp Leu Pro Phe
        20

<210> SEQ ID NO 232
<211> LENGTH: 20
<212> TYPE: PRT
<213> ORGANISM: Staphylococcus_haemolyticus

```
<400> SEQUENCE: 232

Asp Asn Pro Phe Ala Asn Ala Asn Gly Pro Ile Asp Ile Ser Asp Asp
1               5                   10                  15

Asp Leu Pro Phe
            20

<210> SEQ ID NO 233
<211> LENGTH: 20
<212> TYPE: PRT
<213> ORGANISM: Staphylococcus_saprophyticus

<400> SEQUENCE: 233

Asp Asn Pro Phe Ala Asn Ala Asn Gly Pro Ile Asp Ile Ser Asp Asp
1               5                   10                  15

Asp Leu Pro Phe
            20

<210> SEQ ID NO 234
<211> LENGTH: 20
<212> TYPE: PRT
<213> ORGANISM: Staphylococcus_epidermidis

<400> SEQUENCE: 234

Asp Asn Pro Phe Ala Asn Ala Asn Gly Pro Ile Asp Ile Ser Asp Asp
1               5                   10                  15

Asp Leu Pro Phe
            20

<210> SEQ ID NO 235
<211> LENGTH: 20
<212> TYPE: PRT
<213> ORGANISM: Listeria_innocua

<400> SEQUENCE: 235

Ser Asp Ser Phe Ala Asn Glu Gly Lys Pro Ile Asp Ile Asn Pro Asp
1               5                   10                  15

Asp Leu Pro Phe
            20

<210> SEQ ID NO 236
<211> LENGTH: 20
<212> TYPE: PRT
<213> ORGANISM: Listeria_monocytogenes

<400> SEQUENCE: 236

Ser Asp Ser Phe Ala Ser Glu Gly Lys Pro Ile Asp Ile Asn Glu Asp
1               5                   10                  15

Asp Leu Pro Phe
            20

<210> SEQ ID NO 237
<211> LENGTH: 20
<212> TYPE: PRT
<213> ORGANISM: Prosthecochloris_vibrioformis

<400> SEQUENCE: 237

Thr Ser Gln Pro Pro Ser Gly Pro Met Ile Glu Asn Asn Asp Lys Asp
1               5                   10                  15

Asp Leu Pro Phe
            20

<210> SEQ ID NO 238
```

```
<211> LENGTH: 20
<212> TYPE: PRT
<213> ORGANISM: Pelodictyon_luteolum

<400> SEQUENCE: 238

Pro Pro Gln Thr Ala Pro Ser Ala Pro Met Ile Glu Asn Asp Lys Asp
1               5                   10                  15

Asp Leu Pro Phe
            20

<210> SEQ ID NO 239
<211> LENGTH: 20
<212> TYPE: PRT
<213> ORGANISM: Chlorobium_phaeobacteroides

<400> SEQUENCE: 239

Asp Tyr Pro Gln Gln Ser Ser Gly Pro Met Ile Glu Ser Glu Lys Asp
1               5                   10                  15

Asp Leu Pro Phe
            20

<210> SEQ ID NO 240
<211> LENGTH: 20
<212> TYPE: PRT
<213> ORGANISM: Chlorobium_tepidum

<400> SEQUENCE: 240

Tyr Gly Ala Ser Pro Ser Ser Gly Gly Ala Gln Glu Phe Glu Lys Asp
1               5                   10                  15

Asp Leu Pro Phe
            20

<210> SEQ ID NO 241
<211> LENGTH: 20
<212> TYPE: PRT
<213> ORGANISM: Chlorobium_chlorochromatii

<400> SEQUENCE: 241

Pro Pro Ala Thr Pro Thr Val Pro Thr Met Ile Asp Thr Asp Lys Asp
1               5                   10                  15

Asp Leu Pro Phe
            20

<210> SEQ ID NO 242
<211> LENGTH: 20
<212> TYPE: PRT
<213> ORGANISM: Staphylococcus_aureus

<400> SEQUENCE: 242

Thr Gln Thr Gly Asn Asn Pro Phe Asp Asn Thr Glu Glu Asp Phe Ser
1               5                   10                  15

Asp Leu Pro Phe
            20

<210> SEQ ID NO 243
<211> LENGTH: 20
<212> TYPE: PRT
<213> ORGANISM: Lactobacillus_delbrueckii

<400> SEQUENCE: 243

Thr Asn Pro Phe Asp Ser Ser Asp Asp Ala Ile Asn Val Ser Asn Asp
1               5                   10                  15

Asp Leu Pro Phe
```

-continued

```
                    20

<210> SEQ ID NO 244
<211> LENGTH: 20
<212> TYPE: PRT
<213> ORGANISM: Salinibacter_rubber

<400> SEQUENCE: 244

Gly Gly Asp Gly Gln Pro Gly Ser Asp Glu Thr Phe Glu Pro Asp Asp
1               5                   10                  15

Asp Leu Pro Phe
            20

<210> SEQ ID NO 245
<211> LENGTH: 20
<212> TYPE: PRT
<213> ORGANISM: Cytophaga_hutchinsonii

<400> SEQUENCE: 245

Ala Met Glu Ser Ala Gly Ser Phe Glu Pro Gln Thr Ser Gly Ala Asp
1               5                   10                  15

Asp Leu Pro Phe
            20

<210> SEQ ID NO 246
<211> LENGTH: 20
<212> TYPE: PRT
<213> ORGANISM: Methylococcus_capsulatus

<400> SEQUENCE: 246

Gly Gly Ser Gly Ala Gly Ser Ser Gln Phe Asp Glu Gly Phe Asp Asp
1               5                   10                  15

Asp Val Pro Phe
            20

<210> SEQ ID NO 247
<211> LENGTH: 20
<212> TYPE: PRT
<213> ORGANISM: Alkalilimnicola_ehrlichei

<400> SEQUENCE: 247

Gly Gly Arg Gln Asp Asn Met Gly Asp Asp Ala Gly Ala Phe Glu Asp
1               5                   10                  15

Asp Ile Pro Phe
            20

<210> SEQ ID NO 248
<211> LENGTH: 20
<212> TYPE: PRT
<213> ORGANISM: Rhodopirellula_baltica

<400> SEQUENCE: 248

Ser Ser Asp Ser Gln Pro Thr Gly Asp Gly Pro Gly Tyr Asp Glu Pro
1               5                   10                  15

Asp Ile Pro Phe
            20

<210> SEQ ID NO 249
<211> LENGTH: 20
<212> TYPE: PRT
<213> ORGANISM: Synechococcus_WH_8102

<400> SEQUENCE: 249
```

```
Asp Asn Gln Glu Ala Ala Gly Ser Phe Gly Gly Gln Ala Ser Asp Glu
1               5                   10                  15

Glu Ile Pro Phe
            20

<210> SEQ ID NO 250
<211> LENGTH: 20
<212> TYPE: PRT
<213> ORGANISM: Synechococcus_CC9902

<400> SEQUENCE: 250

Asp Asn Gln Glu Ser Gly Gly Asn Phe Gly Gly Gln Ala Ser Asp Glu
1               5                   10                  15

Asp Ile Pro Phe
            20

<210> SEQ ID NO 251
<211> LENGTH: 20
<212> TYPE: PRT
<213> ORGANISM: Synechococcus_CC9311

<400> SEQUENCE: 251

Ser Glu Ala Gly Ser Gly Gly Phe Gly Gly Gly Ser Pro Ser Asp Glu
1               5                   10                  15

Glu Val Pro Phe
            20

<210> SEQ ID NO 252
<211> LENGTH: 20
<212> TYPE: PRT
<213> ORGANISM: Prochlorococcus_marinus

<400> SEQUENCE: 252

Ala Ser Asn Phe Gly Gly Gly Gly Phe Gly Asp Gly Pro Ser Glu Glu
1               5                   10                  15

Glu Val Pro Phe
            20

<210> SEQ ID NO 253
<211> LENGTH: 20
<212> TYPE: PRT
<213> ORGANISM: Arthrobacter_aurescens

<400> SEQUENCE: 253

Asn Pro Ser Ala Asn Ala Gly Ser Ser Trp Gly Asn Ser Pro Asp Ser
1               5                   10                  15

Glu Pro Pro Phe
            20

<210> SEQ ID NO 254
<211> LENGTH: 20
<212> TYPE: PRT
<213> ORGANISM: Arthrobacter_FB24

<400> SEQUENCE: 254

Pro Gly Val Ser Asn Ala Gly Gly Gly Trp Gly Asn Gly Pro Asp Ser
1               5                   10                  15

Glu Pro Pro Phe
            20

<210> SEQ ID NO 255
<211> LENGTH: 20
<212> TYPE: PRT
```

<213> ORGANISM: Mycobacterium_tuberculosis

<400> SEQUENCE: 255

Pro Trp Gly Ser Ala Pro Ala Ser Gly Ser Phe Gly Gly Gly Asp Asp
1

```
<210> SEQ ID NO 261
<211> LENGTH: 20
<212> TYPE: PRT
<213> ORGANISM: Nocardia_farcinica

<400> SEQUENCE: 261

Pro Trp Gly Ser Ala Pro Ala Ser Gly Ser Phe Ser Gly Ala Asp Asp
1               5                   10                  15

Glu Pro Pro Phe
            20

<210> SEQ ID NO 262
<211> LENGTH: 20
<212> TYPE: PRT
<213> ORGANISM: Mycobacterium_ulcerans

<400> SEQUENCE: 262

Gly Ser Ala Pro Ala Ala Gly Ser Phe Gly Gly Gly Arg Met Asp Asp
1               5                   10                  15

Glu Pro Pro Phe
            20

<210> SEQ ID NO 263
<211> LENGTH: 20
<212> TYPE: PRT
<213> ORGANISM: Mycobacterium_leprae

<400> SEQUENCE: 263

Asp Pro Trp Gly Ser Ala Pro Ala Ser Gly Ser Phe Gly Gly Asp Asp
1               5                   10                  15

Glu Pro Pro Phe
            20

<210> SEQ ID NO 264
<211> LENGTH: 20
<212> TYPE: PRT
<213> ORGANISM: Corynebacterium_jeikeium

<400> SEQUENCE: 264

Pro Trp Gly Ser Ala Pro Thr Ser Gly Ser Phe Gly Val Gly Asp Glu
1               5                   10                  15

Glu Pro Pro Phe
            20

<210> SEQ ID NO 265
<211> LENGTH: 20
<212> TYPE: PRT
<213> ORGANISM: Corynebacterium_diphtheriae

<400> SEQUENCE: 265

Asp Pro Trp Asn Ser Ala Pro Gln Ser Gly Phe Gly Asp Gly Asp Asp
1               5                   10                  15

Glu Pro Pro Phe
            20

<210> SEQ ID NO 266
<211> LENGTH: 20
<212> TYPE: PRT
<213> ORGANISM: Salinispora_tropica

<400> SEQUENCE: 266

Pro Trp Ser Ser Ala Pro Gln Ala Gly Gly Phe Gly Gly Ala Glu Gln
1               5                   10                  15
```

Asp Pro Pro Phe
            20

<210> SEQ ID NO 267
<211> LENGTH: 20
<212> TYPE: PRT
<213> ORGANISM: Corynebacterium_efficiens

<400> SEQUENCE: 267

Ala Pro Ala Pro Ser Arg Gly Gly Ser Gly Gly Gly Asn Phe Asp Glu
1               5                   10                  15

Glu Pro Pro Phe
            20

<210> SEQ ID NO 268
<211> LENGTH: 20
<212> TYPE: PRT
<213> ORGANISM: Corynebacterium_glutamicum

<400> SEQUENCE: 268

Asn Ser Ala Pro Pro Ala Gly Ser Gly Gly Phe Gly Gly Ala Asp Asp
1               5                   10                  15

Glu Pro Pro Phe
            20

<210> SEQ ID NO 269
<211> LENGTH: 20
<212> TYPE: PRT
<213> ORGANISM: Rhodococcus_RHA1

<400> SEQUENCE: 269

Ala Pro Gln Ala Ser Gly Ser Phe Gly Gly Ser Gly Gly Gly Ser Asp
1               5                   10                  15

Glu Pro Pro Phe
            20

<210> SEQ ID NO 270
<211> LENGTH: 20
<212> TYPE: PRT
<213> ORGANISM: Streptomyces_avermitilis

<400> SEQUENCE: 270

Gly Ser Ser Gly Gly Ser Ser Gly Gly Ser Gly Gly Gly Tyr Ser Asp
1               5                   10                  15

Glu Pro Pro Phe
            20

<210> SEQ ID NO 271
<211> LENGTH: 20
<212> TYPE: PRT
<213> ORGANISM: Thermobifida_fusca

<400> SEQUENCE: 271

Trp Ala Thr Gly Gly Gly Gly Phe Gly Gly Gly Gly Gly Tyr Ser Asp
1               5                   10                  15

Glu Pro Pro Phe
            20

<210> SEQ ID NO 272
<211> LENGTH: 20
<212> TYPE: PRT
<213> ORGANISM: Frankia_CcI3

```
<400> SEQUENCE: 272

Ala Pro Ile Asp Asp Pro Trp Ser Gln Pro Ala Gly Gly Tyr Ser Asp
1               5                   10                  15

Glu Pro Pro Phe
            20

<210> SEQ ID NO 273
<211> LENGTH: 20
<212> TYPE: PRT
<213> ORGANISM: Nocardioides_JS614

<400> SEQUENCE: 273

Ser Ala Pro Ala Asn Asp Pro Trp Gly Ala Pro Gly Val Gly Ser Asp
1               5                   10                  15

Glu Pro Pro Phe
            20

<210> SEQ ID NO 274
<211> LENGTH: 20
<212> TYPE: PRT
<213> ORGANISM: Acidothermus_cellulolyticus

<400> SEQUENCE: 274

Ala Asn Arg Gly Gly Gly Val Asp Pro Trp Ala Ser Ala Gln Thr Asp
1               5                   10                  15

Glu Pro Pro Phe
            20

<210> SEQ ID NO 275
<211> LENGTH: 20
<212> TYPE: PRT
<213> ORGANISM: Propionibacterium_acnes

<400> SEQUENCE: 275

Ala Asn Arg Gly Gly Gly Val Asp Pro Trp Ala Ser Ala Gln Thr Asp
1               5                   10                  15

Glu Pro Pro Phe
            20

<210> SEQ ID NO 276
<211> LENGTH: 20
<212> TYPE: PRT
<213> ORGANISM: Leifsonia_xyli

<400> SEQUENCE: 276

Pro Ser Ala Gly Thr Asp Val Trp Asn Thr Pro Gly Ala Tyr Asn Asp
1               5                   10                  15

Glu Thr Pro Phe
            20

<210> SEQ ID NO 277
<211> LENGTH: 20
<212> TYPE: PRT
<213> ORGANISM: Aster_yellows_witches_broom

<400> SEQUENCE: 277

Asn Lys Thr Ala Thr Lys Val Ile Val Gln Lys Val Ile Phe Leu Asp
1               5                   10                  15

Asn Lys Asp Lys
            20

<210> SEQ ID NO 278
```

```
<211> LENGTH: 20
<212> TYPE: PRT
<213> ORGANISM: Onion_yellows_2

<400> SEQUENCE: 278

Val Ile Val His Lys Val Ile Phe Leu Asp Asn Lys Ser Gln Thr Asp
1               5                   10                  15

Asn Leu Pro Phe
            20

<210> SEQ ID NO 279
<211> LENGTH: 20
<212> TYPE: PRT
<213> ORGANISM: Anabaena_variabilis

<400> SEQUENCE: 279

Glu Glu Ser Thr Ser Thr Ser Leu Pro Asn Glu Thr Gln Ala Val Ala
1               5                   10                  15

Asn Ala Asn Phe
            20

<210> SEQ ID NO 280
<211> LENGTH: 20
<212> TYPE: PRT
<213> ORGANISM: Nostoc_PCC_7120

<400> SEQUENCE: 280

Glu Glu Ser Thr Ser Thr Ser Ala Pro Asn Glu Thr Gln Ala Val Ala
1               5                   10                  15

Asn Ala Asn Phe
            20

<210> SEQ ID NO 281
<211> LENGTH: 20
<212> TYPE: PRT
<213> ORGANISM: Synechocystis

<400> SEQUENCE: 281

Leu Leu Gly Ser Lys Arg Asp Asn Ala Glu Ala Thr Met Asn Asn Tyr
1               5                   10                  15

Pro Glu Glu Phe
            20

<210> SEQ ID NO 282
<211> LENGTH: 20
<212> TYPE: PRT
<213> ORGANISM: Trichodesmium_erythraeum

<400> SEQUENCE: 282

Glu Leu Leu Gly Ser Lys Arg Asp Ser Glu Gln Ala Ala Leu Ala Ser
1               5                   10                  15

Tyr Asn Glu Phe
            20

<210> SEQ ID NO 283
<211> LENGTH: 20
<212> TYPE: PRT
<213> ORGANISM: Flavobacterium_johnsoniae

<400> SEQUENCE: 283

Ala Lys Asn Thr Asn Phe Asp Ala Pro Ser Glu Gly Leu Pro Ile Asn
1               5                   10                  15

Asp Leu Pro Phe
```

-continued

```
          20

<210> SEQ ID NO 284
<211> LENGTH: 20
<212> TYPE: PRT
<213> ORGANISM: Thermotoga_maritime

<400> SEQUENCE: 284

Leu Glu Ile Pro Glu Glu Asp Phe Ser Ser Asp Thr Phe Ser Glu Asp
1               5                   10                  15

Glu Pro Pro Phe
            20

<210> SEQ ID NO 285
<211> LENGTH: 20
<212> TYPE: PRT
<213> ORGANISM: Syntrophus_aciditrophicus

<400> SEQUENCE: 285

Glu Gly His Phe Ser Pro Phe Asn Asp Leu Pro Pro Leu Pro Glu Asp
1               5                   10                  15

Asp Val Pro Phe
            20

<210> SEQ ID NO 286
<211> LENGTH: 20
<212> TYPE: PRT
<213> ORGANISM: Leptospira_interrogans

<400> SEQUENCE: 286

Val Val Gly Gln Met Ile Arg Phe Asp Gly Leu Pro Gly Lys Lys Glu
1               5                   10                  15

Arg Glu Val Ala
            20

<210> SEQ ID NO 287
<211> LENGTH: 20
<212> TYPE: PRT
<213> ORGANISM: Desulfotalea_psychrophila

<400> SEQUENCE: 287

Ser Phe Pro Glu Pro Thr Gly Pro Asp Ala Tyr Gly Gly Thr Gly Asn
1               5                   10                  15

Asp Val Pro Phe
            20

<210> SEQ ID NO 288
<211> LENGTH: 20
<212> TYPE: PRT
<213> ORGANISM: Onion_yellows_phytoplasma_OY-M

<400> SEQUENCE: 288

Cys Asn Asn Val Gln Phe Leu Glu Ser Lys Lys Asn Pro Asp Asn Ala
1               5                   10                  15

Tyr Asp Asn Phe
            20

<210> SEQ ID NO 289
<211> LENGTH: 20
<212> TYPE: PRT
<213> ORGANISM: Campylobacter_jejuni

<400> SEQUENCE: 289
```

Glu Lys Leu Lys Glu Ile Asp Ile Asp Ala Tyr Asp Ser Asp Asp Thr
1               5                   10                  15

Asn Leu Pro Phe
            20

<210> SEQ ID NO 290
<211> LENGTH: 20
<212> TYPE: PRT
<213> ORGANISM: Thermosynechococcus_elongates

<400> SEQUENCE: 290

Leu Ser Ser Lys Arg Asp Thr Asp Pro Asn Ala Val Pro Ala Gly Tyr
1               5                   10                  15

Val Pro Glu Ile
            20

<210> SEQ ID NO 291
<211> LENGTH: 20
<212> TYPE: PRT
<213> ORGANISM: Shewanella_W3-18-1

<400> SEQUENCE: 291

Pro Ala Asp Asp Ala Ser Ser Gln Ala Asn Trp Ala Gln Thr Tyr Pro
1               5                   10                  15

Glu Pro Asp Phe
            20

<210> SEQ ID NO 292
<211> LENGTH: 20
<212> TYPE: PRT
<213> ORGANISM: Gloeobacter_violaceus

<400> SEQUENCE: 292

Lys Val Asp Gln Leu Glu Leu Leu Gly Arg Ala Ala Arg Pro Asp Glu
1               5                   10                  15

Pro Glu Ser Phe
            20

<210> SEQ ID NO 293
<211> LENGTH: 20
<212> TYPE: PRT
<213> ORGANISM: Shewanella_ANA-3

<400> SEQUENCE: 293

Ala Gln Pro Gln Gly Gly His Gln Gln Asn Thr Gln Gln Gln Ala Tyr
1               5                   10                  15

Asn Tyr His Arg
            20